US009029114B2

(12) United States Patent
Lee et al.

(10) Patent No.: US 9,029,114 B2
(45) Date of Patent: May 12, 2015

(54) **TYPE II RESTRICTION-MODIFICATION SYSTEM METHYLATION SUBUNIT OF *ALICYCLOBACILLUS ACIDOCALDARIUS***

(71) Applicant: Battelle Energy Alliance, LLC, Idaho Falls, ID (US)

(72) Inventors: Brady D. Lee, West Richland, WA (US); Deborah T. Newby, Idaho Falls, ID (US); Jeffrey A. Lacey, Idaho Falls, ID (US); David N. Thompson, Idaho Falls, ID (US); Vicki S. Thompson, Idaho Falls, ID (US); William A. Apel, Jackson, WY (US); Francisco F. Roberto, Highlands Ranch, CO (US); David W. Reed, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 14/055,966

(22) Filed: Oct. 17, 2013

(65) Prior Publication Data

US 2014/0093936 A1    Apr. 3, 2014

Related U.S. Application Data

(62) Division of application No. 13/604,979, filed on Sep. 6, 2012, now Pat. No. 8,569,030, which is a division of application No. 12/800,045, filed on May 5, 2010, now abandoned.

(51) Int. Cl.
| | | |
|---|---|---|
| *C12N 9/00* | (2006.01) | |
| *C12N 1/20* | (2006.01) | |
| *C12N 15/00* | (2006.01) | |
| *C07H 21/04* | (2006.01) | |
| *C12N 15/87* | (2006.01) | |
| *C12N 9/52* | (2006.01) | |
| *C12N 9/10* | (2006.01) | |

(52) U.S. Cl.
CPC ........ *C12N 15/87* (2013.01); *C12N 9/00* (2013.01); *C12N 9/52* (2013.01); *C12N 9/1007* (2013.01)

(58) Field of Classification Search
None
See application file for complete search history.

(56) References Cited

U.S. PATENT DOCUMENTS

| | | | |
|---|---|---|---|
| 4,237,226 A | 12/1980 | Grethlein | |
| 4,581,333 A | 4/1986 | Kourilsky et al. | |
| 4,624,922 A | 11/1986 | Horikoshi et al. | |
| 5,098,825 A | 3/1992 | Tchen et al. | |
| 5,882,905 A | 3/1999 | Saha et al. | |
| 5,916,795 A | 6/1999 | Fukunaga et al. | |
| 5,948,667 A | 9/1999 | Cheng et al. | |
| 6,083,733 A | 7/2000 | Groenberg et al. | |
| 6,268,197 B1 | 7/2001 | Schulein et al. | |
| 6,426,211 B1 | 7/2002 | de Buyl et al. | |
| 6,506,585 B2 | 1/2003 | Danielsen et al. | |
| 6,777,212 B2 | 8/2004 | Asakura et al. | |
| 6,833,259 B2 | 12/2004 | Bhosle et al. | |
| 7,727,755 B2 | 6/2010 | Thompson et al. | |
| 7,858,353 B2 | 12/2010 | Thompson et al. | |
| 7,923,234 B2 | 4/2011 | Thompson et al. | |
| 7,960,534 B2 | 6/2011 | Thompson et al. | |
| 8,071,748 B2 | 12/2011 | Thompson et al. | |
| 8,202,716 B2 | 6/2012 | Thompson et al. | |
| 2003/0134395 A1 | 7/2003 | Shetty et al. | |
| 2003/0233674 A1 | 12/2003 | Gabor et al. | |
| 2003/0233675 A1 | 12/2003 | Cao et al. | |
| 2004/0029129 A1 | 2/2004 | Wang et al. | |
| 2005/0112742 A1 | 5/2005 | Thompson et al. | |
| 2006/0105442 A1 | 5/2006 | Wu et al. | |
| 2006/0211083 A1 | 9/2006 | Katzen et al. | |
| 2007/0082381 A1 | 4/2007 | Wilting et al. | |
| 2007/0134778 A1 | 6/2007 | Benning et al. | |
| 2007/0148728 A1 | 6/2007 | Johnson et al. | |
| 2009/0203107 A1 | 8/2009 | Thompson et al. | |
| 2009/0215168 A1 | 8/2009 | Lee et al. | |
| 2009/0221049 A1 | 9/2009 | Shaw, IV et al. | |
| 2009/0226978 A1 | 9/2009 | Thompson et al. | |
| 2009/0253205 A1 | 10/2009 | Thompson et al. | |
| 2009/0263859 A1 | 10/2009 | Thompson et al. | |
| 2009/0269827 A1 | 10/2009 | Thompson et al. | |
| 2010/0203583 A1 | 8/2010 | Thompson et al. | |
| 2010/0311110 A1 | 12/2010 | Thompson et al. | |
| 2011/0081683 A1 | 4/2011 | Thompson et al. | |
| 2011/0275135 A1 | 11/2011 | Lee et al. | |
| 2012/0015407 A1 | 1/2012 | Thompson et al. | |

FOREIGN PATENT DOCUMENTS

| | | |
|---|---|---|
| DE | 197 17 893 A1 | 1/1999 |
| WO | 81/00577 | 3/1981 |
| WO | 99/06584 A1 | 2/1999 |

(Continued)

OTHER PUBLICATIONS

Michel et al., "Specificity of the protein secretory apparatus: secretion of the heat-labile enterotoxin B subunit pentamers by different species of Gram bacteria," Gene 152 (1995) pp. 41-45.
Miele, E. A. et al., 1983, J. Mol. Biol., 171: 281-295.
Mielenz, 2001, Curr. Op. in Micro., 4:324-329.
Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.
Neddleman and Wunsch, J. Mol. Biol. 48: 443 (1970).
Ng et al., 1981, Applied and Environmental Microbiology, 41(6):1337-1343.
Ohta et al., "Purification and Characterization of an Acidophilic Xylanase from *Aureobasidium pullulans* var. *melanigenum* and Sequence Analysis of the Encoding Gene," Journal of Bioscience and Bioengineering, vol. 92, No. 3, 262-270, 2001.

(Continued)

*Primary Examiner* — Christian Fronda
(74) *Attorney, Agent, or Firm* — TraskBritt

(57) ABSTRACT

Isolated and/or purified polypeptides and nucleic acid sequences encoding polypeptides from *Alicyclobacillus acidocaldarius* are provided. Further provided are methods for modulating or altering recombination inside or outside of a cell using isolated and/or purified polypeptides and/or nucleic acid sequences from *Alicyclobacillus acidocaldarius*.

7 Claims, 228 Drawing Sheets

(56) References Cited

FOREIGN PATENT DOCUMENTS

| WO | 03/068926 | | 8/2003 |
|---|---|---|---|
| WO | 2005/066339 | | 7/2005 |
| WO | 2006/117247 | A1 | 11/2006 |
| WO | 2010/014976 | A2 | 2/2010 |

OTHER PUBLICATIONS

Olins, P. O., and Lee, S. C., 1993, Recent advances in heterologous gene expression in *E. coli*. Curr. Op. Biotechnology 4: 520-525.

Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.

Pajunen et al., Microbiology (2005) 151, 1209-1218.

Patel et al., (2006), "Medium and long-term opportunities and risks of the biotechnological production of bulk chemicals from renewable resources: The potential of white biotechnology". The BREW Project. Final Report prepared under the European Commission's Growth Programme (DG Research), (publica.fraunhofer.de/eprints/N-48834.pdf).

PCT International Preliminary Report on Patentability of the International Search Authority for PCT/US09/32333, dated Aug. 3, 2010.

PCT International Preliminary Report on Patentability of the International Searching Authority for PCT/US09/00442, dated Jul. 27, 2010.

PCT International Preliminary Report on Patentability of the International Searching Authority for PCT/US09/34701, dated Aug. 24, 2010.

PCT International Preliminary Report on Patentability of the International Searching Authority for PCT/US09/35275, dated Aug. 31, 2010.

PCT International Preliminary Report on Patentability of the International Searching Authority for PCT/US09/35331, dated Aug. 31, 2010.

PCT International Preliminary Report on Patentability of the International Search Authority for PCT/US09/35307, mailed Jan. 25, 2011.

PCT International Search Report and Written Opinion of the International Searching Authority for PCT/US10/51095, dated Dec. 2, 2010, 11 pages.

PCT International Search Report and Written Opinion of the International Search Authority for PCT/US11/34852, dated Oct. 21, 2011, 12 pages.

PCT International Search Report and Written Opinion of the International Searching Authority for PCT/US09/00442, dated May 18, 2009, 8 pages.

PCT International Search Report and Written Opinion of the International Searching Authority for PCT/US09/34701, dated Jan. 12, 2010, 10 pages.

PCT International Search Report and Written Opinion of the International Searching Authority for PCT/US09/35275, dated Feb. 25, 2010, 13 pages.

PCT International Search Report and Written Opinion of the International Searching Authority for PCT/US09/35331, dated Feb. 23, 2010, 10 pages.

PCT International Search Report and Written Opinion of the International Search Authority for PCT/US09/35307, dated Jun. 10, 2010, 10 pages.

PCT International Search Report and Written Opinion of the International Search Authority for PCT/US10/25521, dated Jul. 14, 2010, 12 pages.

PCT International Search Report of the International Search Authority for PCT/US10/25521 Jul. 14, 2010.

Pearson and Lipman, Proc. Natl. Acad. Sci. (U.S.A.) 85: 2444 (1988).

Perlack et al., "Biomass as Feedstock for a Bioenergy and Bioproducts Industry: The Technical Feasibility of a Billion-Ton Annual Supply," USDA and DOE, Apr. 2005, 78 pages.

Peyton et al., "Biotransformation of Toxic Organic and Inorganic Contaminants by Halophilic Bacteria," Halophilic Microorganisms, Antionio Ventosa (Ed.), Springer, 2004, pp. 315-331.

Ragauskas et al., "The Path Forward for Biofuels and Biomaterials," Science, Jan. 27, 2006, vol. 311, pp. 484-4589.

Ramos et al., "Biomechanical and Biochemical Pulping of Sugarcane Bagasse with *Ceriporiopsis subvermispora* Fungal and Xylanase Pretreatments," J. Agric. Food Chem. 2001, 49, 1180-1186.

Saeman et al., "Quantitative Saccharification of Wood and Cellulose," Industrial and Engineering Chemistry, Jan. 1945, vol. 17, No. 1, pp. 35-37.

Saha et al., "Dilute Acid Pretreatment, Enzymatic Saccharification, and Fermentation of Rice Hulls to Ethanol," Biotechnol. Prog. 2005, 21, 816-822.

Sanchez-Pescador, R., 1988, J. Clin. Microbiol., 26(10): 1934-1938.

Sa-Pereira et al., "Rapid production of thermostable cellulose-free xylanase by a strain of *Bacillus subtilis* and its properties," Enzyme and Microbial Technology, 30 (2002) 924-933.

Schafer et al., "X-ray Structures of the Maltose-Maltodextrin-binding Protein of the Thermoacidophilic Bacterium *Alicyclobacillus acidocaldarius* Provide Insight into Acid Stability of Proteins," J. Mol. Biol. 2004, 335:261-274.

Schaffer, C. et al., 2001, Prokaryotic glycosylation. Proteomics, 1: 248-261.

Scheffel et al., "Functional reconstitution of a maltrose ATP-binding cassette transporter from the thermoacidophilic gram-positive bacterium *Alicyclobacillus acidocaldarius*," Biochem Biophy Acta, 2004, 1656(1):57-65.

Schell et al., "Dilute-Sulfuric Acid Pretreatment of Corn Stover in Pilot-Scale Reactor," Applied Biochemistry and Biotechnology, vol. 105-108, 2003, pp. 69-85.

Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.

Schwarz, Wolfgang H., "A list of cellulolytic bacteria," Technische Universitat Munchen, Apr. 24, 2003, 8 pages.

Schwermann, B. et al., 1994, Purification, properties and structural aspects of a thermoacidophilic a-amylase from *Alicyclobacillus acidocaldarius* ATCC 27009, insight into acidostability of proteins. Eur. J. Biochem. 226: 981-991.

Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).

Shallom et al., "Microbial hemicellulases," Current Opinion in Microbiology, Current Biology Ltd, GB, vol. 6, No. 3, Jun. 1, 2003, pp. 219-228.

Simpson et al., "An extremely Thermostable xylanase from the thermophilic eubacterium *Thermotoga*," Biochem. J. (1991) 277, 413-417.

Smook, G.A., "Handbook for Pulp & Paper Technologists," Tappi Pr; 2nd Ed. (Jun. 1992) pp. 65-88.

Subramaniyan et al., "Cellulase-free xylanases from *Bacillus* and other microorganisms," FEMS Microbiology Letters 183 (2000) 1-7.

Sunna et al., "Glycosyl hydrolases from hyperthermophiles," Extremophiles (1997) 12-13.

Supplemental European Search Report for EP 06 82 7231, dated Nov. 12, 2009, 6 pages.

Techapun et al., "Production of a cellulose-free xylanase from agricultural waste materials by a thermotolerant *Streptomyces* sp.," Biotechnology Letters 23: 1685-1689, 2001.

Thompson et al., "Comparison of Pretreatment Methods on the Basis of Available Surface Area," Bioresource Technology 39 (1992) 155-163.

Thompson et al., "In Vitro Degradation of Natural Insoluble Lignin in Aqueous Media by the Extracellular Peroxidases of *Phanerochaete chrysosporium*," 1998 John Wiley & Sons, Inc. pp. 704-717.

Thompson et al., "Measurement of fumonsins in corn with a fiberoptic fluoroimmunosensor," SPIE vol. 2980, (2010) pp. 532-538.

(56) References Cited

OTHER PUBLICATIONS

Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.
Thompson et al., "Purification and Characterization of a Novel Thermo-Alkali-Stable Catalase from *Thermus brockianus*," Biotechnol. Prog. 2003, 19, 1292-1299.
Thompson et al., "Thermoacidophilic Cellulases and Hemicellulases from *Alicyclobacillus acidocaldarius*," Idaho National Laboratory, 2006, 1 page.
Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.
Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.
Tsao, GT, MR Ladisch, and HR Bungay, 1987. Biomass Refining, In Advanced Biochemical Engineering, Wiley Interscience, N.Y., 79-101.
Turner et al., "Potential and utilization of thermophiles and thermostable enzymes in biorefining," Microbial Cell Factories, Biomed Central, London, NL, vol. 6, No. 1, Mar. 15, 2007, p. 9.
Uhl et al., "The first description of an archaeal hemicellulase: the xylanase from *Thermococcus zilligii* strain AN1," Extremophiles (1999) 3:263-267.
Uniprot Direct submission Q9RHZ5_ALIAC, "Putative maltose transport membrane protein malF," Nov. 13, 2007. [Retrieved from the Internet Jan. 22, 2010: <http://www.uniprot.org/uniprot/Q9RHZ5.txt?version=30?].
UniProtKB/TrEMBL Q9JRQ1 [online]. Oct. 1, 2000. Available on the internet at <<URL://http://www.uniprot.org/uniprot/Q9JRQ1>>.
Upreti et al., 2003, Bacterial glycoproteins: Functions, biosynthesis and applications. Proteomics, 3: 363-379.
Urdea, M. S., 1988, Nucleic Acids Research, II: 4937-4957.
Vieille and Zeikus, 2001, Micro. and Mol. Biol. Rev., vol. 65, No. 1, p. 1-43.
Viikari et al., "Xylanases in bleaching: From an idea to the industry," FEMS Microbiology Reviews 13 (1994) 335-350.
Walker, G. T. et al., 1992, NAR 20: 1691-1696.
Walker, G.T. et al., 1992, PNAS. USA, 89:392-396.
Walseth, Curtis S., Occurrence of Cellulases in Enzyme Preparations from Microorganisms, TAPPI vol. 35, No. 5, May 1952, pp. 228-233.
Ward et al., "Characterization of a new bacteriophage which infects bacteria of the genus *Acidiphilium*," Journal of General Virology (1993) 74: 2419-2425.
Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.
Whisstock et al. "Prediction of Protein Function from Protein Sequence and Structure" Quarlty Reviews of Biophysics 36, 3 (2003) pp. 307-340 (35 pages).
Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).
Wright et al., "Ethanol from Biomass by Enzymatic Hydrolysis," Chemical Engineering Progress, Aug. 1988, pp. 62-74.
Yuan et al., Expression of acidophilic alpha-amylase from *Alicyclobacillus acidocaldarius*, Sheng Wu Gong Cheng Xue Bao, Jan. 2005, 21(1):78-83. Abstract only.
Database UniProt [Online]. Feb. 10, 2009. XP-002698982. Database accession No. B7DRM6, 1 page.
Extended Supplementary European Search Report for EP 09 75 5308, dated Jun. 18, 2013, 3 pages.
Extended Supplementary European Search Report for EP 09 74 3132, dated Apr. 19, 2013, 4 pages.
Fan et al., "The Nature of Lignocellulosics and Their Pretreatments for Enzymatic Hydrolysis," Advances in Biochemical Engineering/Biotechnology, 1982, vol. 23/1982, 157-187.
Flanagan, et al., "Development of gas phase bioreactors for the removal of nitrogen oxides from synthetic flue gas streams," Fuel 81 (2002) 1953-1961.
Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.
Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.
GenBank: E17054.1 Direct Submission *Alicyclobacillus acidocaldarius* genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2 &tool=Entr.
GenBank: AJ252161.1 *Alicyclobacillus acidocaldarius* maltose/maltodextrine transport gene region(maIEFGR genese, cdaA gene and glcA gene), NCBI, Hulsmann, A. http://www.ncbi.nlm.nih.gov/nuccore/AJ252161 (Jan. 6, 2000).
Gessesse, Amare, "Purification and Properties of Two Thermostable Alkaline Xylanases from an Alkaliphilic *Bacillus* sp.," Applied and Environmental Microbiology, Sep. 1998, pp. 3533-3535.
Glenn et al., "Transformation of *Acidiphilium* by electroporation and conjugation," Can J Microbiol. May 1992;38(5):387-93.
Goldstein et al., "The Hydrolysis of Cellulose with Superconcentrated Hydrochloric Acid," Biotechnology and Bioengineering Symp. No. 13, pp. 17-25 (1983).
Grassin et al., "Chapter 2.13, Fruit Juices," (T. Godfrey and S. West, eds.), Industrial Enzymology, 2nd Ed., pp. 227-264 (1996).
Grethlein, H. E., "Pretreatment for enhanced hydrolysis of cellulosic biomass," Biotechnol. Adv. 1984. 2:43-62.
Grethlein, Hans E., "Comparison of the Economics of Acid and Enzymatic Hydrolysis of Newsprint," Biotechnology and Bioengineering, vol. XX, pp. 503-525 (1978).
Guateli, J. C. et al., 1990, PNAS. USA, 87: 1874-1878.
Hamelinck, CN, G van Hooijdonk, and APC Faaij, 2005, Ethanol from lignocellulosic biomass: techno-economic performance in short-, middle-, and long-term, Biomass Bioenergy, 28:384-410.
Hanselmann, K.W., "Lignochemicals," Experientia 38 (1982) pp. 176-189.
Houghton et al., "Fungal Upgrading of Wheat Straw for Straw-Thermoplastics Production," Applied Biochemistry and Biotechnology, vol. 113-116, 2004, pp. 71-93.
Hulsmann et al., "Maltose and maltodextrin transport in the thermoacidophilic gram-positive bacterium *Alicyclobacillus acidocaldarius* is mediated by a high-affinity transport system that includes a maltose binding protein tolerant to low pH," J. Bacteriology, Nov. 2000, p. 6292-6301.
Huygen, K. et al., 1996, Nature Medicine, 2(8): 893-898.
International Preliminary Report on Patentability and Written Opinion of the International Searching Authority for PCT/US06/42566 datedApr. 23, 2009 (7 pages).
International Search Report and Written Opinion of the International Search Authority for PCT/US09/32333, mailed Jun. 19, 2009, 9 pages.
International Search Report of the International Searching Authority for PCT/US06/42566, dated Jul. 25, 2008.
Ito et al., "Purification and properties of acid stable xylanases from *Aspergillus kawachii*," Bioscience Biotechnology and Biochemistry 56 (4):547-550, Apr. 1992.
Jeffries, 1996, Curr. Op. in Biotech., 7:337-342.
Jones et al., "Cloning and transcriptional analysis of the *Thermoanaerobacter ethanolicus* strain 39E maltose ABC transport system," Extremophiles 2002, 6:291-299.
Keller et al., "Microbial Pretreatment of Biomass: Potential for Reducing the Severity of Thermochemical Biomass Pretreatment," Applied Biochemistry and Biotechnology, vol. 105-108, 2003.

(56) References Cited

OTHER PUBLICATIONS

Kenealy et al., "Rapid 2,2'-bicinchoninic-based xylanase assay compatible with high throughput screening," Biotechnology Letters 25: 1619-1623, 2003.
Kievitis, T. et al., 1991, J. Virol. Methods, 35: 273-286.
Knappert et al., "Partial Acid Hydrolysis of Cellulosic Materials as a Pretreatment for Enzymatic Hydrolysis," Biotechnology and Bioengineering, vol. XXII, pp. 1449-1463 (1980).
Kohler, G. et al., 1975, Nature, 256(5517): 495497.
Kulkarni et al., "Molecular and biotechnological aspects of xylanases," FEMS Microbiology Reviews 23 (1999) 411-456.
Kwoh, D. Y. et al., 1989, PNAS. USA, 86: 1173-1177.
Lau et al., "PCR ligation mutagenesis in transformable streptococci: application and efficiency," Journal of Microbiological Methods 49 (2002) 193-205.
Lauro et al., "Characterization of a β-glycosidase from the thermoacidophilic bacterium *Alicyclobacillus acidocaldarius*," Extremophiles (2006) 10:301-310.
Lauro et al., "Isolation and characterization of a new family 42 beta-galactosidase from the thermoacidophilic bacterium *Alicyclobacillus acidocaldarius*: Identification of the active site residues," Biochimica et Biophysica Acta 1784 (2008) 292-301.
Lavarack et al., "The acid hydrolysis of sugarcane begasse hemicellulose to produce xylose, arabinose, glucose and other products," Biomass and Bioenergy 23 (2002) 367-380.
Lee et al., "Oxygen Effects on Thermophilic Microbial Populations in Biofilters Treating Nitric Oxide Containing Off-Gas Streams," Environmental Progress, vol. 20, No. 3, Oct. 2001.
Lin et al., "Purification, Characterization, and Gene Cloning of Thermopsin, a Thermostable Acid Protease from *Sulfolobus acidocaldarius*," The Journal of Biological Chemistry, 1990, vol. 265, No. 3, pp. 1490-1495.
Liu C, and CE Wyman, 2003, The effect of flow rate of compressed hot water on xylan, lignin, and total mass removal from corn stover, Ind. Eng. Chem. Res., 42:5409-5416.
Lucas et al., C4-Dicarboxylate Transporter/Malic Acid Transport Protein [*Alicyclobacillus acidocaldarius* LAA1], GenBank Direct Submission, Accession No. EED06059, Dec. 17, 2008 (Retrieved from the Internet Dec. 15, 2009: <URL:http://www.ncbl.nlm.nlh.gov/.
Luckow, V. A., 1993, Baculovirus systems for the expression of human gene products. Curr. Op. Biotechnology 4:564-572.
Lynd et al., 2002, Micro. and Mol. Biol. Rev., vol. 66, No. 3, p. 506-577.
Lynd, Lee R., "Overview and Evaluation of Fuel Ethanol from Cellulosic Biomass: Technology, Economics, the Environment, and Policy," Annu. Rev. Energy Environ. 1996, 21:403-65.
Mackenzie et al., "Multiple Chromosomes in Bacteria: The Yin and Yang of trp Gene Localization in Rhodobacter sphaeroides 2.4.1," Genetics 153: 525-538 (Oct. 1999).
Malherbe and Cloete, 2002, Re/View in Environmental Science and Bio/Technology, 1: 105-114.
Manchenko, Gennady P., "Handbook of Detection of Enzymes on Electrophoretic Gels," CRC Press, Inc. 1994, pp. 220-240.
Matthews, J. A. et al., 1988, Anal. Biochem., 169: 1-25.
McCoy, Michael, "Chemical Makers Try Biotech Paths," Chemical Engineering News, Jun. 22, 1998, pp. 13-19.
Merrifield, R. D., 1966, J. Am. Chem. Soc., 88(21): 5051-5052.
Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.
Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).
Badger, P.C., "Ethanol from cellulose: A general review," In: J. Janick and A. Whipkey (eds.), Trands in new crops and new uses. ASHS Press, Alexandria, VA, 2002, pp. 17-21.
Bailey et al., "Interlaboratory testing of methods for assay of xylanase activity," Journal of Biotechnology, 23 (1992) 257-270.
Barany, F., 1991, PNAS. USA, 88: 189-193.
Bergquist et al., "Molecular diversity of thermophilic cellulolytic and hemicellulolytic bacteria," FEMS Microbiology Ecology 28 (1999) 99-110.
Bertoldo et al., 2004, Eng. Life Sci., 4, No. 6.
Bhatia et al., "Microbial beta-Glucosidases: Cloning, Properties, and Applications," Critical Reviews in Biotechnology, 22(4):375-407, Jan. 1, 2002.
BLAST Search of Seq. ID. 36, accessed Apr. 22, 2009, 54 pages.
BLAST Search of Seq. ID. 456, accessed Apr. 22, 2009, 48 pages.
BLAST Search of Seq. ID. 458, accessed Apr. 22, 2009, 59 pages.
BLAST Search of Seq. ID. 460, accessed Apr. 22, 2009, 37 pages.
BLAST Search of Seq. ID. 462, accessed Apr. 22, 2009, 35 pages.
BLAST Search of Seq. ID. 464, accessed Apr. 22, 2009, 45 pages.
Bork, Peer, "Powers and Pitfalls in Sequence Analysis: The 70% Hurdle," Genome Research, 2000, 10:398-400.
Borman, S., 2006, Glycosylation Engineering. Chem. Eng. News, 84(36): 13-22.
Bowie et al., "Deciphering the Message in Protein Sequences: Tolerance to Amino Acid Substitutions," Science, 1990, 247:1306-1310.
Breves et al., "Genes Encoding Two Different beta-Glucosidases of *Thermoanaerobacter brockii* Are Clustered in a Common Operon," Applied and Environmental Microbiology, vol. 63, No. 10, Oct. 1997, pp. 3902-3910.
Broun et al. "Catalytic Plasticity of Fatty Acid Modification Enzymes Underlying Chemical Diversity of Plant Lipids" Science vol. 282 Nov. 13, 1998 pp. 1315-1317 (4 pages).
Buckholz, R. G., 1993, Yeast systems for the expression of heterologous gene products. Curr. Op. Biotechnology 4: 538-542.
Burg, J. L. et al., 1996, Mol. and Cell. Probes, 10: 257-271.
Chu, B. C. F. et al., 1986, NAR, 14: 5591-5603.
Collins et al., "Xylanaes, Xylanase Families and Extremophilic Xylanses," FEMS Microbiology Review, 2005, pp. 3-23.
Cowling, Ellis B., "Physical and Chemical Constrains in the Hydrolysis of Cellulose and Lignocellulosic Materials," Biotechnol. & Bioeng. Symposium No. 5, 163-181 (1975).
Crout et al., "Glycosidases and glycosyl transferases in glycoside and oligosaccharide synthesis," Current Opinion in Chemical Biology, Current Biology LTD, London, GB, vol. 2, No. 1, Feb. 1, 1998, pp. 98-111.
Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.
Database EMBL [Online]. Mar. 16, 2007. XP-002627757. Database accession No. ER073884, 1 page.
Database Geneseq [Online]. May 21, 1998. XP-002627734. Database accession No. AAW35004, 1 page.
Database UniProt [Online]. May 1, 1997. XP-002630045. Database accession No. P96090, 1 page.
Database UniProt [Online]. Oct. 1, 2001. XP-002627736. Database accession No. Q97UI4, 1 page.
Database UniProt [Online]. Feb. 10, 2009. XP-000002659383. Database accession No. B7DT70, 1 page.
Database UniProt [Online]. Jun. 26, 2007. XP-002627735. Database accession No. A5IKZ4, 1 page.
Database UniProt [Online]. Nov. 3, 2009. XP-002627733. Database accession No. C8WTP2, 1 page.
Database Uniprot [Online]. Nov. 3, 2009. Database accession No. C8WVZ2, 2 pages.
Database UniProt [Online]. Feb. 10, 2009. XP-002674095. Database accession No. B7DM51, 1 page.
Database UniProt [Online]. Feb. 10, 2009. XP-002695727. Database accession No. B7DUZ1, 1 page.
Devos et al. "Practical Limits of Functiona Prediction" Proteins: Structure, Function, and Genetics 41 (2000) pp. 98-107 (10 pages).
Duck, P. et al., 1990, Biotechniques, 9: 142-147.

(56) References Cited

OTHER PUBLICATIONS

Eckert et al., "A Thermoacidophilic Endoglucanase (CelB), etc.," Eur. J. Biochem. 270, 2003, pp. 3593-3602.

Eckert et al., "Gene cloning, sequencing, and characterization of a family 9 endoglucanase (CelA) with an unusual pattern of activity from the theremoacidophile *Alicyclobacillus acidocaldarius* ATCC27009," Applied Microbiology and Biotechnology, vol. 60, pp. 428-436 (2002).

Eckert, Kelvin, "Dissertation, Cloning and Characterization of two glycosidases from the acidothermophile *Alicyclobacillus acidocaldarius* ATCC27009," Berlin, Dec. 18, 1971, 113 pages.

Edwards, C. P., and Aruffo, A., 1993, Current applications of COS cell based transient expression systems. Curr. Op. Biotechnology 4: 558-563.

Ehrman, Tina, "Standard Method for Determination of Total Solids in Biomass," Chemical Analysis and Testing Task, Laboratory Analytical Procedure, Oct. 28, 1994, 242 total pages.

EMBL Submission CP001728, Sep. 2009. [Retrieved from the internet: URL:http://www.ebi.ac.uk/Tools/dbfetch/embifetch?style=html&id=CP001728&Submit=Go], 51 pages.

Erlich, H.A., J Clin. Immunol., Nov. 1989; 9(6):437-47.

Extended Supplementary European Search Report for EP 09 70 3173, dated Apr. 20, 2011, 7 pages.

Extended Supplementary European Search Report for EP 09 82 3952, dated Sep. 20, 2011, 7 pages.

Extended Supplementary European Search Report for EP 09 70 9191, dated Mar. 29, 2012, 6 pages.

Extended Supplementary European Search Report for EP 09 75 5307, dated Apr. 18, 2012, 4 pages.

Extended Supplementary European Search Report for EP 10 74 6882, dated Aug. 27, 2012, 9 pages.

FIG. 1

```
gb|AAY21825.1|              ------------------------------------------SVSTTVSSTSS----PST
ref|XP_001743680.1|         -----------------------------------------TTSTTSTTSTTSTNSTNSTT
ref|XP_001525241.1|         ------------------------------------------------------------
RAAC03697                   MLGCVKVGLETGKEAIQRVLNWSCTHFIQRERFMMRKTIAAIVTLGTVSSMLAGTVYAAT
ref|YP_308280.1|            ----------------------------------------TGSSFIEGNVYADDGIDLG
ref|ZP_01916690.1|          ---------------------------------------SGPLQGSGEQGQNTVTA gb|AAY21825.1|              TLTSTSTTNQTTNTTTASSTPANTTLTSTSPTNQTTTTNNSSG---TQTSNTSSTQPPTS
ref|XP_001743680.1|         STTSTTSTTSTTSTTSTTSTTSTTSTTSTTSTSSTGNTSS---SAISNTTANSTDTS
ref|XP_001525241.1|         --TSTTSTTSTTNTNVPANSTASTTTNST--ANSTTSTANNSN---QLAQDKAAKYE---
RAAC03697                   NTTNATSTGNTANTTASATSNATSNTTGSAPTNPNVLTQKSAVYQLIEVFNTIPSWPTGL
ref|YP_308280.1|            WSTPITGDAVTPADINRPGNISGTVTTGAAPQLPNVLTDAEIA---AIVTDIQNETAFAA
ref|ZP_01916690.1|          PNSSESGALTNSAPQNRTSTSTSSNSPGSAPANPGIATQKSAPSEPVRPSRPTPPAPSGS
                              :   :    ..    . . : :    .:       * gb|AAY21825.1|              QSLDTST-----------------------------------------------------
ref|XP_001743680.1|         TSMSPSRT-NGSDTPSSPAPPA--------------------------------------
ref|XP_001525241.1|         ------------------------------------------------------------
RAAC03697                   QSIDPATQNAQWDWKYKPIPPSQWVGLACVFPGDPESKYAADLGIQMTDPNGPVTAGQLA
ref|YP_308280.1|            FSPGAITRSSDWNIKYYPVPAS--------------------------------------
ref|ZP_01916690.1|          SGPQPAAPVSQ------------------------------------------------- gb|AAY21825.1|              -----------
ref|XP_001743680.1|         -----------
ref|XP_001525241.1|         -----------
RAAC03697                   QWIVDWEVKAR
ref|YP_308280.1|            -----------
ref|ZP_01916690.1|          -----------
```

FIG. 2

```
gb|EAZ41188.1|        ----------ARVVHHREHAMRAQAG---------------LDRVEQQQAAMGTGQFTGH
RAAC02297             -MVPFDPSCHARFVHHRNHVLQAETGHLKGGDNGMGYVILALGLVPSVLLVMGAGQGEYA
ref|YP_429214.1|      -----------LLRPAVERCIASWSG---------------GALR-AIEQLGND----I
gb|AAR38445.1|        ---------NGLLVGSYYTLLALGLS----------IIFSLGCVVNLAHGAFYAVGAYL
ref|ZP_01774730.1|    -----------------IARVAAVDRD----------------QLLLVDET-----
ref|ZP_01171092.1|    KRNSELFSLYDMLLSEIEMMQQTRINAYSLIRTLKPYFKELDGTITRLLANWTNDKGPEY gb|EAZ41188.1|        GIERRRHRAAGVAFAHHRLQEHRFDEPLVT-------------------------------
RAAC02297             GIRTRARIAAGWYGAKMRVRKRLEDEQLVSLLRKSGLTLKAYQYHYLRIGLTLVFLLMGV
ref|YP_429214.1|      NLKEADVLIA--------VLMQIVEGGVAK-------------------------------
gb|AAR38445.1|        TVLFTDILGFG--------LAFLITPAVVG-------------------------------
ref|ZP_01774730.1|    -HAFRGRVAGG----------YLHRHHLSQ-------------------------------
ref|ZP_01171092.1|    ALDIFAKEIGTNEAKSLANVLKKFDENKRD------------------------------- gb|EAZ41188.1|        ---------------------------------CGILEHLAQAGL----------------
RAAC02297             VGLLHGRLLPMLFPLVVWFGLEYRRPFPMYYGFLALQKQAALERDKALYLLYRLLLQEAV
ref|YP_429214.1|      -----------------------------LAGVMEEEAL----------------
gb|AAR38445.1|        --------------------------------LIGIAIEALFLR----------------
ref|ZP_01774730.1|    --------------------------------ELPCVGDWVCLEK----------------
ref|ZP_01171092.1|    --------------------------------TIILSLKGMEDMFIN--------------
                                                       :          :

gb|EAZ41188.1|        -----------------------------------------VVRRHGDH------------
RAAC02297             AFRGRPLGVYDMLRRQLHRVPVLSPFLERCLHDWVDDPAVALRRFGDEVGTSQAKALAHM
ref|YP_429214.1|      --------------------------------------------RLDEL------------
gb|AAR38445.1|        ---------------------------------------RLYNKDPILTLLFTFGLA
ref|ZP_01774730.1|    ----------------------------------------APGDDVGVVRALLERRT
ref|ZP_01171092.1|    ----------------------------------------SQIENYRRKRKLYVDLAKL
                                                                   .

gb|EAZ41188.1|        ------------------------------------------------------------
RAAC02297             LIEIEEAGVAVALDVLQTNLERFRADRIAAFRAHLNTRSILATALTMLGLGATSFDLMVV
ref|YP_429214.1|      ------------------------------------------------------------
gb|AAR38445.1|        MSGEQALRLIFGASGIPFSIPEFLSGQLH-------------------------------
ref|ZP_01774730.1|    LLRRKSAGDAIEYQMIASNLD---------------------------------------
ref|ZP_01171092.1|    PIKATHGLIILNFVVVIIFMVSYLMKDS-------------------------------- gb|EAZ41188.1|        ----------------
RAAC02297             IQVYAGALMRASAGG
ref|YP_429214.1|      ----------------
gb|AAR38445.1|        ----------------
ref|ZP_01774730.1|    ----------------
ref|ZP_01171092.1|    ----------------
```

FIG. 3

```
ref|ZP_01900573.1|   ------------------------------------------------------------
RAAC02298            MGGDIVANALNTLAQIVLYGVACAGLLWLFEQVWRDGWAWAKRTYYGIGHRQLLRVSEGF
ref|ZP_01301851.1|   ------------------------------------------------------------
ref|ZP_01171091.1|   ------------------------------------------------------------
ref|ZP_02598168.1|   ------------------------------------------------------------
ref|ZP_01575699.1|   ------------------------------------------------------------ ref|ZP_01900573.1|   ------------------------------------------------------------
RAAC02298            RGRQTTQLPWWMGWHDHLETLLQATLKRPHRDAVSRFIVGSVTAAVIVGVLTSVVTHNPF
ref|ZP_01301851.1|   ------------------------------------------------------------
ref|ZP_01171091.1|   --------------------------------VSTFIVLSLLIGFLTFSLILVKYQDAF
ref|ZP_02598168.1|   ----------------HLELLLSSISKNSKKINVFNFLFASMLVFVITVSVLYFLIHDLV
ref|ZP_01575699.1|   ---------------NHIYKVLTASLSKEISDLGTYSFMIGSISLFIFS-FLTALKLFNFI ref|ZP_01900573.1|   ------------------------------------------------------------
RAAC02298            YALVMFALTVVAPYGVLQIRRYHMSIRNSYDIGTLLSVIVPEYRKQHGSMLHALQ-STVE
ref|ZP_01301851.1|   ------------------------------------------------------------
ref|ZP_01171091.1|   LGLIIGTVVSIIPYIILHVQLRNTRNAVGNQLTEIVELIIHAYGSSSSDMYQALK-VTQS
ref|ZP_02598168.1|   FALGIGITFGILPYVAIRYRLTMLRLKTQYAFLIEYHVLFQNYQSTSKDIYYTML-NAVK
ref|ZP_01575699.1|   ISLGIAIIIAASPYVLLRLKLRSVQIEGSYDANVLVPSITNEYKQHYFNMINAIENCAVR ref|ZP_01900573.1|   ----------IETISYRLSDHTTADDASR--YRSEDNVGEAWQKEPMTRLRTLLMDELII
RAAC02298            HLPPSPIRRAVARLTDRLTDYTTPDDARRALHRFVKELGTSWAAQLASDIEHALLDGVNV
ref|ZP_01301851.1|   -------------LGSRIAKKTLQAMEHH--LVYGAALAGAFA------LLMLAWAWFYF
ref|ZP_01171091.1|   HIAEKELRSILVRLISDLQTARTEEEMRLSIDLFIFTCGNSWSMRLGNIILKSYLHQENV
ref|ZP_02598168.1|   ETKNKELKHIYMKLLSSLQKDRGNLEFERAVNVFSYSINSTFAKRFAKLLKKAHIDRGDI
ref|ZP_01575699.1|   EDIGSYSRKNLFRLSLALKAYYSEEDLDKAIERFVFAYNTEWAMLLGLNIKMAIHKGIVV
                                     :   :                      :     :       .

ref|ZP_01900573.1|   DNAAIELLEKECSEEIDAAVTRYLA-----------------------------------
RAAC02298            E-ASLALLHKEFQEIEDARKSQNLARIDTLLISCVPFLMWPVMMV---LFYLFVSRNIFQ
ref|ZP_01301851.1|   TRTGRGLGSNQFLRGARFGTARQLRR----------LLW--------------------
ref|ZP_01171091.1|   MSALIQLQN-QMVNNQKMLEQEKASSYDAFVDATLTVILFPISLIG--AKFMTKPQSWMA
ref|ZP_02598168.1|   TMSLMDLNA-DIKKRKQDIQTDKTRKLETVILGYSPMVLFP-LMIF--LAYRISGVVDFW
ref|ZP_01575699.1|   SSGLEDILK-KLKDSSEQVEVSKRYNTDAFAIKFLLIPLYIGGILFSISTFDFTLRKYFE
                                                                  :    .

ref|ZP_01900573.1|   ---------------------------------------
RAAC02298            YQFANPTGFTWFLLTLLATLGSFIIGITFYKPKQDI
ref|ZP_01301851.1|   ---------------------------------------
ref|ZP_01171091.1|   LQFGEKATLMLFILTTIMVVISLLVGLIIRKPKNDL
ref|ZP_02598168.1|   YVFQQKTPIILFTISLVMSIFSVLTAIVMSKPRADI
ref|ZP_01575699.1|   YQFLNPIGLRTGIISFMGIIVSFISLRMIRKPKYDI
```

FIG. 4

```
ref|ZP_01171090.1|  ----------------------------------------------------NSEWLERQ
ref|ZP_02598167.1|  -------------------EKAKSVKQTHEFSEVLEIVKKSIENIYEDRGISSDEKIKRQ
RAAC02299           MSVHELLPSEPFRADRYVLETQRERAKDYGEVPFDRVIEAFQQYLGEEVGGKDDVDSQYL
ref|ZP_01575700.1|  -----------------------------------------------------------L
ref|ZP_02849387.1|  --------SARLRLDQSAVTDPLDRGEAAGRGADFGRLAEEIRSYLAAPRGLTEEERRQYS
ref|NP_627754.1|    ------------------------------------------------------------ ref|ZP_01171090.1|  ---HQAIIGDKVAIEYFLAEIEKVLRTK-NITSKDFPSFFNSLSEAIFHEIWGLSVLAKW
ref|ZP_02598167.1|  EIEHNAILGDHEAEKILTKEIEKCLREQ-NLLDVKYPDFFDSLAQALFHEIYGFGAFYKW
RAAC02299           HRKYRALIGDEAAKQYFIHRIHDFLRERPEFQNTRYPRYYPDLPEAIFQHALGFGPMSVW
ref|ZP_01575700.1|  ERHRNAILGKPTEVNYLKDKIREYLKAK-RLENERYPTWYKNLIDAIFHENWGIAGIAEW
ref|ZP_02849387.1|  ETLNRAVLGFASEREQVLAIIADRLIRLRIHQLDGYKHPYATLAEALFAEVIGLNVLELV
ref|NP_627754.1|    ------------------------------------------EQLRSELVGSGPLEPL
                                                                :  :    .  *    :

ref|ZP_01171090.1|  ERYPE-SEACCIRGTQLWIDIDG--QFVKQEEEFESLTVVERIKRAFVIRRPDSVINRES
ref|ZP_02598167.1|  KKYPE-SVSASIIGKEIWFKING--KFVKQEEELRDEEHIYEIFRALEVGHKGLKINHEN
RAAC02299           FANP--TESATVNGTQILFGVKGSNTKVLQPFAFDSIDQVKRLVRTLTLRDPANQVNQTN
ref|ZP_01575700.1|  MDMPE-SSSAKIIGDRIYFFING--KQVLKEQRISK-KRFEQLRQAFMLSDETKRANEN-
ref|ZP_02849387.1|  LARKDGLEEIQVVGSQIYEVRDG--QTMLSSYRFDHERDVERIQQNLVLYNND-RINPRK
ref|NP_627754.1|    LADPSVTDVLVSAPDRVWVDRGG--GLELAPVSFPDAAAVRRLAQRLAT-VAGRRLDDAR
                         .:        *            .   ..:  : :

ref|ZP_01171090.1|  PELEIEREDGSRITMIQ---PPRSRENYIMIRRFIVNKYSLHDQASR--GTIPQEDIPIFQ
ref|ZP_02598167.1|  PRAEIEMKDGTRVNIIR--PPANLFPVIVFRRFIIKNFSFEEQARR--KTISSEDVELME
RAAC02299           HWTQVDMLNGTRVTIFA--PPLSETYVLVFRQYTFHRYTFEHEAEM--RTIPADSVEWWK
ref|ZP_01575700.1|  -YSELYMYSGERVTVYTGRKVIDGQSVMVFRKYVVKVLTFEEQARR--GTIPVELVPALE
ref|ZP_02849387.1|  RWAEVMLRDGSRVTMTG--FGFTSKPTLTIRFFTVRSFSLEALCSAPYHTLSLAMRNMLL
ref|NP_627754.1|    PWVDARLPDGTRLHAVLP-PVAVDCTCLAIRVVRPRAFTLRELAAA--GTVPPGGDRVLR
                         .  *  *:       : :*        .     ::   .    *:.

ref|ZP_01171090.1|  ALARTMANMIVAGRVRSAKSTFMTTLIGERDDSFVGAVLEK-HFEVALSKHFPNRL--FF
ref|ZP_02598167.1|  IISQLYLNMIIAGHVESGKSTMLKTIFASRSPEKIAICIET-SPESFLKKDFPDRL--VY
RAAC02299           LLSRLMLTMVTTGIRRSGKTTFLKVIFGARDPNLEVVTVERGTFEAHLKRDFPERAGRII
ref|ZP_01575700.1|  ALVNCGVKVAFIGPVRSGKSTMLLTWQLYEDPELEGVLIQT-DPEIRIHEVMPKAP--IM
ref|ZP_02849387.1|  DVLEARFNLVIIGPTNSGKTHLMKALIAELPDEERIVTIEG-RFEMMLGRDFPMKN--TV
ref|NP_627754.1|    ALLRARLSFLVSGGTGSGKTTLLSALLGLVGPDERIVLAED---SAELRPDHPHVVRLET
                    :    .. *   *.*: ::.          :        . :            * ref|ZP_01171090.1|  EIQAKEGD----LHKAIPRLLRMEHDFVVVGEIRS-LEIEAYLQSTERGERGSLSTFHLT
ref|ZP_02598167.1|  DMYTINGN----IEDVIYSALRTDHDYIIFQEVRG-IEADGAMKGAERGTTGMMMTYHIT
RAAC02299           ALKSPLDE----MASLFPAFLRSDAHYMMVPEIRS-SEVDLLILSRERGN-GCLASYHSP
ref|ZP_01575700.1|  PLIAGGKE----LFELSSEILKSDADYLVVQEVRDGYTAYIAVEAANKGTNRLKITAHLS
ref|ZP_02849387.1|  EYEADEDDPQHRAEQAFKLALRQSPQRIVHAEIRD-MDANIYVRACTRGHSGSMTTVHAN
ref|NP_627754.1|    RPANQEGAGLVTLEDLVRQALRMRPDRLVVGEVRG-PEVVHLLAALNTGHEGGCGTVHAN
                         .  :: *:*.     :  *   :  * ref|ZP_01171090.1|  DVEQVVEQLARLTLDEFPTRRFEVEVERIARNID-IIITMDTER-DRSKKRVVGVTEVIW
ref|ZP_02598167.1|  DPSRTPEQLAQHIVDAYANRKLENEIRRVAKNLD-LGIIMKNDE-PKNEKRLMSIYEICY
RAAC02299           YVTNIPREIADLALENNPSRDYRATYIRTAQSLD-VAITMWED--PTGRKIVTGVYAYEF
ref|ZP_01575700.1|  NPEDFCYDIANKIQGVFGG-NIDYQMVRVANSFN-FLFEMVQLPGNRSQKRLKSTYEIRY
ref|ZP_02849387.1|  TLEDVPEAITDMCMLDGRGMNPERLTKRIAEYVTQVGIEMRYLG---GRRVIARIGELSW
ref|NP_627754.1|    AAADVPARLEALGTT--AGLNRAALHSQLAAALS-VVLHLVRDR--AGRRRIAEVHVLER
                      :           :  *    . .  :      ..:  :   :

ref|ZP_01171090.1|  DNQQRRHYTQDLIRYSKLKDKYYYSSNI--------------------------------
ref|ZP_02598167.1|  DYKGDKAWINYLMKYNELDERWEYNSEVSEALIKKMK-----------------------
RAAC02299           DHETESYTVTTWMKYHRATDTWTFHAEIPPSMRARLEDTYPDVLAAFEAEFQRLASAYPF
ref|ZP_01575700.1|  DTEANVISYHKICEYNKDTDSWCFSYSVGNKVTELGEFENPKALEVYKNTLKFLSEKYP-
ref|ZP_02849387.1|  AN--NEVNVRDWARFDETSEQWIYPEKPSPKARTRLSE-----------------------
ref|NP_627754.1|    D----------------------------------------------------------- ref|ZP_01171090.1|  -------------
ref|ZP_02598167.1|  -------------
RAAC02299           QGEAKRRVKIGG
ref|ZP_01575700.1|  -------------
ref|ZP_02849387.1|  -------------
ref|NP_627754.1|    -------------
```

FIG. 5

```
ref|ZP_02598166.1|    --------------------------------LLISDRVLPYSELSTI--EFENKKVF
ref|ZP_01171089.1|    --------------------------------AIVIDGKCFPQSELKELRKLYPEIPVF
ref|YP_159112.1|      ---------------GHATSSEPLGAVNGTVPDVVVLDA--FRPANLGALEQLTLRYPQI
ref|ZP_02007550.1|    ---------------------------GQGNDLLILEASRFSSDDLQQLRRLSSEHPET
ref|ZP_02849386.1|    ------------------------------------------------------------
RAAC02300             MIAVGLRESLQRELTGRVEIAEDWHALEGRKVDALLLDAKRVPETELYEIREWFSETPIT ref|ZP_02598166.1|    YMLENQYKPQLESTVKAICNSKDIYLIPPRLVVEQIVDFIDQNLN-LAMVQK-TNILTFF
ref|ZP_01171089.1|    YQFYQVTNEQQMKNLQMICAAHRIVLLSEFLSEKQIEEEVEKHLFAKESVYK-NRIISFF
ref|YP_159112.1|      EPIVITADTSSDFLLQAFRAGVREVLPISPSPEALHAALARITRKRGGSATN-GKILALT
ref|ZP_02007550.1|    LCMLLTEAPSADLLMRAMRAGVQCVLPWPPEAQEFRDEVQRCTSHALSSSHNDGQVVSFL
ref|ZP_02849386.1|    -----------------------------------------------------AAPLITFV
RAAC02300             YIVDEFTS-----ALTAFAAAHNIRLVHVSRVQSYLDEAIGQGQS--------TPILAFW
                                                                            : : : :

ref|ZP_02598166.1|    SSVSNIGTTSTCLSVGKALSQYTNAKVGVLLLNAWDSGTDQLNFKGN---YMDQVKSKLA
ref|ZP_01171089.1|    GTHSGAGVSTTVLNVADLLAQQVNEKVLVLSLNPWDPADYFLPYEGK---YLSDIKIELK
ref|YP_159112.1|      SCKGGSGATFLATNLAWVLAAAHGKRVALIDLNLQFGDAAMYVTDQK---PASNLALVCQ
ref|ZP_02007550.1|    SCRGGSGTTFIAANFAHVLSARHGKRVLLIDLCQQYGDAAFLLTDQS---PPATLANVCN
ref|ZP_02849386.1|    GTTPNIGTTSAAFAAAFRMAEASGRQIGYLCLHLKSAKLHRYLGIAEPAVTLDKLRPELK
RAAC02300             GVYPRLGTTTIALAVAHVLAAQHGKSVGVLGLNAYDPGTVMVPGAEH---HLDDILSYLA
                        . *.:          . ::     . :     :  *                    :

ref|ZP_02598166.1|    SKTISSEQEFLSQFHMVNP-NLYILGGNRDTKMERLFTKEEINYLIEHSKQTFDVVLVDA
ref|ZP_01171089.1|    TGGITEEKLQKAVHHYPN--SFYHLAGNRDIKLQRYYRTEEISTLLDTAKKVFDVILIDA
ref|YP_159112.1|      QIHRLDAAFLQSAMIEVAP-GFHLLAAPDDPAHSTDVRPEHVEAILKVARTNYDFVIVDV
ref|ZP_02007550.1|    QIDRLDAALLDACLTHVSQ-DFDVLAGAGDPIKSGEIKATHLERILALAASMYDVVVFDV
ref|ZP_02849386.1|    SGSLTPGKLQRAVQPVRGMPNLHVLFGNMLRDQAEFYSPEEMKHLLQIAGQTFAMVIIDV
RAAC02300             QQKLDPETLQAAMEFVLR---VKYLPGLQNQTRALAVMPEHVRHLLRVAQSQFEVLVLDV
                              :            . *   .                  .: ::   :  :.::.*.

ref|ZP_02598166.1|    GSHFDNANMVQALNESNLRFLIMNQQTKAIR-KFNQFHRDILYPLGYEKEDLLMIINQFE
ref|ZP_01171089.1|    GTHFDNAAFAQAYKQSDLKFLVTTQEPKGFRGYWPHIFHQLLEPIGGKADEYLLI-----
ref|YP_159112.1|      GRSLD-AVSLKPFDMADMIFPVVQLTLPFIR--EAKRLVEVFVSLGYPMSKVGLVVNRQH
ref|ZP_02007550.1|    GQDIN-PASIVVLDHSNVIYPVLHLSLPYLR--AGRKLMEICHSLGYRAERLRLVINQYD
ref|ZP_02849386.1|    GAYWDNAATICALREADTRIIVTTDALS--------------------------------
RAAC02300             GSALNTALALEGLQAATHRYVIANDLVATQR--QLLRQMDYILRPLGVEPSDLMLVGSQVH
                      *     :  .            :          :

ref|ZP_02598166.1|    DLSHLPTTKDIHKDIDIPLLTTIEKSENGMLS--EIERTVLYDYEDIGYKQSINAVAKSI
ref|ZP_01171089.1|    ------------------------------------------------------------
ref|YP_159112.1|      KNSDIS-LQDVERTVKAKLFKTVPNSYDTVAASVNQGEPIARLAKNSPVTKALREIAESL
ref|ZP_02007550.1|    KHMPIS-QNMMES------------------AFGMPVAHILPYDP---------------
ref|ZP_02849386.1|    ------------------------------------------------------------
RAAC02300             GKGSLAKSVGLMQVTSIPYYPSIDLFAEQSPEPMKVFLAEKTFRKAVETLAQSAMTTPVT ref|ZP_02598166.1|    ASSV-----
ref|ZP_01171089.1|    ---------
ref|YP_159112.1|      VDDP-----
ref|ZP_02007550.1|    ---------
ref|ZP_02849386.1|    ---------
RAAC02300             PEVAASVRA
```

FIG. 6

```
emb|CAE47778.1|      ------------------------------------VVVAK--EDIAEMQTIYDTMVETK
ref|NP_967133.1|     ------------------------------------VVVAK--EDIAEMQTIYDTMVETK
emb|CAE47790.1|      ------------------------------------VVVAK--EDIAEMQTVYDTMVETK
RAAC02301            MKSWVRYTLATTLFVVGVGGSIAYNQFVSPMLTSEWVYVAR--TQLPADTPIQASDVERI
ref|ZP_02756760.1|   IKNKANILLQFSLFILFAGG---VFLFTQSQVKPVAVYQYS--RNIPENTVIQKGDYIKT
ref|ZP_01171088.1|   MKPWLKITLGVLLSVFVIAFIIVWDTVIKDKIDSVEVAIVRPGVVIEKNQVISKDLLMME
                                                         *       :          :

emb|CAE47778.1|      ELPADFIQPDAITIPDEIIGNVAAVPIRKGQMVVKNNLLTPGPDTGISLQVAPSKRAVTI
ref|NP_967133.1|     ELPADFIQPDAITIPDEIIGNVAAVPIRKGQMVVKNNLLTPGPDTGISLQVAPSKRAVTI
emb|CAE47790.1|      ELPADFIQPDAITVPDEIIGNVAAVPIRKGQMIVKNNLLTPGPDTGISLQVAPSKRAVTI
RAAC02301            RVPKSEVSPDAITNAEGLMGTYTAQPVDQNQVLTA---LDTEPDP---FTITPGTEDVPI
ref|ZP_02756760.1|   FKPKDILTKSMITNEKDINGKILTTNVYRSEYAIKNNLEDPAKLDEFAKIDLSNLRKVSI
ref|ZP_01171088.1|   QRNRATLVEGTVYDMDDVVGYEAKQKLYGNSILSERDVEFIPFTP----DPEKGEAIRPI
                      : . :  . :  *        :  ..                 .  .* emb|CAE47778.1|      PVDEVRGVAKLIRPGDRIDIYAAVDSGKGVN-----------------------------
ref|NP_967133.1|     PVDEVRGVAKLIRPGDRIDIYAAVDSGKGVN-----------------------------
emb|CAE47790.1|      PVDEVRGVAKLIRPGDRIDIYAAVDSGKGVN-----------------------------
RAAC02301            PSTWIASVSETLRQGDYVDLIPIAEPQAGSNNVGMLTTTSEASEFKHLLVLSVHTDNNAE
ref|ZP_02756760.1|   PVEMKDAVGGNLKKGDRVDLTFVKQGDSKNNDTS--DSFTYAKTFMQDVLVYNVVDDGGK
ref|ZP_01171088.1|   PASWIYASPSTIRRKDHID-----------------------------------------
                     *       ::    *  :* emb|CAE47778.1|      ------------------------------------------------------------
ref|NP_967133.1|     ------------------------------------------------------------
emb|CAE47790.1|      ------------------------------------------------------------
RAAC02301            VTSQQTGAPQSVGARGNGSGVPASVDVKMTSAEAQALASLIQQKYQLLIVGVSDDNRTGG
ref|ZP_02756760.1|   KYVDQTEGTQSLANEKGEVVESGSLSIVTVAVTAQQAEEI--------------------
ref|ZP_01171088.1|   ------------------------------------------------------------ emb|CAE47778.1|      ---
ref|NP_967133.1|     ---
emb|CAE47790.1|      ---
RAAC02301            GAK
ref|ZP_02756760.1|   ---
ref|ZP_01171088.1|   ---
```

FIG. 7

```
emb|CAJ49597.1|    ------------------------------------------------------------
ref|YP_158155.1|   ------------------------------------------------------------
RAAC02302          MLYLAFPADLRERYAESTWLVYDKQVLETSFAPGDILLLSSWVVPHRAEQLQVIHRARQE
ref|YP_061819.1|   ------------------------------------------------------------
ref|NP_779769.1|   ------------------------------------------------------------
ref|ZP_01171087.1| -EILRMIEQWRFQYNDSLRIVYICERERTDPLLGSLVARN----------VLDIFYTRSI emb|CAJ49597.1|    ------------------------------------------------------------
ref|YP_158155.1|   ------------------------------------------------------------
RAAC02302          GARVIFVGSKEDETDEWKRQLCALGVYDFAFFGDEVVLSVLDDLIEHPRTPLDVRAYVDE
ref|YP_061819.1|   ------------------------------------------------------------
ref|NP_779769.1|   ------------------------------------------------------------
ref|ZP_01171087.1| PTKLLINQILEPPK---FSNVAKIGVTDIDLAN-----------LEYLEEQAEKSGIEDE emb|CAJ49597.1|    ------------------------------------------------------------
ref|YP_158155.1|   ------------------------------------------------------------
RAAC02302          TVWHLAREDPVVVEVETPKADVDEPTQDEAPFRPRWRRPRWGKPSPPAPERLQVVQPRLV
ref|YP_061819.1|   ------------------------------------------------------------
ref|NP_779769.1|   ------------------------------------------------------------
ref|ZP_01171087.1| LTEEHANQPAKPIDIPTSKSKKKVELPSLKLPKPEFHIHVHKPSKIRTEKIAKAIDRKIV emb|CAJ49597.1|    ------------------------------------------------------VPAEQASE
ref|YP_158155.1|   ------------------------------------------------------------VL
RAAC02302          VVLGLWPRAGVTTITYLLAQLFAKQLPTRSVACIEHPRPWPRMWDYFQLDARMPAENYRH
ref|YP_061819.1|   ----------------------LDETRPRIIVRPKTVDDSGFVVKVEGGSEGPVYRV
ref|NP_779769.1|   --------------------------P-DWRVAWA-------MRYGAPAL
ref|ZP_01171087.1| VVISPFERSGSTFVS----HQLAYQIAERKIGITYFENPFKRPYTYDRFGGHLLVPNFKS emb|CAJ49597.1|    ALAQGRADVVLADRVDTAPMGPYWVGSGYSGQ------------PKAVIRS--DTPLRQW
ref|YP_158155.1|   NLANGNPIITETNTLQAEIEGPHYR-------------------PAPVFR-----SVDRW
RAAC02302          WTADGVGQEIEVDGVDLVPLPPGWIGSADYGQPMVQYIFRHMRKPVTLVDVGAQAPSEML
ref|YP_061819.1|   LGAKPERWVAQTDFQNDEAIGYLAARLAKLG-----------VEDQLVRVGAVAGSTVV
ref|NP_779769.1|   TKALDALQAQQVRRIVILPLYPQYSTTT---------------TASVQDV-----VEAW
ref|ZP_01171087.1| LYTSQPNANIDIDRKWTVEGVQIQALNPILEM-----------PYEEKDISIEKFLRLF
                                                                                :

emb|CAJ49597.1|    SEVAGKRVCMAQSN----------NRAEALARRYGATVQT--------------------
ref|YP_158155.1|   LTVAPGKSVPVSPE----------TAAAVRERLLGVL-----------------------
RAAC02302          LGVADRIVCVLDCDPTFLSIAELGNQYRALSAKYGESMVTVLNKWTRYAHYEDLFEDAVK
ref|YP_061819.1|   IGRENGVVFDWEPT--------LTSAAELISSPRGTDARIGVNARPTRAQRREDYFD---
ref|NP_779769.1|   CKRTPQVQVECIQD---------YAEDPAWVAAVAASIRR---HWQAHGRSEKL------
ref|ZP_01171087.1| LSAGDTPILIVDIG---------ADRQRPIYDELLSIASHVLVVMDCD------------ emb|CAJ49597.1|    ------------------------------------------------
ref|YP_158155.1|   ------------------------------------------------
RAAC02302          VPYLAPEMMQQALWAGQFPDVATLTSELHELTERVVTPLLPARVG
ref|YP_061819.1|   ------------------------------------------------
ref|NP_779769.1|   ------------------------------------------------
ref|ZP_01171087.1| ------------------------------------------------
```

FIG. 8

```
ref|YP_001371728.1|    ------------------------------------------------------------
ref|ZP_00630666.1|     ------------------------------------------------------------
ref|YP_674884.1|       ------------------------------------------------------------
ref|YP_001235767.1|    ------------------------------------------------------------
RAAC02303              MKRIGLFRIPTEPKDVFPWLVKRLVLSLGLGGVLGYLALLVVALSLLGFLVGDYQANGRG
ref|NP_046584.1|       ------------------------------------------------------------ ref|YP_001371728.1|    ------------------------------------------------------------
ref|ZP_00630666.1|     ------------------------------------------------------------
ref|YP_674884.1|       ------------------------------------------------------------
ref|YP_001235767.1|    ------------------------------------------------------------
RAAC02303              TVENGNIVLSNATQARETALKNTYQQVADEWQQGLSASQIAQVEQQQVDLPAAVLMGIGK
ref|NP_046584.1|       ------------------------------------------------------------ ref|YP_001371728.1|    ------------------------------------------------------------
ref|ZP_00630666.1|     ------------------------------------------------------------
ref|YP_674884.1|       ------------------------------------------------------------
ref|YP_001235767.1|    ------------------------------------------------------------
RAAC02303              MINNLNPPNAQEYYDYLAPVYTWHTYIDVTITYQTVCSKNGCHVVTHEVDTPVTMLQTAN
ref|NP_046584.1|       ------------------------------------------------------------ ref|YP_001371728.1|    ------------------------------------------------------------
ref|ZP_00630666.1|     ------------------------------------------------------------
ref|YP_674884.1|       ------------------------------------------------------------
ref|YP_001235767.1|    ------------------------------------------------------------
RAAC02303              TWDGTLVDTYKWVTSMSGTTQNGVYTKKIELASSKRTYDWSRVWNLFAHIPTAQHTHIKE
ref|NP_046584.1|       ------------------------------------------------------------ ref|YP_001371728.1|    --------------------------------------------IAPLPGLAQIAVMGRAVA-VHP
ref|ZP_00630666.1|     ------------------------------------------------------------
ref|YP_674884.1|       ------------------------------------------------------------
ref|YP_001235767.1|    ------------------------------------------------------------
RAAC02303              SQEDEDILAGFIGAIDYTISDPEVQKMVTSVLFPDGVVVTDLPHVSTALPSGNAIQNILH
ref|NP_046584.1|       ---------------------------------------------GIVTSTTSSGGTPSSTGGSYSGK ref|YP_001371728.1|    HGAHIEEASQRFGIPAAWIIAVMQVESAGNMHA------ISSAGAMGLMQVMPSTWAELR
ref|ZP_00630666.1|     YAAQVTEASQRFGIPTTWIMAVMRTESAGDLRA------VSSAGAMGLMQVMPDTWAGLR
ref|YP_674884.1|       YAANIHQASRRFGIPAAWIRAVLRTESAGDVHA------ISSEGAMGLMQVMPDTWAELR
ref|YP_001235767.1|    ----IEQASARFDVPAKWIRAVMHVESGGHEYMNG-HLTVSSAGAMGLMQLEPETYQEMA
RAAC02303              YKAEIEAAARMFNIPAVLIAGVMYQESGGNQLDPTGHVLTSSAGAMGLMQVEPSTAAGLT
ref|NP_046584.1|       YSSYINSAASKYNVDPALIAAVIQQESGFNAKAR------SGVGAMGLMQLMPATAKSLG
                           : *:  :.:.   *  .*:  **. .         *. *******:  *  *   :

ref|YP_001371728.1|    IR-HALGR----DPFEPRDNILAGTAYLREMWDRYGN-VAAMLAAYNAGPGRYDEYRATA
ref|ZP_00630666.1|     IR-HGLGH----DPFEPRDNILAGAAYLREMWDRYGN-VAAMLAAYNAGPARYDGYRLAD
ref|YP_674884.1|       VR-YRLGL----DPFDPRDNIIAGTAYLREMFDRYGN-VGAMLAAYNAGPDRYDEYLSKG
ref|YP_001235767.1|    AR-YGLGP----DPFNPLDNIMAGTAYIHQMYEIYG--SPGFLAAYNAGPGRLDDYLDYR
RAAC02303              INGVPVGSNWYADLSNPTTNILLGAELLSELYHEFNENVDETLSAYNAGPGAEEEALSQG
ref|NP_046584.1|       VN-----------NAYDPYQNVMGGTKYLAQQLEKFGGNVEKALAAYNAGPG--------
                         .       :*  *:: *:   : : . :.     *:****** ref|YP_001371728.1|    RPLP--AETRAYVAALT---------------
ref|ZP_00630666.1|     RPLP--AETRAYVAAL----------------
ref|YP_674884.1|       RALP--AETRAYVAALT---------------
ref|YP_001235767.1|    QPLP--AQTRHYVAMIAPQ-------------
RAAC02303              YTVAQNSQTLEYVAAITQQWIPALEPYFGSL
ref|NP_046584.1|       --------------------------------
```

FIG. 9

```
ref|YP_793245.1|     ------------------------------------------------------------
ref|NP_253469.1|     ULATRPSEUDMNASAERUGINSAPAGBEAZHYPTHETTCALPRTEINPACGPSEUDMNAS
ref|YP_386759.1|     ------------------------------------------------------------
ref|ZP_01591801.1|   ------------------------------------------------------------
ref|YP_868126.1|     ------------------------------------------------------------
RAAC02304            ------------------------------------------------------------ ref|YP_793245.1|     ------------------------------------------------------------
ref|NP_253469.1|     AERUGINSACGBEAZHYPTHETICALPRTEINPAGPSEUDMNASAERUGINSASCRESIG
ref|YP_386759.1|     ------------------------------------------------------------
ref|ZP_01591801.1|   ------------------------------------------------------------
ref|YP_868126.1|     ------------------------------------------------------------
RAAC02304            ------------------------------------------------------------ ref|YP_793245.1|     --------------------------------AVIEALATLGDLRDNPRSRHLPRIERY
ref|NP_253469.1|     NIFICANCEE-IDENTITIESPSITIVESGAPSAVIEALATLGDLRDNPRSRHLPRIERY
ref|YP_386759.1|     --------------------------------SLASLAETRDNETGAHIMRTQAY
ref|ZP_01591801.1|   -------------------------------AMAKLAEFRDEDTGGHLERVKEY
ref|YP_868126.1|     --------------------------------IIQKLGLAAEYRDNETGLHITRMSHY
RAAC02304            -----------------------MIIVHSLTSLFESIAFVAEYGEPDADRHVKRVATY
                                                     :.   .:  :    . *:  *    * ref|YP_793245.1|     VRLLAEHLAAQRAFADELTPEAVDLLSKSALLHDIGKVAVPDRVLLNPGQLDAADTALLQ
ref|NP_253469.1|     VRLLAEHLAAQRAFADELTPEAVDLLSKSALLHDIGKVAVPDRVLLNPGQLDAADTALLQ
ref|YP_386759.1|     VRVLARQLRTHVRFRSVLTPEGIEQLCKSAPLHDIGKVGVPDAILRKQGPLTPQEMDQIK
ref|ZP_01591801.1|   CRLLAEDLNRHSPYSDLITAEFIDCIQHAAPLHDIGKVAIPDHILQKPEKLTPEEFDRMK
ref|YP_868126.1|     GRILAQYVCDSQAWC-------EMYFTALPMHDIGKIGIPDSILSKPGKLTDDERRQMQ
RAAC02304            ARFVGEHVLRWSPAA-------CERLALAALVHDVGKVVIPREILRKPGPLMPAERQYVQ
                      *.:.. :               :    :  :**:**:  :*  :* :   *   :  ::

ref|YP_793245.1|     GHTRAGRDALASAERRLGQP-SGFLRFARQIAYSHHERWDGRGFPEGLAGERIPLAARIV
ref|NP_253469.1|     GHTRAGRDALASAERRLGQP-SGFLRFARQIAYSHHERWDGRGFPEGLAGERIPLAARIV
ref|YP_386759.1|     LHTVYGRDALRHASMRLGG--SSFLQMAEELVHTHHECWDGTGYPQQLTGEQIPVAGRLM
ref|ZP_01591801.1|   THTVIGADNLQLVYNNYPG--NLFVGMGIEIALYHHEQWDGSGYPDGLVGKNIPLPARIM
ref|YP_868126.1|     QHASFGAQILGDDD-------DPLLSLAKEIALYHHERWDGTGYPHRLAGEQIPLSARIA
RAAC02304            CHTVYGRDMLVELARRYSGLDGGLFELAQQVALYHHERWDGDGYPEGLCREEIPLAARVV
                      *:   *  * *           . :. :. ::.   ***  ***  *:*. *   :.**:..*:

ref|YP_793245.1|     ALADRYDELTSRHAYRPPLAHAEAVLLIQAGADSEFDPRLVEAFVAVADAFAEVAQ----
ref|NP_253469.1|     ALADRYDELTSRHAYRPPLAHAEAVLLIQAGAGSEFDPRLVEAFVAVADAFAEVAR----
ref|YP_386759.1|     ALADVYDALISRRCYKKPVPHHQAREIILKGRGTRFDPAVVDAFLRAEHDFLAIAAA---
ref|ZP_01591801.1|   ALADVYDALRSDRCYRKAMSHEQARTIILEGDGRHFDPEVVMAFLRVETIFAKTAE----
ref|YP_868126.1|     AIADVFDALTSDRPYKVAWSTQKAFDYIEENAGTQFDPKLTRAFIECKAQVLEVQQ----
RAAC02304            HLVDVIDARLSPRPYKPGQSWHQVKQALVEGMFLDFDGMLVTGLLEVESAFLELVQAQTY
                      :.*   *   *  * *:   . :.    :  .    **  :.   .::    .

ref|YP_793245.1|     ------
ref|NP_253469.1|     ------
ref|YP_386759.1|     ------
ref|ZP_01591801.1|   ------
ref|YP_868126.1|     ------
RAAC02304            RQLVTI
```

FIG. 10

```
ref|YP_645800.1|         ----GHGGMMGGWQGPGGMMGSGPGAWAFLWMLVP-VLFWTGLLVLLVWAVLRLVPPSGG
ref|YP_950098.1|         ----GTPWMMNDY----GMGGMG-LAWIFWLLLIAGVILLAVVLVKAFTRNAGGNAPTDG
RAAC02305                MSVFGVSRMMGGYG--FGMMG--------LYWFLS-VLMLLAAIVLVIWAILRMKP----
ref|ZP_01697403.1|       ---------MYGGY----GMMG--------VFSLIG-MIAQLVIFVLVIFLIVAGIKK---
ref|NP_111721.1|         IGIYGVG-YRGPY---FGMMGLP---YYGMYFFMP-IMAAISILVIILFIYLIAGAF---
dbj|BAB60367.1|          IGIYGVG-YRGPY---FGMMGLP---YYGMYFFMP-IMAAISILVIILFIYLIAGAF---
                                   . :      ** *              ::  ::       :*  .

ref|YP_645800.1|         NCG-RE-APEEKAEEILRRRFARGEIDAEEYEERRRLLEEHHQ-
ref|YP_950098.1|         QGPPRPGAGPARAREILEERYARGEISTEEYQERRRTLEEDSR-
RAAC02305                FGSLAQHEPYDRAVETLRERYARGEISREEYLERLEDLQDHRRS
ref|ZP_01697403.1|       VSEFRPHQREDKSLDILRERYAKGEITEEEFKKMKKDLMD----
ref|NP_111721.1|         HDGSIMSDENSRATEILKERYAKGEISEEEYRKKLDELK-----
dbj|BAB60367.1|          HDGSIMSDENSRATEILKERYAKGEISEEEYRKKLDELK-----
                            .          :: : *..*:*:*** **: :      *
```

FIG. 11

```
ref|ZP_01500882.1|    ------------------------------------------------------------
RAAC02306             MRGIWHFIHHWYLKIPYSPAEAHLFRHVWHMIPFWMPGFTALSIVPAG---YILMILLSV
gb|EAU91762.1|        -----HFVHHR---SPREDAVPLIFAHGWPGNFTERPGFSIARIARVY---HKLMVTLG-
ref|ZP_01076306.1|    ----------------------------IWSMVPFLYVIMILVSIIQPS---FFLFVLINV
ref|YP_173223.1|      ----------------------------FWG--PQTRAENVGLTLFWAG---WWPLLLA-
ref|ZP_01035289.1|    --HLAHHREEYLTDPYDDPEANYLDPTVWARLPLWVRAVLRINNTLAGRMLIGPMVAQAI ref|ZP_01500882.1|    ---------------------------------------------AARFGFTFEGIFRQAVT
RAAC02306             LFSGFEWFKYEKALEVIKERGRKYSYYGLWLAYAIWAPLPWPRAATFGWTVVGWLTIRHF
gb|EAU91762.1|        -------YKHYVAQG------------GDWGSFILRS-----VAIQYPEAVVGLHIN---
ref|ZP_01076306.1|    MFG-WMGITWYMRTLTYKEKAREYVQAARAQGAGLWR-----IILKHILPNTMVMIVTLA
ref|YP_173223.1|      -------FPFVGRLW-----------CAYCPFMIYG-------ELVQWVSLKLWPRSLL
ref|ZP_01035289.1|    FLRADWQAIKQGNRAVLHAWLWHIPAVALVLIWLSFASMPVWAYLLAVWLGLAVLKIRTF ref|ZP_01500882.1|    YKGRNRDTAWFSIVDSEWPA-LRAGFAE-WLD----------------------------
RAAC02306             WKKRRRRIAWMSTLDKADLA-LMPGWAE-WLERQQRIEAVLDRTLPWRRAKAKKASSK
gb|EAU91762.1|        FPAAPIPSPLKNPITLFWLA-IGWLTPE-EKKRINRIKW---------------------
ref|ZP_01076306.1|    PFGVVANISALTALDYLGLG-LMPPTPS-WGDLLQQGKSNMD------------------
ref|YP_173223.1|      PWPRAAAERWGGWFLFGLFA-LILLWEELWH--LEDVAWLS-------------------
ref|ZP_01035289.1|    LEHRAHERASGRTVVIEDRGPLAWIFLNNNLHVVHHMHPEVP----WYRLPALYAARR
                                    .       . :       .
```

FIG. 12

```
ref|YP_503850.1|       -KISKKNYDLVFKEAFSIFDNRSLAFLGID-LPPIISFLVTEIPEVETTDDMMDLNFRLE
ref|YP_517477.1|       --ISYHNNDILMKVLAEQFKNKTLDVFGIK-TAKIKDLIPSVHPAVEANETRNDIIFLLE
ref|YP_001568284.1|    -------------------------------IISVKPIDIPVINVSNQNPDFVFELE
ref|NP_783815.1|       -------------------------------DTKIIAPANTELKTIDIKTNFTDYTFYTE
ref|YP_149134.1|       --ISHHAKDILFKSLSALYQNQALDVYGLHGLPRIKALLPNEFPSVRADERRADTVFLLE
RAAC02289              MRIARSGNDIVAKHLTNALPGEVLSVIGIH-DAHVVRALPTELPTVEVRQEFTDIMLELA
                                                        :           :       *  :

ref|YP_503850.1|       DGSILHLEEEMNLSKRD-LIRFAHYDLRLFRYYD------APVHTVVLTPADSSSGTKVL
ref|YP_517477.1|       DDTLLHLEFQTTAGEQD-LKRFLYYDARLVRRQE------RKVHTIVIYSGRIEQARERL
ref|YP_001568284.1|    DNSLLHLEFQTTWKKAD-LLRFAQYDIALYQKER------RRINTVVMYSGKYESAESEL
ref|NP_783815.1|       NDDYLHFEFQTTNKEED-INRFLFYDASLFYKYG------KKVNTLVVYSSDIKKSKTKV
ref|YP_149134.1|       DDSILLLEYESNERFLDNHLKYLDYACRILHTYYQQEKRIRPIRIVVIYTSDVTTARERL
RAAC02289              DGRLLHLEFQTT-REPN-LYRFGTYDWAMAERYK------RPIRTVILYTRDVTEAPSEL
                       :.  * :* :   :    ::   *   :             :. ::: .   .   :

ref|YP_503850.1|       DIGSLQYNVLQIVLSDRDGDALLSQMRAALEKGEPVNE----LELIFLPLMKSKLTKIELL
ref|YP_517477.1|       ECGSILYQVENIYMKHYNGDQEYNRLKHKIDNHQLLSETDTLKLIFLPLMKSEQKEEELA
ref|YP_001568284.1|    DMGSNKYKVQQIFMIKYDGIKRYEEIKEKIEKEEELTDKDLMDLVFLPLMRNEKSEEEVT
ref|NP_783815.1|       DAGSLKYEIKAFYMSSLNGDEEYNNLKTKIDKGEDLTKEEILSLTFIPLMDSKEDKSTRT
ref|YP_149134.1|       DAGDVFLSSKAVLLGEFNGDAIFHAIEEKVHNGEPLTPEETMKLILVPLMHTRFDRQTMI
RAAC02289              DAGSMRYAVENVYLGHMDGDGALETVKRHLAAHEWTEEDRVRLAFAFHMRFERRTREEAF
                       : *.          .   :*        :.  :. . ..         . :  .    .

ref|YP_503850.1|       RRTIDLEKELPEKDLRNKVRELTLILADKIVDQKILDELWEELRMFKVVKYAEEKGMEKG
ref|YP_517477.1|       IQAAELAKAAPDEKTKLFAIAALIVITDKIMSESNKRKLLEVLKMTQIEQWIREEGRQE-
ref|YP_001568284.1|    KDVFELAIKIPDEDKKEAVIGSLLGFSDNYVRDEYINELKKEVIRMTKIGTSLFEEGVE--
ref|NP_783815.1|       IKSIELAEKMEENNTKLQCITLLYAFLEKFGDAKSKKKFKEVFSMTEIGRMIVEESIEKG
ref|YP_149134.1|       EKTIELAKAIGDEPKQLHIIAGVLTATDKFIDRSYAEKVKEWIKMNKVFRLLVEELEQEK
RAAC02289              GEIVEVVQRVPDVHEQNYLAALILGFSGRVMADEQKEQLRRVLEMTDLLRELEREFEEKG
                        ::       :      :          :       :..   :  * .:    .: :

ref|YP_503850.1|       --------LEKGLEKGIKKGMEKGKKQERETVAKNMLSLGIEDELIIKATGLDQSIIDKL
ref|YP_517477.1|       ------------------GELKGRRDEKRETAQTMLNLGMSPELIAKATKLPLEEILEM
ref|YP_001568284.1|    ----------------------EGEKELTIKILNKRFGRRLTEEIKDRIREADKKTIDYI
ref|NP_783815.1|       RAEGIKKGIEEGIKKGRTEGKTEGKSEILIKQLIKKF-KKVPEEYIQKIKTLSIDTIDII
ref|YP_149134.1|       ----------------EEMLKKVMQEKEQAVQRAIQEKEQAVQRVIQEKEQAVQRA
RAAC02289              ------------IQKGLQQGLQQGELQKAREIAHRLLRKGASVQEVVEITGLSSKDVEEI
                                         .           :.       .  ..

ref|YP_503850.1|       KKSL--------
ref|YP_517477.1|       ------------
ref|YP_001568284.1|    GDNL--------
ref|NP_783815.1|       ALEIFDMEDIK
ref|YP_149134.1|       IQ----------
RAAC02289              RQNLH-------
```

FIG. 13

```
ref|XP_001191064.1|    ------------------------------------------------------------
RAAC02307              MLGYEVIHMHPGVFFMHLRHMLPWWSPAIIAWYGTLFMWAREYPQRYYEDIPASDGSVEV
ref|YP_303751.1|       ------------------------------------------------------------
ref|ZP_01697132.1|     --------------------------EFGQFDEWK---------DLTQLDWMLLD
ref|ZP_01222568.1|     -----VVDMHGNEVMLPMIQVLDMWYPNNLSFLGKLTHWGHQVVKFLTEDPREANTEGGV
ref|XP_001317319.1|    -----------------------------YYN----------HYYEEYIEDHKSGFE ref|XP_001191064.1|    ----------------------------------------------------------GN
RAAC02307              FSRWFGMFFWALVMFYAMWFALPYPGVEILVDLCCIPVMLIVFGMLAIGWVVHLIDEFGS
ref|YP_303751.1|       -SFWIGMVFF-------------------------LLMF--------------VAY
ref|ZP_01697132.1|     FETHRTFFQFT-----------------------KALNAF--------------YQN
ref|ZP_01222568.1|     FPAIFGTVFMVLLMS---------------IIVTPLGVMAAIY--------------LHE
ref|XP_001317319.1|    VNFRWQFGSWG------------------------KFSSY--------------PPL ref|XP_001191064.1|    YQ-RDSSVTQMQTCLEWESLERRRE----KSRLVMLYK------------IYKGKVGLKQ
RAAC02307              YQ-ADEHLEKGLTCAEWEQFKRRREFRDFQLRVNAMYEAIEPERRKQRFIVFEGKRGKKR
ref|YP_303751.1|       YA-SGYGLSEIMIYPSIFSFG---------LVAFGMLG-------------MGPVTIAV
ref|ZP_01697132.1|     TR-SLWRLDHDPEGFEWIDPNNRRQ------SIIIFMR-----------------RGKRK
ref|ZP_01222568.1|     YA-GKNGFTKLIR-VAVINLAGVPS------IVYGVFG----------------LGFFV
ref|XP_001317319.1|    FALVGAGITILIDMCVLSDLR----------ILFTIAN----------------FAYIL ref|XP_001191064.1|    ED--
RAAC02307              GDRA
ref|YP_303751.1|       DSYG
ref|ZP_01697132.1|     GD--
ref|ZP_01222568.1|     YMV-
ref|XP_001317319.1|    ----
```

FIG. 14

```
ref|YP_001662357.1|     -----LKLKKNKEEA-------------VKEE----PELFEK-VPTVVEVIS-SDGYLIE
ref|YP_001666189.1|     -----LKLKKNKEEA-------------VKEE----PELFEK-VPTVVEVIS-PDGYLIE
ref|NP_623664.1|        ------KKKKQKTEK-------------QKENNF--HDPFNH-VSDIKQIIA-SDGIYVD
ref|ZP_02755290.1|      ------KKKKKEKSTAKIIDF--------NKDDILNETNLLDKGIPSLKELIS-PSSFEVD
RAAC02309               MTLFARKKKKKEKKRKRWSWLRAHLRRQKEKRVLAQDPSVIGEHAPTLHDLMTLADGIEMR
ref|YP_001181426.1|     ----------------------------------------EFAPDIYELIL-PDTFHEE
                                                                    . . : :::   :

ref|YP_001662357.1|     KDYIRVG-KKFYRLYVLT-DFPQAVYVGWLEDIKLLG-NVDVSVHLTPVDARDAVNQLTR
ref|YP_001666189.1|     KDYIRVG-KKFYRLYVLT-DFPQAVYVGWLEDIKLLG-NVDVSVHLTPVDARDAVNQLTR
ref|NP_623664.1|        RNYMQIN-DKYVRIYYFT-DYPASVNIGWLEDLKLFS-NANISIHVYPETNANAVKRLTT
ref|ZP_02755290.1|      ADYIKIG-KKYVRSFIMQ-GFPAQVYVGWLDSIFNYEGETDTTIHIDPTDDKIALEEYTR
RAAC02309               ASEIYVSPSGYTKTYYVT-GLPSTVHFGYFQRFFRVGADVHISLHVEPADSAVAMAKRTK
ref|YP_001181426.1|     ADYIYLGAENYCRVYVLDIDYPSEMYVGFFDSLLDKG-EIAISVFIEPRDTGQAIRDITR
                         . : :.  .: : : .  .*::: :        : :::.: *    *:     * ref|YP_001662357.1|     KITQYQSQYMLDDQRGNIYELGILRKAVEDLERLRESIQMNRDKLYYVTAVVSVSADSVE
ref|YP_001666189.1|     KITQYQSQYMLDDQRGNIYELGILRKAVEDLERLRESIQMNRDKLYYVTAVVSVSADSVE
ref|NP_623664.1|        KITQLQSQLMLDEEEGNIAELGILQRASESLEALRENIQMNRDKLFYVTIVIAVYGDSLA
ref|ZP_02755290.1|      KITQFEAQLMSEQEKGNIRNITRLRDKIQELYMERSKLERNTDKLFQVQIACNLYSDSLD
RAAC02309               LMTKIEAEILAEQKAGTNKQIAFLQQEYQLLEKEREELRLGRERIFYATIILAVSSPNRQ
ref|YP_001181426.1|     RINEMKSNAMLQRGE----PDYKLLAQIEWYDALRASLQRGIEKILMAQVFTVVYSKSLE
                         :.: :::  : :            *    :  *  .:.  :::   .    :  .

ref|YP_001662357.1|     ELERSSKILEEVLAGKSIRARRMFLRQSEAFKSFVPILEN--HCEDLSRNFNSGAAASLF
ref|YP_001666189.1|     ELERSSKILEEVLAGKSIRARRMFLRQSEAFKSFVPILEN--HCEDLSRNFNSGAAASLF
ref|NP_623664.1|        ELEHNSKTLEEVLASKSIKARSAIFRQEQGFKSLVPTAEN--YLADSSRNFNVGAAISLF
ref|ZP_02755290.1|      ELNKETQKIDNKLRGRKMYMMPTYLRQDDTYKTVSPYGKS--YVEDMFRNFNSGALTSCF
RAAC02309               EFEAACERIEREGFEG-FLLREAFKEHDLGFRSVAPIGEN--ALRHP-IEMTASALANSF
ref|YP_001181426.1|     QLRENCIRITKFAESLGLNMRCLSFEQAKGYISCLPLGARNLKYIEKFRLMTTSATACLF
                        ::.       :  .    :      .:     ::     *    .:    . .*    * ref|YP_001662357.1|     PFASPEFSHKKGIPLGINLFTGSPVIFDNFIGPPFMTNYNLGIFATSGAGKSFLIKLLSM
ref|YP_001666189.1|     PFASPEFSHKKGIPLGINLFTGSPVIFDNFIGPPFMTNYNLGIFATSGAGKSFLIKLLSM
ref|NP_623664.1|        PFASPEYSHRQGIPVGINLFTGSPVIFDFFIGPPVLPNANIAVFAQAGAGKSFMMKLLAL
ref|ZP_02755290.1|      PFYNSDIRHEKGVFCGINLSTCSPILID-FYDRSKLKNSNITVIGQPGTGKTFFVSLLTM
RAAC02309               PFTNARFSHEYGVPIGVDWSSGHLNRYDAWHPK--LVNANGVIIGKAGAGKSFLVKGLVA
ref|YP_001181426.1|     PVGNTDITYEEGFYIGYNAITNSPVFYNQFDRS--LPNPHMAIFGTTGAGKSTTMKTMLG
                        *  ..    ::.  *. * :  :       : :    . * ::  .*:**   :.  :

ref|YP_001662357.1|     RGALLGIKTVFVDPDGEYSRMVQKMGGSVVKISTETENIINPFDVEEEEDENE----IRY
ref|YP_001666189.1|     RGALLGIKTVFVDPDGEYNRMVQKMGGSVVKISTETENIINPFDVEEEEDENE----IRY
ref|NP_623664.1|        RSALLGVRTVFIDPEGEYKPVVDRVGGVHIKLEPNCKHIINPFDIEVDVDDEG----IEF
ref|ZP_02755290.1|      RSALRGIRTVIIDPESEYGRLTEALGGSRIYLATDSKECINPFDIE-EEDELD----ENF
RAAC02309               RSAAMGIRHVIVDYEGEYTPMVQALGGVVIRLDEHSPYKFNPFELEEEEEKQADGTIRRF
ref|YP_001181426.1|     RMAAYGYNICVLDPEREYEKIINKLGGKYIRIRPGEKLGINPFDVEIEEEEGK-----RF
                        * *  *   . .:* : ** : ::**  : :   :***::*  ::  .:

ref|YP_001662357.1|     VDIVQKIAEIKALVG--MIVEGVMKDKISAEELAAVEEAVRDEYE-ARGINKSPESLYEK
ref|YP_001666189.1|     VDIVQKIAEIKALVG--MIVEGVMKDKISAEELAAVEEAVRDEYE-ARGINKSPESLYEK
ref|NP_623664.1|        IDLLQKANEIKGLVS--MIIEKISKTPLTAYELSLIEETILEEYR-ARGITRNPESLYEQ
ref|ZP_02755290.1|      LPTGIKLVDVKGKIADLLNLIAVMAGGCLSGAQTSTVAQLLQELYE-SFGITKNPKSLYVT
RAAC02309               VDVKEKISDMERLIVS-MAHLHAGHDLLDSYTRNAINDMLQELYERDFGFTSDPESLYER
ref|YP_001181426.1|     IDLNSKVADIRFILN--IISEYYVGRRLDGVQMAIIERIVRKLYY-DKGITSDPESLYTS
                        :    *  ::. :    :          :  .     :    . * *:. .*:*** ref|YP_001662357.1|     N---IADSEEFYFK--KKKEMPTLSSFVERLKKNPRGER------IAAVMKPFLKGGTLG
ref|YP_001666189.1|     N---IADSEEFYFK--KKKEMPTLSSFVERLKKNPRGER------IAAVMKPFLKGGTLG
ref|NP_623664.1|        S---TQEIDGKYYIGTRQKQMPTLSSFTKRLSEKPGGEK------LAQILKPYLKGGTMG
ref|ZP_02755290.1|      EP-YFDKNTKEFIHEGRKKTMPIFSDFYNSLSEYAEKNSDIEVMDLVRVLKMFKKGGVYD
RAAC02309               HETWQRDAKGDRLVRRVKRPQPRFSDFYVKLEERAASDS--RLEELAMRLRRFREGGTEG
ref|YP_001181426.1|     AR---TDEKGRLIVCKIKKELPTLSELREELFKESETQA------LAKAMEVFVGEGSLS
                        .        ::    *  :*.:  *  : .            :.  :.  :   *   .
``` continued →

FIG. 14 continued

```
ref|YP_001662357.1|    IFDGQT---NVS-LEDSYLVNFDVSEIRDR-FLRTYAMYVITNWIWEKFVKKDVK-QKKRV
ref|YP_001666189.1|    IFDGQT---NVS-LEDSYLVNFDVSEIRDR-FLRTYAMYVITNWIWEKFVKKDVK-QKKRV
ref|NP_623664.1|       LFDGQS--NVD-LKDALLISFDVSGIMDE-FLKTYALYVVTNWVWEKFVKKNIK-QKKFV
ref|ZP_02755290.1|     LFDCYTSSNISNFKNSPIVTFDVSKLEEN-ILRPIGMYVALSWTWEKFGKKDPY-INKRI
RAAC02309              MFDCYS---NVELQDVPVVSFDLSHLPEKSMARLLGMQVVLEWIMEKFIKKNVH-LKKRV
ref|YP_001181426.1|    LFDCQT----TIDADDKIIAFDLKEFERDNFLKFFASVNILSWIWNKFSNAKLKGQKKVV
                       :**   :      :  :: **:. :    : :  .   .* :** :  .    :* :

ref|YP_001662357.1|    VVDEAWMFMKY-----KDTAYFLENLSRRARKRNTSLTVASQSFIEFSNSQEGKAVLTNS
ref|YP_001666189.1|    VVDEAWMFMKY-----KDTAYFLENLSRRARKRNTSLTVASQSFIEFSNSQEGKAVLTNS
ref|NP_623664.1|       IVDEAWMFMKY-----EHTANFLENLARRARKRNTSLTTASQSFMEFANSQQGRAVLTNA
ref|ZP_02755290.1|     VCDEAWMLVSKNMAGSEYSAKFLETASRRIRKRMGGLLVASQKFTEFVESTQGQAVLTSA
RAAC02309              VIDEAQKMLEH-----LYHAIFMEDVFRRIRKRSGSAVAASQDFRKFAESEQGRAILQNS
ref|YP_001181426.1|    IFDEAWMFTRY-----QASAEYLEFISRKGRKYKISLMIASQTLLEFLQNDTGRAIINMC
                       : ***   :          * ::*   *: **   .   *** : :* :.  *:*:: .

ref|YP_001662357.1|    AAVFLMKQAATDIDSVQEVFHLSQGERDFLTSCGVGEALFLVG-----------------
ref|YP_001666189.1|    AAVFLMKQAATDIDSVQEVFHLSQGERDFLTSCGVGEALFLVG-----------------
ref|NP_623664.1|       ATVFLLRQSPTDIDAVQEVFHLSKGEREFLLSSGIEA-----------------------
ref|ZP_02755290.1|     ETKIFLGQDTTDIDSIQNMFKLSEGEKLFLLRADKGEMLVRIQGESTVVKVLAFDFEKKL
RAAC02309              DTKILLRQDKLDKEAVIENFGLEEHEFEELIAFRDGQARWWVGGEVFYNQLIPFADEFEL
ref|YP_001181426.1|    ASKILMRQESDMAAQIAEFFRLSERTVEIITSAAQGQGTIINPRKIFIQVTPFDFEWEY
                         : :::  *           : :  * *.:         :       *:

ref|YP_001662357.1|    ----------------------
ref|YP_001666189.1|    ----------------------
ref|NP_623664.1|       ----------------------
ref|ZP_02755290.1|     IEKR------------------
RAAC02309              FTTRFVQSDAELAMQRRWLA
ref|YP_001181426.1|    VTT-------------------
```

FIG. 15

```
ref|ZP_00874806.1|              ------------------------------------KAQKQEIKPSTVNTLAY
gb|ABV55445.1|                  ------------------------------------KTQKQEISPSTVNTLAY
ref|NP_735797.1|                ----------------LNLLMKPKTSSKQKKEKTKKREVLPTTLNTLAY
gb|AAG38042.1|AF295925_7        ------------------------------------KEEVLPSTANTLSY
RAAC02310                       MGSAVKFIVLGAALAVMLVILILRDQRKQQGQGRRSKRKVTPSLQEFLPI
ref|XP_001247966.1|             -------------------------------------------------- ref|ZP_00874806.1|              QGLFQNGLMQVSPSYFSQTYLLGDVNYQTVGLDDKGAIVEKYSDLINSLD
gb|ABV55445.1|                  QGLFQNGLMQVSPSYFSQTYLLGDVNYQTVGLDDKGAIVEKYSDLINSLD
ref|NP_735797.1|                QGLFPNGLMQVSPDYFSQSYLLGDVNYQTVGLEEKEAIVEKYSNLINSLD
gb|AAG38042.1|AF295925_7        QALYQNGLMQVKEDYFSQSYLLGDVNYQTVGLEDKGAIIEKYSDLIKSLD
RAAC02310                       EGFHESGAVIVN-GRFRRLIRVGDLNLYAMSMDEIVAVRERFKAMLMRLD
ref|XP_001247966.1|             ---------------QVRRAVVTAFMKHAQRQLEEGVSAGEAIKQLLT---
                                                  . :    . ::    :::   :  . ::

ref|ZP_00874806.1|              DKTNFQLTIFNQKVNLEKFRKSILYPLQE-------DGFDAYRDELNRMM
gb|ABV55445.1|                  DKTNFQLTIFNQKVNLEKFRKSILYPLQE-------DGFDTYRDELNRMM
ref|NP_735797.1|                DKTNFQLTIFNKKVNLEQFRKSVLYPLQE-------DGFDSYREELNRMM
gb|AAG38042.1|AF295925_7        DQTNFQLTIFNKRLNLEKFRHSVLYEEKE-------DGYDSYRKELNRMM
RAAC02310                       NP--FQISVQARRANYTDFVAYAESTIDESVKVYDNPAFTAYAEDLKTYL
ref|XP_001247966.1|             ----------------------------------------KYKEMLARIV
                                                                          *  . *    :

ref|ZP_00874806.1|              DANLEAGENNFSAVKFLSFGKSD--QTPKLAFRSLSQIGEYFKSGFSEID
gb|ABV55445.1|                  DANLEAGENNFSAVKFLSFGKSD--QTPKLAFRSLSQIGEYFKSGFSEID
ref|NP_735797.1|                DSNLEAGENNFSAVKLISFGKSD--QAPKLAYRSLSQIGEYFKSGLSEIE
gb|AAG38042.1|AF295925_7        NQNLDSGENNFSAVKLISFGRKD--SNPKQAYRSLSQIGEYFKSGFSEID
RAAC02310                       REEAMKPRTDRENLIVIGVLPKVGGEDEKLQLERLAREQSFVESGLSAMG
ref|XP_001247966.1|             FDRETDEKPDQVDLLLL-------FQQDLVERSKGGTILLFVAKELYDLE
                                  .    . : .:           .        .    :. . :  :

ref|ZP_00874806.1|              VSLGLLGGEERVNVLADMLRGENHLPFSYKD-------------------
gb|ABV55445.1|                  VSLGLLGGEERVNVLADMLRGENHLPFSYKD-------------------
ref|NP_735797.1|                ASFTLLTGEERVNNLADMLRGENHLPFTYKDLV-----------------
gb|AAG38042.1|AF295925_7        ARFESLAGEERVNLLADMLRGEHHLPFSYRDLTR----------------
RAAC02310                       LPYEVLEPVQVVEAVQNFWNRERAVSQRYRDAVRRRTHAPRVDGLDVEVS
ref|XP_001247966.1|             IVED--------EAFEQWWDNERSTATEALKKVRQQT-QPFIDWMMTEES
                                 :   . :      *.    .

ref|ZP_00874806.1|              --------------
gb|ABV55445.1|                  --------------
ref|NP_735797.1|                --------------
gb|AAG38042.1|AF295925_7        --------------
RAAC02310                       DLVRTQEEEGKEA
ref|XP_001247966.1|             DEEESDEESGEE-
```

FIG. 16

```
ref|YP_001205829.1|    --------LPIVEGVTTVFGVRTPRNEYFTAVICWVA--IGLLWFLVNRTRRGKAVMAAS
ref|YP_001240062.1|    --------LPIVEGVTTVFGVRTPRNEYFTAVICWVA--IGLLWFLVNRTRRGKSVMAAS
RAAC02311              -MLEVHSPIPMTEGETLVFGIRTKHIAHFSIGVCLTAPMAALAWFLLPLLHEPKLLVLFL
ref|YP_359336.1|       -VLPFYVSIPVLESLRLLFGGIGALAGFLFPVISGGL--ISAP-VSVPLWHTPLLPVLFL
ref|YP_001451893.1|    ----------------ILIGVLAGYALSFAMGVVDTAPIAEAHWFALPTFYTPR----FE
ref|YP_466026.1|       APILFSGGRPLAADLSDAVGRFG--LAPLVAAAGAAA--LRARWRAAPE-RRPEVLLLAT
                                       .*             :

ref|YP_001205829.1|    MNPRGVTLLGIELSS-----IYLTVW----------------------------------
ref|YP_001240062.1|    MNPRGVTLLGIELSS-----IYLTVW----------------------------------
RAAC02311              WGGAGVVFAKVPVAN-----RPLAEWLWLSFRYARRPKLILYDREFRIRVHRKRAAERWG
ref|YP_359336.1|       INSFGVAFAAIPALF-----APGSEILAFIFNLA--------------------------
ref|YP_001451893.1|    WFA---ILTILPAAL-----VVIAE-----------------------------------
ref|YP_466026.1|       WGGLAFALALARNRFDVYAAAPLAVWCWLGLRHVQASRL---------------------
                                  :                :

ref|YP_001205829.1|    --
ref|YP_001240062.1|    --
RAAC02311              AR
ref|YP_359336.1|       --
ref|YP_001451893.1|    --
ref|YP_466026.1|       --
```

FIG. 17

```
ref|ZP_02850831.1|         ------------------------------LSGFLADVSYS--LSFVLNG------
RAAC02312                  MSMKRWITQVGKSLYAGSVVLASTAMSAEASTSGITNPLSSSSSS--VSSVLNQAL----
ref|NP_279998.1|           -----------------------------ATIGGIATTLGFSSQT--MAAILGGVFGLQ-
ref|XP_001637270.1|        ---------------------------------------------VGVLLGTALN---
ref|YP_001506532.1|        --------QLGSSLLLNTIVLVLVTATAGAASTPLAVARRALARPSLIALVLALALRPVG
ref|ZP_02248080.1|         -----------GKLETIGSAMVAQNAAAAAPTTTGVIPAAADEISV--LQAPLFTAYG---
                                                                         :    * ref|ZP_02850831.1|         ----VTSGVFAL---FFLFY-LQR--VGTGSGDHSAELMRKKQAAGGASLWLLVTDVRLY
RAAC02312                  --GWLDDAIFAVAGALFLFH-LYKAIIGLMAGSHHAQ---RREEAKSHLVWVAISGVMLG
ref|NP_279998.1|           -SAWLTYGIFAAIGAVFLVD-VWL---GLRSG--------IRNAARATMLLIGVAMAVL-
ref|XP_001637270.1|        ----LTDWIFAVSGGMFLFVSLAETMPELFASAAH-----QREESRGKVLLAQNAGLLAG
ref|YP_001506532.1|        FPAWLDEALASIGATLTPLA-LFS--VGLQLRLPAVR-RWRRELALGLVVKLAVAPVVVL
ref|ZP_02248080.1|         ---TLYQQVSAEAAAVYDLF-VKT--LGVSAGTYA-----ATEAANSSAAALPLSGI---
                                : :      .  .  :                        : :  .        :

ref|ZP_02850831.1|         LFMALGGMLINLGNS-
RAAC02312                  GGAILAGALYNLGKSF
ref|NP_279998.1|           ---VVVG---------
ref|XP_001637270.1|        -----FGTMLTLAAF-
ref|YP_001506532.1|        GCYALAGAL-------
ref|ZP_02248080.1|         ----------------
```

FIG. 18

```
ref|YP_245669.1|    ------------------------------------------------------------
RAAC02313           MRQSSNAPDSVRGESWPKVGAICSFPSCTLVPSRPVQARGGEGMAGSTASNVTQTITQLG
ref|ZP_02369868.1|  --RGALAARIGAAFDLPTLGRTLVVCAPAIALYG-ATGDARWLLASIATIAIAIAVERVG
ref|YP_438666.1|    --RGALAARIGAAFDLPTLGRTLVVCAPTIALYG-ATGDARWLLASIATIAIAIAVERVG
ref|NP_695275.1|    ---------------------------------------------------------VSVLG
emb|CAB06069.2|     ------------------------------------------------------------ ref|YP_245669.1|    ----------AVLVLFFGGFGTAIDVDGADQIIILGWGAVFSSILGIIGSVVVKSKSG--
RAAC02313           FAP---VNPWALLNRVTSGFGHLIEVVFAWVYFLSEIGVLAGALVWLVGSIGSHARIK--
ref|ZP_02369868.1|  IAP---LGALAQGAAIIAGFLSLSCALNAWPAFVAGCAALAAAAVALSRFGARLRSLGNF
ref|YP_438666.1|    IAP---LGALAQGAAIIAGFLSLSCALNAWPAFVAGCAALAAAAVALSRFGARLRSLGNF
ref|NP_695275.1|    FVPHMFANPWGSLMAVLVALFLSVPAAFIYRKIRTRKGAAIGILVGAVLAIVVALVSN--
emb|CAB06069.2|     SLP----STWR-IPSTCSEHSEGSDCSTNSNVTMSLLKLLDCFFRPFLPREGLKKIPS-- ref|YP_245669.1|    --IGGAFMLIAAIIGFLCI-------FAIYILPGALLAI------
RAAC02313           --RTGAHITLYAIVGFL---------AAVILPGVILAIDSTFQR
ref|ZP_02369868.1|  VFIPSLYLTCEAAAAHLSAPRLVPYLCAAMLPPIALSCIATLR-
ref|YP_438666.1|    VFIPSLYLTCEAAAAILSAPRLVPYLCAAMLPPIALSCIATLR-
ref|NP_695275.1|    ----LIVTPIYAHMTYQAV-------AAMILP-ILLP-------
emb|CAB06069.2|     -------EKLSHIPELI---------EPWFIFSLVWSVGATGDH
                                              ::        .
```

FIG. 19

```
ref|ZP_01058859.1|        ------------------------IGEDILPENVDFEVIDGFTKVTDKDAAIYTRRL
RAAC02314                 MERVEYVDRVKHVWSEYRTNDEELAFALGIDEEAESVDVSTKDGITNVT-----VFTTEA
ref|YP_754274.1|          ------------------------LSPNRWQHSLQVAET-ALQMAG---QYELELEQ
ref|XP_503244.1|          ------------------------NLTANVEIDGKQYNTFTEPPKALAGER--AKVKFPIKD
ref|NP_218466.1|          ------------------------DLIVRLAKLKHVNPQVLQVMS----DSLHKKF
ref|NP_126488.1|          ---------------ARKILEVLIDSDVNVYINDVVASEVIFIYLKLTTGKSYLTLKK
                                                                  .        :        .

ref|ZP_01058859.1|        AKEEGFFLGNSAGAAIKGLLQLKQHFK---------------------------------
RAAC02314                 VYHFGTFRADYVGHASRALVQLLQHFRVNLPIDFIVAHQTFHVYLKGGKVVAGEKEYPIA
ref|YP_754274.1|          VYLTALLHDYAKGLSGQFLLRLAEENNL----IEDEVDREVPDLLH--------------
ref|XP_503244.1|          MTEFLHGGEENVTMIERLMTELERDPVLNVSGDYDMPKEQLRETAVARIAALSGHWKKDT
ref|NP_218466.1|          AALHLSQRRDLDGHA--VLAAILKKMER------ATEHSILHALAEKN------------
ref|NP_126488.1|          NPVIVRSVDKTSVYELLGMFKFLETNEFVFSIAKRLIDK-YGLLPNDALILATAIFY---
                                     :     :    .

ref|ZP_01058859.1|        ------------------------------------------------------------
RAAC02314                 ERSEGYELVEPVEWMIASSVLDVVLRLAEEYEVTPEQIVESAVGTFYALLSVAEENDVEP
ref|YP_754274.1|          ------------------------------------------------------------
ref|XP_503244.1|          EKEALL------------------------------------------------------
ref|NP_218466.1|          ------------------------------------------------------------
ref|NP_126488.1|          ------------------------------------------------------------ ref|ZP_01058859.1|        ------------------------------
RAAC02314                 ETVISMLTELMHRHAEHTNEHELSTLNR
ref|YP_754274.1|          ------------------------------
ref|XP_503244.1|          ------------------------------
ref|NP_218466.1|          ------------------------------
ref|NP_126488.1|          ------------------------------
```

FIG. 20

```
ref|ZP_02854145.1|      ---MGTTISFGIQKGGVGKTTTTAITSYILSKE--HKTLAVDFDSQGNLTRFLTQQNIYNF
RAAC02315               MERVGCTISVGLQKGGVGKSTTTALTSYILAEQGHRVLAVDFDSQGNLTQLLTQRSPYDF
ref|YP_145847.1|        ------TITMGIQKGGCGKSTTTGVLAYLLSRDGYRVLAVDMDSQGNLTELLSRKPSNEF
ref|YP_799230.1|        ---MGKIVSISNQKGGVGKTTTSINLAANLASIGKKVLIIDMDPQGNSGSGLGIEINTLV
ref|NP_714527.1|        --QMGKIVSISNQKGGVGKTTTSINLAANLASIEKKVLIIDMDPQGNSGSGLGLEIHKTN
ref|YP_536482.1|        ---MGTVIAIANQKGGVGKTTTSVNLGACLARAGQKVLLIDTDAQGNATSGIGVRKHNIE
                           ::.. **** **:**:      .  *:    :.* :* *.***      :  .

ref|ZP_02854145.1|      TEKTVLEAVKAKDPRPYIYKISDNLHILPAEDFLATFSRFLYQ---------EYQG-NKA
RAAC02315               VHRTSLEACKERDPRPYIHAISDNLHLLLPAEDFLSQFDKWIYT---------EVHVSQQM
ref|YP_145847.1|        TEKSVLEAMQERDPEPYIVKVNDRLDLLPANNFLATFPRWIYTGETYLGKYIRYKG-KPT
ref|YP_799230.1|        KTSYELLLGESSTNECIQRTNVSNLHIIPSNINLSGAEADLLVED-------------QRE
ref|NP_714527.1|        KTSYELLLGEASVNECIQRTNVSNLHIIPSNINLSGAEADLLAED-------------QRE
ref|YP_536482.1|        NDVYDVIVSELPIREAIMPTYIDNLDVVPATIQLAGAEIELTAQM-------------ARE
                                  :      :   .     ..*.::*:    *:             :

ref|ZP_02854145.1|      LLLKETLDVVREQYNYITIDLPPHLGDQTINGLSASDYAVVLLQSEPFALDALDRYLEVL
RAAC02315               VILKNTLDVVKSDYDYILIDLPPNLGGLTLNGVCASDYCVVVCQSEPFAYDALDRYMEII
ref|YP_145847.1|        LILDDTLDKIRHRYDFIVIDTPPSLSEQTTNALCASQYVIMMFECSNWCYSAVPNFMESV
ref|YP_799230.1|        YRLKNAVSELRSEYDYILIDCPPSLGILTINALCAADSVMITLQTEYFALEGLTQLMKII
ref|NP_714527.1|        YRLKNAISDLRTEYDYILIDCPPSLGILTINALCAADSVMITLQTEYFALEGLTQLMKII
ref|YP_536482.1|        KKLYDAVQDVKEEYDFILIDCPPSLGLLTINAFTASDSILIPVQSEYYALEGLSQLMNTI
                           *  :::.   ::     *::*  **  **  *  *.. *::     ::   :  .:.   ..: .  .::  :

ref|ZP_02854145.1|      MGVQKKANSNMKLIGILSTMLDSRAAIDSEIINKARKDYEDVVFETIIRRRNRIKEFSLF
RAAC02315               QAAQQRVNPNLRIAGILISLLDARTAIGNYITERIREEYQDFVFDTVIRRKSRIIEFSVE
ref|YP_145847.1|        EGARVHGRHNTRLLGILRTMNDVRRNDAKAFNEMIEEDYPNEVFKTIITRKAPIGRLSLY
ref|YP_799230.1|        SLVQNQLNPSLELEGVLLTMFDKRTNLANQVAEDVKSYFKDKVYTTIIPRNVKLSE----
ref|NP_714527.1|        SLVQNQLNPSLELEGVLLTMFDKRTNLANQVAEDVKSYFKDKVYTTIIPRNVKLSE----
ref|YP_536482.1|        QLVQKHFNPDLQIEGVLMTMLDARTNLGNQVVEEVKKFFKEKVYKTVIPRNVRLSEAPSH
                         .:   :.....: *:*  ::  * *       . .  :.. :  *:  *:*  *.   :  .

ref|ZP_02854145.1|      GIEERT-KVDREALKYYKNFTKELISRVQK
RAAC02315               GIKIQT-KADREAIAMYESFVEELKARVSR
ref|YP_145847.1|        GFEENN-ELN-QALEQYENFYKEMMERV--
ref|YP_799230.1|        ------------------------------
ref|NP_714527.1|        ------------------------------
ref|YP_536482.1|        GMSIIDYDPRSRGAEEYEALAKEV------
```

FIG. 21

```
ref|XP_624126.2|         ------------------------------LSQPHTTIP-----------------A
RAAC02316                --------------------MSAADKKKRFESLMPSRTETPPHKSEVIDTLMGQTYDADD
ref|ZP_01893908.1|       -------------------------------PFMEEDTTP--------------------
ref|XP_001444409.1|      -------------------------------LGISKTATE--------------------
ref|ZP_02180762.1|       -------------------------------TYDQEGAVY-------------------
ref|ZP_02077766.1|       LGSTQKEQKYEMEDYTESVQKQAEAADELAKSLNDAEEAAKNSYADKIGDIGTVEKYLQK ref|XP_624126.2|         LHPPNVPLVSS------SHTTSPAVASLGVTPAAPSNGATTTSYP-PSIPMAAYP-----Q
RAAC02316                IGTPKTRMESLHKESVSHTSEVVYPPMSNTTTTDDNGTTDNSFD-IAARIRAFEE--QRR
ref|ZP_01893908.1|       -DTSSTSDDSS------DDDDDDDDSEEETESGPDPEETRLRFELLKEKLDAAD-----A
ref|XP_001444409.1|      ---EQIKEAYA------QKAQKLYPNVTTSVAIND-VQAQQGFQDVAEAFAVLS---QIQ
ref|ZP_02180762.1|       -----THVAKD------HQKKAMKFIQDQLFTTPTWMLDEDIFN----KIESAG-----S
ref|ZP_02077766.1|       LREMSGETGYVDN---VNLAKMYVEEINSLLPETVQLTADGRVEWLKNTDAIYQEIAALK ref|XP_624126.2|         TQPSYPPLYTPYTAL---------------------------------------------
RAAC02316                SRPSYDELYTKHTFLIRKDLMERLERASARHSRGFKTRFINELLEAGLTQLEIED
ref|ZP_01893908.1|       SLAKHGRGHKKTQEALN-EL----------------------------------------
ref|XP_001444409.1|      SRNAYDLLNKEQPELLYGEEMERYKQSFQRNDDG--------------------
ref|ZP_02180762.1|       IERVRGMQTRTLNNMLDFGRMQRMLEN---------------------------
ref|ZP_02077766.1|       EEARVKAYQELYTQAVRDEIKARTDLTMTTEELNKKVQRLNELKADGISEDEIEE
```

FIG. 22

```
emb|CAJ50746.1|              ----------------------------------------AADLAQDTFVRVLRHRRELPGV
gb|AAM28266.1|               ----------------------------------------AADLAQDTFVRVLRHRRELPGV
RAAC02290                    MTSGMRRFTNSSRTAEEVTGMEGHYTYALMGPTSEHTVACDLAPDTFVEVLRGAMEAIGV
ref|XP_816394.1|             --RGAN-LSNEERTNETIVR----------------QYETALENIIGTLQDRLTILRE
ref|XP_001585185.1|          -YIEMSAFGRESHPRVQALR----------------HDRDRSPPDPNATDPEVIEHLKT
gb|EAU92316.1|               ---THSAFGPTVSFEE--------------------AQRIERETAEHLLKSRKLSLIV emb|CAJ50746.1|              RE----PRAYLVTIAGRLLLNHYRRRS---LERAYEEALAVMPLESAPSPEQRLL-----
gb|AAM28266.1|               RE----PRAYLVTIAGRLLLNHYRRRS---LERAYEEALAVMPLESAPSPEQRLL-----
RAAC02290                    RLDELVLRIYVQEGAGGWQLVHGRVKD---AREAQQTCLLPMPPE-PPSGDPEVLDDATY
ref|XP_816394.1|             EYAS-FLKVSEEETANEKEVLNEHEQDSQRVRQTFRTAALTLQRVFWSTREKEVPEVISE
ref|XP_001585185.1|          QLKDADDLMDLIVARYRVLENENGEPNTERVEVAERRLEECMDLVDGPLGQKEAFDN---
gb|EAU92316.1|               DLDQTIVHATVDPTVGEWIAEGEAWEAR--QERRNKVKTTTPDSDDSDSSDDSDDDEDDE
                                                                           .   .     :

emb|CAJ50746.1|              ------------------------------------------------------------
gb|AAM28266.1|               ------------------------------------------------------------
RAAC02290                    QDIGYAALNLYRVLWQSRQRIKASSLKTKVRVRQSLRALDERMRLVEQAVEGTEWWDLFR
ref|XP_816394.1|             LDN---------------AAAAAEKSRAAVKVTLALLDSRLQSFSEQKE-------WM
ref|XP_001585185.1|          ------------------LKALLSESREALKVKMNEWNEKDKERDWAVES------LE
gb|EAU92316.1|               CNPNWEALKDVKKFTLGPESFNAPSVKGRSKGKHRMVEQEGCMYYIKPRPG--------W emb|CAJ50746.1|              ------------------------------------------------------------
gb|AAM28266.1|               ------------------------------------------------------------
RAAC02290                    LRYQQGKKLVACAMELHMSSRTLNRQISDMAGHVGRMLSTVLKERELAELMQAAKRVPMM
ref|XP_816394.1|             ETHQQSLEDLLVSLR-QLNKRAFERQLSLMNERVARPSST--------------------
ref|XP_001585185.1|          KLLKESEEREAALAGLLHATQEDMRREGKRAAKVAEIEEK--------------------
gb|EAU92316.1|               KEFLENAAKKYEMHVYTMGTRAYAQEVCAAIDPDGKLFGSRLLSRDESGSLTQKSLQRLF emb|CAJ50746.1|              -------------------
gb|AAM28266.1|               -------------------
RAAC02290                    PGKATARVIRLEQRELWS
ref|XP_816394.1|             -------------------
ref|XP_001585185.1|          -------------------
gb|EAU92316.1|               PCDTSMVVIIDDRADVW-
```

FIG. 23

```
ref|YP_001210712.1|   ------------------------------------------------------------
ref|ZP_01593342.1|    ------------------------------------------------------------
RAAC02317             MWFKYTQKQQTTQPCAGFSSLRTMGRFPSRRKVFFRPPLQGGTNMAYTPAKVRKGWSENW
ref|ZP_02727046.1|    ---------------------------------------------------------KEW
ref|ZP_02758954.1|    -----------------------------------------------------------W
ref|ZP_00235902.1|    -----------------------------------------------------------F ref|YP_001210712.1|   ----DAIFERHDLTTLQKLVYIYFCRRANNNG-QSTPSYDDIAKDCGCHRSSAIEAVNTL
ref|ZP_01593342.1|    ---PNAISRSTELSSTAKLVFGKLCQYAGQNG-QAYPSYKTLAGDVGVERRQAIRAVKEL
RAAC02317             FRCPNSIYDIDYISGYAKAVYIFLCRCADGEG-QSFPGYNAIAKAIGFGRTRTIEAIKEL
ref|ZP_02727046.1|    FWLENDLVDREDLGIYEKMIYIVLARYSDNES-CCFPSYKTIALKCGCSERQAKSVVKIL
ref|ZP_02758954.1|    FWLENDLVDREDLGIYEKMIYIVLARYSDNES-CCFPSYKTIALKCGCSERQAKSVVKIL
ref|ZP_00235902.1|    FMIDNEVIDNGELDVYAFKTYAVIVRYANKKTKSAFPSLNTLAKRVGCGKKKVIECIKIL
                          :   :        :  : : :. :   . *. . :*   *  .   :: * ref|YP_001210712.1|   GKMG-LVVKHRRKRHNGSDTSNMYVVFPP--------------------------------
ref|ZP_01593342.1|    VDYG-LIKPVGRKKGDGGFTSNIYAFLWHQTFSDDGLTDPG----DKNDTRGGVTNVTTP
RAAC02317             EQAGLLVKEHRRNEETGEYYSNLYTVIHPDDVAFRGGMSPHGIPMSRDDTPLSPDDIPMS
ref|ZP_02727046.1|    ENKGLIKKENRIKSNSNEKESNIYFVL---------------------------------
ref|ZP_02758954.1|    ENKGLIKKENRIKSNSNEKESNIYFVL---------------------------------
ref|ZP_00235902.1|    VEKGYVSKTLR-KDNKGDHLSNLYHLLPTSNISKKQG-----------------------
                      . *  :      :   .   **:* .:

ref|YP_001210712.1|   ------------------------------------------------------------
ref|ZP_01593342.1|    QCHKRHHLVS------DMSP---KENHTRESNSETTTTEEIRLLLSGTPLSKISEKEVRI
RAAC02317             PHDRRVSPGGREVRSIDQDPPTKIYIHTRSQAAATLATSNNEHLTSNTALEEVCETVNEA
ref|ZP_02727046.1|    ------------------------------------------------------------
ref|ZP_02758954.1|    ------------------------------------------------------------
ref|ZP_00235902.1|    ------------------------------------------------------------ ref|YP_001210712.1|   ------------------------------------------------------------
ref|ZP_01593342.1|    LIKR---------HGNERVMQAADIAAEKWRRERKEIKNPGGYLQTFCVNLVV-------
RAAC02317             LVQLGIRAQKKTLLHWLQIATPEEIIEAASLATREGVKSPAGYIGTVLRNGLVRVEKSTA
ref|ZP_02727046.1|    ------------------------------------------------------------
ref|ZP_02758954.1|    ------------------------------------------------------------
ref|ZP_00235902.1|    ------------------------------------------------------------ ref|YP_001210712.1|   ----------------
ref|ZP_01593342.1|    ----------------
RAAC02317             KHKDPRYNEFYKLFP
ref|ZP_02727046.1|    ----------------
ref|ZP_02758954.1|    ----------------
ref|ZP_00235902.1|    ----------------
```

FIG. 24

```
ref|ZP_02171383.1|        -----------VYLARGSTDLRKSIDGLAAIVQEGFELDPFSSSLFVFCNRYRDKIKILY
RAAC02319                 MLAFDWTSDHRVYLACGATDMRKSIDGLAALVQASFQLDPFSPCLFVFCNRQRDKLKILH
ref|YP_431168.1|          ----------RVYLACGATDLRKSIDGLAVLVKEGFELDPFSSCLFVFCNRNRDKLKILH
ref|YP_001212944.1|       ----------RVYLALGATDLRKSIDGLAVLVKEGFELDPFSSCLFVFCNRKCDKLKILH
ref|YP_754944.1|          -------SNRQVYLACGSTDLRKSIDGLAVLVKEAFELNPFSPCLFVFCNRQRNKLKILQ
ref|YP_754864.1|          -------SNRLVYLACGSTDLRKSIDGLAVLVKESFHLDPFSPCLFVFCNRKRDKLKILQ
                                     ****  *::******.:*:  .*.*:*..****   :*:*** ref|ZP_02171383.1|        WDHNGFWLYYRRLEKGRFPWPTSGSDEPMIITERQLRWLLDGLPLDQKGAHR--------
RAAC02319                 WSHNGFWLYYRRLERGRFDWPETGDAKTMVITRRELNWLLDGLPLEQPRAHRAVYVRSAI
ref|YP_431168.1|          WEHNGFWLYYRRLEKGKFVWPQDTTSSTITITRRELRWLLDGLPLKQPQAHPEVKARTIL
ref|YP_001212944.1|       WDHNGFWLHYRRLEKGKFHWPADAGSPTLVISRRELRWLLDGLSLKQPKAHPEVKARTIL
ref|YP_754944.1|          WDHNGFWLYYRRLERGKFEWPA-ADSQVVSISYREFRWLLDGLSLKQKQAHKAVKERTII
ref|YP_754864.1|          WEHNGFWLHYRRLERGKFDWPT-AHTDVVSISYREFRWLLDGLSLKQNQAHKAVKQR---
                          *.******:*****:*:* **         : *: *::.******.*.*   **
```

FIG. 25

```
ref|ZP_01287154.1|    ---------------------------RSKRRFWAAHVAAWEKSGLTQTAYCREHG-LSR
ref|ZP_01287577.1|    ---------------------------RSKRRFWAAHVAAWEKSGLTQTAYCREHG-LSR
ref|YP_754945.1|      --------------------------MSSNERKAWWEERLAEHEASGQRVTAWCEENS-ITP
ref|YP_754863.1|      --------------------------MVNNDLRSLWEQRLADYETSGKSIATWCREHS-IRN
ref|YP_431169.1|      --------------------------MTKAELQELWASRIAEYKMSGQSVKEWCATHEGVSP
RAAC02320             MAFILPSVENVVIKPREGSCMREHMSHQERRELWRERIAAFYDSGQSASQFCAEHG-LKP
                                                  . :  ::*    **     :*  :  :

ref|ZP_01287154.1|    HAFGWWRRKFRDQPASEQPLLQVPTVARPTAAT-AAADFSGLRLLLPRG-LQLEINQGF
ref|ZP_01287577.1|    HAFGWWRRKFRDQPASEQPLLQVPTVTRPTAAT-AAADFSGLRLLLPRG-LQLEINQGF
ref|YP_754945.1|      RQFYYWRRKLR-----TEHVEKEQPVKWLSLKYESRQLGIAGDAIAVHVGQATVEIRKGF
ref|YP_754863.1|      NQFYYWRKKLR-----MDQVENNQPVKWLPLEVE--QANLAPGSIGVHVGQATVEIKPGF
ref|YP_431169.1|      RQLWYWLRKYKN----QNGVLSAQSTRWLPVEIS-EQTSNVSNSLLVRIGPAIIEVSPSF
RAAC02320             HQFWYWLRRLRN-----ETAPGTQATSFVSVVTTSSPSDASRSPLTLRVGSVEIDVHPGY
                      . : :* ::  :          :     ..  .      .    : :  *   :::  .:

ref|ZP_01287154.1|    DAATLGRVI-------
ref|ZP_01287577.1|    DAATLGRVI-------
ref|YP_754945.1|      DRELFCEIIQVLQTI-
ref|YP_754863.1|      DPHLLRQIVKVLQTI-
ref|YP_431169.1|      DPVLLSQVVKVLVALC
RAAC02320             DASTLAELIRLVMHVC
                      *    :  .::
```

FIG. 26

```
ref|NP_982177.1|      TEINBACILLUSCEREUSSCRESIGNIFICANCEE-IDENTITIESPSITIVESCAPSQY
ref|ZP_02595431.1|    ------------------------------------------------------------QY
RAAC02321             ------------------------------------------------------MNEKPQA
ref|YP_001108426.1|   ------------------------------------------------------------
emb|CAN89659.1|       ------------------------------------------------------------
ref|NP_927486.1|      -------------------------------------------------------KKPSGS ref|NP_982177.1|      VLVISPRDNE--VDLVKELGYGVILIRKNISFDEMFSVEVPVEIDLNDEEIVVGKCKELS
ref|ZP_02595431.1|    VLVISPRDNE--VDLVKELGYGVILIRKNISFDEMFSVEVPVEIDLNDEETVVGKCKELS
RAAC02321             VVVIGTREHEGEVELVRALGYRVLLLNTKINIEDALVADVPVELDLNDETLVISKVIDLT
ref|YP_001108426.1|   --------------------------------------------ETNDVAALAEHVARLQ
emb|CAN89659.1|       --------------------------------------------IRCDTNSDAALRAALQDRF
ref|NP_927486.1|      IELKKAKELGAYIIFIGSR-----KYYNKVSDNDLLYIDEFFEADTNDDELVINMVEYIN
                                                                  : *.   :

ref|NP_982177.1|      EKYNVVGVYTLNEYRIPLAAKVGEILEINSFLSYETAITCRNKKLARKKLNNSNVSSVKF
ref|ZP_02595431.1|    EKYNIVGVYTLNEYRIPLAAKVGEILEINSFLSYETAIICRNKKLARKKLNDSNVSSVKF
RAAC02321             NHYYIKAVFTLNEYRVPLSARIAETLGLQRTISYEAAQNCRNKKLTRRTLMRNGIQAMKF
ref|YP_001108426.1|   PVLGFDGVLTSCDYYLPAVAHIAARLGLPGAP-PEAVERACSKDLTRRALREAGVPGPAF
emb|CAN89659.1|       RREEIAGVTTTSDFYVPAAARLARWLGLPGNP-PEAVTACRDKSALRALLRRAGVHQPRY
ref|NP_927486.1|      AKKKIQGVITFMEFYVPLVAKVAETLGLKGIT-YENALRARNKHLMRESFRQKNVPIPKY
                       . * *   :: :*  *::. * :          *  . .*   *  :  .:   :

ref|NP_982177.1|      ILIRKLDNLNEKLEGFSFPVIVKPSNDSGSKNVYLCKDYNEVKQAVDVISNSKLNLVGQT
ref|ZP_02595431.1|    VLIRELDNLNEKLEDFSFPVIVKPSNDSGSKNVYLCKDYNEVKQAVDVISHSKLNLVGQT
RAAC02321             ATVKTPAEALDVIADMDLPVVVKPANDAGSHLVYRCDTLQEVWEAVEAIAQTPYNWVGQN
ref|YP_001108426.1|   ALAESAAGLEEAAAALGYPLVLKPVDLCAGMFVRKVTDDVELRDAYAALRQFPVNARGQR
emb|CAN89659.1|       AVVREPGEVAAAVARTGLPCVVKPADDSGSVNVLLCTDEAQARAQAERILAVTTNVRGMP
ref|NP_927486.1|      ALISNIDSAKIEAAKIGYPNIIKPINMAGSRGVLRNDNVIELERNFREVCEITP-PFGVK
                       . *  ::** :...  *          :         :    :          * ref|NP_982177.1|      LDPEAIVEEYLDGPEYSIESYTIDGKTTIVGVTEKVVTPFPLSVEVGHNFPAVLEEDIET
ref|ZP_02595431.1|    LDPEAIVEEYLDGPEYSIESYTIDGKTTIVGVTEKVVTPFPLSVEVGHNFPAVLEEDIET
RAAC02321             RDPEILIEEYLVGKEYSVEACTIQGETHILAITEKETTTTNVSVEIGHTVPAILEEEQVS
ref|YP_001108426.1|   RNPLVLLEELLTGPEVSVETVTSRGRTSVIGVTDKSIAGAPWFVETGHMFPAALDLDTER
emb|CAN89659.1|       TARTVLVEEYLDGPEYSVEMFSQDGEAVCVGITAKSVTGDPHFVEHRHLFPAPLPAATAE
ref|NP_927486.1|      KSSLFLIEEYLEGQEYSIESISFNGVVNIVTITKKYVSSNGYFVELGHTLPANIPLQQKI
                      ::** * * * *:*    : * .  ::*  :*         **    * .** :

ref|NP_982177.1|      SIHETVINALDVIGVDFGVTHTEVKVTSDGPKVIEVNARPGGDRITDLVEYVTGIDLRRI
ref|ZP_02595431.1|    SIHETVINALDVIGVDFGVTHTEVKVTSDGPKVIEVNARPGGDRITDLVEYVTGIDLRRI
RAAC02321             SIHDLVKKALRALGVDNCVTHTEIKLDGNSLRIVEVNARPAGDKIPLLVRAVTGYDLREL
ref|YP_001108426.1|   AVVETAVAANVEALGLDNVVGHTELKLTPDGPRIVEVNPRPAGNQITELVRRVTGIDLAAA
emb|CAN89659.1|       RITETVMAALDAAGIRLGATHTEVKLTGSGPAVIEINPRPAGGMIPELVRLASGVDLLEQ
ref|NP_927486.1|      EIEKVVTQALFALGIYNGGGHTEVKVTSDGVKVIEVGARLGGDHIPELVEMATGIDMWKA
                                :   . *:   *:    ***:*:  ..   ::*:..* .*. *. **. .:* *:

ref|NP_982177.1|      ALRINLGLPIKNSCCNKELVPSSSIRFLIADKEGYISFNEN----FRAESIKEIHWYVNK
ref|ZP_02595431.1|    ALRINLGLPIKNSCCNKELVSSSIRFLIADKEGYISFNEN----FRAESIKEIHWYVNK
RAAC02321             ALHIALGGQFENAPRHEVLAPVAAIRFLIADKHGVVSYDSRGV--LEFEEMKYIEFFTKN
ref|YP_001108426.1|   YAQVALG-EEPALERAETGAGSAAISFLLPPKEGVIGEVVGVQDLDGADGVVDWKFKSS-
emb|CAN89659.1|       QLKAATG-QAPDLKPGHG--AHAGIQFLLADADGVLDAVDGVARARAVDGVEAVTVTVAP
ref|NP_927486.1|      VIQVSLN---ISPDLSKKFSKYAAISYITAPS-GIVKKVNYIKN-------GFIHFDVNV
                            :  .               :.* ::       *  :

ref|NP_982177.1|      GERVNKTTSNFDRIGYYIVDGNKKESSKKIADSLNECFELAISEL
ref|ZP_02595431.1|    GERVNKTTSNFDRIGYYIVDGNTKESSKKIADSLNGCFELAISEL
RAAC02321             GYVVKKTTSNYNRLGYFVVFGKNRDHVETVNRKILSKLNLRISDI
ref|YP_001108426.1|   GHRSGPATSNNNYLGHVMVTAPDPGRARAKAEALVGGLDVRYAE-
emb|CAN89659.1|       GAVVRRARSAGDRVGHVIACRPGPEQVTAALDEARDLLRLTVGE-
ref|NP_927486.1|      GEHIESLKNSSQRLEYAIACGVTAEQAEFESHHLKENIIIEIA--
                      *        .  : :: :.         :   :   .
```

FIG. 27

```
ref|YP_504284.1|      -----SLYVAVFSTMLGIGIVIPLLPRFAETLGASGFGIGMIFSSFALSRAFAMPFFGRY
ref|ZP_02131576.1|    -KIFITLFFSIFTSVTGVGIVVPLLPVYANNLGASGFMVGMIFGSFSLSRILFLPYFGKR
ref|YP_001046337.1|   -RIYNVLFISVFATMLGLGIVSPLLPIYAENLGATGIWLGIIFSAFALSRSVFMPVIGRI
ref|ZP_02132246.1|    --ILVLLSVSVGVSMIGLGIIWPLIPVYAVELGAGGFMVGLIIASFNLSKAAFGPFMGRF
ref|ZP_01288161.1|    -RLLLPLLFSVFIALLGIGIIVPVMPIFATSLGASGLALGFIIASFSITRGLCQPGVGML
RAAC02322             MKIVYTLSFAVFLLVTGTGIVAPLIGPYAHSLGAGGFWIGLLFSGFYIVRLLVGTPVGRL
                             * .::    :  * **: *::   :*  *** *: :*:::..*  : :    . .* ref|YP_504284.1|      SDICGRRQFIIIGLLLYAIFSLLYVPAGSVLELSGIRFLQGIASAMVFPIAMAYIGDIAP
ref|ZP_02131576.1|    SDMIGRKPFITIGLFAYSLVSIAFMFSHGVTQLVVIRFIQGIASAMILPVCQAYIGEIAP
ref|YP_001046337.1|   SDRRGRKWIILIGMFAYAVLSLAYIIVDSVYSLTAVRFAHGLASAMVVPIAMAYVADLSE
ref|ZP_02132246.1|    SDSLGRKKFITVGLIAYTCMSVMYVLAGSAETLIAVRIFHGMASVMVVPIAMALAADIAP
ref|ZP_01288161.1|    SDRWGRKGFLLGGLLIFGVVGLLIPQAVSVENLVLIRALHGVGSAMIVPVAMAYVSDLAP
RAAC02322             ADHQGPKRVLIYSLILYPLISIAYWSAHSVGVLFAARLLHGLASAMMLPMAMTYVGAITP
                      :*   *  :  .:     .:: :   ..:    ..   *    *  :*:.*.:.*:. :   . ::

ref|YP_504284.1|      PGMEGRYLGTFTSSLFLGMGLGPFLGGIVTDIAGMDTAFICMGALTGVALLTCIFFLP--
ref|ZP_02131576.1|    QGREGFFMGLFNISMYSSLSLGPILGGVVNDHFGLQTAFACMGVLSLLAFFMAQHFLPPV
ref|YP_001046337.1|   KGREGSHMGNFSISMFLGMGMGPLLGGFLNDAFGLDSVFYVMAGLSAFATILVGISLP-E
ref|ZP_02132246.1|    KHELGLYMGTLNMAVMLGLGAGPVLGGALRDHFGMDSAFIAMGLLALITCILVVIVIPSD
ref|ZP_01288161.1|    VGEEGRYMGLLNTAIFAGIGSSGPLLGGIFTDLWGMPSAFYAMSTLSFLALGLILLQMPAM
RAAC02322             PGQEGRYMGIYNTFLFIAGGIGPLLGGLLASELSPNAAFLSLSLLAIGSLLLVIPLPR--
                         * .:*  .  :  .  . **.***  . .   .  :.*   :. *:   :

ref|YP_504284.1|      ----GYQGSRKEQSSILHLLIHPGLRTPLLYQMMNAFANGTFMVFLPVIAAHVGNLSAGE
ref|ZP_02131576.1|    KEE-PRQERGREPVTYRILAKNAGIMGAVLLRTTYTFCIGAIWGFLPVYADAHFNLSSSA
ref|YP_001046337.1|   AKRGTFTVQEGNPVPMRKILTLPVMRGVMVFAFISALGRGGMMVFIPVFG-PLIAISPTE
ref|ZP_02132246.1|    AETRSFKENQAR-SSVGQIVRHRIALGIIFMRFLAASGQAVYTFLPLLG-LKMDMSSSQ
ref|ZP_01288161.1|    PAASRTGNADGLFTVMGKMLANRSTTGLLLARMATMLIMVPTMAFLPLLMTQAFQASGMQ
RAAC02322             VSSASKEKNGMNHWGMGDLIISPGILALAVLNVENAVLDVFQVSFFPVFA-QNRGLSLLA
                                    :             .                     *:*:        * ref|YP_504284.1|      TGLVISVSVLSTALLQRVCGRLADRFDKYLLIATGCLTVTVALALVPGFEGLWSYLFFAL
ref|ZP_02131576.1|    IGFLIMLGVLTSGVLTTPMGWLADRVDKRLLCVIGSVMISVAVYSFTADGFWHLFASNM
ref|YP_001046337.1|   VGIVLSANTFLMALLQVPMGRITDTGNKVVLIVAGSAITALAIGAIPFSGSFGPLLAITS
ref|ZP_02132246.1|    VGILLSANIFLIAFLQRFSGRLADRVNPKYLVIFGTFLAGFAVLGMPMVKGFFLVLVLNI
ref|ZP_01288161.1|    IGTVIAVRTLINASLQGYCGRLADRYDKLRLLRYGCLVISGVMCLIPLAGHYWVLLLLFA
RAAC02322             IGFLIAINSIVIGASQVPCGWLVDRTNKYYLVLVSGIVTSVLLTMFPLCRKLWVITMLMI
                       * ::      :   .        *  :.*    :       *           :  ..

ref|YP_504284.1|      LMGIGGGISVPAMYALVTIAG-RDVGQGAAMGTINMVMSMGMIISPVVCGLFMDQTGISS
ref|ZP_02131576.1|    AFGIGGGIMAPALTAICVIEGHKERAMGSVMALLTIGHSLGMLAGSVATGVLMDMFSLSA
ref|YP_001046337.1|   LVGIGGAIQQPAIMALTVDAG-RTIGMGTSMGAYNTVFGIGMIIAPLMGGVFMDYIGIDA
ref|ZP_02132246.1|    VMGAANGLALPGGLVITAQLG-RTMGMASLMSITDAAWSLGMIVSPILSGIILDVYGLPY
ref|ZP_01288161.1|    VLGLGEAIIWPTLGALATEEG-RVYGQGTMMGVFNLAMSAGVLGGALGAGFATDLLGLTW
RAAC02322             LIGFSSAITIAASSALSTMLG-RTGGMGHVMGFLNSATSFGMIVGPIVSGIILDKLNVYF
                      .*  . .:    .  .:  *   . .   *.    . *:: ..:  *.   *   .:

ref|YP_504284.1|      VFYLSAVIVLVVTPVF--------------------
ref|ZP_02131576.1|    AFTASAVLAILGTVVF--------------------
ref|YP_001046337.1|   VFYVGGAISLLGTGIFAVMMQRNARAADRKDIP----
ref|ZP_02132246.1|    VFLMGSALIL--------------------------
ref|ZP_01288161.1|    SFPVIGLLVLLLTFLAIGMIAADRLA----------
RAAC02322             TFYFNSIVWLVSTMLFAMLWMVHNRRISKKQDVPISY
                      *       . : :
```

FIG. 28

```
ref|ZP_01287831.1|   ------------------------------------------------------------
ref|YP_076198.1|     ------------------------------------------------------------
ref|NP_634267.1|     ------------------------------------------------------------
ref|YP_446560.1|     ------------------------------------------------------------
ref|ZP_01106621.1|   ---------------SSCCGATTPSNKVYNIMMDDYTETDGYVEDADLGLGCGLPTEFAKI
RAAC02323            MRKNVNANCCSAEPEPLTPAKRVIKDFYDTVAVGSGPYPASTDRFSPAAPTEKILEYVKR ref|ZP_01287831.1|   -----VLDLGSGGGFDCFLAARQVGETGRVIGVDMTPEMISQARANATKSGD---RNVEF
ref|YP_076198.1|     -----VLDLGSGAGFDCFLAARQVGESGRVIGVDMTPEMLARARENARKGGF---ANVEF
ref|NP_634267.1|     -----VLDLGSGGGFDCFLAAQKIGSSGKVIGVDMTLEMVEKAQANARKYGY---SNVEF
ref|YP_446560.1|     ----RVLDLGSGAGMDAFVARRTVGPDGHVHGVDFAEEMVAKARANADTLDY---DNVTF
ref|ZP_01106621.1|   KKGDTVIDLGSGAGNDCFVARHETGSEGKVLGIDFTPIMIEKARINAEKLGY---NNVEF
RAAC02323            TNCRRILDVGCGMGTTLLRMAQEHVSGVQFIGVDFSEKMIERARTSSLSLHDDLRKKIGF
                          ::*:*.* *     :    :    :. *:*::  *: :*: .: .    :: * ref|ZP_01287831.1|   RLGEIENLPVADGAVDVIISNCVINLSPEKRRVFAFAYRILKAGGRLAISDVVATAELPE
ref|YP_076198.1|     RLGEIEHLPVADESVDVIISNCVINLSPEKEQVFREAFRVLRPGGRIAVADMVSLAPLPP
ref|NP_634267.1|     RHGDIESLPVKDSSVDVIISNCVINLAPDKEKVFREAFRVLKPEGRMYISDMVLLDELPE
ref|YP_446560.1|     EVGDIEALPVESGAFDVILSNCVLNLVPDKEAAFAQMHRALRPGGRFSVSDVVHAGALPD
ref|ZP_01106621.1|   REGDIDAMPVSDEVADVIVSNCVLNLVPNKNKVIGEMFRVLKPGGHFSVSDIVLVGNLPE
RAAC02323            FVANAESLPYMEGQFDFVFSECVLNLIPEREKAIAEVMRVLAPGGMFVYTDFVAFSPISN
                         .: :  :*  .    *.:.*:**:** *::.  .: :    *  * . * :  :*.*    :.

ref|ZP_01287831.1|   AVRKDMALYTGCIAGASLVSDIEQMLTEVGF-TEIRVSTKDESKSF--------------
ref|YP_076198.1|     EVREDLALYAGCVAGVATVGELRTMLTEAGF-VDI-------------------------
ref|NP_634267.1|     ELKNDSELLAGCIAGAVLKEEYLGLLKKAGFSVEILNEDLDISKRQYRDLPVESLKLK--
ref|YP_446560.1|     GLREAAELYVGCVAGAMERDMYLDRLREAGF-----------------------------
ref|ZP_01106621.1|   ALKADAEMYAGCVAGAIQKEDYLKIIEDKGFMNLK-------------------------
RAAC02323            SIRDNLNLVSGCRAGSKTLSENIRLLEETGFVKIECIDFTSDKNKRYADLMNESEQIRRE
                        ::      :   * **  **         :  .  **

ref|ZP_01287831.1|   ------------------------------
ref|YP_076198.1|     ------------------------------
ref|NP_634267.1|     ------------------------------
ref|YP_446560.1|     ------------------------------
ref|ZP_01106621.1|   ------------------------------
RAAC02323            FEEFRNLYPDAAAFLDERVGYYLILGCKPI
```

FIG. 29

```
ref|ZP_02595423.1|    MNILLVSNFEGGFQPNTIATAATPLVKAGFDVEILDTYVEG-LVEEKFKDKQLVAISVPL
ref|NP_982173.1|      MNILLVSNFEGGFQPNTIATAATPLVKAGFNVEILDTYVEG-LVEEKFKDKQLVAISVPL
ref|ZP_02367476.1|    ------------------------------------------------------------
RAAC02324             MKILLVSVFEGGFQPQTIATAAGALSEIGVEIDALDVYIED-LRFNKVSDANLVAISVPL
ref|YP_001616264.1|   MNVLLVSTYESGFQSLGTSVAAAHLLEADVRVNALDLSVTPTPDIDDLCRHDLVGFHLPM
ref|YP_827637.1|      MRVLLVSTYEMGRQPFGLASPAAWLRAEGHEVTQADVSCTP-MPKDAVEAAGLIAFFLPM ref|ZP_02595423.1|    FDAVTAGIEVAKKVAEINPDAHITFFGQHATINANRLAGRYSDSCISGEWEHPLTLLAKH
ref|NP_982173.1|      FDAVTAGIEVAKKVAEINPDAHITFFGQHATINANRLAGRYSDSCISGEWEHPLTLLAKH
ref|ZP_02367476.1|    ------------------------------------------------------------
RAAC02324             FDSIQPAIALSKEIRKINPRTHVTFFGQHATIHAQKLASTYGDSCIRGDWEYPLINLARY
ref|YP_001616264.1|   FHSVPAAVRVAGRLRQQEKAPKIFFYGLYADLFREKLLGRHGDYVLGTDWEDQIVPLVK-
ref|YP_827637.1|      HTATKLFLRLVDRVRAVNPRAHLCAYGLYAPLNERLLRGAGVGTVLGGEFESGLRDLARR ref|ZP_02595423.1|    LSGETQESLPGVLSAEQAIKGESVHPYMARNHLDIPSRHLLPALHKYPQKQINRLLGSDQ
ref|NP_982173.1|      LSGETQESLPGVLSAEQAIKGESVHPYMARNHLDIPSRHLLPALHKYPQKQINRLLGSDQ
ref|ZP_02367476.1|    ------------------------------------------------------------
RAAC02324             LMGNNSE-LVGVLLADDAKKGKSTPVYIGRNDLRVPARSILPPLDKYPQPHVERIMGSKQ
ref|YP_001616264.1|   ------------RSPDPSVVQLQKRGFARQNRYRTPARQVLPHLGNYAKLVED---GAHM
ref|YP_827637.1|      LS----------SGDPAPAAPPVTISIERQQFLVPDRKGLPPLGAYAQLVVG---NGTR ref|ZP_02595423.1|    VVGSTEIARGCHHKCLYCSVFAAYDGKVILVPEEIVLQDVRNLVEGGMTHLTFIDADFFN
ref|NP_982173.1|      VVGSTEIARGCHHKCLYCSVFAAYDGKVILVPEEIVLQDVRNLVEGGMTHLTFIDADFFN
ref|ZP_02367476.1|    ------------------MYAAYDGKVIMVTDDIVVEDVRNLVKQGMEHLTFTDAEFFN
RAAC02324             VVGATEIARGCHHKCLYCSVFAAYNGKVVLIPEDIVLEDAKNLVEQGMTHLSFIDADFFN
ref|YP_001616264.1|   LAGCVEATRGCAHHCTHCPIPPVYGGKVTIIPFEVVLADIDNLVLMGARHVSFVDPDFLN
ref|YP_827637.1|      RVGYTEASRGCKHLCRHCPVVPVYNGRFRIVQADIVLEDIRRQVAAGAAHITFGDPDFFN
                                        : ..*.*:. ::   ::*:  *   . *   *  *::* *.:*:* ref|ZP_02595423.1|    AKYHGIKILRKLHEEFPELTYDFTTRVDHILENKKTLAEMKELGVKFITSALEFPSEEVL
ref|NP_982173.1|      AKYHGIKILRKLHEEFPELTYDFTTRVDHILENKKTLAEMKELGVKFITSALEFPSEEVL
ref|ZP_02367476.1|    AKNHGVRIMRRLHEEFPHLTYDFTTRVDHILEHEDAIREMSGLGLRFITSALEFPTQKVL
RAAC02324             AKWHGIKIIRKLHEKYPFLTYDFTTRVDHILENRDTFREMVNLGVKFVTSALEFPSEELL
ref|YP_001616264.1|   VPRHGLSIMKAVNDKYPFLTYDFVAKVSHFRRHEQYVRELAKLGLKFVLTAMEFNDNEVL
ref|YP_827637.1|      GPGHAVPIVEALHREWPWLSYDVTIKVEHLLKHRDLLPVLKETNCAFVTSAIESLDDEVL
                      *.: *:. ::   ::* *:**..  :*.*:  .:... .  :     *: :*:*    :::* ref|ZP_02595423.1|    DAVAKDTSVADIEQGIAYLREIDIKLNPTFIMFNPWTTFEDLTTFRSFVEDNELGNIIDP
ref|NP_982173.1|      DAVAKDTSVADIEQGIAYLREIDIKLNPTFIMFNPWTTFEDLTTFRSFVEDNELGNIIDP
ref|ZP_02367476.1|    DIVAKEISVDDIEMAIRRLKAIGVKLNPTFIMYNPWVSKEDILSFKAFIERNDLEDVVDP
RAAC02324             DEVEKQITVNDIREAIKFLREIGMKLNPTFIMFNPWTRLEDLIEFRAFIEDNNLQDLIDP
ref|YP_001616264.1|   DILKKKHDIDDLDWSIGLFHELGVHLKPTFVMVNPWAEVGDIMDLLEFVETRGLIDAVDP
ref|YP_827637.1|      VKLAKGHTRAGFLEALVLMRAVDLPLSPTFIPFHPWTTLESYREFLRTLAENGLASQITP
                       : *    .:  .:  :: :.: *.*: :.  :**.  .     .  . *  . * ref|ZP_02595423.1|    IQYETRLYLYKGSPLLHKQSIQDLE--LTEYEFHYDWKHPDSKIDELYFEMLTPPEEGIF
ref|NP_982173.1|      IQYETRLYLYKGSPLLRKQSIQDLE--LTEYEFHYDWKHPDSKIDELYFEMLTPPEEGIF
ref|ZP_02367476.1|    IQYETRLHLYKGSPLLNRASTAGLK--LTEREFHFDWSHPDPAVDEMYYANVTPPEPGVF
RAAC02324             VQYQTRLHLYKGSPLLIKKSVKNLE--LTELEFHYEWKHPDPRVDELYSQLHKPVENGVM
ref|YP_001616264.1|   IQYKIRLLLFNNSPLMDSVGLYASL--GEESDYYTEWRHRNPAVEELHREICRWVDEAV-
ref|YP_827637.1|      IQLAIRLLIPEGSLLMELPEVRALVGLFDARALSYPWRNPDPGLDRLCATIQATIKRGEK
                      :*  **  :.  *    *:           *   :..  ..:                ..

ref|ZP_02595423.1|    KRCCLKC
ref|NP_982173.1|      KRCCLKC
ref|ZP_02367476.1|    KRCCLKC
RAAC02324             KRCCLKC
ref|YP_001616264.1|   -------
ref|YP_827637.1|      HR-----
```

FIG. 30

```
ref|NP_982172.1|      .MMVIFASATHGKATKSFAGVAIGSTVALEAMFGGPISGASMNPARSFGPALISGTFEYLW
RAAC02326              MTVILGSAVHGKAIKPFAGIAIGATVALDALFGGPISGASMNPARSFGPAVVSGMFHFLW
ref|ZP_01872101.1|     MIVIYTSAIHGKAIKSFAGIAIGFTVGIEAMIGGAISGASMNPARSIGPAIVSGNLDSLW
ref|NP_922949.1|       MLVICGSALDARAPRGFAGLAIGLTVGLEAGFGGPISGASMNPARSFGPALVAGAWEAHW
emb|CAO48005.1|        MFVISGVATDNRAIGELAGLAVGATVLLNVMFAGPISGASMNPARSLGPAIVSNTYRGIW
sp|P08995|NO26_SOYBN   MFVICGVATDNRAVGEFAGIAIGSTLLLNVIIGGPVTGASMNPARSLGPAFVHGEYEGIW
                        * **    *  .:*     :**:*:* *: ::. :.*.::********:*.: .       * ref|NP_982172.1|       IYLVATTLGALLAAIVYKFI--
RAAC02326              IYFVATVLGAVIASAIYRIIRF
ref|ZP_01872101.1|     LYIVASILGAIVAGVVF-----
ref|NP_922949.1|       VYWLAPIAGALLAGWVWHQMR-
emb|CAO48005.1|        IYLLAPTCGAISGAWVYNIIRF
sp|P08995|NO26_SOYBN   IYLLAPVVGAIAGAWVYNIVRY
                       :* :*.  **:  .. ::
```

FIG. 31

```
ref|ZP_01090358.1|   ------------------------------------------------------------IR
ref|ZP_01856486.1|   ------------------------------------------------------------IK
ref|ZP_02736297.1|   ----------------------------------------------------------MTVR
ref|ZP_01311632.1|   ----------------------------------------------------------MSCR
ref|NP_982171.1|     EINBACILLUSCEREUSSCRESIGNIFICANCEE-IDENTITIESPSITIVESGAPSTAR
RAAC02327            ----------------------------------------------------------MSVK
                                                                                :

ref|ZP_01090358.1|   FVMIGGFLGAGKTTTIGRLAQHYRDQGLNVGIVTNDQATDLVDTQMLRSQGFRVGEVAGA
ref|ZP_01856486.1|   FIMVGGFLGAGKTTTLGRLAKYYSDQGLNVGVVTNDQAADLVDTNALRSQGLHVGEVAGA
ref|ZP_02736297.1|   FVMVGGFLGAGKTTTLGRLARHYQQQGKRVGVVTNDQAHDLVDTNTLRAQGLSVEEVPGA
ref|ZP_01311632.1|   LILVGGFLGAGKTTLLAETAHKLSLQGLKVGLITNDQATNLVDTRMLVRSGAGVAEVSGS
ref|NP_982171.1|     LVLLGGFLGAGKTTTMIKSALKLEKEGYRVAIVTNDQGKELIDTELARANGLESKEVTGG
RAAC02327            LVLLGGFLGAGKTTTLIRAAHMFQSAGQNVAVITNDQGTELIDTELSRLNELNTEEVTGG
                     ::::.*********    :  .  *     .*.::****. :*:**.       **.*.

ref|ZP_01090358.1|   CFCCNFNELTGTVEKLAAEDRPDIVIAEPVGSCTDLVATVVQPLVRMFDAQFDVAPYGVI
ref|ZP_01856486.1|   CFCCHFNALMDTIEELGSEQKPDVILAEPVGSCTDLVATVIQPIKRLFDADFSILPYTVL
ref|ZP_02736297.1|   CFCCRFDDLVGRVGSLEAGERPDVILAEPVGSCTDLVATVIQPLKDLYSGRFEVAPYAVL
ref|ZP_01311632.1|   CFCCNFQGLLDAMDQLKKTFDADIVLAEPVGSCTDLSATIIQPLKDKLQSKLLISPLTVL
ref|NP_982171.1|     CFCCQFDDLYNNLNTLMKEKQPDVIIAEAVGSCTDLAATVIQPLKQYYADKFKTAPLTIV
RAAC02327            CFCCRFNELYDKLISLKSQFRPDVIIAEAVGSCTDLAATVIRPLKQYYGKEFDVAPLTVV
                     ****.*: *   .   :  *     .*::**.******* **:::*:      :  * ::

ref|ZP_01090358.1|   LKPSHGLRILQGEDSGG---FSPKAAYIFKKQLEEADFVIINRIDELDAEKVDLLASLITE
ref|ZP_01856486.1|   MKPSHGLKILKNDKGSS---FSPKAAYILKKQLEEADLILINRIDELSAEEVDEITALVNE
ref|ZP_02736297.1|   FKPSHGLRILRNQAAGG---FSPKAAYIFKKQLEEADAIVINRVDELDPAQIDELSLLVTQ
ref|ZP_01311632.1|   ADPIKLGAILAG-GTAG---LHDDAAYIYRKQLEEADLILISKVDLLTLPMVDDLLIRVRK
ref|NP_982171.1|     VEPARLLHELNLDENTKPFFSQSVSYIFEKQLAEADIIALNKVDRYSEEEIAKLKAYLQQ
RAAC02327            VDPGRILSEIGPKEKIN--FSRSVSYIFDKQLSEADIIALNKIDKYEERCINDLEDYLQK
                     .*  :     :         :  ..:**  *** ***  :  .:.:*    :  :  : :

ref|ZP_01090358.1|   AFPGTPILRTSAKTGAGFDALVELIDQRGEFGKKILDIDYDVYAEGEAELGWLNSSLKAT
ref|ZP_01856486.1|   QFPGTPVLRTSALTGEGFEPLLEFLEQDGDFGSKILDIDYDIYAEGEAELGWLNSSVHIS
ref|ZP_02736297.1|   QFPGTPVLRASATTGAGFDALTELLDQTGAFGRKILDIDYDIYAEGEAELGWLNATARLT
ref|ZP_01311632.1|   AFPSAIVQPLSAERNVGLDYWLDHVLHKTTAGNTLLDIDYDRYAEGEAVLGWLNARFELR
ref|NP_982171.1|     RYPQTIIQTFSAERGDNLEALTHTWLTTDLGGDKVLDIDYELYAEGEAQLAWMNILGDIK
RAAC02327            RYPTAVIHTFSAHRGDNMERLLDLWRTLNISGEKALDIDYDKYAQGEAKLAWLNSLIDLS
                     :*  :  :  **   ..::      .    *  .***** :* :* *.*:* ref|ZP_01090358.1|   ASEAF--DLDAFLMAIMNAMQKTLANSHAETAHLKTIGLWEG-FYGVANLVSSDTAPILS
ref|ZP_01856486.1|   AENSF--SLDQLLDVISQLQTSFKEKSVETAHLKTIGLWEG-FFGVANLVSNDSEPRLS
ref|ZP_02736297.1|   SDEPF--DLDALLTSVLGELAVVCRSLGGEVAHLKLIGMDDASAFAVGNVISSSDTAPKLS
ref|ZP_01311632.1|   TTAG---TWRTFAEAIMTRLHHQFAERNLPIGHVKLIVESES-QVLFANLTGTEIEPKIR
ref|NP_982171.1|     AEQD--INPREWAEKLLDNLNKHFIREKMAIAHLKVHVGFEG-GYVKASMVQTGDAPTFT
RAAC02327            VDEANHFDAKLWMHMFLDKLHEHFLREKMAIAHLKVYVGSDN-GFIKASIVETGDTPTYI
                                .:  :             .*:*     :       ..:  .:  * ref|ZP_01090358.1|   LPSNCQAKEADVVVNARVGISPEELRQQVDDAIDAAAKKFGVRIERQQTQYFRPGRPVPT
ref|ZP_01856486.1|   LSSDCTVTEADLIVNARVACDPEALTAQVKQVLQNCAQALNAKLEFRQTQSFRPGRPVPT
ref|ZP_02736297.1|   LPSGLRPREADLIVNARVAIDPAVLEAEVKRVVALESAKVGVIAEFRTSQSLRPGRPVPT
ref|ZP_01311632.1|   GEMTSTP-HATMTINARVETSPEELRQIIWQALQQSSDGINVYQEQWN--CLKPGRPEPT
ref|NP_982171.1|     VENVKEGKEFRIVLNIRIEATPAILNLVVADSIGAINKELGSNWSETYNECFSPLPPKPV
RAAC02327            VKEPVNGQEFRVVINIRIETEPELLSLVVADALAIVNKEMKVKWKQTYHECFSPLPPNPT
                         . :.:* *:     * *  :                .            :*   * * *.

ref|ZP_01090358.1|   HR------
ref|ZP_01856486.1|   HR------
ref|ZP_02736297.1|   HR------
ref|ZP_01311632.1|   YR------
ref|NP_982171.1|     HRL-----
RAAC02327            HRLRVAAK
                     :*
```

FIG. 32

```
ref|XP_955124.1|      ----------------------------------------ELCDPVLEAN-GLKVAAKSTFGDM
ref|XP_763458.1|      ----------------------------------------ELCDPVLEAN-GLKVAAKSTFGDM
ref|XP_666904.1|      ----------------------------------------NTNLEEN-ELSDKTINLIQNL
RAAC02328             MIRGEEILLRKIVVEVLPKYSS-ENCCSVDGEETTIDCCNPLVEAN-ELKDKIKNVLGDL
ref|NP_982170.1|      --------LIEIFPSVVTNQTD-CCDSDNNSEEGCCEESNQFFEESLELKEQLKEHFDKL
ref|XP_845342.1|      ------------LAEALERYSDSEQLCSCTLRVFSVFPSSPYVDMN-AIASLFKNTESEA
                                                          .  .:  .   :     .   .

ref|XP_955124.1|      IIVELYKAAYVLGLWDVAAYNCLKT-CKRRGY----------------------------
ref|XP_763458.1|      IIVELYKAAYVLGLWDVAAYNCLKT-CKRRGY----------------------------
ref|XP_666904.1|      VIIHFSD--LIINQLPLNSVNHTESLCKER------------------------------
RAAC02328             VVTHVFD--YTLSVDWSLAVNRLRQLFKERGFRGLSEMDNILEVVTPVVIVNGNLVSFVC
ref|NP_982170.1|      VNVHLYN--YELSMDRVLAQKKLSQLTQERGFGNISE-DSVLRYVTPAVVVNGTLVSFAT
ref|XP_845342.1|      VAIEAIH--FLCSVA--MSVKTLKQLIHTTGC--VQRVLEVMRKYAGNASIQEYACSLLS
                      :  :.   .      .        : :        :

ref|XP_955124.1|      -----------------
ref|XP_763458.1|      -----------------
ref|XP_666904.1|      -----------------
RAAC02328             PFDFEKIVSRIMTMSYE
ref|NP_982170.1|      KPQMESVL---------
ref|XP_845342.1|      YLSFDSETITSFI----
```

FIG. 33

```
ref|YP_079109.1|         --INIRKAISADLPFILTIYNQGIEDRIATLEQDLKEMSDIEIWFQEHQGRYSVLVAE-S
RAAC02332                MMVTVRVATHRDLPSILAIYNQGIEDRVATLEQDLKDMDYITNWFNEHTNRYPVFVAE-Y
ref|ZP_01858609.1|       --IIIRKAEIRDIDRILTIYNQGIEDRVATLETEPKDRTYMAEWLKAHQGRYTGIVAE-L
gb|AAV70501.1|           ----IRKATEQDAQEIMTIYNEGIEDRIATLETEIKTDKYVMEWLFQREKRYSVIVME-E
ref|YP_001319533.1|      MAYTVRIAELQDLKSITEIYNEGIEDRIATLETKIKSEAEMIPWLQQRSEKHKVITIENE
ref|ZP_00539168.1|       ----IRPVKEDDLKDILAIYNEGIEDRIATLETDTKELSFMEDWYRERTPRYAGFVAY-E
                             :*   .   *   * :***:****:****  . *    :   *    :   ::  :.

ref|YP_079109.1|         KGEIVGWASLNPYSHRCAYQGVADLSVYVDRACRGKGIGGLLLQALEKTAKENSFYKIVL
RAAC02332                QNNIIGWADLHPYSHRCAYGGVAELSVYVHRGWRAKGVGQALLSALEAFARKHDFHKLVL
ref|ZP_01858609.1|       EGEVIGWASLNPYSPRKAYAGVADISVYIERNSRGKGIGRKLLSSLEVKARENGFHKLVL
gb|AAV70501.1|           NSHIVGWASINPYSHRCAYRGVGELSIYIKREYRGKGLGQKLLLALEKTGQKNEFYKFVL
ref|YP_001319533.1|      RDEVLGWASLNPFNSRCCYDGVADFSIYIKRQMRGMGLGKLLLKALIEVAREQDIHKLVL
ref|ZP_00539168.1|       GTTILGFISLDPYNPRPVYQSVGELSVYITRTHRGQGIGRQLLHVIEEHAITQGFHKLIL
                           ::*:  .:.*:.   *   *  .*.::*:*:  *   *.:*    **        :     .   :  ::*::* ref|YP_079109.1|         FTFPFNELGQNLYNKMGYRQVGIFKNQGILDGRFIDVMAMEKLL-----
RAAC02332                ATFPFNSAGLALYRKMGFREVGVFMNHGRLDGKWVDVLWMEKLLELKVE
ref|ZP_01858609.1|       FTFPFNKLGQQLYQKCGYREVGTFKNQGILDGIYVDVMAMEKLL-----
gb|AAV70501.1|           FTFSFNNLGQGLYRKMGYREVGVFEKQGIMDGEHVDVMIMEKLLSVE--
ref|YP_001319533.1|      STFKSNEAGQRLYESFGFREVGTYKNQGILDGKFVDVTIMEKLL-----
ref|ZP_00539168.1|       FTFPFNKIGQKLYIRSGFRIVGTFKEQGMLNGYYVDVLAMEKLLPKTID
                          **  *.    *   **  *:*  **  : ::*   ::*    :**  *****
```

FIG. 34

```
ref|YP_001358015.1|      ---ILIDTNVVVRFLTRDNEKYFLKSVAIFQDIEDGKMEAMLMDFIVAEIVSVL--HRIYK
ref|ZP_02178354.1|       ----LIDANVILRYLLRDNKELYAKAEEVFNDMMEGKTKILILESVIAEVVYVL-QRIYN
ref|YP_001356736.1|      ----LVDTNVLVRLFTQDNEEMFREAFSFFEKVANFEIQAVISEGVLLESWFVL-QKVYE
ref|YP_001485227.1|      ----VVDTNVIVRFLTNDDEEQSKKAFEIFKRAVNQEITLFLTPIVIIECTWVLGMKRYG
RAAC02334                MKSVLLDTNVILRFLLDDHPHHSPAATNLFMKAEQGEIKLVIDPMIVAECCYVLEGKVYQ
ref|ZP_02013298.1|       MKTWLLDANGILRFLRNDDAVQSPQSKKLLERANAGEVRLLISVLTVAEVFYAL-RASYK
                             ::*:* ::* : *.       :  .:     :  .:    : *    .*   * ref|YP_001358015.1|      HSKKEIATTLKKLLLYDHLYTENKLITFEALEIYAEKNIDFADAVLYAKQRLEGFEIISF
ref|ZP_02178354.1|       VSRKEISEILRKLIELRGVKVHNKGQMLNALEIFSEKKLDFVDCILCAHR--EENEVITF
ref|YP_001356736.1|      MKKDEIIKRLLTIVTLRNVILEDKLAFIEALHILKERNIDFIDAMLCVKSNIKGYKVFSF
ref|YP_001485227.1|      YSHEEIADNLTTIITSPGVKTLESDVVLKALHEYKTNRIDFADAYLAAVSTKNGVPCLTW
RAAC02334                FSKELIASHLTPVLTHEGVQCEALMTVLDGLDIYVEHRLDFADAYLIALARNHRFEVATF
ref|ZP_02013298.1|       MTRPAAAQVLMRFVLTGVAEVEREDVLLDALQRVVSANVDLGDAVLAVEAVRHGEGVASF
                          .:      *   .:            :...*.     .:*: *. * .   .   ::

ref|YP_001358015.1|      DKDIEK--------
ref|ZP_02178354.1|       DKGLRR--------
ref|YP_001356736.1|      DNDIQR--------
ref|YP_001485227.1|      NSK-----------
RAAC02334                DNKMARIENVVFQDL
ref|ZP_02013298.1|       DKDFSRFTDV----
                         : .
```

FIG. 35

```
dbj|BAF91394.1|      ------------------------------KNMIPKISDFGMARIFARDETEANTKKVV
dbj|BAF91409.1|      ------------------------------KNMIPKISDFGMARIFARDETEANTKKVV
gb|AAL17690.1|       ---ARGLVYLHQDSRFRIIHRDMKAGNILLDKNMIPKISDFGLARIIARDQTEASTDNPI
ref|NP_001058416.1|  ------------------------------------------------------------
dbj|BAD45624.1|      ------------------------------------------------------------
RAAC02335            MHTSRGVGYMNPDEPVFEILALVWEA-----KRRLPKVSDYRRIARKRQTESPDHVIQRY dbj|BAF91394.1|      GTYG-----YMSPEYTMHGIFSEKTDVFSFGVIVLEIVSGKKNK----------------
dbj|BAF91409.1|      GTYG-----YMSPEYAMHGIFSEKSDVFSFGVIVLEIVSGKKNR----------------
gb|AAL17690.1|       GTYG-----YMSPEYAMYGILSEKTDVFSFGVIVLEIVTGKRNR----------------
ref|NP_001058416.1|  ------------------------------------------------------------
dbj|BAD45624.1|      ------------------------------------------------------------
RAAC02335            GTWSRVLEDFFQAYFTLHGYPTIPDYLFGALFSRAKVVRDKRGRWYLRFVSDDTTQIEIL dbj|BAF91394.1|      -----------------GLYNLSFENNLLSYVWSQWK---EGRALEIVDPVIVDSLSSLP
dbj|BAF91409.1|      -----------------GLYNLSFENNLLSYVWSQWK---EGRALEIVDPVIIDSLSSLP
gb|AAL17690.1|       -----------------GFYQSTPEDNLVCYAWTHWA---QGRALEIVDPVIVDSLS---
ref|NP_001058416.1|  -----------------TVIMRCTQVALLCAQE-----DPADRPTMTDVTAMLDSESIML
dbj|BAD45624.1|      -----------------TVIMRCTQVALLCAQE-----DPADRPTMTDVTAMLDSESIML
RAAC02335            RSFMRRSAATLVNRGKPSLYLRCYDVDLICAYEHACKTEPVFRPTVDFVRGYIDTHSHFR
                                      .    :  *:.         *.           :*: * dbj|BAF91394.1|      STFQPQEVLKCIQIGLLCVQEHA-------------------------------------
dbj|BAF91409.1|      STFQPQEVLKCIQIGLLCVQEHA-------------------------------------
gb|AAL17690.1|       STFQPKEVLKCIQIGLLCIQERAVHRPTMSSV----------------------------
ref|NP_001058416.1|  SDPKEPTELTHGGAPVLTGHRHILVTQAR-------------------------------
dbj|BAD45624.1|      SDPKEPTELTHGGAPVLTGHRHILVTQAR-------------------------------
RAAC02335            KDPSGRDRLTLTGPLVPECHDFLVALGARNTRVSRVKDSYRMNVHAGSLRRIREALYPPG
                      .  *.      :   :

dbj|BAF91394.1|      ---------------
dbj|BAF91409.1|      ---------------
gb|AAL17690.1|       ---------------
ref|NP_001058416.1|  ---------------
dbj|BAD45624.1|      ---------------
RAAC02335            CVCNPEIRARIFTV
```

FIG. 36

```
ref|YP_517489.1|       ----------------------------------------------------------------
ref|ZP_01370335.1|     ----------------------------------------------------------------
ref|YP_517477.1|       ----DILMKVLAEQFKNKTLDVFGIKTAKIKDLIPSVHPAVEANETRNDIIFLLEDDTLL
gb|ACA46983.1|         ---KDVLFKTLSEMFKDKALIMYGLDYPKIVEMLPNEFPEVKADERRADSIFLLEDGSIL
ref|YP_001568284.1|    ------------------------------------------------DFVFELEDNSLL
RAAC02336              MPVQDTLMKALTRSLSGGALDVLGVHGVDLVEPFATELP----ANTLRMDRVWRTVDGNLF ref|YP_517489.1|       ------------------YDARLASRQE------RQIRTFVVYSGHIEQAKERLDCGSI
ref|ZP_01370335.1|     ------------------YDARLASRQE------RQIRTFVVYSGHIEQAKERLDCGSI
ref|YP_517477.1|       HLEFQTT-AGEQDLKRFLYYDARLVRRQE------RKVHTIVIYSGRIEQARERLECGSI
gb|ACA46983.1|         LLEYESNNRITENMYKYIDYVLRISRKYYEENKSIKKINVAVIYASNIERAEDHFNIGSV
ref|YP_001568284.1|    HLEFQTTWKKAD-LLRFAQYDIALYQKER------RRINTVVMYSGKYESAESELDMGSN
RAAC02336              HLEFQTK--RESTLHRFLEYDARLANEHR------TRIRTVVLYHASVASAPDELDIGTA
                                                  *    :    .          ::..  *:*  .     *   ..::  *:

ref|YP_517489.1|       LYQVENIYMKDYNGDQEYNRLKAKIESGQLLNETDTLKLIFLPLMKSRQQEEDLAIQAAE
ref|ZP_01370335.1|     LYQVENIYMKDYNGDQEYNRLKAKIESGQLLNETDTLKLIFLPLMKSRQQEEDLAIQAAE
ref|YP_517477.1|       LYQVENIYMKHYNGDQEYNRLKHKIDNHQLLSETDTLKLIFLPLMKSEQKEFELAIQAAE
gb|ACA46983.1|         GIDVKSVFMKNYDGDTIYKEVEQKIKNGINLKDIDLMNLILLPLMKSIKDKHELIKDTIE
ref|YP_001568284.1|    KYKVQQIFMIKYDGIKRYEEIKEKIEKEEELTDKDLMDLVFLPLMRNEKSEEEVTKDVFE
RAAC02336              LYRVENVFLRHLDGDQALNEVEHHLRAG-QWEPGDRMRLGLALNMR-LENQAHAFERVRE
                        *:.::: . :*      :.:: ::         * : * :   *:  :.: .   . * ref|YP_517489.1|       LAKAT-DEKTKVFAIAALIVITDKIISESNKRKLLEVLK-MTQIEQWIREEGREEGRQEG
ref|ZP_01370335.1|     LAKAT-DEKTKVFAIAALIVITDKIMSESNKRKLLEVLK-MTQIEQWIREEGREEGRQEG
ref|YP_517477.1|       LAKAAPDEKTKLFAIAALIVITDKIMSESNKRKLLEVLK-MTQIEQWIREEG----RQEG
gb|ACA46983.1|         LAKEVKDEKNQYFIIAGVLTSTDKFIDEKYANTVRSWLR-MTKVEK-IFEKE----KEEA
ref|YP_001568284.1|    LAIKIPDEDKKEAVIGSLLGFSDNYVRDEYINELKEVIR-MTKIGTSLFEEG----VEEG
RAAC02336              LIPQVPDETERDLVVSAILVLGDQGLTEEQRALLRKELRNVSKLAEELYEEG----REEG
                        *   **   :   :..::  *:  : :.    : . :: ::::   : *:          :*.

ref|YP_517489.1|       ELKGRQEEKRETARTMLSMGMSPEVIAKATKLSQEEILRIEKEMKN
ref|ZP_01370335.1|     ELKGRQEEKRETARTMLSMGMSPEVIAKATKLSQEEILRIEKEMKN
ref|YP_517477.1|       ELKGRRDEKRETAQTMLNLGMSPELIAKATKLPLEEILEMAK----
gb|ACA46983.1|         MNQAEKSKAIEIAKNLMDI-LSVEMIAKKTGLSIEEVEKL------
ref|YP_001568284.1|    ----------------------------------------------
RAAC02336              RMVGRMEERMEIALNMLRKGMSVEDISDTTGLTKQEIEELARKQSH
```

FIG. 37

```
gb|AAB91591.1|        MSPFGQQLRELRRARKLTVNQLAVYSGISSATISKIENGKRGTPKPATIKKLAAVLKVPY
ref|NP_391247.1|      MSPFGQQLRELRRARKLTVNQLAVYSGISSATISKIENGKRGTPKPATIKKLAAVLKVPY
ref|YP_001422657.1|   MNTFGKQLRELRRARKLTVNQLAVYSGVSSATISRIENGHRGIPKPATIRKLADTLKIPY
ref|YP_093160.1|      MTNFGHHLRQLRERKKLTVNQLAMYSGVSSAGISRIENGKRGVPKPATIRKLADALKVPY
ref|NP_391246.1|      MESFGEQLRALREERKLTVNQLATYSGVSAAGISRIENGKRGVPKPATIKKLAEALKIPY
RAAC02292             MSQFGQYLRKLRKERNLTINQLALYSGVSSALTSRIENGQRGRPKPDTLKKLASALKVPY
                      *  **. ** **. ::**:****.***:*:*.**:****:** *** *::*** .**:**

gb|AAB91591.1|        ENLMAAAGHIRAFPEEIREASES---------------------------------
ref|NP_391247.1|      ENLMAAAGHIQAFPEEIREASE----------------------------------
ref|YP_001422657.1|   EELMARAGHIKAFQEEIRETSES---------------------------------
ref|YP_093160.1|      EELMASAGYISAS--TVQEARS----------------------------------
ref|NP_391246.1|      EGLMYKAGYIEE--------------------------------------------
RAAC02292             EDLLLHAGVLNEQISRTSESRDLKPVDPSWYKRQVPIPVLGSIRAGTPVEMLALNSSEFV
                      * *:    **  :

gb|AAB91591.1|        ---------------------------------------------------------
ref|NP_391247.1|      ---------------------------------------------------------
ref|YP_001422657.1|   ---------------------------------------------------------
ref|YP_093160.1|      ---------------------------------------------------------
ref|NP_391246.1|      ---------------------------------------------------------
RAAC02292             LVDSDLLGNHEGFALEVVGDSMIGDYIFPGDLVIVKYTSNFSPQDICVVAINGEEATLKR gb|AAB91591.1|        ---------------------------------------------
ref|NP_391247.1|      ---------------------------------------------
ref|YP_001422657.1|   ---------------------------------------------
ref|YP_093160.1|      ---------------------------------------------
ref|NP_391246.1|      ---------------------------------------------
RAAC02292             VKCQGDICILTPSNPSMEPMVYNSVDVHVIGVVVEVRRRLRNK
```

FIG. 38

```
ref|YP_195796.1|    ------------------------------------------------------
ref|NP_817052.1|    ------------------------------------------------------
ref|NP_664934.1|    ------------------------------------------------------
ref|ZP_02626811.1|  MYEEYLKHFDLHVSDDIKNFVEETLKDKEYLFVRNEYEPEPISNLKVKVQYGYCSHCRKE
gb|ACA41259.1|      ----------AHFPAEVPEHVQFEADEKALLLSRYIFVSSGKN------RTGYCTHCRNT
RAAC02337           ----MSHDFFAHFPTEPSAALIEYARDVAFLRSRYLFVWRDGK-----VQMAYCTHCRET ref|YP_195796.1|    ------------------------------------------------------
ref|NP_817052.1|    ------------------------------------------------------
ref|NP_664934.1|    ------------------------------------------------------
ref|ZP_02626811.1|  FKTG---EYLKHNEVIICPNCGAEIMVKNIGRGKKCLMNDFCFYWFDKSVLDPEIVTCKG
gb|ACA41259.1|      FPIE---NPIKQNGKECPACFSKCRYKKAWLGRKALIDTACILHCQKSVLNPSVVTVEW
RAAC02337           YPLGSDKDTYRHNEQATCRQCGSTCVVKHRGRGRRHLIDTAYIVWYEKSMVDAQTVVATW ref|YP_195796.1|    ------------------------------------------------------
ref|NP_817052.1|    ------------------------------------------------------
ref|NP_664934.1|    ------------------------------------------------------
ref|ZP_02626811.1|  YYFSKKYDEDYKNPKYEYNLNSLYVFNTKDNTSKMFKRNWYTVESWFERSSIFDFNINWL
gb|ACA41259.1|      LYASRDYRESFENVSTEYAAVARYVFDYDRKVCQKIE-GGSGCRWWTESGFSTPSFLQNR
RAAC02337           YYAWRDYSGDFHDVETQFQPRARYVFVPGR-GGSMMRLDWSGEWQPRRNVHPLPVGMMGW ref|YP_195796.1|    ------------------------------------------------------
ref|NP_817052.1|    ------------------------------------------------------
ref|NP_664934.1|    ------------------------------------------------------
ref|ZP_02626811.1|  GNKLCYCSFESLDEAVKDTIFQYSNYKRRCGYKS-IVRYLDAFNKYQWIEQLEKMGFDRL
gb|ACA41259.1|      SFMSRNIMHGTFEDGISGTPFQYSGWQR-YDYED-VLKYLPLVAKYPSVEILTKAGLDSF
RAAC02337           RTVDVWCSHESIQTAVAGTPLQYSGWETYCDQYNTLLTFFDLASRYPCVEYLTKLGFSRL ref|YP_195796.1|    ------------------------------------------------------
ref|NP_817052.1|    ------------------------------------------------------
ref|NP_664934.1|    ------------------------------------------------------
ref|ZP_02626811.1|  VETLENRWTTDYSINYRGKDIFKKLKLNRGEVKQLTNEQKRELDSFVLRIYQLNRDNGFN
gb|ACA41259.1|      VKAKIYGYKTYSAVNWSKSKLHHIFKMSKQDLQMLREKNFVSSVYYVGDFLFNAWVVQQW
RAAC02337           VMAKLDGLRTFGAIHWRGRTMEQVLRMPRADVHAFRKLADVIEP-LSLRSYQTWRRLGWK ref|YP_195796.1|    ------------------APMINEIEKYVHYSQIKQLPKEVNLT-----KFQKWFIRKGE
ref|NP_817052.1|    ------------------APMINEIEKYVHYSQIKQLPKEVNLT-----KFQKWFIRKGE
ref|NP_664934.1|    -PTCCCUSPYGENESMGASSCRESIGNIFICANCEE-IDENTIT-----IESPSITIVES
ref|ZP_02626811.1|  PSFVEAYEVYEMCRYSDSSGLNNLIKIVGTNKVIKYCEKQYNSF-----NESNSYYNKAS
gb|ACA41259.1|      RKEKSKMNIDELQKNMQIFSVKDDLKTFKFIRRFTSLHRLFNYANKQFEKDEKHFIRRHQ
RAAC02337           VSPEEAHLLRELLIPHHWREIQVRASLASEVEIAKYLLKQLRKG---------EYRSISY ref|YP_195796.1|    RFDYYMDYLHMLEELNTPLNNDSVLYPENLQVAHDNAMNTLNLLKSEIEEKQYQERKNQI
ref|NP_817052.1|    RFDYYMDYLHMLEELNTPLNNDSVLYPENLQVAHDNAMNTLNLLKSEIEEKQYQERKNQI
ref|NP_664934.1|    GAPSYIDYLSMLDELGIEIDTDNLIMPKDLVKAHDNVVKLVNQKKSEIEKRKFKNRLKSL
ref|ZP_02626811.1|  VISKWNDYLKNCEKLNWSIRDKSILLPKNLVKAHNHTTSLINAEKNKFADQKIKRRLPGL
gb|ACA41259.1|      VLITWSDYLNDCQKLKIHID-EAIIFPKNLRKAHEETIKRVKHYEDELMRKKAKERYEKI
RAAC02337           ALIEWIDYLRFCSELGIPLNTTRNVFPSNLREMHDEMMRRVRIKRDERLNAQIQARLAEL
                            : ***    .:*     : *.:*    *:.     :.    ..:   : : * ref|YP_195796.1|    KALEAEIDDLLFLTPHSLQE-IIQEGSILRHCVGSQHYIERHTQGKTTIVFIRRKEKPDM
ref|NP_817052.1|    KALEAEIDDLLFLTPHSLQE-IIQEGSILRHCVGSQHYIERHTQGKTTIVFIRRKEKPDM
ref|NP_664934.1|    SKYEQTIGDYCFRAPVDSGE-LIREGKTLSHCVGSARYTQAHASGKTTIIFIRRKSDSDK
ref|ZP_02626811.1|  KKKYFFKDKDFFIRPAESSEDLINEGGTLNHCV-AVHYMKPYANKETDILMIRRIDNPTV
gb|ACA41259.1|      KHYEFELGQLKIVVPYTPKE-IIDEGNKLSHCV--GGYAERHADGQTTILFVRNIKEPDE
RAAC02337           EPFGYT-DEHFMIRPARSVQELFDEGQALHHCVG--SYAAKYASGETNLFLMRRVSAPDT
                    .      ..  :    *  :  :: **  * *** *    ::. :* :..:*.  . .

ref|YP_195796.1|    PYFTLEYRNQQVIQIQGKCNR---------------------
ref|NP_817052.1|    PYFTLEYRNQQVIQIQGKCNR---------------------
ref|NP_664934.1|    PFYTMEYKAGHIVQVRGKHNQSATEEVQKVVDQWLAIVNKNYKHA------
ref|ZP_02626811.1|  PLVTMEIKNGQVKQAYGKNDTIPKKDVEKFIEKFKTEILEKINSSKKNK--
gb|ACA41259.1|      SFYTVEVKNEKVLQVRGIKNKPATEDVQTFIDEFKKQKLTKKKARK-----
RAAC02337           PYCTVEMRDSALIQARGERNRLLREDEQTFVDQFVRHVARMHKRAQRRKAS
                    . *:*  :   :  *     :
```

FIG. 39

```
RAAC02338              ------------------------------------------------
gb|ACA41261.1|         ------------------------------------------------
ref|ZP_02626812.1|     ------------------------------------------------
ref|XP_001701427.1|    ------------------------------------------------
sp|Q2M3V2|ANR43_HUMAN  ------------------------------------------------
ref|NP_664935.1|       PRTEINSTREPTCCCUSPYGENESSSI-GBAATUNKNWNPHAGEPRTEIN RAAC02338              ------------------------------------------------
gb|ACA41261.1|         ------------------------------------------------
ref|ZP_02626812.1|     ------------------------------------------------
ref|XP_001701427.1|    ------------------------------------------------
sp|Q2M3V2|ANR43_HUMAN  ------------------------------------------------
ref|NP_664935.1|       STREPTCCCUSPYGENESMGASGBABFPHAGEPRTEINSTREPTCCCUSP RAAC02338              ------------------MYEKAVEKITL-EMSANEHHPYVQVIG-----
gb|ACA41261.1|         ------------------MVEQAMAKLSA-ELRVERVNPYVAAVG-----
ref|ZP_02626812.1|     ------------------AVEKIKE-EMS-KESNPYIAYIG-----
ref|XP_001701427.1|    ------------------DMAARYLSTQE-ALLVATMSIHNGYGI-----
sp|Q2M3V2|ANR43_HUMAN  ------------------VLGFLQEHGGKVRN-SELLSRFKPLLDAGDP----
ref|NP_664935.1|       YGENESMGASSCRESIGNIFICANCEIDENTITIESPSITIVESGAPSEK RAAC02338              --RFLLVHLEQHPEHAKN----------------LLEEEKTILKSLDTM
gb|ACA41261.1|         --NFLMDFLEDNPSSAEK----------------FLAEGKTIIGSMKEV
ref|ZP_02626812.1|     --NYVLENIEVNKPAAFK----------------IAVGSKTISESFKKV
ref|XP_001701427.1|    --RLTWTQRPPRPQPPNR----------------LAPGAGTIGSSGASP
sp|Q2M3V2|ANR43_HUMAN  --RGRAARRDRFKQFVNN----------------VAVVKELDGVKFVVL
ref|NP_664935.1|       ALSKMLDEMNKKHSAAEDAIHNWLSDQDDEELFKGILDDKKSIKDAMKYC
                                                       :

RAAC02338              RRYAETQRVGNVAVISDADGFGIVLQYFDCWDGKPFEIPPEPQPPARVAA
gb|ACA41261.1|         R-------------------------------------------------
ref|ZP_02626812.1|     QGEARKIAQNGIAMLAEREVISIVTKYFE---------------------
ref|XP_001701427.1|    QASPRAS--GTVPSAGTTAAASDAD-------------------------
sp|Q2M3V2|ANR43_HUMAN  RKKPRPPEPEPAPFGPPGAAAQPSKPTSTVLPRSAS--APGAPPLVRV--
ref|NP_664935.1|       INQAQKQKTGNCAMVDDKTVFGWVRVYFT---GKTKKIEPVQATVTVSQE RAAC02338              PTRVTSAKSAQASKKSTAPALTQLSLFDDAEGGEAL
gb|ACA41261.1|         ------------------------------------
ref|ZP_02626812.1|     ------------------------------------
ref|XP_001701427.1|    ------------------------------------
sp|Q2M3V2|ANR43_HUMAN  ------------------------------------
ref|NP_664935.1|       NTKVIPKK----NKKSKGVVEGQLDLF---------
```

FIG. 40

```
gb|AAU83457.1|      --IKGKVVLIPFPFDDLSAEKVRPAVCLTEPIGPHHHVILAFITSQIPQKLLETDLVLDA
emb|CAJ70907.1|     ------KVVLVNFPFDDLSTSKVRPAVCLTNPIGSHSHVILAFISSRIPSDLLETDLIIDT
RAAC02339           MKMKHKIVLIPFPFDDLQSHKVRPALCLTDPISAHDHVVVAFISSQVPTHLLPTDIVLRA
ref|YP_183482.1|    MNLKGKFVLVPFPFTNLKATKLRPALVLYE---GKEDVVVAFVSSRIDTFDPGTDVRIET
ref|ZP_00514953.1|  ---KGDIVLVPFPFTDLSTTKLRPAVVLWVDL-SGIDVTVCFISSQNVNHVTPEEFVIET
ref|YP_322920.1|    ---KGDIVLVPFPFTDLTGTKLRPGLILWVDN-SGNDITLCFISSQDVTNLTSGEFVLDP
                        ..**: *** :*    *:**.: *       .: :.*::*:        :. : .

gb|AAU83457.1|      GQPDFALVGLNVSSTLRLHRLMTVTTSLILRELGELPFDMKTEVDKRLRKLFGV-----
emb|CAJ70907.1|     SHEGFSGTGLKVASTLRLHRLMTVTTSLCQRELGELSPKFLSEVNNKLKKLF-------
RAAC02339           GTDAFAPTGLKVSSVIRLHRMVSMTTRIIRYELGHIADETRDLVESKLIQLFNLQHRLR
ref|YP_183482.1|    SHPQFRGIGLKVPSIIKLTKIATLHKGLLIGVLGELPEDLVQEVNSKL-----------
ref|ZP_00514953.1|  TNSEFSKTGLKVTSKVRVSRMVTIERNLITRRLGKLDISLLNKLNDCLKRVFQL-----
ref|YP_322920.1|    SDAEFAGTGLKLTSKVRVTRLVTLERRLITRRIGKLGVNQIQQLNLLMIQAFQL-----
                        **:: * ::: :: ::    :   :*.: .    :: :
```

FIG. 41

```
ref|ZP_02432977.1|    --EKLKEITDRLEQGIAELFDSERYREYLKVMSKFHNYSFRNTVLIAMQKPDASLVAGFS
ref|ZP_02085861.1|    --EKLKEITDRLEQGIAELFDSERYREYLKVMSKFHNYSFRNTVLIAMQKPDASLVAGFS
ref|ZP_02207628.1|    --EKLKEITDRLEQGIAELFDSERYKEYLKVMSKFHNYSFRNTVLIAMQKPDASLVAGFS
ref|ZP_02429891.1|    --EKLKEITDRLEQGITELFDSERYKEYLRVMSKFHNYSFNNTLLIAMQKPDASLIAGFN
ref|ZP_01731985.1|    ---KTALAFQQLEQGLAELLESGDWQRYLKVQSEFHNYSFNNVLLILSQFPEASRVAGYQ
RAAC02340             MNEKVKAAMERLEHGLETLLSTEEWRKFLQFQAAFHHYSFSNTLLIMCQKPDATYVAGYN
                              *  ::**:*:   *:..   ::.:*:.  :  **:***  *.:**    * *:*:  :**:.

ref|ZP_02432977.1|    AWKNNFERNVMKGQKGIKIIAPSPYKIKQEMQKIDPHTQKPVIGKDGKPVTEEKEVTIPA
ref|ZP_02085861.1|    AWKNNFERNVMKGQKGIKIIAPSPYKIKQEMQKIDPHTQKPVIGKDGKPVTEEKEVTIPA
ref|ZP_02207628.1|    AWKNNFERNVMKGQKGIKIIAPSPYKIKQEMQKIDPHTQKPIIGKDGKPVTEEKEVTIPA
ref|ZP_02429891.1|    AWKNNFGRNVMKGQKGIKILAPSPFKIKKEMEKIDPQTQKPVIGKDGKPVTEEKEITIPA
ref|ZP_01731985.1|    HWQ-ELGRQVKKGSKSIKILAP-------LKCK---------TEKENDNGELEAKTGIFG
RAAC02340             TWR-ELGRYVKKGEHGIEIFAP-------LLKKKSNKADIPREESEETSQEEENKRIIYG
                       *:  ::  *  **.::.*:*:**        *              .:  .   * :  * .

ref|ZP_02432977.1|    YKVVSVFDVSQTEGKELPDIAVDE-LTGDVDRYKDFFAALEKTSPVPIAFENIEGGSHG-
ref|ZP_02085861.1|    YKVVSVFDVSQTEGKELPDIAVDE-LTGDVDRYKDFFAALEKTSPVPIAFENIEGGSHG-
ref|ZP_02207628.1|    YKVVSVFDVSQTEGKELPDIAIDE-LPGDVDRYKDFFAALEKTSPVPIAFENIEGGSHG-
ref|ZP_02429891.1|    FKMVSVFDVSQTEGKEIPNIAVDS-LTGDVERYKDVFAALEKTSPVPVGFEKIEGGAHG-
ref|ZP_01731985.1|    FRTVNIFDISQTQGEDLPERTSP--LTGDDDGLIDRLMAFSLNNNVPVFFKGLLGNANGC
RAAC02340             YRIVYVFDVSQTDGKPLPTVESPQIISGDSD-LYEKLLQVCP---YPVSEVVSLGSARG-
                      ::  * ::*:*: :*         :.** :  : :    .  *:    *.::* ref|ZP_02432977.1|    --YYHLEDKRIAINEG--MSELQTLKTAIHEIAHAKLHDIDLNAPKDEQQPHVDRRTREV
ref|ZP_02085861.1|    --YYHLEDKRIAINEG--MSELQTLKTAIHEIAHAKLHDIDLNAPKDEQQPHVDRRTREV
ref|ZP_02207628.1|    --YYHLEDKRIAINEG--MSELQTLKTAIHEIAHAKLHDIDLNAPKDEQQPHIDRRTREV
ref|ZP_02429891.1|    --YYHLEDKRIALDEG--MSELQTLKTLIHEIAHAKLHDIDLNAPLEDLENRPDRRTREV
ref|ZP_01731985.1|    CRYDALSGHPIEIVVDPLLPKQHQAKTLCHEIGHSLLHSR------TQYNNHIPRSKAEL
RAAC02340             -EFD-LETNQIKIVQT--LPEAHKAKTLIHEWAHGLLHTN------GPLN-PAHKPLIEL
                        :  *. : *  :      :.:  :    ** **.*. **            :    : *:

ref|ZP_02432977.1|    EAESVAYTVCQHYGLDTSDYSFGYVAGWSSGRELS-ELKSSLETIRSAAAEIINSIDENL
ref|ZP_02085861.1|    EAESVAYTVCQHYGLDTSDYSFGYVAGWSSGRELS-ELKSSLETIRSAAAEIINSIDENL
ref|ZP_02207628.1|    EAESVAYTVCQHYGLDTSDYSFGYVAGWSSGRELS-ELKSSLETIRSAAAEIINSIDENL
ref|ZP_02429891.1|    QAESIAYTVCQHYGLDTSDYSFGYVAGWSAGRELA-ELKSSLETIRSTAAEIINSIDEHI
ref|ZP_01731985.1|    EAESVAFIVLNYFGIDSRDYSFPYVAGWQQGEDALENLRQSGMRIQKAANKVI-------
RAAC02340             EAESTAFVVSHALGLDTTDYSFAYIAGWS-GKEAVNALKACGTRIQQAANSILLALEDQA
                      :***  *: *   *:*: ****  *:***. *.:    *:    *::* .::

ref|ZP_02432977.1|    AELQKA-
ref|ZP_02085861.1|    AELQKA-
ref|ZP_02207628.1|    AELQKA-
ref|ZP_02429891.1|    AELQKA-
ref|ZP_01731985.1|    -------
RAAC02340             QDFKTAM
```

FIG. 42

```
ref|ZP_00231288.1|       -----------LEVVRIEQIIREAEEG-VDYIIRSPEDGAKIASRFIGRDDREVFFVMCL
ref|YP_001113884.1|      ------------------------------ITRCPEDVCGLVMEDLRDLDREHFLALLL
ref|YP_001213007.1|      ----------------LKIVKEASVLY-AARRISSPDDAAGFVRDFIEDADREKFLIICL
RAAC02341                MEVGRKSNMSSITVVRVELVKERSLEYEGSRLIRCAEDAANILRGYIGNADREMFVVMVL
ref|ZP_02596024.1|       -----------VDIVKLKMIKESSLLY-KERRVKSPEDASLLFRQFLDGADREYFIVLCL
ref|NP_150014.1|         --------MKKIDVVKVYVKKEQSLQI-EKDIIKKPEQVFEVVKNFLGEVDREYLIVIVL
                                    :   .::    .     :    *** :. : * ref|ZP_00231288.1|       NTKNNVVAVHRCHVGSLNSSIVHPREVFKSAILNNVASVILAHQHPSGDIKPSMEDINVT
ref|YP_001113884.1|      NTKNQVLARETISIGTLNSSVVHPRELFKVAIRRSAASMILVHNHPSGDPTPSREDIVLT
ref|YP_001213007.1|      NTRNEPTAVHTVAVGTLNSSQVHPREVFKVALLANSAGIILAHNHPSGDPAPSREDIEIT
RAAC02341                SAKHIVNAINTVSLGILDSSIVHPREVFKPAILSNAASVIVGHNHPSGDPEPSPEDVAVT
ref|ZP_02596024.1|       DIKNQPTTINVCHIGSLNSSIVHPREVLKPAIISNAASIIVAHNHPSNDPTPSSEDLEVT
ref|NP_150014.1|         DVKNKINSISVASVGTLNSSIVHPREVFKTAILANGASITLAHNHPSGDTSPSKDDINIT
                         .  ::    :       :* *: ***::* *:   .*.:*: *:***.*  ** :*:  :* ref|ZP_00231288.1|       KRLVEAGKLLGIEVLDHLIVNSDNSFTSLKER---
ref|YP_001113884.1|      KRLIEAGEIIGIDVLDHIIIG-DNKFTSLKSKGLI
ref|YP_001213007.1|      RRLKECGDLLGISVLDHIVIGSGGQYTSLLQKLLI
RAAC02341                RRLVDAGKILGIDVLDHIVIGDEGRFVSLKARELL
ref|ZP_02596024.1|       KRLIEAGKVVGIEVLDHLIVC-EESFVSLKEK---
ref|NP_150014.1|         TRIKECGVLMGIELLDHVILG-DEKFISLK-----
                         *: :.* ::**.:***:::       : **
```

FIG. 43

```
ref|ZP_01273840.1|      --------------LNNVLRAISSKTTIPILTGLKMVVN--EDNIVLTGSNSDITIESVIN
ref|YP_001270615.1|     --------------LNNVLRAISSKTTIPILTGLKMVVN--EDNIVLTGSNSDITIESVIN
ref|NP_783868.1|        MKFTINRSAFIKELNNVQRAISSKTTIPILTGLKLDVN---TDAITLTGSDADISIETTIP
ref|YP_805310.1|        MKFTITRSTFLKTLNDVSRAISTKTTIPILTGLKIVLN--DSGLILTGSDADISIESRIN
ref|YP_803555.1|        MKFTIARNTFIKKLNAVQRAISSKTTIPILTGLKIEAE--EDRLILTGSNTDISIETTIS
RAAC02342               MKATFRHGDLEKILRQLLRVVPNSTNKAVLKHVLIEAKREEDRVDFYASSEDMSLRRTLC
                         *. : *.:...*. .:*. : :    .  : .. .*. *:::. :

ref|ZP_01273840.1|      ANDADNDLTIEDTGAIVLPARFFSDIVKKLPDKKVTIEVTSGFQADITSGSAKFQINGQD
ref|YP_001270615.1|     ANDADNDLTIEETGAIVLPARFFSDIVKKLPDKKVTIEVTSGFQADITSGSAKFQINGQD
ref|NP_783868.1|        ASDDNNTLVVEDAGSIVLPARFFSEIVKKLPEDTMTVNVVDGFQTQITSGAASFTINGLD
ref|YP_805310.1|        ATDENNDLQIGSTGEIVLPARFFSEIVKRLPESTMTLEVKDNFQVTITSGASEFTINGLD
ref|YP_803555.1|        TNDEEAHLNIESTGAVVLTARFFGDIVKKLPDNTMLLEVKDGFQTTITSGASEFKINGLD
RAAC02342               VEATDSSVEIARSGSCLLPAKELYEVIKRANGPITVETTTD--RTVITFGKTKFELVGLQ
                         .  :  : : :* :*.*: : :::*:    .. :: ** * :.* : * :

ref|ZP_01273840.1|      AENFPHLPEIETNKS-VTLPNDILKEVIRQTVIAVSKQESRPILAGVHMTLKDGILTAVA
ref|YP_001270615.1|     AENFPHLPEIETNKS-VTLPNDILKEVIRQTVIAVSKQESRPILAGVHMMLKDGVLTAVA
ref|NP_783868.1|        PENYPHLPEIDTTNT-ITLAGDVLKELIGQTVIAVSNQESRPILTGVHFILANGEFLAVA
ref|YP_805310.1|        ANNYPRLPEITADAA-LSVSADVLRQLINQTVIAVSNQESRPILTGVHLTITGDQLVAVA
ref|YP_803555.1|        ANNFPHLPEVDSQTT-ITLKADVFSEMINETVIAVSNQESRPILTGIHFTIEGNKLSAVA
RAAC02342               PRLFQPYGDADDEVTTATVLAPHLYRLIRRTSYAAGKSQTRPILTGVQLTLADGIHLSAVA
                        .. :   :       :   : ::    : ..:*  .*  *...::**** :*:::  : ... :  *** ref|ZP_01273840.1|      TDSHRLAQRKVVLENIDNGIDFDVIIPGKSMEELSGMI--SDVHEDVQMQVTENQVLFIF
ref|YP_001270615.1|     TDSHRLAQRKVVLENIDNGIDFDVIIPGKSMEELSGMI--SDVHEDVQMQVTENQVLFIF
ref|NP_783868.1|        TDSHRLSQRRIKLPEANN-ANYDVIIPGKSLTELSRMI--GDNNPDVQMRLSENQVLFVL
ref|YP_805310.1|        TDSHRLAQRSLTLPTASA-SDYDIIIPGKSLTELSRML--SDDVEKIEIRIAENQVLFVF
ref|YP_803555.1|        TDSHRLSQRVINLPEPIK-MPEDIIIPGKSLLELSRML--DDEIDTITLQISENQALFTF
RAAC02342               TDALRLAQYTVSCEDVNG-EDRQLVIPAVLLDTLATALPASDDDEEVTFTLGTSSCTVSW
                        **: **:.*  :           :::**.  *:  .*    :  :.      :  :

ref|ZP_01273840.1|      GNTHFYSRL--LEGNYPETSQLIPQTADTTVELEAGTFLSSIERASLLSHESRNDVVKLS
ref|YP_001270615.1|     GNTHFYSRL--LEGNYPETSQLIPQTADTTVELEAGTFLSSIERASLLSHESRNDVVKLS
ref|NP_783868.1|        GNTSFYSRL--LEGNYPDTSRLIPKESNTTVEISAPALSAAIERASLLSHESRNNVVRFS
ref|YP_805310.1|        GQTAFYSRL--LEGNYPDTSRLIPTSSNTQAEFDAPALLASIQRASLLSHESSNNVVRLV
ref|YP_803555.1|        DETLFYSRL--LEGLYPDTSRLIPKESSTEMEFEAPELLASIERASLLSHAGRNNVVKLT
RAAC02342               GDDAFHMALRGLEGTYPDTARLIPERTAHRVVVERQALLTACERVAILSEADHQ---RAE
                        .: *:  *  *** **:*::***  :   ..    : :::**. : : :

ref|ZP_01273840.1|      LKPSENLVRISGDSPDIGTVEEEVVTSALDGNDLEISFNPNYMKDALRSFG-QATIKISF
ref|YP_001270615.1|     LKPSENLVRISGDSPDIGTVEEEVVTSALDGNDLEISFNPNYMKDALRSFG-QATIKISF
ref|NP_783868.1|        VNPTDKTITIFGNSPDVGEVTEQLQPTDLSGDELEISFNPDYMKEALRSFG-QAMIKISF
ref|YP_805310.1|        LNIADQKATIYGNSPDVGNVEEVLSFNKLSGEDLEISFNPDYMKDALQGFG-QTAIEVDF
ref|YP_803555.1|        INAANKQAIISGDSPEVGNVEEEVVTKDIVGEDLEISFNPDYLKDALRSFG-HTSIKMAF
RAAC02342               FRFTMSGLTVSATSTQYGHAEETLETIQGTKDDVELLCNVHYWIAALKALDGIAQVEIGL
                        ..  :  .  :  *.: * .*  :     :::*:  *  .*   **:. :.  : ::: :

ref|ZP_01273840.1|      TSPLRPFTLVPTEDQ---------------------
ref|YP_001270615.1|     TSPLRPFTLVPTEDQ---------------------
ref|NP_783868.1|        TMALRPFTLVPTEEGENFIQLI--------------
ref|YP_805310.1|        TAPLRPFTLVPTEDK---------------------
ref|YP_803555.1|        TSALRPFTLVPTEDQ---------------------
RAAC02342               NGPLQPCLLRPVGEEGVGLIATVARSSAPTETKRQAS
                        . .*:*  * *. :
```

FIG. 44

```
ref|YP_429218.1|        ------------------------------------VQRALEMAVRAAAMQVTPDSQAAGHPR
ref|YP_001112194.1|     ------------------------------------AAKSAVMQVTKESQADGRPR
ref|YP_001112320.1|     ------------------------------------ALALAARSAAGQVVPVSNASNNPR
RAAC02293               MKWILMALSLVVLQFWTHEQVLNLEMETVVYHRIVNAMVLASQDAVEDVIPSSTANGEPI
ref|ZP_01171099.1|      --------------------LNFTFDSTATRGLRDSLELATHDAGLQIYNEELVNGNIV
ref|ZP_02598174.1|      ------------------LTLNMNIATYAKSSKYLKEDLEVAVHDASLELKKDELANGKLV
                                                            *  :  *    ::    .  . ..

ref|YP_429218.1|        INIVAANIAFRRELASNLGLDANTLAPLKGSAMKTRP-----------------
ref|YP_001112194.1|     INTTNAQAVFQQQLAKNLGLDETTLNPLSGS----------------------
ref|YP_001112320.1|     VHADNAHSTFKKILAKNLGLDEVTLNPLPGS----------------------
RAAC02293               FDQTEAAQTFRMTLANNLGLDPNTLQPLSNSTFHVAPKILDEEFYDWSNT-TFPYHYVNS
ref|ZP_01171099.1|      FDQSEARRVLEESLKKNLLLDAS-LQPKPDSFFQDTVQIKFVDYLDDNNTPEFPTNYINE
ref|ZP_02598174.1|      FDPIKAKQTFKESLKDNTGFQEG-TDYK---------ILEFQVLDQSNS-KFPVKYKAN
                        ..    *   .:.   *  .*   ::

ref|YP_429218.1|        ---------------------------------------
ref|YP_001112194.1|     ---------------------------------------
ref|YP_001112320.1|     ---------------------------------------
RAAC02293               AYGINETLDAPSMVVVVQFTMPSYAANVPPFTITVPMVQSYAGS
ref|ZP_01171099.1|      QYDIVDTVDGPAIVVLETTGPRY-----------------
ref|ZP_02598174.1|      TLKFQDTFQNPTLVAIIETTTKKY----------------
```

FIG. 45

```
ref|ZP_02327783.1|   ------------------------------------------IKFKTLFLHNFKSHRDLE
ref|ZP_02846176.1|   ------------------------------------------IRLIQEQLINYAGIKDRT
ref|ZP_00235040.1|   SCRESIGNIFICANCEE-IDENTITIESPSITIVESGAPSMKIVFKQLTLENFKNHKNLV
ref|NP_623604.1|     ------------------------------------------MIIKSITLKNFKSHKNTI
RAAC02346            ------------------------------------------MKILSIQLENFRSFTEAS
ref|ZP_02082031.1|   ------------------------------------------MKIKGVTFTDFRNHKAPQ
                                                               :  :   : ::  .

ref|ZP_02327783.1|   INFG-ELTKITGENTKGKSSILEAIPWLFYSVDMLG-----SKSDPTPINYEYDHTLVKL
ref|ZP_02846176.1|   ITFG-NVTNLSGKNGEGKSSIGGAPIWILFGKDLYGNDYTKDKYSPRPSNYKYDRVYASI
ref|ZP_00235040.1|   VDYE-QVTQISGKNGFGKTSIGEAVTWLLYGTDLLG-----TKIEPQPLG-TEEEVHVSL
ref|NP_623604.1|     INFNDKNTVIYCDNGTGKTSIGEAIAWCLTGANLFG----TENVTNKLVTIGKNEMSVTL
RAAC02346            FQFH-DITVISGIINGAGKSTLAEAVVWCLFGTDIAG----RQKQDEKLMRLGEKRMAVTV
ref|ZP_02082031.1|   SYTFGDISYITGHNGTGKTTMAHGICYALYGVSYYG-----EQKIERLMNEKATGTQVQL
                        .  :  : *.*  **:::  .  :: .  *          :              . :

ref|ZP_02327783.1|   HFA-VDGKDILLGRGIE-KGKATYYINEVPAKAKEYEELVKSLFDKDLFLSLYNPSYYFT
ref|ZP_02846176.1|   LLS-IDGTEYKFAREIDEKKKNNFYVNDIPKSATDFSAAVVALITQDEFMSLYFPAYFFG
ref|ZP_00235040.1|   LIN-ADGKDLLLTKKQK--KTAKYAINEVPRKATEFADMIDSLFEKNLFYSLYSPGYFFS
ref|NP_623604.1|     VIE-KDGKEYEITRSKK---KNEIEITINGVKSTQIDLYTQFVQDKDIFFTVFNPLYFTT
RAAC02346            TWL-IHGKSVVISRTRASRQGSTLLLVNGKRAQPGQIEGWFGTVQE---FLSVFVPGYFSS
ref|ZP_02082031.1|   DFTDQNGTTHTLIRNRS-GDKTALLLDGYTVRQCGDIDR---IFCDKETFLSMFNPTYLTE
                      .*.  ::  :                :                   *  :::  *  * ref|ZP_02327783.1|   LKWNEQRELLLRYVSAPANKEVFAQLPKQQAEKLG-------------------------
ref|ZP_02846176.1|   LKWTEQRELLMKGATAPLTKAVLKEIEKLYADKLE-------------------------
ref|ZP_00235040.1|   QHWQTQREQLLSYVTEPGEKEVLEEMNEIDRTLLS-------------------------
ref|NP_623604.1|     LAPRDAKAILYKVLPEVSNEEVFEKLSPEVAETLKKNGFNNANTFIEKQREILKDWEDGL
RAAC02346            LEPKEAKTVLSRCVPDIPKEDVLARMTSVHASMLA-------------------------
ref|ZP_02082031.1|   RLGEKGRPLILKYLQPVSANAVLEQMSETYREYLDGIDLNTFPPEAKLKEFRG-------
                      :   :          : *:  .:          * ref|ZP_02327783.1|   ------------------ELVKKHSLADLEKIHRDNKNKKDKAYIAAQSRTKTLI-----
ref|ZP_02846176.1|   ------------------PLLKKNSLSDLESKHKQDKTRLEKAHTEAGGATKKLR-----
ref|ZP_00235040.1|   ------------------TELNKHLLDDLEAVNRETFKNSDKQYERASERVLTLK-----
ref|NP_623604.1|     LKSEGNIEILRQIINAKIPEMKSFDETQLKELEKKLMEFQKNQNIEIEKELAILK-----
RAAC02346            --------------------RDQFVMGLDSIEFAMQKVRDEIKECEAERLRLEG-----
ref|ZP_02082031.1|   -------------AVRQAEEQEAYLQGNIDSFEEASRTAEQKLSELYADKAAIEKKRKVL
                                           .          :: .          .  :

ref|ZP_02327783.1|   --EQLQLLPQSPPNLKN---IQDDYDRFLAEIKVIDSMLPKADENNGK--IIKLESQIEH
ref|ZP_02846176.1|   --EMLERMPAVEGELTE---LETQAEALRVEIAKEDAIVAAAWQTNTS--YRELESALFY
ref|ZP_00235040.1|   --EQLSNASEVNMDIKE---ITEQKDALIAERTAIELKEDKNVQLRND--YADAEQKINA
ref|NP_623604.1|     --EQYKNPPIEKPQLKDTSILQKTREELLQEYKQIQEQIKNLKPQYIT--CNKCGNKIDV
RAAC02346            --QCQAYQAVLRRGEPQ----PYVPSVTDEERARYEAAKRELMELEAS--QGNRKERLRD
ref|ZP_02082031.1|   SDKQFEGIEVEDLSIQRNMLLEKLSSVPKGENPKVTQLQEKIEELRHKPYVSKYTQAMAE
                         :                            .  *                 . . :

ref|ZP_02327783.1|   LKEQRDQIKEQIRELIIN--EPIDD---RCRACGQTLQGEAKAAAEADKQRRVDQLIEEFNN
ref|ZP_02846176.1|   TQHEVDSSKAAWPALKD--EAIND--TCRTCAQPLQEDAIKAVIADKEKRIAAYRSKHSN
ref|ZP_00235040.1|   LKERILRKREEALNVRE--QKIEE--NCEYCGQTLQGDSIEHAIQYRKEHYNRLVTAGKI
ref|NP_623604.1|     TAKEKQLLLAKLQEIKE--KGTKT--AAELKAVIEENEKAEKEFKEKVNKYRKALEIKIK
RAAC02346            LYARRDSLGRAFRALRDSLPQADT--HCHTCGQPLPEDQAARILQEIAQKRKASLAKMKE
ref|ZP_02082031.1|   NAAEVKNLSERYKALVNRVKGLRPGAQCPACLMRITEQNLPEVRNRMLAELKSLAEQGKE
                             ::     .         :                   :        .

ref|ZP_02327783.1|   VIT---------------------------------KRKELEAHLTQIEHI
ref|ZP_02846176.1|   LQS---------------------------------IRDEAKAALAAAKWV
ref|ZP_00235040.1|   MVE---------------------------------ELEASKARLAKLENP
ref|NP_623604.1|     RLE---------------------------------NALNTNANKEQIQQI
RAAC02346            LYD---------------------------------EGNQVQAEIAKLEAM
ref|ZP_02082031.1|   RVAQGKELAGMDYQSKTVFEQFKADDLKKLYEELKGLKTEAAGKTDGEELRAALDKVEEL
                                                          .*     :
``` continued →

FIG. 45 continued

```
ref|ZP_02327783.1|        ---------DVSKQREEVRELEVRLDQLDEVISNHKSREQLQG--QIDHAETDEAAILTS
ref|ZP_02846176.1|        ---------DVTERQANVRALEDQRDLITEKIRAHKDRARFEV--ELQQSEETEATTLIS
ref|ZP_00235040.1|        ---------EKNFDRVKYKEIDEKILELSGYIQSVGQTEKLHK--QIADAELEQQRIRKQ
ref|NP_623604.1|          ---------MQQIERLRFEERE-VISHNESVKALLRQKEEAKK--KLKEVEEDIKLAEQQ
RAAC02346                 PDYDAPHPELVEFVQTMEARLKDEHYREVAYAAQLRAYEQAKG--HFTQAQEDLQATAEH
ref|ZP_02082031.1|        QK-------YGNLDEDEYTELNCLSAELAGIEAQTQAVQDMCDERKLEDAYAQQEVCKGQ
                                        .    .                               .: .

ref|ZP_02327783.1|        LNESIFIIDAIKAFAAKEAEMMADKVQALFTTLSLRLFKTNKTDGEIKPDFEIEMDGKPY
ref|ZP_02846176.1|        LRESTLILDAIKAYKAKEAELQAAEIQSNFTRLSVRLFKYVKSNDAYEPDFSIQMDGKDY
ref|ZP_00235040.1|        RNKSQSIVEAIKRFKAKRSDLMVGKVNGLFENITIKLYEVLKN-GTEKPTFEVEWQQKPY
ref|NP_623604.1|          INEVKTLIEYAKAFNAKKLELEATEINKYLNKVSLQLWKIVQSTGEIKDDFKILYDGKEF
RAAC02346                 LEGLKQRLQALQEFRFEYLRAQHEQLNGLFRHVAIHLMDVNKETGEVREAFRIEWKGRPY
ref|ZP_02082031.1|        ILKYKNVISALGEFICKRTEIAVSSLQ--MPNVKIKLFDVVRSTGEVINVFKFTYKGRDY
                           :.    :  :         .::  :  ::*  . :   *  .  .::

ref|ZP_02327783.1|        RKLSLSESIRAGLELRDVLSQQSGIIAPCMVDNAESITQFKQP--NGQLIVSRV------
ref|ZP_02846176.1|        AFLSTGEKIAAGLELAEVLHKQSGIIAPVFIDN---------------------------
ref|ZP_00235040.1|        SKLSTAEKIIAGIEFANALSLKAETIIPLFADNAESVIELPKP--TGQLITATVKKTKFT
ref|NP_623604.1|          NILSYSERIKAGLEIANLIMGLTKIKFPIFIDNAESI-----------------------
RAAC02346                 RLLSYSEKIRCDIEIGRALAQAKGEAMPVYVDNAESVQRLMDETFSGQVIAAYVADGPLT
ref|ZP_02082031.1|        STLSLSEKTLAGIEITAMIRKITGIDCPICVDNTESIAAFNSVSMPSQTLLLRFVKGQPL
                           ** .*   ..:*:    :        *   ** ref|ZP_02327783.1|        ----------
ref|ZP_02846176.1|        ----------
ref|ZP_00235040.1|        VKGVSE----
ref|NP_623604.1|          ----------
RAAC02346                 VSKMPEAQGA
ref|ZP_02082031.1|        TVQSRNRA--
```

FIG. 46

```
ref|YP_113896.1|        ---------------------------------------PWLVNVAKG-DLKLVGVEA
RAAC02347               MRPSTLYYNGVQMNPVRGGPSMEDKKVLKTVIRNGVTFDNYPVYVSEAYG-DSYLMKHEE
ref|XP_001383704.2|     -----------------------NKSVPSFIIRKPINMNGYDYSVFTNYPTEIDLQHGEH
ref|XP_001664270.1|     --------------------------------------------SDSSG-DDHLMKPEE
ref|XP_761114.1|        -------------------------KEIADRGAKADKEWTELFKAYG-EKYPNEHAE
ref|XP_001015776.2|     -----------------------------VQRNGDLESKKISKVVLKSG-ITFLDIQIK ref|YP_113896.1|        VTSEQAACRTAEWEKAADRAPAGLIG---PTQLDLPATAPAEERLMS----------
RAAC02347               LAEQIASCIPQAWRKAA-RFDCNLIA---EFQDDMDETSEDEQRLLSKFERWMSRHN
ref|XP_001383704.2|     LPPAIKESQIKSWESAERISTNVIFGNSSESEDDIDELDEDEHTEASRSSKVNSRKN
ref|XP_001664270.1|     LDLRSNFFDKIESTKRQSGEPAPQFD--CNAGMRLSDSSDDDQAEEPIPSSIQK--
ref|XP_761114.1|        IARRIAGKLPEGWKS------------------------------------------
ref|XP_001015776.2|     VQRDLKLGYTENFRLFN-REGVEMFE------NDIPFLQNNCYLLASMGEEYDSTS-
                        :
```

FIG. 47

```
ref|YP_503850.1|        -KISKKNYDLVFKEAFSIFDNRSLAFLGID-LPPIISFLVTEIPEVETTDDMMDLNFRLE
ref|YP_517477.1|        --ISYHNNDILMKVLAEQFKNKTLDVFGIK-TAKIKDLIPSVHPAVEANETRNDIIFLLE
ref|YP_001568284.1|     -------------------------------IISVKPIDIPVINVSNQNPDFVFELE
ref|NP_783815.1|        ------------------------------DTKIIAPANTELKTIDIKTNFTDYTFYTE
ref|YP_149134.1|        --ISHHAKDILFKSLSALYQNQALDVYGLHGLPRIKALLPNEFPSVRADERRADTVFLLE
RAAC02289               MRIARSGNDIVAKHLTNALPGEVLSVIGIH-DAHVVRALPTELPTVEVRQEFTDIMLELA
                                                         :          :      *  :

ref|YP_503850.1|        DGSILILEEEMNLSKRD-LIRFAHYDLRLFRYYD------APVHTVVLTPADSSSGTKVL
ref|YP_517477.1|        DDTLLHLEFQTTAGEQD-LKRFLYYDARLVRRQE------RKVHTIVIYSGRIEQARERL
ref|YP_001568284.1|     DNSLLHLEFQTTWKKAD-LLRFAQYDIALYQKER------RRINTVVMYSGKYESAESEL
ref|NP_783815.1|        NDDYLHFEFQTTNKEED-INRFLFYDASLFYKYG------KKVNTLVVYSSDIKKSKTKV
ref|YP_149134.1|        DDSILLLEYESNERFLDNHLKYLDYACRILHTYYQQEKRIRPIRIVVIYTSDVTTARERL
RAAC02289               DGRLLHLEFQTT-REPN-LYRFGTYDWAMAERYK------RPIRTVILYTRDVTEAPSEL
                        :.  * :* :   :    :  :: *  :               :. ::: .    :

ref|YP_503850.1|        DIGSLQYNVLQIVLSDRDGDALLSQMRAALEKGEPVNE---LELIFLPLMKSKLTKIELL
ref|YP_517477.1|        ECGSILYQVENIYMKHYNGDQEYNRLKHKIDNHQLLSETDTLKLIFLPLMKSEQKEEELA
ref|YP_001568284.1|     DMGSNKYKVQQIFMIKYDGIKRYEEIKEKIEKEEELTDKDLMDLVFLPLMRNEKSEEEVT
ref|NP_783815.1|        DAGSLKYEIKAFYMSSLNGDEEYNNLKTKIDKGEDLTKEEILSLTFIPLMDSKEDKSTRT
ref|YP_149134.1|        DAGDVFLSSKAVLLGFFNGDAIFHAIEEKVHNGEPLTPEETMKLILVPLMHTRFDRQTMI
RAAC02289               DAGSMRYAVENVYLGHMDGDGALETVKRHLAAHEWTEEDRVRLAFAFHMRFERRTREEAF
                        :  *.       .  :   *        :  :        . : .

ref|YP_503850.1|        RRTIDLEKELPEKDLRNKVRELTLILADKIVDQKILDELWEELRMFKVVKYAEEKGMEKG
ref|YP_517477.1|        IQAAELAKAAPDEKTKLFAIAALIVITDKIMSESNKRKLLEVLKMTQIEQWIREEGRQE-
ref|YP_001568284.1|     KDVFELAIKIPDEDKKEAVIGSLLGFSDNYVRDEYINELKEVIRMTKIGTSLFEECVE--
ref|NP_783815.1|        IKSIELAEKMEENNTKLQCITLLYAFLEKFGDAKSKKKFKEVFSMTEIGRMIVEESIEKG
ref|YP_149134.1|        EKTIELAKAIGDEPKQLHIIAGVLTATDKFIDRSYAEKVKEWIKMNKVFRLLVEELEQEK
RAAC02289               GEIVEVVQRVPDVHEQNYLAALILGFSGRVMADEQKEQLRRVLEMTDLLRELEREFEEKG
                         ::     :   :                 .     :       .   . :

ref|YP_503850.1|        --------LEKGLEKGIKKGMEKGKKQERETVAKNMLSLGIEDELIIKATGLDQSIIDKL
ref|YP_517477.1|        -------------------GELKGRRDEKRETAQTMLNLGMSPELIAKATKLPLEEILEM
ref|YP_001568284.1|     -------------------EGEKELTIKILNKRFGRRLTEEIKDRIREADKKTIDYI
ref|NP_783815.1|        RAEGIKKGIEEGIKKGRTEGKTEGKSEILIKQLIKKF-KKVPEEYIQKIKTLSIDTIDII
ref|YP_149134.1|        -------------------EEMLKKVMQEKEQAVQRAIQEKEQAVQRVIQEKEQAVQRA
RAAC02289               ----------IQKGLQQGLQQGELQKAREIAHRLLRKGASVQEVVEITGLSSKDVEEI
                                             :     .    .      . :

ref|YP_503850.1|        KKSL------
ref|YP_517477.1|        ----------
ref|YP_001568284.1|     GDNL-------
ref|NP_783815.1|        ALEIFDMEDIK
ref|YP_149134.1|        IQ---------
RAAC02289               RQNLH------
```

FIG. 48

```
ref|NP_607899.1|
ref|NP_269831.1|   SINGLE-STRANDDNA-BINDINGPRTEINSTREPTCCCUSPYGENESMGASREFYPSIN
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   GLE-STRANDDNA-BINDINGPRTEINSTREPTCCCUSPYGENESMGASREFYPSINGLE
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   -STRANDDNA-BINDINGPRTEINSTREPTCCCUSPYGENESMGASREFYPSINGLE-ST
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   RANDDNA-BINDINGPRTEINSTREPTCCCUSPYGENESMGASSPPSSBSTRPSINGLE-
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   STRANDEDDNA-BINDINGPRTEINSSBHELIX-DESTABILIZINGPRTEINSPPSSBS
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   TRPSINGLE-STRANDEDDNA-BINDINGPRTEINSSBHELIX-DESTABILIZINGPRT
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   EINSPQXASSBSTRPSINGLE-STRANDEDDNA-BINDINGPRTEINSSBHELIX-DEST
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------ ref|NP_607899.1|   ------------------------------------------------------------
ref|NP_269831.1|   ABILIZINGPRTEINGBAAKPUTATIVESINGLESTRANDBINDINGPRTEIN-PHAGEA
gb|AAF98351.1|     ------------------------------------------------------------
ref|ZP_01171110.1| ------------------------------------------------------------
ref|XP_414088.2|   ------------------------------------------------------------
RAAC02348          ------------------------------------------------------------
``` continued →

FIG. 48 continued

```
ref|NP_607899.1|      ----------------------------------------------------------------
ref|NP_269831.1|      SSCIATEDSTREPTCCCUSPYGENESMGASGBAAMPUTATIVESINGLESTRANDDNABI
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      NDINGPRTEINSTREPTCCCUSPYGENESMGASDBBACPUTATIVESINGLESTRANDBI
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      NDINGPRTEINPHAGEASSCIATEDSTREPTCCCUSPYGENESSSI-GBAATPHAGESIN
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      GLE-STRANDDNABINDINGPRTEINSTREPTCCCUSPYGENESMGASGBAAXPHAGESI
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      NGLE-STRANDDNABINDINGPRTEINSTREPTCCCUSPYGENESMGASGBAAZPHAGES
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      INGLE-STRANDDNABINDINGPRTEINSTREPTCCCUSPYGENESMGASCBABFSINGL
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      ESTRANDBINDINGPRTEINSTREPTCCCUSPYGENESMGASGBABFSINGLESTRANDB
gb|AAF98351.1|        ----------------------------------------------------------------
ref|ZP_01171110.1|    ----------------------------------------------------------------
ref|XP_414088.2|      ----------------------------------------------------------------
RAAC02348             ---------------------------------------------------------------- ref|NP_607899.1|      ----------------------------------------------------------------
ref|NP_269831.1|      INDINGPRTEINSTREPTCCCUSPYGENESMGASGBABFSINGLESTRANDBINDINGPR
gb|AAF98351.1|        ----------------------------------------------------------------
ref|ZP_01171110.1|    ----------------------------------------------------------------
ref|XP_414088.2|      ----------------------------------------------------------------
RAAC02348             ----------------------------------------------------------------
``` continued →

FIG. 48 continued

```
ref|NP_607899.1|    ------------------------------------------------------------
ref|NP_269831.1|    TEINSTREPTCCCUSPYGENESMGASGBABFSINGLESTRANDBINDINGPRTEINSTRE
gb|AAF98351.1|      ------------------------------------------------------------
ref|ZP_01171110.1|  ------------------------------------------------------------
ref|XP_414088.2|    ------------------------------------------------------------
RAAC02348           ------------------------------------------------------------ ref|NP_607899.1|    --------------------------------------------------GAPSVTEV
ref|NP_269831.1|    PTCCCUSPYGENESMGASSCRESIGNIFICANCEIDENTITIESPSITIVESGAPSVTEV
gb|AAF98351.1|      ----------------------------------------------------VTEV
ref|ZP_01171110.1|  ----------------------------------------------------VTEV
ref|XP_414088.2|    ------------------------------------------------------------
RAAC02348           ----------------------------------------------------MAEV ref|NP_607899.1|    VADNFQMLESRATREGGSTGSFNGGFNNNTSSSNSYSAPAQQTPNFGRDDSPFGNSNPMD
ref|NP_269831.1|    VADNFQMLESRATREGGSTGSFNGGFNNNTSSSNSYSAPAQQTPNFGRDDSPFGNSNPMD
gb|AAF98351.1|      VADNFQMLESRATREGGSTGSFNGGFNNNTSSSNSYSAPAQQTPNFGRDDSPFGNSNPMD
ref|ZP_01171110.1|  IARYVQFLDSKKNNQSQEQRRPES--NNTPSGRNSNNNPYAD-PYFEGEP----------
ref|XP_414088.2|    ------KYAEEGEGKQSEEEAKASA-----KIKKNSAPLPAEQ-P---------------
RAAC02348           VAEGVRFLDRGEGNQSAKSASAAP------PVKNNTSPAPSKQ-PDFGPYDDPFADDLPPG
                         :  :      .:. .               *:    *   : * ref|NP_607899.1|    ISDDDLPF
ref|NP_269831.1|    ISDDDLPF
gb|AAF98351.1|      ISDDDLPF
ref|ZP_01171110.1|  ISDDDLPF
ref|XP_414088.2|    --------
RAAC02348           FEED-LPF
```

FIG. 49

```
ref|YP_001038860.1|        ------------------------------IEKFQMVVQKTLNEGHDYDIIPGT-SKPSLLK
ref|YP_001396671.1|        ------------------MEIGEVRNTLGKIAQFQSIIQKTLKNGHDYGEIGGV-TKPTLLK
ref|YP_001254879.1|        ---------------------------QKIATFQAVIQKNLKDGHDFGVVAGAGSKPTLLK
ref|YP_754926.1|           ---------------------------KQRLELLQEFVKEMMIPGQDYGIVPGV-SKPSLFK
ref|YP_001396310.1|        ------------ISIVPDFAITLNDAKNRVELLQSFVKEMMIINIDYGFIPNC-SKPSLFK
RAAC02349                  MALPERQLPRAYCAGVNMVMDFGALRQRLEELRQFVKEYMVPGEDYGIIG-D-SKPTLFK
                                                       :  ::  .::: :   .  *:.  :     :**:*:* ref|YP_001038860.1|        PGAEKILVLLGLTS-EYEIIEKIENYEKGIFA-YTVRCILS--KNGKKVTEGLGSCNSKE
ref|YP_001396671.1|        PGAEKILMLMGLTS-EYNIIEKIEDYDKGIFA-YTIKCILR--KNGQKITEGVGSCNSKE
ref|YP_001254879.1|        PGGEKICMMFGLNP-EYEFLERTEDYKDGFFA-YNIKCTLY--RNGNPVSQGVGNCNSME
ref|YP_754926.1|           PGAEKLTDIFGFSK-QVEILNRTENWENGLFN-YEVKVSLINKRNQLIEAEGIGCCNSKE
ref|YP_001396310.1|        SGAEKLCDIFGFSK-KIETLNRVEDWEKALFH-YEIKTTLINKKTGLIEAEGIGSCNNRE
RAAC02349                  PGAEKLCDVYGLSAGEAHIEFTRDDTKTPIYISYRVSLPLISRIDGKIIMVGVGSANSWE
                           .*.**:  :  *:.  : .:   ::   ::   *   *        *:*  .*. * ref|YP_001038860.1|        DKYRWRWVSEKDLPPNVDKDMLKSKTNEYG---QKLYRIENDEIFTQANTILKIAKKRAQ
ref|YP_001396671.1|        DKYRWRWVKEDDLPMGIDKDAVKSKVDNYG---HTKYKVENDDICSQANTILKMAKKRAQ
ref|YP_001254879.1|        KKYRY--INVDAVPDGIDPSTVEKVTTRYG---TVKYKIPNPHIADLVNTILKMAKKRAF
ref|YP_754926.1|           KRYRS-----------------QDPYN------------------TVNTVLKMAKKRAL
ref|YP_001396310.1|        RKYKN-----------------QDGYS------------------IVNNILKMAKKRAF
RAAC02349                  KKYRWRWVTERELPPDLPKETLKQATFDGKYGSYIKYRIPNDEIDDLDNTLLKMAKKRAL
                            :*:                  .                          *.:**:****

ref|YP_001038860.1|        IDAVLTVAALSEIFTQDVEDMQEF---LQNEQLETMKAEEAVNVKVTFGKHKGKTLGEIY
ref|YP_001396671.1|        VDATLTVASLSEIFTQDIEDMAQF---QERE-----------------------------
ref|YP_001254879.1|        IDAVLQVASLSDVFTQDLEEMQE-------------------------------------
ref|YP_754926.1|           IDAVLSATRSSGLFTQDVEDLDISESWVRSPQPQATKTVRGVKPD-SLSVANITQPQLRK
ref|YP_001396310.1|        IDAVLSATRSSGLFTQDMED----------------------------------------
RAAC02349                  IDAVLSATRSSALFTQDIEDLED----LTIRQPESVDRRQRTQPDRSTGSPDISQAQKNL
                           :**.*  .:    *  :****:*:

ref|YP_001038860.1|        SQAPDYVQWLAQNARNDVLRKAANMVMNGKGNESQQEAQRSEDL--------
ref|YP_001396671.1|        ------------------------------------------------
ref|YP_001254879.1|        ------------------------------------------------
ref|YP_754926.1|           VQALAEAIGMTPHQLQALIQDMFRVNHTTRLSKNQASALIQHLLS------
ref|YP_001396310.1|        ------------------------------------------------
RAAC02349                  ILRKAQERGMDTEALNAFVLQATGKGELDSLTKQEASKLIDLLTSGKPRER
```

FIG. 50

```
emb|CAJ73677.1|         --------------MTNYNFGEILLLKFPYSDGKGDAKRPVVVLAQTDL-EDIVTAKVTSM
emb|CAJ73386.1|         -------------------GEIILVRFPHTDLQDISKRPALILYDSGD-QDILIARITTQ
ref|YP_001655174.1|     -------PQKTKVYMTIIKGGEFWVAKILFTDGTSSKKRPVLILWVDG--DDVVVTAVTSA
RAAC03270               MPFTMKPSDTYWNLMNVRRGQIYLMKVQFSDLSGEKIRPVVVIGTDRVDDDVTVVFVTSS
emb|CAJ74660.1|         ------------------------MQYPFSGVSVQKVRPAVVVNAPHVSHDLLVVPLTSK
ref|ZP_00516046.1|      -------------MANYWKNDVILVRYPFSDLSNSKIRPAIIVSSPHTSQDVLITPLTSK
                                                 : .:.      **.:::   .*:   . :*:

emb|CAJ73677.1|         -EQRGEYDIAIDAWKDVGLLYPSVVRIDKLATLSKQRVEKRFGTLVGSYKPEIISRIK--
emb|CAJ73386.1|         -EYTTGTDYKIVEWKSCGLLVESFIRISKQATIEKKYVIKPLGTLAEAELNAVKSIIKN-
ref|YP_001655174.1|     -MPRTQTDILLKDWANSGLRVPSTVRLSRLDCLEKNLLAKLGRISNEDAVYLLRAWDDY
RAAC03270               -PPRLRYDVQITEWSVAGLLKPSTVRASKFLTVHKGRFLKPLGTLTDSDLQAVMTAVRSY
emb|CAJ74660.1|         TTSLLKGEFVLTDWTLAGLNVVTAVKRG-IYTVHQSLIIKRLGKLSHADSQKIEVALKEW
ref|ZP_00516046.1|      TQLLEGEFILSDWKKAGLNVETAVKRG-IYTIYQGLILKKVGKLVDADTTKLEQSLRQW
                         :  :  *    **    : ::  .     ::  .     .* :   :

emb|CAJ73677.1|         --
emb|CAJ73386.1|         --
ref|YP_001655174.1|     I-
RAAC03270               LL
emb|CAJ74660.1|         L-
ref|ZP_00516046.1|      L-
```

FIG. 51

```
sp|P26545|VE2_HPV5B      -STTRSRSTSVGKTRALTSRSRS-RGRSPSTCRRGG---GRSPRRRSRSPSTYSSCTTQR
ref|NP_041368.1|         -STTRSRSTSLTKTRALTSRSRS-RGRSPTTCRRGG---GRSPRRRSRSPSTSSSCTTQR
ref|XP_001371550.1|      -SRTRSPARRGGRSRSRTPARRGGRSRSRTPARRGGRSRSRTPARRGRS----RSRTPAR
sp|P36786|VE2_HPV19      RSRSKSKSRSRSRSRSLSSNRRS-RSKSR---RKAS-----TTRGRGRGSPTATSDQSSR
RAAC03271                MSRTRSTATNAGKKAARSPFTHG-CAESRSRQRKPN----CTRRGHGSATYTPQNGSPPP
ref|XP_001131003.1|      -TRERARPSPPPESAARARVTHK-AADPRPGVSRAT----TAREQRGETHGAPYAPAPPP
                             : ::.    ..: :   :   . .      :        : :.            .

sp|P26545|VE2_HPV5B      SQRARAESPTTRGARGSRG--SRGGSRGGRL------RRRGRSSSSSS----
ref|NP_041368.1|         SQRARAESSTTRGARGSRG--SRGGSRGGRG------RRRGRSSSSSS----
ref|XP_001371550.1|      RGRTRSRTPARRGRSRTRSPVRRGRSHSRTP------QRRGRSGSSSER---
sp|P36786|VE2_HPV19      SPSATSSTTSLRSRGSSRVGRSRGG-RSRVG------RSRGRGKRSR-----
RAAC03271                NSPSLASRRASRGACQKAWTHWHGDVSAKQCSIGFGKNTRGMSASSASRPSG
ref|XP_001131003.1|      -PPPRQPKRSERTR-------HRGA---------------------------
                                   . : *           :*
```

FIG. 52

```
ref|YP_941474.2|     ----------------------------------------------------------
gb|AAZ42391.1|       ----------------------------------------------------------
prf||2123261AD       ----------------------------------------------------------
ref|NP_498368.2|     ----------------------------------------------------------
RAAC02294            MCSRLRDSRLRPRKALCRAADGARGRSSRMRSAIIFALMFFFILSWNYQPYMDVINGARL
ref|ZP_01171098.1|   ---------------------------------------------FTPFFVYLDSLHR ref|YP_941474.2|     -----------VSEAAFRQYSKTKDPETLVQYIATMLSSSSNHVVING-ITMR--SGSP-I
gb|AAZ42391.1|       -----------VSEAAFRQYSKTKDPETLVQYIATMLSSSSNHVIING-ITMR--SGSP-I
prf||2123261AD       -----------SHMKKVIVFILLY-P--FLLLWNVIISEKYLDFIFGG-FVISYIKRVPWA
ref|NP_498368.2|     -----------SHMKKVIVFILLY-P--FLLLWNVIISEKYLDFIFGG-FVISYIKRVPWA
RAAC02294            EYLQAVAETAISEAKIKGYFSATDLSNIQQAVATHLGYPVSEVQVQG-TTLPTTRGNP-I
ref|ZP_01171098.1|   AVVALVLQQGLKEAAIEGYFSQEIVEGMKDTLEQDYKFERNLIEITTPDSSPQTRGEY-L
                                  .  :                :                  . .

ref|YP_941474.2|     DLEEYVPLAVTF-YVMA---------------------
gb|AAZ42391.1|       DLEEYVPLAVTF-YVMA---------------------
prf||2123261AD       SLSKFQIISYVFTFSVTLVTN-----------------
ref|NP_498368.2|     SLSKFQIISYVFTFSVTLVTN-----------------
RAAC02294            DIQISIPTHINL-FSMAPASNQATLTAYESADSEALNPS
ref|ZP_01171098.1|   EVEISVPRGPMFILNIFNQGP-----------------
                     .:.              :   :
```

FIG. 53

```
ref|YP_430185.1|       ------------------------------------------------------------
emb|CAO81523.1|        ------------------------------------------------------------
ref|YP_001233893.1|    ------------------------------------------------------------
ref|YP_001603689.1|    ------------------------------------------------------------
ref|YP_719187.1|       ------------------------------------------------------------
RAAC02353              MNEVNTMENLRAVYVNTFAEGSRSTDPIQLSVDELKMAARGWKRAKTVIHVHLLGMQQKL ref|YP_430185.1|       ------------------------PASLVERGYVEDLNAYLGQTLRLRVIELDRSKNKV
emb|CAO81523.1|        ------------------------------------------------------------
ref|YP_001233893.1|    ---------------------------------------DTFDLYIERYEDKDGSI
ref|YP_001603689.1|    ----------------------------------------------------EDRDGSI
ref|YP_719187.1|       -------------------------------------------------DAVEDGFGET
RAAC02353              VDGTTRDILVGDIGPAKVMLPVDPEYSALEDGEDPMSLTDRWICGIVEDFDLQDEGDSTI ref|YP_430185.1|       VLSRKAILEEEYEKQR-QATWNSLEVGQVRKGIVRRLTNFGAFVDLGGVDGLLHVSEISW
emb|CAO81523.1|        -------LEEMREQERKETALAKLKVGDIVKGKVLRMTTFGAFIDLGGIEGLMHVSEISW
ref|YP_001233893.1|    VLSR----EKARREEAWTALERAYEQQARVNGVIHGRVKGGFTVDLGGATAFLPGSQVDI
ref|YP_001603689.1|    VLSR----EKARREEAWTNLEKAFEGNQRVNGTIYGRVKGGFTVDLGGAMAFLPGSQVDI
ref|YP_719187.1|       KLSR----EKAVRQESWIDLEKAYEEQATVIGLINGKVKGGFTVELNGVRAFLPGSLVDT
RAAC02353              LLNR----KKGLERLRELNAERVSKPGNRAIGVIVGIRRGAYVLNVGGYTALMPKAWYDW
                          :       :  ..      :        * :    . :::.* .::   :   .

ref|YP_430185.1|       GRVEHPRDALSEGQEIEVKILGIDREEGKVSLGRKQLLPNP----WDTAAERYPVGTIVE
emb|CAO81523.1|        QHIVRPQDELKKGQEIEVKILDIKGE--KIALSRKVLLEDP----FEVAMKELHEGDIIN
ref|YP_001233893.1|    RPVRDVTPLMGVQQ--PFQILKMDRARGNIVVSRRAVLEETRAEQRSELIQGLKEGQILD
ref|YP_001603689.1|    RPVRDVTPLMGVPQ--PFQILKMDRARGNIVVSRRAVLE---------------------
ref|YP_719187.1|       RPTREADHLLGKEQ--EFKVIKLDQKRNNVVVSRRAVIESENSQEREEILANLAEGSEVK
RAAC02353              DDSKRDQGTIGEEFPVQIQPSKVEDR---IVVSRCHLMENP----NVPSSLRFDRGTILR
                            :            .:   :.      : :.*  ::

ref|YP_430185.1|       GKILRLAP--------FGAFVEVEPGIEGLVHISQLA-DRHVDKPEDVVSIGDIIPVKVL
emb|CAO81523.1|        CRVLRLHN--------FGAFAELKPGVEGLIPISEMSRNRNISHPRDIVKEGDWVQQIL
ref|YP_001233893.1|    GVVKNITD--------YGAFVDLG-GVDGLLHVTDIA-WRRINHPAEALTI---------
ref|YP_001603689.1|    ------------------------------------------------------------
ref|YP_719187.1|       GTVKNLTD--------YGAFVDLG-GVDGLLHITDMA-WKRVKHPGEIVSVGDEITVKVL
RAAC02353              ATVAFIRNGLIRAEVYPGFLVSVDPVILRQIPKPGDRITVRILGQNKNGYYGMMVDHQPQ ref|YP_430185.1|       G-----
emb|CAO81523.1|        -----
ref|YP_001233893.1|    -----
ref|YP_001603689.1|    -----
ref|YP_719187.1|       KFDKD
RAAC02353              SVG--
```

FIG. 54

```
ref|YP_001251565.1|   ------------------PVYIPQDVRVGHTFVVGTTRVGKTRLASILINQDIRNGD--
ref|YP_126374.1|      ------------------PVYIPQDVRVGHTFVVGTTRVGKTRLASILINQDIRNGD--
ref|YP_123382.1|      ------------------PVYIPQDVRVGHTFVVGTTRVGKTRLASILINQDIRNGD--
ref|YP_001251158.1|   -------------------VYIPQEVRVGHTFVVGTTRVGKTRLASILINQDIRNGD--
RAAC02354             MVTHMLTDIKLERHAVPYAPVWIPGRERTGNVLVEGGPGTGKTYCLKTMLHQDIQAMVDG
ref|YP_001438903.1|   ------------------------------IILEDVTGAGKTEAALVLAHRLMAAGQAR
                                                    ::  .  .*** :  :: :

ref|YP_001251565.1|   ----AVIVVDPKGDQDLVRDMMAACKVSGRTEDFKIVH--LGFPEQSAQYNPLKNFDQIS
ref|YP_126374.1|      ----AVIVVDPKGDQDLVRDMMAACKVSGRTEDFKIVH--LGFPEQSAQYNPLKNFDQIS
ref|YP_123382.1|      ----AVIVVDPKGDQDLVRDMKAACKVSGRTEDFKIVH--LGFPEQSAQYNPLKNFDQIS
ref|YP_001251158.1|   ----AVIVVDPKGDLDLVRDMYSACKASGRLHDFRVVH---LGFPELSAHYNPLKNYDQVS
RAAC02354             QQDCRMIVISPEGSMCDIEDCTSRLQVDWIKIYSRALH--VSSPYEKAFFSALRNLLMVS
ref|YP_001438903.1|   ----GLYIGLP--TMATANAMYARMSQAWLRLYREGSHPSLVLAHSARKLSAGFNASIWV
                          : :  *       .    :  .       . *  :  .      ..  * ref|YP_001251565.1|   -EVATRITDAISAE----------------------------------------------
ref|YP_126374.1|      -EVATRITDAISAE----------------------------------------------
ref|YP_123382.1|      -EVATRITDAISAE----------------------------------------------
ref|YP_001251158.1|   -EVATRVTDAIQAE----------------------------------------------
RAAC02354             PDDSQSTCDRVLAEYGLLKPFLYCSRQNTKIVSLYTGYQEIDTFIGAAFVHYLACNMSKI
ref|YP_001438903.1|   HELLPNDSGDEAAAYEGCAAWFAQSPKKALLAETGVGTLDQAMMAVMAFKH---QNLHLL
                           :         .    * ref|YP_001251565.1|   ------------------------------------------------------------
ref|YP_126374.1|      ------------------------------------------------------------
ref|YP_123382.1|      ------------------------------------------------------------
ref|YP_001251158.1|   ------------------------------------------------------------
RAAC02354             TMKPTILYVDELHRYAAYAPHAVAKLFECGAEHGISLIAAVQSTEQLNTAESPCLSELVN
ref|YP_001438903.1|   GLNDKVLIADEIHSYDAYMSHVVEKLVETRARYGN---ATILLSATLSQAQRDRLIAAFY ref|YP_001251565.1|   -------------------------------------
ref|YP_126374.1|      -------------------------------------
ref|YP_123382.1|      -------------------------------------
ref|YP_001251158.1|   -------------------------------------
RAAC02354             RNTRFHVKMRTSEDRDTLRLAPNQALWITSTTRHVIEVSPQFRN
ref|YP_001438903.1|   KG--------LNTTRESPRLGPDDYPWIT---------------
```

FIG. 55

```
ref|ZP_02602342.1|    ------------------------------------------------------------
ref|ZP_02597242.1|    ------------------------------------------------------------
ref|ZP_02524501.1|    ------------------------------------------------------------
gb|ACA42232.1|        ------------------------------------------------------------
ref|ZP_02758276.1|    ------------------------------------------------------------
RAAC02355             MYALAYWRAKRKEHRRMPEVPALVRVSIAHSTWFMVVIGAIGAFALYRSVFRALGRMAQL ref|ZP_02602342.1|    -------VEIGPHIEHKEMVRIKGKDRTLN-------------CIIIGPIGSGK-------
ref|ZP_02597242.1|    -------VEIGPHIEHKEMVRIKGKDRTLN-------------CIIIGPIGSGK-------
ref|ZP_02524501.1|    -------VDIGPHIKHKEMIRIKGKDRTLN-------------GITIGPIGSGK-------
gb|ACA42232.1|        ----LILFVLPALISGLMIFIQVRDFMVH--------------KDMLSESFMTW-------
ref|ZP_02758276.1|    --KIESINGEAGETLDTPVFIPLKDRFLH--------------MLILGPTGCGK-------
RAAC02355             GTLAVIAMAGFGVVKLHGLIAAWQNRMLHPSTPKAATTATNSHAIINPLTSGTGPKLPLS
                                                   :    ::   ::            ::.

ref|ZP_02602342.1|    -----------------------------------------TSSLIIPMINQDLHWMARFI
ref|ZP_02597242.1|    -----------------------------------------TSSLIIPMINQDLHWMARFI
ref|ZP_02524501.1|    -----------------------------------------TSSLIIPMINQDLHWMVRFI
gb|ACA42232.1|        -----------------------------------------KAPIIRRFTHKKLLGTADII
ref|ZP_02758276.1|    -----------------------------------------TSQTIIPMINQDLQNKE---
RAAC02355             ALNATNPLVHENAWVIALALVAGVLGLLAFFVYRGLSPTAKAQFLQRMQATDFDRSTHRR
                                                              .:   :   :    .:

ref|ZP_02602342.1|    N---------------------------KFINVFKKKDYHTEEVKGTFLN---------
ref|ZP_02597242.1|    N---------------------------KFINVFKKKDYHTEEVKGTFLN---------
ref|ZP_02524501.1|    N---------------------------KFENTYKKNNYDTEEVKGTFLN---------
gb|ACA42232.1|        IGYQFKTMIP------------IVLKEAQRFLHEAVIGATGSGKTSTALLLRIAQDLIN
ref|ZP_02758276.1|    ------------------------------------------------------------
RAAC02355             DDDPNKFSLVGVEVGIRKDNGRPIRIEGKDRFINTLVLGSTGTGKTSRIMLKAVYQDLRS ref|ZP_02602342.1|    --------GVTVIEPSNDLCQKVFKLVQAHKIPESAVYYIDPTNPDTKNINILRGPVDKV
ref|ZP_02597242.1|    --------GVTVIEPSNDLCQKVFKLVQAHKIPESAVYYIDPTNPDTKNINILRGPVDKV
ref|ZP_02524501.1|    --------GITVIEPSNDLCQKVFKLVQAHKIPESSIYYIDPTNPDTKNINILRGPVDKV
gb|ACA42232.1|        IATGRRKMGLVFLEPKGDGVDDVLKMCKKLKIPDEKIKVIDATKAFTIKFNPFIGPSAPA
ref|ZP_02758276.1|    --------IGVTVLEPKSDLAEKVYQMAKIHNR---EVIYFNPLLADCPYFNPLFGHESEV
RAAC02355             MANG-TPMDVIAMDPDGGFAQAAVNMANQLGVET-IIMDLRGTMPSTVSFSPFGGEIADI
                          .: ::*... : . ::    :   :   . : . * ref|ZP_02602342.1|    AEVFAMVIQGLSESNNAFFEQAQRNHLKQHIYLLKLHNPQKD-----------------
ref|ZP_02597242.1|    AEVFAMVIQGLSESNNAFFEQAQRNHLKQHIYLLKLHNPQKD-----------------
ref|ZP_02524501.1|    AEVFAMVIQGLSESNNAFFEQAQRNHLKQHIYLLKLHNPQKD-----------------
gb|ACA42232.1|        AATFEGTINALSGDQDDFYKGQQNEAASTLTKLAKIAFGEKTNIFHIQRMFSDPRYLANI
ref|ZP_02758276.1|    IENMATTFNMLNPDSPQFFKDMSDGLIRKSVKLLKRLYGDDA-----------------
RAAC02355             IDNVRAALQEKMGKQDGFFQNAQDDLVRTVIQVQVPLWPEAD-----------------
                           . .::   ..  *::  .          :         :

ref|ZP_02602342.1|    -----------------VTFDDLIEMYD----DVEHVHRMHKLLKVQVEKLYDFVQSGAAS
ref|ZP_02597242.1|    -----------------VTFDDLIEMYD----DVERVHRMHKLLKVQVEKLYDFVQSGAAS
ref|ZP_02524501.1|    -----------------VTFDDLIDMYD----DVEHVIRMHKLLKVQVEKLYDFVQSGVAS
gb|ACA42232.1|        VESIREQITTNREKQFREQKDLIMLLDSLGTSVEHIEQTEHELMFKLKNLSNSSAINENQ
ref|ZP_02758276.1|    ---------------------TLIDLND-------LVWNSNGIGKKIVNEFSKLPVKNPLQ
RAAC02355             -------------------FLQFADLVT----DPLHFRAICSMVQDCAAQEAGTAKKKRKS
                                           :  :                .           :

ref|ZP_02602342.1|    R------DQKNEYKIIKGIHEWFDNTIREKLDFQGEPAVYKSGKYRGQPMHYDR------
ref|ZP_02597242.1|    R------DQKNEYKIIKGIDEWFDNTIREKLDFQGEPAVYKSGKYRGQPMHYDR------
ref|ZP_02524501.1|    R------DQKNEYKIIKGIDEWFDNTIREKTGFQGEPAVYKSGKYRGKPMHYDR------
gb|ACA42232.1|        KKLNEIQELKKRNNLLRAQQTFIDNTEQIIFYFENEVLLYKVDQRTQQPILYPKNHIYAN
ref|ZP_02758276.1|    Q------------------KENEEIAIWFLTDYYSGMTGDRKGT---------------
RAAC02355             E-------MDEAMSMWEHERPEVEARFHRLTPHEKSMVLSAARSFLMDTATEQK------
                      .                      .       .    .  .

```
ref|ZP_02602342.1|    -------EEEYVKGLRNILKDLASNVLIRRVLFGKSD----FDFDVHLEQG--GILLVNT
ref|ZP_02597242.1|    -------EEEYVKGLRNILKDLASNVLIRRVLFGKSD----FDFDVHLEQG--GILLVNT
ref|ZP_02524501.1|    -------EEEYVKGLRNILKDLASNVLIRRVLFGKSD----FDFDVHLEQG--GILLVNT
gb|ACA42232.1|        QQMVESKKDKFVTGAKKYLNDIALNDLLKNLFIGAEGE-EVFDADEFLREG--GVLLVNT
ref|ZP_02758276.1|    ------KTYEHCSGVRTQISKLVSNEYLRKALNPPRGHGTDIDFDKALEEG--LVITMTT
RAAC02355             ----LEKLETITKGLKIVVNELATNPRLRQVFKTDELP--PFDFQGFLAAGKEQPGRLVV
                           .*   :  :..:. *  ::. :          :* :  *  *      : .

ref|ZP_02602342.1|    AKGELADLSNVLGKFVLLSMQNAVFRRD--PNVSPYHHIIVDEFPDYVVRPFKEFPAQSR
ref|ZP_02597242.1|    AKGELADLSNVLGKFVLLSMQNAVFRRD--PNVSPYHHIIVDEFPDYVVRPFKEFPAQSR
ref|ZP_02524501.1|    AKGELADLSNVLGKFVLLSMQNAVFRRE--PNISPYHHIIVDEFPDYVVRPFKEFPAQSR
gb|ACA42232.1|        SLAELDELSLMFGQFFIRQFQSAIFRRP--QEGRIPIFFYIDEFPLYVNEAFERILTLGR
ref|ZP_02758276.1|    TQGSLRDLGKFLGYFIILQLQSSVFRRPGDEDSRRENMLYIDEFQVYANQGFGEMLTQGR
RAAC02355             VVTGNRPAGKLFGKLFLVTLKMYALEREGTEDTRRPVYLYVDEFAVYGTESFTEMFSQAR
                         . .:* :.:  ::     :.*      :      : :*** *  . * .: : .* ref|ZP_02602342.1|    KYKVILTIASQTLSQLALD-FTEQYMFTLLGSFRNKMIFGDVTPYDAKIFSDMFGEKEEF
ref|ZP_02597242.1|    KYKVILTIASQTLSQLALD-FTEQYMFTLLGSFRNKMIFGDVTPYDAKIFSDMFGEKEEF
ref|ZP_02524501.1|    KYKVILTIASQTLSQLALD-FTEQYMFTLLGSFRNKMIFGDVTPYDAKIFSDMFGETEEF
gb|ACA42232.1|        SYNVGAVIAMQSIGQLEG--VKAGYQDIILGNASSKTVFGRGPNKDNEYFSLEFGEKEIN
ref|ZP_02758276.1|    SYRVASHLATQARDQMSVGREGDSFLELVSANARNKIIYPGISITDAKYYSEEFGEELRT
RAAC02355             KYRVGMMLAIQARAQLLD--VSKKFMDVVEGSCRNKIYFPAPSPDDARFLEHALGSVKNI
                       .*.*   :* *:  *:      :   :  ..  .*  :    . *  .  . :*.

ref|ZP_02602342.1|    KEAESEQGIS---------------------------------------------------
ref|ZP_02597242.1|    KEAESEQGIS---------------------------------------------------
ref|ZP_02524501.1|    KESESEQGIS---------------------------------------------------
gb|ACA42232.1|        EESLNESASPMTSEDQKWGYRLNTAKKKVARFSTTAIRE-LPFKHMIVQIVDETNSIAPP
ref|ZP_02758276.1|    TIGKSYSKDRYFSSFSDEKMTTKVDERYEPRFSPSNLIY-RDFGQITHCLVKNNTVQIPA
RAAC02355             RETYSENKLSWFFDTRNLDRRVSTQETIDPRYRLEDISYGLSKDEAIFAMTVDNQVQAPC
                                       .  .

ref|ZP_02602342.1|    -------------------------------------------------------------
ref|ZP_02597242.1|    -------------------------------------------------------------
ref|ZP_02524501.1|    -------------------------------------------------------------
gb|ACA42232.1|        LKAVGRFVNEARFIKPYLNLKKSDIKSNQE-------------------------------
ref|ZP_02758276.1|    LAQIEY-------------------------------------------------------
RAAC02355             VGITSYADEWVKKQRGFFDVRRSQNRSQRQPTPINVAVKVVEHGVSERRSMPEPRDETYV ref|ZP_02602342.1|    -------------------------------------------------------------
ref|ZP_02597242.1|    -------------------------------------------------------------
ref|ZP_02524501.1|    -------------------------------------------------------------
gb|ACA42232.1|        -------------------------------------------------------------
ref|ZP_02758276.1|    -------------------------------------------------------------
RAAC02355             PSPASPSKVRPTADRNAKINVQAFARAIQEAAFHMSDASRADTVDVEPVETHTETSPQQG ref|ZP_02602342.1|    -------------------------------------------------------------
ref|ZP_02597242.1|    -------------------------------------------------------------
ref|ZP_02524501.1|    -------------------------------------------------------------
gb|ACA42232.1|        -------------------------------------------------------------
ref|ZP_02758276.1|    -------------------------------------------------------------
RAAC02355             ETSPYASPNESTAQEAERPIEEPAIVRIDLRPQRPPKRCPQCEAELTLTPDERKWRCPRC ref|ZP_02602342.1|    -------
ref|ZP_02597242.1|    -------
ref|ZP_02524501.1|    -------
gb|ACA42232.1|        -------
ref|ZP_02758276.1|    -------
RAAC02355             GFERKNR
```

FIG. 56

```
ref|NP_347717.1|        ------------------------------------------AVGLAVGVLGALM
ref|YP_429187.1|        ---------------------------------------------IGRGIVG---
ref|YP_423535.1|        -----------------------------------------MMVVSHVVLGVSA
RAAC02356               MMGRSHMAIGAVGAVAATPLVLHERWESLRDLLTHPWASMPHIVVVQAAFVAATVVGALV
ref|YP_645289.1|        ------------------------------------------------------------
ref|ZP_01860459.1|      ---------------------------------------------IGAGGISGLI ref|NP_347717.1|        PDIDTSRSKVSYNLRKIV----------------VYAALVIVGAYILMANFYPEVEKTNL
ref|YP_429187.1|        --------------------------------------IAILGAWHQTR-----------
ref|YP_423535.1|        WTLAQRAG------------------------LAVPLGPEGAAAAALG----------
RAAC02356               PDLDQQDAKLTYTIEIVFGLPVLALAIVVMVLMIIWATSLTAWGIALLLMFIFGAAHNVTR
ref|YP_645289.1|        ------------------------------------------------------------
ref|ZP_01860459.1|      PDLDVDGKLSNTFTSSYK---------------FLMTLVQFIGVAVIVYSWWAGTDQEMW ref|NP_347717.1|        FLKNMGVYKLKDYIPYNLKLSNAGLLIIVGCIIFSKFTKHRSFSHSILGLILFTVGVKLL
ref|YP_429187.1|        -------------LPLLLPAG--------VAFVALAFLPHRGITHSALGLVLAWLAIKTL
ref|YP_423535.1|        ----------ALLPDIDHPSSWLGRRLWPISKPISMVLGHRGLTHSLLAVMGGLAVLMLV
RAAC02356               MLGLGALATILLDLAYHHRMPMEAAVLLAAWMVATMPAKHRTFTHSLLGLAVFGAGCYLS
ref|YP_645289.1|        -----------------LRAT---------SFVLVRTVGHRTLTHSLLGLALFCAPVWLL
ref|ZP_01860459.1|      KG--------IAAGLGIMLVSSFIKKRHLLTVAGGGALAGGMFLAETWLQLLGIYIVIASL
                                           ::.: *  :

ref|NP_347717.1|        LG-----NIFIY----FAVGFISHMVADTFTNSGIEVFYPIKKKISLKLVHTGSMLDHFTG
ref|YP_429187.1|        G------WPQVP---FLIGYGIHLAEDLLTPSGIPLLYPWQERMRIPLAQTGGIIDRTLG
ref|YP_423535.1|        EPGRGLVRLAEP---LALGYLSHLAADALTPAGVPLLWPWKQRFGVGLCSTGGVMEWLV-
RAAC02356               EPALSHLHLGVAAYGLILGYVLHMAADFIAG-GVPLLWPWGKRQGVHLVKSFSAVDYLIG-
ref|YP_645289.1|        LGG--YPAFALA---LAAGYASHLLADALNTRGVPLLWPLGK------------------
ref|ZP_01860459.1|      VSHRSYTHSLIG--LAFFAVIAYYLQASIKTEGILLACTGG--YVSHLIADMKWLPFNKR
                              .   :     :     *:  :   .

ref|NP_347717.1|        GLAFIVFLAIIL-
ref|YP_429187.1|        LAALALFL-----
ref|YP_423535.1|        -------------
RAAC02356               GIGIFTFVGLALV
ref|YP_645289.1|        -------------
ref|ZP_01860459.1|      GIKLFLPVSRKE-
```

FIG. 57

```
ref|NP_217638.1|      PRTEINTBHGMYCBACTERIUMTUBERCULSISSTRHAARLEMGBABQHYPTHETICALP
ref|ZP_00876805.1|    ------------------------------------------------------------
ref|NP_856790.1|      ------------------------------------------------------------
gb|EAY58379.1|        ------------------------------------------------------------
ref|ZP_01505670.1|    ------------------------------------------------------------
RAAC02357             --MVCDMAIRYDGWSIAAQYRRCGKSACRVCREGPGHGPYWYGSKTVDGRRLTKYFGKVP ref|NP_217638.1|      RTEINMRAMYCBACTERIUMTUBERCULSISHRAGBABRHYPTHETICALPRTEINTBFG
ref|ZP_00876805.1|    ------------------------------------------------------------
ref|NP_856790.1|      ------------------------------------------------------------
gb|EAY58379.1|        ------------------------------------------------------------
ref|ZP_01505670.1|    ------------------------------------------------------------
RAAC02357             PVEQEIAQDEPSVLKELSRLREENENLRAQVAQLQAELAALRTPPALSDPPHPLEETKEA ref|NP_217638.1|      MYCBACTERIUMTUBERCULSISFSCRESIGNIFICANCEIDENTITIESPSITIVESGA
ref|ZP_00876805.1|    ------------------------------------------------------------
ref|NP_856790.1|      ------------------------------------------------------------
gb|EAY58379.1|        ------------------------------------------------------------
ref|ZP_01505670.1|    ------------------------------------------------------------
RAAC02357             SQDELTIHEQPRRRASVRSSDELTKADVEAIWCEETEGLDEEPDILAEVHDALVRNLFPV ref|NP_217638.1|      PSSISENYRRCGKPN--CVCAQEGHPGHGPRYL------------WTRTVAGRGTKGRQ
ref|ZP_00876805.1|    --SIENYRRCGKPN--CVCAQEGHPGHGPRYL------------WTRTVAGRGTKGRQ
ref|NP_856790.1|      --SISENYRRCGKPN--CVCAQEGHPGHGPRYL------------WTRTVAGRGTKGRQ
gb|EAY58379.1|        --SISENYRRCGKPN--CVCAQEGHPGHGPRYL------------WTRTVAGRGTKGRQ
ref|ZP_01505670.1|    --SLIERYKRCGKPG--CKCADG--PGHGPKYY------------LSVSFPGRRPQMDY
RAAC02357             PTQDTTRLKTGTNPRKPYVCPFRATKRGGRLTFGSADKLVRTAIPWLIQSVKHQREWREL
                            .   :*    *.       *               :.  :

ref|NP_217638.1|      LSVEEVDKVRAELANYHRFA------------------------QVSEQIVAVNEAI
ref|ZP_00876805.1|    LSVEEVDKVRAELANYHRFA------------------------QVSEQIVAVNEAI
ref|NP_856790.1|      LSVEEVDKVRAELANYHRFA------------------------QVSEQIVAVNEAI
gb|EAY58379.1|        LSVEEVDKVRAELANYHRFA------------------------QVSEQIVAVNEAI
ref|ZP_01505670.1|    VPQADYTDVAEHLANYHRVR------------------------EIIEEICEINREL
RAAC02357             SRRRQQDRIAELLSTYRRMDTLELVHLVERMERAILMGDRTGWTVRLEELDEHVEVIRQV
                       :    :  *:.*:*.                          :  ::   :.  :

ref|NP_217638.1|      CEARPPNP
ref|ZP_00876805.1|    CEARPPNP
ref|NP_856790.1|      CEARPPNP
gb|EAY58379.1|        CEARPPNP
ref|ZP_01505670.1|    LRRR----
RAAC02357             LQERNT--
                       . *
```

FIG. 58

```
ref|YP_655149.1|      ------------------------------------------------------
ref|NP_943831.1|      ------------------------------------------------------
ref|YP_001456771.1|   ------------------------------------------------------
RAAC02358             MRPVQRAIPGPVKRWKFRLVVSRHSSQVPNSNRPCRCDHSTGTPPVPTARTNIVRPAEGR
ref|YP_024839.1|      ------------------------------------------------------
ref|XP_748956.1|      ------------------------------------------------------ ref|YP_655149.1|      ------------ELRPYQREAVEAIESHWSQGVTRVGVVLPTGTGKSTVIGRTAVNGYQN
ref|NP_943831.1|      ------------MRPYQREAVEAIESHWSQGVTRVGVVLPTGTGKSTVIGRTAVNGYQN
ref|YP_001456771.1|   ------------ELRAYQTEAVNAVLGEWVDGK-RTCVVLPTGTGKSTVIAKLAEIAYKA
RAAC02358             ALNDVEGISVAIQLRPYQQAAVDAFFQALAEGRKRQLIVLPTGAGKTIVFGSVARRFHEE
ref|YP_024839.1|      ------------LRPYQEKALEGIEKAEREGVRRPLVVLPTGTGKTVVFSHGIKNRADR
ref|XP_748956.1|      ---------SPKLVLRDYQEECIQSVLKYLDEGHKRLGISLATGAGKTVIFTELIGRIPSR
                                 :*  **   .::..    :*   *    :  *.**:**:  ::      .

ref|YP_655149.1|      R---EPVLMVAHRGELIDQMAGTIFEVDPSIPRSHVGIVRAEMDDHSAPIVVATLQTLAT
ref|NP_943831.1|      R---EPVLMVAHRGELIDQMAGTIFEVDPSIPRSHVGIVRAEMDDHSAPIVVATLQTLAT
ref|YP_001456771.1|   G---QRVILLAHRRELLDQMAQSIRMVAPQIPTDDIGFVQAERDQPERPIVCASFQTLMS
RAAC02358             VSRERPILVIAHRTELLDQAEQKIHFVWP---EAFIGRIQGARNEQLGDVLLASTQTLVA
ref|YP_024839.1|      G----RSLVLVHRDELVRQTIEKIGMVAP---ELTTGVVKADENGLDADVVVASVQTAQV
ref|XP_748956.1|      NEIGDKSLIIVHRKELVEQAAQHCRRAYP--DRTVEIEMGHSHASGAGDIVVASVQTLTR
                          :::.** **: *          .*          :        ::   *:  **

ref|YP_655149.1|      AHRREAVGFRR------RILWDEVHHAGAECFHTTFTELGGYTDAL----FAGFTATMRR
ref|NP_943831.1|      AHRREAVGFRR------RILWDEVHHAGAEGFHTTFTELGGYTDAL----FAGFTATMRR
ref|YP_001456771.1|   ASRLQAVGERT------VVLVDEVHHSAASTYAEILSAPN-FDGAF----KAGFTATLQR
RAAC02358             GRRIPQPG---------LIIYDECHHSRAEGALGVLERLGVFESDGPP--LLGVTATPSR
ref|YP_024839.1|      DRRLAQLVEAAKRSPFGTVWVDEAHHAPAPSWTKVLTGLGSFNPYGPL--TVGFTATPER
ref|XP_748956.1|      GNRLAKFDPKR----FKLLLVDEAHHIVASSYREVLKHFGADETSADSPVLVGVSATFSR
                             *             :    *       :  .              *.:**   * ref|YP_655149.1|      DDKGKSPVGLGDVIEKV-----VYEKDILWAIDSGYLVRPRGLTVRTKNLNALDDVRTVA
ref|NP_943831.1|      DDKGKSPVGLGDVIEKV-----VYEKDILWAIDSGYLVRPRGLTVRINNLNALDDVRTVA
ref|YP_001456771.1|   ADGG-----LADYWDSI-----AFERDLRWALDEGFLVPPQGKTVVIPGLDTTN-IKLRN
RAAC02358             SDRT----ELGDIFEHL-----TYERTILDMLMDGYLSDVRGVKVEVPGLNLGA-IRTTA
ref|YP_024839.1|      DKKTLGVWERLAAFMSIREAIYGNGKRGKDGHEGGYLVPILPAVVVETEMDLTR-VRKTG
ref|XP_748956.1|      SDGLK----LGAAIDHI-----VYHKDYIDMINDNWLAN-AVFTTVRSEANLSKVKKDSF
                                        :             :              .:*     :            :

ref|YP_655149.1|      GDFQQSDLAEVM--EAATEYVVDAIKLHAADRR-PIIFAASVDAAHHIADALTAADFPAV
ref|NP_943831.1|      GDFQQSDLAEVM--EAATEYVVDAIKLHAADRR-PIIFAASVDAAHHIADALTAADFPAV
ref|YP_001456771.1|   GDYAAGDLSEVM--MSSVDSTVEAIHTHAPDRR-MLIFGAGVEHCQALSDTLSATGIHTA
RAAC02358             GDYNSKDLSYVMNIESALDAVVDAVVTHAPGRK-CLVFAVDVKHAHALAERFQKRGIACA
ref|YP_024839.1|      GDFSEGDLGREMEESGAIAQIADAYLINAHDRK-GVAFTPTVATAHALAAALCARGIRTE
ref|XP_748956.1|      GDFAIGPLSKAVNTENVNNITVRAWLANAQDRKSTLVFCVDVAHTKALTETFRNYGIDAR
                      **:    *.  :           . *  .*:. :*      *     :::  :       .:

ref|YP_655149.1|      AVTGSMSYAERQPVYEAYRNGTAKALVTVQVLTEGADFPMCDCVVLARPTRSRNLYSQMI
ref|NP_943831.1|      AVTGSMSYAERQPVYEAYRNGTAKALVTVQVLTEGADFPMCDCVVLARPTRSRNLYSQMI
ref|YP_001456771.1|   LVVGSTSSEERTELFEEFTAGRVQALVTVQVLTEGTDLPACDCVVLARPTRSAVLFTQMV
RAAC02358             AVDGAMKAEERAAILQAFAENRLCVLVNCQILTEGYDQPDVDCVVIARPTRSQALYVQMV
ref|YP_024839.1|      ALDGTTTHKDERRAILRRLKTGETQVVTNCGVLTEGFDEPSISCVVVARPTKFHGLYVQMI
ref|XP_748956.1|      YITAKTPKDVRMEQLRAFRNGEYPVLLNCGLFTEGTDIPNIDCVLLARPTRSRNLLIQMI
                      :  .    *    .      .:  ::*** * *  .**::**** *  **:

ref|YP_655149.1|      GRALRLYDGKQDALVLDLAGSS------------------RSMKLVNLTQLV-------
ref|NP_943831.1|      GRALRLYDGKQDALVLDLAGSS------------------RSMKLVNLTQLV-------
ref|YP_001456771.1|   GRALRLHQDKNDALVLDLAGST------------------RDVAMVTLSSLV-------
RAAC02358             GRALRLHPDKTDALVLDLTGAS------------------DDKSLQTFARLMRTQRKTA
ref|YP_024839.1|      GRCTRLYPGKKDLMILDLVAAS------------------RRHEFVGYVDLG-LDLDEG
ref|XP_748956.1|      GRGLRLYPGKEDCHIIDMVATLNTGVLSTPTLFGLHPDEILQNAKAKDLRDMPLEKTTTG
                      **. **: .* *    ::*:...:
``` continued →

FIG. 58 continued

```
ref|YP_655149.1|          ------------------------------------------------------------
ref|NP_943831.1|          ------------------------------------------------------------
ref|YP_001456771.1|       ------------------------------------------------------------
RAAC02358                 THALVGAEEGEDAVPMEDGESVGEWLTRVAQKRELAEQVAQAINLFANRSRYRWVRVKDN
ref|YP_024839.1|          KKPKEGEPERQACPTCEEPCEVTEHRCALCHRYLPVAVTAEGGSRHENCQANGSGRVN--
ref|XP_748956.1|          TGTALAGEETEEPPPTPDDLDVNLTFTKYDTIYDLIADLKSEKHIRSLSPHVWVRVGDHR ref|YP_655149.1|          ------------------------------------------------------------
ref|NP_943831.1|          ------------------------------------------------------------
ref|YP_001456771.1|       ------------------------------------------------------------
RAAC02358                 FAIAYGHDGWAYLYRDGDEFWPVLELKNEKFMPLHDRSLPLEYAQGVVEGFLSLFESSLI
ref|YP_024839.1|          -------------------VFGESRLRWLPVGPAWVLGAGKEIVVMVPEGVDTWKLAAYE
ref|XP_748956.1|          YVLSDASGWLTIDKEEDTSRAYRPRLNPDPTSIANTPDEPYIFTVRHVAKFKNSDDSIMH ref|YP_655149.1|          ------------------------------------------------------------
ref|NP_943831.1|          ------------------------------------------------------------
ref|YP_001456771.1|       ------------------------------------------------------------
RAAC02358                 TKEADWRNAPMTERQKYVLQKYRIRYDDTWTRGMAADALGQRFAAKRVRVLQKNFDAQ--
ref|YP_024839.1|          NGRVEVLHEEIPSDWAMGIGEDRAKAFQKLVERQARWLNEPVSISQKGRLVREGLPEK--
ref|XP_748956.1|          TRPRLIATAPDFETALRAADTFATKEFEERYVSVRQTWRQLPATEAQVRFLNKAKVRHGS ref|YP_655149.1|          ----------------------------------------
ref|NP_943831.1|          ----------------------------------------
ref|YP_001456771.1|       ----------------------------------------
RAAC02358                 KWRDVLAQPHGQAWLEHRLMALRARAQSRARVAQTS
ref|YP_024839.1|          HLPRVKTKGEAADLLTRISGKRAVRKL---------
ref|XP_748956.1|          IQRKHLTRGQAADLITKLKFGGKQRFEARRAERL--
```

FIG. 59

```
ref|YP_001086797.1|    ----------------------------------------------------------
ref|ZP_01805266.1|     ----------------------------------------------------------
ref|ZP_01966753.1|     ----------------------------------------------------------
ref|ZP_01188985.1|     ----------------------------------------------------------
ref|YP_001681547.1|    ----------------------------------------------------------
RAAC02361              MDTQCIEVRCGSARHHLSYEDLFTPEVQSLFEECYALGVEVRCLCNPDRPVPMHLRRVRI ref|YP_001086797.1|    ----------------------------------------------------------
ref|ZP_01805266.1|     ----------------------------------------------------------
ref|ZP_01966753.1|     ----------------------------------------------------------
ref|ZP_01188985.1|     ----------------------------------------------------------
ref|YP_001681547.1|    ----------------------------------------------------------
RAAC02361              RPPTYTVVTNPLGIHHPNCPRFRQSRHPSASHKTRDAQAVETTPNHIEEWLPHRRIFVPT ref|YP_001086797.1|    LDTLNPAQREAVEKTEGPVLILAGAGSGKTKVLTTRIAYLIEDKGVQAPNILAITFTNKA
ref|ZP_01805266.1|     LDTLNPAQREAVEKTEGPVLILAGAGSGKTKVLTTRIAYLIEDKGVQAPNILAITFTNKA
ref|ZP_01966753.1|     -DTLNPQQEAVFHTEGPLLILAGAGSGKTRVLTHRIAYLIEEKGVNPWNILAITFTNKA
ref|ZP_01188985.1|     LTGLNPEQKKAVEHFEGPLLILAGAGSGKTRVLTHRIAYLIENYGVNPLQILAVTFTNKA
ref|YP_001681547.1|    LHSLNPVQREAVLHQEGPLLLLAGAGSGKTRVLTHRIGHLIEQCRVSPFIILAITFTNKA
RAAC02361              LDQLNDAQREAATHKNGPCMVVAAAGSGKTAMLIARIQHLIN-QGVRPGDILACTFTRKA
                        *  **   *::*.  :  :**  :::*.******  :*   **  :**:    *   . *** *** **.**

ref|YP_001086797.1|    ANEMRERVEQNIGPETKDMWISTFHCCVRILRKDINKIGYNRSFVIYDSADQVTLVKDC
ref|ZP_01805266.1|     ANEMRERVEQNIGPETKDMWISTFHCCVRILRKDINKIGYNRSFVIYDSADQVTLVKDC
ref|ZP_01966753.1|     AEEMRQRVDSLVGIGAESIWVSTFHSMCVRILRKDINKIGYNRSFVIYDSADQVTLVKDC
ref|ZP_01188985.1|     AGEMKERVDNLLCGMAGDLWVSTFHSLCARILRKEIGKIGYDNNFVIFDTDDQQKLISRI
ref|YP_001681547.1|    AAEMRERLGRLIGPRAHDVWVSTFHSTCMRILRKDGEKLGYDRSFVIYDYDDQQRLLKEC
RAAC02361              AQEMTDRLLAAVGERGKAVTIGTIHSVAYRMVTPELG--EDWRVLSDPTWMIERVLEEPS
                         * ** :*:  :*    :  : .*:**  .  *::        . :        :  * .

ref|YP_001086797.1|    LKELNLSDKVFEPKAVISAISGAKDKLYTPKQFKDINMADNRMVKIADIYALYQDRLKRN
ref|ZP_01805266.1|     LKELNLSDKVFEPKAVISAISGAKDKLYTPKQFKDINMADNRMVKIADIYALYQDRLKRN
ref|ZP_01966753.1|     CRKTDIDTKRFKERMLLSVISSAKNEMILPEEFELNAGGDFVQLKIAKVYKEYEAQMRAN
ref|ZP_01188985.1|     LKELNLDPKKTRPRAILSEISRAKNELIDPRSYANNVG-DYFQDITARIYPLYQERLKES
ref|YP_001681547.1|    LKELNIDEKRFKPQAVGAAISSAKNRLVGPVAFERQAY-DHFAQISAKVYHIYQKKLKAH
RAAC02361              GKNPHGVGPVMKLGEAISAIAKAKADALGP---------HQVSDPLTKVYAAYETLKAER
                        ::  .       .      :  *: **    *             : :*  *:

ref|YP_001086797.1|    SALDFDDLIKTVELFKANDEVLAYYRSRFRYIMVDEYQDTSKAQYELIKLLAREHQNIC
ref|ZP_01805266.1|     SALDFDDLILKTVELFKANDEVLAYYRSRFRYIMVDEYQDTSKAQYELIKLLAREHQNIC
ref|ZP_01966753.1|     NALDFDDLLVKTVQLLETQPDVRENYQERFRYIMVDEYQDTNTVQFRLVSLLAGKYRNLC
ref|ZP_01188985.1|     NALDFDDLIMKTIEVFVDNPMVLEYYQERFKYILVDEYQDVNFAQYKLVQLLANKYRNLC
ref|YP_001681547.1|    NAMDFDDLLVNGVCLFREFPHVLDNYQDRFRYIHVDEYQDTNHAQYVLVKLLADKYRNLC
RAAC02361              KTLDFEDMILHAIRLFRTDEAFAKRWRQRWRYVMVDEFQDTNTAQWLFLLELVKAHNNLF
                       .::*:::*   :  : ::    :    .   :: *:*:  ***:**..  .*: **  *.  .:*:

ref|YP_001086797.1|    VVGDDDQSIYGWRGADIRNILEFEKDYDNVHVVKLEQNYRSTQVILDAANKVISNNIERK
ref|ZP_01805266.1|     VVGDDDQSIYGWRGADIRNILEFEKDYDNVHVVKLEQNYRSTQVILDAANKVISNNIERK
ref|ZP_01966753.1|     VVGDDDQSIYKFRGANIRNILDFEKEFSDAKVIKLEQNYRSVGNVLEVANSVIRNNKGRK
ref|ZP_01188985.1|     VVGDPDQGIYGFRCADIRNILNFEEDYPEARVIKLEQNYRSKEKILKAAHHVIRNNTARK
ref|YP_001681547.1|    VVGDDDQSIYGWRGADIQNILDFERDYPEAVVLKLEQNYRSTGKILEAANNAVVGNNRGRK
RAAC02361              VVGDDWQSIYYFRGARPDLMKEFLRRFPDAKRVTLETNYRSHDLIVDVGRRIIRLNDGHQ
                       ****  *.**  ****     : * .  :.  ..:** **** ::....  ::   *  ::

ref|YP_001086797.1|    RKK---LWSEKKEGELIKIQLTGSEIEEADFIADSIAQIARKENRPYKDFAVLYRANAQA
ref|ZP_01805266.1|     RKK---LWSEKKEGELIKIQLTGSEIEEADFIADSIAQIARKENRPYKDFAVLYRANAQA
ref|ZP_01966753.1|     EKT---LWTDNEKGEKIRLRQFDTAYDEAQFIAEDIKDETAQG-ANYSDHAVLYRTNAQS
ref|ZP_01188985.1|     EKR---LWTKRGKGEDLKLYVAFDDKEASYVCRKIKELKREKNYKFSDFAVLYRTNSQS
ref|YP_001681547.1|    SKK---LWTQNPSGQPIVAYQGETEHDEARYIVRTIKRLSESENRPYRDFAILYRTNAQS
RAAC02361              LPKRVVAHRSMPEGAIAQIVTVRSDLEEARFVAQELQRLRKEHGVSWSDCAVLYRTNIQS
                            .*                  :**  ::       :       . *  *:****:* *:

```
ref|YP_001086797.1|    RPVEDALNRSQIPYNIYGGTKFYERKEIKDLLAYLRVIQNPQDDISIKRIINVPRRGIGL
ref|ZP_01805266.1|     RPVEDALNRSQIPYNIYGGTKFYERKEIKDLLAYLRVIQNPQDDISIKRIINVPRRGIGL
ref|ZP_01966753.1|     RLLEEKFVAMNIPYKIVGGINFYSRREIKDVLSYLKTIDNGKDDLAVRRIINVPKRGIGL
ref|ZP_01188985.1|     RSVEEMMVKYAIPYQIVGGFRFYDRMEIKDILAYLRVIYNPSDEVSLLRIINRPKRGIGQ
ref|YP_001681547.1|    RVLEEHFMYAGIPYRIFGGLRFYERKEIKDIVAYLRFISNPADAVSFRRVVNVPKRGIGD
RAAC02361              RLFEEALADADIPYHVVGDKHFYESPDVKIILDYLRTTQDTSDPTVWGHLLNRPKRYIPI
                       *  .*: :     ***.: *. .**.   ::* :: **:    : *     :::* *:* * ref|YP_001086797.1|    RTIEKIEDRANLKQESIYSVLIDIETNSDISTKARASISGFVDIIGTLRTIKEVYPVSKL
ref|ZP_01805266.1|     RTIEKIEDRANLKQESIYSVLIDIETNSDISTKARASISGFVDIIGTLRTIKEVYPVSKL
ref|ZP_01966753.1|     TTINRIQESAAARGIGFYDALSAPDLIPGIGRSASK-LDSFAALIEYFKGRSEESGVTDL
ref|ZP_01188985.1|     GTISKLSRYARERGISLYKAGTEAESNPYLTASFKKRVKAFFDLLEELREKSETLSIDTL
ref|YP_001681547.1|    ATVQKLLEHADSEGWTVGEALARVGEVPGLSR-AVKALSAFGQMIEELRREAPSLLVTQI
RAAC02361              DVVHEVQHGG----------------WEAVVAHPKCRAFVTTIDTLRRIEE--PSKAI
                       .: .:   .                          .*   :  ::           :

ref|YP_001086797.1|    IEKVLDTTGYMDELVEIRNKNEKDLTGKGEEAQDRIDNLREFISIALEFESSNDDTYENK
ref|ZP_01805266.1|     IEKVLDTTGYMDELVEIRNKNEKDLTGKGEEAQDRIDNLREFISIALEFESSNDDTYENK
ref|ZP_01966753.1|     LTEVIEKTGYTESLEADDP---------EELEARVQNIDELVSKAAVYEESCSDRGERP
ref|ZP_01188985.1|     THQVVTRTGYQRELNEEGT---------QQARNRLENIQELFS---VIEEFMKG-NENK
ref|YP_001681547.1|    VEAILNRTGYVRELEAEKT---------EEAKGRIENIKEFLS---VTKEFDRT-ADDK
RAAC02361              QWLVDNHPGLVRQQDEDEP---------------IKWVDSLIAS----------ASRYK
                          :    .*  .                        :. : .:.:

ref|YP_001086797.1|    DLETFLTSIALTSESNDE-EDNDRVSLMTIHTSKGLEFPVVFLTGMEEGLFPISRAIKSM
ref|ZP_01805266.1|     DLETFLTSIALTSESNDE-EDNDRVSLMTIHTSKGLEFPVVFLTGMEEGLFPISRAIKSM
ref|ZP_01966753.1|     TLSGFLEEVALVADIDSVAEDRDYVILMTLHSAKGLEFPHVYLAGMEDGLFPSYMSISGD
ref|ZP_01188985.1|     TLGAFLEEVSLISDVDNMEDNQNVVTLMTLHSAKGLEFPVVFIIGMEEGLFPHANSMM--
ref|YP_001681547.1|    TLEEFLAGVSLVSDTDNYNEDEDAVVLMTMHSAKGLEFPVVFVAGMEEGVFPHSRVQF--
RAAC02361              TVASFLRFVDWIIE-KSKEPKDEAVQLMTIHKAKGLEWTTVFVAGLAEGLLPHKKALK--
                         :  **   :    :  ..   . : * ***:*.:****:. *:: *: :*::* ref|YP_001086797.1|    SDSQIEEERRLCYVGITRAKEELYM---------------------
ref|ZP_01805266.1|     SDSQIEEERRLCYVGITRAKEELYM---------------------
ref|ZP_01966753.1|     DPEELEEERRLCYVGVTRAEEKLTLTCAR-----------------
ref|ZP_01188985.1|     DHEELEEERRLCYVGITRARDELYLTRAR-----------------
ref|YP_001681547.1|    EETQVEEERRLCYVAITRARERLYLARA------------------
RAAC02361              -GEELREETRLCYVAATRARDNLYLMAAKWYGDKEREVSRYVNAVKNP
                       ::.** *****. ***.:.*  :
```

FIG. 60

```
ref|ZP_02406784.1|      ----RRHARRRGGGDDRRIAVVEQRLHARQIVVVHVDRAHLMRIRAELAAEPRRE-VLLQ
ref|YP_335221.1|        ----RRHARRRGGGDDRRIAVVEQRLHARQIVVVHVDRAHLMRIRAELAAEPRRE-VLLQ
ref|ZP_02485527.1|      ----RRHARRRGGGDDRRIAVVEQRLHARQIVVVHVDRAHLMRIRAELAAEPRRE-VLLQ
ref|ZP_02509777.1|      ----RRHARRRGGGDDRRIAVVEQRLHARQIVVVHVDRAHLMRIRAELAAEPRRE-VLLQ
RAAC02362               MFPVPYILLIRTYVRIRGVRMNRPTALLRQLLILELIQAHIVRERARVKAQMRAEGLHIV
ref|YP_157691.1|        -------------VQILDVRLKRVDL---PLEVSESVYRRMEAERKRVANELRSEGGAIA
                                             : :.      : :.     ::    * .:  : * *     :

ref|ZP_02406784.1|      ERREHVVQQPDVRVVRAHERDHVQPAFAQQQLQ--AERA-----
ref|YP_335221.1|        ERREHVVQQPDVRVVRAHERDHVQPAFAQQQLQ--AERA-----
ref|ZP_02485527.1|      ERREHVVQQPDVRVVRAHERDHVQPAFAQQQLQ--AERA-----
ref|ZP_02509777.1|      ERREHVVQQPDVRVVRAHERDHVQPAFAQQQLQ--AERA-----
RAAC02362               ERQDGDMDIRVEFRVGDHYDEAVFMRKMLEAEAANRAKRTGMISR
ref|YP_157691.1|        EKIRADADRQREVIIAEAYRDAQQAKGAGDAKAT------GI---
                        *:       . : :. :   :              : :
```

FIG. 61

```
ref|ZP_02329650.1|      --KRVIF-LADCQSFYASVEKAHHPEYRNR----------PLVVAGDPARRSGIVLAACPL
ref|YP_001421775.1|     -------LVDMQSFYASVEKAEAPHLKSR----------PVIVSGDPERRSGVVLAACPL
ref|YP_177318.1|        -------LVDMESFYASIEHAANPQYDGR----------PLVVSGDVNRRSGVILAACPL
ref|NP_243607.1|        MDKVIF-MVDMESFFASVERANHPELSGR----------PLLVSGDPERRSGVILAACPV
ref|YP_001681084.1|     -------LADMNSFYASVEMAHNPTLRGQ----------PVLVCGDPERRHGIILAASRE
RAAC02363               MTKLIYGLVDMQSFYASCEVASREEYAARRKEFDDSTDPPLVVSGDPARRSGIILAATPT
                          .*  ::  *      :              *::*.     *::*** ref|ZP_02329650.1|      AKKYGITTAERLGEAINKCPDLVVVRPRMQEYIKVSLQITEILQSYTDLVEPLSVDEQHL
ref|YP_001421775.1|     AKRYGVKNAERLWEAQAKCPDAVIVRPRMQRYIDVSVMITELFERYTDLVEPYSIDEQFL
ref|YP_177318.1|        AKAKGVRNAERLFEAQQKCPDLVVVKPHMQRYVDISLQISKILGTFTDLVEPYSIDEQFM
ref|NP_243607.1|        AKARGVTNGERLWEAQQKCPEAVVVRPHMQQYVTVSVQITEILERFTDLIEPFSIDEQFM
ref|YP_001681084.1|     AKRRGVKTAMTVGEARAICPDAVCVRPRMSLYLEVSWQIQQIARTLSPLVEPYSVDELFI
RAAC02363               AKRYGVENAMRLGEALRLYPRLIVVRPHMAFYLHVSVRIQMLMQQCFPFQEQFSVDEGFI
                        **  *:   ..  :  **       *    : *:*:*   *:  :*    :    * *:** .:

ref|ZP_02329650.1|      DVTASIKLLGSPQEIAKSIQSRVWNETGVYTRIGISENKVLAKMACDNFAKKNGDGIFYL
ref|YP_001421775.1|     DVTGSRRLFGDPFTIAKSIQQAIMREFGIYARVGIGPNKALSKMACDHFAKKNASGIHRL
ref|YP_177318.1|        DVTGSQKLFGPPYEIAEKVKQAIMDRFGVKARVGIGENKVLAKLACDNFAKKSSEGIYWL
ref|NP_243607.1|        DVTHSQRLFGAPREIAQKVQQAIWHETGVRARIGMGESKVLAKMACDNFAKKMPSGVFHL
ref|YP_001681084.1|     DVRGAEHIWGDAVEAAGIFRQRVWEAVKVPCSVGVGPNKFLSKMACDVEAKKSPSGVALW
RAAC02363               AFPYPSNLFPDPIAAARNLQARIWDQFRIRARIGLAPNKWLAKMAN-KAAKKTPGGIVWW
                        .   ..:     .  *   .:   :      :  :*::. .*   *:*:*     ***   *:

ref|ZP_02329650.1|      PKTEMEQKLWPLPVNKMYHIGSRMTRHLKRMGIHTIGDIACASVLRLQKRWGINGEVIWR
ref|YP_001421775.1|     DMSNIRQDLWPLPVGKLFGIGKRMEHHLRRMGISTIGGLAGHPAELLKKRWGINGELLQR
ref|YP_177318.1|        RKDSLDLDLWCLPIEKLFGVGRKMSVHLRNMGIRTIGQLAQTDGARIKKRFGVHGQVLWM
ref|NP_243607.1|        TKERMERLLWPLPIECLYGVGRQMTKYFRNQGIRTIGQLANTSLERIKGKWGVNGHVLWL
ref|YP_001681084.1|     RVDDVEAKLHPLPIGKMFMVGSRMERHFRNMGLLTIGDLAHYPVDYLMRRFGLRGAVYIN
RAAC02363               REEDIPSVLHPLPVEEMWGLKRRAEVLRRKFKCETIGDVARLPVGVLKAEFGVWGEVIHR
                          :    *  **:  ::    : .       *** :*    :          .:*:  *  :

ref|ZP_02329650.1|      IANGLDDSPVTPDT-YIGQKGVGHQMTLPRDYMTINELLVPLLELSELVCQRCRAKGYMG
ref|YP_001421775.1|     TARGIDPSPVTVNT-HSRQKAIGHNMTLPRDYSRFEDIKVVLLELSEEVARRARFKQYIG
ref|YP_177318.1|        SANGEDYSPVTRAA-HARRKGYGNGMTLPRDYVKKEDICVVLLELCEEVCARLRQDGWMG
ref|NP_243607.1|        TAHGIDPSPVTPHS-HDKQKGIGHGMTLPHDYVKAEDIHVVLLELCEEVCKRARRAHLMG
ref|YP_001681084.1|     LAWGRDGSPVRPDS-LEQTKSVGHSVTLPRDYHHSDDIELVLLELTDEVCRRARKLGKAG
RAAC02363               WANGIDVSDINPDSYHAPHKGFSHRTTLPRDFYERSEIAVVILELLDEVCHRLRQAHQAG
                          * *    *        *     *:    ***:*  .  :: .:*** : *. *  *   * ref|ZP_02329650.1|      QVVSVGCQGTDFDYPTGFHRQMKLEDPTNLSDEVNRAVVLFKRHWNGLPVRKISVSLTG
ref|YP_001421775.1|     HTVSIRGADFEFPSDFHRQRKLVSPTNFGMDIFKTAVKLFKEHWNGEPVRSAGVSLSQ
ref|YP_177318.1|        STVSLSVNGADFVEKRGFHRQYTIPFETNITMEVYEAACALLERFWDGYPIRRLSIGVSN
ref|NP_243607.1|        RTVAIGVSGANMETPTGFHRQMKLTNHTNITMEVYEGAATLFERFWDGKPIRRLHVNLSN
ref|YP_001681084.1|     RTVSVGLR--AYDLTRGFYRQTTLPSPSNLSGPVFEKAQLLFRRHWDGRPVRTVTVDLSG
RAAC02363               RRVGLGLTYEGLTG--GFYRARTLPRATNDPAELYPVLLALLDEHWDGSGVRAVSVAVDM
                        *.:.       .*:*    .:    :*       *:  ..:* :*   :     : :

ref|ZP_02329650.1|      LVRDDTFQLVLFED---RMKKLALEKALDGIKDRFGNASIMRAVSLTAAGQAKDRSMKIG
ref|YP_001421775.1|     LEPCDYVQLSLFDA---QEKKISLGKVLDDIHERYGPASLLHAASLTEAGQAFHRAEKIG
ref|YP_177318.1|        LQSDQNWQLSLFDDNASRDRLSTIGYVMDGIRQKYGKLAIQRASSLQKASQLRDRSQKIG
ref|NP_243607.1|        LTSDEAWQLSFFGN---RDRAHQLGYTMDTIKEKFGDTAIRRAVSFLSASQAEERAKKIG
ref|YP_001681084.1|     LEEDGTLQQELFRD---MDRQDRVSRTMDRIRDAMGTTAIVRASSLLPAGQARDRAVKIG
RAAC02363               LQFRETLQLSLFEN---VPARTRLYETVDEIRARFGETSIMRAVSLTRAGQLRERSLRIG
                         *     * :*    *  :*        :   .:* *:   *  :: :*   *:.  .*: :**

ref|ZP_02329650.1|      GHY-
ref|YP_001421775.1|     GHY-
ref|YP_177318.1|        GHY-
ref|NP_243607.1|        GHY-
ref|YP_001681084.1|     GHY-
RAAC02363               GHYA
                        ***
```

FIG. 62

```
ref|ZP_01860132.1|     -RDRGRIKWTS--MMLPEHVKVLRDWAKEDSYEQRKEIDEQHLEELSEITAEAMEYGRLV
ref|ZP_01171904.1|     IRDRGRIKWTS--MMLPEHVKLLRDWAKEDTYEKPKELDEQQLEQMNETLAEAMEFGQAV
ref|YP_079689.1|       LRDRGSIKWVS--MMLPEHVELLREYHESFQKIKKPILDEQKYEEFNEIICEAMAENRFL
ref|ZP_02329649.1|     -------LWESSRMMLPEHREQLLEQRRELKKHAKPLLDEQRLEELSTILNYALATKHKV
ref|YP_001487332.1|    -------MWESSRMMLPEHREQLLAQKRKKKEYTPPPLSTDQLEEMNFLITQSITEDQAI
RAAC02364              MNIRDGNIFEAMRLVLPEHRALMAQIQRERMKRKPMLTEERLEEMQYVLSEAIREGRIV
                              : :   ::****   :    ..    :   :: *::.    ::   : :

ref|ZP_01860132.1|     TITHYVGRRHELLIGRI-------------------------------------
ref|ZP_01171904.1|     AITHFRTHRHELVIGNIHYWDEIGQKLHVIDHFGEVHRIPLNTVADV-----
ref|YP_079689.1|       QFAYYRQGEVKTLAGRIHYADALKRELRIVSRADEICILKIEDIIEIEYD--
ref|ZP_02329649.1|     RFTVYDVYEDQHIAGVLIKYDPLTRSLGVISEANKAMHIMLENIIDVRLE--
ref|YP_001487332.1|    CVTYAAAGRKEQFWGWVKTIHYETQRIKIVND-EDVLNLSLQQ---------
RAAC02364              RVTMFTPERDVVLVGRVS---ARGRELR-VRTAAGVHIVDVRDVVGVEMERS
                        .:         .   . * :
```

FIG. 63

```
ref|YP_161675.1|      ------------------------------------------------------------
RAAC02366             MRSSKTMHKEGDLLVVDTWTGREERFSYDEASAKRSEWLSQYENRERYRFYCLCRGHERI
gb|ABH06559.1|        ------------------------------------------------------------
gb|AAB95339.1|        ------------------------------------------------------------
ref|YP_001202661.1|   ------------------------------------------------------------
ref|ZP_01614696.1|    ------------------------------------------------------------ ref|YP_161675.1|      ------------------------------------------------------------
RAAC02366             RLHLVKREHWHLASNPGQARLHAPHCGFYRNEVVRIVERRKKQFGIETVETVNEKGERVA
gb|ABH06559.1|        ------------------------------------------------------------
gb|AAB95339.1|        ------------------------------------------------------------
ref|YP_001202661.1|   ------------------------------------------------------------
ref|ZP_01614696.1|    ------------------------------------------------------------ ref|YP_161675.1|      ------------------------------------------------------------
RAAC02366             SLIFHVDDFFSADQEQTEEHEPPTPNMSSAAETERTILPEKRIIVRGERKERGKLTFSGF
gb|ABH06559.1|        ------------------------------------------------------------
gb|AAB95339.1|        ------------------------------------------------------------
ref|YP_001202661.1|   ------------------------------------------------------------
ref|ZP_01614696.1|    ------------------------------------------------------------ ref|YP_161675.1|      ------------------------------------------------------------
RAAC02366             LREWYRVGLQWYEHHQQRQAKNVSELLYGMWRVMLDGTITFHDGKDPRALLFIPNRYVEP
gb|ABH06559.1|        ------------------------------------------------------------
gb|AAB95339.1|        ------------------------------------------------------------
ref|YP_001202661.1|   ------------------------------------------------------------
ref|ZP_01614696.1|    ------------------------------------------------------------ ref|YP_161675.1|      ------------------------------------------------------------
RAAC02366             WHGERQKIVVGQLGDRSRSGSGEFWRVDGIYAKGTSLRANWNVLVSEVHLCPNPHIGALV
gb|ABH06559.1|        ------------------------------------------------------------
gb|AAB95339.1|        ------------------------------------------------------------
ref|YP_001202661.1|   ------------------------------------------------------------
ref|ZP_01614696.1|    ------------------------------------------------------------ ref|YP_161675.1|      ------------------------------------------------------------
RAAC02366             ALRVKHETDQLMSVCPAKQALIVERDGCAWVDSLVEYQFHEILMNGLQRRPDVKVEKPLE
gb|ABH06559.1|        -----EQTEKSHPRSP-----------------------NVLSVALSQRTTAPEEELNP
gb|AAB95339.1|        ------------------------------------------------------------
ref|YP_001202661.1|   DNLSEYHSILMTSEDP-----------------------DPDLEGEAAKEAREKDEADD
ref|ZP_01614696.1|    ---YRNEVMWLYQHKN-----------------------KHYRVKNLQDALEQG-YTVAA ref|YP_161675.1|      ---------PDFIL-TDVAPEVVIEVLGMSGNADYDARIAEKRAHY--LAS-G-IPLLEW
RAAC02366             GLVEYDGRRPDYVLRMEGKPPLIIEIWGMSGKTDYDESKEKRQAFYRQLEKRGELRFLEW
gb|ABH06559.1|        KILALQNAQRKRKIEHDGS---LFQAVGIGTLLQQPDDRATTTS----------LSWKRV
gb|AAB95339.1|        ------EEQTKGAITFES----VAREWHAAN-KKWTEEHSRRV-----------LKSLED
ref|YP_001202661.1|   RRLSYLGTQLDLLLNQKKP--LQKALWGISDEILALDTKEERQA----------------
ref|ZP_01614696.1|    HVGSYYGEQFEHLKNIYPK----QIIFTGAAKTRFALLAKQRV----------------- ref|YP_161675.1|      D-------------------
RAAC02366             DSRNPRERAAVLRNIGLWMKK
gb|ABH06559.1|        KGCKSSEQNGMEQKTIIFIPS
gb|AAB95339.1|        N---------------LF---
ref|YP_001202661.1|   ---------------------
ref|ZP_01614696.1|    ---------------------
```

FIG. 64

```
ref|ZP_02093159.1|    ------------------------------------------------------------
ref|ZP_02091713.1|    ------------------------------------------------------------
ref|ZP_02423704.1|    -----------------------------------------------------------A
ref|ZP_02026447.1|    ------------------------------------------------------------
ref|YP_001127515.1|   -------------------------------------------------------PEAIEE
RAAC02367             MYDGRQTVVREATALQQPQWTRDIVMVNPNELVPHPRRDEAGERYDTPEAMDNLPTNLVS ref|ZP_02093159.1|    ---SVEQYGVLSPLIARPRP--EGGYEIISGHRRQHAAQLAGLDTLPVIVRQMDDDAAVL
ref|ZP_02091713.1|    ---SVEQYGVLSPLIARPRP--EGGYEIISGHRRQHAAQLAGLDTLPVIVRQMDDDAAVL
ref|ZP_02423704.1|    LAESIKMHGVVSPIIVRPLENTADEYEIISGHRRVMASRKAGITEVPALVVSLDRDAAAI
ref|ZP_02026447.1|    LTESIRERGVLLPILVRKTN--DEEYEIISGHRRTHAARLAGLEKVPVIIRELSNDDATI
ref|YP_001127515.1|   LKQSILQHGILQPLIVRRSL---KGFEIVVGERRYRAAKEANLPSVPVVVRELTDEQMME
RAAC02367             LQANILQNGIREPLLVQRST-----NILMTGHFRRAVAIQAGWTEVPVQYLDVTDEEAYA
                       .:    *:   *::.:       ::  *.*  .:  *.   .:*.   .:  :

ref|ZP_02093159.1|    LMVDSNLQR------ENILPSERAFAYKMKLEALKNQGARSDLTSVQVAP--------KL
ref|ZP_02091713.1|    LMVDSNLQR------ENILPSERAFAYKMKLEAIERTVGRPKNVG-QVVPD----YFGKR
ref|ZP_02423704.1|    VLVDSNLHR------EHILPSEKAFAYKMKAEALAHKGYRTDLTSVQVAP--------KL
ref|ZP_02026447.1|    VMVDSNIQR------EEILPSEKAYAFQMKLEAIHHKGIKG----------------AE
ref|YP_001127515.1|   FALLENLQR------EDLNPIEEAMAYKMLMDKLH-------------------------L
RAAC02367             IMLADNWERNTGIMEDYMAVARNMFYFALRLKLLNEIDDDSVDISPSRKQEGTVPSFSSE
                       .  :  .*  .*         : :      ..   :   . :

ref|ZP_02093159.1|    STEKIGEEVGMSKDNVKRYIRLTNLVPELLDMVDEKKIAFNPAVELSYLDEAQQRDFLE-
ref|ZP_02091713.1|    STEIVAEGTGESYKQVQRFIRLTNLIPELLDMVDEKKIAFNPAVELSYLDESQQRDFLE-
ref|ZP_02423704.1|    ATEQIAEDAGTSKDTIKRYIRLTNLIPEILQYVDDGRIAFTPAVELSYLNEQEQYDLL--
ref|ZP_02026447.1|    SREVVGEANGLSGRQVSRYIKLTNLLPELLEMVDKKKIAIKLAVEIAELSESEQQEILDY
ref|YP_001127515.1|   TQEEIASRVGKSRPHIANHLRLLSLPPEVQKLLIDGTLSMGHGRALLGLKKKGKMKSIVE
RAAC02367             IVHLVSKKFERSRAVVRKHFALLKLIPELQHWISEKKIGFEGGAMLAGMSEQAQRDFMRD
                       . :..    *   : ..:  *.* **:  . :   . .  :   :   ..:   : :

ref|ZP_02093159.1|    ------------------------------------------------------AMNDTQNA
ref|ZP_02091713.1|    ------------------------------------------------------AMQDTQNA
ref|ZP_02423704.1|    ------------------------------------------------------
ref|ZP_02026447.1|    FNLGYKVS-----------------------------------LEQVKAIKNKEKS
ref|YP_001127515.1|   R--------------------------------------------------TVREGLNV
RAAC02367             YADWPKISDSDIKAFRNTWESIVERQTNGLGAAEKPISIPEPSSETLVAEWEEMRSDESV ref|ZP_02093159.1|    PSLSQA------------------------------------------------------
ref|ZP_02091713.1|    PSLSQA------------------------------------------------------
ref|ZP_02423704.1|    ------------------------------------------------------------
ref|ZP_02026447.1|    TDIIERPEEKTKESTKVTISRKKLKQYFP--------ENYTKAEMENIIYQLLEKWKSDG
ref|YP_001127515.1|   RQLEKLVQQMNENVSRETSKRKPPEKSVF--------IRESESLLRE-------------
RAAC02367             PHITKYASDAYELSVVADGGRHQPMYSAEKRSISIVDVPEHKTLLARNRLALLVKKQRRA ref|ZP_02093159.1|    ------------------------------------------------------------
ref|ZP_02091713.1|    ------------------------------------------------------------
ref|ZP_02423704.1|    ------------------------------------------------------------
ref|ZP_02026447.1|    YDI---------------------------------------------------------
ref|YP_001127515.1|   ------------------------------------------------------------
RAAC02367             MERMTNELSQQAEALMEEIKEGGLQEMMEDIEQLEFHTKGMLALIENLKLHDREAVQRLS ref|ZP_02093159.1|    ----------
ref|ZP_02091713.1|    ----------
ref|ZP_02423704.1|    ----------
ref|ZP_02026447.1|    ----------
ref|YP_001127515.1|   ----------
RAAC02367             DIFEEFEDHA
```

FIG. 65

```
ref|ZP_00960984.1|    -PQICKGAPMAPRKL-YAGAKLRETRSRLGLTQKDFAARLGVSLPYLNQMENNNRPVSTT
ref|ZP_01903846.1|    -------------------AKLRETRQRLGLTQKDFATKLGVSLPYLNQMENNNRPVSTT
ref|ZP_01880414.1|    -------------------AKLRETRQRLGLTQKDFAGKLGVSLPYLNQMENNNRPVSTT
ref|ZP_01035782.1|    -------------------AKLRETRQRLGLTQKDFAGKLGVSLPYLNQMENNNRPLSTT
RAAC02370             MPRLSKDALVPPEKRDTFIAWLINKRDELGFTQKDMADFLGLSLSYYNAIENRKRNLSAK
ref|ZP_01742943.1|    -------------------RRIDLGLRQGDLALKVGISPAYLNLIEHNKRRIGGK
                                         *   **: *  *;*    :*:*  .*  *  :*:..*  :. .

ref|ZP_00960984.1|    VVLALAQE----------------------------------------------------
ref|ZP_01903846.1|    VVLALAQE----------------------------------------------------
ref|ZP_01880414.1|    VVLALAQE----------------------------------------------------
ref|ZP_01035782.1|    VVLALAQE----------------------------------------------------
RAAC02370             LVIQLASKLPQGPRFAVQLLGPEVVGKYMNLIQLPPEKEEEYEAEDALLDAIQQREKSAT
ref|ZP_01742943.1|    LLVSLAATLAVEPIALTQGGAAAVVAGLKNAASNAPQIDVEEANVDQFL-----------
                      ::: **

ref|ZP_00960984.1|    ------------------------------------------------------------
ref|ZP_01903846.1|    ------------------------------------------------------------
ref|ZP_01880414.1|    ------------------------------------------------------------
ref|ZP_01035782.1|    ------------------------------------------------------------
RAAC02370             DYLGLLRSVLHHSNAVMAVSVQPNLCWFGLTPEDVAIITPVTDLKALIPGQLVYVVDRTA
ref|ZP_01742943.1|    ------------------------------------------------------------ ref|ZP_00960984.1|    ------------------------------------------------------------
ref|ZP_01903846.1|    ------------------------------------------------------------
ref|ZP_01880414.1|    ------------------------------------------------------------
ref|ZP_01035782.1|    ------------------------------------------------------------
RAAC02370             QAGEFAFVRALHGKELTSVESTLMMMLDLPRDTTQLFEWGIDPRRALMSWNADDPNLMVC
ref|ZP_01742943.1|    ------------------------------------------------------------ ref|ZP_00960984.1|    ------------------------------------------------------------
ref|ZP_01903846.1|    ------------------------------------------------------------
ref|ZP_01880414.1|    ------------------------------------------------------------
ref|ZP_01035782.1|    ------------------------------------------------------------
RAAC02370             EVVTICKASPSRIVPLTSPGYEEWSLLERKTILQQGIVYNRLRQEMKETLQKFRRIMATQ
ref|ZP_01742943.1|    ------------------------------------------------------------
```

FIG. 66

```
ref|ZP_01551668.1|      ------------------------------------------------------
RAAC02371               MRMGKADEWEARSEQRADEVSRALVRMGVMTHGQLTRLLGINPKSERDLIRRWWDRFEEQ
ref|ZP_02756730.1|      ------------------------------------------------------
ref|YP_521772.1|        ------------------------------------------------------
ref|ZP_02833143.1|      ------------------------------------------------------
ref|YP_887014.1|        ------------------------------------------------------ ref|ZP_01551668.1|      -------------IKQNNFSEAIKLGESLIANSGQLDHIRINKK---------------
RAAC02371               HNVAKWVASSRYSVPGNRVMRLVRLTDAALTEWAEREGIRRARNRVKPRMLAQTINMGEV
ref|ZP_02756730.1|      -----------YAIIGKRIRNYRKRAGYSQEALAKKAGLFHAYLG---------------
ref|YP_521772.1|        --------MNIGMAREQDKLAMQSSLPTEAQRVLVREHPCKSVELLR-------------
ref|ZP_02833143.1|      ---MADLQAPEWVGAECARRTLSRLSPRKLSTMKAPVIFANEVATG--------------
ref|YP_887014.1|        -KNPRLADDIVSAVAELGPATAGQIEAHLEAEPRGRKGPWWDRSDT-------------- ref|ZP_01551668.1|      -----------LIECSMMLSQIDKANLYKKLSLNDPDYKFYQALIYQKLSRNEKAMK--I
RAAC02371               LIALRRDGALYDEWDMMLPQDGDEGLHAWLVKQDDPDYRMGLFLLPTRLTQEEQGKKGLI
ref|ZP_02756730.1|      ----------------QIERGESKASLRSIFKIANALEMPLEILFENIIQNEKDPE---
ref|YP_521772.1|        ---------------LMGVSDEDQLDIVRWHHEVNESHGLAHNVMARRLLRLADGFV---
ref|ZP_02833143.1|      ---------------LFGHLVGAIAGGAVYRKSTFLLDSLGKQILPEWLTIEEHPHL---
ref|YP_887014.1|        ------------KWVAEALFAAGILTTATRVGFARHYDLAENVLPPEVLAREVGDE---
                                           :    ::      :

ref|ZP_01551668.1|      YQELIR--------------------------------------------SGYRNA
RAAC02371               YHGVIRRVIQNTKIRDTLFLVPRKYYTVALRLLSYIEQVGGGLYVLPFEAFLKNPGWYLD
ref|ZP_02756730.1|      ------------------------------------------------------
ref|YP_521772.1|        ------------------------------------------------------
ref|ZP_02833143.1|      ------------------------------------------------------
ref|YP_887014.1|        ------------------------------------------------------ ref|ZP_01551668.1|      SIYQN--------------------LGYEFASLG-----QHKLAQNYYTEAINI-----
RAAC02371               SIYRGESQQRASLIDVLRPVRKLNMPLQYQFAALVQLPDGRYRMIDTYTSGDVKRVQNWI
ref|ZP_02756730.1|      --------------------------TLSSEA--------YELIDSLTSKEQKAIIKLL
ref|YP_521772.1|        -----------------------------------AKMAARKTRLAMSPLGAAK
ref|ZP_02833143.1|      ------------------------------------RKGLASSPFDSEGVRTER
ref|YP_887014.1|        ---------------------------------------EAVRELALRAATAL---- ref|ZP_01551668.1|      ------------------------------------------------------
RAAC02371               RFVLGYQVPNTGQVAGADVYVFDETMREGLDAVLRMKSKKRFDVSMVEVHAWPEGMVTPK
ref|ZP_02756730.1|      KEIIEYR-----------------------------------------------
ref|YP_521772.1|        SVFLG-------------------------------------------------
ref|ZP_02833143.1|      RDIVKDGVL---------------------------------------------
ref|YP_887014.1|        ------------------------------------------------------ ref|ZP_01551668.1|      ------------------------------
RAAC02371               PGRDELRDAFDEVDDSHIDWDAWLNEPW
ref|ZP_02756730.1|      ------------------------------
ref|YP_521772.1|        ------------------------------
ref|ZP_02833143.1|      ------------------------------
ref|YP_887014.1|        ------------------------------
```

FIG. 67

```
ref|YP_324842.1|      ------------------------------------------------------
ref|NP_486002.1|      ------------------------------------------------------
RAAC02372             MAKRMHPVNKLNLEMLKNSNDPLDMLRQWGILMSTVYETLTQLTMNEDDE
ref|ZP_01733540.1|    ------------------------------------------------------
ref|XP_660834.1|      ------------------------------------------------------
sp|Q7ZXB1|MCM7B_XENLA ----------------------------------------------------GL ref|YP_324842.1|      ------------------------------------------------------
ref|NP_486002.1|      ------------------------------------------------------
RAAC02372             LVTEYLSGI-EELDDKIQEYLYEEAAARIAHFDERTSKVVFDQWPTGLCL
ref|ZP_01733540.1|    -------------NPVHHYKMNVGLLQQNDYADFIVVEDLVNFKVSKTF
ref|XP_660834.1|      ------------SRNDQELAKYGAVALRLAMLVGALVDAEERRQELQ---
sp|Q7ZXB1|MCM7B_XENLA LSETYLESHRLVKMNKTEDDELGTEELSEEELRQITEEDFYEKLAASIAP ref|YP_324842.1|      -------------------HGSKDQQHPLYNR----DRPF-I---------
ref|NP_486002.1|      -------------------HGSKDQQHPLYNR----DRPF-I---------
RAAC02372             VPSNFGFEIRNLPVWMLGHGAKRKHHPLYHR----DRPF-IRRRQLWYWL
ref|ZP_01733540.1|    ING----------ELVAENGISNVKHVPFDR----PNNFNITTKTISDFE
ref|XP_660834.1|      ----------------GNGRSVSYSIAWMS----EEQQ----QRLQEIL
sp|Q7ZXB1|MCM7B_XENLA --------------EIYGHEDVKKALLLLLVGGVDHSPRGMKIRGNINVC
                                                  :

ref|YP_324842.1|      ------------------------------------------------------
ref|NP_486002.1|      ------------------------------------------------------
RAAC02372             VHELKWNYLNSVASWDDSLLPKNPPRYAHMNIRFMSRNDYEIRDLDNYVV
ref|ZP_01733540.1|    IES-TASKIRVIE-----------------------------------
ref|XP_660834.1|      GQRHPETYLSVRY-----------------------------------
sp|Q7ZXB1|MCM7B_XENLA LMGDPGVAKSQLLSYIDR------------------------------- ref|YP_324842.1|      ------------------------------------------------------
ref|NP_486002.1|      ------------------------------------------------------
RAAC02372             SLPMIVNALVANGLIQSDRPGYFTYSVEWVQKHEQDEVQEPTTTLRVRYL
ref|ZP_01733540.1|    ------------------------------------------------------
ref|XP_660834.1|      ------------------------------------------------------
sp|Q7ZXB1|MCM7B_XENLA ------------------------------------------------------ ref|YP_324842.1|      --------
ref|NP_486002.1|      --------
RAAC02372             ERPNVSTL
ref|ZP_01733540.1|    --------
ref|XP_660834.1|      --------
sp|Q7ZXB1|MCM7B_XENLA --------
```

FIG. 68

```
ref|YP_001236354.1|    ---------VVRTGAAMTIRFRRITDG---DLPAIRNWLH-QPHIRQW----WGDPDEQY
RAAC02296              MGEFMCHPPVLRIGARREIRGRRIREGRHPGLSDLREFLLTEPHIRHR----QADHDDHH
ref|XP_001563017.1|    -----------HLSSHVAER-NDQHER----VDDWRGVPPKLPGSSYR----YEERHPQQ
ref|ZP_01776409.1|     ----LCQPP--RLHDRRRHRGRRLREQG--RPGQIRGVLDLHQDGRQQPLEAERDQPEVT
ref|ZP_01565636.1|     --------------RREQHDQRQHGR----RADFHPVLLADEHHGQR----AADEQDHR
ref|XP_001615133.1|    ---------------KSSLKGAKKKKGRGSYTDDLAEHETTWENKKRR---RSAEGDNHD
                                      :                                  :

ref|YP_001236354.1|    GLIDGDRDEP--------------------------------
RAAC02296              EQPDDDLPHPPR---LLSCST-IRFESEHFTPRVRHIFIHLHSRA
ref|XP_001563017.1|    RHMAHHHHQPA-----------------------------
ref|ZP_01776409.1|     APPDIGLKPPLKGTGSARCRSPFSELAARLRPKKWRLFVELH---
ref|ZP_01565636.1|     PREPREQPHPQR----------QVRAARFE--------------
ref|XP_001615133.1|    EQEDDEEYEPKR-------KVPRKDMDDDYEHNT-----------
                                  *
```

FIG. 69

```
ref|YP_001376930.1|    ------------------------------------------------KLKTYKVEG
RAAC02373              MLTIGLDVGNGSIGLCVRDGDTLVQDTTPSVYGRVDPTRQVLSVPGKSAPRKVDVFTFGG
gb|AAW81277.1|         ------------------------------------------------------------
ref|YP_001312077.1|    ------------------------------------------------------------
ref|ZP_02852259.1|     ---VGIDLGYGYVKFIDGKEP----KMFPSVVGYGNSQKYKSALQLDLNPLDDLQIKIGD
ref|YP_001642790.1|    ------------------------------------------------------VYTYEG ref|YP_001376930.1|    TEYVWGDDIIKVNN--TLNTYAQQNRYKTNQYKTLSKIALAEMAAKTNVKS--YDEILVI
RAAC02373              EHFVLGYKNVHAMHSTPIGAYDREQRYASRQFETLAKLALLDAATRTGRTG--VIEVVVA
gb|AAW81277.1|         ------------------------RYNSEAFKLLANFALGLLASDFKIANNQVLEVVVT
ref|YP_001312077.1|    --------------------------------------------------------VRVI
ref|ZP_02852259.1|     EHFFIGDLAIRQSEVASRSLGKDRSQDKNARVLMLTALSLLSSWDKQ--------GFNLV
ref|YP_001642790.1|    IRYVIGEAQG------ISSSARNDDRYSSAGYRTETILAISQLVKDGS-------EIVVG
                                                                                . :

ref|YP_001376930.1|    TGVPSEEIG---TKAVDEIKEVYQGAHDLEVNGKKVSINVVDVIVLAQPVGTVMSRYLDE
RAAC02373              CGTPSEDFT---TRTVEIMQRWFSEPVTGAKNGEQVVVMIKRLEVIPQPFGVFLDAYLDQ
gb|AAW81277.1|         AGLPTGDYAD--QERLRSLLKVLEGQHQVTIDDQIVTVRVRKVYILPQPIGTLYNELLDD
ref|YP_001312077.1|    TGLPAQFFA---EQKNSLIKALENRRVFMKLNGENRSFTITKVIVFPQSAG---------
ref|ZP_02852259.1|     TGLPTNFYAAFAEEWESTLNGEFKTKMKIGGGKTQERSFQIEEVTTLPQPFGTLYDQVLNS
ref|YP_001642790.1|    TGLPSEDYKN--GDNHEKVKRNLVGEHTVQIDGKTKTFSILRVYTPMQPIGSVVNRIYDY
                        * *:           :        .    .   .: .:     *.  * ref|YP_001376930.1|    DGFVADDTYED--MTVGIIDIGTGTTDLDVISMLRREKE-STSVPKGMHDVYEPIVAKIK
RAAC02373              DGLVVDEELEK--QDVLVIDSGSGTLDLSEIHRLELTR--QTSIPAGLNDVYQLILEEIR
gb|AAW81277.1|         QGFIKNKALLD--EKVGIVDVGGGTILIDTILNFELSGKNRQQFNTGVNDLYEAIASRIE
ref|YP_001312077.1|    -LFLYDKSLVE--KDTLVVDIGGGTLDIAYMSNGQFKEG--RTYPLGVNPTYDVLLQELT
ref|ZP_02852259.1|     VGKVVDRDLTD--SKIGIVDIGFKTTDLAVSDGMEFINPLSFSTTTGLSNVNRLVNEKLR
ref|YP_001642790.1|    NLKVRKDMESERTARKLVIDIGFGTTDVCEAEGLRIVRY--DGVQVGMLEANRIIKDELS
                                       ::*  *   *  :     .         *:      :   .:

ref|YP_001376930.1|    K-----------ETS---ATINDYKLEKVFEEGAYQASKRMDPID-FNDE--KTASIKE
RAAC02373              R-----------EEPKVYATAYDLEAQLRAQDGAQEFWFEYGALR-MNITNLRERAMRQ
gb|AAW81277.1|         G-----------DVS-----LYQLEKELRHGNQQHQWSYRFSKNRQDDITELVGKESDR
ref|YP_001312077.1|    K-----------YGVN-------YSNRMKAEQIIADKAIFVEGKE-IDVSKDIDNVLSL
ref|ZP_02852259.1|     H-----------EFKID-------REEHQLDDCINSQKIMVAGKS-EDISSWVREALQT
ref|YP_001642790.1|    KRGARGIVSLLHMDTLLRNAKREYVKDEFTDKEILSKVIIEIGGKE-YEIKDLMEQALEY
                                                                   .    :   .    :

ref|YP_001376930.1|    VYDFIVNGVNNAWKTFDRFDEVLVSDGGANTF-HELLEEWIGKVTKLEES--QTANVEGF
RAAC02373              VWDRMQQGIQYAYPDRSSFGRVILAGGSGEAF-RNYFLAWMPSIRIAPEP--QLAVARGL
gb|AAW81277.1|         FTRRLVANVTSTLKNLDSIDTLFFTGGGANLINQKILKTTFTNAAIVKDT--EVANVNGF
ref|YP_001312077.1|    RAGEIINAIKQAFPEQSKYSRFVFIGGGALLLKNY-------------------------
ref|ZP_02852259.1|     VSDKISVEIESKWDYRD-FDTLLLTGGGGEML-YPYLKDKFPNLVLVEDP--QTANVRGY
ref|YP_001642790.1|    TARIVMQRVDNLGYVLKDYDVVLFTGGSLLAL-HKYIKPYLTGVNTKAEQGAQTANVKGY
                         :      :            .   ....*.   :

ref|YP_001376930.1|    YRYGKFEVGEE-
RAAC02373              YKYALAQGAEES
gb|AAW81277.1|         YKYGLSQQVQE-
ref|YP_001312077.1|    ------------
ref|ZP_02852259.1|     QKLA--------
ref|YP_001642790.1|    TKYAMIQDAK--
```

FIG. 70

```
ref|XP_001467069.1|     LVSTWPQSRRFLESRILQTADMQAEDMISGDGGS-----QHIEDDSVSVTPSTS------
ref|YP_001208199.1|     --------------------------QGAGGL-----SGMQSSSPSSSSSTP------
ref|YP_946581.1|        --------RRLAERLTARLNEIYAERQLMAVGGSEWAAPGAAPQSNPGIPASTA------
ref|YP_001376929.1|     ---------MANKTYLLSYDDVLDKDIKEWLESL-----PRNRKAEMVRAI---------
RAAC02374               ---------MTIRRYVLSYDDEYDREIAEVIEQT-----PKRRRAERVRQLILLGIQAEA
gb|EAU86007.1|          -------QTVIVKRRAKPEPTGYDGNPTNAAASP-----AFSTTTQLTASPPSL------ ref|XP_001467069.1|     ----------------------APS-PAPRSAAATGAPPLAPR-----
ref|YP_001208199.1|     ----------------------SSTGLEPRSGGAGGGQPLMPNVRITP
ref|YP_946581.1|        ----------------------TPAHMMAQAGSSTGADPVLAR-----
ref|YP_001376929.1|     ------------------------------------------------
RAAC02374               EMRGEGGMKPVQTGSPASDDSSIPPSPQTPQSGSSTGKRPVIPRITPKS
gb|EAU86007.1|          ----------------------FPNSPPTGTSSGIRPLIPHIVPPS
```

FIG. 71

```
ref|XP_975359.1|       ------------------------------------------------------------
RAAC02375              MCKMWTKRWTDFLAVSILTATVTGCGTIPHAVSQTSSTAIPAPSVHAVVDRLPGHLQAKL
ref|ZP_02840410.1|     ---------------------------------------IPAKAGEAHLERLLRHVHSR-
ref|ZP_01467536.1|     ---------------------------------------QGKLNRIDVASKRVTPIPFHV
ref|YP_001016790.1|    ---------------------------------------PLRLRCWRISMRTMVQRAAAE
ref|XP_001315633.1|    ---------------------------------------LQAEFINFENAEN ref|XP_975359.1|       ----------------------------------------------------RRKSKEENK
RAAC02375              IGFDVRKKRVSHLPIAVKGTNVLYISPMEQYAIQQFQQIWPRLKAYPVVVWTGVTKAQAE
ref|ZP_02840410.1|     AGLEAAPSRIED--------------------QLDHV------------ARTVKGRNL
ref|ZP_01467536.1|     KGTRTLFARVIIS-------------------PQAQAVVPERFPVKMLRWVQVSPKGDR
ref|YP_001016790.1|    LGIEVIPSRRTY--------------------ALLDWLAERE--------RDVYPLEEG
ref|XP_001315633.1|    IGFSLKQS------------------------SKLVIS-----------EQRSNKNYQ ref|XP_975359.1|       LDREKSDYAPESVPIVGEE-------NGVHYYEDGHFWMEVPG-LLPESEEED------
RAAC02375              MVWRKEGYPGDPLPSQQTEYVSQTIPTPDAYHRDGKAWVEVPG-ILPASQLEDWVTFFR
ref|ZP_02840410.1|     LFVVADEIPASPALEQLLR--------RLRAQHEILWLTIR-----DAE---------
ref|ZP_01467536.1|     VVYQALGHLYTRELPDGLP---------RRLTKQTEHFEMHPS-FSRDGKSIV------
ref|YP_001016790.1|    YMAGPLAPPPTPIPTPPVP-------LPEAVRGDAWSWASLPLGLLREAQ---------
ref|XP_001315633.1|    KFWQRL-WSAMTMPLALWEG--------ATSKKIEMIYQRD----------------
                                                          :
```

FIG. 72

```
ref|ZP_01091610.1|    ------------------------------------------------------------
RAAC03273             MDMAWEPSQDPYTLLQDFSCFYGTDVKGPNSVLTQKDMMAIRNNIVEVSRGWRQLGPNKV
ref|YP_944003.1|      ------------------------------------------------------------
ref|YP_502758.1|      ------------------------------------------------------------
ref|YP_462360.1|      ------------------------------------------------------------
gb|EAU81483.1|        ------------------------------------------------------------ ref|ZP_01091610.1|    ------------------------------------------------------------
RAAC03273             ELLEPLMDPSAVSGAFV-YLAKHHEDWSLSDWPKVYLAFIRTVDSQTLTFEPNGNVIYTY
ref|YP_944003.1|      ------------------------------------------------------------
ref|YP_502758.1|      --------PSEVSGNFLSALNKLSLDDYSKIITSIESGFSTNLDSIIQLLERKCQIILYG
ref|YP_462360.1|      ------------------------------------------------------------
gb|EAU81483.1|        ------------------------------------------------------------ ref|ZP_01091610.1|    ---------------------------------------------------------RL
RAAC03273             KRGTGLTPNVTGVFEKGVDTVYSSYSYSDQIGVEAYKEDDPSLNSKIFYEPDYQVFSPKT
ref|YP_944003.1|      ------------------------------------------------------------
ref|YP_502758.1|      PPGTGKT----------------------------------------------YSVQSLTK
ref|YP_462360.1|      ------------------------------------------------------HSYR
gb|EAU81483.1|        ------------------------------------------------------------ ref|ZP_01091610.1|    HRSNYTYTYT----ASGGTLSFSQWACVALTFDG-----------YQYRFYKNGFLISTH
RAAC03273             HLSNYHYSYPGYVPPSNGQIAFELWGTVCDPYTARVGGAIFIEGMYEFTYY-NGHLVNAH
ref|YP_944003.1|      -----SYSYN----DEVGTLDY-ILASASLK--------------DKIVDSMYWNIN
ref|YP_502758.1|      KTASTPYIST---TKDYGNIQFFWLITYKDKYDDIS---------TINSKSIYTYQWKSN
ref|YP_462360.1|      AGAGLTYNLT--EISDLG-LDYAYSKSDYDEEDK-----------VDSTKDTVSMAYR
gb|EAU81483.1|        ----YPGYIP----PSSAQIESALRGTIYDALIRR----------IMWEGVRGKWGVPST
                              . . :

ref|ZP_01091610.1|    GIGGSPVNNPAASVWIGD---
RAAC03273             QIGQESENYPSEVTRYGD---
ref|YP_944003.1|      SSESSLFEYSTKYTGYLP---
ref|YP_502758.1|      YNYSKYFYMINEGDYFAIYLW
ref|YP_462360.1|      HFFRERRDIVTVTPFYSRY--
gb|EAU81483.1|        HQGEDGEERYSEIDTWG----
```

FIG. 73

```
ref|YP_074959.1|      ------------------------------------------------------------
ref|ZP_01846154.1|    NTEGRASECATALYTICREGINMETHYLBACTERIUMSP-GBACAINTEGRASECATALY
ref|YP_594046.1|      ------------------------------------------------------------
RAAC02967             ------------------------------------------------------------
sp|Q45618|TRA6_BACST  ------------------------------------------------------------
ref|YP_828009.1|      ------------------------------------------------------------ ref|YP_074959.1|      ------------------------------------------------------------
ref|ZP_01846154.1|    TICREGINMETHYLBACTERIUMSP-GBACAHYPTHETICALPRTEINMMETHYLBACTE
ref|YP_594046.1|      ------------------------------------------------------------
RAAC02967             ------------------------------------------------------------
sp|Q45618|TRA6_BACST  ------------------------------------------------------------
ref|YP_828009.1|      ------------------------------------------------------------ ref|YP_074959.1|      ---MAP-----------------------------------------YRPMAKAAATVRF
ref|ZP_01846154.1|    RIUMSP-SCRESIGNIFICANCEE-IDENTITIESPSITIVESGAPSLRPSAPLPIERRF
ref|YP_594046.1|      ---VRPFRR--------------------------------------TQVSAARVTTRF
RAAC02967             ---MKPLR---------------------------------------PVVSAKATERF
sp|Q45618|TRA6_BACST  ---MKPFR---------------------------------------ETAKKKYTVRY
ref|YP_828009.1|      -----PWR---------------------------------------EEGRERAFVRF
                         *                                            *:

ref|YP_074959.1|      ETPPGKQAQVDWADFGYIEVD--GRRLKLYCFIMVLAYSRAMYLEFVTATDMKTFMRCHI
ref|ZP_01846154.1|    ETPPGEQAQVDLARFEVVFADEPGVTRIVWLFAMVLGHSRYLWARFVVHQDLQTVLRCHI
ref|YP_594046.1|      ETAPGEQAQVDFGRYSYLNLE--GQTRSIWAFVMVLGWSRALYVEFIRKADTASFIRCHL
RAAC02967             ESDPGEQAQIDLGAFLYYDSH--GQRRTIWAFAMVLAYSRMLYVEFIKAADQLHILQALR
sp|Q45618|TRA6_BACST  ETLPGEQMQVDWKEVGEVVIE--GKKVKLSLFVATLGYSRMKYAVFTTSQDQEHLMECLI
ref|YP_828009.1|      ETGPGEQSQMDWGHFGN--WD--GR--RLYGFALTLCYSRMRYIEFTQSQDIHHLLACMV
                      *:  **:* *:*           .   *   :  * .*  **   :  *     .: .

ref|YP_074959.1|      NAFKFFGGVPHEILYDNVKTVVKDRDDDNRPVFNERFLDFSSYYGFRPRLCLPYHAWTKG
ref|ZP_01846154.1|    AAFQALGGAPREILYDRMKTAVIGEDPDGLVIYNRSLLDLARHYGFLPRACRPYRAKTKG
ref|YP_594046.1|      NAFAYFGGMTQSILYDNTKQVVLERDETGQPVWNPQFLDFSLRLCFSIRLCRPYRPRTKG
RAAC02967             NDLEFFGGVPRVMLSDNCSPLVVANDGQGHVDWQPAYLDFAKFYGFVPKACPRRSRTKG
sp|Q45618|TRA6_BACST  QSFKYFGGVPKKVLFDNMKTVTDGREQ-GVVKWNQRFSEFASYYCFIPKVCRPYRAQTKG
ref|YP_828009.1|      HAFRYFGGVTESVLTDRMKTVLIDQTG-GELHFNQKFLQFAAYYGFVPRVCRPYRPETKG
                       :**  .. :* *.   .     ::   :::   ** : * :. *** ref|YP_074959.1|      KVERPVRYIRQNFW---
ref|ZP_01846154.1|    KVERPFRYLREDFF---
ref|YP_594046.1|      KVESGVGYVEKNFW---
RAAC02967             KVERPIRYIRDSFWPVA
sp|Q45618|TRA6_BACST  KVERAIQYIMDHFY---
ref|YP_828009.1|      KIESSVRFVKQNFWP--
                      *:*  . :: . *:
```

FIG. 74

```
ref|YP_148969.1|      ------------------------YLQLAHNEWDPKAKYAKAKVIYSFGREDEVDRAVLER
ref|YP_001126171.1|   ------------------------YLQLAHNEWDPKAKYAKAKVIYSFGREDEVDRAVLER
ref|YP_146154.1|      ------------------------------------------------------------
ref|YP_146741.1|      ------MYIRRVTRKNKDGTTVAYLQLAHNEWDPKAKYAKAKVIYSFGREDEVDRAVLER
RAAC03589             MPYHVGMYIRVIRRKNKNGSVTGYVQLAHNFRDPNTGQPKAKVLYTFGREDEIDLEALRR
ref|ZP_02130848.1|    ------MYIRTISRKNKDGSKVEYVQLAHNYRDPKSKQARAEVLYSFGRKDQLDMEAIRR ref|YP_148969.1|      LAKSISRFLSPEQAWEIETLTGEVSDDFQFQSSKRLGGAWLLDQLWRQLGLGEILHSLFA
ref|YP_001126171.1|   LAKSISRFLSPEQAWEIETLTGEVSDDFQFQSSKRLGGAWLLDQLWRQLGLGEILHSLFA
ref|YP_146154.1|      ----------------------------------------------------------VC
ref|YP_146741.1|      LAKSISRFLSPEQAWEVEKLTGEASDDFQFQSCKHLGGVWLLDQLWRQLGLGEILHSLFT
RAAC03589             LAQSIHRFVG--DEFTAGRGQSERIQTTLLDS-RPMGGAYLLDELWRQLGLDEVLRERLA
ref|ZP_02130848.1|    LAKSVERFLAKTGDVETQCKLQFPGEDVRFVESRPMGGVFVLKKIWDRLRISECLDKALA ref|YP_148969.1|      SRHHQIPLERLIFAMVANRALHPSSKLAMEEWVEKDVHIPHLPQVASHQLYRAMDELLAV
ref|YP_001126171.1|   SRHHQIPLERLIFAMVANRALHPSSKLAMEEWVEKDVHIPHLPQGASHQLYRAMDELLAV
ref|YP_146154.1|      SRHHQIPLERLIFAMVANRALHPSSKLAMEEWVEKDVHIPHLPQVASHQLYRAMDELLAV
ref|YP_146741.1|      SRHHQISLERLIFAMVANRALHPSSKLAMEEWVEKDVYIPHLPQVASHQLYRAMDELLAV
RAAC03589             DRKFKAAVERVIFAMVANRALAPSSKLAMEEWVDREVALPGMTELDVWQAYRAMDFLHDV
ref|ZP_02130848.1|    DRQYTAPIGDAVFAMVANRALAPDSKLAVEDWAAKDVHLEIDQPLKVQHLYRAMDFLLEN
                       .*:.  .:  :*********  *.****:*:*. .:* :        :  * ***** * ref|YP_148969.1|      QPELERQVFHAVADLLNLEVDLIYFDTTSSYFEVDPSETPEGESLRKQGFSKDKRPDLVQ
ref|YP_001126171.1|   QPELERQVFHAVADLLNLEVDLIYFDTTSSYFEVDPSETPEGESLRKQGFSKDKRPDLVQ
ref|YP_146154.1|      QPELERQVFHAVADLLNLEVDLIYFDTTSSYFEVDPSETPEGESLRKQGFSKDKRPDLVQ
ref|YP_146741.1|      QPELERQVFHAVADLLNLEVDLIYFDTTSSYFEVDPSETPEGESLRKQGFSKDKRPDLVQ
RAAC03589             AEDLQYEVFRRVSDLLNLDVDLLFFDTTSTYFET---EDESDDSLRRKGYSKDHRPDLPQ
ref|ZP_02130848.1|    QEAIQKEVFWSTANLLNLEVDLVFFDTTSTYFER---DEEDEEGLKRYGHSKDKRKDLPQ
                       ::  :  .:::*::***:*    :      .:.*::  *.**:* ** * ref|YP_148969.1|      IVIGLAVTREGVPIRAWVWPGNTMDMTVIKQVKQDLIGWKLGRVISVMDRGFSSEENLRI
ref|YP_001126171.1|   IVIGLAVTREGVPIRAWVWPGNTMDMTVIKQVKQDLIGWKLGRVISVMDRGFSSEENLRI
ref|YP_146154.1|      IVIGLAVTREGVPIRAWVWPGNTMDMTVIKQVKQDLIGWKLGRVISVMDRGFSSEENLRI
ref|YP_146741.1|      IVIGLAVTREGIPIRAWVWPGNTMDMTVIKQVKQDLIGWKLGRVISVMDRGFSSEENLRI
RAAC03589             VVIGLAVTRDGIPVRCWTWPGNTADMSVVEEVKQDLIGWRLGRVITVVDRGFVSESNLRI
ref|ZP_02130848.1|    VVVGLAVTKEGLPIRSWVFPGNTPDVNTVEQIQKEMNDWKLGRVVWAMDRGMTSEENRAI
                       :*:*****::*:*:*.*.:****  *:..::::::: .*:**: .:*: **.*  * ref|YP_148969.1|      LQQAGGHYIVGEKMRSGKAAVEEALNRRGRYQQVRENLHIKEIIVGDGEARQRYVLVYNP
ref|YP_001126171.1|   LQQAGGHYIVGEKMRSGKAAVEEALNRRGRYQQVRENLHIKEIIVGDGEARQRYVLVYNP
ref|YP_146154.1|      LQQAGGHYIVGEKMRSGKAAVEEALNRRGRYQQVRENLHIKEIIVGDGEARQRYVLVYNP
ref|YP_146741.1|      LQQAGGHYIVGENMRSGKAAVEEALSRRGRYHEVDENLHIKEIIVGDGEARQRYVLVYNP
RAAC03589             LQRAGGHCIAGEKMTSGKPAVEAALARPGRFRELRPNLKVKEVVVGDGEARVRYVLAFNP
ref|ZP_02130848.1|    LQRGGGNYILGEKLR-GSNMSKAVLGSPGRFTTVRDNLEIKEVTAGDGACRRYVIVRNP
                       **:.**: * **::  *.  . .*   **   * .   **.:***  .* .*** ** :. **

ref|YP_148969.1|      SEAERQRKEREKLLESLKEELEGLRQLPNEAHHKATCRLRSHPSYGKYLRQLKDGTLRID
ref|YP_001126171.1|   SEAERQRKEREKLLESLKEELEGLRQLPNEAHHKATCRLRSHPSYGKYLRQLKDGTLRID
ref|YP_146154.1|      SEAERQRKEREKLLESLKEELEGLRQLPNEAHHKATCRLRSHPSYGKYLRQLKDGTLRID
ref|YP_146741.1|      GEAERQRKERETLLESLKEELEGLRQLPNEAHHKATCRLRSHPSYGKYLRQLKDGTLRID
RAAC03589             EEAKRDEARREAMLRELRMELERLKELQGEAHTKAHCRLASHPTFKRYLKQDRWGNLRID
ref|ZP_02130848.1|    KQVKRDQATRERLIRRAEQEIEATGDLTGKKHTKAACALLSHRSMGKYVRELKSGKLKIN
                       :..:**:. **    ::.   .*:* :* .: *  ** *  **  :*:::  :  *.*:*:

ref|YP_148969.1|      KQAVREAEKYDGKYLIRTSDDTLSAEDVALGYKQLVDIEQAFRTLK-------
ref|YP_001126171.1|   KQAVREAEKYDGKYLIRTSDDTLSAEDVALGYKQLVDIEQAFRTLK-------
ref|YP_146154.1|      KQAVREAEKYDGKYLIRTSDDTLSAEDVALGYKQLVDIEQAFRTLK-------
ref|YP_146741.1|      KQAVRDAEKYDGNYLIRTSDDTLSAEDVAIGYKQLVDIEQAFRTLK-------
RAAC03589             PEAVRQAAHLDGKYLIRTSDDTLSTEDVALGYKQLLMVESALRTLKKFWTSVP
ref|ZP_02130848.1|    KAKITEEEKLDGKYLLSCSDDTLSPEETALGYKQLLEVERAFRTLK-------
                       : :   **:**  ******.::*******: :* *:****
```

FIG. 75

```
ref|ZP_01665148.1|      ----------------------------------------------------------------
ref|YP_001111903.1|     ----------------------------------------------------------------
ref|YP_753434.1|        ----------------------------------------------------------------
ref|YP_753226.1|        EFYPHYPTHETICALPRTEINSWLSYNTRPHMNASWLFEISUBSPWLFEISTRGETTING
ref|YP_752864.1|        ----------------------------------------------------------------
RAAC03695               ---------------------------------------------------------------- ref|ZP_01665148.1|      ----------------------------------------------------------------
ref|YP_001111903.1|     ----------------------------------------------------------------
ref|YP_753434.1|        ----------------------------------------------------------------
ref|YP_753226.1|        ENGBABIHYPTHETICALPRTEINSWLSYNTRPHMNASWLFEISUBSPWLFEISTRGETT
ref|YP_752864.1|        ----------------------------------------------------------------
RAAC03695               ---------------------------------------------------------------- ref|ZP_01665148.1|      ----------------------------------------------------------------
ref|YP_001111903.1|     ----------------------------------------------------------------
ref|YP_753434.1|        ----------------------------------------------------------------
ref|YP_753226.1|        INGENGBABIHYPTHETICALPRTEINSWLSYNTRPHMNASWLFEISUBSPWLFEISTRG
ref|YP_752864.1|        ----------------------------------------------------------------
RAAC03695               ---------------------------------------------------------------- ref|ZP_01665148.1|      ----------------------------------------------------------------
ref|YP_001111903.1|     ----------------------------------------------------------------
ref|YP_753434.1|        ----------------------------------------------------------------
ref|YP_753226.1|        ETTINGENGBABIHYPTHETICALPRTEINSWLSYNTRPHMNASWLFEISUBSPWLFEIS
ref|YP_752864.1|        ----------------------------------------------------------------
RAAC03695               ---------------------------------------------------------------- ref|ZP_01665148.1|      ----------------------------------------------------------------
ref|YP_001111903.1|     ----------------------------------------------------------------
ref|YP_753434.1|        ----------------------------------------------------------------
ref|YP_753226.1|        TRGETTINGENGBABIHYPTHETICALPRTEINSWLSYNTRPHMNASWLFEISUBSPWLF
ref|YP_752864.1|        ----------------------------------------------------------------
RAAC03695               ---------------------------------------------------------------- ref|ZP_01665148.1|      --------------------EAXTRANSPSASEISFAMILYPRTEINTHERMSINU---
ref|YP_001111903.1|     ----------------------------------------------------------------
ref|YP_753434.1|        ----------------------------------------------------------------
ref|YP_753226.1|        EISTRGETTINGENGBABIHYPTHETICALPRTEINSWLSYNTRPHMNASWLFEISUBSP
ref|YP_752864.1|        ----------------------------------------------------------------
RAAC03695               ---------------------------------------------------------------- ref|ZP_01665148.1|      ------SCARBXYDIVRANSNRGBEAXTRANSPSASEISFAMILYPRTEINTHERMSINU
ref|YP_001111903.1|     ----------------------------------------------------------------
ref|YP_753434.1|        -------------------IHYPTHETICALPRTEINSWLSYNTRPHMNASWLFEISU
ref|YP_753226.1|        WLFEISTRGETTINGENGBABIHYPTHETICALPRTEINSWLSYNTRPHMNASWLFEISU
ref|YP_752864.1|        ----------------------------------------------------------------
RAAC03695               -----------------------------------------------MLPRRFFMDNref|ZP_01665148.1|      ----SCARBXYDIVRANSNRSCRESIGNIFICANCEE-IDENTITIESPSITIVESCAPS
ref|YP_001111903.1|     ----------------------------------------------------------------
ref|YP_753434.1|        BSPWLFEISTRGETTINGENSCRESIGNIFICANCEE-IDENTITIESPSITIVESGAP-
ref|YP_753226.1|        BSPWLFEISTRGETTINGENSCRESIGNIFICANCEE-IDENTITIESPSITIVESGAP-
ref|YP_752864.1|        ----------------------------------------------------------------
RAAC03695               ---------TVDFLEPFAESRVLVRQG----FFEHKEGLHPNLRERKWYPANHFKGAKSN
``` continued →

FIG. 75 continued

```
ref|ZP_01665148.1|      MYIRQKPLFSFDTLMQYQPKTRLAMVFESIDLHPLLKTLPIKSIR--GPKGYSSAALIKA
ref|YP_001111903.1|     MYLLQPNLFSFEELLKFEPETKLQKVLSVLDLSPALN-VVKRAVL--GPKGHCVGNMIRA
ref|YP_753434.1|        -SIRQNCIFSFEDALKIQPKSRLEKIINTLDLKPVLCKLDKPGEIRVGPKPYPAYAMLNA
ref|YP_753226.1|        -SIRQNCIFSFEDALKIQPKSRLEKIINTLDLKPVLCKLDKPGEIRVGPKPYPAYAMLNA
ref|YP_752864.1|        --IRQGYVFSFEDAINLQPRSRLEIVLATLDFDDVITVLDKENKQHRGPTGYPFESKLNA
RAAC03695               VYVRQAWLFSFDEWMEMSPCERRELFFSTLDLSPYAAKLRSSTPQ--GAKPISREAILRA
                         :  *  :***:   ::  .*  :   .: :*:      :     *..      :.* ref|ZP_01665148.1|      FLAMRLCSIPTVTLLVERLKTDLVFRYECGFSLEQPVPSLATFSRFFQKIAETDS-----
ref|YP_001111903.1|     LVAKQLEQIPTVAALVKRLSNDIRFRFQCGFSLSKPIPSESTFSRLIQKLAATDETNKTE
ref|YP_753434.1|        LIAMRLENMGTFTQLVERLTYDPHLRYVCGFEPFGTAPSKSCFSRFYSKLAQSGC-----
ref|YP_753226.1|        LIAMRLENMGTFTQLVERLTYDPHLRYVCGFEPFGTAPSKSCFSRFYSKLAQSGC-----
ref|YP_752864.1|        LIAMRVYNMATFTELVERLTHDPVLRYNCGFDVFGKVPSIATFSRFYERLTQSEV-----
RAAC03695               FLAAPLEGISTFTQLHRRLESDLRFRYQCGFSLHESIPSVSTLSRVFQAIVDKGV-----
                        ::*   :  :  *.: *.** *  :*: ***.   **  : :**. . :.

ref|ZP_01665148.1|      --LQVLFSALVDTAIQDKVISGEVVAIDASAIDSYEKPVPKKELNSNGDSATWGAKLDTH
ref|YP_001111903.1|     SVMKQIFDNLVKSAKDMGLIDSNCVAIDSSKIDAYEKSKPKKDLQGD-KTANWGAKRDTH
ref|YP_753434.1|        --LETLFTSLVKQAEEMGLLDLSSVAIDATKVEAYEKSVPRKNIIQDGNVADWGIKSDTN
ref|YP_753226.1|        --LETLFTSLVKQAEEMGLLDLSSVAIDATKVEAYEKSVPRKNIIQDGNAADWGIKSDTN
ref|YP_752864.1|        --LRELFKKQVTTAESMGLIDTSSIAIDASKVDANEKSVPRKNIKDDGQSANWGSKLDTN
RAAC03695               --AATLFAELVRQCRDEGLIECEHVAIDSTAIHAYERKHPRSGVQPS-NRANWGAKFDAF
                          :*    *    .  . ::.  :***:: :.: *:  *:. :   . .   * ** *:

ref|ZP_01665148.1|      GNQHVWFGYKLHLAVDTKSELPIAVKVTPANRNDVTQAIPLMDEIK------HQPKYYCM
ref|YP_001111903.1|     GNQISWFGYKAHVAVDCHSELPIAIMVTPANTHDAKMAIPLIELVNKALEDSKKPKYYTM
ref|YP_753434.1|        GNPIKWFGYKLHIGTDVKSGLPIAMKVTPANYSDSSVALELVEKCCANTQ--SKIVYFLM
ref|YP_753226.1|        GNPIKWFGYKLHIGTDVRSGLPIAMKVTPANCSDSSVALELVEKCCANTQ--SKIVYFLM
ref|YP_752864.1|        GNQITWFGYKLHIATDVKSELPVALSITPASTNDGIMAESILEECSNNLN--SKPQYYLM
RAAC03695               GNKLAWFGYKVHLAVDAKSELPMALTVTPANVYDGEMAIPLMEELHHHDW---RIRFVLM
                          ***  *:..* :* **:*: :***. *   *    :        :    :  * ref|ZP_01665148.1|      DMGYDAKDVYQAAY-ERQAQAIIPLNRRKEKLPPEGMDENRTPTCSMGYPMVYWGCEREK
ref|YP_001111903.1|     DMGYDSKDIYSVVMNDFNAQAIIPINSRGSKDHPEGCDFDGTPICSMGQRMVFWGSDAKA
ref|YP_753434.1|        DAGYDHREIYSVIRDKYHAQAIIALNKRGAKQPPEGFDWDGTPICSARYRMVYWGS--YQ
ref|YP_753226.1|        DAGYDHREIYSVIRDKYHAQAIIALNKRGAKQPPEGFDWDGTPICSARYRMVYWGS--YQ
ref|YP_752864.1|        DAGYDQKSIYELIRKDYKAQAIIPLNHRGAKEPPEGLDWDATPICSAGYRMAYWGG--SN
RAAC03695               DAGYDQTKNYEAAR-ALGAQAIIPMNRRNEKEPPEGMDFDGTPRCTMGYRMTYWGV--HN
                        * ***   .  *.       ****.:*  *  *   *** *:  ** *:    *.:**

ref|ZP_01665148.1|      GILKFRCPHVCGKVNCPNGSAWCSPSNYGLVIKKKVEDDPRSFCTPHRGTREWEKLYAER
ref|YP_001111903.1|     GTNKYRCPHVMGKCDCPYGSAWCSPSSYGLVVKTKVKDDPRMNCIPARGTKNWQSLYNKR
ref|YP_753434.1|        GVNKFRCPHIMGKCDCPFGSAWCSDSNYGMVVKTKVKDDPRLFSSPHRGSANWQKQYNLR
ref|YP_753226.1|        GVNKFRCPHIMGKCDCPFGSAWCSDSNYGMVVKTKVKDDPRLFSSPHRGSANWQKQYNLR
ref|YP_752864.1|        GVNKFRCPHVMGKCDCPFGSSWCSDSNYGMVVKTRARQDSRLFIVPHRGTSNWKLLYNKR
RAAC03695               AWLKFRCPHATGQVDCPLGMAACSASYYGMVVKKHIDEDVRRYANPHRGSRTWKMLYDER
                         . *:****  *: :  * * * **:*:*:::*.:  *    * **: *    * * ref|ZP_01665148.1|      TSVERAFSRLKEQLGANT-VRVQGIKKVTAHLMLCCIALLAGTIAVNR--------
ref|YP_001111903.1|     TSVERCFGRLKQHLGANS-IRTRGLEKVTLHITLSCIALLAGSIAVAKTKRIEQAA
ref|YP_753434.1|        TYSERCFSRFKENLGLEDGLNVRKITKVETHAYLCAITMIAAVIAINQ--------
ref|YP_753226.1|        TYSERCFSRFKENLGLEDGLNVRKITKVETHAYLCAITMIAAVIAINQ--------
ref|YP_752864.1|        TSVERCFGRLKEHLGLETGLNVRGIKKVKTHAYLSVITMIASVIAINKDKSSTDIA
RAAC03695               TAVERCFARLKEWLTLDG-VHVRGIEKVTVHAYIHAIVLLASALAMHRTNRIEQVA
                        *  **.**.*:*: *     :   :  **  *  :   *.::*. .*::   :
```

FIG. 76

```
ref|YP_754943.1|    ---------------------------------LNAKVKWYEEQFRLSRQKQFGASSEK------
ref|YP_754865.1|    ANCEE-IDENTITIESPSITIVESGAPSLNAKVKWYEEQYRLSRQKQFGTSSEK------
ref|YP_431166.1|    ------------------------------------------------------------
RAAC02318           ---------------------------------MRQQVAYLEEQIHLLRHRLFGASSEKRRKTQA
ref|ZP_02171171.1|  ---------------------------------MQKKKFGTSSEK-----T
ref|YP_519650.1|    ---------------------------IKQQNQWLMEQFRLLKHKQYGASSEQ------ ref|YP_754943.1|    -TTPEQINLFNEAEDITDPKLEEPS-------------LETVTYQRKKKQAGQREDKLKD
ref|YP_754865.1|    -TTPEQINLFNEAEDIVDPEIKEPD-------------IETITYERKKKQPGQKADKLKD
ref|YP_431166.1|    ------------------------------------------------------------
RAAC02318           ESDSVQLSLFNEAEVEADAQSSEETGEADTKAPSEDVETETITYERRKPRAVRERDAWLY
ref|ZP_02171171.1|  DERFEQGSLFNESEKEQDAAEEEPT-------------VEAITYERKKKRKARKD---LT
ref|YP_519650.1|    -HSAEQMDLFNEAEATAELSAPEPP-------------LTEVKTHYRKRTRLTTDK---LP ref|YP_754943.1|    L--PVEIIEYRLEKHEQICPCCQGELHEMSIQVRHEIKIIPAQAISVKHVQYIYACRRCE
ref|YP_754865.1|    L--PVEVIEYRLLEHEQVCPCCQGSLHEMSTQIRQEIKVIPAQVKVVQHVQYIYSCRQCE
ref|YP_431166.1|    ---------------------------MSTEVRQELKIIPAQVKVVKHIRYVYACRHCE
RAAC02318           QGEADEVVEYRLSDDERVCPKCAGELHEMSREITRRVKIIPAQMKKVEYVRYVYACRHCE
ref|ZP_02171171.1|  ENLYTETVTYTLPVEDQVCSCCNGELHIMKTQVKDELEIIPAEVKVKRYETTIYSCRHCE
ref|YP_519650.1|    EDLPVEVMEYELPEPERRCPECSGELHTMGRDIWEELKIIPAKAVIVRHIQHVYACRCCE
                                              *  ::  .:::***:     .:    :*:** **

ref|YP_754943.1|    KENITTPIIKAEMPKPILPGSLASPSILAYIMDQKYTNSLPLYRQEQQFSRLGIELSRQT
ref|YP_754865.1|    KENITTPIIKAQMPNPILPGSLASPSILAYIMDQKYTNSMPLYRQFQQLSRLGIELSRQT
ref|YP_431166.1|    REELTTPVVTAPMPAPVLPGSPVSPSLLAYVMHQKYGEGLPLYRQEQQFKSLGLELSRQT
RAAC02318           AQDVETPVVRAPTPKPVQAKSLATPEAVAYVMTKKFVDGMPLYRQEQQFARHGYPLSRQT
ref|ZP_02171171.1|  RTGTRNPIVKAPSPERPFPGSLASPSIVSYMINQKFVQGVPLYRQEQEFKRMDVPISRQT
ref|YP_519650.1|    ATSEHVPMLKAQRPSPVIKGGFACAETIAHLAVQKFMMGSPLYRQEQEWKHNGILLSRQT
                      *::  *   *     .   ..::::  :*:  . *******:  :    :****

ref|YP_754943.1|    MANWLLAAADPWLKIIYDRLHEQLLEKDILHADETTLQVLKEPGRRAESKSYMWLYRT-G
ref|YP_754865.1|    MANWVLNVADPWLKIIYDRLHVELLDRDILHADETTLQVLKEPGRSAETKSYMWLYRT-G
ref|YP_431166.1|    LANWVLHGANTWLTHIYDRLHEYLLKRDILHADETTLQVLREPGREAATKSFLWLYRT-G
RAAC02318           LANWVVHAAETWLEPLYAKLRQVLLAQRYLHADETTLQVLHEAGRAAQTQSYMWVYRS-G
ref|ZP_02171171.1|  MSNWIIEASEQMLEPIWDLMIRILTSLDVLHADETTVQVLKEDGKEAAAKSYMWLYRS-G
ref|YP_519650.1|    MSNWLIKASQDWLEPLYEAMKLRLCEHDVLHGDFTTLQVLKEPGKTAQSKSYMWLYRTSG
                     ::**::  ::  *   ::   :      *  .:*:*  *:  * ::*::*:**: * ref|YP_754943.1|    RDGPPIVLYDYQTTRASKHPDSFLSGFKGYLQTDGYSGYGSLT--SVTLAGCWAHARRKFT
ref|YP_754865.1|    RDGPPIVLYEYQTTRASKHPDRFLSGFKGYLQTDGYSAYGKLT-GITLVGCWAHARRKFT
ref|YP_431166.1|    RDGPSIVLYDYQTTRASKHPCRFLAGFKGYLHVDGYAGYNELP-DVTLVGCWAHARRKFD
RAAC02318           TDEPPVVLYDYQETRNAEHPQRFLAGFQGYLHVDGYAGYEGLP-DVTLAGCWAHARRKFD
ref|ZP_02171171.1|  SHDVPIVIYDYQPGRASKYPRRFLEGFTGYLHVDGYGGYHALKPKVELVGCWAHLRRKFF
ref|YP_519650.1|    EAKHPLVIYEYQPDRKHNHPQTFLKEFSGYLHTDGYEAYHKLPGNIIVVGCAAHLRRKFF
                     .:*:*:**  *  ::*   **    *   *:.*  .*      :  :.:   **** ref|YP_754943.1|    EALKALPAEQKDKPVAASI------------------------
ref|YP_754865.1|    EALKALPAAQKDKPVAA---------------------------
ref|YP_431166.1|    EALKALPEDKRNAAVAA---------------------------
RAAC02318           EALKAVPPKERKGKTAAEAIAWRKPTCASLTTSHTPRSPRTFQTSKE
ref|ZP_02171171.1|  DAVQTLPDDRDSTTSAAK--------------------------
ref|YP_519650.1|    DALKTLPKDRQADSNAAKGVAY----------------------
                    :*::::*   .       **
```

FIG. 77

```
ref|ZP_02171383.1|          -----------VYLARGSTDLRKSIDGLAAIVQEGFELDPFSSSLFVFCNRYRDKIKILY
RAAC02319                   MLAFDWTSDHRVYLACGATDMRKSIDGLAALVQASFQLDPFSPCLFVFCNRQRDKLKILH
ref|YP_431168.1|            -----------RVYLACGATDLRKSIDGLAVLVKEGFELDPFSSCLFVFCNRNRDKLKILH
ref|YP_001212944.1|         -----------RVYLALGATDLRKSIDGLAVLVKEGFELDPFSSCLFVFCNRKCDKLKILH
ref|YP_754944.1|            -------SNRQVYLACGSTDLRKSIDGLAVLVKEAFELNPFSPCLFVFCNRQRNKLKILQ
ref|YP_754864.1|            -------SNRLVYLACGSTDLRKSIDGLAVLVKESFHLDPFSPCLFVFCNRKRDKLKILQ
                                         ****  *::*******.:*: .*.*:*..*****   :*:*** ref|ZP_02171383.1|          WDHNGFWLYYRRLEKGRFPWPTSGSDEPMIITERQLRWLLDGLPLDQKGAHR--------
RAAC02319                   WSHNGFWLYYRRLERGRFDWPETGDAKTMVITRRELNWLLDGLPLEQPRAHRAVYVRSAI
ref|YP_431168.1|            WEHNGFWLYYRRLEKGKFVWPQDTTSSTITITRRELRWLLDGLPLKQPQAHPEVKARTIL
ref|YP_001212944.1|         WDHNGFWLHYRRLEKGKFHWPADAGSPTLVISRRELRWLLDGLSLKQPKAHPEVKARTIL
ref|YP_754944.1|            WDHNGFWLYYRRLERGKFEWPA-ADSQVVSISYREFRWLLDGLSLKQKQAHKAVKERTII
ref|YP_754864.1|            WEHNGFWLHYRRLERGKFDWPT-AHTDVVSISYREFRWLLDGLSLKQNQAHKAVKQR---
                            *.******:*****:*:* **         : *: *:::******.*.*    **
```

FIG. 78

```
ref|ZP_02734990.1|   ------------------DIGSEADRYVEKSRAPNTRRAQRSDWKDFSSWCAKYARSP--
ref|YP_713924.1|     ------------------ELAARVGDYARASRSASTWRAYDSDLRQFRAWCARRPAAPSA
RAAC02333            MQEIMDTNVSSTIHVGLTELSASANKYVLNSKARNTIRAYQSDWRSFCTWCDERHLSS--
ref|YP_008142.1|     ------------------DLVKTAKEYATFARSFNTNKSYRSDWDDFVFWCQEKNLRP--
ref|ZP_01265219.1|   --------------ITDIKALQEETLLNLQSSKANNTVRAYKSDFNDFGLFCAKNGFKS--
ref|YP_266430.1|     --------------ITDINALKKETLLNLQSSKSINTARAYKSDFTDFSLFCVKNGFKS--
                                       :::  .   ::: . ::  **  .*  :*  .   .

ref|ZP_02734990.1|   LPAAPDTVAYYLADRSQE-----------LKTSTLQRRLMSISDAHRTAGFDSPTKSAQ
ref|YP_713924.1|     LPATAATVAGYLATLADAG----------YKPSTIRRRLAAISVAHQLAQHPNPAAAPE
RAAC02333            LPAEPKTVALYLSDMADRG----------YRTSTIGRHMISIGLAHRTKGFPSPTSDET
ref|YP_008142.1|     LPALPQTIVVYLISRADNAWINQKGKLQKPLKISSLSRRLTSISQAHKLAKQPFDKNCPE
ref|ZP_01265219.1|   LPSEPKIVSLYLTHLSTKD-----------VRMSTLKRRLVSIGVIHKLKGHYLDTKHPS
ref|YP_266430.1|     LPSEPKIVSLYLTYLSTKE-----------VKMSTLKRRLVSIGVIHKLKGHYLDTKHPA
                     **:  . :  **   :             :  *:: *:: :*.  *:

ref|ZP_02734990.1|   VKLVWAGIRRDKGVAQNHKKPTLTKHIREMVEHLPQG------LLGVRDRALLLLGFAGA
ref|YP_713924.1|     VGAVWDGIRRTRGVRPTRKTALDTDLLTRVVAGLRDDD-----LADIRDRALLLVGFAGC
RAAC02333            VRAVWRGIRNTLGVAPQGKSPILVEDLRRMLQHVPND------LMGLRDRALLLIGFAGA
ref|YP_008142.1|     IQEVWKGIKNKLGSAQIRKDPILLDDLRKMIESINNDNSKANSLSGMRDKALLLLGFVGA
ref|ZP_01265219.1|   IVENIMGIKRRKGSIQRGKKPLLINNLKKIINVIDQQKKEE--IKKLRDRSIILIGFSGG
ref|YP_266430.1|     IIENIMGIKRRKGSIQKGKKPLLINNLKQIIDVIDQQKKEE--IKKIRDRSIILIGFSGG
                     :     **:.   *     *  .   .: ..:  ::           :  :**::::*:** * ref|ZP_02734990.1|   MRRSELVGIDATDVALTDEGLVVTIRKSKTDQVQEGRTLGIPYGEHEGTCPVRAVLAWVD
ref|YP_713924.1|     LRRSELVGLDVADLVETADGLILTVRRSKTDQEGEGALVGIAYGSYRPTCPVRAWRAWAQ
RAAC02333            FRRSEIVALNVEDVEFVREGLVITLRRSKTDQEGEGRKVGIPYGSFIETCPVRALQAWLN
ref|YP_008142.1|     FRRSELVSLTIDDIKFVREGLQITLRKSKTDQEGKERIIAIPYGSNILTCPVRTLNDWLD
ref|ZP_01265219.1|   FRRNEIVSLDYEDLDFVQEGLKINLRRSKTDQFGEGFVKGLPYFQNPQYCPVISIHKWIE
ref|YP_266430.1|     FRRNEIVSLDFDDLDFVSEGLKINIKRSKTDQFGEGFTKALPYFDSSQYCPVVSLRNWLE
                     :**.*:*.: *:    .:** :.::::****    :.  * .   ***  : *  :

ref|ZP_02734990.1|   QAAILEGPLFRSVNKHGHVMGTRLSDRTVAEVVKRSLVAAGHTARGYAAHSLRAGLITQA
ref|YP_713924.1|     AADLRQGPAFRAVSRHGHVGATRLYPGSVARVVQRRVAAAGLDPADFAGHSLRSGFATAA
RAAC02333            ATGIDSGPLFRRVTKGHDVRDARLSDKTVARIVKRYVRLIGLDQRHFAGHSLRAGLATSA
ref|YP_008142.1|     CSKISEGLLFRPINRHCGIMDKALTSKSVALIIKRNKHLE-NQKNSFSGHSLRAGFATTA
ref|ZP_01265219.1|   ISKIKSGALFRRFIKGSKISDNRLTDQTVALIVKLKLAGIDCKNYSGHSLRSGFATSA
ref|YP_266430.1|     ISRSGSVFRRFIKGSKLSENRLTDQTVALLIKEYLSMLGIDTKNYSGHSLRSGFATSA
                     :  :  .*  **  . :   .:  *   :  :::.      ::.**:*:  *  * ref|ZP_02734990.1|   AIAGASDRDIQDQSGHKSLLVMRRYIRDGSLF-RQNVAAKVGL
ref|YP_713924.1|     ARAGVADRSIMRQGRWRSSASLDGYVRAGRLFDRDNPSGRVGL
RAAC02333            ALAGVSERDIMAQTGHRSPMMVRRYIRDSNLF-RSNAAARIGL
ref|YP_008142.1|     AIFGVPEHLIMKQTGHKSFDTIRRYI-----------------
ref|ZP_01265219.1|   AESGAEERSIMAMTGHKSTEMVRRYIKEANLF-KNNALKNI--
ref|YP_266430.1|     AESGVEERNIMAMTGHKSTEMVRRYIKDANLF-RNNALNKI--
                     *  *.  ::  *      :*   :    *:
```

FIG. 79

```
ref|YP_001036724.1|    TRANSPSASEMUTATRTYPECLSTRIDIUMTHERMCELLUMATCCGBABNTRANSPSASE
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    MUTATRTYPECLSTRIDIUMTHERMCELLUMATCCGBABNTRANSPSASEMUTATRTYPE
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    CLSTRIDIUMTHERMCELLUMATCCGBABNTRANSPSASEMUTATRTYPECLSTRIDIUM
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    THERMCELLUMATCCGBABNTRANSPSASEMUTATRTYPECLSTRIDIUMTHERMCELLU
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    MATCCGBABNTRANSPSASEMUTATRTYPECLSTRIDIUMTHERMCELLUMATCCGBABN
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    TRANSPSASEMUTATRTYPECLSTRIDIUMTHERMCELLUMATCCGBABNTRANSPSASE
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    MUTATRTYPECLSTRIDIUMTHERMCELLUMATCCSCRESIGNIFICANCEE-IDENTIT
ref|YP_001039064.1|    ------------------------------------------------------------
ref|YP_001039349.1|    ------------------------------------------------------------
RAAC03703              ------------------------------------------------------------
ref|YP_076118.1|       ------------------------------------------------------------
ref|YP_074958.1|       ------------------------------------------------------------ ref|YP_001036724.1|    IESPSITIVESGAPSMATNNRMALLEQLSKYVVEKDKDFLKEALTLLINALMDAEVTSII
ref|YP_001039064.1|    --------------MATNNRMALLEQLSKYVVEKDKDFLKEALTLLINALMDAEVTSII
ref|YP_001039349.1|    --------------MATNNRMALLEQLSKYVVEKDKDFLKEALTLLINALMDAEVTSII
RAAC03703              ----MTNTKSRRHATMASLNSFAVLEWIRKMQDVDQIDFLRELMQLVTQFLIDAEAAEKI
ref|YP_076118.1|       ------SNTSQRGNPQVTNFRIALEELLRK-SGVDDVDFLREGVRVLAQGLMELEVSQQI
ref|YP_074958.1|       -------------------LEELLRK-TGVDDFDFLREGLRVLAQGLMELEVSQRI
                                         : * : *    .: ***:*  : ::  : *:: *.:. * continued →
```

FIG. 79 continued

```
ref|YP_001036724.1|    GAEKYERNNNRNNYRNGYRLREWDTRVGTLQLSIPKLRHGSYFPSLLEPRKMSEKALLNV
ref|YP_001039064.1|    GAEKYERNNNRNNYRNGYRLREWDTRVGTLQLSIPKLRHGSYFPSLLEPRKMSEKALLNV
ref|YP_001039349.1|    GAEKYERNNNRNNYRNGYRLREWDTRVGTLQLSIPKLRHGSYFPSLLEPRKMSEKALLNV
RAAC03703              GAERYERTESRVTQRNGYRSRAWDTRLGTVDLKIPKLRQGSFFPSILEPRRRAEQALASV
ref|YP_076118.1|       GAERYERSSERSNYRNGYRERQWDTRVGTIDLQIPKLRKGSYMPSWLEPRRRAEKALVAV
ref|YP_074958.1|       GADRYERSAERSTYRNGYRERQWDTRVGTIDLQIPKLRKGSYMPSFLEPRRRAEKALVAV
                       ::*  .* .***** *.**:::*.***:::.**.  :*:** * ref|YP_001036724.1|    VQEAYVHGVSTRKVDELVEALGMKGIDKSEVSRISKQLDEFVEEFKNRRLEGEYPYLWLD
ref|YP_001039064.1|    VQEAYVHGVSTRKVDELVEALGMKGIDKSEVSRISKQLDEFVEEFKNRRLEGEYPYLWLD
ref|YP_001039349.1|    VQEAYVHGVSTRKVDELVEALGMKGIDKSEVSRISKQLDEFVEEFKNRRLEGEYPYLWLD
RAAC03703              IQEAYVKGVSTRKVDDLVRALGLDGISKSEVSRLCQLIDEEVRQFKERPLEREYPYVWLD
ref|YP_076118.1|       VQEAYIQGVSTRKVDELVQALGMTGVSKSQVSRLCAELDEVVEAFRNRPLEGRYPYVWLD
ref|YP_074958.1|       VLEAYVNGVSTRKVDDLVQALGMTGVSKSQVSRLCAELDEVVQAFRNRPLESRYPYVWLD
                       :.*::****:..*** *:::*:.   :** *. *::*..:*:*** ref|YP_001036724.1|    ATFPKVREGGRVCSMALVIAVGVNQQGEREILGFDVGMSEDGAFWEEFLRRLVARGLKGV
ref|YP_001039064.1|    ATFPKVREGGRVCSMALVIAVGVNQQGEREILGFDVGMSEDGAFWEEFLRRLVARGLKGV
ref|YP_001039349.1|    ATFPKVREGGRVCSMALVIAVGVNQQGEREILGFDVGMSEDGAFWEEFLRRLVARGLKGV
RAAC03703              ATFPKVREGGRVQSMALVIAIGVTDTGEREVLGFDVGTSEDGAFWSDFLRSLKARGLRGV
ref|YP_076118.1|       AKYEKVRENGRVSSMALVIAMGVREDGDREILGLDVGPSEDGAFWTAFLRQLVARGLKGV
ref|YP_074958.1|       AKYVKVRENGRVCTMALVVAVGVREDGDREVLGLDVGPSEDGAFWTAFLRQLVTRGLKGV
                       *.: .****.***.*** : *:**:**:**.******* ***   *.:****:**

ref|YP_001036724.1|    RLVISDAHEGLKAAIKKILTGSAWQRCRVHFMRNVLSQVPKHYQGMVSSIIRTIFAQNDQ
ref|YP_001039064.1|    RLVISDAHEGLKAAIKKILTGSAWQRCRVHFMRNVLSQVPKHYQGMVSSIIRTIFAQNDQ
ref|YP_001039349.1|    RLVISDAHEGLKAAIKKILTGSAWQRCRVHFMRNVLSQVPKHYQGMVSSIIRTIFAQNDQ
RAAC03703              RLVVSDAHAGLRQAISEVLTGATWQRCKVHTIRNVLSQVPKREQSMVASIIRTIFTQPTQ
ref|YP_076118.1|       LLVISDNHVGLREAIRTVFSGASWQRCRVHFMRNLLGYVPKNLQSMVSAAVRTIFAQPDQ
ref|YP_074958.1|       LLAISDSHVGLQEAIRTVLSGASWQRSRVHFMRNLLGYVPKHWQSMVAAAVRTIFAQPDQ
                        *.:** * :    ::* *:*.:.:**:* .***.  *.::.:**.*  * ref|YP_001036724.1|    ESAREQLRHVVDELKNRFPKAMKILEEAEEEILAYMAFPREHWAQIHSTNPLERLNREIR
ref|YP_001039064.1|    ESAREQLRHVVDELKNRFPKAMKILEEAEEEILAYMAFPREHWAQIHSTNPLERLNREIR
ref|YP_001039349.1|    ESAREQLRHVVDELKKRFPKAMKILEEAEEEILAYMAFPREHWAQIHSTNPLERLNREIR
RAAC03703              EAAREQLRRVVAELRGRFPKAMDILEAAEEDVLAFMALPIEHWRQICSTNPLERLNREMR
ref|YP_076118.1|       QAAKSQLAVVVENLRKQFPRAAQLLEDAEEDILAYMAFPTEHWRLHSTNPLERLNREIG
ref|YP_074958.1|       QAARRQLAVVADNLRPQFPRAAQLLEEAEDDILAYMAFPTEHWRQHSTNPLERLNREIG
                       ::*: ** .*. :*: :**:* ..:** **::*:* *** ::.*********:

ref|YP_001036724.1|    RRTDVVCIFPNREAVIRLVGAMLMEQNDEWKVG-RRYFSLESMSKITSINEFTLTPVALL
ref|YP_001039064.1|    RRTDVVCIFPNRKAVIRLVGAMLMEQNDEWKVG-RRYFSLESMSKITSINEFTLTPVALL
ref|YP_001039349.1|    RRTDVVCIFPNREAVIRLVGAMLMEQNDEWKVG-RRYFSLESMSKITSINEFTLTPVALL
RAAC03703              RRMDVVGIFPNRASVVRLAGAILQEQHEEWLVS-RRYFSLESMAKLKPNRPF-LAAEAML
ref|YP_076118.1|       RRTEIVGIFPNREALIRLAGAVMIEQQEEWMTAPRRYFSQASMAKLYAHDPSLGRPELL-
ref|YP_074958.1|       RRTDVVGIFPNREAFIRLAGAVLIEQQDEWTAAPRRYFSQASMAKL---------------
                       ** ::* *****  :.:**.**.::** **:* .. *****  **:*:

ref|YP_001036724.1|    HK
ref|YP_001039064.1|    HK
ref|YP_001039349.1|    HK
RAAC03703              QK
ref|YP_076118.1|       --
ref|YP_074958.1|       --
```

FIG. 80

```
ref|YP_001039349.1|    ----------------------------------------------------------------
ref|YP_001036724.1|    TRANSPSASEMUTATRTYPECLSTRIDIUMTHERMCELLUMATCCGBABNTRANSPSASE
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ----------------------------------------------------------------
ref|YP_001036724.1|    MUTATRTYPECLSTRIDIUMTHERMCELLUMATCCGBABNTRANSPSASEMUTATRTYPE
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ----------------------------------------------------------------
ref|YP_001036724.1|    CLSTRIDIUMTHERMCELLUMATCCGBABNTRANSPSASEMUTATRTYPECLSTRIDIUM
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ----------------------------------------------------------------
ref|YP_001036724.1|    THERMCELLUMATCCGBABNTRANSPSASEMUTATRTYPECLSTRIDIUMTHERMCELLU
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ----------------------------------------------------------------
ref|YP_001036724.1|    MATCCGBABNTRANSPSASEMUTATRTYPECLSTRIDIUMTHERMCELLUMATCCGBABN
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ----------------------------------------------------------------
ref|YP_001036724.1|    TRANSPSASEMUTATRTYPECLSTRIDIUMTHERMCELLUMATCCGBABNTRANSPSASE
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ----------------------------------------------------------------
ref|YP_001036724.1|    MUTATRTYPECLSTRIDIUMTHERMCELLUMATCCSCRESIGNIFICANCEE-IDENTIT
ref|YP_001039064.1|    ----------------------------------------------------------------
RAAC03568              ----------------------------------------------------------------
ref|YP_076118.1|       ----------------------------------------------------------------
ref|YP_074958.1|       ---------------------------------------------------------------- ref|YP_001039349.1|    ---------------MATNNRMALLEQLSKYVVEKDKDFLKEALTLLINALMDAEVTSII
ref|YP_001036724.1|    IESPSITIVESCAPSMATNNRMALLEQLSKYVVEKDKDFLKEALTLLINALMDAEVTSII
ref|YP_001039064.1|    ---------------MATNNRMALLEQLSKYVVEKDKDFLKEALTLLINALMDAEVTSII
RAAC03568              ----MTNTKSRRHATMASLNSFAVLEWIRKMQDVDQIDFLRELMQLVTQFLIDAEAAEKI
ref|YP_076118.1|       ------SNTSQRGNPQVTNFRIALEELLRK-SGVDDVDFLREGVRVLAQGLMELEVSQQI
ref|YP_074958.1|       ---------------------LEELLRK-TGVDDFDFLREGLRVLAQGLMELEVSQRI
                                            :  *: *       .: ***:*  : :: :  *:: *..  * continued →
```

FIG. 80 continued

```
ref|YP_001039349.1|    GAEKYERNNNRNNYRNGYRLREWDTRVGTLQLSIPKLRHGSYFPSLLEPRKMSEKALLNV
ref|YP_001036724.1|    GAEKYERNNNRNNYRNGYRLREWDTRVGTLQLSIPKLRHGSYFPSLLEPRKMSEKALLNV
ref|YP_001039064.1|    GAEKYERNNNRNNYRNGYRLREWDTRVGTLQLSIPKLRHGSYFPSLLEPRKMSEKALLNV
RAAC03568              GAERYERTESRVTQRNGYRSRAWDTRLGTVDLKIPKLRQGSFFPSILEPRRRAEQALASV
ref|YP_076118.1|       GAERYERSSERSNYRNGYRERQWDTRVGTIDLQIPKLRKGSYMPSWLEPRRRAEKALVAV
ref|YP_074958.1|       GADRYERSAERSTYRNGYRERQWDTRVGTTDLQIPKLRKGSYMPSFLEPRRRAEKALVAV
                       ::*. .*. ***** * **:::*.***::: **: :*:**  * ref|YP_001039349.1|    VQEAYVHGVSTRKVDELVEALGMKGIDKSEVSRISKQLDEFVEEFKNRRLEGEYPYLWLD
ref|YP_001036724.1|    VQEAYVHGVSTRKVDELVEALGMKGIDKSEVSRISKQLDEFVEEFKNRRLEGEYPYLWLD
ref|YP_001039064.1|    VQEAYVHGVSTRKVDELVEALGMKGIDKSEVSRISKQLDEFVEEFKNRRLEGEYPYLWLD
RAAC03568              IQEAYVKGVSTRKVDDLVRALGLDGISKSEVSRLCQLIDEEVRQFKERPLEREYPYVWLD
ref|YP_076118.1|       VQEAYIQGVSTRKVDELVQALGMTGVSKSQVSRLCAELDEVVEAFRNRPLEGRYPYVWLD
ref|YP_074958.1|       VLEAYVNGVSTRKVDDLVQALGMTGVSKSQVSRLCAELDEVVQAFRNRPLESRYPYVWLD
                       : *::****:.***: *:.:*:.    :**  *. *.::*  .*:*** ref|YP_001039349.1|    ATFPKVREGGRVCSMALVIAVGVNQQGEREILGFDVGMSEDGAFWEEFLRRLVARGLKGV
ref|YP_001036724.1|    ATFPKVREGGRVCSMALVIAVGVNQQGEREILGFDVGMSEDGAFWEEFLRRLVARGLKGV
ref|YP_001039064.1|    ATFPKVREGGRVCSMALVIAVGVNQQGEREILGFDVGMSEDGAFWEEFLRRLVARGLKGV
RAAC03568              ATFPKVREGGRVQSMALVIAIGVTDTGEREVLGFDVGTSEDGAFWSDFLRSLKARGLRGV
ref|YP_076118.1|       AKYEKVRENGRVSSMALVIAMGVREDGEREILGLDVGPSEDGAFWTAFLRQLVARGLKGV
ref|YP_074958.1|       AKYVKVRENGRVCTMALVVAVGVREDGDREVLGLDVGPSEDGAFWTAFLRQLVTRGLKGV
                       *.:: ****.***  :****:*:** :  *:**:**:***  *** ****** *** * :***:**

ref|YP_001039349.1|    RLVISDAHEGLKAAIKKILTGSAWQRCRVHFMRNVLSQVPKHYQGMVSSIIRTIFAQNDQ
ref|YP_001036724.1|    RLVISDAHEGLKAAIKKILTGSAWQRCRVHFMRNVLSQVPKHYQGMVSSIIRTIFAQNDQ
ref|YP_001039064.1|    RLVISDAHEGLKAAIKKILTGSAWQRCRVHFMRNVLSQVPKHYQGMVSSIIRTIFAQNDQ
RAAC03568              RLVVSDAHAGLRQAISEVLTGATWQRCKVHTIRNVLSQVPKREQSMVASIIRTIFTHPTQ
ref|YP_076118.1|       LLVISDNHVGLREAIRTVFSGASWQRCRVHFMRNLLGYVPKNLQSMVSAAVRTIFAQPDQ
ref|YP_074958.1|       LLAISDSHVGLQEAIRTVLSGASWQRSRVHFMRNLLGYVPKHWQSMVAAAVRTIFAQPDQ
                       *.:** * :    :::*::*.: :**:*.:.  ***.  *.:: :**::   * ref|YP_001039349.1|    ESAREQL-
ref|YP_001036724.1|    ESAREQL-
ref|YP_001039064.1|    ESAREQL-
RAAC03568              EAGREQLP
ref|YP_076118.1|       QAAKSQL-
ref|YP_074958.1|       QAARRQL-
                       ::.:  **
```

FIG. 81

```
ref|YP_516922.1|      MFARIKTAYNRDGSPRRYLQIVESRREEGKVRQKVLCNLGRVEDLQNGKLDDLIRSLAKF
ref|YP_519084.1|      MFARIKTAYNRDGSPRRYLQIVESRREEGKVRQKVLCNLGRVEDLQNGKLDDLIRSLAKF
ref|ZP_01370818.1|    MFARIKTAYNRDGSPRRYLQLVESRREEGKVRQKVLCNLGRVEDLQNGKLDDLIRSLAKF
ref|ZP_01372264.1|    MFARIKTAYNRDGSPRRYLQLVESRREEGKVRQKVLCNLGRVEDLQNGKLDDLIRSLAKF
ref|YP_519534.1|      MFARIKTAYNRDGSPRRYLQLVESRREEGKVRQKVLCNLGRVEDLQNGKLDDLIRSLAKF
RAAC03707             MFAQIVSTKKPDGKTYKYLHIVESYREGRTVKKRRVASLGNISQYSEREIEQIIRTLESL
                      ***::*  ::  : **..  :**::*** **  .*::: :..**.:..  .: :::::**:*  .:

ref|YP_516922.1|      SDKLAVVDAAEDLFADWSKEYGPSMVFNRLWDNLGLHKILDGLFSERELSIDVREAIFCM
ref|YP_519084.1|      SDKLAVVDAAEDLFADWSKEYGPSMVFNRLWDNLGLHKILDGLFSERELSIDVREAIFCM
ref|ZP_01370818.1|    SDTLAVVDAAEDLFADWSKEFGPSMVFRRLWENLGLHTILDGLFNERDLSIDVQEAIFCM
ref|ZP_01372264.1|    SDTLAVVDAAEDLFADWSKEFGPSMVFRRLWENLGLHKIFAGLFNERDLSIDVQEAIFCM
ref|YP_519534.1|      SDTLAVVDAAEDLFADWSKEFGPSMVFRRLWENLGLHKILSGLFNERELSIDVQEAIFCM
RAAC03707             LQHR-TTGSLEDFEAQQVLHFGVPYVVQFLWNQLGLTEAIRDALRAREVTFDVARYVQAM
                       :    ...:  **: *:    .:* . *.. :*    :  . :  *:::**   . : .* ref|YP_516922.1|      VLNRLTEPTSKLGVSDWKDSVYRPDF--ETLKLHHFYKAIDFLDENKDTIEEQLFFHHTN
ref|YP_519084.1|      VLNRLTEPTSKLGVSDWKDSVYRPDF--ETLKLHHFYKAIDFLDENKDTIEEQLFFHHTN
ref|ZP_01370818.1|    VLNRLTEPTSKLGVSDWKDSVYRPEF--ESLKLHHFYKAIDFLDENKDTLEEQLFFHHTN
ref|ZP_01372264.1|    VLNRLTEPTSKLGVSDWKDSVYRPEF--ESLKLHHFYRAIDFLDENKDTLEEQLFFHHTN
ref|YP_519534.1|      VLNRLTEPTSKLGVSDWKDSVYRPEF--ESLKLHHFYKAIDFLDENKESIEEQLFFHQTN
RAAC03707             VIHRLVDPSSKLRLFHTLDDLYLPDWGGEPWQLQHFYRALDYLVDIKPQLERVLYARLTD
                      *::**.:*:***  :  .  *:* *::   *. :*:***:*:*:*  : *  :*. *:  : *:

ref|YP_516922.1|      LFTQQLDLVFFDTTSTYVEGDAGAFDLLEYGHSKDHRPDRLQVMIGILMSRDGIPIAHHV
ref|YP_519084.1|      LFTQQLDLVFFDTTSTYVEGDAGAFDLLEYGHSKDHRPDRLQVMIGILMSRDGIPIAHHV
ref|ZP_01370818.1|    LFTQQLDLVFFDTTSTYVEGDAGAFDLLEYGHSKDHRPDRLQVMIGLLMSRDGIPIAHHV
ref|ZP_01372264.1|    LFTQQLDLVFFDTTSTYVQGDAGAFDLLEYGHSKDHRPDRLQVMIGILMSRDGIPIAHHV
ref|YP_519534.1|      LFTQQLDLVFFDTTSTYVEGDAGAFDLLEYGHSKDHRPDRLQVMIGILMSRDGIPIAHHV
RAAC03707             LLNFRLSLVLYDLTSTHLNGHA---CPLGEHGYSRTHRPDLEQVELGLLVTPEGIPITHEV
                      *:.  :*.**::*  ***::.*.*     *  *:*:*: **     :*:*::  :****:*.* ref|YP_516922.1|      FPGNTPDTDAFIEAVSDLKKRFNIQRVIVVGDRGMMGKRTLELLEELQLQYILGVRMRN-
ref|YP_519084.1|      FPGNTPDTDAFIEAVSDLKKRFNIQRVIVVGDRGMMGKRTLELLEELQLQYILGVRMR--
ref|ZP_01370818.1|    FPGNTSDTDAFIEAVSDLKKRFTIQRVIVVGDRGMMGKRTLELLEELQLHYILGVRMRN-
ref|ZP_01372264.1|    FPGNTPDTDAFIEAVSDLKKRFTIQRVIVVGDRGMMGKRTLELLEELQLHYILGVRMRN-
ref|YP_519534.1|      FPGNTPDTDAFIEAVRDLKKRFTIQRVIVVGDRGMMGKRTLELLEELELHYILGVRMRN-
RAAC03707             FAGNVSDKQTVPDILKRLKEDFAVEQCVFVGDRGMVTEKNMALMAEAGFPYIVGFHKRGR
                      *.**..*..::.  :  :  **:  *  :::  :.****** : ::.:  *:  *   : **:*.: * ref|YP_516922.1|      --IKAGPDLANSPEPYAFIKDNLKVKEVVHQ---------EKRYIVCLNEEEAKRDQLVR
ref|YP_519084.1|      ------------------------------------------------------------
ref|ZP_01370818.1|    --VKAGPELATSPEPYVFTKDNLKVKEVLHQ---------GKRYIVCLNEEEAKRDQWVR
ref|ZP_01372264.1|    --IKAGPELAASAQPYPFVKDNLKVKEVLHQ---------EKRYIVCLNEEEAKRDQLVR
ref|YP_519534.1|      --IKAGPELAASPEPYTFLKDNLKVKEVLHQ---------EKRYIVCLNEEEAKRDRLVR
RAAC03707             IVSDALLEQFADVNAYHELKDNLRYLEVPAASVDDVEKAEGVRYILCYNPEKARQDAAFR ref|YP_516922.1|      E-----------------------------------------------------------
ref|YP_519084.1|      ------------------------------------------------------------
ref|ZP_01370818.1|    E-----------------------------------------------------------
ref|ZP_01372264.1|    E-----------------------------------------------------------
ref|YP_519534.1|      E-----------------------------------------------------------
RAAC03707             ESALEEAETGLKALAESLAKPKRGRKPTDKGVMLKVADLLTRKGVEAFFQVDYKDGILTY ref|YP_516922.1|      --------
ref|YP_519084.1|      --------
ref|ZP_01370818.1|    --------
ref|ZP_01372264.1|    --------
ref|YP_519534.1|      --------
RAAC03707             RRDEDAIT
```

FIG. 82

```
ref|ZP_02171383.1|      ----------VYLARGSTDLRKSIDGLAAIVQEGFELDPFSSSLFVFCNRYRDKIKILY
RAAC03173               MLAFDWTSDHRVYLVCGATDMRKSIDGLAALVQASFQLDPFSPCLFVFCNRQRDKLKILH
ref|YP_431168.1|        ----------RVYLACGATDLRKSIDGLAVLVKEGFELDPFSSCLFVFCNRNRDKLKILH
ref|YP_001212944.1|     ----------RVYLALGATDLRKSIDGLAVLVKEGFELDPFSSCLFVFCNRKCDKLKILH
ref|YP_754944.1|        -------SNRQVYLACGSTDLRKSIDGLAVLVKEAFELNPFSPCLFVFCNRQRNKLKILQ
ref|YP_754864.1|        -------SNRLVYLACGSTDLRKSIDGLAVLVKESFHLDPFSPCLFVFCNRKRDKLKILQ
                                   ***. *::*******.:*: .*.*:*..****  :*:*** ref|ZP_02171383.1|      WDHNGFWLYYRRLEKGRFPWPTSGSDEPMIITERQLRWLLDGLPLDQKGAHR--------
RAAC03173               WSHNGFWLYYRRLERGRFDWPETGDAKTMVITRRELNWLLDGLPLEQPKAHRAVPVRSAI
ref|YP_431168.1|        WEHNGFWLYYRRLEKGKFVWPQDTTSSTITITRRELRWLLDGLPLKQPQAHPEVKARTIL
ref|YP_001212944.1|     WDHNGFWLHYRRLEKGKFHWPADAGSPTLVISRRELRWLLDGLSLKQPKAHPEVKARTIL
ref|YP_754944.1|        WDHNGFWLYYRRLERGKFEWPA-ADSQVVSISYREFRWLLDGLSLKQKQAHKAVKERTII
ref|YP_754864.1|        WEHNGFWLHYRRLERGKFDWPT-AHTDVVSISYREFRWLLDGLSLKQNQAHKAVKQR---
                        *.******:*****:*:* **           : *: *::.******.*.*   **
```

FIG. 83

```
ref|NP_634718.1|            ---------------------------------------MLKTEEWLLIRDLYSQGFSISEIA
ref|NP_616807.1|            ---------------------------------------MLKTEEWLSTRDLYSQGFSISEIS
gb|AAR99616.1|              ---------------------------------------IKEMYERGMSISDIA
sp|Q45618|TRA6_BACST        ---------------------------------------IKEMYERGMSISDIA
ref|YP_074959.1|            ---------------------------------------MLRSGETLEIRQMYAGGLSISEIA
RAAC02966                   MRIPQDHRPQFLKIIGMNSPPPCRIVAPVIRSWEVPVMREDERMEIRQLYEAGVSISELA.
                                                                    *::*  *.***:::

ref|NP_634718.1|            KQTGFDRKTVRKYLRLKTLPEPQKRSG-----RKSKLDPFKPYIQEKLKEGPYT------
ref|NP_616807.1|            RRTGYARETVRKYLKKKTAPEPQKRPP-----KPSKLDPFKPYIQEKLKEGPYT------
gb|AAR99616.1|              RELGIDRKTVRKYIHSPNPPSKSKRKQ-----RKSKLDPFKPYLQKRM------------
sp|Q45618|TRA6_BACST        RELGIDRKTVRKYIHSPNPPSKSKRKQ-----RKSKLDPFKPYLQKRM------------
ref|YP_074959.1|            RRTGRDRKTIRKWLRTNTMPKPAKRK------RSSMLDQHEAFTLEQMQKGVTSASK---
RAAC02966                   RRFGYDRKTIRSALNSSLEEKQGERASRGERKKGSKLEPYKDYVKQRMQLGVSTLNEFCE
                            :. *  *:*:*.  :.       . :*       : * *: .: :    :::

ref|NP_634718.1|            -----------------
ref|NP_616807.1|            -----------------
gb|AAR99616.1|              -----------------
sp|Q45618|TRA6_BACST        -----------------
ref|YP_074959.1|            -----------------
RAAC02966                   RFGSRAIPAVSPSSVSS
```

FIG. 84

```
ref|YP_148444.1|        MEERLVSGEVLGEETALEPSLRPQYLHEYIGQDKIKENLKVFIEAAKLREETLDHVLLYG
ref|NP_980798.1|        MDERLLSGESAYEDADLEYSLRPQTLRQYIGQDKAKHNLEVFIEAAKMREETLDHVLLYG
sp|Q9KDI8|RUVB_BACHD    MEERMVSAEAQTEEAAVEQGIRPHSFEQYIGQEKVKQNLKVFIEAAKMREEALDHVLLYG
ref|YP_430545.1|        --ERLVAGNLHNEDQELELSLRPRCLAEYIGQEHVKETLGIFIQAARERGEALDIIVLLYG
ref|YP_001211577.1|     MKDRLISAVARPEDADVDTSLRPRLLAEYIGQEKVKETISVFIQAARGRGEPLDHVLLFG
RAAC00757               MDERLISAEWMREDAQLDT-IRPRFLDDYIGQRAAVENLRIFIQAAKERGEPLDHVLLYG
                          :*::.    *:   ::  :: : :     ..: ::**: * *.******:* ref|YP_148444.1|        PPGLGKTTLAVIIANEMGVKLRATSGPALERPGDLAALLTSLEPGDVLFIDEIHRLPRAV
ref|NP_980798.1|        PPGLGKTTLANIIANEMGVNVRTTSGPAIERPGDLAAVLTSLQPGDVLFIDEIHRLHRSI
sp|Q9KDI8|RUVB_BACHD    PPGLGKTTLSTIIANELGVQMRTTSGPAIERPGDLAAILTALEPGDVLFIDETHRLNRMV
ref|YP_430545.1|        PPGLGKTTLAGIIANELGVQLRVTSGPALERAGDLAAILTNLQPRDVLFIDEIHRLPRQV
ref|YP_001211577.1|     PPGLGKTTLANIIANEMGVSIRTTSGPAVERPGDLAAILTSLSQGDILFIDEIHRLSRTV
RAAC00757               PPGLGKTSLAMIIANELGVQIRVTSGPAIERAGDLAAILTNLQPGDVLFIDEIHRLSPSV
                        *******:*: *****:**.:*.***** **.***** **  *.:********    :

ref|YP_148444.1|        EEVLYPAMEDYCLDITIGKGPDARTLRLDLPPFTLVGATTRAGALSAPLRDRFGVISRLE
ref|NP_980798.1|        EEVLYPAMEDFCLDIVIGKGPSARSVRLDLPPFTLVGATTRAGALSAPLRDRFGVLSRLE
sp|Q9KDI8|RUVB_BACHD    EEVLYPAMEDYCLDIVIGKGPTARSVRLDLPPFTLVGATTRAGMLSSPLRDRFGVMARLE
ref|YP_430545.1|        EEILYPAMEDFVLDIILGKGPGARSIRLDLPPFTLVGATTRAGLLSSPLRDRFGINSRLE
ref|YP_001211577.1|     EEVLYPAMEDYALDIVIGKGPGARSLRLELPPRFTLVGATTRAGLLTSPLRDRFGVISRLE
RAAC00757               EEVLYPAMEDFAIDIVIGKGPSARSVRLDLPPFTLIGATTRAGLLSHPLRDRFGVMHLD
                        **:*******: :** :****  **::**:**  ***.*******  *: ******:  :*:

ref|YP_148444.1|        YYHVDQLAQIIERAAAILQIGIEREAALELARRRARGTPRIANRLLRRVRDFAQVRGEGGI
ref|NP_980798.1|        YYTVDQLSEIVERTAEVFEVEIDSLAALEIARRRARGTPRIANRLLRRVRDFAQVRGNGTV
sp|Q9KDI8|RUVB_BACHD    YYNVEELTTIIERTATIFDTELERDASIEIARRSRGTPRIANRLLRRVRDFAQVSGDMRL
ref|YP_430545.1|        FYQVAELEEIIRRAATILQVAIEPEGAREIARRRARGTPRVANRLLKRVRDYAEIRAGGVI
ref|YP_001211577.1|     YYRPEDLVLIVNRSARILGIEITAEGAFEIARRSRGTPRVANRLLKRVRDYAQVRANGVI
RAAC00757               YYPVRDLAEIVKRNARILQLSITEDGCAEIARRARGTPRIANRLLKRVRDIAQVAGWPEI
                        :*    :*  *:.* * ::    :    ..*:***:*****:****.****  *::  .  :

ref|YP_148444.1|        TLPLAVEALERLQVDRLGLDQIDHKLLSAMIEKFAGGPVGLETLAAVIGEEAQTIEEVYE
ref|NP_980798.1|        TMEITQMALELLQVDRLGLDHIDHKLLLGIIEKFRGGPVGLETVSATIGEESHTIEDVYE
sp|Q9KDI8|RUVB_BACHD    SSSRATESLERLQVDRLGLDHIDHKLIKGIMTKFNGGPVGLETISATIGEETDTIEEVYE
ref|YP_430545.1|        TREVAREALELLQVDAAGLDSSDRRLLLTLIRKFNGGPVGLETLAAAISEEPDTIEDVYE
ref|YP_001211577.1|     TCEVAVEALKFLEVDPLGLDFADRRLLLTIIQKFGGGPVGLETIATAVNEEPETVEDVYE
RAAC00757               DAARAAEALAQLHVDPLGLDATDKRILEAAMDKFGGGPVGLDTLAAAVGEEPSTLEDVYE
                           :*    *.  *    *::::   :   ****:*:::: .**.  *:*:*** ref|YP_148444.1|        PYLMQIGLLQRTPRGRVVTPAAYTHLGMEVP--
ref|NP_980798.1|        PYLLQIGFLQRTPRGRIVTPLAYEHFGMEMP---
sp|Q9KDI8|RUVB_BACHD    PYLLQIGFLQRTPRGRVVTPLAYEHFNMEVPN-
ref|YP_430545.1|        PFLLQMGYLQRTPRGRVATPGAYAHLG------
ref|YP_001211577.1|     PYLIQLGMLARTPRGRVTTPLAFRHLG------
RAAC00757               PYLLQIGFLKRTPRGRVVMPSAYRHLGRAVPSG
                        *:*:*:* * *****:.  *  *: *:.
```

FIG. 85

```
ref|YP_234498.1|        --------MIGRLRGSLAEKQPPHLVLDVNGVGYEVEVPMTTLYRLPHVGETVTLHTHLVV
ref|YP_275913.1|        --------MIGRLRGSLAEKQPPHLVLDVNGVGYELEVPMTTLYRLPHVGETVTLHTHLVV
ref|NP_793742.1|        --------MIGRLRGAIAEKQPPHLVLDVNGVGYELEVPMTTLYRLPHVGETVTLHTHLVV
ref|YP_001186768.1|     --------VIGRLRGTLAEKQPPHLLLDVNGVGYELEVPMTTLYRLPAVGETLTLHTHQVV
ref|ZP_00991066.1|      --------MIGRLRGTLIEKQPPELLIEVSGVGYEVQMPMSCFYELPNVGEEAIIYTHFVV
RAAC00756               MGTGAFSVIAFLRGRVAFLGPGYVDLDVRDVGYRVHVCDRTQAAL-NLGDTAFLYTHHHV
                            :*. ***  :    *  : ::*  .***.:.:      *  :*:   ::**  * ref|YP_234498.1|        REDAHLLYGFYEKRERELFRELIRLNGVGPKLALALMSGLEVDELVRCVQAQDTSALTRI
ref|YP_275913.1|        REDAHLLYGFYEKRERELFRELIRLNGVGPKLALALMSGLEVDELVRCVQAQDTSALTRI
ref|NP_793742.1|        REDAHLLYGFYEKRERELFRELIRLNGVGPKLALALMSGLEVDELVRCVQAQDTSALTRI
ref|YP_001186768.1|     REDAHLLYGFFEKRERELFRELIRLNGVGPKLALALMSGLEVDELVRCVQAQDTAALTKV
ref|ZP_00991066.1|      REDAQLLYGFNTVKERALFREVIKANGVGPKLGLGILSGMTASQFVQSVEREDISTLVKL
RAAC00756               REDGWALYGFETIEERALFERLVAVSGIGPKLALQVIGAAGVGEIVAAILAEDAESLSRL
                        ***.  ****    .** **..::  .*:****.*  ::..  ..::* .:  :*  :* ::

ref|YP_234498.1|        PGVGKKTAERLLVELKDRFKAWEALPGTFTLVSNGPNQAEP-VASAESDAVSALISLGYK
ref|YP_275913.1|        PGVGKKTAERLLVELKDRFKAWESLPGTFTLVSNGPNQAEP-VASAESDAVSALISLGYK
ref|NP_793742.1|        PGVGKKTAERLLVELKDRFKAWESLPGTFTLVSNGPNHADP-VASAESDAVSALISLGYK
ref|YP_001186768.1|     PGVGKKTAERLLVELKDRFKAWETMPAIATLVVE-PRLGAT-VSSAENDAVSALISLGYK
ref|ZP_00991066.1|      PGVGKKTAERLVVEMKDRLKGWGAGDLFTPATDAAPMDSMPTVHDAEEEAVSALLALGYK
RAAC00756               PGIGRKLASRLVVELREKLDDLAPAALRAPAPASSPQ------GSAAEDAVSALVALGYR
                        **:*:*  *.**:**:::::.    .       *         .*  .:*****::***:

ref|YP_234498.1|        PQEASKAVSAIKEKDLSSADLIRRAL---------------
ref|YP_275913.1|        PQEASKAVSAIKEKDLSSADLIRRAL---------------
ref|NP_793742.1|        PQEASKAVSAIKEKDLSSADLIRRAL---------------
ref|YP_001186768.1|     PQEASRAVAAVKEDGLSSEDLIRRAL---------------
ref|ZP_00991066.1|      PTQASKVVAQVAKGGMTSEQLIREAL---------------
RAAC00756               PREAEEAVSAVGRGRQSVEDTIKAALTYLYARDARTEPLSQP
                        *  :*...*:  : .    :  : *:  **
```

FIG. 86

```
ref|YP_644098.1|         ------------------------ILGIDPGTATMGWGVVRQ-EGSRLRYVQHGATTTP
RAAC00755                ------------------------MESLRILGVDPGLARLGFGIIERGPGDSLHHVAHGCIETG
ref|YP_074988.1|         ------------------------MRILGIDPGTARMGYGIVEDAGAGRERAVEYGCLETP
ref|ZP_02848139.1|       ------------------------MRVLGIDPGIAIAGFGFIDK-DGHKLKPVQYGCIQTA
ref|YP_518701.1|         EE-IDENTITIESPSITIVESGAPSILGIDPGTATMGYGLIEK-KGNRLFPVDYACWRTP
ref|YP_001180347.1|      ------------------------MRVLGIDPGIALTGYGIIESKNGSEFKVIDYGRIETS
                                                 ::* * *:*.:     .   : :.   * ref|YP_644098.1|         SGWGMPRRLDRLFAGVTELIRGYRPSAVAVEELFFNTNVTTAITVGQARGVALLAAYRAG
RAAC00755                ADTPLPERLRHIFQQLTELCRTHRPAVMAVEELFFSRNTTTAFTVGQARGVALLAGAEAG
ref|YP_074988.1|         PDMRPELRLQALYRGLADLMARHRPDALAVEELFFGRNVTTAIHVGQARGVVLLAAADSG
ref|ZP_02848139.1|       AHTPQEERLVQIYDSAVALMDKYKPDTVAVEKLFFNRNVTTAFAVGQARGVIILAAAQRG
ref|YP_518701.1|         AHTPMPERLLMLYHEIEAYIKEKQPHHVAVEELFFNRNTTTAISVGQARGVVLLAAAQCG
ref|YP_001180347.1|      SSLKKSMRLLHLYTELCSIISLYQPDVVAIEELFFSKNSKTAITIGEARGVIILTCIQNN
                              .  **  ::          :*  :*:*:***.  *  **: :*:****  :*:    .

ref|YP_644098.1|         VEVFEYTPLQVKQAITSYGRADKRQVQEMVRALLGLRSIPRP------------------
RAAC00755                LAVMEYTPMQVKQAVTGYGRADKRQVQEMVRLLLRLTSVPKPDDAADALAVAIAHAHAGR
ref|YP_074988.1|         VPVREFTPMQVKMAVTGYGRANKAQVQRMVQALLGLPEIPKP------------------
ref|ZP_02848139.1|       LPVAEYTPLQVKQAVVGYGKAEKRQVQEMVKMFLKLSAIPKP------------------
ref|YP_518701.1|         LPVYEYTPLQVKQAVAGYGRADKQQIQQMVRALLGLQEIPKP------------------
ref|YP_001180347.1|      LSIYEYTPLQVKQSITGYGRADKTQIQKMVKSLLGLSEIPKP------------------
                          :  :::*  ::..**:*:*  *:*.**:  :* *   :*:* ref|YP_644098.1|         -------------------------
RAAC00755                IGELEARLAAGKRTGWVWERGRFR
ref|YP_074988.1|         -------------------------
ref|ZP_02848139.1|       -------------------------
ref|YP_518701.1|         -------------------------
ref|YP_001180347.1|      -------------------------
```

FIG. 87

```
ref|YP_146341.1|        ---------------VFIYLRKSRKDIEEEKKAAESGASYDTLQRHRDNLLAVARKEGHNIL
ref|YP_001373830.1|     ---------------VFIYLRKSRKDLEEEKKAMEHGQHYDTLERHRTQLLELAHKEHHNII
ref|ZP_02261478.1|      ---------------VCIYLRKSRKDVEEERRAIEEGSSYNALERHRKRLFAIAKAENHNII
ref|ZP_02257063.1|      ---------------VCIYLRKSRKDVEEERRAIEEGSSYNALERHRKRLFAIAKAENHNII
ref|YP_001513188.1|     ----------MEKVSIYLRKSRADIEAESRGEGE-----TLAKHRSTLLKVAKEKKLSIV
RAAC01468               MTPVSTFPTGLEHVAIYLRKSRADLEAEARGEGE-----TLTKHRRALLELAKQYHYSID
                                       * ******* *:* *  :.       :* :** *: :*:    .* ref|YP_146341.1|        GIFEEIVSGESIAERSEIQKLLRELETGVADAVLVMDIDRLGRGDMLDQGILDRAFRYSG
ref|YP_001373830.1|     DIFEEVVSGEYISERPMMQKLLREVETGIADAVLVMDLDRLGRGDMVDQGTIYRVFRYSE
ref|ZP_02261478.1|      DIFEEVASGESIQERPQMQQLLRKLEGNEIDGVLVIDLDRLGRGDMLDAGMIDRAFRYSS
ref|ZP_02257063.1|      DIFEEVASGESIQERPQMQQLLRKLEGNEIDGVLVIDLDRLGRGDMLDAGMIDRAFRYSS
ref|YP_001513188.1|     KIYEEIVSGESLMHRPEMLELLKNVESKKYDAVLVMDVDRLGRGNMQEQGLILETFKKSC
RAAC01468               HIYEEIVSGELIVDRPEVQRLLHAVREGKYSAVLVMDIDRLGRGNQIDQGIIQQAFKQSG
                         *::.*  : .*. :  :: :.    ..*:*:******:   :  * ..*: * ref|YP_146341.1|        TKIITPTEVYDPESETWELVFGVKSIVSREELKVITKRLQGGRRDSAAKGRSISKKPPYG
ref|YP_001373830.1|     TFIITPTEVINPNDENQELTFSIKSLIAREELKTIVKRMQRGRKASAKEGKSISRVPAYG
ref|ZP_02261478.1|      TKIITPTDVYDPDEESWELVFGIKSLISRQELKSITKRLQNGRIDSVKEGKHIGKKPPYG
ref|ZP_02257063.1|      TKIITPTDVYDPDDESWELVFGIKSLISRQELKSITKRLQNGRIDSVKEGKHIGKKPPYG
ref|YP_001513188.1|     TKIITPRKIYNLDDEFDEEYSEFEAFMARKELKMINRRLQNGRVRSIEDGNYISPNPPYG
RAAC01468               TLIITPRKVYNLEDELDEEFSEFEQFMARRELKIITRRMQRGRKLSAKEGKSITPYVPFG
                        * ****  .: :  :.*     .:  :::*.*** * *:*:  ** * .*.  *   .:* ref|YP_146341.1|        YLRDEQ---LKLYPDPETSWVVVKIFEMVRDGHGRQAIAAELDRLGVKPPDEKRAFWSPS
ref|YP_001373830.1|     YLRDNN---LKLYPDPEKSWVIPKIFELMANGIGRQAIAQELDRLGIAPPEGE--YWNPS
ref|ZP_02261478.1|      YLKDEN---LRLYPDPEKAWIVKKIFELMCDGKGRQMIAAELDRLGIDPPVTKRGAWDSS
ref|ZP_02257063.1|      YLKDEN---LRLYPDPEKAWIVKKIFELMCDGKGRQMIAAELDRLGIDPPVTKRGAWDSS
ref|YP_001513188.1|     YEIDEGKDYRTLKPHPEQAEVVKMIFEWYVSGLGSGKIANKLNDLGYKSYTGIP--WRSS
RAAC01468               YKRDEN---LKLYPDPETAPIVRQIFEWSAEGLGLIIKIAKKLNEMGVPAPRSCG--WQRT
                         *  *:    * *.** :  :  ***   .*  * ** :*: :*   .        *  :

ref|YP_146341.1|        TISAIIKNEVYLGHIIWGKVKYIKQNGRYKRK---KMPRERWYVKENAHAPLVSKELWEA
ref|YP_001373830.1|     TISSIIKNEVYLGHIIWGKIRYIKQNGKYIRK---KVSKERWQRHDNAHPPLVSEELFQK
ref|ZP_02261478.1|      TITSIIKNEVYTGVIVWGKFKHKKRNGKYTRH---KNPQEKWIMYENAHEPIISKELFDA
ref|ZP_02257063.1|      TITSIIKNEVYTGVIVWGKFKHKKRNGKYTRH---KNPQEKWIMYENAHEPIISKELFDA
ref|YP_001513188.1|     SVLNMLKNLVYTGKVVWGRKDIKKSTEVGKVKDTVTRPKEEWIIADGKHPALVSEELFEK
RAAC01468               TVQHILKNEVYLGRIVWDKKRDVKTTEG-KYR-SIKRPREEWIVHENAHEPIISQELWDR
                        :: :::** ** * ::*.: :       * .    :   .:*.*   :. * .:*:**::

ref|YP_146341.1|        ANKAYRSRWRPSTVESKPLANPLAGLLKCEVCGYTMWYQPRKDRPHHPLVRCPNPKCKGVQ
ref|YP_001373830.1|     ANTAHSKRWRPPTIKTKKLSNPLAGLLLCELCGHSMLYQPRKDRPNPQVRCVQPSCKGVQ
ref|ZP_02261478.1|      ANEAHSSRHKPAVITSKELTNPLAGIIKCKLCGYTMLIQTRKDRPHNYLRCNNPACKGKQ
ref|ZP_02257063.1|      ANEAHSSRHKPAVITSKKLTNPLAGILKCKLCGYTMLIQTRKDRPHNYLRCNNPACKGKQ
ref|YP_001513188.1|     AQEILNKRYHVPYQLENGITNPLAGLTRCENCGASMVLRPYPDKD-HQVMCYNN-CGNKS
RAAC01468               VVEIRKVNDHR-TKDNYDLKNPFAGILRCKQCGRVMKRQPRPNRNGDTLQCYTTGCPTRE
                         . :    :          : :::  *: **  :  :: *     *   * ref|YP_146341.1|        KGALLPLVEEKILQSLAEFVDQFEVQE---DRKEQRSV-----IPLKQKAIEKKEKELRE
ref|YP_001373830.1|     KGASLALVEQRILDGLKQTIESFEIQANMVQQKKRKKN-----IHLQQKALEKKEQQMIN
ref|ZP_02261478.1|      KQSVFNLVEEKLLYSLQQIVDEYQAQKVEEVEIDDSKL-----ISFKEKAIISKEKELKE
ref|ZP_02257063.1|      KQSVFNLVEEKLLYSLQQIVDEYQAQKVEEVEIDDSKL-----ISFKEKAIISKEKELKE
ref|YP_001513188.1|     --SKLKYVEKEVLAGLAEWCLQYRAQWDIDNKSKRKKSKLTSSIPVLEKAVENLQKELVE
RAAC01468               --VLLSRLEDRVLQSIEEFVQSYAAQSSVKKRADNRQKKLFA----LHRQKKSIQSKLSK
                            :  :*..:*  :  : :  .  *   .   .         .:   .   . :.:: :

ref|YP_146341.1|        LHKQKDALHDLLERGVYTIETFLERQQTIVSRIKKTQEEIDQLREEIAKEQLKEKNISEY
ref|YP_001373830.1|     LQKQKNNLHDLLEKGVYDVETFLERQKSIAVRLKTTQKAIEELKHEIKKILEKEKHIHEF
ref|ZP_02261478.1|      LQAQKGNLHDLLEQGIYTVEIFLERQKNLVERITSIENDIEVLQKEIETEQIKEHNKTEF
ref|ZP_02257063.1|      LQAQKGNLHDLLEQGIYTVEIFLERQKNLVERITSIENDIEVLQKEIETEQIKEHNKTEF
ref|YP_001513188.1|     LENQKNSLHDFLERGIYVDVTYLERSQNLATRIDATKVSLSKAKLVLGQEMQRFEKAQID
RAAC01468               LETQKNRLFDFLEQGIYDVQTFIERSKLVGEQIDQAKEELKICEQAIEREMLQQQHEEEL
                        *. ** .* *:**:*:*   *::** . :    .     :   ::    :  :::    :

ref|YP_146341.1|        VPTVKKVLDAYRLTDDVEKKNRLLKSVLEKATYLRKPEWTKKDQFTIQLYPRI
ref|YP_001373830.1|     VPRIKNVLEAYYATNDIEKKNRLLKSVLEKATYLRKKIWQRKDEFLIELYTRI
ref|ZP_02261478.1|      IPALKTVIESYHKTTNIELKNQLLKTILSTVTYYRHPDWKTN-EFEIQVYFKI
ref|ZP_02257063.1|      IPALKTVIESYHKTTNIELKNQLLKTILSTVTYYRHPDWKTN-EFEIQVYFKI
ref|YP_001513188.1|     IPRIEKVLDVYPKINDPAHKNELLKSVLDYAAYSKDKSK-RNDDFSLRLF---
RAAC01468               IPAISEAIAMYRTASNAEIKNMALKSVIKEIHYYRPRSWSKSKEFEIDIYFRI
                        :* :..: .:       :  ** .:**.:::   *      .   * : :
```

FIG. 88

```
ref|YP_753434.1|      ----------------------------------------------------------------
ref|YP_753226.1|      EFYPHYPTHETICALPRTEINSWLSYNTRPHMNASWLFEISUBSPWLFEISTRGETTING
ref|YP_752864.1|      ----------------------------------------------------------------
ref|ZP_01665148.1|    ----------------------------------------------------------------
ref|YP_001111903.1|   ----------------------------------------------------------------
RAAC03178             ---------------------------------------------------------------- ref|YP_753434.1|      ----------------------------------------------------------------
ref|YP_753226.1|      ENGBABIHYPTHETICALPRTEINSWLSYNTRPHMNASWLFEISUBSPWLFEISTRGETT
ref|YP_752864.1|      ----------------------------------------------------------------
ref|ZP_01665148.1|    ----------------------------------------------------------------
ref|YP_001111903.1|   ----------------------------------------------------------------
RAAC03178             ---------------------------------------------------------------- ref|YP_753434.1|      ----------------------------------------------------------------
ref|YP_753226.1|      INGENGBABIHYPTHETICALPRTEINSWLSYNTRPHMNASWLFEISUBSPWLFEISTRG
ref|YP_752864.1|      ----------------------------------------------------------------
ref|ZP_01665148.1|    ----------------------------------------------------------------
ref|YP_001111903.1|   ----------------------------------------------------------------
RAAC03178             ---------------------------------------------------------------- ref|YP_753434.1|      ----------------------------------------------------------------
ref|YP_753226.1|      ETTINGENGBABIHYPTHETICALPRTEINSWLSYNTRPHMNASWLFEISUBSPWLFEIS
ref|YP_752864.1|      ----------------------------------------------------------------
ref|ZP_01665148.1|    ----------------------------------------------------------------
ref|YP_001111903.1|   ----------------------------------------------------------------
RAAC03178             ---------------------------------------------------------------- ref|YP_753434.1|      ----------------------------------------------------------------
ref|YP_753226.1|      TRGETTINGENGBABIHYPTHETICALPRTEINSWLSYNTRPHMNASWLFEISUBSPWLF
ref|YP_752864.1|      ----------------------------------------------------------------
ref|ZP_01665148.1|    ----------------------------------------------------------------
ref|YP_001111903.1|   ----------------------------------------------------------------
RAAC03178             ---------------------------------------------------------------- ref|YP_753434.1|      ----------------------------------------------------------------
ref|YP_753226.1|      EISTRGETTINGENGBABIHYPTHETICALPRTEINSWLSYNTRPHMNASWLFEISUBSP
ref|YP_752864.1|      ----------------------------------------------------------------
ref|ZP_01665148.1|    EAXTRANSPSASEISFAMILYP---------RTEINTHERMSINU---------------
ref|YP_001111903.1|   ----------------------------------------------------------------
RAAC03178             ---------------------------------------------------------------- ref|YP_753434.1|      --------------------IHYPTHETICALPRTEINSWLSYNTRPHMNASWLFEISU
ref|YP_753226.1|      WLFEISTRGETTINGENGBABIHYPTHETICALPRTEINSWLSYNTRPHMNASWLFEISU
ref|YP_752864.1|      ----------------------------------------------------------------
ref|ZP_01665148.1|    -------SCARBXYDIVRANSNRGBEAXTRANSPSASEISFAMILYPRTEINTHERMSINU
ref|YP_001111903.1|   ----------------------------------------------------------------
RAAC03178             --------------MLLSNGTTYMQERVHWGVHHIAPVNCMHLHNIKFFRSESTRFPKNref|YP_753434.1|      BSPWLFEISTRGETTINGENSCRESIGNIFICANCEE-IDENTITIESPSITIVESGAP-
ref|YP_753226.1|      BSPWLFEISTRGETTINGENSCRESIGNIFICANCEE-IDENTITIESPSITIVESGAP-
ref|YP_752864.1|      ----------------------------------------------------------------
ref|ZP_01665148.1|    ----SCARBXYDIVRANSNRSCRESIGNIFICANCEE-IDENTITIESPSITIVESGAPS
ref|YP_001111903.1|   ----------------------------------------------------------------
RAAC03178             ------FVRYLNEPFAESRVLVRQG------FFEHKEGLHPNLRERKWYPANHFKGAKSN
``` continued →

FIG. 88 continued

```
ref|YP_753434.1|      -SIRQNCIFSFEDALKIQPKSRLEKIINTLDLKPVLCKLDKPGEIRVGPKPYPAYAMLNA
ref|YP_753226.1|      -SIRQNCIFSFEDALKIQPKSRLEKIINTLDLKPVLCKLDKPGEIRVGPKPYPAYAMLNA
ref|YP_752864.1|      --IRQGYVFSFEDAINLQPRSRLEIVLATLDFDDVITVLDKENKQHRGPTGYPFESKLNA
ref|ZP_01665148.1|    MYIRQKPLFSFDTLMQYQPKTRLAMVFESIDLHPLLKTLPIKS--IRGPKGYSSAALIKA
ref|YP_001111903.1|   MYLLQPNLFSFEELLKFEPETKLQKVLSVLDLSPALNVVKRAV---LGPKGHCVGNMIRA
RAAC03178             VYVRQAWLFSFDEWMEMSPCERRELFFSTLDLSPYAAKLRSSTP--QGAKPISREAILRA
                        : * :***:  :: .*  .  .  :*:       *..         :.* ref|YP_753434.1|      LIAMRLENMGTFTQLVERLTYDPHLRYVCGFEPFGTAPSKSCFSRFYSKLAQS-------
ref|YP_753226.1|      LIAMRLENMGTFTQLVERLTYDPHLRYVCGFEPFGTAPSKSCFSRFYSKLAQS-------
ref|YP_752864.1|      LIAMRVYNMATFTELVERLTHDPVLRYNCGFDVFGKVPSIATFSRFYERLTQS-------
ref|ZP_01665148.1|    FLAMRLCSIPTVTLLVERLKTDLVFRYECGFSLEQPVPSLATFSRFFQKIAET-------
ref|YP_001111903.1|   LVAKQLEQIPTVAALVKRLSNDIRFRFQCGFSLSKPIPSESTFSRLIQKLAATDETNKTE
RAAC03178             FLAAPLEGISTFTQLHRRLESDLRFRYQCGFSLHESIPSVSTLSRVFQAIVDK-------
                      ::*   :  : *.: * .**   *  *:  ***.        **  :**..  . .

ref|YP_753434.1|      GCLETLFTSLVKQAEEMGLLDLSSVAIDATKVEAYEKSVPRKNIIQDGNVADWGIKSDTN
ref|YP_753226.1|      GCLETLFTSLVKQAEEMGLLDLSSVAIDATKVEAYEKSVPRKNIIQDGNAADWGIKSDTN
ref|YP_752864.1|      EVLRELFKKQVTTAESMGLIDTSSIAIDASKVDANEKSVPRKNIKDDGQSANWGSKLDTN
ref|ZP_01665148.1|    DSLQVLFSALVDTAIQDKVISGEVVAIDASAIDSYEKPVPKKELNSNGDSATWGAKLDTH
ref|YP_001111903.1|   SVMKQIFDNLVKSAKDMGLIDSNCVAIDSSKIDAYEKSKPKKDLQGD-KTANWGAKRDTH
RAAC03178             GVAATLFAELVRQCRDEGLIEGEHVAIDSTAIHAYERKHPRSGVQPS-NRANWGAKFDAF
                         : *    *  . ..  ::. . :***::  :.: *:  *:.    . .  * ** *:

ref|YP_753434.1|      GNPIKWFGYKLHIGTDVKSGLPIAMKVTPANYSDSSVALELVEKCCANTQS--KIVYFLM
ref|YP_753226.1|      GNPIKWFGYKLHIGTDVRSGLPIAMKVTPANCSDSSVALELVEKCCANTQS--KIVYFLM
ref|YP_752864.1|      GNQITWFGYKLHIATDVKSELPVALSITPASTNDGIMAESILEECSNNLNS--KPQYYLM
ref|ZP_01665148.1|    GNQHVWFGYKLHLAVDTKSELPIAVKVTPANRNDVTQAIPLMDEIKH------QPKYYCM
ref|YP_001111903.1|   GNQISWFGYKAHVAVDCHSELPIAIMVTPANTHDAKMAIPLIELVNKALEDSKKPKYYTM
RAAC03178             GNKLAWFGYKVHLAVDAKSELPMALTVTPANVYDGEMAIPLMEELHHHDWR---IRFVLM
                          *** *:..* :* **:*: :***. *   *    :::        :   * ref|YP_753434.1|      DAGYDHREIYSVIRDKYHAQAIIALNKRGAKQPPEGFDWDGTPICSARYRMVYWGSY--Q
ref|YP_753226.1|      DAGYDHREIYSVIRDKYHAQAIIALNKRGAKQPPEGFDWDGTPICSARYRMVYWGSY--Q
ref|YP_752864.1|      DAGYDQKSIYELIRKDYKAQAIIPLNHRGAKEPPEGLDWDATPICSAGYRMAYWGGS--N
ref|ZP_01665148.1|    DMGYDAKDVYQAAYER-QAQAIIPLNRRKEKLPPEGMDENRTPTCSMGYPMVYWGCEREK
ref|YP_001111903.1|   DMGYDSKDIYSVVMNDFNAQAIIPINSRGSKDHPEGCDFDGTPICSMGQRMVFWGSDAKA
RAAC03178             DAGYDQTKNYEAARAL-GAQAIIPMNRRNEKEPPEGMDFDGTPRCTMGYRMTYWGVH--N
                      * ***   .*.     ***** .:* *   * *** * ** *: *   *.:**

ref|YP_753434.1|      GVNKFRCPHIMGKCDCPFGSAWCSDSNYGMVVKTKVKDDPRLFSSPHRGSANWQKQYNLR
ref|YP_753226.1|      GVNKFRCPHIMGKCDCPFGSAWCSDSNYGMVVKTKVKDDPRLFSSPHRGSANWQKQYNLR
ref|YP_752864.1|      GVNKFRCPHVMGKCDCPFGSSWCSDSNYGMVVKTRARQDSRLFIVPHRGTSNWKLLYNKR
ref|ZP_01665148.1|    GILKFRCPHVCGKVNCPNGSAWCSPSNYGLVIKKKVEDDPRSFCTPHRGTREWEKLYAER
ref|YP_001111903.1|   GTNKYRCPHVMGKCDCPYGSAWCSPSSYGLVVKTKVKDDPRMNCIPARGTKNWQSLYNKR
RAAC03178             AWLKFRCPHATGQVDCPLGMAACSASNYGMVVKKHLDEDVRRYANPHRGSRTWKMLYDER
                      . :**** *:  :** * :  ** *.**:*:*. :* *      * **:   *: *  * ref|YP_753434.1|      TYSERCFSRFKENLGLEDGLNVRKITKVETHAYLCAITMIAAVIAINQ--------
ref|YP_753226.1|      TYSERCFSRFKENLGLEDGLNVRKITKVETHAYLCAITMIAAVIAINQ--------
ref|YP_752864.1|      TSVERCFGRLKEHLGLETGLNVRGIKKVKTHAYLSVITMIASVIAINKDKSSTDIA
ref|ZP_01665148.1|    TSVERAFSRLKEQLGANT-VRVQGIKKVTAHLMLCCIALLAGTIAVNR--------
ref|YP_001111903.1|   TSVERCFGRLKQHLGANS-IRTRGLEKVTLHITLSCIALLAGSIAVAKTKRIEQAA
RAAC03178             TAVERCFARLKEWLTLDG-VHVRGIEKVTVHAYIHAIVLLASALAMHRTNRIEQVA
                      *  **.*.*:*:  *   :    :...: :  ** *   *  *.::*..:*  :
```

FIG. 89

```
ref|YP_001126744.1|     ------------------------------------------------------
gb|AAB52611.1|          ------------------------------------------------------
sp|P52026|DPO1_BACST    ------------------------------------------------------
gb|ABM97416.1|          ------------------------------------------------------
dbj|BAF33373.1|         -----------------------MNFVNIIINSLKCVNSACVPLGVRPFSC
RAAC01937               MNFHPRHGPVRTFHWLSAPPRRTYSLLHCLRSMNFVNIIINSLKCVNSACVPLGVRPFSC ref|YP_001126744.1|     ---------------------------------KLVLIDGNSVAYRAFFALPLLHNDKG
gb|AAB52611.1|          ---------------------------------KLVLIDGNSVAYRAFFALPLLHNDKG
sp|P52026|DPO1_BACST    ---------------------------------NKLVLIDGNSVAYRAFFALPLLHNDKG
gb|ABM97416.1|          ---------------------------------NKLVLIDGNSVAYRAFFALPLLHNDKG
dbj|BAF33373.1|         RHKTTRADKGNVIEWSGTTVRQTARSLGWPMPASKLVLIDGNSILYRAFFALPPLTARDG
RAAC01937               RHKTTRADKGNVIEWSGTTVRQTARSLGWPMPASKLVLIDGNSILYRAFFALPPLTARDG
                                                         *******: ***** *   .* ref|YP_001126744.1|     IHTNAVYGFTMMLNKILAEEQPTHLLVAFDAGKTTFRHETFQEYKGGRQQTPPELSEQFP
gb|AAB52611.1|          IHTNAVYGFTMMLNKILAEEQPTHLLVAFDAGKTTFRHETFQEYKGGRQQTPPELSEQFP
sp|P52026|DPO1_BACST    IHTNAVYGFTMMLNKILAEEQPTHILVAFDAGKTTFRHETFQDYKGGRQQTPPELSEQFP
gb|ABM97416.1|          IHTNAVYGFTMMLNKILAEEEPTHMLVAFDAGKTTFRHEAFQEYKGGRQQTPPELSEQFP
dbj|BAF33373.1|         TPTNAVYGFTTMILRLMSDEKPTHLAVAFDKSKTTFRHADFAAYKGTRQETPDELVQQFP
RAAC01937               TPTNAVYGFTTMILRLMSDEKPTHLAVAFDKSKTTFRHADFAAYKGTRQETPDELVQQFP
                         ******** *:  :::::*:*:   .****  *  * :  :*** ref|YP_001126744.1|     LLRELLKAYRIPAYELDHYEADDIIGTLAARAEQEGFEVKIISGDRDLTQLASRHVTVDI
gb|AAB52611.1|          LLRELLKAYRIPAYELDHYEADDIIGTLAARAEQEGFEVKIISGDRDLTQLASRHVTVDI
sp|P52026|DPO1_BACST    LLRELLKAYRIPAYELDHYEADDIIGTMAARAEREGFAVKVISGDRDLTQLASPQVTVEI
gb|ABM97416.1|          LLRELLRAYRIPAYELNYYEADDIIGTLAARAEQEGFEVKVISGDRDLTQLASPHVTVDI
dbj|BAF33373.1|         LARRTLEALSIPMVEIDQYEADDVIGTLAKRAAEAGFDVRVVSGDKDLLQLVDDRIHVLL
RAAC01937               LARRTLEALSIPMVEIDQYEADDVIGTLAKRAAEAGFDVRVVSGDKDLLQLVDDRIHVLL
                        * *. *.*  **  *:::*****:***:* **  . ** *:::***:** ** ..  :: * :

ref|YP_001126744.1|     TKKGITDIEPYTPETVREKY-GLTPEQIVDLKGLMGDKSDNIPGVPGIGEKTAVKLLKQF
gb|AAB52611.1|          TKKGITDIEPYTPETVREKY-GLTPEQIVDLKGLMGDKSDNIPGVPGIGEKTAVKLLKQF
sp|P52026|DPO1_BACST    TKKGITDIESYTPETVVREKY-GLTPEQIVDLKGLMGDKSDNIPGVPGIGEKTAVKLLKQF
gb|ABM97416.1|          TKKGITDIEPYTPETVREKY-GLTPEQIVDLKGLMGDKSDNIPGVPGIGEKTAVKLLRQF
dbj|BAF33373.1|         TRKGITEMEHFDEQAVARRYPGLKPAQVIDLKGLMGDPSDNIPGVPGVGEKTALKLLASF
RAAC01937               TRKGITEMEHFDEQAVARRYPGLKPAQVIDLKGLMGDPSDNIPGVPGVGEKTALKLLASF
                        *:****::*  :   ::* .:* **.*  *::******* ******:* .* ref|YP_001126744.1|     GTVENVLASIDEVKGEKLKENLRQHRDLALLSKQLASICRDAPVELSDDIVYEGQDREK
gb|AAB52611.1|          GTVENVLASIDEVKGEKLKENLRQHRDLALLSKQLASICRDAPVELSDDIVYEGQDREK
sp|P52026|DPO1_BACST    GTVENVLASIDEIKGEKLKENLRQYRDLALLSKQLAAICRDAPVELTDDIVYKGEDREK
gb|ABM97416.1|          GTVENVLASIDEIKGEKLKETLRQHREMALLSKKLAAIRRDAPVELSDDIAYQGEDREK
dbj|BAF33373.1|         GTVEGVYDHLDEVQGQKLRERLEQHREDAFLSKRLATIACDAPIEVDLETLRYEGPDPAR
RAAC01937               GTVEGVYDHLDEVQGQKLRERLEQHREDAFLSKRLATIACDAPIEVDLETLRYEGPDPAR
                        ****.*   :**::*:**:* *.*:*: *:****  ***:*: *: : *:*  *   :

ref|YP_001126744.1|     VIALFKELGFQSFLEKMAAPAAEGEKP-------------LEEMEFAIVDVI-----TEE
gb|AAB52611.1|          VIALFKELGFQSFLEKMAAPAAEGEKP-------------LEEMEFAIVDVI-----TEE
sp|P52026|DPO1_BACST    VVALFQELGFQSFLDKMAVQTDEGEKP-------------LAGMDFAIADSV-----TDE
gb|ABM97416.1|          VVALFKELGFQSFLEKMESPSSEEEKP-------------LAKMAFTLADRV-----TEE
dbj|BAF33373.1|         AIAWFRELDFRSLVDKISEEMSHDSTPTPSPAAASGASSEWSSFAYGLIEDAGAWQEAIS
RAAC01937               AIAWFRELDFRSLVDKISEEMSHDSTPTPSPAAASGASSEWSSFAYGLIEDAGAWQEAIS
                        .:* *:**.*:*::::*:::*:        . ...*            : : :    : .

ref|YP_001126744.1|     MLADKAALVVEVMEENYHDAPIVGIALVNEHGRFFMRPETALADSQFLAWLADETKKKSM
gb|AAB52611.1|          MLADKAALVVEVMEENYHDAPIVGIALVNEHGRFFMRPETALADSQFLAWLADETKKKSM
sp|P52026|DPO1_BACST    MLADKAALVVEVVGDNYHHAPIVGIALANERGRFFLRPETALADPKFLAWLGDETKKKTM
gb|ABM97416.1|          MLADKAALVVEVEENYHDAPIVGIAVVNEHGRFFLRPETALADPQFVAWLGDETKKKSM
dbj|BAF33373.1|         SFSEPVGVMMDLADPDYHRAEIRGMAVATPKRAYYVRFGERLELSDVRPWLVSD-RPKVA
RAAC01937               SFSEPVGVMMDLADPDYHRAEIRGMAVATPKRAYYVRFGERLELSDVRPWLVSD-RPKVA
                        :::  ..:::::   :** * *:*:..  :    :::*      *  ... .**  : : *
``` continued →

FIG. 89 continued

```
ref|YP_001126744.1|    FDAKRAVVALKWKGIELRGVA--FDLLLAAYLLNPAQDAGDIAAVAKMKQYEAVRSDEAV
gb|AAB52611.1|         FDAKRAVVALKWKGIELRGVA--FDLLLAAYLLNPAQDAGDIAAVAKMKQYEAVRSDEAV
sp|P52026|DPO1_BACST   FDSKRAAVALKWKGIELRGVV--FDLLLAAYLLDPAQAAGDVAAVAKMHQYEAVRSDEAV
gb|ABM97416.1|         FDSKRAAVALKWKGIELCGVS--FDLLLAAYLLDPAQGVDDVAAAAKMKQYEAVRSDEAV
dbj|BAF33373.1|        FDLKSMAFALDAHGIGLTSECGWQDVKLAAYLLNPQDG------------EVELSDVFA
RAAC01937              FDLKSMAFALDAHGIGLTSECGWQDVKLAAYLLNPQDG------------EVELSDVFA
                       ** *  ..**.:** *         *: ******:*            *.  **  .

ref|YP_001126744.1|    YGKGVKRSLPDEQTLAEHLVRKAAAIWALEQPFMDDLRNNEQDQLLTKLEQPLAAILAEM
gb|AAB52611.1|         YGKGVKRSLPDEQTLAEHLVRKAAAIWALEQPFMDDLRNNEQDQLLTKLEQPLAAILAEM
sp|P52026|DPO1_BACST   YGKGAKRTVPDEPTLAEHLVRKAAAIWALEEPLMDELRRNEQDRLLTELEQPLAGILANM
gb|ABM97416.1|         YGKGAKRAVPDEPVLAEHLVRKAAAIWALERPFLDELRRNEQDRLLVELEQPLSSILAEM
dbj|BAF33373.1|        RERGQELPAWEEGEREKWLAYTASQLPPLFESLAYTIRMQEMERLYQEVELPLAFVLAKM
RAAC01937              RERGQELPAWEEGEREKWLAYTASQLPPLFESLAYTIRMQEMERLYQEVELPLAFVLAKM
                         :*  : .  :*    : *. .*: :.*  ..:   :* :* ::*  ::* : ::* ref|YP_001126744.1|    EFTGVNVDTKRLEQMGSELAEQLRAIEQRIYELAGQEFNINSPKQLGVILFEKLQLPVLK
gb|AAB52611.1|         EFTGVNVDTKRLEQMGSELAEQLRAIEQRIYELAGQEFNINSPKQLGVILFEKLQLPVLK
sp|P52026|DPO1_BACST   EFTGVKVDTKRLEQMGAELTEQLQAVERRIYELAGQEFNINSPKQLGTVLFDKLQLPVLK
gb|ABM97416.1|         EFAGVKVDTKRLEQMGEELAEQLRTVEQRIYELAGQEFNINSPKQLGVILFEKLQLPILK
dbj|BAF33373.1|        EITGFYVNREKLVAFGQELTERIKRITQEIYDLAGTSFNLNSPKQLGEILFDKLGLPALK
RAAC01937              EITGFYVNREKLVAFGQELTERIKRITQEIYDLAGTSFNLNSPKQLGEILFDKLGLPALK
                       *::*. *:  ::*   :* **:*:::  :  :.**:*** .**:******  :**:** ** **

ref|YP_001126744.1|    KTKTGYSTSADVLEKLAPHHEIVENILHYRQLGKLQSTYIEGLLKVVRPDTGKVHTMFNQ
gb|AAB52611.1|         KTKTGYSTSADVLEKLAPHHEIVENILHYRQLGKLQSTYIEGLLKVVRPDTGKVHTMFNQ
sp|P52026|DPO1_BACST   KTKTGYSTSADVLEKLAPHHEIVEHILHYRQLGKLQSTYIEGLLKVVHPVTGKVHTMFNQ
gb|ABM97416.1|         KTKTGYSTSADVLEKLAPYHEIVENILHYRQLGKLQSTYIEGLLKVVRPDTKKVHTIFNQ
dbj|BAF33373.1|        KTKTGYSTSADVLEKLAPMHEIVQKILDYRLLAKLQSTYVEGLLKVIRKETGRVHTRFHQ
RAAC01937              KTKTGYSTSADVLEKLAPMHEIVQKILDYRLLAKLQSTYVEGLLKVIRKETGRVHTRFHQ
                       ****************  :. *  *.***:***:: :  * :*** *:* ref|YP_001126744.1|    ALTQTGRLSSAEPNLQNIPIRLEEGRKIRQAFVPSEPDWLIFAADYSQIELRVLAHIADD
gb|AAB52611.1|         ALTQTGRLSSAEPNLQNIPIRLEEGRKIRQAFVPSEPDWLIFAADYSQIELRVLAHIADD
sp|P52026|DPO1_BACST   ALTQTGRLSSVEPNLQNIPIRLEEGRKIRQAFVPSEPDWLIFAADYSQIELRVLAHIAED
gb|ABM97416.1|         ALTQTGRLSSTEPNLQNIPIRLEEGRKIRQAFVPSESDWLIFAADYSQIELRVLAHIAED
dbj|BAF33373.1|        TLTATGRLSSSEPNLQNIPIRLEEGRRLRQVFEPTYKDWVIFAADYSQIELRILAHLSGD
RAAC01937              TLTATGRLSSSEPNLQNIPIRLEEGRRLRQVFEPTYKDWVIFAADYSQIELRILAHLSGD
                       : ** ********::.* *:  :**:* * ref|YP_001126744.1|    DNLIEAFQRDLDIHTKTAMDIFHVSEEEVTANMRRQAKAVNFGIVYGISDYGLAQNLNIT
gb|AAB52611.1|         DNLIEAFQRDLDIHTKTAMDIFHVSEEEVTANMRRQAKAVNFGIVYGISDYGLAQNLNIT
sp|P52026|DPO1_BACST   DNLIEAFRRGLDIHTKTAMDIFHVSEEDVTANMRRQAKAVNFGIVYGISDYGLAQNLNIT
gb|ABM97416.1|         DNLMEAFRRDLDIHTKTAMDIFQVSEDEVTPNMRRQAKAVNFGIVYGISDYGLAQNLNIS
dbj|BAF33373.1|        EALIDAFRRDMDIHTRTAADVFEVPPEQVTSLMRRQAKAVNFGIVYGISDFGLAQNLNIP
RAAC01937              EALIDAFRRDMDIHTRTAADVFEVPPEQVTSLMRRQAKAVNFGIVYGISDFGLAQNLNIP
                         : *:.**:*.:.:***: *:*:**  *:*.*.  ::. *****:***** ref|YP_001126744.1|    RKEAAEFIERYFASFPGVKQYMENIVQEAKQKGYVTTLLHRRRYLPDITSRNFNVRSFAE
gb|AAB52611.1|         RKEAAEFIERYFASFPGVKQYMENIVQEAKQKGYVTTLLHRRRYLPDITSRNFNVRSFAE
sp|P52026|DPO1_BACST   RKEAAEFIERYFESFPGVKRYMENIVQEAKQKGYVTTLLHRRRYLPDITSRNFNVRSFAE
gb|ABM97416.1|         RKEAAEFIERYFESFPGVKRYMENIVQEAKQKGYVTTLLHRRRYLPDITSRNFNVRSFAE
dbj|BAF33373.1|        QKEAKRFIESYFEKFPGVKRYMDEIVKQARERGYVTTLMNRRRYLPDIHSRNYQLRSFAE
RAAC01937              QKEAKRFIESYFEKFPGVKRYMDEIVKQARERGYVTTLMNRRRYLPDIHSRNYQLRSFAE
                       :*  .*  .*:::**::*::*****: ****  *::: ***** ref|YP_001126744.1|    RTAMNTPIQGSAADIIKKAMIDLAARLKEEQLQARLLLQVIIDELILEAPKEEIERLCELV
gb|AAB52611.1|         RTAMNTPIQGSAADIIKKAMIDLAARLKEEQLQARLLLQVHDELILEAPKEEIERLCELV
sp|P52026|DPO1_BACST   RTAMNTPIQGSAADIIKKAMIDLSVRLREERLQARLLLQVHDELILEAPKEEIERLCRLV
gb|ABM97416.1|         RMAMNTPIQGSAADIIKKAMIDLNARLKEERLQARLLLQVHDELILEAPKEEMERLCRLV
dbj|BAF33373.1|        RTAMNTPIQGSAADLIKLAMVRIDRAMRDAQMDARMLLQVHDELIFECPKDELAALEVLV
RAAC01937              RTAMNTPIQGSAADLIKLAMVRIDRAMRDAQMDARMLLQVHDELIFECPKDELAALEVLV
                       * **********::  ::    :::  :::********:*.**:*:  * ** ref|YP_001126744.1|    PEVMEQAVTLRVPLKVDYHYGPTWYDAK
gb|AAB52611.1|         PEVMEQAVTLRVPLKVDYHYGPTWYDAK
sp|P52026|DPO1_BACST   PEVMEQAVTLRVPLKVDYHYGPTWYDAK
gb|ABM97416.1|         PEVMEQAVTLRVPLKVDYHYGPTWYDAK
dbj|BAF33373.1|        RDNMENAMTLSVPLKVDTAYGPTWYDAK
RAAC01937              RDNMENAMTLSVPLKVDTAYGPTWYDAK
                       : **:.*:** ******   *********
```

FIG. 90

```
ref|ZP_00651175.1|      -----AHRIALDPNNVQATHLSRVAGVARFAYNWALAEWRHQYEACTLDSALPKPSQHSL
gb|ACA11657.1|          -----AHRIALDPNNVQATHLSRVAGVARFAYNWALAEWRHQYEACTLDSALPKPSQHSL
ref|YP_001681573.1|     MKINRAYRYELKPNVAQRILLAQHAGTARFAYNWGLARRITLYEAEKKS-----TNAIAQ
RAAC01372               MKIHRAYRYELAPNRMQRVMLAKHAGVARFAYNWGLARRIALHEEAGQS-----TNAIEQ
ref|YP_473713.1|        ------------NNRQKTLAAQHAGVARHAYNWGLAICKQAVESKQKL-----PTAIDL
ref|YP_475384.1|        ------------NNRQKTLAAQHAGVARHAYNWGLAICKQAVESKQKL-----PTAIDL
                                     *   * :: **.**.****.**     *              ..

ref|ZP_00651175.1|      RRQLNAIKREQFPWMGEVTKNAPQMAIIQLGQAFQNFFAG-----RAKYPKFRKKGAHDR
gb|ACA11657.1|          RRQLNAIKREQFPWMGEVTKNAPQMAIIQLGQAFQNFFTG-----RAKYPKFRKKGAHDR
ref|YP_001681573.1|     HRELNQLKQTEFPWMYEVSKCAPQEALRDLDKAFKNFFRGLKLGQKVGFPRFKKKGQDDS
RAAC01372               HRELNRLKKTDFPWMYEVSKCAPQEALRDLDRAFQHFFRGLNEGRKVGFPRFKKKGRDDS
ref|YP_473713.1|        HKRLVAEVKKENPWYYQVSKCAPQQALRNLEQAFKRWRSG-----LGKFPRFKRKGVRDS
ref|YP_475384.1|        HKRLVAEVKKENPWYYQVSKCAPQQALRNLEQAFKRWRSG-----LGKFPRFKRKGVRDS
                        ::.*     :  :  **  :*:* ***  *: :* :**:..  *      :*:*::** * ref|ZP_00651175.1|      FTLTNDQFDLDASRIRIPRLGWVRMRETLRFAGRIMSATVSRVAARWFVSITVDVPDPSH
gb|ACA11657.1|          FTLTNDQFDLNASRIRIPRLGWVRMRETLRFAGRIMSATVSRVAARWFVSITVDVPDPSH
ref|YP_001681573.1|     FRLT-GAIKVNGKAVQLPRLGVIRLKEEPWIRGRILSATVSREADRWFVSLACEVEIPDP
RAAC01372               FRLT-GSIRVLDNAVQLPRLGRIRLKEKPYVEGRILSATVKREADRWYVSLATETEIPDP
ref|YP_473713.1|        FYLE-GSIRISGDRIKVPILGWLRCAELLPTA-TPKNVVISLRAGHWYVSFKYEAPAP-Q
ref|YP_475384.1|        FYLE-GSIRISGDRIKVPILGWLRCAELLPTA-TPKNVVISLRAGHWYVSFKYEAPAP-Q
                        * *   .  :   .    ::: * **  :*    *      ...:.   * :*:**:  :. * ref|ZP_00651175.1|      LPQAENQGVVGVDLGVLALATLSTGETICGPRPHRALLGRVRRLSRSVSRKVKDSANRHK
gb|ACA11657.1|          LPQAENQGAVGVDLGVLALATLSTGETICGPRPHRALLGRVRRLSRSVSRKVKDSANRHK
ref|YP_001681573.1|     APVLGP--IVGIDVGLNHFAVLSDGTKVEAPKPLDKFLKRLRRLSKKHSRKQKGSTNRKK
RAAC01372               VPPSGE--PVGVDLGVSWFLTLSDGTKIKAPKPLRRYLRRLERLSKRHSRKKPGSRNRRK
ref|YP_473713.1|        VEKTGE--VVGVDLGINRLATCSDGEVFENPKPYYKAKKRLARLQRRLSRKQKGSANRKK
ref|YP_475384.1|        VEKTGE--VVGVDLGINRLATCSDGEVFENPKPYYKAKKRLARLQRRLSRKQKGSANRKK
                              **:*:*:   :  . * *   .  *:*    *: .:   *  .*  **:* ref|ZP_00651175.1|      AKATLAHLHARIAAIRLDALIKLTSDLTRRFHTIGIENLNVKGMVKNRHLARSIADMGFF
gb|ACA11657.1|          AKATLAHLHARIAAIRLDALHKLTSDLTRRFHTIGIENLNVKGMVKNRHLARSIADMGFF
ref|YP_001681573.1|     SALALARLHRRIRNIRQDFLHKLTTNLAKTKSEIVMEDLNVRGMMRNGSLARHIADVGWG
RAAC01372               SALALARLHRRIRQDFLHKVTTELAKTKRAIVMEDLHVRGMVQNRALARAISDMCFG
ref|YP_473713.1|        AVAQLAKAHKRVADIRQDNLHKLTTYLAKKYRVVVIEDLQVKNLLKNHKLAGALSDCGFY
ref|YP_475384.1|        AVAQLAKAHKRVAGIRQDNLHKLTTYLAKKYRVVVIEDLQVKNLLKNHKLAGALSDCGFY
                        :   **:  * ::   **  *  ***:*: *::      : :*:*:*..:::*   ** ::* *:

ref|ZP_00651175.1|      EFRRQLEYKAAMRGGQVVVADRFFASSKMCSTCCHTLKELPLSVRQWACLGCGTRHDRDV
gb|ACA11657.1|          EFRRQLEYKAAMRGGQVVVADRFFASSKMCSTCCHTLKELPLSVRQWACLGCGTRHDRDV
ref|YP_001681573.1|     EFRRQLGYKTAWYGSKLTLVHRFYPSSKTCSACGYVREELPLSVREWDCPSCGVHHDRDH
RAAC01372               EFRRMLTYKCAWYGSELIIAPRFYASSKTCSACGYVISELPLSVREWTCPACSTRHDRDI
ref|YP_473713.1|        EFRRQLEYKARLYGCQVVVADRFYPSSQLCSRCGHR-QKMPLQERMFCCPCCGLELDRDL
ref|YP_475384.1|        EFRRQLEYKARLYGCQVVVADRFYPSSQLCSRCGHR-QKMPLQERMFCCPCCGLELDRDL
                        **** * **       * ::  :. :.:   :   .::**. * :  *.  *** ref|ZP_00651175.1|      NAAVNLKNMA--VSSTVS--ACGEECTG-----
gb|ACA11657.1|          NAAVNLKNMA--VSSTVS--ACGEEGTG-----
ref|YP_001681573.1|     NAAKNL------------------------
RAAC01372               NAAKNLLRIG--TASSAGSDACGDPSGGAALGC
ref|YP_473713.1|        NAALNLLRWYRTTSSSGGSDACGDPSGG-----
ref|YP_475384.1|        NAALNLLRWYRTTSSSGGSDACGDPSGG-----
                        *** **
```

FIG. 91

```
ref|ZP_01695687.1|    ----------------VGPSQLLSKLCDEIELEKTINDLVKWDSVRCHISPGTRIKALVLN
ref|ZP_01695982.1|    ----------------VGPSQLLSKLCDEIELEKTINDLVKWDSVRCHISPGTRIKALVLN
ref|ZP_01695971.1|    ----------------VGPSQLLSKLCDEIELEKTINNLVKWDSVRCHISPGTRIKALVLN
ref|ZP_01695655.1|    --------------------PQSCKLCDEIELEKTINNLVKWDSVRCHISPGTRIKALVLN
ref|YP_430569.1|      ----------MRFFRAGPAALISRLCDVLKIAEIIDAVVDWDPAQCHLSPGNRVKALIIN
RAAC00062             MREAFQLFGPVRSYVMGPAPVLARLIDELKWVEIIDEFVPRP--DSKLSVGLRTKALLVN
                                   .:*  *  ::   : *: .*      .::*  *  ***::* ref|ZP_01695687.1|    ILCSGKPLYKVHEFYQNLDSEMLF--DTSVSPDQLNDDALGRALDYLYEA-EAWKVYSTL
ref|ZP_01695982.1|    ILCSGKPLYKVHEFYQNLDSEMLF--DTSVSPDQLNDDALGRALDYLYEA-EAWKVYSTL
ref|ZP_01695971.1|    ILCSGKPLYKVHEFYQNLDSEMLF--DTSISPDQLNDDALGRALDYLYKA-EAWKVYSTL
ref|ZP_01695655.1|    ILCSGKPLYKVHEFYQNLDSEMLF--DTSISPDQLNDDALGRALDYLYKA-EAWKVYSTL
ref|YP_430569.1|      LLVDREALYHVERFYENQDLEVLFGAEQQVRPEDFNDDALGRALDKLFTSGQLKKLFSSI
RAAC00062             IGTNREALYRVEEFYAQRDVEVLLG--SGVSADDLHDDALARALDALYDA-GLEALYARI
                      :  . :.**:*..**  :  * *:*:      . .:::****.****  *:  :    ::: :

ref|ZP_01695687.1|    ALKTLKKLNLP-----IGILHNDTTSISVYGEYKQPKEDGLQITYGYSKAHRPDLKQIVL
ref|ZP_01695982.1|    ALKALKKLNLP-----IGILHNDTTSISVYGEYKQPKEDGLQITYGYSKAHRPDLKQIVL
ref|ZP_01695971.1|    ALKALKKLNLP-----IGVLHNDTTSISVYGEYKQPKEDGLQITYGYSKAHRPDLKQIVL
ref|ZP_01695655.1|    ALKALKKLNLP-----IGVLHNDTTSISVYGEYKQPKEDGLQITYGYSKAHRPDLKQIVL
ref|YP_430569.1|      ALTAAATHNVS-----IAGIHVDTTSISVQGAYDG--EGDLDITFGFSKDHRPDLKQFLI
RAAC00062             ALHTLRRLRVLSDSNELPIHADTTSLSMTGEYLD--QTAFRIDRGFSKDHRPDLKQIVF
                      **  :    .:        : :* ****:*: * *    :   : *  *:** *******:::

ref|ZP_01695687.1|    GMGVTPERIPIPILAKVENGNTSDKSWNVEFIQKMRKILSHEDWKNLIYQADSALITTENLA
ref|ZP_01695982.1|    GMGVTPERIPIPILAKVENGNTSDKSWNVEFIQKMRKILSHEDWKNLIYQADSALITTENLA
ref|ZP_01695971.1|    GMGVTPERIPIPILAKVENGNTSDKSWNVEFIQKMRKILSHEDWKNLIYQADSALITTENLA
ref|ZP_01695655.1|    GMGVTPERIPIPILAKVENGNTSDKSWNVEFIQKMRKILSHEDWKNLIYQADSALITTENLA
ref|YP_430569.1|      GLTVNRDGLPILAQSLDGNSSDKSWYPQVIEELVQTFKPEKLKEVIFVADCALVTKDNLA
RAAC00062             GL-CTVHGLGLCANVNPGNLDDHTWNFENIQQLLSQLDEETRKRSVYADAALVTKDNLE
                      *:  . .   :  : *:    **  .*:*    *  *::: ..  .   *.  ::  **.**:*..**

ref|ZP_01695687.1|    EIQQQN-----LSFISRLPDTFGLSTELKKEAWLLNN-WERVGSLSNKKDAAIYQIQAFE
ref|ZP_01695982.1|    EIQQQN-----LSFISRLPDTFGLSTELKKEAWLLNN-WERVGSLSNKKDAAIYQIQAFE
ref|ZP_01695971.1|    EIQQQN-----LSFISRLPDTFGLSTELKKEAWLLNN-WERVGSLSNKKDAAIYQIQAFE
ref|ZP_01695655.1|    EIQQQN-----LSFISRLPDTFGLSTELKKEAWLLNN-WERVGSLSNKKDAAIYQIQAFE
ref|YP_430569.1|      LLVQEEGNKPALQFISLLPENFGLNKEIKAEAFRTGT-WQEIGKLSPKKDAACYKSQSFV
RAAC00062             LLAEED-----FHFISRLPGTYKLSEDLKRAAWEKENSWKEVGRLAEAEDSAHYRIQAFR
                       : :::       : *   .: *.  :: *  *:    .  *::.* *:  :*:* *:  *:* ref|ZP_01695687.1|    RQIQNLPYRFLVVHSNNLDQRKEKTLNRAIEKEEIQLKKEIEKLSKVIFHCKEDALEAIQ
ref|ZP_01695982.1|    RQIQNLPYRFLVVHSNNLDQRKEKTLNRAIEKEEIQLKKEIEKLSKVIFHCKEDALEAIQ
ref|ZP_01695971.1|    RQIQNLPYRFLVVHSNNLDQRKEKTLNRAIEKEEIKLKKEIEKLSKVIFHCKEDALEAIQ
ref|ZP_01695655.1|    RQIQNLPYRFLVVHSNNLDQRKEKTLNRAIEKEEIQLKKEIEKLSKVIFHCKEDALEAIQ
ref|YP_430569.1|      REIDGRDYRLIVVHSTTLDKRKENSLLKKWAKQREVLEKAAKDLSRRPFACKADARKAIE
RAAC00062             RTLYGRTYRFVVVRSSSLDTRKERKLKEVLKREKAALEKAAKAMSQNVYSCEQDAQMAMQ
                      *  :   .  **::**:*..** ***..*   ::.   *:*   : :*:    : *: ** *::

ref|ZP_01695687.1|    SFKKKQKASYFCYKLNVQMSDQPIKRKKRGRPKKDEQTK-REQIYQIQLESFEKDHDFIE
ref|ZP_01695982.1|    SFKKKQKASYFCYKLNVQMSDQPIKRKKRGRPKKDEQTK-REQIYQIQLESFEKDHDFIE
ref|ZP_01695971.1|    SFKKKQKASYFCYKLNVQMSDQPIKRKKRGRPKKDEQTK-REQIYQIQLESFEKDHDFIE
ref|ZP_01695655.1|    SFKKKQKASYFCYKLNVQMSDQPIKRKKRGRPKKDEQTK-REQIYQIQLESFEKDHDFIE
ref|YP_430569.1|      LFLREYR-----------------------------------------------------
RAAC00062             TFMHEHRATLHPISARICAEQVQAKRARRGRPRKDDPPPPVHTQYRVEVAILPPSEERVQ
                      * ::  :

ref|ZP_01695687.1|    NKKKMLSTFVLITNKLDEETLSNQEVLRVYKGQSAAETRFRLIKDSQMIDAIYLKTPERV
ref|ZP_01695982.1|    NKKKMLSTFVLITNKLDEETLSNQEVLRVYKGQSAAETRFRLIKDSQMIDAIYLKTPERV
ref|ZP_01695971.1|    NKKRMLSTFVLITNKLDEETLSNQEVLRVYKCQSAVETRFRLIKDSQMIDAIYLKTPERV
ref|ZP_01695655.1|    NKKKMLSTFVLITNKLDEETLSNQEVLRVYKGQSAAETRFRLIKDSQMIDAIYLKTPERV
ref|YP_430569.1|      ------------------------------------------------------------
RAAC00062             QWREKEATFVLITDIRDDQRVSDEQILRLYKEQHEVEARFRYLKSPYHVGPIYLHKPTRV
``` continued →

FIG. 91 continued

```
ref|ZP_01695687.1|    EALGIVYVMALLIYGILEYRVRKELKEKNLSLILKGKRKLYQPTGQALLEQLEDITVILI
ref|ZP_01695982.1|    EALGIVYVMALLIYGILEYRVRKELKEKNLSLILKGKRKLSQPTGQALLEQLEDITVILI
ref|ZP_01695971.1|    EALGIVYVMALLIYGILEYRVRKELKEKNLSLILKGKRKLYQPTGQALLEQLEDITVILI
ref|ZP_01695655.1|    EALGIVYVMALLIYGILEYRVRKELKEKNLSLILKGKRKLYQPTGQALLEQLEDITVILI
ref|YP_430569.1|      ------------------------------------------------------------
RAAC00062             KAFGFVMLLSLLLYSVLEYLIREKMKRETEPLMLPGNRKSFRPTGLAILEMLDGVTTVHM ref|ZP_01695687.1|    NQNQQKIRLLPDNIDSQAKKIIELCGYDLSIY-------
ref|ZP_01695982.1|    NQNQQKIRLLPDNIDSQAKKIIELCGYDLSIY-------
ref|ZP_01695971.1|    NQNRQKLRLLPDNIDSQAKKIIELCGYDLSIY-------
ref|ZP_01695655.1|    NQNRQKLRLLPDNIDSQAKKIIELCGYDLSIY-------
ref|YP_430569.1|      ---------------------------------------
RAAC00062             QVGDTWQRVPATPHNPQIMRVLKLLNMDLSIYTEAQKTA
```

FIG. 92

```
ref|ZP_01665148.1|    ------------------------------------------------------------
RAAC02377             ------------------------------------------------------------
ref|YP_754667.1|      ------------------------------------------------------------
ref|YP_753226.1|      EFYPHYPTHETICALPRTEINSWLSYNTRPHMNASWLFEISUBSPWLFEISTRGETTING
ref|YP_752864.1|      ------------------------------------------------------------
ref|YP_001111903.1|   ------------------------------------------------------------ ref|ZP_01665148.1|    ------------------------------------------------------------
RAAC02377             ------------------------------------------------------------
ref|YP_754667.1|      ------------------------------------------------------------
ref|YP_753226.1|      ENGBABIHYPTHETICALPRTEINSWLSYNTRPHMNASWLFEISUBSPWLFEISTRGETT
ref|YP_752864.1|      ------------------------------------------------------------
ref|YP_001111903.1|   ------------------------------------------------------------ ref|ZP_01665148.1|    ------------------------------------------------------------
RAAC02377             ------------------------------------------------------------
ref|YP_754667.1|      ------------------------------------------------------------
ref|YP_753226.1|      INGENGBABIHYPTHETICALPRTEINSWLSYNTRPHMNASWLFEISUBSPWLFEISTRG
ref|YP_752864.1|      ------------------------------------------------------------
ref|YP_001111903.1|   ------------------------------------------------------------ ref|ZP_01665148.1|    ------------------------------------------------------------
RAAC02377             ------------------------------------------------------------
ref|YP_754667.1|      ------------------------------------------------------------
ref|YP_753226.1|      ETTINGENGBABIHYPTHETICALPRTEINSWLSYNTRPHMNASWLFEISUBSPWLFEIS
ref|YP_752864.1|      ------------------------------------------------------------
ref|YP_001111903.1|   ------------------------------------------------------------ ref|ZP_01665148.1|    ------------------------------------------------------------
RAAC02377             ------------------------------------------------------------
ref|YP_754667.1|      ------------------------------------------------------------
ref|YP_753226.1|      TRGETTINGENGBABIHYPTHETICALPRTEINSWLSYNTRPHMNASWLFEISUBSPWLF
ref|YP_752864.1|      ------------------------------------------------------------
ref|YP_001111903.1|   ------------------------------------------------------------ ref|ZP_01665148.1|    --------------------EAXTRANSPSASEISFAMILYPRTEINTHERMSINUSCA
RAAC02377             ------------------------------------------------------------
ref|YP_754667.1|      ------------------------------------------------------------
ref|YP_753226.1|      EISTRGETTINGENGBABIHYPTHETICALPRTEINSWLSYNTRPHMNASWLFEISUBSP
ref|YP_752864.1|      ------------------------------------------------------------
ref|YP_001111903.1|   ------------------------------------------------------------ ref|ZP_01665148.1|    RBXYDIVRANSNRGBEAX--------TRANSPSASEISFAMILYPRTEINTHERMSINU
RAAC02377             ------------------------------------------------------------
ref|YP_754667.1|      ------------------------------------------------------------
ref|YP_753226.1|      WLFEISTRGETTINGENGBABIHYPTHETICALPRTEINSWLSYNTRPHMNASWLFEISU
ref|YP_752864.1|      ------------------------------------------------------------
ref|YP_001111903.1|   ------------------------------------------------------------ ref|ZP_01665148.1|    ----SCARBXYDIVRANSNRSCRESIGNIFICANCEE-IDENTITIESPSITIVESG-AP
RAAC02377             -----------------------------------------------------------M
ref|YP_754667.1|      ------------------------------------------------------------
ref|YP_753226.1|      BSPWLFEISTRGETTINGENSCRESIGNIFICANCEE-IDENTITIESPSITIVESGAPS
ref|YP_752864.1|      ------------------------------------------------------------
ref|YP_001111903.1|   ------------------------------------------------------------
``` continued →

FIG. 92 continued

```
ref|ZP_01665148.1|    SMDMGYDAKDVYQAAY-ERQAQAIIPLNRRKEKLPPEGMDENRTPTCSMGYPMVYWGCER
RAAC02377             LMDAGYDQTKNYEAAR-ALGAQAIIPMNRRNEKEPPEGMDFDGTPRCTMGYRMTYWGAEG
ref|YP_754667.1|      LMDAGYDHREIYSVIRDKYHAQAIIALNKRGAKQPPEGFDWDGTPICSARYRMVYWGS--
ref|YP_753226.1|      LMDAGYDHREIYSVIRDKYHAQAIIALNKRGAKQPPEGFDWDGTPICSARYRMVYWGS--
ref|YP_752864.1|      LMDAGYDQKSIYELIRKDYKAQAIIPLNHRGAKEPPEGLDWDATPICSAGYRMAYWGG--
ref|YP_001111903.1|   -MDMGYDSKDIYSVVMNDFNAQAIIPINSRGSKDHPEGCDFDGTPICSMGQRMVFWGSDA
                       ** ***    .  *.        *****.:*  *   *  *** **  : **  *:    *.:**

ref|ZP_01665148.1|    EKGILKFRCPHVCGKVNCPNGSAWCSPSNYGLVIKKKVEDDPRSFCTPHRGTREWEKLYA
RAAC02377             D--WLKFRCPHATGQVDCPLGMAACSASNYGMVVKKRLDEDVRRYANPHRGSRTWKMLYD
ref|YP_754667.1|      YQGVNKFRCPHIMGKCDCPFGSAWCSDSNYGMVVKTKVKDDPRLFSSPHRGSANWQKQYN
ref|YP_753226.1|      YQGVNKFRCPHIMGKCDCPFGSAWCSDSNYGMVVKTKVKDDPRLFSSPHRGSANWQKQYN
ref|YP_752864.1|      SNGVNKFRCPHVMGKCDCPFGSSWCSDSNYGMVVKTRARQDSRLFIVPHRGTSNWKLLYN
ref|YP_001111903.1|   KAGTNKYRCPHVMGKCDCPYGSAWCSPSSYGLVVKTKVKDDPRMNCIPARGTKNWQSLYN
                         *:****  *:  :**  *  :  **  *.**:*:*.:    :*   *       * **:  *:    * ref|ZP_01665148.1|    ERTSVERAFSRLKEQLGANT-VRVQGIKKVTAHLMLCCIALLAGTIAVNR--------
RAAC02377             ERTAVERCFARLKEWLTLDG-VHVRGIEKVTAHAYINASVLLASALAMHRTNRIEQVA
ref|YP_754667.1|      LRTYSERCFSRFKENLGLEDGLNVRKITKVETHAYLCAITMIAAVIAINQ--------
ref|YP_753226.1|      LRTYSERCFSRFKENLGLEDGLNVRKITKVETHAYLCAITMIAAVIAINQ--------
ref|YP_752864.1|      KRTSVERCFGRLKEHLGLETGLNVRGIKKVKTHAYLSVITMIASVIAINKDKSSTDIA
ref|YP_001111903.1|   KRTSVERCFGRLKQHLGANS-IRTRGLEKVTLHITLSCIALLAGSIAVAKTKRIEQAA
                       **   **.*.*:*:   *     :   :..:  :   **   *   :     .::*.  :*:   :
```

FIG. 93

```
ref|YP_754865.1|        ANCEE-IDENTITIESPSITIVESGAPSEEQYRLSRQKQFGTSSEKTTPEQIN-------
ref|YP_754943.1|        -------------------------------EEQFRLSRQKQFGASSEKTTPEQIN-------
ref|YP_431166.1|        ------------------------------------------------------------
RAAC03117               --------------------------MEEQIHLLRHRLFGTSSEKRRKPQTDPDSIQLP
ref|ZP_02171171.1|      ------------------------------MQKKKFGTSSEKTDERFEQGS-----
ref|YP_001318017.1|     ----------------------------EEQFRLSQAQKYGSSSEKTDPDQMS------- ref|YP_754865.1|        LFNEAEDIVDPEIKEPDIE-------------TITYERKKKQPGQKADKLKDL--PVEVI
ref|YP_754943.1|        LFNEAEDITDPKLEEPSLE-------------TVTYQRKKKQAGQREDKLKDL--PVEII
ref|YP_431166.1|        ------------------------------------------------------------
RAAC03117               LFNEAEVEADAQASEETVEGNAEATSEGVETETITYERRKPRAARERDAWLYQGEADEVV
ref|ZP_02171171.1|      LFNESEKEQDAAEEEPTVE-------------AITYERKKKRKARKD---LTENLYTETV
ref|YP_001318017.1|     IFNEAEKFSVKLDEEPEAE------------EVLTKRRTGKSKSKKK----YEDLPIEEV ref|YP_754865.1|        EYRLLEHEQVCPCCQGSLHEMSTQIRQEIKVIPAQVKVVQHVQYIYSCRQCEKENITT--
ref|YP_754943.1|        EYRLEKHEQICPCCQGELHEMSIQVRHEIKIIPAQAISVKHVQYIYACRRCEKENITT--
ref|YP_431166.1|        --------------------MSTEVRQELKIIPAQVKVVKHIRYVYACRHCEREELTT--
RAAC03117               EYRLSDDERVCSKCAGELHEMSREITRRVKIIPAQMKKVEYVRYVYTCRHCEAQDVET--
ref|ZP_02171171.1|      TYTLPVEDQVCSCCNGELHIMKTQVKDELEIIPAEVKVKRYETTIYSCRHCERTGTRN--
ref|YP_001318017.1|     HYTLSDEERQCPKCDHTLHEMKTEVRKELKIIPAQVKVVHHIKQVYACRGCDAIDSDNGG
                                           *. ::  .:::***:    .:   :*:** *:     .

ref|YP_754865.1|        PIIKAQMPNPILPGSLASPSILAYIMDQKYTNSMPLYRQEQQLSRLGIELSRQTMANWVL
ref|YP_754943.1|        PTIKAEMPKPILPGSLASPSILAYIMDQKYTNSLPLYRQEQQFSRLGIELSRQTMANWLL
ref|YP_431166.1|        PVVTAPMPAPVLPGSPVSPSLLAYVMHQKYGEGLPLYRQEQQFKSLGLELSRQTLANWVL
RAAC03117               PVVRAPMPKPVQAKSLATPEAVAYVMAKKFVDGMPLYRQEQQFARHGYPLSRQTLANWVV
ref|ZP_02171171.1|      PIVKAPSPERPFPGSLASPSIVSYMINQKFVQGVPLYRQEQEFKRMDVPISRQTMSNWII
ref|YP_001318017.1|     TIITAPMPKPVLPGSMVSPSVLAFIMENKYNQALPLYRQEASFVNYGIDLSRQNMASWII
                         .::   *    *   .   *  .:*. :::::  :*: :.:******   .:     :***.::.*::

ref|YP_754865.1|        NVADPWLKIIYDRLHVELLDRDILHADETTLQVLKEPGRSAETKSYMWLYRTGRD-GPPI
ref|YP_754943.1|        AAADPWLKIIYDRLHEQLLEKDILHADETTLQVLKEPGRRAESKSYMWLYRTGRD-GPPI
ref|YP_431166.1|        HGANTWLTHIYDRLHEYLLRKDILHADETTLQVLREPGREAATKSFLWLYRTGRD-GPSI
RAAC03117               HAAETWLEPLYAKLRQVLLAQRYLHADETTLQVLHEAGRAAQTQSYMWVYRSSMN-GPPL
ref|ZP_02171171.1|      EASEQMLEPIWDLMIRILTSLDVLHADETTVQVLKEDGKEAAAKSYMWLYRSGSH-DVPI
ref|YP_001318017.1|     QGAEKWLSPLYDRMHTHLKQSPVIHADESPLKVLDEKDK---SQSYMWLYATAETSEYPI
                                ::  *    ::   :   *    :****::.:** *  .:   ::*::*:* :.      .:

ref|YP_754865.1|        VLYEYQTTRASKHPDRFLSGFKGYLQTDGYSAYGKLT-GITLVGCWAHARRKFTEALKAL
ref|YP_754943.1|        VLYDYQTTRASKHPDSFLSGFKGYLQTDGYSGYGSLT-SVTLAGCWAHARRKFTEALKAL
ref|YP_431166.1|        VLYDYQTTRASKHPCRFLAGFKGYLHVDGYAGYNELP-DVTLVGCWAHARRKFDEALKAL
RAAC03117               VLYDYQETRSAEHPRRFLAGFQGYLHVDGYAGYEGLP-DVTLVGCWAHARRKFDEALKAV
ref|ZP_02171171.1|      VIYDYQPGRASKYPRRFLEGFTGYLHVDGYGGYHALKPKVELVGCWAHARRKFFDAVQTL
ref|YP_001318017.1|     YLYEYQPSRAKKHPKQFLEGFTGFLQTDGYAGYNGVE-NVVQVGCLAHARRKYTDAIKAL
                        :*:**  *: ::*    ** **  *:*:.***..*    :    .**  ******: :*::::

ref|YP_754865.1|        PAAQKDKPVAASVGLEYCNRLFAIERQLKD--VSDKERYDKRLEKSKPLLDEFYIWLKKQ
ref|YP_754943.1|        PAEQKDKPVAASIGLGYCNKLFAIERQLKD--MSCQERYEKRLELTRPLLNEFYAWLKRQ
ref|YP_431166.1|        PEDKRNAAVAAREGLEFCNRLFTIERDLKD--KTPEERYQLRQVRSKPVLDAFLAWLKTQ
RAAC03117               PSKERKGKTAAEEGLSYCNALYAVEKKLKN--ASAEERQRVRMAKSKPILDAFLAWLEKQ
ref|ZP_02171171.1|      PDDRDSTTSAAKKGLNAIDELYRIEREIQNEYKTPEEFYEARKERIEPPLEAFSAWVESM
ref|YP_001318017.1|     PEGSDVSLTKANEGLSLLRKIYRLEKSFKE--MEPEVRYEARIEQTQPVLDAYKTWLEVE
                         *              *  **     ::  :*:.:::       :          *       .*  *: :   *::

ref|YP_754865.1|        KQQTLPKSTFGQAITYCLNQWDCLNSFLLDGRLEIDNNRAERSIKPFVIGRKNWLFTNTP
ref|YP_754943.1|        RQQTLPKSMFGQAITYCLNQWDALNTFLLDGRLEIDNNRAERSIKPFVIGRKNFLFSNTP
ref|YP_431166.1|        KSRVLPKSSFGQAINYCLGQWDKLTAFLQDGRLELDNNRSERSIKPFVIGRKNWLFANTP
RAAC03117               EQQVLPKSALGRAVSYVLKQWPKLIRYVENGYLEIDNNRCERSLKPFVIGRKNWLFANTP
ref|ZP_02171171.1|      KPKILSKSLLGKAVIYASNQMEHLRTFLKDGRLAIDNNRAERSIKPFVLGRKNWIFSNTP
ref|YP_001318017.1|     EKRTLPKSKLGQAISYSLKQWDKLAAFMKDGRIAIDNNLAERGTKPFVLGRKNYLFAKSP
                        .  :*.**  :*:* : *       *  :: :* : :*** .**.:****:****:*::*
``` continued →

FIG. 93 continued

```
ref|YP_754865.1|      RGARGSAIIYSVIETAKENNLKPYNYMFYLFEQLPNVDTGDQAAIDRLLPWSDTLPE---
ref|YP_754943.1|      RGARGSAIIYSIIETAKENNLKPYDLVYLFEQLPNVDTSDQTAVDRLMPWSDTLPEGCR
ref|YP_431166.1|      RGAKASAITYSIIETAKDNGLNPFQYLIYLFERLPNLDLKDKDALDQLLPWSASLP----
RAAC03117             RGARASAVTYSIVETAKENGLNPTAYLTYLFERMPNIDLKDEAAFEALLPWSEGLPEGIR
ref|ZP_02171171.1|    RGAKSSSIIYSMIETAKENQLKPQAYLNYLFENLP---SSKQSEMEQFLPWSDSLPRMIF
ref|YP_001318017.1|   KGATASALCYSIIETAKANKLIPFQYLTYLFEQLPNLDIEDPEALDAMLPWAESLPNEVR
                      :**  .*:: **::****  *  *    *: ****.:*   .    .: ::**:  **

ref|YP_754865.1|      ---
ref|YP_754943.1|      I--
ref|YP_431166.1|      ---
RAAC03117             VRK
ref|ZP_02171171.1|    V--
ref|YP_001318017.1|   ---
```

FIG. 94

```
ref|NP_780819.1|       ----IQIFQNYSVFIVLGLIIATIILFFIVVVQAKAINRLEKRYRKFMRGVDNKNLEELI
ref|YP_699899.1|       ----LNILTQYSTYITIGLIVLVLIQFILLIVALRSLSKVENKFRKIMRGVNNKNLEELI
ref|YP_001514390.1|    MAFITNILEEYRDILFIASLGLNILTIIFLIINMGISSNLKEKYRKLVRGTDGKQIESIL
ref|YP_077153.1|       ------LLQQDPLLVAFTALGFCIVAIVIMLIVLVRQSILLRRYRSLLRGNTNASLEDLL
RAAC00037              MAMGLSILQPYALDIALFSGILAIICLVIASVALSRSARLKRKFNRLKEVTSAADLERVF
ref|YP_001663996.1|    ----LDIISQNATLIILFLSVLSIIELIFILIINGKFLRLNRTYNKIIKTLEKGDVFDIF
                         ::     : :       :: :.:  :         : . :. :  .    .:  ::

ref|NP_780819.1|       NTYLDKVDKASEECQYAKELYKSLEDRLNICVQKIAIIRYRAFEDVGSDLSFSVALLDYK
ref|YP_699899.1|       NSYLDKVEEVKKDSEETLETNKMLKAQIEKCTQKVSVIRYKAFEDVGSDLSFSVALLDGE
ref|YP_001514390.1|    FEHLDKIEDVHQRLNQFEGKLEIFNNRLSFCVQRVGIIRYNAFDDTGSDLSYSIALLDEN
ref|YP_077153.1|       IQQQQATADLRAAQESIRRRLSDLESASQKYLQRIGIVRYNAFPDVGADLSFSCALLDGE
RAAC00037              EETKDAVRKLEMKLREAEEHLRIVEEALQSKVSTPAILRYNAFAEVGSDLSYSVALIDGK
ref|YP_001663996.1|    SRILTENEEIKNKLDKLRMDLNSLDKETKTAIKKVGIVRYNAFSDVGSDLSFSIALLDSN
                           .           ..    .   . .::**.** :.*:***:* **:*  :

ref|NP_780819.1|       DSGIIITGIYGRNESTTYAKPIDKGISRYELSEEE----NHVLKEAM---------
ref|YP_699899.1|       NNGVILTGIYGRDYSTTYAKPIDKGISRYDLSEEE----LHVLNAAM---------
ref|YP_001514390.1|    NDGIIITGIYGRIETVSYAKPVKNGVSNYSLSVEE----LQALERA----------
ref|YP_077153.1|       DNGVVVTSLYGRSECRTYAKPIRGGSSSYALTDEE----KQALRLA----------
RAAC00037              GDGVVITSIYGREDSVTYGKPVQGGDSPYMLTEEERAVIEEALRGAPRRRTTAQIS
ref|YP_001663996.1|    DNGIVLSGIYGRNETATFAKPIERGQSKYPLSAEE----VQAIERAKRKA------
                       ..*::::.:***    ::.**:    *  * * *:  **       ...:. *
```

FIG. 95

```
ref|NP_387885.1|        MYIQNLELTSYRNYDHAELQFENKVNVIIGENAQGKTNLMEAIYVLSMAKSHRTSNDKEL
ref|YP_001419683.1|     MYIQNLELTSYRNYERAELQFENKVNVIIGENAQGKTNLMEAIYVLSMAKSHRTSNDKEL
ref|YP_077286.1|        MYIQNLTLSSYRNYERLDLQFENKVNVIIGENAQGKTNLMEAIYVLAMAKSHRTSNDKEL
ref|ZP_02326643.1|      MFLQRLTLHHYRNYQHVELVTDRNVNIFVGPNAQGKTNLLESIYVLALTKSHRTHHDKFL
ref|YP_803557.1|        MYLKTLELHNFRNYADLVVEFGSGINVLLGENAQGKTNLLESIYFLALTRSHRTNSDRDL
RAAC00054               MDIRRVELHDFRNYAKAEIELSPGVNVLVGENGQGKTNALEAMLLIAVGKSHRAHRDRDL
                        *   ::   :  *  :***        :     :*::::* *.*****  :*:: .:::   :***:     *::* ref|NP_387885.1|        IRWDKDYAKIEGRVMKQNGAIPMQLVISKKGKKGKVNHIEQQKLSQYVGALNTIMFAPED
ref|YP_001419683.1|     IRWDEDYAKIEGRVMKRNGDIPMQLVISKKGKKGKVNHIEQQKLSQYVGALNTIMFAPED
ref|YP_077286.1|        IRWDEDYAKIEGRVIKKNGSVPIQLVISKKGKKGKVNHIEQQKLSQYVGAVNTIMFAPED
ref|ZP_02326643.1|      IQWEGESALLQGDVEKKYGSYSLDLAISSKGKKAKINGLEQKKLSQFIGALNVVLFAPED
ref|YP_803557.1|        ISWKTKAARVSGSVQKEHTVTPLEINLSSKGKNAKVNHLEQSRLSQYVGQLNVILFAPED
RAAC00054               IRWEQDRARILLEASTRYGDRRLTLELGPEGRRAFANGVQVGRMTEFVGQVQVVLFAPED
                        * *. . *  :    . ..     :  : :. :*:..   * ::   ::::::*  ::.:**** ref|NP_387885.1|        LNLVKGSPQVRRRFLDMEIGQVSPVYLHDLSLYQKILSQRNHFLKQLQ-TRKQTDRTMLD
ref|YP_001419683.1|     LNLVKGSPQVRRRFLDMEIGQVSAVYLYDLSLYQKILSQRNHFLKQLQ-SRKQTDRTMLD
ref|YP_077286.1|        LNLVKGSPQVRRRFLDMEIGQVSPVYLHDLSLYQKILSQRNHFLKQLQ-TRKQTDQTMLD
ref|ZP_02326643.1|      LEIIKGNPGIRRRFLDMEIGQVYPGYLYDLSQYQKVLAQRNNMLKKAFPAPSAEHAAMLD
ref|YP_803557.1|        LSIVKGSPAVRRKFIDMEFGQMSSKYLYNSAQYRSVLKQRNQYIKQLQFNPKG-DQVYLD
RAAC00054               LDLVKGSPRVRRRFLDTELGQMEPLYLHHLSLYNRALLQRNRWLKTAP---LSPDDDVLA
                        *.::**.* :**:*:* *:: . :.  : *. * ***.   :*          .    * ref|NP_387885.1|        VLTDQLVEVAAKVVVKRLQFTAQLEKWAQPIHAGISRGLEELTLKYHTALD-VSDPLDLS
ref|YP_001419683.1|     VLTDQLIEAAAKVVAKRLQFTAQLEKWAQPIHSGISRGLEELTLKYHTALD-VSDPKDLS
ref|YP_077286.1|        VLTEQLTEFAAKVVMKRLQFVDQLEKWAQPIHSGISRGLEELTLKYHTSLH-VSDSPDLS
ref|ZP_02326643.1|      IWNEQLAQFGVKIMKKRQNFIKKLQNWAEQIHDGITNGGEELTIRYQPSFA-VQDFEDET
ref|YP_803557.1|        VLSDQLAAHGAEIIFQRIQFLKKLEKWSQEVHKEISQGKEKLSFQYVSPIS-SDQADTTE
RAAC00054               TFDRQIAFHGAHVIHRRLRFLARLRAYAARIYSDIASGREEFALAYRSSVSGVEEGMSVE
                           *:      ...::  :*  .*  :*. ::  ::  *:  *  *::::  *  ...   .:

ref|NP_387885.1|        KIGDSYQEAFSKLREKEIERGVTLSGPHRDDVLFYVNGRDVQTYGSQGQQRTTALSLKLA
ref|YP_001419683.1|     KIGNSYQESFSKLKEKEIERGVTLFGPHRDDVLFYVNGRDVQTYGSQGQQRTTALSLKLA
ref|YP_077286.1|        KMINSYQETFSKLRDKEIERGVSLSGPHRDDVLFYVNGRDVQTYGSQGQQRTTALSLKLA
ref|ZP_02326643.1|      VLMEQFMIKLSQIKDQEIRRGVSLAGPHRDDLLFYINDKEVQTYGSQGQQRTTALSLKLA
ref|YP_803557.1|        KIYAALQALFQKREKELQQGKTLVGPHLDDVRFMVNDKNVSTFGSQGQQRTTALSVKLA
RAAC00054               EMADTVQRALEKNRAQDLRFGTTSAGPHRDDILLFLDGREVHTAASQGQQRTIALSLRLA
                         :         :.:  :  :::.  *   :   *** **: :  ::.:: * *.****** ***:**

ref|NP_387885.1|        EIDLIHEEIGEYPILLLDDVLSELDDYRQSHLLHTIQGRVQTFVTTTSVDGIDHETLRQA
ref|YP_001419683.1|     EIDLIHEEIGEYPILLLDDVLSELDDYRQSHLLHTIQGRVQTFVTTTSVDGIDHDTLHQA
ref|YP_077286.1|        EIDLIQEEIGEYPILLLDDVLSELDDYRQSHLLHTIQGRVQTFVTTTSVDGIDHKTLNEA
ref|ZP_02326643.1|      EIELIHSEVGEYPILLLDDVLSELDEYRQTQLIQTFQKKVQTFITTTGLESVHLDQLEDA
ref|YP_803557.1|        EIDLMKEETGEYPVLLLDDVLSELDDSRQTHLLTAIQNKVQTFITTTSLSGVAQQLINEP
RAAC00054               EIDFMHEELGEYPVLLLDDVLSELDDLRQRNLVLGMSRKVQTVITTTSLNRLG-QELDDF
                        **::::.* ****:************: ** .*:  :. .***.****.. :  . : :

ref|NP_387885.1|        GMFRVQNGALVK---
ref|YP_001419683.1|     GMFRVENGTLVK---
ref|YP_077286.1|        EIFRVENGTLSD---
ref|ZP_02326643.1|      SVFRV----------
ref|YP_803557.1|        HVFNIDHGVLMQSK-
RAAC00054               RLFRVCSGIIAEERV
                         :*.:
```

FIG. 96

```
gb|AAR99616.1|           ------------------------------------------IKEMYERGMSISDIA
sp|Q45618|TRA6_BACST     ------------------------------------------IKEMYERGMSISDIA
ref|YP_074959.1|         --------------------------------------MLRSGETLEIRQMYAGGLSISEIA
ref|YP_075129.1|         ---------------------------------------------MYAAGLSISEIA
RAAC03102                MRIPQDHRPTFLKIIGMNSPPPCRIVAPVIRSWEVPVMREDERMEIRQLYEAGVSISELA
ref|YP_359963.1|         ------------------------------------------LHELQARGKSIRAIA
                                                                   :   * **  :* gb|AAR99616.1|           RELGIDRKTVRKYIHSPNPPSKSKR-----KQRKSKLDPFKPYLQKRMLEDGVFNSEKLF
sp|Q45618|TRA6_BACST     RELGIDRKTVRKYIHSPNPPSKSKR-----KQRKSKLDPFKPYLQKRMLEDGVFNSEKLF
ref|YP_074959.1|         RRTGRDRKTIRKWLRTNTMPKPAK------RKRSSMLDQHEAFTLEQMQK-GVTSASKML
ref|YP_075129.1|         RRTGRDRKTIRKWLRTNAMPKPAK------RKRSSMLDQHKAFILEQMQK-GVTNASKML
RAAC03102                RRFGYDRKTIRNALNSSVEEKQGERASRGERKRGSKLEPYKDYVKQRMQL-GVLNAERIL
ref|YP_359963.1|         RETGHSRNTVRKYLRAEGIPERKPR-----PKRGSKLDPYKDTIQELMNL-GIFNCEVIY
                         *. *  .*:*:*: :.:            :* * *: .:    : *    *: ... :

gb|AAR99616.1|           FEIRQQGYTGGKTILKDYMKPFRETAKKKYTVRYETLPGEQMQVD---------------
sp|Q45618|TRA6_BACST     FEIRQQGYTGGKTILKDYMKPFRETAKKKYTVRYETLPGEQMQVD---------------
ref|YP_074959.1|         YLLQQRGFKGKIRIVRAFMAPYRPMAKAAATVRFETPPGKQAQVDWADFGYIEVDGRR--
ref|YP_075129.1|         YLLQQRGFKGKIRIVRAFMAPYRPMAKAAATVRFETPPGKQAQVDWADFGYIEVDGRR--
RAAC03102                REIREQGYTGGITVLREFMKPLRPVVSAKATERYESDPGEQAQIDLGAFPYYDSHGQRRT
ref|YP_359963.1|         ERIKEEGYTGGRTILRDYVRQFRPPKQVPAVCRYETKPGQQAQVDWGEYTYID-------
                         ::.*: *   :::  ::   *     .  .*:*: **:* *:* gb|AAR99616.1|           -
sp|Q45618|TRA6_BACST     -
ref|YP_074959.1|         -
ref|YP_075129.1|         -
RAAC03102                I
ref|YP_359963.1|         -
```

FIG. 97

```
ref|YP_074959.1|      MVLAYSRAMYLEFVTATDMKTFMRCHINAFKFFGGVPHEILYDNVKTVVKDRD-------
ref|YP_594046.1|      MVLGWSRALYVEFIRKADTASFIRCHLNAFAYFGGMTQSILYDNTKQVVLERDETG----
ref|ZP_02516401.1|    -VLGYSRMLYIEFTDNMRYDTLETCHRNAFRFFGGVPREVLYDNMKTVVLQRD-------
ref|ZP_02335796.1|    -VLGYSRMLYIEFTDNMRYDTLETCHRNAFRFFGGVPREVLYDNMKTVVLQRD-------
ref|ZP_02563000.1|    -VLGYSRMLYIEFTDNMRYDTLETCHRNAFRFFGGVPREVLYDNMKTVVLQRD-------
RAAC03103             MVLAYSRMLYVEFIKAADQLHILQALRNALEFFGGVPRVMLSDNCSPLVVANDGQGHVDC
                       .:  :*:         :   : :***:.: :* **  .*   .* ref|YP_074959.1|      ----------------------------
ref|YP_594046.1|      ----------------------------
ref|ZP_02516401.1|    ----------------------------
ref|ZP_02335796.1|    ----------------------------
ref|ZP_02563000.1|    ----------------------------
RAAC03103             NRLISILPSSTDSCPRHVGLAGAAPRAR
```

FIG. 98

```
ref|YP_001039349.1|    ------------------------------------------------------------
ref|YP_001036724.1|    TRANSPSASEMUTATRTYPECLSTRIDIUMTHERMCELLUMATCCGBABNTRANSPSASE
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ------------------------------------------------------------
ref|YP_001036724.1|    MUTATRTYPECLSTRIDIUMTHERMCELLUMATCCGBABNTRANSPSASEMUTATRTYPE
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ------------------------------------------------------------
ref|YP_001036724.1|    CLSTRIDIUMTHERMCELLUMATCCGBABNTRANSPSASEMUTATRTYPECLSTRIDIUM
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ------------------------------------------------------------
ref|YP_001036724.1|    THERMCELLUMATCCGBABNTRANSPSASEMUTATRTYPECLSTRIDIUMTHERMCELLU
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ------------------------------------------------------------
ref|YP_001036724.1|    MATCCGBABNTRANSPSASEMUTATRTYPECLSTRIDIUMTHERMCELLUMATCCGBABN
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ------------------------------------------------------------
ref|YP_001036724.1|    TRANSPSASEMUTATRTYPECLSTRIDIUMTHERMCELLUMATCCGBABNTRANSPSASE
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ------------------------------------------------------------
ref|YP_001036724.1|    MUTATRTYPECLSTRIDIUMTHERMCELLUMATCCSCRESIGNIFICANCEE-IDENTIT
ref|YP_076075.1|       ------------------------------------------------------------
ref|YP_074958.1|       ------------------------------------------------------------
ref|YP_076118.1|       ------------------------------------------------------------
RAAC03341              ------------------------------------------------------------ ref|YP_001039349.1|    ---------------MATNNRMALLEQLSKYVVEKDKDFLKEALTLLINALMDAEVTSII
ref|YP_001036724.1|    IESPSITIVESGAPSMATNNRMALLEQLSKYVVEKDKDFLKEALTLLINALMDAEVTSII
ref|YP_076075.1|       ---------SRRRIPQVTTFRIALEELLRKTGVD-DFDFLREGLRVLAQGLMELEVSQRI
ref|YP_074958.1|       ----------------------LEELLRKTGVD-DFDFLREGLRVLAQGLMELEVSQRI
ref|YP_076118.1|       -------SNTSQRGNPQVTNFRIALEEELLRKSGVD-DVDFLREGVRVLAQGLMELEVSQQT
RAAC03341              ----MTNTKSRRHATMASLNSFAVLEWIRKMQDVDQIDFLRELMQLVTQFLIDAEAAEKI
                            : * :*        : ***:*  : ::  *:: *.:. * ref|YP_001039349.1|    GAEKYERNNNRNNYRNGYRLREWDTRVGTLQLSIPKLRHCSYFPSLLEPRK
ref|YP_001036724.1|    GAEKYERNNNRNNYRNGYRLREWDTRVGTLQLSIPKLRHGSYFPSLLEPRK
ref|YP_076075.1|       GADRYERSAERSTYRNGYRERQWDTRVGTIDLQIPKLRKGSYMPSFLEPRR
ref|YP_074958.1|       GADRYERSAERSTYRNGYRERQWDTRVGTIDLQIPKLRKGSYMPSFLEPRR
ref|YP_076118.1|       GAERYERSSERSNYRNGYRERQWDTRVGTIDLQIPKLRKGSYMPSWLEPRR
RAAC03341              GAERYERTESRVTQRNGYRSRAWDTRLGTVDLKIPKLRQGSFFPSILEPRR
                       **::***. .*  . ***** * *****:** ::*.*****:**  ****:
```

FIG. 99

```
ref|YP_001125185.1|    ------------------MSDYLVIVESPTKAKTIERYLGKKYTVKASMGHVRDLPKSQMG
ref|YP_147064.1|       ------------------MSDYLVIVESPTKAKTIERYLGKKYTVKASMGHVRDLPKSQMG
ref|NP_389494.1|       ------------------MSDYLVIVESPAKAKTIERYLGKKYKVKASMGHVRDLPKSQMG
ref|YP_091420.1|       ------------------MSEYLVIVESPAKAKTIERYLGKKYKVKASMGHVRDLPKSQMG
ref|YP_001486753.1|    ------------------MADYLVIVESPAKAKTIERYLGKKYKVKASMGHIRDLPKSQLG
RAAC02852              MNQGQGLPRLRRMEDRGVSDYLVIVESPAKAKTIGKYLGSKYTVKASMGHVRDLPKSQLG
                                         : :*****.* :*..***:*****:* ref|YP_001125185.1|    VDINDGYTPKYITIRGKGQVIKELKTAAKKAKKVFLAADPDREGEAIAWHLANMLDLDIH
ref|YP_147064.1|       VDIDHGYEPKYITIRGKGQVIKELKTAAKKAKKVFLAADPDREGEAIAWHLAHMLDLDIH
ref|NP_389494.1|       VDIEQNFEPKYITIRGKGPVLKELKTAAKKAKKVYLAADPDREGEAIAWHLAHSLDLDLN
ref|YP_091420.1|       VDIEQNFEPKYITIRGKGPVLKELKTAAKKAKKVYLAADPDREGEAIAWHLAHSLDLDLN
ref|YP_001486753.1|    VDTEHDFEPRYITIRGKGPVLKELKTAAKKAKKVYLAADPDREGEAIAWHLAHSLDLDLS
RAAC02852              VDVEHGFEPKYITIRGKGDVIKALREASKKAKKVYLAADPDREGEAIAWHLQHLLDLNPD
                       **  ...: *:******  *:.* *: *:****:****************  : ***:

ref|YP_001125185.1|    SDCRVVFHEITKDAIKQSFQQPRSINMNLVDAQQARRVLDRLVGYNISPLLWKKVKKGLS
ref|YP_147064.1|       SDCRVVFHEITKDAIQQSFQQPRAINMNLVDAQQARRVLDRLVGYNISPLLWKKVKKGLS
ref|NP_389494.1|       SDCRVVFNEITKDAIKESFKHPRMINMDLVDAQQARRILDRLVGYKISPILWKKVKKGLS
ref|YP_091420.1|       SDCRVVFNEITKDAIKESFKHPRMINMDLVDAQQARRILDRLVGYKISPILWKKVKKGLS
ref|YP_001486753.1|    SDCRVVFNEITKDAIKDSFKHPRMINMDLVDAQQARRILDRLVGYKISPILWKKVKKGLS
RAAC02852              DDCRVVFHEITKDAVKQAFQHPRKINLDLVNAQQTRRILDRLVGYKLSPLLWRKVKKGLS
                       .***.****:::*::*:  :::*. ******:.::***** ref|YP_001125185.1|    AGRVQSVALRLIIDREKEIRQFQPEEYWTIQAKFQKGKEAFAASFYGVDGEKLELKTEAD
ref|YP_147064.1|       AGRVQSVALRLIIDREREIREFQPEEYWTIQATFQKEGETFAASFYSIDGQKRDLKTEAD
ref|NP_389494.1|       AGRVQSVALRLIIDREKEINDFKPEEYWTIDGTFLKGQETFEASFFGKNGKKLPLNSEAD
ref|YP_091420.1|       AGRVQSVALRLIIDREKEINDFIPEEYWTIEGSFLKGKETFEASFFGINGEKHQLKSEDD
ref|YP_001486753.1|    AGRVQSVALRLIIDRENEINEFKPEEYWTIDGTFLKGKESFEASFFGVNGKKHPLKTKED
RAAC02852              AGRVQSVALRLIVDRENEIRTFQPEEYWTVDAHGQVHGKKLVARFYGYGEEKTPLPNEAA
                       ************:***.**.** * ******::.       :  : * *:. . :* * ..:

ref|YP_001125185.1|    VKEVLARLNGRAFTVKTVTKRERRRSPVPPFTTSSLQQEAARKLNFRTKKTMMVAQQLYE
ref|YP_147064.1|       VKAVLDRLNGTAFAVKTVTKRERKRSPVPPFTTSSLQQEAARKLNFRTKKTMMIAQQLYE
ref|NP_389494.1|       VKEILSQLKGNQYTVEKVTKKERKRNPALPFTTSTLQQEAARKLNFRAKKTMMIAQQLYE
ref|YP_091420.1|       VKQILSRIKGNKFEVKKVTKKERKRNPALPFTTSTLQQEAARKLNFRAKKTMMIAQQLYE
ref|YP_001486753.1|    VKEILSKLKGSKFSVEKVTKKERKRNPAVPFTTSTLQQEAARKLNFRAKKTMMIAQQLYE
RAAC02852              VRELLSRVEGHSLVVRRVKKSERKRNPAAPFTTSSLQQEAARKLGFRAYKTMQIAQQLYE
                       *: :* :::*    *.  *.* **:*.*. ***:*****.: * :**** ref|YP_001125185.1|    GIDLGGEGTVGLITYMRTDSTRIAETAQQEAAAYIEATFGAQYVHQEKRKEKKSTNAQDA
ref|YP_147064.1|       GIDLGSEGTVGLITYMRTDSTRVAETAQQEAAAYIEATFGAMYVNQEKRKEKKSTNAQDA
ref|NP_389494.1|       GIDLGGEGTVGLITYMRTDSTRISNTAVDEAAAFIDQTYGKEFLGGKRKPAKKNENAQDA
ref|YP_091420.1|       GIDLGKEGTVGLITYMRTDSTRISNTAQEEAASFIGEQYGKEFLGSKRKPAKKNENAQDA
ref|YP_001486753.1|    GIDLGKEGTVGLITYMRTDSTRISNTAIEEVSAFIDQTYGKNFLNTTKRTVKKNENAQDA
RAAC02852              GLDVPGEGTVGLITYMRTDSTRIAQSAQEEARAYIRQSFGEDYVPDRPRQYAKNEDAQDA
                       *:*: ******************:::*  :*. ::*   :  ::     *. :**** ref|YP_001125185.1|    HEAIRPTSAFRDPDKVKPYLTRDQFRLYKLIWERFIASQMAAAVLDTMSVELENNGVLFR
ref|YP_147064.1|       HEAIRPTSAFRDPDKVKPYLTRDQFRLYKLIWERFIASQMAAAVLDTMSVELENNGVVFR
ref|NP_389494.1|       HEAIRPTSVLRKPSELKAVLGRDQMRLYKLIWERFVASQMAPAVLDTMSVDLTNNGLTFR
ref|YP_091420.1|       HEAIRPTSVLRKPSDLKAVLGRDQLRLYKLIWERFVASQMAPATLDTMSVDLENNGLTFR
ref|YP_001486753.1|    HEAIRPTSTLRKPADVKHVLSRDQLRLYKLIWERFVASQMAPAVLDTMSVDLDNNGLTFR
RAAC02852              HEAIRPTSVMRHPDRLKDHLSRDQYRLYKLIWERFVASQMESAVLDTTSVDLEANGAWFR
                       ********.:*.*    :* * * ******:** .*.* :* ref|YP_001125185.1|    ASGSKVKFPGFMKVYIEGTDDQTEEQD-RLLPDLEEGEAVESEMIEPKQHFTQPPPRYTE
ref|YP_147064.1|       ASGSKVKFPGFMKVYIEGTDDQTEEQD-RILPDLEEEETVESETIESKQHFTQPPPRYTE
ref|NP_389494.1|       ANGSKVKFSGFMKVYVEGKDDQMEEKD-RMLPDQEGDTVLSKDIEPEQHFTQPPPRYTE
ref|YP_091420.1|       ANGSKVKFSGFMKVYVEGKDDQMEEKN-KMLPDLAEGDTVLSKDIEPEQHFTQPPPRYTE
ref|YP_001486753.1|    ANGSKVKFPGFMKVYVEGKDDQLEEKD-KMLPDLKEGDTVLSKDIEPEQHFTQPPPRYTE
RAAC02852              ATGSVVRFPGFMALYTEGRDDDADEEEGKLLPPLQEGDVVQVKTWKPEQHFTQPPPRYTE
                       *.** *:*.*:*. :* ** ** *:*    :** * *  *. :   *:.**********
``` continued →

FIG. 99 continued

```
ref|YP_001125185.1|    ARLVKTLEELGIGRPSTYAPTLDTIQKRNYVVLENKRFVPTELGEIVVELILEFFPEIID
ref|YP_147064.1|       ARLVKTLEELGIGRPSTYAPTLDTIQKRNYVVLENKRFVPTELGEIVVELMLEFFPEIID
ref|NP_389494.1|       ARLVKTLEERGIGRPSTYAPTLDTIQRRGYVALDNKRFVPTELGQIVLDLIMEFFPEIIN
ref|YP_091420.1|       ARLVKTLEELGIGRPSTYAPTLDTIQKRGYVALDNKRFIPTELGEIVLDLIMEFFPEIIN
ref|YP_001486753.1|    ARLVKTLEELGIGRPSTYAPTLDTIQKRGYVALDNKRFIPTELGEIVLNLIIEFFPEIIN
RAAC02852              STLVKAMEELGIGRPSTYAPTIDILLKRGYVTLDQKRFVPTELGETVVNILKEHFPQLID
                       :  ***::**  **********:*   :*.**.*::***:*****:**:::  *.**:*:

ref|YP_001125185.1|    VEFTAKMEKELDEIEEGKVEWIKVVDEFYREFEKRLKVAEKEMREVEIKDEPAGIDCDVC
ref|YP_147064.1|       VEFTAKMEKELDEIEEGKVEWIKVVDEFYREFEKRLKVAEKEMRAVEIKDEPAGIDCEVC
ref|NP_389494.1|       VEFTAKMERDLDHVEEGNTEWVKIIDNFYTDFEKRVKKAESEMKEVEIEPEYAGEDCELC
ref|YP_091420.1|       VEFTAKMEKELDDVEDGNIQWVQIIDSFYKDFEKRVEKAEAEMQEVEIEPEYAGVDCEAC
ref|YP_001486753.1|    VEFTAKMEKELDSVEEGTIEWVRIIDSFYQDFAKRVEKAEAEMQEVEIEPEYAGVDCEEC
RAAC02852              VSFTADMESRLDKVEEGNANWIELLDQFYHDFEKDLKKAESALGHVELKDEVSDVRCEKC
                       *.*.   **  :*:*.  :*:.::*.**  :*  *  ::      : :: * :.   *: * ref|YP_001125185.1|    GSPMVYKMGRFGKFIACSNFPECRHTKPIVKEIGVKCPKCHEGNIVERNSKRKRVFYGCD
ref|YP_147064.1|       GSPMVYKMGRFGKFIACSNFPECRHTKPIVKEIGVKCPKCREGNIVERSTKRKRVFYGCD
ref|NP_389494.1|       SSPMVYKMGRYGKFLACSNFPDCRNTKPIVKQIGVKCPSCGEGNIVERKSKKKRVFYGCD
ref|YP_091420.1|       GHPMVYKMGRYGKFMACSNFPDCRNTKPIVKEIGVKCPSCKTGNIVERKSKKRRIFYGCD
ref|YP_001486753.1|    GHPMVYKMGRYGKFMACSNFPDCRNTKPIVKDIGVKCPTCHEGNTVERKSKKRRIFYGCD
RAAC02852              GRLMVYKTGRYGKFLACPGFPECRNTKPILKEIPVSCPKCGKP-LVERKGKSRKVFYGCS
                       .  **** **:***:**..**:**:****:*  *  *.**.*       :***. * :::****.

ref|YP_001125185.1|    RFPECDFVSWDKPLARPCPKCGGLLVEKKLKKGVQVQCT---------------
ref|YP_147064.1|       RFPDCDFVSWDKPLARPCPKCAGLLVEKVLKKGVQVQCT---------------
ref|NP_389494.1|       RYPDCEFVSWDKPIERKCPKCGKMLVEKKLKKGIQVQC----------------
ref|YP_091420.1|       RYPECEFVSWDKPLERKCPKCEDMLVEKKLKKGVQVQCVN--------------
ref|YP_001486753.1|    RFPECEFVSWDKPIERKCPKCENMLVEKKLKKGMQVQCVN--------------
RAAC02852              GYPECDYVLWQRPTGQTCPVCGHPMIEKGGKGKTVVVCSNEKAHPMVATEAQAK
                       :*:*:**  *::*    : **  *   ::** *     * *
```

FIG. 100

```
ref|YP_001125186.1|    -----ALQLFLEYLQIEKNYSQYTIVCYRRDIEQFLQFMNEEGIDEL-NEVAYSDVRLYL
ref|NP_243331.1|       -------------------SPHTIVNYELDLRHFRDFMEQQSIPSF-AAVSYAFVRHYL
ref|YP_175772.1|       ------------------TIDHYRKDVQQFAAFMSAAGIAEI-KDVKHQDVRLFI
ref|ZP_01775043.1|     -------------------SPHTLAAYRSDLEQFLSFLAREREAPRAEEVDHLAIRRYL
ref|YP_740910.1|       -------------------SPHTLQAYQRDLTRFHHWCAENGLADR-DAVSAHDIRRFA
RAAC02854              MTQSVGDAVKVFLDDAALRFSPRTVRSYGQDLEAFRQWLDDRGVYDL-DALSTRDVRMHA
                                           *:   *   *:  *   :           :  :* .

ref|YP_001125186.1|    TKLYGQQLASRSVARKISSLRSFYKFLLREGWTAENPFALAALPKKEQKIPNFLYREELE
ref|NP_243331.1|       TVLYEQEYARSTVSRKLSTLRSFYQFLVREKWVMENPFLLAHTPKGVKKLPSFLYEEEME
ref|YP_175772.1|       SELVDKKYARKSIARKLSALRSFGKFLMEEGHISENPFLHTHLPKQKTRLPTFLYEEEME
ref|ZP_01775043.1|     AQLH-KGCAKSSIGRKLSAIRALFRYLMREGKLEKNPAELVSTPKKEKRLPFHLNIDQVS
ref|YP_740910.1|       AARHRQGLAPGSVQRTLSSLRSLFRYLVREGRLTGNPAEGVAAPRRPRRLPGVLSPDEAA
RAAC02854              SDLLAKGAAKSSVARRLSCLRTFLRFCAERGWVRQVMAKNVRLPKRDRRLPRYLHEEEVA
                        :    :  *  :: * :* :*::  ::   ..      .  *:   ::*  *   ::

ref|YP_001125186.1|    ALFRVNDGNTAVGQRNAALLELLYATGARVSECCHIRLSDLDFAASTVLIHGKGNKQRYV
ref|NP_243331.1|       QLLDALNGDSPLQLRNRALFETIYASGLRVSECCGLKLQDVDLSIGTVFVFGKGRKERYV
ref|YP_175772.1|       HWLLALPANKPLEKRDKAIIELLYATGMRVSECSMLALDQWDRVSETVRVFGKGRKERYV
ref|ZP_01775043.1|     ALVTAPAGSSGLPLRDRAVLETLYSCGIRVSELTGMNVGDMDLAAGLARVMGKGGKERLV
ref|YP_740910.1|       RLLEGSPEDDPLALRDRALYELIYSSGLRLAEAVGLDLGRLDLTEGLVFVVGKGAKTRRV
RAAC02854              ALIDHVGGDDFVALRDRALLEFLYATGVRVSECVHLDIGDLDLSAGFARVLGKGGRERYV
                        .      .  : *:  *: *:*:  * :*   :    . : *      . : ***   :  * * ref|YP_001125186.1|    PFGRPAREALERYIGGGRRELVGKLPADHR--YLFVNARGNPLTPRGVRYILDRIVETAA
ref|NP_243331.1|       PIGSFACDAIQEYIENGREKLLKKSKSVDLPGDLFLNYRGGPLTERGVRKILHQALDQAA
ref|YP_175772.1|       PVGKMAVSAVESYIHEARPKLLR---ANDPTSHLFLNYRGGALSDRSIRKIVEKRLDEAA
ref|ZP_01775043.1|     PVGSCARSALAAYLAER-------ADPGPAEPLILN-ARGGRLTRRSVARIVDAHMLLIA
ref|YP_740910.1|       PVGGKAREALQAWLAVRP------ALAGADEPAVFVSQRGGRLSARSVQARLARLATLSG
RAAC02854              MVGRRAVDALRRYLPLR--------DRMARCSAVFINRRGGRLTDRSVRRVLERRIQEVP
                        . *    *  .*:   ::                 ::      **. *:  * .:    :

ref|YP_001125186.1|    LTQNISPHVLRHTFATHLLNEGADLRSVQELLGHAHLSSTQVYTHVTKDRL---------
ref|NP_243331.1|       LSTRVSPHSLRHSFATHLLNNGADLRVVQDLLGHENLSTTQVYTHVTKDRL---------
ref|YP_175772.1|       MQKKISPHAIRHSFATHLLNAGADLRAVQELLGHQSLKTTQVYTHVSKERL---------
ref|ZP_01775043.1|     AMRKVSPHTLRHTFATHLLEGGADLRAIQELLGHASLSTTQKYTHVSIDKL---------
ref|YP_740910.1|       VGRPVHPHMLRHSFASHLLESSGDLRAVQELLGHADIATTQVYTHLDFQHL---------
RAAC02854              GLRSIHVHGLRHSFATHMLNGGADLRSVQELLGHASLSSTQIYTHTSREQLARAYYAAHP
                            :   * :::*: .  :*** :*:** :  : ***    ::* ref|YP_001125186.1|    ----------------
ref|NP_243331.1|       ----------------
ref|YP_175772.1|       ----------------
ref|ZP_01775043.1|     ----------------
ref|YP_740910.1|       ----------------
RAAC02854              RARRGTQGRESSEDGV
```

FIG. 101

```
ref|ZP_01666445.1|      ------------------------------------------------------------
ref|ZP_01665334.1|      ------------------------------------------------------------
ref|YP_001211938.1|     DINACTIVATEDDERIVATIVESPELTMACULUMTHERMPRPINICUMSIDBBAFTRANS
dbj|BAD22831.1|         ------------------------------------------------------------
RAAC03166               ------------------------------------------------------------
gb|EAY56013.1|          ------------------------------------------------------------ ref|ZP_01666445.1|      ------------------------------------------------------------
ref|ZP_01665334.1|      ------------------------------------------------------------
ref|YP_001211938.1|     PSASEANDINACTIVATEDDERIVATIVESPELTMACULUMTHERMPRPINICUMSIDBB
dbj|BAD22831.1|         ------------------------------------------------------------
RAAC03166               ------------------------------------------------------------
gb|EAY56013.1|          ------------------------------------------------------------ ref|ZP_01666445.1|      ------------------------------------------------------------
ref|ZP_01665334.1|      ------------------------------------------------------------
ref|YP_001211938.1|     AFTRANSPSASEANDINACTIVATEDDERIVATIVESPELTMACULUMTHERMPRPINIC
dbj|BAD22831.1|         ------------------------------------------------------------
RAAC03166               ------------------------------------------------------------
gb|EAY56013.1|          ------------------------------------------------------------ ref|ZP_01666445.1|      ---------------------------------------------MAQYQINIDSKILHQL
ref|ZP_01665334.1|      ------------------------------------------------------------
ref|YP_001211938.1|     UMSISCRESIGNIFICANCEE-IDENTITIESPSITIVESGAPSMAQYQITVNQELLHQL
dbj|BAD22831.1|         ---------------------------------------------MAQYQITLDSQLLHQL
RAAC03166               ----------------------------MVECETEKKPLHQEG-YRMAQYQITVDDEILEGL
gb|EAY56013.1|          -----------------------------------------------MAELNLTLNPDLLPNL ref|ZP_01666445.1|      FLSNAKDAAMASFLEEVLNQILQAQATEQLRAERYERTDERQGYRNGVYPHRLTTRVGTI
ref|ZP_01665334.1|      ------------------------------------------------------------
ref|YP_001211938.1|     FLSNNKDSGIAALLESVLNQILQAQATEQLQAGPYERTDERKGYRNGTYPHQLTTRVGTI
dbj|BAD22831.1|         FLSNAHDAGVAKLLESVLNQVLQAQATEQLGAEPYERTEERQGYRNGTYPHQLTTRVGTI
RAAC03166               FQ---RDGGVAKLVESVLNQILQAQVQEQLKAAPYERTKERQGYRNGTVTRTLTTRVGRL
gb|EAY56013.1|          LTE--GGDGLKKLVESVLNQVLEAQMTEHLGADRHERTEERAGYRNGVRERTLTTRVGTV ref|ZP_01666445.1|      TLKVPRFRDGKFSTEMFARYQRSEQALVLTLMEMVVNGVSTRKVAQITEELCGSEFSKST
ref|ZP_01665334.1|      -------------MFARYQRSEQALVLTLMEMVVNGVSTRKVAQITEELCGSEFSKST
ref|YP_001211938.1|     TLRVPRFRNGQFSTEMFARYQRSEQALVLTLMEMVINGVSTRKISQITEELCGAEFSKST
dbj|BAD22831.1|         TLRVPRIRNGKFSTELFARYQRSEQALVLALMEMVVNGVSTRKVAQITEELCGTEFSKST
RAAC03166               VLRVPRVRNGQFSTELFARYQRSEQAFIIALMEMVVNGVSTRDVAKITEQLCGTTFSKST
gb|EAY56013.1|          ILRVPQTRDCSFSTDLFKRYQRSEQALVLSMMEMVVQGVSTRKVANITEELCGTRFSKST
                        :* ******:::::*.:::*:*:  *** ref|ZP_01666445.1|      VSDLCKRLDPIVHAWNERPLKDQKYPFVMVDAMVIKVREEEERVRSRGVMIAVGINAEGYR
ref|ZP_01665334.1|      VSDLCKRLDPIVHAWNERPLKDQKYPFVMVDAMVIKVREEEERVRSRGVMIAVGINAEGYR
ref|YP_001211938.1|     VSDLCKKLDPLVISWNNRDLREMRYPFILVDALVLKVREDGRVRSRGVMIAIGLNTEGYR
dbj|BAD22831.1|         VSELCKRLDPVVTAWNNRPLDDHPFPFVIVDALVLKVREESRVRSRGALIGIGVNTDGYR
RAAC03166               VSELCKRLDPIGQGWNHRSLAEHRYPFLLVDALVLRIREEGRDRSRAAMIAVGINEEGYR
gb|EAY56013.1|          VSQLSTGLSARVQAWKNRKLSS-PYPFVLIDALVIRVRKNESVSPMAALIATGITAEGQR
                        :.. *.. .*:.* * .  :::::*::*::   ...*. *:. :* * ref|ZP_01666445.1|      EVLGIMLGDSESEASWSEFFSWLKRRGLCGVDLIISDHHGGLIRAIRQYFQGVTWQRCQT
ref|ZP_01665334.1|      EVLGIMLGDSESEASWSEFFSWLKRRGLCGVDLIISDHHGGLIRAIRQYFQGVTWQRCQT
ref|YP_001211938.1|     EVLGIMLGDSESEASWSEFFSWLKNRNLRGVDLVVSDDHSGLVKAVRNHFQGVTWQRCQT
dbj|BAD22831.1|         EVLGLMLGDSESEASWSEFFGWLKSRGLQGVDLIVSDDHGGLIRAIRRHFQGVTWQRCQT
RAAC03166               GILGLMLGDSESEASWREFFAWLKNRGLRGVDVVVSDSHGGLVKALHTEFQGCTWQRCQT
gb|EAY56013.1|          EILGLTLGDSENEASWDDMLRDLKHRGLSGVDLIVSDDHKGLKNAAWKHFQGVRWQRCQV
                        :**: *****.****  :::  ** *.* ***:::** * **  . *  *** *****.
``` continued →

FIG. 101 continued

```
ref|ZP_01666445.1|    HFIRNILDATPKSLQPEILARVRAILAAPDRETAVMLLNETLAAYETKAPKAMAILEAGF
ref|ZP_01665334.1|    HFIRNILDATPKSLQPEILARVRAILAAPDRETAVMLLNETLAAYETKAPKAMAILEAGF
ref|YP_001211938.1|   HFMRNIMDSAPKSVKEELYPRLRAILDAPDIGSARLLLNQTLEAFEKKAPRAMRVLEMGF
dbj|BAD22831.1|       HFIRNILDATPKELQDEVHSWVRAILDAPDLDTARLLLNQVLETYETKAPKAMAILEACF
RAAC03166             HFMRNLLDATPKALQEEVYQQVRAVLDAPDLKTARLLKDAFVEAYAEKAPKAVQVLEDGF
gb|EAY56013.1|        HFLRNILGHAPASQRGPLAQALSRLFRSETMEEARMVRNEILRTFEKKAPKAMECLEEGF
                      **:**::. :*      :  :   :  ::  :     * ::  : ::  ***:*:  ** **

ref|ZP_01666445.1|    DDAIAVLALPEKYRKRLRTTNGVERLNEEVRRRERVIRIFPNRASALRLIGALLMEIDDK
ref|ZP_01665334.1|    DDAIAVLALPEKYRKRLRTTNGVERLNEEVRRRERVIRIFPNRASALRLIGALLMEIDDK
ref|YP_001211938.1|   DDATAVLVLPEKYRLRLRTTNGVERLIEEVRRRERVIRIFPNRESVVRLIGALLMEIDDK
dbj|BAD22831.1|       EDATAVLLLPEKYRKRLRTTNALERLNEEIRRRERVIRIFPNRESAMRLIGALLMEID--
RAAC03166             DDVTAVLVLPERYRRRLRTTNGVERLNEEIRRRERVIRIFPNRESAIRLLGALLMEIDEE
gb|EAY56013.1|        DETLNILTFPKKYRVRLRSTNSQERLNEEIRRRERVIRIFPNEESAIRLIGALLSEFHEQ
                      ::.   :* :*::** ***:**. *** **:**********. *.:**:****  *:.

ref|ZP_01666445.1|    WASGKKYLDMTDYWDWRERQ---------------
ref|ZP_01665334.1|    WASGKKYLDMTDYWDWRERQ---------------
ref|YP_001211938.1|   WAAGKKYLDMAEYLQWQKEQKHDR-----------
dbj|BAD22831.1|       -----------------------------------
RAAC03166             WTTGRKYLNMDEYEAWKKAQEASRGSTQACAATA
gb|EAY56013.1|        WSTGKKYLDMTEYHEWKKQESFKTSSTLA-----
```

FIG. 102

```
ref|ZP_02327778.1|    MDELKIHKHEWKKE--KLFVGDKWRGGDKQYVFHAGFGKPLYHTYPTQWWGEFIKRHNLK
ref|ZP_02327484.1|    MDELKVHEYEWKKE--KLSVGDKWRGGDRQYVFHACFGKPFHHTYPTEWWNGFTKRHNLK
ref|ZP_02330756.1|    MVELKEYEREWKKE--KLSVGDKWIGGDRRYVFHAGLGKPYFYSYPSEWWSKFIKRHDLK
ref|ZP_02330395.1|    MQELKVHEREWKKE--KLFMGDKWLGGDRQYVFHAGYGKPFFHTTPTKWWRSFISRNKLK
ref|ZP_02326400.1|    --DELSKFEIIWNEE--KETAGQKWEERKHSFIFHNGLGKPFYRTVPSQRWLQFIRANNLP
RAAC02961             MNELSKYREIWIKERWHLQQSGKWQGGEKQFLFHNGFGEKYYPSTPSLHWRRFLDKHGLP
                        **.  ..  * :*    :   . .:  :: * *:  . : *:   *   *    : * ref|ZP_02327778.1|    RVRFHDLRHSSATLLIEAGASMKAIQERLGHSKHQTTADIYAHITKKVSRETAEKFDKFA
ref|ZP_02327484.1|    RVRFHDLRHSSATLLIEAGASMKAVQQRLGHSKHQTTADIYAHVTKKVSRDTAEKFNKFA
ref|ZP_02330756.1|    RVRFHDLRHSSATLLIEAGASMKAIQQRLGHSKHQTTADVYAHVTKKVSRETAEKFDKFA
ref|ZP_02330395.1|    YIRLIDLRHSSATLLIEAGAPMKAIQKRLGHSKHQTTADIYAHVTKKVSRDTAEKFDKFA
ref|ZP_02326400.1|    HIRLHDLRHTVATLLLEEGVRLKVIQERHGHANYQTTADIYSHVTKRLTEDAVDKFEKFG
RAAC02961             RIRLHDLRHTTATILREDGADLKSIQERLRHTRLSITADLYTHETEAVSRETADRLEKLN
                      :*:*****:  **:*   * *.  :* :*:*    *:..  ***:*:* *:  :: .:..:::*:

ref|ZP_02327778.1|    P--------
ref|ZP_02327484.1|    PNNIRPQSV
ref|ZP_02330756.1|    PDSIRPQSV
ref|ZP_02330395.1|    PNNIRPQSV
ref|ZP_02326400.1|    P--------
RAAC02961             PFRSRSQSI
                      *
```

FIG. 103

```
ref|YP_146129.1|       ------------------------------------------------------------
sp|O87703|DNLJ_BACST   ------------------------------------------------------------
gb|ABN05294.1|         ------------------------------------------------------------
ref|YP_001124385.1|    ------------------------------------------------------------
ref|ZP_01169975.1|     ------------------------------------------------------------
RAAC02202              MGARRDRRQVGRGRIAGTRRALRRPHRREAAVCQVRADSQGGSLSGFKHPMQCVIRSVMR ref|YP_146129.1|       ----------QQAERRAAELRELLHRYGYEYYVLDRPSVPDAEYDRLMQELMAIEEQYPE
sp|O87703|DNLJ_BACST   ----------QQAERRAAELRELLNRYGYEYYVLDRPSVPDAEYDRLMQELIAIEEQYPE
gb|ABN05294.1|         ----------QQAERRAAELRELLHRYGYEYYVLDRPSVPDAEYDRLMQELIAIEEQYPE
ref|YP_001124385.1|    ----------QQAKRRAAELRELLNRYGYEYYVLDRPSVPDAEYDRLMQELIAIEKQYPE
ref|ZP_01169975.1|     -------MDLQNAEARVKELHNLLNQYGYEYYVLDKPSVPDSFYDRLLKELMELENEHPQ
RAAC02202              VVDAKSALSLEEARARAKVLREQIEYHNRKYYLEDNPEISDAEWDALMRDLIELERKYPE
                              ::*. *.  *:: :. :. :**:   ..*.::*:*:* *:::*: :*.:**:

ref|YP_146129.1|       LKTSDSPTQRIGGPPLEAFRKVTHVVPMMSLANAFDEGDLRDFDRRVRQEVGE-AAYVCE
sp|O87703|DNLJ_BACST   LKTSDSPTQRIGGPPLEAFRKVAHRVPMMSLANAFGEGDLRDFDRRVRQEVGE-AAYVCE
gb|ABN05294.1|         LKTSDSPTQRIGGPPLEAFRKVTHVVPMMSLANAFDEGDLRDFDRRVRQEVGE-AAYVCE
ref|YP_001124385.1|    LKTSDSPTQRIGGPPLEAFRKVTHRVPMMSLANAFNEGDLRDFDRRVRQEVGE-AAYVCE
ref|ZP_01169975.1|     LKTADSPTQRVGGEILDMFEKVEHQTPMLSLGNAFNEEDLRSFDRRVRQTAGENLSYVCE
RAAC02202              LVDPASPTQRVGAPALEGFAKVVHEVPMLSLANAYSTEDLLDWDRRVRQAVGDDVRYVCE
                       *  . ****:*:.  *: *  . .:.:.   .:*** .*: **** ref|YP_146129.1|       LKIDGLAVSVRYEDGYFVQGATRGDGTTGEDITENLRTIRSLPLRLKEPVSLEARGEAFM
sp|O87703|DNLJ_BACST   LKIDGLAVSVRYEDGYFVQGATRGDGTTGEDITENLKTIRSLPLRLKEPVSLEARGEAFM
gb|ABN05294.1|         LKIDGLAVSVRYEDGYFVQGATRGDGTTGEDITENLRTIRSLPLRLKEPVSLEARGEAFM
ref|YP_001124385.1|    LKIDGLAVSVRYEDGYFVQGATRGDGTTGEDITENLKTIRSLPLRLNEPVSLEARGEAFM
ref|ZP_01169975.1|     LKIDGLAVALKYEDGLFIQGATRGDGTIGEDITVNLRTIRSIPLRLSEPVSIEVRGEAFM
RAAC02202              LKVDGLAVALRYQDGRLVLGATRGDGSVGEDITANIRTIRNVPLELSEPVSLEVRGEAYM
                       :***::::*:  :: ***: *** *::*.:.*.****:*.****:* ref|YP_146129.1|       PKASFLRLNEERKARGEELFANPRNAAAGSLRQLDPKVAASRQLDLFVYGLANAEELGIE
sp|O87703|DNLJ_BACST   PKASFLRLNEERKARGEELFANPRNAAAGSLRQLDPKVAASRQLDLFVYGLADAEALGIA
gb|ABN05294.1|         PKASFLRLNEERKARGEELFANPRNAAAGSLRQLDPKVAASRQLDLFVYGLANAEELGIE
ref|YP_001124385.1|    PKASFLRLNEERQARGEELFANPRNAAAGSLRQLDPKVAASRQLDLFVYGLANAEELGIE
ref|ZP_01169975.1|     PGRSFEALNKGKEERGEEPFANPRNAAAGSLRQLDPRIAASRNLDIFLYGISNTGDTGVE
RAAC02202              PKREFMRLNELREQQGEPLFANPRNAAAGSLRQLDPAVAASRRLGVIVYQLVRAEAHGCE
                       *  .*  : :: :  **************.:**.*.::::*  :      * ref|YP_146129.1|       SHSEALDYLQALGFKVNPERRRCANIDEVIAFVNEWHEKRPQLPYEIDGIVIKVDSFAQQ
sp|O87703|DNLJ_BACST   SHSEALDYLQALGFKVNPERRRCANIDEVIAFVSEWHDKRPQLPYEIDGIVIKVDSFAQQ
gb|ABN05294.1|         SHSEALDYLQALGFKVNPERRRCANIDEVIAFVNEWHEKRPQLPYEIDGIVIKVDSFAQQ
ref|YP_001124385.1|    SHSAALSYLQSLGFKVNPERRRCATIDEVIAFVNEWKEKRPQLPYEIDGIVIKVDSFAQQ
ref|ZP_01169975.1|     SHSAGLDYLETLGFKTNKERRKCASIEEVIEYVSSWTEKRPNLDYDIDGIVIKVDSLALQ
RAAC02202              THSQALDYVARLGLPAHRERHVCANIEDVIAYIEAWADKRHELPYATDGMVVKVDSLALQ
                       :** .*.*:  :.:  : **.*::** ::. * :** :* * *  **:*:****:* * ref|YP_146129.1|       RELGATAKSPRWAIAYKFPAEEVVTTLIGIEVNVGRTGVVTPTAILEPVRVAGTTVQRAT
sp|O87703|DNLJ_BACST   RALGATAKSPRWAIAYKFPAEEVVTTLIGIEVNVGRTGVVTPTAILEPVRVAGTTVQRAT
gb|ABN05294.1|         RELGATAKSPRWAIAYKFPAEEVVTTLIGIEVNVGRTGVVTPTAILEPVRVAGTTVQRAT
ref|YP_001124385.1|    RQLGATAKSPRWAIAYKFPAEEVVTTLIGIEVNVGRTGAVTPTAILEPVRVAGTTVQRAT
ref|ZP_01169975.1|     EELGATAKSPRWAIAYKFPAEEVVTTLRDIELSVGRTGVVTPTALLEPVRVAGTTVQRAS
RAAC02202              ARLGATAKSPRWAIAYKYAAEQAETTLRAIELNVGRTGVVTPTAVFDPVQLAGTTVSRAS
                         **************: .**: ***  **:.***** *****::.**: *******.**:

ref|YP_146129.1|       LHNEDFIREKDIRIGDAVIIKKAGDIIPEVVGVVVDRRDGDETPFAMPTHCPECESELVR
sp|O87703|DNLJ_BACST   LHNEDFIREKDIRIGDAVIIKKAGDIIPEVVGVVVDRRDGDETPFAMPTHCPECESELVR
gb|ABN05294.1|         LHNEDFIREKDIRIGDAVIIKKAGDIIPEVVGVVVDRRDGDETPFVMPTHCPECESELVR
ref|YP_001124385.1|    LHNEDFIREKDIRIGDAVIIKKAGDIIPEVVGVVVDRRDGDEVPFTMPTHCPECESELVR
ref|ZP_01169975.1|     LHNEDLIREKDIKIGDKVVKKAGDIIPEVVNVLAEQRTGEEREFIMPTHCPECGSELVR
RAAC02202              LHNEDLVREKDIRVGDVIVVQKAGDIIPEVIRSLPERRTEPLPEFRMPETCPQCGSRLVR
                       *****::*****: ***  :::*********:    : ::*   *  **:*  *.:***
``` continued →

FIG. 103 continued

```
ref|YP_146129.1|         LEGEVALRCLNPNCPAQLRERLIHFASRAAMNIEGLGEKVVTQLFNAGLVRDVADLYRLT
sp|O87703|DNLJ_BACST     LEGEVALRCLNPNCPAQLRERLIHFASRAAMNIEGLGEKVVTQLFNAGLVRDVADLYCLT
gb|ABN05294.1|           LDGEVALRCLNPKCPAQLRERLIHFASRAAMNIEGLGEKVVTQLFNAGLVHDVADLYRLT
ref|YP_001124385.1|      LDGEVALRCLNPKCPAQLRERLIHFASRSAMNIEGLGEKVVTQLFNAGLVHDVADLYQLT
ref|ZP_01169975.1|       LEGEVALRCINPKCPAQIREGLIHFVSRNAMNIDGLGEKVVSQLFAKELIKDVADLYKLT
RAAC02202                LDGEVAWRCINPDCPALLREGLIHFCSRDAMNIEGLGEQWITVLLDRGLVRTHADLYRLR
                         *:** : * :   **:**: :: *:   *:: **** * ref|YP_146129.1|         KEQLIGLERMGEKSATNLLAAIEASKQNSLERLLFGLGIRYVGAKAAQLLAEHFETMERL
sp|O87703|DNLJ_BACST     KEQLVGLERMGEKSAANLLAAIEASKQNSLERLLFGLGIRYVGAKAAQLLAEHFETMERL
gb|ABN05294.1|           KEQLIGLERMGEKSATNLLAAIEASKQNSLERLLFGLGIRYVGAKAAQLLAEHFETMERL
ref|YP_001124385.1|      KEQLVGLERMGEKSAANLLAAIEASKQNSLERLLFGLGIRYVGAKAAQLLAEHFETMERL
ref|ZP_01169975.1|       HEALIGMERMGEKSVNNLVQAIEASKQNSLEKLLFGLGIRHVGAKAAKTLAQHFSSMDNL
RAAC02202                KADLVQLDRMGDKLADKLLHNIQESKRNSLERLLFGLGIRHVGEKAAKTLAEHFVTIDAL
                         :  *: ::***:*  . :*:  *: ::****:  *::**  ::: * ref|YP_146129.1|         ERATKEELMAVPEIGEKMADAITAFFAQPEATELLQELRAYGVNMAYKGPKRSAEAPADS
sp|O87703|DNLJ_BACST     ERATKEELMAVPEIGEKMADAITAFFAQPEATELLQELRAYGVNMAYKGPKRSAEAPADS
gb|ABN05294.1|           EKATKEELMAVPEIGEKMAGSIIAFFSQPEAAELLHELRLYGVNMAYKGPKRAAEAPADS
ref|YP_001124385.1|      EAATKDELMAVPEIGEKMADSITTYFSQPEAVELLNELRTYGVNMAYKGRKRTAETPASS
ref|ZP_01169975.1|       MAASEDDLTAINEIGGKMAGAIVAFFFQEEAKELIRELKESGVNMEYKGPKPVAAEDSDS
RAAC02202                MSASEEDLMAVPDIGPKVAQSIRQYFDTPRVRQLIQELKDLGVNMTYLGPQKVSDGP---
                         *::::* *: :** *:* :*  :  .. :*:.**: **** * *  :  :

ref|YP_146129.1|         AFAGKTVVLTGKLASMSRNEAKEEIERLGGRVTGSVSRSTDLVIAGEDAGSKLEKAQQLG
sp|O87703|DNLJ_BACST     AFAGKTVVLTGKLASMSRNEAKEQIERLGGRVTGSVSRSTDLVIAGEDAGSKLEKAQQLG
gb|ABN05294.1|           AFAGKTVVLTGKLASMSRNEAKEEIERLGGRVTGSVSRSTDIVIAGEDAGSKLEKAQQLG
ref|YP_001124385.1|      VLAGKTVVLTGKLASMSRNEAKEQIERLGGRVTGSVSRSTDTVIAGEDAGSKLDKAQQLG
ref|ZP_01169975.1|       FFAGKTIVLTGKLSILSRNEAKEKIEALGGNVSGSVSKKTDLLIAGEDAGSKLAKAQDLG
RAAC02202                -LAGKTVVLTGVLQAADRKQATAWIEQMGGKVASSVSAKTDVLIAGDKAGSKLAKAQEIL
                         : ****:**** *   .*::*.  **  :**.*::*** .**::***:*****  ***::

ref|YP_146129.1|         -------IEIWDESRFLQEIN-----
sp|O87703|DNLJ_BACST     -------IEIWDESRFLQEIN-----
gb|ABN05294.1|           -------IEIWDESRFLQEIN-----
ref|YP_001124385.1|      -------IEIWDETRFLQ--------
ref|ZP_01169975.1|       -------IDIWNEEQLVEE-------
RAAC02202                RNHPDAKLEIWDEAAFLRLVDEAGLR
                                ::*:** ::.
```

FIG. 104

```
ref|ZP_01695687.1|    ---------VGPSQLLSKLCDEIELEKTINDLVKWDSVRCHISPGTRIKALVLNILCSGK
ref|ZP_01695982.1|    ---------VGPSQLLSKLCDEIELEKTINDLVKWDSVRCHISPGTRIKALVLNILCSGK
ref|ZP_01695971.1|    ---------VGPSQLLSKLCDEIELEKTINNLVKWDSVRCHISPGTRIKALVLNILCSGK
ref|ZP_01695655.1|    ------------PQSCKLCDEIELEKTINNLVKWDSVRCHISPGTRIKALVLNILCSGK
ref|YP_430569.1|      ----MRFFRAGPAALISRLCDVLKIAEIIDAVVDWDPAQCHLSPGNRVKALIINLLVDRE
RAAC03682             MFGPVRSYVMGPAPVLARLIDELKWVEIIDEFVPRP--DSKLSVGLRTKALLVNIGTNRE
                            .:*  *  ::   : *:  .*     .::* * * ***::*:     . :

ref|ZP_01695687.1|    PLYKVHEFYQNLDSEMLF--DTSVSPDQLNDDALGRALDYLYEA-EAWKVYSTLALKTLK
ref|ZP_01695982.1|    PLYKVHEFYQNLDSEMLF--DTSVSPDQLNDDALGRALDYLYEA-EAWKVYSTLALKALK
ref|ZP_01695971.1|    PLYKVHEFYQNLDSEMLF--DTSISPDQLNDDALGRALDYLYKA-EAWKVYSTLALKALK
ref|ZP_01695655.1|    PLYKVHEFYQNLDSEMLF--DTSISPDQLNDDALGRALDYLYKA-EAWKVYSTLALKALK
ref|YP_430569.1|      ALYHVERFYENQDLEVLFGAEQQVRPEDFNDDALGRALDKLFTSGQLKKLFSSIALTAAA
RAAC03682             ALYRVEEFYAQRDVEVLLG--SGVSADDLHDDALARALDALYDA-GLEALYARIALHTLR
                      .**:*..**  : * *:*:     : .:::****.**** *: :     ::: :** :

ref|ZP_01695687.1|    KLNLP-----IGILHNDTTSISVYGEYKQPKEDGLQITYGYSKAHRPDLKQIVLGMGVTP
ref|ZP_01695982.1|    KLNLP-----IGILHNDTTSISVYGEYKQPKEDGLQITYGYSKAHRPDLKQIVLGMGVTP
ref|ZP_01695971.1|    KLNLP-----IGVLIHNDTTSISVYGEYKQPKEDGLQITYGYSKAHRPDLKQIVLGMGVTP
ref|ZP_01695655.1|    KLNLP-----IGVLHNDTTSISVYGEYKQPKEDGLQITYGYSKAHRPDLKQIVLGMGVTP
ref|YP_430569.1|      THNVS-----IAGIHVDTTSISVQGAYDG--EGDLDITFGFSKDHRPDLKQFLIGLTVNR
RAAC03682             RLRVLSDSNELIPIHADTTSLSMTGEYLD--QTAFRIDRGFSKDHRPDLKQIVFGL-CTV
                       .:     :* ****:*:  * *    :  : * *:** ******:::*:  .

ref|ZP_01695687.1|    ERIPILAKVENGNTSDKSWNVEFIQKMRKILSHEDWKNLIYQADSALITTENLAEIQQQN
ref|ZP_01695982.1|    ERIPILAKVENGNTSDKSWNVEFIQKMRKILSHEDWKNLIYQADSALITTENLAEIQQQN
ref|ZP_01695971.1|    ERIPILAKVENGNTSDKSWNVEFIQKMRKILSHEDWKNLIYQADSALITTENLAEIQQQN
ref|ZP_01695655.1|    ERIPILAKVENGNTSDKSWNVEFIQKMRKILSHEDWKNLIYQADSALITTENLAEIQQQN
ref|YP_430569.1|      DGLPILAQSLDGNSSDKSWYPQVIEELVQTFKPEKLKEVIFVADCALVTKDNLALLVQEE
RAAC03682             HGLGLCANVNPGNLDDHTWNFENIQQLLSQLDEETRKRSVYVADAALVTKDNLELLAEED
                       . :  *:    **  .:*    : *::   .:.  *  *. ::  **.**:*.:**   : :::

ref|ZP_01695687.1|    ------LSFISRLPDTFGLSTELKKEAWLLNN-WERVGSLSNKKDAAIYQIQAFERQIQNL
ref|ZP_01695982.1|    ------LSFISRLPDTFGLSTELKKEAWLLNN-WERVGSLSNKKDAAIYQIQAFERQIQNL
ref|ZP_01695971.1|    ------LSFISRLPDTFGLSTELKKEAWLLNN-WERVGSLSNKKDAAIYQIQAFERQIQNL
ref|ZP_01695655.1|    ------LSFISRLPDTFGLSTELKKEAWLLNN-WERVGSLSNKKDAAIYQIQAFERQIQNL
ref|YP_430569.1|      GNKPALQFISLLPENFGLNKEIKAEAFRTGT-WQEIGKLSPKKDAACYKSQSFVREIDGR
RAAC03682             ------FHFISRLPGTYKLSEDLKRAAWEKENSWKEVGRLAEAEDSAHYRIQAFRRTLYGR
                      :  ***   ** .: *. ::* *:     . *:..:*  *:   :*:* *: *:* * :  .

ref|ZP_01695687.1|    PYRFLVVHSNNLDQRKEKTLNRAIEKEEIQLKKEIEKLSKVIFHCKEDALEAIQSFKKKQ
ref|ZP_01695982.1|    PYRFLVVHSNNLDQRKEKTLNRAIEKEEIQLKKEIEKLSKVIFHCKEDALEAIQSFKKKQ
ref|ZP_01695971.1|    PYRFLVVHSNNLDQRKEKTLNRAIEKEEIKLKKEIEKLSKVIFHCKEDALEAIQSFKKKQ
ref|ZP_01695655.1|    PYRFLVVHSNNLDQRKEKTLNRAIEKEEIQLKKEIEKLSKVIFHCKEDALEAIQSFKKKQ
ref|YP_430569.1|      DYRLIVVHSTTLDKRKENSLLKKWAKQREVLEKAAKDLSRRPFACKADARKAIELFLREY
RAAC03682             TYRFVVVRSSSLDTRKERKLKEVLKREKAALEKAAKAMSQNVYSCEQDAQMAMQTFMHEH
                      **::**:*:..** ***.:*  .   ::.   *:*  : :*:    *: ** *:: *  ::

ref|ZP_01695687.1|    KASYFCYKLNVQMSDQPIKRKKRGRPKKDEQTK-REQIYQIQLESFEKDHDFIENKKKML
ref|ZP_01695982.1|    KASYFCYKLNVQMSDQPIKRKKRGRPKKDEQTK-REQIYQIQLESFEKDHDFIENKKKML
ref|ZP_01695971.1|    KASYFCYKLNVQMSDQPIKRKKRGRPKKDEQTK-REQIYQIQLESFEKDHDFIENKKRML
ref|ZP_01695655.1|    KASYFCYKLNVQMSDQPIKRKKRGRPKKDEQTK-REQIYQIQLESFEKDHDFIENKKKML
ref|YP_430569.1|      R-----------------------------------------------------------
RAAC03682             RATLHPISARICAEQVQAKRARRGRPRKDDPPPVHTQYRVEVAILPPSEERVQQWREKE
                                                                                 :

ref|ZP_01695687.1|    STFVLITNKLDEETLSNQEVLRVYKGQSAAETRFRLIKDSQMIDAIYLKTPERVEALGIV
ref|ZP_01695982.1|    STFVLITNKLDEETLSNQEVLRVYKGQSAAETRFRLIKDSQMIDAIYLKTPERVEALGIV
ref|ZP_01695971.1|    STFVLITNKLDEETLSNQEVLRVYKGQSAVETRFRLIKDSQMIDAIYLKTPERVEALGIV
ref|ZP_01695655.1|    STFVLITNKLDEETLSNQEVLRVYKGQSAAETRFRLIKDSQMIDAIYLKTPERVEALGIV
ref|YP_430569.1|      ------------------------------------------------------------
RAAC03682             ATFVLITDIRDDQRVSDEQILRLYKEQHEVEARFRYLKSPYHVGPIYLHKPTRVKAFGFV
``` continued →

FIG. 104 continued

```
ref|ZP_01695687.1|    YVMALLIYGILEYRVRKELKEKNLSLILKGKRKLYQPTGQALLEQLEDITVILINQNQQK
ref|ZP_01695982.1|    YVMALLIYGILEYRVRKELKEKNLSLILKGKRKLSQPTGQALLEQLEDITVILINQNQQK
ref|ZP_01695971.1|    YVMALLIYGILEYRVRKELKEKNLSLILKGKRKLYQPTGQALLEQLEDITVILINQNRQK
ref|ZP_01695655.1|    YVMALLIYGILEYRVRKELKEKNLSLILKGKRKLYQPTGQALLEQLEDITVILINQNRQK
ref|YP_430569.1|      ------------------------------------------------------------
RAAC03682             MLLSLLLYSVLEYLIREKMKRETEPLMLPGNRKSFRPTGLAILEMLDGVTTVHRQVGDTW ref|ZP_01695687.1|    IRLLPDNIDSQAKKIIELCGYDLSIY-------
ref|ZP_01695982.1|    IRLLPDNIDSQAKKIIELCGYDLSIY-------
ref|ZP_01695971.1|    LRLLPDNIDSQAKKIIELCGYDLSIY-------
ref|ZP_01695655.1|    LRLLPDNIDSQAKKIIELCGYDLSIY-------
ref|YP_430569.1|      ---------------------------------
RAAC03682             QRVPATPHNPQIMRVLKLLNMDLSIYTEAQKTA
```

FIG. 105

```
ref|ZP_01695687.1|         ---------VGPSQLLSKLCDEIELEKTINDLVKWDSVRCHISPGTRIKALVLNILCSGK
ref|ZP_01695982.1|         ---------VGPSQLLSKLCDEIELEKTINDLVKWDSVRCHISPGTRIKALVLNILCSGK
ref|ZP_01695971.1|         ---------VGPSQLLSKLCDEIELEKTINNLVKWDSVRCHISPGTRIKALVLNILCSGK
ref|ZP_01695655.1|         -------------PQSCKLCDEIELEKTINNLVKWDSVRCHISPGTRIKALVLNILCSGK
ref|YP_430569.1|           ----MRFFRAGPAALISRLCDVLKIAEIIDAVVDWDPAQCHLSPGNRVKALIINLLVDRE
RAAC03770                  MFGPVRSYVMGPAPVLARLIDELKWVEIIDEFVPRP--DSKLSVGLRTKALLVNIGTNRE
                               .:* *  ::  : *:  .*       .::* * * ***::*:  . :

ref|ZP_01695687.1|         PLYKVHEFYQNLDSEMLF--DTSVSPDQLNDDALGRALDYLYEA-EAWKVYSTLALKTLK
ref|ZP_01695982.1|         PLYKVHEFYQNLDSEMLF--DTSVSPDQLNDDALGRALDYLYEA-EAWKVYSTLALKALK
ref|ZP_01695971.1|         PLYKVHEFYQNLDSEMLF--DTSISPDQLNDDALGRALDYLYKA-EAWKVYSTLALKALK
ref|ZP_01695655.1|         PLYKVHEFYQNLDSEMLF--DTSISPDQLNDDALGRALDYLYKA-EAWKVYSTLALKALK
ref|YP_430569.1|           ALYHVERFYENQDLEVLFGAEQQVRPEDFNDDALGRADLKLFTSGQLKKLFSSIALTAAA
RAAC03770                  ALYRVEEFYAQRDVEVLLG--SGVSADDLHDDALARALDALYDA-GLEALYARIALHTLR
                            .**:*..**  : * *:*:      :  .::::****.**** *: :   ::: :** :

ref|ZP_01695687.1|         KLNLP-----IGILHNDTTSISVYGEYKQPKEDGLQITYGYSKAHRPDLKQIVLGMGVTP
ref|ZP_01695982.1|         KLNLP-----IGILHNDTTSISVYGEYKQPKEDGLQITYGYSKAHRPDLKQIVLGMGVTP
ref|ZP_01695971.1|         KLNLP-----IGVLHNDTTSISVYGEYKQPKEDGLQITYGYSKAHRPDLKQIVLGMGVTP
ref|ZP_01695655.1|         KLNLP-----IGVLHNDTTSISVYGEYKQPKEDGLQITYGYSKAHRPDLKQIVLGMGVTP
ref|YP_430569.1|           THNVS-----IAGIHVDTTSISVQGAYDG--EGDLDITFGFSKDHRPDLKQFLIGLTVNR
RAAC03770                  RLRVLSDSNELIPIHADTTSLSMTGEYLD--QTAFRIDRGFSKDHRPDLKQIVFGL-CTV
                            .:      :  :* ****:*: * *      *  *:** ******:::*:   .

ref|ZP_01695687.1|         ERIPILAKVENGNTSDKSWNVEFIQKMRKILSHEDWKNLIYQADSALITTENLAEIQQQN
ref|ZP_01695982.1|         ERIPILAKVENGNTSDKSWNVEFIQKMRKILSHEDWKNLIYQADSALITTENLAEIQQQN
ref|ZP_01695971.1|         ERIPILAKVENGNTSDKSWNVEFIQKMRKILSHEDWKNLIYQADSALITTENLAEIQQQN
ref|ZP_01695655.1|         ERIPILAKVENGNTSDKSWNVEFIQKMRKILSHEDWKNLIYQADSALITTENLAEIQQQN
ref|YP_430569.1|           DGLPILAQSLDGNSSDKSWYPQVIEELVQTFKPEKLKEVIFVADCALVTKDNLALLVQEE
RAAC03770                  HGLGLCANVNPGNLDDHTWNFENIQQLLSQLDEETRKRSVYVADAALVTKDNLELLAEED
                            . : :*:    **  .*::*   : *::: . :  * *. :: **.**:*.**   : :::

ref|ZP_01695687.1|         -----LSFISRLPDTFGLSTELKKEAWLLNN-WERVGSLSNKKDAAIYQIQAFERQIQNL
ref|ZP_01695982.1|         -----LSFISRLPDTFGLSTELKKEAWLLNN-WERVGSLSNKKDAAIYQIQAFERQIQNL
ref|ZP_01695971.1|         -----LSFISRLPDTFGLSTELKKEAWLLNN-WERVGSLSNKKDAAIYQIQAFERQIQNL
ref|ZP_01695655.1|         -----LSFISRLPDTFGLSTELKKEAWLLNN-WERVGSLSNKKDAAIYQIQAFERQIQNL
ref|YP_430569.1|           GNKPALQFISLLPENFGLNKEIKAEAFRTGT-WQEIGKLSPKKDAACYKSQSFVREIDGR
RAAC03770                  -----FHFISRLPGTYKLSEDLKRAAWEKENSWKEVGRLAEAEDSAHYRIQAFRRTLYGR
                                : *** **  .: *:  ::*  *: .  *:. :* *::*:* *: *:* * :  .

ref|ZP_01695687.1|         PYRFLVVHSNNLDQRKEKTLNRAIEKEEIQLKKEIEKLSKVIFHCKEDALEAIQSFKKKQ
ref|ZP_01695982.1|         PYRFLVVHSNNLDQRKEKTLNRAIEKEEIQLKKEIEKLSKVIFHCKEDALEAIQSFKKKQ
ref|ZP_01695971.1|         PYRFLVVHSNNLDQRKEKTLNRAIEKEEIKLKKEIEKLSKVIFHCKEDALEAIQSFKKKQ
ref|ZP_01695655.1|         PYRFLVVHSNNLDQRKEKTLNRAIEKEEIQLKKEIEKLSKVIFHCKEDALEAIQSFKKKQ
ref|YP_430569.1|           DYRLIVVHSTTLDKRKENSLLKKWAKQREVLEKAAKDLSRRPFACKADARKAIELFLREY
RAAC03770                  TYRFVVVRSSSLDTRKERKLKEVLKREKAALEKAAKAMSQNVYSCEQDAQMAMQTFMHEH
                            **::**:*..**  ***..*  .    ::. *:*   : :*:   *: ** *::  * ::

ref|ZP_01695687.1|         KASYFCYKLNVQMSDQPIKRKKKRGRPKKDEQTK-REQIYQIQLESFEKDHDFIENKKKML
ref|ZP_01695982.1|         KASYFCYKLNVQMSDQPIKRKKKRGRPKKDEQTK-REQIYQIQLESFEKDHDFIENKKKML
ref|ZP_01695971.1|         KASYFCYKLNVQMSDQPIKRKKKRGRPKKDEQTK-REQIYQIQLESFEKDHDFIENKKRML
ref|ZP_01695655.1|         KASYFCYKLNVQMSDQPIKRKKKRGRPKKDEQTK-REQIYQIQLESFEKDHDFIENKKKML
ref|YP_430569.1|           R-----------------------------------------------------------
RAAC03770                  RATLHPISARICAEQVQAKRARRGRPRKDDPPPPVHTQYRVEVAILPPSEERVQQWREKE
                                                                                       :

ref|ZP_01695687.1|         STFVLITNKLDEETLSNQEVLRVYKGQSAAETRFRLIKDSQMIDAIYLKTPERVEALGIV
ref|ZP_01695982.1|         STFVLITNKLDEETLSNQEVLRVYKGQSAAETRFRLIKDSQMIDAIYLKTPERVEALGIV
ref|ZP_01695971.1|         STFVLITNKLDEETLSNQEVLRVYKGQSAVETRFRLIKDSQMIDAIYLKTPERVEALGIV
ref|ZP_01695655.1|         STFVLITNKLDEETLSNQEVLRVYKGQSAAETRFRLIKDSQMIDAIYLKTPERVEALGIV
ref|YP_430569.1|           ------------------------------------------------------------
RAAC03770                  ATFVLITDIRDDQRVSDEQILRLYKEQHEVEARFRYLKSPYHVGPIYLHKPTRVKAFGFV
``` continued →

FIG. 105 continued

```
ref|ZP_01695687.1|      YVMALLIYGILEYRVRKELKEKNLSLILKGKRKLYQPTGQALLEQLEDITVILINQNQQK
ref|ZP_01695982.1|      YVMALLIYGILEYRVRKELKEKNLSLILKGKRKLSQPTGQALLEQLEDITVILINQNQQK
ref|ZP_01695971.1|      YVMALLIYGILEYRVRKELKEKNLSLILKGKRKLYQPTGQALLEQLEDITVILINQNRQK
ref|ZP_01695655.1|      YVMALLIYGILEYRVRKELKEKNLSLILKGKRKLYQPTGQALLEQLEDITVILINQNRQK
ref|YP_430569.1|        ------------------------------------------------------------
RAAC03770               MLLSLLLYSVLEYLIREKMKRETEPLMLPGNRKSFRPTGLAILEMLDGVTTVHMQVGDTW ref|ZP_01695687.1|      IRLLPDNIDSQAKKIIELCGYDLSIY-------
ref|ZP_01695982.1|      IRLLPDNIDSQAKKIIELCGYDLSIY-------
ref|ZP_01695971.1|      LRLLPDNIDSQAKKIIELCGYDLSIY-------
ref|ZP_01695655.1|      LRLLPDNIDSQAKKIIELCGYDLSIY-------
ref|YP_430569.1|        ---------------------------------
RAAC03770               QRVPATPHNPQIMRVLKLLNMDLSIYTEAQKTA
```

FIG. 106

```
ref|YP_001666203.1|     ------------------------------------------------------------
ref|YP_001512589.1|     ------------------------------------------------------------
ref|NP_842969.1|        EINTEGRASEFAMILYBACILLUSANTHRACISSTRAREFZPPRPHAGELAMBDABASIT
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        E-SPECIFICRECMBINASEPHAGEINTEGRASEFAMILYBACILLUSANTHRACISSTR
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        AREFZPPRPHAGELAMBDABASITE-SPECIFICRECMBINASEPHAGEINTEGRASEFA
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        MILYBACILLUSANTHRACISSTRAREFZPPRPHAGELAMBDABASITE-SPECIFICRE
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        CMBINASEPHAGEINTEGRASEFAMILYPRTEINBACILLUSANTHRACISTSIANKVSK
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        II-IGBAAPPRPHAGELAMBDABASITE-SPECIFICRECMBINASEPHAGEINTEGRAS
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        EFAMILYBACILLUSANTHRACISSTRAMESGBAATPRPHAGELAMBDABASITE-SPEC
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        IFICRECMBINASEPHAGEINTEGRASEFAMILYBACILLUSANTHRACISSTRAMESAN
ref|ZP_02596019.1|      ------------------------------------------------------------
ref|YP_430640.1|        ------------------------------------------------------------
RAAC02738               ------------------------------------------------------------
``` continued →

FIG. 106 continued

```
ref|YP_001666203.1|     ------------------------------------------------------------
ref|YP_001512589.1|     ------------------------------------------------------------
ref|NP_842969.1|        CESTRGBAATPRPHAGELAMBDABASITE-SPECIFICRECMBINASEPHAGEINTEGRA
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        SEFAMILYBACILLUSANTHRACISSTRSTERNEGBEDRPRPHAGELAMBDABASITE-S
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        PECIFICRECMBINASEPHAGEINTEGRASEFAMILYBACILLUSANTHRACISSTRAGB
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        EDRPRPHAGELAMBDABASITE-SPECIFICRECMBINASEPHAGEINTEGRASEFAMIL
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        YBACILLUSANTHRACISSTRAGBEDRPRPHAGELAMBDABASITE-SPECIFICRECMB
ref|ZP_02596019.1|      ------------------------------------------------------------
ref|YP_430640.1|        ------------------------------------------------------------
RAAC02738               ------------------------------------------------------------ ref|YP_001666203.1|     ------------------------------------------------------------
ref|YP_001512589.1|     ------------------------------------------------------------
ref|NP_842969.1|        INASEPHAGEINTEGRASEFAMILYBACILLUSANTHRACISSTRASCRESIGNIFICAN
ref|ZP_02596019.1|      ------------------------------------------------------------
ref|YP_430640.1|        ------------------------------------------------------------
RAAC02738               ------------------------------------------------------------ ref|YP_001666203.1|     ----------------------------YSIVVDIGRDEN-GKRKQKWISGFKTKKEAEK
ref|YP_001512589.1|     -----------------------KKNHKWYIVVDS-IDEN-GKRKRKWISGFNTQKFAEK
ref|NP_842969.1|        CEE-IDENTITIESPSITIVESGAPSEKWSFTIDIGKDPITGKRKQKTASGFKTKKEAER
ref|ZP_02596019.1|      ------------------TVKKDDKTKTWYFVLTHGKKED-GKPRQFKKRGFKTKQEALK
ref|YP_430640.1|        ----------------------------WTAQITVGIDHE-GKQRRLTLYG-KSKKEVLE
RAAC02738               ---------MTTGRVFSYTTKSNEKKYGYTITITPADPQT-GRYPQVTRKGFKSERAAKS
                                                    :   :        *:  :    * :::: .

ref|YP_001666203.1|     ALAEIIAKIEKNELELTN-LTLGQFLNKWYETHCELKLAPKTLKSYKELIELYFKPYLGD
ref|YP_001512589.1|     KLPEILQQLNTNTFVDTNNITLRDYMQLWLEDYAKPNVAPTTYDKYTYAAN-KVSEILGN
ref|NP_842969.1|        ACNELIHQFNTGSLVDDKNFTLSEYLQEWLENTAKQRVRETTFTNYKRAINSRIIPVLGS
ref|ZP_02596019.1|      ALHELEHSLMTGTYIAPTKMLYGEYLLNQWLEDKQTKVKKQTLQTYRWLVEKHIIPAIGN
ref|YP_430640.1|        KLTQALYQQQNGGFIEPSKITVEQWLNRWLTDYAKPHLRQSTWESYETVLRLHVIPTLGS
RAAC02738               AMMEHLRSLEDTPVVHAKSFTLHEWASRWFADKS-SSLRPWTRRTYHHVLQAYILPELGK
                           :   .         . :   ::            :   *  .*    .  .   :*.
``` continued →

FIG. 106 continued

```
ref|YP_001666203.1|    IELTKLKPVMIQNYYNKLK-ELGLSDTTINYHHRVLKSALKKAVVWQLISKNPCDYVEPP
ref|YP_001512589.1|    MKLQQIKPIHIQQLVNKLN-NSDVTPSTVLSYYRVLNTAINQAVKWQFIQYNPCVAVTPP
ref|NP_842969.1|       HKLKDLKPLHGQRFVKSLI-DEGLSPAYIEYIFIVLKGSLEDAVRWELLFKNPFQHVEIP
ref|ZP_02596019.1|     MELTQLTPMAIQKLYNQLTKEKALSDENIQKVHTLINDSLKKAERWGITSKNPASLVDRP
ref|YP_430640.1|       IPLKKLQPADIQRLYASKL-ESGLSPTRVRYIHVVLHEAMSQARESGLLLQNPTEAAKPP
RAAC02738              MPISKIEARHIQALYRKLS--NRLKPVTVHRIHRVLKTCLLAAVKAGYLDKSPFLNVEPP
                        :  .:  .       *    .:.   :   .:::  .: *    :   .*   .   * ref|YP_001666203.1|    KKNKNEITVWSINDVKKAKE--IFKDTPIYLHFMLALYTGMRIGEICGLKWEDIDFNNKT
ref|YP_001512589.1|    RNTKNKMMILDQDEIQILLD--KSKDHVLYPVIVLALLCGLRRGEILGLQWENIDFFSGV
ref|NP_842969.1|       RPRKVVNSTWSIEETKKFLNRTKFENVIYYHLFLLALNTGMRRGEILGLKWKNFDLNEGK
ref|ZP_02596019.1|     KAEKKEIKVWDVKEVQTFLK-HAQSHSRYYIAFLLALTTGMRQGEILGLRWRDVDFETGC
ref|YP_430640.1|       RHPKKKVQPLNPEQVKRFLE--TAKQDPLYPAFLLALGTGLRRGEILGLRWQDLDLQKGI
RAAC02738              EHKTPPKPVLSVNDAFRLLAWLREHRPTSYMAAFLAIHTGMRMGEIAGLQWRDIDLDTGV
                       .  .       . .:        *    .**:    *:* *** **:*.:.*:

ref|YP_001666203.1|    CTVKRQYQQVGGKEIIK-EPKSETSIRVIPLHSDVIEVLKEEKKKQLQNRMLLGEKYNKK
ref|YP_001512589.1|    IHLENNLVMANNESILK-ETKTSTGRRAVDISSNVVEVLKKVKKQKMSYKLLYGSSYHDS
ref|NP_842969.1|       ISVTETLIYDENGFRFT-EPKTHGSKRLISIDQNLCKEFKSYKAKQNEFKLLFGQSYEDN
ref|ZP_02596019.1|     IRITQTLSS-DGKEILP-YTKTKSGSRTVDLPEETIIQLKKHRKLIESEKLEAGSEVYNN
ref|YP_430640.1|       LQVRQSLIRTREGLKFE-EPKTEKSRRQIPLPPSVVAALKRHKAWVNQNKLILGPDYEDH
RAAC02738              IQLERTRYRPKGGQDFLGPPKTFGSRRRIVVTREVVDELRRWK--QSQQEIERESWTPES
                        :  .           :  .*:  . *  : :      ::  :    ..:        .

ref|YP_001666203.1|    YEGYISVWEDGRMKTPEYVSKKFSKILKAYPELPQIRFHDLRHSCASFLVQAGVPMKVVS
ref|YP_001512589.1|    --NFVCTWEDGRPFRPDYIPKAFAKILVS-ANLPKIRFHDLRHTHASILLKSGIHPKVVQ
ref|NP_842969.1|       --DLVFAKETGQPILPRTMTTTFNQFIKK-ADVPQIRFHDLRHTHATILLKLGINPKIVS
ref|ZP_02596019.1|     -WDLVVCTELGTPTNKSNIRRSFNSIIKK-AKIPKIRFHDMRHTHATLLLLQGVNPKIVS
ref|YP_430640.1|       --DLVFPVENGRPRDPKGFAEYFNRLLDK-AGLPHIRLHDLRHTHATLLLLEGVHPKVVQ
RAAC02738              ---FVVRLPNSAPPSPASFNNAIQNARKE-LGLPPVSFHGLRHTHATWLLESGVDLKIVS
                             :        .   :     :   *  : :*.:** *: *:   *: *:*.

ref|YP_001666203.1|    EILGHSQIGITMDLYSHVLLDSKKEAIKKLEEYLQ--------------
ref|YP_001512589.1|    ERLGHSSISITLDTYSHLVPSLQKSAAEKMATM----------------
ref|NP_842969.1|       ERLGHSSIKTTLDTYSHVTIDMQESAVLKLSEALKS-------------
ref|ZP_02596019.1|     ERLGHADVRITLDTYSHLLPSMQKDTAIKFGEML---------------
ref|YP_430640.1|       ERLGHSTVSITLDIYSHILPGLQEKAAERIDGLLQPK------------
RAAC02738              ERLGHSSITITADIYAHVTDALQREAIEKLQRMMRSRRTNNSGSDDEEDL
                       * ***:  :   * * *:*:         :..:   ::
```

FIG. 107

```
ref|YP_001114460.1|    ------------------------------------------------------------
ref|YP_001111555.1|    TRANSPSASEISFAMILYPRTEINDESULFTMACULUMREDUCENSMI-GBABTRANSPS
ref|YP_001112147.1|    ------------------------------------------------------------
ref|YP_001111684.1|    ------------------------------------------------------------
ref|YP_001113963.1|    ------------------------------------------------------------
RAAC02514              ------------------------------------------------------------ ref|YP_001114460.1|    ------------------------------------------------------------
ref|YP_001111555.1|    ASEISFAMILYPRTEINDESULFTMACULUMREDUCENSMI-GBABTRANSPSASEISFA
ref|YP_001112147.1|    ------------------------------------------------------------
ref|YP_001111684.1|    ------------------------------------------------------------
ref|YP_001113963.1|    ------------------------------------------------------------
RAAC02514              ------------------------------------------------------------ ref|YP_001114460.1|    ------------------------------------------------------------
ref|YP_001111555.1|    MILYPRTEINDESULFTMACULUMREDUCENSMI-GBABTRANSPSASEISFAMILYPRT
ref|YP_001112147.1|    ------------------------------------------------------------
ref|YP_001111684.1|    ------------------------------------------------------------
ref|YP_001113963.1|    ------------------------------------------------------------
RAAC02514              ------------------------------------------------------------ ref|YP_001114460.1|    ------------------------------------------------------------
ref|YP_001111555.1|    EINDESULFTMACULUMREDUCENSMI-SCRESIGNIFICANCEE-IDENTITIESPSIT
ref|YP_001112147.1|    ------------------------------------------------------------
ref|YP_001111684.1|    ------------------------------------------------------------
ref|YP_001113963.1|    ------------------------------------------------------------
RAAC02514              ------------------------------------------------------------ ref|YP_001114460.1|    --------VSRTYKGTDGYAPIFAYLAKEGYCVNTELRQGSEHCQKNTSEFVAESIRYAR
ref|YP_001111555.1|    IVESGAPSVSRTYKGTDGYAPIFAYLAKEGYCVNTELRQGSEHCQKNTSEFVAESIRYAR
ref|YP_001112147.1|    --------VSRTYKGTDGYAPIFAYLAKEGYCVNTELRQGSEHCQKNTSEFVAESIRYAR
ref|YP_001111684.1|    --------VSRTYKGTDGYAPIFAYLAKEGYCVNTELRQGSEHCQKNTSEFVAESIRYAR
ref|YP_001113963.1|    --------VSRTYKGTDGYAPIFAYLAKEGYCVNTELRQGSEHCQKNTSEFVAESIRYAR
RAAC02514              --------MSRTYKGHDGYAPIFAYLGQEGYVVNVQLREGSTHVQKGTSTFLRESIQYAR
                               :**** ****.:*  .::** * . *: *:* ref|YP_001114460.1|    KITQLPLLLRMDSGNDSASNIEICLNDDTKADFIIKRNLRKETPEGWLLLAKNNKDIYCQ
ref|YP_001111555.1|    KITQLPLLLRMDSGNDSASNIEICLNDDTKADFIIKRNLRKETPEGWLLLAKNNKDIYCQ
ref|YP_001112147.1|    KITQLPLLLRMDSGNDSASNIEICLNDDTKADFIIKRNLRKETPEGWLLLAKNNKDIYCQ
ref|YP_001111684.1|    KITQLPLLLRMDSGNDSASNIEICLNDDTKADFIIKRNLRKETPEGWLLLAKNNKDIYCQ
ref|YP_001113963.1|    KITQLPLLLRMDSGNDSASNIEICLNDDTKADFIIKRNLRKETPEGWLLLAKNNKDIYCQ
RAAC02514              QVTELPLLVRLDAGNDSAENIAVCRSQDSRAEFIIKRNLRKESPAAWLEIAQRHG--TCH
                       ::*:****:*:*:****.** :* ..:*::*:***********:* .** :*:.:   *:

ref|YP_001114460.1|    E-REGKKVYYGSMMKYKKELKREIRVVYKITERTFGKDGQIFLVPQVEAETYWTSLPDPP
ref|YP_001111555.1|    E-REGKKVYYGSMMKYKKELKREIRVVYKITERTFGKDGQIFLVPQVEAETYWTSLPDPP
ref|YP_001112147.1|    E-REGKKVYYGSMMKYKKELKREIRVVYKITERTFGKDGQIFLVPQVEAETYWTSLPDPP
ref|YP_001111684.1|    E-REGKKVYYGSMMKYKKELKREIRVVYKITERTFGKDGQIFLVPQVEAETYWTSLPDPP
ref|YP_001113963.1|    E-REGKKVYYGSMMKYKKELKREIRVVYKITERTFGKDGQIFLVPQVEAETYWTSLPDPP
RAAC02514              EPRPGKKVYHGSLMCPVKGVSEPVRMVFEVIERTTTADGQILLVPDIEVSAYWTSLPDDP
                       * * ***::*      * :..  :*:*::: *    :*:*...:******* * ref|YP_001114460.1|    HVIERLYHEHGTSEQFHSELKTDLDLERLPSGKFDTNNLILHFGVVAYNLLRMIGQSTTR
ref|YP_001111555.1|    HVIERLYHEHGTSEQFHSELKTDLDLERLPSGKFDTNNLILHFGVVAYNLLRMIGQSTTR
ref|YP_001112147.1|    HVIERLYHEHGTSEQFHSELKTDLDLERLPSGKFDTNNLILHFGVVAYNLLRMIGQSTTR
ref|YP_001111684.1|    HVIERLYHEHGTSEQFHSELKTDLDLERLPSGKFDTNNLILHFGVVAYNLLRMIGQSTTR
ref|YP_001113963.1|    HVIERLYHEHGTSEQFHSELKTDLDLERLPSGKFDTNNLILHFGVVAYNLLRMIGQSTTR
RAAC02514              AVIIRLYHDHAVMEQFHSEIKTDLDAERLPSGKFATNNLVLHFVCVAYNLLRVIGQESLK
                       ** ****:*..  *****:****** *******.****:***   *******:***:: :

ref|YP_001114460.1|    MQHVPLRKQAERRRIRTVIQ-
ref|YP_001111555.1|    MQHVPLRKQAERRRIRTVIQ-
ref|YP_001112147.1|    MQHVPLRKQAERRRIRTVIQ-
ref|YP_001111684.1|    MQHVPLRKQAERRRIRTVIQ-
ref|YP_001113963.1|    MQHVPLRKQAERRRIRTVIQ-
RAAC02514              RNDAPLRKKAERRRIRTVIRT
                       :..  ****:*********:
```

FIG. 108

```
ref|YP_001111555.1|    TRANSPSASEISFAMILYPRTEINDESULFTMACULUMREDUCENSMI-GBABTRANSPS
ref|YP_001114460.1|    ------------------------------------------------------------
ref|YP_001111684.1|    ------------------------------------------------------------
ref|YP_001113963.1|    ------------------------------------------------------------
dbj|BAD18231.1|        ------------------------------------------------------------
RAAC02515              ------------------------------------------------------------ ref|YP_001111555.1|    ASEISFAMILYPRTEINDESULFTMACULUMREDUCENSMI-GBABTRANSPSASEISFA
ref|YP_001114460.1|    ------------------------------------------------------------
ref|YP_001111684.1|    ------------------------------------------------------------
ref|YP_001113963.1|    ------------------------------------------------------------
dbj|BAD18231.1|        ------------------------------------------------------------
RAAC02515              ------------------------------------------------------------ ref|YP_001111555.1|    MILYPRTEINDESULFTMACULUMREDUCENSMI-GBABTRANSPSASEISFAMILYPRT
ref|YP_001114460.1|    ------------------------------------------------------------
ref|YP_001111684.1|    ------------------------------------------------------------
ref|YP_001113963.1|    ------------------------------------------------------------
dbj|BAD18231.1|        ------------------------------------------------------------
RAAC02515              ------------------------------------------------------------ ref|YP_001111555.1|    EINDESULFTMACULUMREDUCENSMI-SCRESIGNIFICANCEE-IDENTITIESPSIT
ref|YP_001114460.1|    ------------------------------------------------------------
ref|YP_001111684.1|    ------------------------------------------------------------
ref|YP_001113963.1|    ------------------------------------------------------------
dbj|BAD18231.1|        ------------------------------------------------------------
RAAC02515              ------------------------------------------------------------ ref|YP_001111555.1|    IVESGAPSFEIEQGDEELTTHSGLALIGALLTNTKIKTRLNNTMSAEQKK-PHISNGSVG
ref|YP_001114460.1|    --------FEIEQGDEELTTHSGLALIGALLTNTKIKTRLNNTMSAEQKK-PHISNGSVG
ref|YP_001111684.1|    --------FEIEQGDKELTTHSGLALIGALLTNTKIKTRLNNTMSAEQKK-PHISNGSVG
ref|YP_001113963.1|    --------FEIEQGDEELTTHSGLALIGALLTNTKIKTRLNNTMSAEQKK-PHISNGSVG
dbj|BAD18231.1|        ------VKFILENSDDTLTTHSGLGLIGLLLSKTKFHKRFSSLKVPEIKSSPKILNGDVT
RAAC02515              ------MRFIIEESDEVIVTHSGMTLVGVLLDKTRIGERLNHTRLPGMGK-PNISNRDVA
                             * :*:.*.  :.****: *:* ** :*::   *:.    .    .*:* * .* ref|YP_001111555.1|    IAYIGLLCQGKSDFDHIEPFREDNFFAISLNIKETPSSPTLRQRLDMVAKDKQWNNILLE
ref|YP_001114460.1|    IAYIGLLCQGKSDFDHIEPFREDNFFAISLNIKETPSSPTLRQRLDMVAKDKQW------
ref|YP_001111684.1|    IAYIGLLCQGKSDFDHIEPFREDNFFAISLNIKETPSSPTLRQRLDMVAKDKQWNNILLE
ref|YP_001113963.1|    IAYIGLLCQGKSDFDHIEPFREDNFFAISLNIKETPSSPTLRQRLDMVAKDKQW------
dbj|BAD18231.1|        TSYVGLLCQGKNDFDHIEQFRDDPFFYRALDIKLVPSSPTLRQRLDQIAKVTGW------
RAAC02515              YSYIGLLCQGKTDFDHIEAFRDDEFFTALQVDNVPSSPTLRQRLDMVAGKSGWESILRE
                       :*:*****.** :* **  :*::. .********** :*  .  * ref|YP_001111555.1|    ESAGLIKKTNAPLTPVYLGQ------
ref|YP_001114460.1|    --------------------------
ref|YP_001111684.1|    ESAGLIKKTNAPLTPVYLGLENRT--
ref|YP_001113963.1|    --------------------------
dbj|BAD18231.1|        --------------------------
RAAC02515              ESARLLRALDVTLHPIELGEPAERRT
```

FIG. 109

```
ref|YP_001212947.1|    ------------------------IKYCLSQWDKLEAFLQDGRLELDNNRSERSIK
ref|YP_431166.1|       ------------------------INYCLGQWDKLTAFLQDGRLELDNNRSERSIK
ref|YP_754943.1|       ------------------------ITYCLNQWDALNTFLLDGRLEIDNNRAERSIK
ref|YP_754865.1|       ANCEE-IDENTITIESPSITIVESGAPSITYCLNQWDCLNSFLLDGRLEIDNNRAERSIK
RAAC02530              ------------------------MSYCLKQWPKLVRYMEDGHLEIDNNRCERSLK
ref|YP_001318017.1|    ------------------------ISYSLKQWDKLAAFMKDGRIAIDNNLAERGIK
                                               :.*.* **   *   ::  ::  :*  **.:* ref|YP_001212947.1|    PFVIGRKNWLFANTPRGARASAIVYSIVETAKENGLNPFHYLSYLFEKLPNLDTKDENAL
ref|YP_431166.1|       PFVIGRKNWLFANTPRGAKASAITYSIIETAKDNGLNPFQYLIYLFERLPNLDLKDKDAL
ref|YP_754943.1|       PFVIGRKNFLFSNTPRGARGSAIIYSIIETAKENNLKPYDYLVYLFEQLPNVDTSDQTAV
ref|YP_754865.1|       PFVIGRKNWLFTNTPRGARGSAIIYSVIETAKENNLKPYNYMFYLFEQLPNVDTGDQAAI
RAAC02530              PFVIGRKNWLFANTPRGARASAIAYSIVETAKENGLNPFAYLEYLFEKLPNMDTDDKTAM
ref|YP_001318017.1|    PFVLGRKNYLFAKSPKGATASALCYSIIETAKANKLIPFQYLTYLFEQLPNLDIEDPEAL
                       ***:****:**:::*:** .**: **::****  * * *: *: ****:***:*  * *:

ref|YP_001212947.1|    DKLLPWSDSLPSVCRVNK
ref|YP_431166.1|       DQLLPWSASLP-------
ref|YP_754943.1|       DRLMPWSDTLPEGCR---
ref|YP_754865.1|       DRLLPWSDTLP-------
RAAC02530              AALLPWSETLPAHIRRRK
ref|YP_001318017.1|    DAMLPWAESLPNEVRHK-
                        ::**:  :**
```

FIG. 110

```
ref|YP_001036724.1|    TRANSPSASEMUTATRTYPECLSTRIDIUMTHERMCELLUMATCCGBABNTRANSPSASE
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    MUTATRTYPECLSTRIDIUMTHERMCELLUMATCCGBABNTRANSPSASEMUTATRTYPE
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    CLSTRIDIUMTHERMCELLUMATCCGBABNTRANSPSASEMUTATRTYPECLSTRIDIUM
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    THERMCELLUMATCCGBABNTRANSPSASEMUTATRTYPECLSTRIDIUMTHERMCELLU
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    MATCCGBABNTRANSPSASEMUTATRTYPECLSTRIDIUMTHERMCELLUMATCCGBABN
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    TRANSPSASEMUTATRTYPECLSTRIDIUMTHERMCELLUMATCCGBABNTRANSPSASE
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    MUTATRTYPECLSTRIDIUMTHERMCELLUMATCCSCRESIGNIFICANCEE-IDENTIT
ref|YP_001039064.1|    ------------------------------------------------------------
ref|YP_001039349.1|    ------------------------------------------------------------
RAAC02533              ------------------------------------------------------------
ref|YP_076118.1|       ------------------------------------------------------------
ref|YP_076073.1|       ------------------------------------------------------------ ref|YP_001036724.1|    IESPSITIVESGAPSLDEFVEEFKNRRLEGEYPYLWLDATFPKVREGGRVCSMALVIAVG
ref|YP_001039064.1|    ---------------LDEFVEEFKNRRLEGEYPYLWLDATFPKVREGGRVCSMALVIAVG
ref|YP_001039349.1|    ---------------LDEFVEEFKNRRLEGEYPYLWLDATFPKVREGGRVCSMALVIAVG
RAAC02533              ---------------MDETVQQFKERPLEREYPYVWLDATFPKVREGGRVQSMALVIAIG
ref|YP_076118.1|       ---------------LDEVVEAFRNRPLEGEYPYVWLDAKYEKVRENGRVSSMALVIAMG
ref|YP_076073.1|       ---------------LDEVVQAFRNRPLEGRYPYVWLDAKYVKVRENGRVSSMALVVAVG
                                      :**  *:  *::* **  .***:****.:  ****.*** *****:*:*
``` continued →

FIG. 110 continued

```
ref|YP_001036724.1|    VNQQGEREILGFDVGMSEDGAFWEEFLRRLVARGLKGVRLVISDAHEGLKAAIKKILTGS
ref|YP_001039064.1|    VNQQGEREILGFDVGMSEDGAFWEEFLRRLVARGLKGVRLVISDAHEGLKAAIKKILTGS
ref|YP_001039349.1|    VNQQGEREILGFDVGMSEDGAFWEEFLRRLVARGLKGVRLVISDAHEGLKAAIKKILTGS
RAAC02533              VSDTGEREVLGFDVGTSEDGAFWTDFLRDLKTRGLRGVRLVVSDAHAGLRQAIAEVLTGA
ref|YP_076118.1|       VREDGEREILGLDVGPSEDGAFWTAFLRQLVARGLKGVLLVISDNHVGLREAIRTVFSGA
ref|YP_076073.1|       VREDGDREILGLDVGPSEDGAFWTAFLRQLVARGLKGVLLAISDSHVGLQEAIRTVLSGA
                       * : *:**:**:*** *******  *** * :***:** *.:** * **: **   :::*:

ref|YP_001036724.1|    AWQRCRVHFMRNVLSQVPKHYQGMVSSIIRTIFAQNDQESAREQLRHVVDELKNRFPKAM
ref|YP_001039064.1|    AWQRCRVHFMRNVLSQVPKHYQGMVSSIIRTIFAQNDQESAREQLRHVVDELKNRFPKAM
ref|YP_001039349.1|    AWQRCRVHFMRNVLSQVPKHYQGMVSSIIRTIFAQNDQESAREQLRHVVDELKKRFPKAM
RAAC02533              TWQRCKVHAIRNVLSQVPKKEQPMMASILRTIFTQPTQDAAREQLRRVVGEFRRRYPKAM
ref|YP_076118.1|       SWQRCRVHFMRNLLGYVPKNLQSMVSAAVRTIFAQPDQQAAKSQLAVVVENLRKQFPRAA
ref|YP_076073.1|       SWQRCRVHFMRNLLSYVPKHWQSMVAAAVRTIFAQPDQQAARRQLAVVADNLRPQFPRAA
                       :**: :**:*.  ***: * *::: :*****:*  *:*:  **  *. ::: ::*:* ref|YP_001036724.1|    KILEEAEEEILAYMAFPREHWAQIHSTNPLERLNREIRRRTDVVCIFPNREAVIRLVGAM
ref|YP_001039064.1|    KILEEAEEEILAYMAFPREHWAQIHSTNPLERLNREIRRRTDVVCIFPNRKAVIRLVGAM
ref|YP_001039349.1|    KILEEAEEEILAYMAFPREHWAQIHSTNPLERLNREIRRRTDVVCIFPNREAVIRLVGAM
RAAC02533              AILADAEEDVLAFMALPFEHWRQICSTNPLERLNREMRRRMNVVGIFPNRDSVVRLVGAI
ref|YP_076118.1|       QLLEDAEEDILAYMAFPTEHWRRLHSTNPLERLNREIGRRTEIVGIFPNREALIRLAGAV
ref|YP_076073.1|       QLLEEAEDDILAYMAFPTEHWRQLHSTNPLERLNREIGRRTDVVGIFPNREAVIRLAGAV
                       :* :**::**:*:*:* *** ::  ***********: **  ::* *****.:::**.**:

ref|YP_001036724.1|    LMEQNDEWKVG-RRYFSLESMSKITSINEFTLTPVALLHK
ref|YP_001039064.1|    LMEQNDEWKVG-RRYFSLESMSKITSINEFTLTPVALLHK
ref|YP_001039349.1|    LMEQNDEWKVG-RRYFSLESMSKITSINEFTLTPVALLHK
RAAC02533              LQEQHEEWLVS-RRYFSLESMAKLKPQ-QPMLSAQALLQK
ref|YP_076118.1|       MIEQQEEWMTAPRRYFSQASMAKLYAH-DPSLGRPELL--
ref|YP_076073.1|       LIEQQDEWTAAPRRYFSQASMAKLYTS-NQSVSGTDFL--
                       : **::**  .. ***** **:*: .  :   :*
```

FIG. 111

```
ref|YP_076118.1|        ------------------------------------------------------------
ref|YP_074958.1|        ------------------------------------------------------------
ref|YP_001036724.1|     TRANSPSASEMUTATRTYPECLSTRIDIUMTHERMCELLUMATCCGBABNTRANSPSASE
ref|YP_001039064.1|     ------------------------------------------------------------
ref|YP_001039349.1|     ------------------------------------------------------------
RAAC02534               ------------------------------------------------------------ ref|YP_076118.1|        ------------------------------------------------------------
ref|YP_074958.1|        ------------------------------------------------------------
ref|YP_001036724.1|     MUTATRTYPECLSTRIDIUMTHERMCELLUMATCCGBABNTRANSPSASEMUTATRTYPE
ref|YP_001039064.1|     ------------------------------------------------------------
ref|YP_001039349.1|     ------------------------------------------------------------
RAAC02534               ------------------------------------------------------------ ref|YP_076118.1|        ------------------------------------------------------------
ref|YP_074958.1|        ------------------------------------------------------------
ref|YP_001036724.1|     CLSTRIDIUMTHERMCELLUMATCCGBABNTRANSPSASEMUTATRTYPECLSTRIDIUM
ref|YP_001039064.1|     ------------------------------------------------------------
ref|YP_001039349.1|     ------------------------------------------------------------
RAAC02534               ------------------------------------------------------------ ref|YP_076118.1|        ------------------------------------------------------------
ref|YP_074958.1|        ------------------------------------------------------------
ref|YP_001036724.1|     THERMCELLUMATCCGBABNTRANSPSASEMUTATRTYPECLSTRIDIUMTHERMCELLU
ref|YP_001039064.1|     ------------------------------------------------------------
ref|YP_001039349.1|     ------------------------------------------------------------
RAAC02534               ------------------------------------------------------------ ref|YP_076118.1|        ------------------------------------------------------------
ref|YP_074958.1|        ------------------------------------------------------------
ref|YP_001036724.1|     MATCCGBABNTRANSPSASEMUTATRTYPECLSTRIDIUMTHERMCELLUMATCCGBABN
ref|YP_001039064.1|     ------------------------------------------------------------
ref|YP_001039349.1|     ------------------------------------------------------------
RAAC02534               ------------------------------------------------------------ ref|YP_076118.1|        ------------------------------------------------------------
ref|YP_074958.1|        ------------------------------------------------------------
ref|YP_001036724.1|     TRANSPSASEMUTATRTYPECLSTRIDIUMTHERMCELLUMATCCGBABNTRANSPSASE
ref|YP_001039064.1|     ------------------------------------------------------------
ref|YP_001039349.1|     ------------------------------------------------------------
RAAC02534               ------------------------------------------------------------ ref|YP_076118.1|        ------------------------------------------------------------
ref|YP_074958.1|        ------------------------------------------------------------
ref|YP_001036724.1|     MUTATRTYPECLSTRIDIUMTHERMCELLUMATCCSCRESIGNIFICANCEE-IDENTIT
ref|YP_001039064.1|     ------------------------------------------------------------
ref|YP_001039349.1|     ------------------------------------------------------------
RAAC02534               ------------------------------------------------------------ ref|YP_076118.1|        ------------------------LEELLRKSGVDDVDFLREGVRVLAQGLMELEVSQQI
ref|YP_074958.1|        ------------------------LEELLRKTGVDDFDFLREGLRVLAQGLMELEVSQRI
ref|YP_001036724.1|     IESPSITIVESGAPSMATNNRMALLEQLSKYVVEKDKDFLKEALTLLINALMDAEVTSII
ref|YP_001039064.1|     ---------------MATNNRMALLEQLSKYVVEKDKDFLKEALTLLINALMDAEVTSII
ref|YP_001039349.1|     ---------------MATNNRMALLEQLSKYVVEKDKDFLKEALTLLINALMDAEVTSII
RAAC02534               ---------------MALLNSFAVLEWIRKMQDEDHIDVLRELMQLVAQFLIDAEAVEKI
                                                ** : :    .. *.*:* : :: : *:: *. . *
``` continued →

FIG. 111 continued

```
ref|YP_076118.1|       GAERYERSSERSNYRNGYRERQWDTRVGTIDLQIPKLRKGSYMPSWLEPRRRAEKALVAV
ref|YP_074958.1|       GADRYERSAERSTYRNGYRERQWDTRVGTIDLQIPKLRKGSYMPSFLEPRRRAEKALVAV
ref|YP_001036724.1|    GAEKYERNNNRNNYRNGYRLREWDTRVGTLQLSIPKLRHGSYFPSLLEPRKMSEKALLNV
ref|YP_001039064.1|    GAEKYERNNNRNNYRNGYRLREWDTRVGTLQLSIPKLRHGSYFPSLLEPRKMSEKALLNV
ref|YP_001039349.1|    GAEKYERNNNRNNYRNGYRLREWDTRVGTLQLSIPKLRHGSYFPSLLEPRKMSEKALLNV
RAAC02534              GAERYERTDSRVTQRNGSRSRTWDTRLGTVDLKIPKLRQGSFFPSLLEPRRRAEQALAAV
                       ::*. .* . *** * * **:::*.***::: **: :*:** * ref|YP_076118.1|       VQEAYIQGVSTRKVDELVQALGMTGVSKSQV
ref|YP_074958.1|       VLEAYVNGVSTRKVDDLVQALGMTGVSKSQV
ref|YP_001036724.1|    VQEAYVHGVSTRKVDELVEALGMKGIDKSEV
ref|YP_001039064.1|    VQEAYVHGVSTRKVDELVEALGMKGIDKSEV
ref|YP_001039349.1|    VQEAYVHGVSTRKVDELVEALGMKGIDKSEV
RAAC02534              IQEAYVKGVSTRKVDDLVRALGLEGISKSEV
                       : ***::*********:**.***: *:.**:*
```

FIG. 112

```
ref|YP_148733.1|      ---------------MDMTLTAKIKIYPTAEQAEVLKATLSAYRQACNAVSVVIFDT-KVL
ref|YP_146224.1|      ---------------MDMTLTAKIKIYPTAEQAEVLKATLSAYRQACNAVSVVIFDT-KVL
ref|ZP_02171259.1|    ---------------MKLTLTAKTKIVPTVEQEDTLRKTAHAYRDACNAVSFVVFDE-NTL
ref|NP_977687.1|      -----------------TITAKIQIHVSDNQAESLKITTNAYRKACNWLSKHIFET-KNL
RAAC02562             MSAIPPPSEGEVNGMELTRTVRVRLDPTPEQASALALTIEANRQALDYVSRIAFER-RIR
ref|ZP_02619781.1|    ---------------MEIVRTLKIKLNINQEEKNMINSTLEAFLKALNYASQVAFNNGEIT
                                     . * : :: . :: . : * * .* : * *: .

ref|YP_148733.1|      AQAKLHDMTYRLLRSNYALRSQMAQSVIKTVIARYRSLKSNGHEWTLVRFKKPEYDLVWN
ref|YP_146224.1|      AQAKLHDMTYRLLRSNYALRSQMAQSVIKTVIARYRSLKSNGHEWTLVRFKKPEYDLVWN
ref|ZP_02171259.1|    VQAKLHKRTYRELRSTFGLKSQMAQSALKTVIATYKTNQSNGHERSQVQFKKPQFDLVFN
ref|NP_977687.1|      NQVNLNNLYYSDLRNQFRLKSQMAQSVMKTVIARYKSAKSNGHEWSLIDFKLAEYDLVWN
RAAC02562             NAFDLQRIVYRTIRTRFGLRAQMACTVCRTVAAVYKSMKSNGNANALAKFKHAKPVFQWN
ref|ZP_02619781.1|    NKPKLQKLVYDDLRTKFNLKSQMAVNTCTTVCSSYVTQHSNKVFNSLAVYKSPKAIYSYG
                       .*:   *  :*. : *::*** ..  ** : * : :**    :  :* .:    :.

ref|YP_148733.1|      RDYSIVQG--LFSVNTLEGRIKVPFEPKG-MEPYFDGSWTFGTAKLVYKHNKFFLHIPMT
ref|YP_146224.1|      RDYSIVQG--LFSVNTLEGRIKVSFEPKG-MEPYFDGSWTFGTAKLVYKHNKFFLHIPMT
ref|ZP_02171259.1|    RDYSLTKG--LFSVNTLEGRIKVPFYTEG-LEPYFDGTWTFGTAKLVHKYGKWFLHIPVS
ref|NP_977687.1|      RDYSLTKN--QFSVNTLEGRLKLNYERKA-MKKYFNSTWKFGTAKLVHKYKKWFLHIPMT
RAAC02562             KDYVLRSG--LAYITTLDGRLRIPFRVEPPYQRYLQDGWTFGAAELVQKRHGWFLHVSVS
ref|ZP_02619781.1|    RDYSFLNDGQTISINTIAKRIKVHFKVNNYFKKYLTKEWSFGSLEIVERENSYYAHITVS
                      :** : ..   :.*: *::: : *: **,**:  :*  * :: : *:.::

ref|YP_148733.1|      KTIPTVDEHNIRQVVGVDVGVNFLAAAYDSQGKTTFFNGRKIKHMRAKYKRMRKTLQQKG
ref|YP_146224.1|      KTIPTVDEHNIRQVVGVDVGVNFLAVAYDSQGKTIFFNGRKIKHMRAKYKRMRKTLQQKG
ref|ZP_02171259.1|    KDVQEANLDNINQVVGIDMGVNFTATTYDSNGQTRFFNGKQIKHKRAKYKQMRKELQQKQ
ref|NP_977687.1|      KEYQTLDFADVNNIVGVDLGINFLATTYDSQSKTTFYNGNIVKHKRGKFKATRKQLQTRQ
RAAC02562             KTVPDP-VGDFDAVIGVDQGMRFLVTAS-CGNEVMFIRGGKVKQTRLRYVRLRASLQRKG
ref|ZP_02619781.1|    KEVQEKPLNEFKNIIGIDLGQNFIATFYDSKGKIKFFKGRYLKDMRAKYTRLRKQLQRKG
                       *        :: ::*:* *  .*    ..     . :  .* .*: *     *  ** :

ref|YP_148733.1|      TASARRKLKTIGQRENRWMTDVNHAVTKALV---RQYGERTLFVLEDLTGIREKTERVRI
ref|YP_146224.1|      TASARRKLKTIGQRENRWMTDVNHAVTKALV---RQYGERTLFVLEDLTGIREKTERVRI
ref|ZP_02171259.1|    TPSARRKLKKIGQRENRWMQNINYCISKALV---EQYGKDTLFVMEDLTGVRNATEKVRV
ref|NP_977687.1|      TPSSRRKKIKQISRENRYVPTDVMFVQITKALV---EAYPRGTMFVLEDLTGVRSATEKVRV
RAAC02562             TRSAKRRLKAIGRRESRFMTDVNHQIAKAVVRFAKAQGQRPLIVLEDLTGS-NLSVRFRM
ref|ZP_02619781.1|    TYNAHKKIVTINQREQRTMTYINHKISKEIV--EYAKQNNAIIAMENLTGI-NLSCKVKK
                      * .:::::  *. **.* : :*: ::* :*           .::: :***   .: ::.

ref|YP_148733.1|      HDRYETVSWAFYQFRQLLEYKARLHGSKVMVVAPHYTSLTCPKCGHTEKANRNKRTHTFC
ref|YP_146224.1|      HDRYETVSWAFYQFRQMLEYKARLHGSKVIVVAPHYTSLTCPKCGHTEKANRKKRTHTFC
ref|ZP_02171259.1|    KDRYQTVSWSFNDLRQKIAYKAQKTGALGIAVDPGYTSQTCPKCGHTEKANRNKKTHTFC
ref|NP_977687.1|      KNRYVSVSWAYQFRQMLEYKAELNGGQKVIVVDPKYTSQTCPKCGNIEKANRNKKLHTFK
RAAC02562             KDQYWRMSWAFRQLADFIRYKAEEVGIAVMVIDPTGTSETCPKCGHCEAANRSRKHEFR
ref|ZP_02619781.1|    DNRYYRVSWAFNQLQQFIEYKAVQAGLKVIYINPKYTSQTCPICGHIHKDNRNKKLHIFK
                       .::*  :**:*  ::  : :  ***    *   :  :   *  : . .:: * * ref|YP_148733.1|      CRTCGYTSNDDRIGAMNLQRKGIE--------
ref|YP_146224.1|      CRTCGYTSNDDRIGAMNLQRKGIE--------
ref|ZP_02171259.1|    CQTCQYTSNDDRIGAMNLQRKGI---------
ref|NP_977687.1|      CKNCQYQSNDDRISAMNLHRKGIK--------
RAAC02562             CKKCGYRCNDDLAASRVIAQKGLECLRQSQSA
ref|ZP_02619781.1|    CRACGCTLNDDLIGAKNIQHKGYD--------
                      *: *   ***   .:  : :**
```

FIG. 113

```
ref|YP_516922.1|    ---MFARIKTAYNRDGSPRRYLQIVESRREEGKVRQKVLCNLGRVEDLQNGKLDDLIRSL
ref|YP_520815.1|    ------------------------------------------------------------
ref|YP_519534.1|    ---MFARIKTAYNRDGSPRRYLQLVESRREEGKVRQKVLCNLGRVEDLQNGKLDDLIRSL
ref|ZP_01372264.1|  ---MFARIKTAYNRDGSPRRYLQLVESRREEGKVRQKVLCNLGRVEDLQNGKLDDLIRSL
ref|ZP_01370818.1|  ---MFARIKTAYNRDGSPRRYLQLVESRREEGKVRQKVLCNLGRVEDLQNGKLDDLIRSL
RAAC03229           MILLFAQIVSTKKPDGKTYKYLHIVESYREGRTVKKRRVASLGNISQYSEREIEQIIRTL ref|YP_516922.1|    AKFSDKLAVVDAAEDLFADWSKEYGPSMVFNRLWDNLGLHKILDGLFSERELSIDVREAI
ref|YP_520815.1|    ----------------------------LWDNLGLHKILDGLFSERELSIDVREAI
ref|YP_519534.1|    AKFSDTLAVVDAAEDLFADWSKEFGPSMVFRRLWENLGLHKILSGLFNERELSIDVQEAI
ref|ZP_01372264.1|  AKFSDTLAVVDAAEDLFADWSKEFGPSMVFRRLWENLGLHKIFAGLFNERDLSIDVQEAI
ref|ZP_01370818.1|  AKFSDTLAVVDAAEDLFADWSKEFGPSMVFRRLWENLGLHTILDGLFNERDLSIDVQEAI
RAAC03229           ESLLQHRTTG-SLEDFEAQQVLHFGVPYVVQFLWNQLGLTEAIRDALRAREVTFDVARYV
                                                **::***   :  :   *:::***  .  :

ref|YP_516922.1|    FCMVLNRLTEPTSKLGVSDWKDSVYRPDF--ETLKLHHFYKAIDFLDENKDTIEEQLFFH
ref|YP_520815.1|    FWMVLNRLTEPTSKLGVSDWKDSVYRPDF--ETLKLHHFYKAIDFLDENKDTIEFQLFFH
ref|YP_519534.1|    FCMVLNRLTEPTSKLGVSDWKDSVYRPEF--ESLKLHHFYKAIDFLDENKESIEEQLFFH
ref|ZP_01372264.1|  FCMVLNRLTEPTSKLGVSDWKDSVYRPEF--ESLKLHHFYRAIDFLDENKDTLEEQLFFH
ref|ZP_01370818.1|  FCMVLNRLTEPTSKLGVSDWKDSVYRPEF--ESLKLHHFYKAIDFLDENKDTLEEQLFFH
RAAC03229           QAMVIHRLVDPSSKLRLFHTLDDLYLPDWGGEPWQLQHFYRALDYLVDIKPQLERVLYAR
                     ::** :*:***   .  *:* *::    *. :*:****:*:* :  *. .  *: :

ref|YP_516922.1|    HTNLFTQQLDLVFFDTTSTYVEGDAGAFDLLEYGHSKDHRPDRLQVMIGILMSRDGIPIA
ref|YP_520815.1|    HTNLFTQQLDLVFFDTTSTYVEGDAGAFDLLEYGHSKDHRPDRLQVMIGILMSRDGIPIA
ref|YP_519534.1|    QTNLFTQQLDLVFFDTTSTYVEGDAGAFDLLEYGHSKDHRPDRLQVMIGILMSRDGIPIA
ref|ZP_01372264.1|  HTNLFTQQLDLVFFDTTSTYVQGDAGAFDLLEYGHSKDHRPDRLQVMIGILMSRDGIPIA
ref|ZP_01370818.1|  HTNLFTQQLDLVFFDTTSTYVEGDAGAFDLLEYGHSKDHRPDRLQVMIGLLMSRDGIPIA
RAAC03229           LTDLLNFRLSLVLYDLTSTHLHG--HACPLGGHGYSRTHRPDLEQVELGLLVTPEGIPIT
                    *:*::  :**:: :  ***::.*     *   *:*:*: ****    **  **:*:****:

ref|YP_516922.1|    HHVFPGNTPDTDAFIEAVSDLKKRFNIQRVIVVGDRGMMGKRTLELLEELQLQYILGVRM
ref|YP_520815.1|    HHVFPGNTPDTDAFIEAVSDLKKRFNIQRVIVVGDRGMMGKRTLELLEELQLQYILGVRM
ref|YP_519534.1|    HHVFPGNTPDTDAFIEAVRDLKKRFTIQRVIVVGDRGMMGKRTLELLEELELHYILGVRM
ref|ZP_01372264.1|  HHVFPGNTPDTDAFIEAVSDLKKRFTIQRVIVVGDRGMMGKRTLELLEELQLHYILGVRM
ref|ZP_01370818.1|  HHVFPGNTSDTDAFIEAVSDLKKRFTIQRVIVVGDRGMMGKRTLELLEELQLHYILGVRM
RAAC03229           HEVFAGNVSDKQTVPDILKRLKEDFAVEQCVFVGDRGMVTEKNMALMAEAGFPYIVCFHK
                    *.**.**..*::.  : :   **: *    :.******: :::*:  *:   :**:*.:

ref|YP_516922.1|    RN---IKAGPDLANSPEPYAFIKDNLKVKEVVHQ---------EKRYIVCLNEEEAKRDQ
ref|YP_520815.1|    RN---IKAGPDLANSPEPYAFIKDNLKVKEVVHQ---------EKRYIVCLNEEEAKRDQ
ref|YP_519534.1|    RN---IKAGPELAASPEPYTFLKDNLKVKEVLHQ---------EKRYIVCLNEEEAKRDR
ref|ZP_01372264.1|  RN---IKAGPELAASAQPYPFVKDNLKVKEVLHQ---------EKRYIVCLNEEEAKRDQ
ref|ZP_01370818.1|  RN---VKAGPELATSPEPYVFTKDNLKVKEVLHQ---------GKRYIVCLNEEEAKRDQ
RAAC03229           RGRIVSDALLEQFADVNAYHELKDNLRYLEVPAASVDDVEKAEGVRYILCYNPEKARQDA
                    *.   .*  :   ..:*    **:            ***:*  *:*::* ref|YP_516922.1|    LVREQIEIKLRS----------KLEHG---------SIKDLIGNSEYKKYINVTAEAAT
ref|YP_520815.1|    LVREQIEIKLRS----------KLEHG---------SIKDLIGNSEYKKYINVTAEAAT
ref|YP_519534.1|    LVREQIEMKLRS----------KLEHG---------SIKDLIGHSEYKKYINVTAEAAT
ref|ZP_01372264.1|  LVREHIEMKLRS----------KLEHG---------GIKDLIGHSEYKKYINVTAEAAT
ref|ZP_01370818.1|  WVREQIEVKLRS----------KLEHG---------SIKDLIGHSEYKKYLNVSAEAAT
RAAC03229           AFRESALEEAETGLKALAESLAKPKRGRKPTDKGVMLKVADLLTRKGVEAFFQVDYKDGI
                    .**   : .:           * ::*           : **: ..  : :::*  :  .

ref|YP_516922.1|    IN----TDKLKQAAVFDGLYILQTNTELPTEEVATAYRDLWQIERAFRNLKSTLDLRPVY
ref|YP_520815.1|    IN----TDKLKQAAVFDGLYILQTNTELPTEEVATAYRDLWQIERAFRNLKSTLDLRPVY
ref|YP_519534.1|    MN----TDKLKQAAVFDGLYILQTNTELPTEEVATAYRDLWQIERAFRNLKSTLDVRPVY
ref|ZP_01372264.1|  IN----TDKLKQAAVFDGLYILQTNTELPTEEVATAYRDLWQIERAFRNLKSTLDLRPVY
ref|ZP_01370818.1|  IN----TDKLKQAAVFDGLYILQTNTELPTEEVATAYRDLWQIERAFRNLKSTLDLRPVY
RAAC03229           LTYRRDEDAITKEALRDGKFLIRTNTDLPAADVVQSYKTLMGIERAFHQIKNFLDVGPIY
                    :.     *  *:  *: **  **  :::::*:** :*  .*::* *  *****:::*  **:  *:*
``` continued →

FIG. 113 continued

```
ref|YP_516922.1|      HWKERRISGHIMLCFLALVVQIKFQKLLES------------------------CGSEY
ref|YP_520815.1|      HWKERRISGHIMLCFLALVVQIKFQKLLES------------------------CGSEY
ref|YP_519534.1|      HWKERRISGHIMLCFLALVIQIRFQKLLEN------------------------CASEY
ref|ZP_01372264.1|    HWKERRISGHIMLCFLALVIQIRFQKLLEN------------------------CASEY
ref|ZP_01370818.1|    HWKERRISGHIMLCFLALVVQIRFQKLLEN------------------------CASEY
RAAC03229             HWNEQRVRGHIFVCVLAYLFEQEMQVLYRRQWAHDKAVAESLACVEEQAKVLAELESRWY
                      **:*:*:  ***::*.**  ::  ..:*  *  .                    .   * ref|YP_516922.1|      GYTEVIRALRKVHAVKLKIKDQDHLVRTEIHGAAAMAFKAVGLRIPER------------
ref|YP_520815.1|      GYTEVIRALRKVHAVKLKIKDQDHLVRTEIHGAAAMAFKAVGLRIPER------------
ref|YP_519534.1|      GYTEVIRALRKVHAVKLKLKDQDHLVRTEIHGAAAMAFRAVGLRIPER------------
ref|ZP_01372264.1|    GYTEVIRALRKVHAVKLKLKDQDHLVRTEIHGAAAMAFKAVGLRIPER------------
ref|ZP_01370818.1|    GYTEVIRALRKVHAVKLKLKDQDHLVRTEIHGAAAMAFRAVGLRVPER------------
RAAC03229             TGEAIVRELRRWKAVRATFLDKEFVSVTKATDQAKAILTSLGIPTPNKTLSVTKVPSMTP
                      :.* **: :**: .: *::..:  *:  . *   : ::*:  *::

ref|YP_516922.1|      --
ref|YP_520815.1|      --
ref|YP_519534.1|      --
ref|ZP_01372264.1|    --
ref|ZP_01370818.1|    --
RAAC03229             DE
```

FIG. 114

```
ref|YP_001125159.1|    -------VTAVKGIGEETAAALADLGITTVGELLNYAPYRYDDYEQKDLAAVRHEEKVTV
ref|YP_147039.1|       -------VTAVKGIGEETAAALADIGIATVGELLAYAPYRYDDYEQKDLAAVRHEEKVTV
ref|ZP_02849289.1|     MTLEQYSVRQIKGVSAPKEEELHAFGVHTVADLLDYFPFRYEDYRIRELAEIKDGEKVTV
ref|ZP_02329219.1|     MDLNQIPVTRVSGVGPQKAEDLAALGIHTAAQLIAYFPFRYEDYRLRDLSEVKDGERITV
ref|NP_816723.1|       -------VSVLPGVGPKRAENLQELGIATIEDLLTYYPFRYDDIQEKDLSEIQDQEKVTL
RAAC00160              MSLRSLSVRALPGVGPQKERALEALGIRTVDDLLHTYPFRYDERAEKPFSEWRDGDRVTA
                              *   *:.     *   :*: *  :*:     *:**::    :  ::  :::* ref|YP_001125159.1|    EGKVHSAPLLTYYGKKKSRLSFRLLTG-RYLITVVCFNRPYLKGKITLNETVTVIGKWDR
ref|YP_147039.1|       EGKVYSAPLLTYYGKKKSRLSFRMLAD-RYLITVVCFNRPYLKEKIALNETVTVIGKWDR
ref|ZP_02849289.1|     QGTIRGNGILQRYGKNKSRLTCKIEVD-HMLVTAVWFNRHFLQGQLTPGREIMLTGKWEQ
ref|ZP_02329219.1|     QGNLIGAPVLQRYGR-KSRLSCKVVID-HFFVTAVWFNRPFLKDKLASCKEIRLTGKWDA
ref|NP_816723.1|       KGLVVSEAVVSRYGYKKSRLTFRMMQE-HAVINVSFFNQPFLKDKVVLSEEIAVYGKWDA
RAAC00160              RAVVEG-PVQVRWRGSKSIMTARVRVDGQHPVVCLWFSQHYLRSKLSDGRFIVVTGKWNE
                           :  .  :      **  ::  ::     :  :  *.: :*:  :    .. : ***:

ref|YP_001125159.1|    HRQTINAYELRFGAAPE----ATGIEPVYSVRSPLTVKTMRRLIKAAFAQFGMHIPDLLP
ref|YP_147039.1|       HRQTINAYELRFGPAPE----TTGIEPVYSVRSPLTVKTMRRLMKAAFEQFGEHIPDPLP
ref|ZP_02849289.1|     QRLQMTVSESEFADKSTGMVKSGTLQPVYSVCGGITQAWMRKTIKQALLQYGSMIEEVLP
ref|ZP_02329219.1|     RRKQLTVSESEFPGNDS---LTGTLQPVYSLTGSLTQKSIRKMIQQALKQFGNLIQEVLP
ref|NP_816723.1|       KRKSLNGMKILASKGDN-----EDFAPIYHVNKKVRQSTLVQLIRTAFEEYGSLVEEILP
RAAC00160              ALRRLVASETSFDAGTQ----APSLVPVYRASKELSTKAIHQLILKALEQYAEEIQESLP
                         :     :              : *:*     :  : ::  *: ::.   : : **

ref|YP_001125159.1|    PALRRAYRLIDKQEAVRALHFPRSREELHQARRRLVYEEFLLYQLKMQALRKVMRDERRG
ref|YP_147039.1|       PALRRAYRLVDKQEALRALHFPRTREELHQARRRLIYEEFLLYQLKMQALRRLMRDERRG
ref|ZP_02849289.1|     HELVERHGLMARRDAVQRIHDPEEVKEGLEARRRMVYEELFLFQLKLQAYRSLTRKRGDG
ref|ZP_02329219.1|     ADFVKRYQLLPRKQAVALIHQPSGLEDGKQARRRMVYEELFFFQLKMHAFKAITRKRADG
ref|NP_816723.1|       NDLLEKYRLMPRKEAMWAMHFPSNPEESHQAKRRVVFEEFFLFQLKMQGLKKQEKAEKNG
RAAC00160              YALVRKYRLWTHRDALFGMHRPKSLEDVRQARRRLVFEEFLLFQIQLQWLRAK-REEPAG
                          : .: *   ::::*:  :*  *    ::  :*:::::::*:::        * ref|YP_001125159.1|    IIHSFPEEQLASFLSGLPFSLTNAQRRVIREILDDMRAPRQMNRLLQGDVGSGKTVVAAV
ref|YP_147039.1|       VVHSFSEERLSSFLSGLPFVLTNAQRRVIGEILADMRSPRQMNRLLQGDVGSGKTVVAAV
ref|ZP_02849289.1|     IVHQVNGETIRNFAATLPFELTDGQKKVVNEIMSDMRQPAAMNRLLQGDVGSGKTVVAAI
ref|ZP_02329219.1|     LAQQVDLPKIRSFVKSLPFELTPSQKQVVGELLHDMQQPYTMNRLLKGDVGAGKTVVAAT
ref|NP_816723.1|       LAIQYDVDRLKTFTQGLPFELTGAQKKVTNEICRDLRSPKHMQRLLQGDVGSGKTVVAAI
RAAC00160              RAQPVPSDALTAFEALLPGMTNAQRRACEDILRDLQRPVPMTRLTQGDVGSGKTWVALF
                                 :     *      **  :  .*::::  *   *   *:****:***:** **

ref|YP_001125159.1|    ALYAAVLSGFQGALMVPTEIAEQHVRSLAELFADTGVTVELLTSSVKGKRRKELLAKLE
ref|YP_147039.1|       ALYAAALSGFQGALMVPTEILAEQHARSLAELFADTDVTIALLTSSVKGKQRKAVLAELE
ref|ZP_02849289.1|     ALYCTIKAGHQGALMVPTEIHLRSLQKLFADTGIEVALLTGSLTEKKRRDVLAGLQ
ref|ZP_02329219.1|     ALYATVTAGCQGALMVPTEIAEQHKKSLSRMFKPYGIETALLTGSSTDKKRREILAGVQ
ref|NP_816723.1|       ALYATMTAGFQGALMVPTEILAQQHMESLQQLFDPLEVRTALLTGSTKTKERRLJLEELA
RAAC00160              ACFAVHLARGQSALMAPTEILAEQHARLAHELLGSAGVRVELLTGSVTGRERDRVLAGLA
                        * ::..  :.***.******:: .::*   *  .      ***.*  ..:*  :*   :

ref|YP_001125159.1|    DGTVDIVIGTHALIQEGVQFRQLGLVITDEQHRFGVEQRRVLREKGHAPDVLMMTATPIP
ref|YP_147039.1|       EGTIDIVVGTHALIQEGVQFRRLGLVITDEQHRFGVEQRRVLREKGHAPDVLMMTATPIP
ref|ZP_02849289.1|     MGMIDILVGTHALIQDDVFFRSLGLVVTDEQHRFGVNQRSILRRKGMNPDVLTMTATPIP
ref|ZP_02329219.1|     MGLIQVLIGTHALIQEDVFFRKLGLVVTDEQHRFGVSQRSILRRKGMNPDVLSMTATPIP
ref|NP_816723.1|       NGEIDIVVGTHALIQQDVSFHQLGLVITDEQHRFGVNQRKILREKGLKPDVLFMTATPIP
RAAC00160              SGDVSLAVGTHALLSEGVEFRDLALLVTDEQHRFGVAQRARLREKGRAPDVLMLSATPIP
                         * ::.:  :****:.:: *: *:*:.:.::******  **  ****  **** ::****

ref|YP_001125159.1|    RTLAITAFGDMDVSVLDEMPAGRKKVETYWVKHNQFARVLDFIEKELRRGHQAYVICPLI
ref|YP_147039.1|       RTLAITAFGDMDVSVLDEMPAGRKKVETYWVKHHQFSRVLDFIEKELRRGHQAYVICPLI
ref|ZP_02849289.1|     RTLAITAFGDMDVSTIKERPHGRKPIKTYWVKHDMMERVLGFIRREVGEGRQAYVICPLI
ref|ZP_02329219.1|     RTLAITAFGDLDVSTLREMPKGRKPIKTYWVHDMLERVLGFIQKEAAGCRQAYVICPLI
ref|NP_816723.1|       RTLAITAYGEMDVSIIDEMPAGRIPIETRWIRPPQLDTVLEWMEKELARGIQAYIICPLI
RAAC00160              RTLALAIYGDMVSILNELPKGRKPVQTIAVPSKDDETVLRLIRRELARGHQAYIVAPAI
                       ****:: ::::***  : * **  *  **   ::*    :.:*   *:****: *. *
``` continued →

FIG. 114 continued

```
ref|YP_001125159.1|    EESEKLDVQNAIDVHSQLVYYYRGKYEVGLMHGRLSADEKEAVMRAFSENRIHVLVSTTV
ref|YP_147039.1|       EESDKLDVQNAIDVHSQLVHYYRGKYEIGLMHGRLSADEKERVMRAFSENRIHVLVSTTV
ref|ZP_02849289.1|     EESDKLDVQNAIDLYVQMQQAFP-DLKVGLLHGRLSASEKDEVMRGFGANETQLLVATTV
ref|ZP_02329219.1|     EESDKLDVQNAIDVHVQLQQHFP-DLNIGLLHGRMTAAEKDDTMRSFKDGSIQVLVSTTV
ref|NP_816723.1|       EESEALDVKNATEIFEHMQSFYSPRYQVGLLHGKMKNQEKDDIMQEFKDNQLQLLVSTTV
RAAC00160              EASERDDVASVTELYERVREHLA-GFRVELLHGRMPSADKERMMRAFRDGDIHALVATTV
                       *  *:  **  .. ::. ::         .: *:**::      :*: *   .   : :* ref|YP_001125159.1|    VEVGVNVPNATVMVIYDAERFGLAQLHQLRGRVGRGDAQSYCILIADPKSEIGKERMHIM
ref|YP_147039.1|       VEVGVNVPNATVMVIYDAERFGLAQLHQLRGRVGRGDAQSYCILIADPKSEVGKERMRIM
ref|ZP_02849289.1|     VEVGVDVPNATLIIIMDAERFGLSQLHQLRGRVGRGAHQSFCVLVADPKSENGRERMKVM
ref|ZP_02329219.1|     IEVGVDVPNATLMVVYDADRFGLSQLHQLRGRVGRGEHQSFCVLIADPKTEVGKERMQAM
ref|NP_816723.1|       IEVGVNVPNATVMLIMDADRFGLAQLHQLRGRVGRGSSASYCILVANPKNEMGVERMKIM
RAAC00160              IEVGIDVPNATVMAIYGAERFGLAQLHQLRGRVGRGPHPSYCLLIHDASSEAARARIETM
                       :*::***:: :   .*:**:***********     *:*:*: :...* .   *:. * ref|YP_001125159.1|    TETTDGFVLAEKDLELRGPGDFFGTKQSGLPEFQFGDPVHDYRILEVARRDAAKLVSSAA
ref|YP_147039.1|       TETADGFVLAEKDLELRGPGDFFGTKQSGLPEFRYGDPVHDYRILEVARRDAAKLVSSAA
ref|ZP_02849289.1|     TETNDGFEVSRRDLELRGPGDFFGTKQSGLPEFKIADMAAEYEMLELARDDAAELTGRDD
ref|ZP_02329219.1|     TETTDGFEIARRDLELRGPGDFFGTKQSGLPEFRIADLMCDFEIMEIARDDAADLVAKPE
ref|NP_816723.1|       TETTNGFVLSERDLELRGPGEVFGARQSGVPQFAVGDIVTDFNILEVARQEASALWKVKE
RAAC00160              LQTNDGFEIAERDLELRGPGELFGLRQSGLPEFALGDLARDYRIMEVAREEALALLRRDD
                       : *  :  ::.:***:   :***:*:*   .*      :::.::*:** :*    * ref|YP_001125159.1|    FWRDEAYAGLRAELE----------
ref|YP_147039.1|       FWRDEAYAGLRAELE----------
ref|ZP_02849289.1|     FWTNPLFERMR--------------
ref|ZP_02329219.1|     FWTAAEYVPLRQFLQK---------
ref|NP_816723.1|       WWQYPAYQGLANRVKPQDEAAQFFD
RAAC00160              FWYAPWAEGLRNALKEAMDKVSYRD
                       :*                :
```

FIG. 115

```
ref|YP_148969.1|        ------------------YLQLAHNEWDPKAKYAKAKVIYSFGREDEVDRAVLERLAKSIS
ref|YP_001126171.1|     ------------------YLQLAHNEWDPKAKYAKAKVIYSFGREDEVDRAVLERLAKSIS
ref|YP_146154.1|        ------------------------------------------------------------
ref|YP_146741.1|        MYIRRVTRKNKDGTTVAYLQLAHNEWDPKAKYAKAKVIYSFGREDEVDRAVLERLAKSIS
RAAC03182               MYIRVIRRKNKNGSVTGYVQLAHNFRDPNTGQPKAKVLYTFGREDEIDLEALRRLAQSIH
ref|ZP_02130848.1|      MYIRTISRKNKDGSKVEYVQLAHNYRDPKSKQARAEVLYSFGRKDQLDMEAIRRLAKSVE ref|YP_148969.1|        RFLSPEQAWEIETLTGEVSDDFQFQSSKRLGGAWLLDQLWRQLGLGEILHSLFASRHHQI
ref|YP_001126171.1|     RFLSPEQAWEIETLTGEVSDDFQFQSSKRLGGAWLLDQLWRQLGLGEILHSLFASRHHQI
ref|YP_146154.1|        ---------------------------------------------------VCSRHHQI
ref|YP_146741.1|        RFLSPEQAWEVEKLTGEASDDFQFQSCKHLGGVWLLDQLWRQLGLGEILHSLFTSRHHQI
RAAC03182               RFVGDEFTAGRGQSEGIQT---TLLDSRPMGGAYLLDELWRQLGLDEVLRERLADRKFKA
ref|ZP_02130848.1|      RFLAKTGDVETQCKLQFPGEDVRFVESRPMGGVFVLKKIWDRLRISECLDKALADRQYTA
                                                                      . .*:.

ref|YP_148969.1|        PLERLIFAMVANRALHPSSKLAMEEWVEKDVHIPHLPQVASHQLYRAMDELLAVQPELER
ref|YP_001126171.1|     PLERLIFAMVANRALHPSSKLAMEEWVEKDVHIPHLPQGASHQLYRAMDELLAVQPELER
ref|YP_146154.1|        PLERLIFAMVANRALHPSSKLAMEEWVEKDVHIPHLPQVASHQLYRAMDELLAVQPELER
ref|YP_146741.1|        SLERLIFAMVANRALHPSSKLAMEEWVEKDVYIPHLPQVASHQLYRAMDELLAVQPELER
RAAC03182               AVERVIFAMVANRALAPSSKLAMEEWVDREVALPGMTELDVWQAYRAMDFLHDVAEDLQY
ref|ZP_02130848.1|      PIGDAVFAMVANRALAPDSKLAVEDWAAKDVHLELDQPLKVQHLYRAMDFLLENQEAIQK
                          .:  :*********  *.****:*:*.  ::*  :         :  *****  *         ::

ref|YP_148969.1|        QVFHAVADLLNLEVDLIYFDTTSSYFEVDPSETPEGESLRKQGFSKDKRPDLVQIVIGLA
ref|YP_001126171.1|     QVFHAVADLLNLEVDLIYFDTTSSYFEVDPSETPEGESLRKQGFSKDKRPDLVQIVIGLA
ref|YP_146154.1|        QVFHAVADLLNLEVDLIYFDTTSSYFEVDPSETPEGESLRKQGFSKDKRPDLVQIVIGLA
ref|YP_146741.1|        QVFHAVADLLNLEVDLIYFDTTSSYFEVDPSETPEGESLRKQGFSKDKRPDLVQIVIGLA
RAAC03182               EVFRRVSDLLNLDVDLLFFDTTSTYFET---EDESDDSLRRKGYSKDHRPDLPQVVIGLA
ref|ZP_02130848.1|      EVFWSTANLLNLEVDLVFFDTTSTYFER---DEEDEEGLKRYGHSKDRKDLPQVVVGLA
                         :   .:::*::***:*    :   . .*::  *.***:*  **  *:*:*** ref|YP_148969.1|        VTREGVPIRAWVWPGNTMDMTVIKQVKQDLIGWKLGRVISVMDRGFSSEENLRILQQAGG
ref|YP_001126171.1|     VTREGVPIRAWVWPGNTMDMTVIKQVKQDLIGWKLGRVISVMDRGFSSEENLRILQQAGG
ref|YP_146154.1|        VTREGVPIRAWVWPGNTMDMTVIKQVKQDLIGWKLGRVISVMDRGFSSEENLRILQQAGG
ref|YP_146741.1|        VTREGIPIRAWVWPGNTMDMTVIKQVKQDLIGWKLGRVISVMDRGFSSEENLRILQQAGG
RAAC03182               VTRDGIPVRCWTWPGNTADMSVVEEVKQDLIGWRLGRVITVVDRGFVSESNLRILQRAGG
ref|ZP_02130848.1|      VTKEGLPIRSWVFPGNTPDVNTVEQIQKEMNDWKLGRVVWAMDRGMTSEENRAILQRGGG
                        **::*:*:*.*.*.:****  *:...::::::   .*:****.  .:***. ** .*  ***:.**

ref|YP_148969.1|        HYIVGEKMRSGKAAVEEALNRRGRYQQVRENLHIKEIIVGDGEARQRYVLVYNPSEAERQ
ref|YP_001126171.1|     HYIVGEKMRSGKAAVEEALNRRGRYQQVRENLHIKEIIVGDGEARQRYVLVYNPSEAERQ
ref|YP_146154.1|        HYIVGEKMRSGKAAVEEALNRRGRYQQVRENLHIKEIIVGDGEARQRYVLVYNPSEAERQ
ref|YP_146741.1|        HYIVGENMRSGKAAVEEALSRRGRYHEVDENLHIKEIIVGDGEARQRYVLVYNPGEAERQ
RAAC03182               HYIAGEKMTSGKPAVEAALARPGRFRELRPNLKVKEVVVGDGEARVRYVLAFNPEEAKRD
ref|ZP_02130848.1|      NYILGEKLR-GSNMSKAVLGSPGRFTTVRDNLEIKEVTAGDGACRRRYVIVRNPKQVKRD
                        :** **::  *.    : .*   **:  :  **.:**:  .***  .*  ***:.   **  ::*:

ref|YP_148969.1|        RKEREKLLESLKEELEGLRQLPNEAHHKATCRLRSHPSYGKYLRQLKDGTLRIDKQAVRE
ref|YP_001126171.1|     RKEREKLLESLKEELEGLRQLPNEAHHKATCRLRSHPSYGKYLRQLKDGTLRIDKQAVRE
ref|YP_146154.1|        RKEREKLLESLKEELEGLRQLPNEAHHKATCRLRSHPSYGKYLRQLKDGTLRIDKQAVRE
ref|YP_146741.1|        RKERETLLESLKEELEGLRQLPNEAHHKATCRLRSHPSYGKYLRQLKDGTLRIDKQAVRD
RAAC03182               EARREAMLRELRMELERLKELQGEAHTKAHCRLASHPTFKRYLKQDRWGNLRIDPEAVRQ
ref|ZP_02130848.1|      QATRERLIRRAEQEIEAIGDLTGKKHTKAACALLSHRSMGKYVRELKSGKLKINKAKITE
                        .  **  ::.  . *:*  :  :*  .:   *  ** * **  :  :*::: :  *.*:*:   : :

ref|YP_148969.1|        AEKYDGKYLIRTSDDTLSAEDVALGYKQLVDIEQAFRTLKSTLELRPMYHRLEDRIRAHV
ref|YP_001126171.1|     AEKYDGKYLIRTSDDTLSAEDVALGYKQLVDIEQAFRTLKSTLELRPMYHRLEDRIRAHV
ref|YP_146154.1|        AEKYDGKYLIRTSDDTLSAEDVALGYKQLVDIEQAFRTLKSTLELRPMYHRLEDRIRAHV
ref|YP_146741.1|        AEKYDGNYLIRTSDDTLSAEDVAIGYKQLVDIEQAFRTLKSTLELRPMYHRLEDRIRAHV
RAAC03182               AAHLDGKYLIRTSDDTLSTEDVALGYKQLMVESAFRTLKTTLDIRPVYHRKDERIRSHV
ref|ZP_02130848.1|      EEKLDGKYLLSCSDDTLSPEEIALGYKQLLEVERAFRTLKSTLDLRPVYHRKDERIRSHV
                        :  **:***  ****** .*::*:****   :* ******:*** :**:**:** ::***:**
``` continued →

FIG. 115 continued

```
ref|YP_148969.1|        LLSWLALLLVRIVEIRTHESWPKVR--------------DECE----------------
ref|YP_001126171.1|     LLSWLALLLVRIVEIRTHESWPKVR--------------DECE----------------
ref|YP_146154.1|        LLSWLALLLVRIVEIRTHESWPKVR--------------DECE----------------
ref|YP_146741.1|        LLSWLALLLVRIVEIRTHESWPKVR--------------DECE----------------
RAAC03182               LLCWLALLLVRIAEVQIGRSWPDIRSHVQGNAPSDAFRRDRCAAHRNDRGAAGDPASLED
ref|ZP_02130848.1|      TLCWLALLLVRLIELETGMTWNQVR-----------------------------------
                        *.********: *:.    :* .:* ref|YP_148969.1|        ------------------------------------
ref|YP_001126171.1|     ------------------------------------
ref|YP_146154.1|        ------------------------------------
ref|YP_146741.1|        ------------------------------------
RAAC03182               QGTAEDPEGRTSNTRAVDTTRVIHRSHESTSDMGLWDFV
ref|ZP_02130848.1|      ------------------------------------
```

FIG. 116

```
ref|YP_148733.1|      ------MDMTLTAKIKIYPTAEQAEVLKATLSAYRQACNAVSVVIFDTKVLA-QAKLHDM
ref|YP_146224.1|      ------MDMTLTAKIKIYPTAEQAEVLKATLSAYRQACNAVSVVIFDTKVLA-QAKLHDM
ref|ZP_02171259.1|    ------MKLTLTAKTKIVPTVEQEDTLRKTAHAYRDACNAVSEVVFDENTLV-QAKLHKR
ref|NP_977687.1|      ---------TITAKIQIHVSDNQAESLKITTNAYRKACNWLSKHIFETKNLN-QVNLNNL
ref|ZP_02619781.1|    ------MEIVRTLKIKLNINQEEKNMINSTLEAFLKALNYASQVAFNNGEITNKPKLQKL
RAAC03163             MREVNGMELTRTIRVRLEPTPEQASALARTVEANRQALDYVSRIAFERKIRN-RVALHRA
                            . *  :  ::   . :: .  :  *  *   . * . *    *:    :  *:

ref|YP_148733.1|      TYRLLRSNYALRSQMAQSVIKTVIARYRSLKSNGHEWTLVRFKKPEYDLVWNRDYSIVQG
ref|YP_146224.1|      TYRLLRSNYALRSQMAQSVIKTVIARYRSLKSNGHEWTLVRFKKPEYDLVWNRDYSIVQG
ref|ZP_02171259.1|    TYRELRSTFGLKSQMAQSALKTVIATYKTNQSNGHERSQVQFKKPQFDLVFNRDYSLTKG
ref|NP_977687.1|      YYSDLRNQFRLKSQMAQSVMKTVIARYKSAKSNGHEWSLIDFKLAEYDLVWNRDYSLTKN
ref|ZP_02619781.1|    VYDDLRTKFNLKSQMAVNTCTTVCSSYVTQHSNKVFNSLAVYKSPKAIYSYGRDYSFLND
RAAC03163             AYRTIRTRFGLRAQMACTVCRVVAGVYKSMKSNGNEDTPAEFKRAKPVFQWNKDYVLRNG
                        *  :*.   : *::***   . .* . * : **    :   :*  .:   :.:** : :.

ref|YP_148733.1|      --LFSVNTLEGRIKVPFEPK-GMEPYFDGSWTFGTAKLVYKHNKFFLHIPMTKTIPTVDE
ref|YP_146224.1|      --LFSVNTLEGRIKVSFEPK-GMEPYFDGSWTFGTAKLVYKHNKFFLHIPMTKTIPTVDE
ref|ZP_02171259.1|    --LFSVNTLEGRIKVPFYTE-GLEPYFDGTWTFGTAKLVHKYGKWFLHIPVSKDVQEANL
ref|NP_977687.1|      --QFSVNTLEGRLKLNYERK-AMKKYFNSTWKFGTAKLVHKYKKWFLHIPMTKEYQTLDF
ref|ZP_02619781.1|    GQTISINTIAKRIKVHFKVNNYFKKYLTKEWSFGSLEIVERENSYYAHITVSKEVQEKPL
RAAC03163             --VAHITTIDGRLRIPFRVEPPYRRYLQDGWTFGAAELVRKRHGWYLHVSVSKSVPD-HA
                        :.* : *::: :         . *:   *.** ::*  :    ::*::.: :* ref|YP_148733.1|      HNIRQVVGVDVGVNFLAAAYDSQGKTTFFNGRKIKHMRAKYKRMRKTLQQKGTASARRKL
ref|YP_146224.1|      HNIRQVVGVDVGVNFLAVAYDSQGKTIFFNGRKIKHMRAKYKRMRKTLQQKGTASARRKL
ref|ZP_02171259.1|    DNINQVVGIDMGVNFTATTYDSNGQTRFFNGKQIKHKRAKYKQMRKELQQKQTPSARRKL
ref|NP_977687.1|      ADVNNIVGVDLGINFLATTYDSQSKTTFYNGNIVKHKRGKFKATRKQLQTRQTPSSRKKI
ref|ZP_02619781.1|    NEFKNIIGIDLGQNFIATFYDSKGKIKFFKGRYLKDMRAKYTRLRKQLQRKGTYNAHKKI
RAAC03163             DDFDAVIGVDQGMRFLVTAS-CGDQVMFIRGGRVKQTRLRYVRLRASLQRKGTRSAKRRL
                       :.   ::*:*  *  .*  ..   . .: * .*  :*. *   ::  *   **  :  *   .:::::

ref|YP_148733.1|      KTIGQRENRWMTDVNHAVTKALVRQYGER---TLFVLEDLTGIREKTERVRIHDRYETVS
ref|YP_146224.1|      KTIGQRENRWMTDVNHAVTKALVRQYGER---TLFVLEDLTGIREKTERVRIHDRYETVS
ref|ZP_02171259.1|    KKIGQRENRWMQNINYCISKALVEQYGKD---TLFVMEDLTGVRNATEKVRVKDRYQTVS
ref|NP_977687.1|      KQIGSRENRYVTDVNHQITKALVEAYPRG---TMFVLEDLTGVRSATEKVRVKNRYVSVS
ref|ZP_02619781.1|    VTINQREQRTMTYINHKISKEIVEYAKQNN--AIIAMENLTGIN-LSCKVKKDNRYYRVS
RAAC03163             KAIGRRESRFMTDVNHQIAKAVVRFAQAQGQRPLIVLEDLTGSN-LSVRFRLKDRYWRMS
                       *.  **.*   :  :*:  ::* :*.        .::.:*:*   .  : :.: ..:  :* ref|YP_148733.1|      WAFYQFRQLLEYKARLHGSKVMVVAPHYTSLTCPKCGHTEKANRNKRTHTFCCRTCGYTS
ref|YP_146224.1|      WAFYQFRQMLEYKARLHGSKVIVVAPHYTSLTCPKCGHTEKANRKKRTHTFCCRTCGYTS
ref|ZP_02171259.1|    WSFNDLRQKIAYKAQKTGALGIAVDPGYTSQTCPKCGHTEKANRNKKTHTFCCQTCQYTS
ref|NP_977687.1|      WAFYQFRQMLEYKAELNGQKVIVVDPKYTSQTCPKCGNIEKANRNKKLHTFKCKNCQYQS
ref|ZP_02619781.1|    WAFNQLQQFIEYKAVQAGLKVIYINPKYTSQTCPICGHIHKDNRNKKLHIFKCRACGCTL
RAAC03163             WAFRQLTDFIRYKAEEAGIAVMFIDPTGTSETCPKCGHCETANRSRKRHEFRCKKCGYRC
                       *:*  ::   : :  ***   *    :  : *   * :  .. .:: * * *: * ref|YP_148733.1|      NDDRIGAMNLQRKGIE--------
ref|YP_146224.1|      NDDRIGAMNLQRKGIE--------
ref|ZP_02171259.1|    NDDRIGAMNLQRKGI---------
ref|NP_977687.1|      NDDRISAMNLHRKGIK--------
ref|ZP_02619781.1|    NDDLIGAKNIQHKGYD--------
RAAC03163             NDDLAASRVIAQKGLECLRQSQSA
                      ***  .:   :   :**
```

FIG. 117

```
ref|YP_148733.1|       --YSIVQGLFSVNTLEGRIKVPFEPKG-MEPYFDGSWTFGTAKLVYKHNKFFLHIPMTKT
ref|YP_146224.1|       --YSIVQGLFSVNTLEGRIKVSFEPKG-MEPYFDGSWTFGTAKLVYKHNKFFLHIPMTKT
ref|ZP_02171259.1|     --YSLTKGLFSVNTLEGRIKVPFYTEG-LEPYFDGTWTFGTAKLVHKYGKWFLHIPVSKD
ref|YP_001396471.1|    --YSLNKNIFSINSLQGRLKIPYQSKG-MEKYFDGSYSFGTAKLVYKFNKYFLHIPVTKD
ref|ZP_02619781.1|     -----------INTIAKRIKVHFKVNNYFKKYLTKEWSFGSLEIVERENSYYAHITVSKE
RAAC01387              MVYVLRSGLAHITTFDGRLRIPYHVEPPYLRYLQDGWTFGAAELVQKRHRWYLHVSVSKT
                              :.::   *:::  :  :       *:    ::**: ::*  :     :: *:.::* ref|YP_148733.1|       IPTVDEHNIRQVVGVDVGVNFLAAAYDSQGKTTFFNGRKIKHMRAKYKRMRKTLQQKGTA
ref|YP_146224.1|       IPTVDEHNIRQVVGVDVGVNFLAVAYDSQGKTIFFNGRKIKHMRAKYKRMRKTLQQKGTA
ref|ZP_02171259.1|     VQEANLDNINQVVGIDMGVNFTATTYDSNGQTRFFNGKQIKHKRAKYKQMRKELQQKQTP
ref|YP_001396471.1|    YPQTTPFEINKIVGIDLGINFLATTYDSFGKATFYQGRHIKAKRGHYKILRKQLQECGSK
ref|ZP_02619781.1|     VQEKPLNEFKNIIGIDLGQNFIATFYDSKGKIKFFKGRYLKDMRAKYTRLRKQLQRKGTY
RAAC01387              APD-PVGDFDAVIGIDQGMRFLITASCGN-QVMFIRGGKVKQTRLRYVRLRASLQRKGTR
                         ::  ::*:*  *  .*  .   .  :   *  .*  :*  * :* :*  **.  :

ref|YP_148733.1|       SARRKLKTIGQRENRWMTDVNHAVTKALVRQYG---ERTLFVLEDLTGIREKTERVRIHD
ref|YP_146224.1|       SARRKLKTIGQRENRWMTDVNHAVTKALVRQYG---ERTLFVLEDLTGIREKTERVRIHD
ref|ZP_02171259.1|     SARRKLKKIGQRENRWMQNINYCISKALVEQYG---KDTLFVMEDLTGVRNATEKVRVKD
ref|YP_001396471.1|    SAKRRIKSIGSRENRYVSDINHQITKSLVDKYG---TNTLFVLEDLTNVRTATEKVTINN
ref|ZP_02619781.1|     NAHKKIVTINQREQRTMTYINHKISKEIVEYAKQ--NNAIIAMENLTGIN-LSCKVKKDN
RAAC01387              SAKRRLKAIGRRESRFMADVNHQIAKAVIRFAQTQGQRPLIVLEDLTGSN-LSVRFRLKD
                       .*::::  *. **.* :   :*: ::* ::           .::.:*:**.   :  :  .:

ref|YP_148733.1|       RYETVSWAFYQFRQLLEYKARLHGSKVMVVAPHYTSLTCPKCGHTEKANRNKRTHTFCCR
ref|YP_146224.1|       RYETVSWAFYQFRQMLEYKARLHGSKVIVVAPHYTSLTCPKCGHTEKANRKKRTHTFCCR
ref|ZP_02171259.1|     RYQTVSWSFNDLRQKIAYKAQKTGALGIAVDPGYTSQTCPKCGHTEKANRKKTHTFCCQ
ref|YP_001396471.1|    RYVSVSWAFYQFRQLLEYKAQMNGSIVMAVNPKYTSQTCPKCGHIEKANRDKKNHIFKCK
ref|ZP_02619781.1|     RYYRVSWAFNQLQQFIEYKAVQAGLKVIYINPKYTSQTCPICGHIHKDNRNKKLHIFKCR
RAAC01387              QYWRMSWSFRQLADFIRYKAEEAGIAVMLVDPAGTSETCPKCGHCEPANRSRKRHFFRCK
                       :*   :**:* :: :  : ***        * : : :** *** ***  . **.::  *  * *:

ref|YP_148733.1|       TCGYTSNDDRIGAMNLQRKGIE--------
ref|YP_146224.1|       TCGYTSNDDRIGAMNLQRKGIE--------
ref|ZP_02171259.1|     TCQYTSNDDRIGAMNLQRKGI---------
ref|YP_001396471.1|    NCSYQSNDDRIGAINLWRKGIEYIEQS---
ref|ZP_02619781.1|     ACGCTLNDDLIGAKNIQHKGYD--------
RAAC01387              RCGYRCNDDLAASRVIAQKGLECLRQSQSA
                        *   ***  .:    :  : :**
```

FIG. 118

```
gb|AAL87775.1|AF403183_11      ------------------------------------------------
ref|ZP_01368657.1|             REFZPTRANSPSASEISDESULFITBACTERIUMHAFNIENSEDCB-GBE
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             ATTRANSPSASEISDESULFITBACTERIUMHAFNIENSEDCB-GBEATT
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             RANSPSASEISDESULFITBACTERIUMHAFNIENSEDCB-GBEATTRAN
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             SPSASEISDESULFITBACTERIUMHAFNIENSEDCB-GBEATTRANSPS
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             ASEISDESULFITBACTERIUMHAFNIENSEDCB-GBEATTRANSPSASE
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             ISDESULFITBACTERIUMHAFNIENSEDCB-GBEATTRANSPSASEISD
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             ESULFITBACTERIUMHAFNIENSEDCB-GBEATTRANSPSASEISDESU
ref|YP_517288.1|               ------------------------------------------------
ref|YP_517659.1|               ------------------------------------------------
ref|YP_001212990.1|            ------------------------------------------------
RAAC03385                      ------------------------------------------------ gb|AAL87775.1|AF403183_11      ------------------------------------------------
ref|ZP_01368657.1|             LFITBACTERIUMHAFNIENSEDCB-GBEATTRANSPSASEISDESULFI
ref|YP_517288.1|               ------------------------------------------------
ref|YP_517659.1|               ------------------------------------------------
ref|YP_001212990.1|            ------------------------------------------------
RAAC03385                      ------------------------------------------------
``` continued →

FIG. 118 continued

```
gb|AAL87775.1|AF403183_11     ------------------------------------------------
ref|ZP_01368657.1|            TBACTERIUMHAFNIENSEDCB-SCRESIGNIFICANCEE-IDENTITIE
ref|YP_517288.1|              ------------------------------------------------
ref|YP_517659.1|              ------------------------------------------------
ref|YP_001212990.1|           ------------------------------------------------
RAAC03385                     ------------------------------------------------ gb|AAL87775.1|AF403183_11     --------------MLQHNSLPEQHQNQLSLIFSSLKLSQLLRAAGIRKSY
ref|ZP_01368657.1|            SPSITIVESGAPSMLQHNSLPEQHQNQLSLIFSSLKLSQLLRAAGIRKSY
ref|YP_517288.1|              --------------MLQHNSLPEQHQNQLSLIFSSLKLSQLLRAAGIRKSY
ref|YP_517659.1|              --------------MLQHNSLPEQHQNQLSLIFSSLKLSQLLRAAGIRKSY
ref|YP_001212990.1|           ----------------------QFYSRVDNFLSRHEIGKILRRSNFQKEK
RAAC03385                     --------------MVRDSQHPDQLQSMVTAFFMEYHIGKLLRQSNITKQA
                                             *  .  :   ::   .:.::** :.: *.

gb|AAL87775.1|AF403183_11     GVSSFVVFQIIFQLVFQGRNLFRLLEGSRAESLPGKDVVYRFLNDSRYNW
ref|ZP_01368657.1|            GVSSFVVFQIIFQLVFQGRNLFRLLEGSRAESLPGKDVVYRFLNDSRYNW
ref|YP_517288.1|              GVSSFVVFQIIFQLVFQGRNLFRLLEGSRAESLPGKDVVYRFLNDSRYNW
ref|YP_517659.1|              GVSSFVVFQIIFQLVFQGRNLFRLLEGSRAESLPGKDVVYRFLNDSRYNW
ref|YP_001212990.1|           GFSCLELFKFIFLLVFKGKNLYRTLQSEAEPGRPEKDTIYRFLNSFRYNW
RAAC03385                     GIPVLEVFRLLFALVFHQRSLKRVLEQLAMN-QFGKDTVYRFLNSPRHNW
                              *..  :  :*:::* ***: :.* * *:      **.:*****. *:**

gb|AAL87775.1|AF403183_11     RRFYQLLSLKMVGRFEK-LTSAQRIRVFIVDDSVMERERSKKVELLARVF
ref|ZP_01368657.1|            RRFYQLLSLKMVGRFEK-LTSAQRIRVFIVDDSVMERERSKKVELLARVF
ref|YP_517288.1|              RRFYQLLSLKMVGRFEK-LTSAQRIRVFIVDDSVMERERSKKVELLARVF
ref|YP_517659.1|              RRFYQLLSLKMVGRFEK-LTSAQRIRVFIVDDSVMERERSKKVELLARVF
ref|YP_001212990.1|           RKFLLILSSSVINETIEPLTSRNWKNVLVLDDSLYSRNRSKAVELLARVK
RAAC03385                     RRFLLLLSSAVVRRTAR-LTSEDRADVFIVDDSLFSRSRSKKVELLAKVY
                              *:*  :  ::  .   *  :   *:::***:.*.* ***:* gb|AAL87775.1|AF403183_11     DHV-----------------------------------------------
ref|ZP_01368657.1|            DHV-----------------------------------------------
ref|YP_517288.1|              DHV-----------------------------------------------
ref|YP_517659.1|              DHV-----------------------------------------------
ref|YP_001212990.1|           DHV-----------------------------------------------
RAAC03385                     DHVLRSNLLTEQPASIPSGDYYFDGMVYSPAGVNRPYAHPDKGYYGISPY
                              *** gb|AAL87775.1|AF403183_11     --------------------------------------------------
ref|ZP_01368657.1|            --------------------------------------------------
ref|YP_517288.1|              --------------------------------------------------
ref|YP_517659.1|              --------------------------------------------------
ref|YP_001212990.1|           --------------------------------------------------
RAAC03385                     VTWHRVGNQDLHCQIDYYDSQSILEAPAWAVGSGVGALVGGMVTDGNLTG gb|AAL87775.1|AF403183_11     --------------------------------------------------
ref|ZP_01368657.1|            --------------------------------------------------
ref|YP_517288.1|              --------------------------------------------------
ref|YP_517659.1|              --------------------------------------------------
ref|YP_001212990.1|           --------------------------------------------------
RAAC03385                     SVIGAIIGGALGAYYGAQVERLADENGCIWFTIDNNPPIVNLGTWWAPEW gb|AAL87775.1|AF403183_11     -------------------------
ref|ZP_01368657.1|            -------------------------
ref|YP_517288.1|              -------------------------
ref|YP_517659.1|              -------------------------
ref|YP_001212990.1|           -------------------------
RAAC03385                     YMDVRYIELGPWATTNFYYYLGGVY
```

FIG. 119

```
ref|YP_001126171.1|    MDELLAVQPELERQVFHAVADLLNLEVDLIYFDTTSSYFEVDPSETPEGESLRKQGFSKD
ref|YP_148969.1|       MDELLAVQPELERQVFHAVADLLNLEVDLIYFDTTSSYFEVDPSETPEGESLRKQGFSKD
ref|YP_146154.1|       MDELLAVQPELERQVFHAVADLLNLEVDLIYFDTTSSYFEVDPSETPEGESLRKQGFSKD
ref|YP_146741.1|       MDELLAVQPELERQVFHAVADLLNLEVDLIYFDTTSSYFEVDPSETPEGESLRKQGFSKD
ref|ZP_02172080.1|     MDELLSVQKQLEDRVFDHVSNLLNLEVDLLYFDTTSSYFEVASDETPEEDDFRLQGYSKD
RAAC03398              MDFLHDVAEDLQYEVFRRVSDLLNLDVDLLFFDTTSTYFETE-DES--DDSLRRKGYSKD
                       ** *  *   *  :*: .**  *::**:*::***:*.  .*:    :..:* :*:*** ref|YP_001126171.1|    KRPDLVQIVIGLAVTREGVPIRAWVWPGNTMDMTVIKQVKQDLIGWKLGRVISVMDRGFS
ref|YP_148969.1|       KRPDLVQIVIGLAVTREGVPIRAWVWPGNTMDMTVIKQVKQDLIGWKLGRVISVMDRGFS
ref|YP_146154.1|       KRPDLVQIVIGLAVTREGVPIRAWVWPGNTMDMTVIKQVKQDLIGWKLGRVISVMDRGFS
ref|YP_146741.1|       KRPDLVQIVIGLAVTREGIPIRAWVWPGNTMDMTVIKQVKQDLIGWKLGRVISVMDRGFS
ref|ZP_02172080.1|     KRSDLVQVVIGLAVTREGIPIKVWTWPGNTMDMNVVEEVKKDLMGWRLGRVVKVMDRGFS
RAAC03398              HRPDLPQVVIGLAVTRDGIPVRCWTWPGNTADMSVVEEVKQDLIGWRLGRVITVVDRGFV
                       :*.**  *:********:*:*::  *.***  .*::::.:**: :*:**** ref|YP_001126171.1|    SEENLRILQQAGGHYIVGEKMRSGKAAVEEALNRRGRYQQVRENLHIKEIIVGDGEARQR
ref|YP_148969.1|       SEENLRILQQAGGHYIVGEKMRSGKAAVEEALNRRGRYQQVRENLHIKEIIVGDGEARQR
ref|YP_146154.1|       SEENLRILQQAGGHYIVGEKMRSGKAAVEEALNRRGRYQQVRENLHIKEIIVGDGEARQR
ref|YP_146741.1|       SEENLRILQQAGGHYIVGENMRSGKAAVEEALSRRGRYHEVDENLHIKEIIVGDGEARQR
ref|ZP_02172080.1|     SEKNLRILQRGAGHYIIGERMRSGKKDVEEALSKRGRFHKVRENLHVKESIVGDGEARKR
RAAC03398              SESNLRILQRAGGHCIAGEKMTSGKPAVEAALARPGRFRELRPNLKVKEVVVGDGEARVR
                       .**:.. * **.* *     :  ::::   :: :****** * ref|YP_001126171.1|    YVLVYNPSEAERQRKEREKLLESLKEELEGLRQLPNEAHHKATCRLRSHPSYGKYLRQLK
ref|YP_148969.1|       YVLVYNPSEAERQRKEREKLLESLKEELEGLRQLPNEAHHKATCRLRSHPSYGKYLRQLK
ref|YP_146154.1|       YVLVYNPSEAERQRKEREKLLESLKEELEGLRQLPNEAHHKATCRLRSHPSYGKYLRQLK
ref|YP_146741.1|       YVLVYNPGEAERQRKERETLLESLKEELEGLRQLPNEAHHKATCRLRSHPSYGKYLRQLK
ref|ZP_02172080.1|     YVIAFNPDEAIRDREKRQEIVRSVEEQLHHLKQLPNEAHHKQACALRAHKVYGKYIRQLK
RAAC03398              YVLAFNPEEAKRDEARREAMLRELRMELERLKELQGEAHTKAHCRLASHPTFKRYLKQDR
                       **:..:** ** *:. .*: ::..:.  :*. *:*  .*** *    *  :*   : :*::*  :

ref|YP_001126171.1|    DGTLRIDKQAVREAEKYDGKYLIRTSDDTLSAEDVALGYKQLVDIEQAFRTLKSTLELRP
ref|YP_148969.1|       DGTLRIDKQAVREAEKYDGKYLIRTSDDTLSAEDVALGYKQLVDIEQAFRTLKSTLELRP
ref|YP_146154.1|       DGTLRIDKQAVREAEKYDGKYLIRTSDDTLSAEDVALGYKQLVDIEQAFRTLKSTLELRP
ref|YP_146741.1|       DGTLRIDKQAVRDAEKYDGNYLIRTSDDTLSAEDVAIGYKQLVDIEQAFRTLKSTLELRP
ref|ZP_02172080.1|     DGTLKLNKQAVREADEKYDGKYLIRTSDDTLSIEDVALGYKQLLQVEDAFRTMKTTLVLRP
RAAC03398              WGNLRIDPEAVRQAAHLDGKYLIRTSDDTLSTEDVALGYKQLLMVESAFRTLKTTLDIRP
                       *.*::: :***:*  : **:*********** ****:*****: :*.**** *:** :**

ref|YP_001126171.1|    MYHRLEDRIRAHVLLSWLALLLVRIVEIRTHESWPKVRDECERLMLGHFSSKNGDLYQRT
ref|YP_148969.1|       MYHRLEDRIRAHVLLSWLALLLVRIVEIRTHESWPKVRDECERLMLGHFSSKNGDLYQRT
ref|YP_146154.1|       MYHRLEDRIRAHVLLSWLALLLVRIVEIRTHESWPKVRDECERLMLGHFSSKNGDLYQRT
ref|YP_146741.1|       MYHRLEDRIRAHVLLSWLALLLVRIVEIRTHESWPKVRDECERLMLGHFSSKNGDLYQRT
ref|ZP_02172080.1|     MYHRLEDRIRAHVIISWLALLLVRMIELDTNESWNTVRRNIQRLQAGHFTTSDGDLYRTT
RAAC03398              MYHRKDERIRSHVLLCWLALLLVRIAEVQTGRSWPDIRSHMQAMHQVTKSTPDGIVVQRT
                       ** ::*:::.******:   : * .**  :* .  : :      :: :* : : * ref|YP_001126171.1|    ELTAKQALFLAALGLEPPPKILGIHPRT---
ref|YP_148969.1|       ELTAKQALFLAALGLEPPPKILGIHPRT---
ref|YP_146154.1|       ELTAKQALFLAALGLEPPPKILGIHPRT---
ref|YP_146741.1|       ELTAKQAQLFAALGLEPPPKILGIHPR----
ref|ZP_02172080.1|     TPTAKQKEIFRNTGTEIPPEILAIRPKS---
RAAC03398              ETTEVQWEILRALRITEPPRILRMEPRTRGL
                         *    *  ::         **.**  :.*:
```

FIG. 120

```
ref|YP_148969.1|      --PSSKLAMEEWVEKDVHIPHLPQVASHQLYRAMDELLAVQPELERQVFHAVADLLNLEV
ref|YP_146154.1|      --PSSKLAMEEWVEKDVHIPHLPQVASHQLYRAMDELLAVQPELERQVFHAVADLLNLEV
ref|YP_001126171.1|   --PSSKLAMEEWVEKDVHIPHLPQGASHQLYRAMDELLAVQPELERQVFHAVADLLNLEV
ref|YP_146741.1|      --PSSKLAMEEWVEKDVYIPHLPQVASHQLYRAMDELLAVQPELERQVFHAVADLLNLEV
ref|ZP_02172080.1|    LAPSSKLVMEEWLSEDVYLPDMPVFKSHQLYRSMDELLSVQKQLEDRVFDHVSNLLNLEV
RAAC03177             MAPSSKLAMEEWVDREVALPGMTELDVWQAYRAMDFLHDVAEDLQYEVFRRVSDLLNLDV
                       **.**:..:* :* :.     * : * *   *:..** *::****:* ref|YP_148969.1|      DLIYFDTTSSYFEVDPSETPEGESLRKQGFSKDKRPDLVQIVIGLAVTREGVPIRAWVWP
ref|YP_146154.1|      DLIYFDTTSSYFEVDPSETPEGESLRKQGFSKDKRPDLVQIVIGLAVTREGVPIRAWVWP
ref|YP_001126171.1|   DLIYFDTTSSYFEVDPSETPEGESLRKQGFSKDKRPDLVQIVIGLAVTREGVPIRAWVWP
ref|YP_146741.1|      DLIYFDTTSSYFEVDPSETPEGESLRKQGFSKDKRPDLVQIVIGLAVTREGIPIRAWVWP
ref|ZP_02172080.1|    DLLYFDTTSSYFEVASDETPEEDDFRLQGYSKDKRSDLVQVVIGLAVTREGIPIKVWTWP
RAAC03177             DLLFFDTTSTYFETE--DEPE-DGLRRKGYSKDHRPDLPQVVIRLAVTDGIPVRCWTWP
                      **:.******:***.   : ** ..:* :*:***:*.** *:** *****:*:*:: *.**

ref|YP_148969.1|      GNTMDMTVIKQVKQDLIGWKLGRVISVMDRGFSSEENLRILQQAGGHYIVGEKMRSGKAA
ref|YP_146154.1|      GNTMDMTVIKQVKQDLIGWKLGRVISVMDRGFSSEENLRILQQAGGHYIVGEKMRSGKAA
ref|YP_001126171.1|   GNTMDMTVIKQVKQDLIGWKLGRVISVMDRGFSSEENLRILQQAGGHYIVGEKMRSGKAA
ref|YP_146741.1|      GNTMDMTVIKQVKQDLIGWKLGRVISVMDRGFSSEENLRILQQAGGHYIVGENMRSGKAA
ref|ZP_02172080.1|    GNTMDMNVVEEVKKDLMGWRLGRVVKVMDRGFSSEKNLRILQRGAGHYIIGERMRSGKKD
RAAC03177             GNTADMSVVEEVKQDLIGWRLGRVITVVDRGFVSESNLRILQRAGGHYIAGEKMTSGKPA
                      *..*::::*:::****:.*:** .****::... .* *** ref|YP_148969.1|      VEEALNRRGRYQQVRENLHIKEIIVGDGEARQRYVLVYNPSEAERQRKEREKLLESLKEE
ref|YP_146154.1|      VEEALNRRGRYQQVRENLHIKEIIVGDGEARQRYVLVYNPSEAERQRKEREKLLESLKEE
ref|YP_001126171.1|   VEEALNRRGRYQQVRENLHIKEIIVGDGEARQRYVLVYNPSEAERQRKEREKLLESLKEE
ref|YP_146741.1|      VEEALSRRGRYHEVDENLHIKEIIVGDGEARQRYVLVYNPSEAERQRKERETLLESLKEE
ref|ZP_02172080.1|    VEEALSKRGRFHKVRENLHVKESIVGDGEARKRYVIAFNPDEAIRDREKRQEIVRSVEEQ
RAAC03177             VEAALARPGRFRELRPNLKVKEVVVGDGEARVRYVLAFNPEEAKRDEARREAMLRELRME
                      ** ** :  **:::: **::** :******* ***:..** **  *:.  .*:   :...:   :

ref|YP_148969.1|      LEGLRQLPNEAHHKATCRLRSHPSYGKYLRQLKDGTLRIDKQAVREAEKYDGKYLIRTSD
ref|YP_146154.1|      LEGLRQLPNEAHHKATCRLRSHPSYGKYLRQLKDGTLRIDKQAVREAEKYDGKYLIRTSD
ref|YP_001126171.1|   LEGLRQLPNEAHHKATCRLRSHPSYGKYLRQLKDGTLRIDKQAVREAEKYDGKYLIRTSD
ref|YP_146741.1|      LEGLRQLPNEAHHKATCRLRSHPSYGKYLRQLKDGTLRIDKQAVRDAEKYDGNYLIRTSD
ref|ZP_02172080.1|    LHHLKQLPNEAHHKQACALRAHKVYGKYIRQLKDGTLKLNKQAVRDAEKYDGKYLIRTSD
RAAC03177             LERLKELQGEAHTKAHCRLASHPTFKRYLKQDRWGNLRIDPEAVRQAAHLDGKYLIRTSD
                      *. *::* .***  *   *  *   : :*::*   : *.*::: :**  :   :******* ref|YP_148969.1|      DTLSAEDVALGYKQLVDIEQAFRTLKSTLELRPMYHRLEDRIRAHVLLSWLALLLVRIVE
ref|YP_146154.1|      DTLSAEDVALGYKQLVDIEQAFRTLKSTLELRPMYHRLEDRIRAHVLLSWLALLLVRIVE
ref|YP_001126171.1|   DTLSAEDVALGYKQLVDIEQAFRTLKSTLELRPMYHRLEDRIRAHVLLSWLALLLVRIVE
ref|YP_146741.1|      DTLSAEDVAIGYKQLVDIEQAFRTLKSTLELRPMYHRLEDRIRAHVLLSWLALLLVRIVE
ref|ZP_02172080.1|    DTLSIEDVVLRPMKTTLVLRPMYHRLEDRIRAHVIISWLALLLVRMIE
RAAC03177             DTLSTEDVALGYKQLLMVESAFRTLKTTLDIRPMYHRKDERIRSHVLLCWLALLLVRIAE
                      ** .***: :*.****:*: :** ::*:::.******:. * ref|YP_148969.1|      IRTHESWPKVRDECERLMLGHFSSKNGDLYQRTELTAKQALFLAALGLEPPPKILGIHPR
ref|YP_146154.1|      IRTHESWPKVRDECERLMLGHFSSKNGDLYQRTELTAKQALFLAALGLEPPPKILGIHPR
ref|YP_001126171.1|   IRTHESWPKVRDECERLMLGHFSSKNGDLYQRTELTAKQALFLAALGLEPPPKILGIHPR
ref|YP_146741.1|      IRTHESWPKVRDECERLMLGHFSSKNGDLYQRTELTAKQAQLFAALGLEPPPKILGIHPR
ref|ZP_02172080.1|    LDTNESWNTVRRNIQRLQAGHFTTSDGDLYRTTTPTAKQKEIFRNTGTEIPPEILAIRPK
RAAC03177             VQTGRTWADIRSHMQAMHRVTKSTPEGIVVQRTETTEVQREILRALRITEPPRILRMEPR
                      : *  ..:*  :*  . :  ::  :: :  * * *  *   :: :*  * ** **:.*:

ref|YP_148969.1|      T---
ref|YP_146154.1|      T---
ref|YP_001126171.1|   T---
ref|YP_146741.1|      ----
ref|ZP_02172080.1|    S---
RAAC03177             TRGL
```

FIG. 121

```
ref|YP_074105.1|         ------------------------------------------------------------
ref|YP_076073.1|         ------------------------------------------------------------
ref|YP_001036724.1|      TRANSPSASEMUTATRTYPECLSTRIDIUMTHERMCELLUMATCCGBABNTRANSPSASE
ref|YP_001039064.1|      ------------------------------------------------------------
ref|YP_001039349.1|      ------------------------------------------------------------
RAAC03588                ------------------------------------------------------------ ref|YP_074105.1|         ------------------------------------------------------------
ref|YP_076073.1|         ------------------------------------------------------------
ref|YP_001036724.1|      MUTATRTYPECLSTRIDIUMTHERMCELLUMATCCGBABNTRANSPSASEMUTATRTYPE
ref|YP_001039064.1|      ------------------------------------------------------------
ref|YP_001039349.1|      ------------------------------------------------------------
RAAC03588                ------------------------------------------------------------ ref|YP_074105.1|         ------------------------------------------------------------
ref|YP_076073.1|         ------------------------------------------------------------
ref|YP_001036724.1|      CLSTRIDIUMTHERMCELLUMATCCGBABNTRANSPSASEMUTATRTYPECLSTRIDIUM
ref|YP_001039064.1|      ------------------------------------------------------------
ref|YP_001039349.1|      ------------------------------------------------------------
RAAC03588                ------------------------------------------------------------ ref|YP_074105.1|         ------------------------------------------------------------
ref|YP_076073.1|         ------------------------------------------------------------
ref|YP_001036724.1|      THERMCELLUMATCCGBABNTRANSPSASEMUTATRTYPECLSTRIDIUMTHERMCELLU
ref|YP_001039064.1|      ------------------------------------------------------------
ref|YP_001039349.1|      ------------------------------------------------------------
RAAC03588                ------------------------------------------------------------ ref|YP_074105.1|         ------------------------------------------------------------
ref|YP_076073.1|         ------------------------------------------------------------
ref|YP_001036724.1|      MATCCGBABNTRANSPSASEMUTATRTYPECLSTRIDIUMTHERMCELLUMATCCGBABN
ref|YP_001039064.1|      ------------------------------------------------------------
ref|YP_001039349.1|      ------------------------------------------------------------
RAAC03588                ------------------------------------------------------------ ref|YP_074105.1|         ------------------------------------------------------------
ref|YP_076073.1|         ------------------------------------------------------------
ref|YP_001036724.1|      TRANSPSASEMUTATRTYPECLSTRIDIUMTHERMCELLUMATCCGBABNTRANSPSASE
ref|YP_001039064.1|      ------------------------------------------------------------
ref|YP_001039349.1|      ------------------------------------------------------------
RAAC03588                ------------------------------------------------------------ ref|YP_074105.1|         ------------------------------------------------------------
ref|YP_076073.1|         ------------------------------------------------------------
ref|YP_001036724.1|      MUTATRTYPECLSTRIDIUMTHERMCELLUMATCCSCRESIGNIFICANCEE-IDENTIT
ref|YP_001039064.1|      ------------------------------------------------------------
ref|YP_001039349.1|      ------------------------------------------------------------
RAAC03588                ------------------------------------------------------------ ref|YP_074105.1|         ---------------VISDAHEGLRQAIAEVLQGAAWQRCRVHFMRNLLGYVPKPAQSMV
ref|YP_076073.1|         ----------------ISDSHVGLQEAIRTVLSGASWQRCRVHFMRNLLSYVPKHWQSMV
ref|YP_001036724.1|      IESPSITIVESGAPSVISDAHEGLKAAIKKILTGSAWQRCRVHFMRNVLSQVPKHYQGMV
ref|YP_001039064.1|      ---------------VISDAHEGLKAAIKKILTGSAWQRCRVHFMRNVLSQVPKHYQGMV
ref|YP_001039349.1|      ---------------VISDAHEGLKAAIKKILTGSAWQRCRVHFMRNVLSQVPKHYQGMV
RAAC03588                ---------------MVSDAHAGLRQAISEVLTGATWQRCKVHTIRNVLSQVPKREQSMV
                                         :**:* **: **  :* *::****:** :**:*. ***  *.**
``` continued →

FIG. 121 continued

```
ref|YP_074105.1|        AALVRTVFAQPDIEAAREQLDRVVASLGRRYPKVAALLSEAAEDVLAYMAFPREHWQKIH
ref|YP_076073.1|        AAAVRTIFAQPDQQAARRQLAVVADNLRPQFPRAAQLLEEAEDDILAYMAFPTEHWRQLH
ref|YP_001036724.1|     SSIIRTIFAQNDQESAREQLRHVVDELKNRFPKAMKILEEAEEEILAYMAFPREHWAQIH
ref|YP_001039064.1|     SSIIRTIFAQNDQESAREQLRHVVDELKNRFPKAMKILEEAEEEILAYMAFPREHWAQIH
ref|YP_001039349.1|     SSIIRTIFAQNDQESAREQLRHVVDELKKRFPKAMKILEEAEEEILAYMAFPREHWAQIH
RAAC03588               ASIIRSIFTQPTQEAAREQLRRVVAELRGRFPKAMDILEAAEEDVLAFMALPIEHWRQIC
                        ::  :*::*:*     ::**.**   *, .*   ::*:,    :*. *  :::**:**:* *** ::

ref|YP_074105.1|        STNPLERLMREIGRRVDVVGIFPNAAAALRLIGAVLQEQEDEWRVQ-RRYLSMQSMAKLA
ref|YP_076073.1|        STNPLERLNREIGRRTDVVGIFPNREAVIRLAGAVLIEQQDEWTAAPRRYFSQASMAKL-
ref|YP_001036724.1|     STNPLERLNREIRRRTDVVCIFPNREAVIRLVGAMLMEQNDEWKVG-RRYFSLESMSKIT
ref|YP_001039064.1|     STNPLERLNREIRRRTDVVCIFPNRKAVIRLVGAMLMEQNDEWKVG-RRYFSLESMSKIT
ref|YP_001039349.1|     STNPLERLNREIRRRTDVVCIFPNREAVIRLVGAMLMEQNDEWKVG-RRYFSLESMSKTT
RAAC03588               STNPLERLNREMRRRMDVVGIFPNRASVVRLAGAILQEQHEEWLVS-RRYFSLESMAKLK
                        ********  **:  ** *** ****   :.:**  **:*  **.:**   .  ***:*   **:*:

ref|YP_074105.1|        ------LTPSEP---
ref|YP_076073.1|        ---------------
ref|YP_001036724.1|     SINEFTLTPVALLHK
ref|YP_001039064.1|     SINEFTLTPVALLHK
ref|YP_001039349.1|     SINEFTLTPVALLHK
RAAC03588               P-NRPLLAAEAMLQK
```

FIG. 122

```
ref|NP_634718.1|           ---------------------------------MLKTEEWLLIRDLYSQGFSISEIA
ref|NP_616807.1|           ---------------------------------MLKTEEWLSIRDLYSQGFSISEIS
ref|YP_074959.1|           --------------------------------MLRSGETLEIRQMYAGGLSISEIA
gb|AAR99616.1|             ----------------------------------------IKEMYERGMSISDIA
sp|Q45618|TRA6_BACST       ----------------------------------------IKEMYERGMSISDIA
RAAC03818                  MRIPQDHRPQFLKIIGMNSPPPCRIVAPVIRSWEVPVMREDERMEIRQLYEAGVSISELA
                                                                   *:::*   *.***:::

ref|NP_634718.1|           KQTGFDRKTVRKYLRLKTLPEPQ--KRSGRKSKLDPFKP----
ref|NP_616807.1|           RRTGYARETVRKYL-----------------------------
ref|YP_074959.1|           RRTGRDRKTIRKWLRTNTMPKPA--KRKR--------------
gb|AAR99616.1|             RELGIDRKTVRKYIHSPNPPSKS--KRKQ--------------
sp|Q45618|TRA6_BACST       RELGIDRKTVRKYIHSPNPPSKS--KRKQ--------------
RAAC03818                  RRFGYDRKTIRNALNSSLERSRAQERRVGSERKVPSWSPTRIT
                           :. *   *:*:*: :
```

FIG. 123

```
ref|YP_594046.1|   LKGRIEQGVLSAVVLFREVQERGYQGQYTVVKDFVRPFRRTQVSAARVTTRFETAPGEQA
RAAC03819          MKQRMQLGVLNAERILREIREQGYTGGITVLREFMKPLR--PVVSAKATERYESDPGEQA
ref|YP_074959.1|   --EQMQKGVTSASKMLYLLQQRGFKGKIRIVRAFMAPYR--PMAKAAATVRFETPPGKQA
ref|YP_359963.1|   IQELMNLGIFNCEVIYERIKEEGYTGGRTILRDYVRQFR--PPKQVPAVCRYETKPGQQA
ref|YP_361300.1|   IQELMNLGIFNCEVIYERIKEEGYTGGRTILRDYVRQFR--PPKQVPAVCRYETKPGQQA
ref|NP_622784.1|   ----INMGIFNCEVIYERIKEEGYTGGKTILRDYVRQFR--PSKHIQAVCRYETKSGEQA
                       ::  *:  ..   :       :::.*: *    :::  ::     *        .. *:*:  .*:*:**

ref|YP_594046.1|   QVDFGRYSYLNLE-GQTRSIWAFVMVLGWSRALYVEFIRKADTASFIRCHLNAFAYFGGM
RAAC03819          QIDLGAFPYYDSH-GQRRTIWAFAMVLAYSRMLYVEFIKAADQLHILQALRNALEFFGGV
ref|YP_074959.1|   QVDWADFGYIEVD-GRRLKLYCFIMVLAYSRAMYLEFVTATDMKTFMRCHINAFKFFGGV
ref|YP_359963.1|   QVDWGEYTYIDEETGEIRKLYVFVMVLGYSRAIYVEFTNRCDVRTFIRCLIHGFEYFGGV
ref|YP_361300.1|   QVDWGEYTYIDEETGEIRKLYVFVMVLGYSRAIYVEFTNRCDVHTFIRCLIHGFEYFGGV
ref|NP_622784.1|   QVDWGEYNYIDQETGEVRKLYLFVMVLGYSRAMYVEFTNRCDVHTFNRCLIHGFEYFGGV
                   *:*  .  :   *  :  .  *.  .::  *  ***.:**  :*:**    *     :  :.   ..: :***:

ref|YP_594046.1|   TQSILYDNTKQVVLERDETG-----------------------------------
RAAC03819          PRVMLSDNCSPLVVANDGQGHVDCNRLISILPSSTDSCPRHVGLAGAAPRAR
ref|YP_074959.1|   PHEILYDNVKTVVKDRD------------------------------------
ref|YP_359963.1|   TDIVLTDRMKTVIL---------------------------------------
ref|YP_361300.1|   TDIVLTDRMKTVIL---------------------------------------
ref|NP_622784.1|   TDVVLTDRMKTVIIGTDANKKPIWNAVFEDLAATLGFVPR-------------
                      .  :*  *. . .  ::
```

FIG. 124

```
ref|ZP_01695687.1|   LVLNILCSGKPLYKVHEFYQNLDSEMLF--DTSVSPDQLNDDALGRALDYLYEA-EAWKV
ref|ZP_01695982.1|   LVLNILCSGKPLYKVHEFYQNLDSEMLF--DTSVSPDQLNDDALGRALDYLYEA-EAWKV
ref|ZP_01695971.1|   LVLNILCSGKPLYKVHEFYQNLDSEMLF--DTSISPDQLNDDALGRALDYLYKA-EAWKV
ref|ZP_01695655.1|   LVLNILCSGKPLYKVHEFYQNLDSEMLF--DTSISPDQLNDDALGRALDYLYKA-EAWKV
ref|YP_430569.1|     LIINLLVDREALYHVERFYENQDLEVLFGAEQQVRPEDFNDDALGRALDKLFTSGQLKKL
RAAC03823            MLVNIGTNREALYRVEFFYAQRDVEVLLG--SGVSADDLHDDALARALDALYDA-GLEAL
                     :::*:  . :.**:*..** : * *:*:     : .::::****.**** *: :    :

ref|ZP_01695687.1|   YSTLALKTLKKLNLP-----IGILHNDTTSISVYGEYKQPKEDGLQITYGYSKAHRPDLK
ref|ZP_01695982.1|   YSTLALKALKKLNLP-----IGILHNDTTSISVYGEYKQPKEDGLQITYGYSKAHRPDLK
ref|ZP_01695971.1|   YSTLALKALKKLNLP-----IGVLHNDTTSISVYGEYKQPKEDGLQITYGYSKAHRPDLK
ref|ZP_01695655.1|   YSTLALKALKKLNLP-----IGVLHNDTTSISVYGEYKQPKEDGLQITYGYSKAHRPDLK
ref|YP_430569.1|     FSSIALTAAATHNVS-----IAGIHVDTTSISVQGAYDG--EGDLDITFGFSKDHRPDLK
RAAC03823            YARIALHTLRRLRVLSDSNELIPIHADTTSLSMTGEYLD--QTAFRIDRGFSKDHRPDLK
                     ::  :**  :   .:     :  :* ****:*: * *       : *  *: **** ref|ZP_01695687.1|   QIVLGMCVTPERIPILAKVENGNTSDKSWNVEFIQKMRKILSHEDWKNLIYQADSALITT
ref|ZP_01695982.1|   QIVLGMCVTPERIPILAKVENGNTSDKSWNVEFIQKMRKILSHEDWKNLIYQADSALITT
ref|ZP_01695971.1|   QIVLGMGVTPERIPILAKVENGNTSDKSWNVEFIQKMRKILSHEDWKNLIYQADSALITT
ref|ZP_01695655.1|   QIVLGMGVTPERIPILAKVENCNTSDKSWNVEFIQKMRKILSHEDWKNLIYQADSALITT
ref|YP_430569.1|     QFLIGLTVNRDGLPILAQSLDGNSSDKSWYPQVIEELVQTFKPEKLKEVIFVADCALVTK
RAAC03823            QIVFGL-CTVHGLGLCANVNPGNLDDHTWNFENIQQLLSQLDEETRKRSVYVADAALVTK
                     *:::*:   .  . : *:     ** .*::*  : *:::  :. * *:. :: **.**:*.

ref|ZP_01695687.1|   ENLAEIQQQN-----LSFISRLPDTFGLSTELKKEAWLLNN-WERVGSLSNKKDAAIYQI
ref|ZP_01695982.1|   ENLAEIQQQN-----LSFISRLPDTFGLSTELKKEAWLLNN-WERVGSLSNKKDAAIYQI
ref|ZP_01695971.1|   ENLAEIQQQN-----LSFISRLPDTFGLSTELKKEAWLLNN-WERVGSLSNKKDAAIYQI
ref|ZP_01695655.1|   ENLAEIQQQN-----LSFISRLPDTFGLSTELKKEAWLLNN-WERVGSLSNKKDAAIYQI
ref|YP_430569.1|     DNLALLVQEEGNKPALQFISLLPENFGLNKEIKAEAFRTGT-WQEIGKLSPKKDAACYKS
RAAC03823            DNLELLAEED-----FHFISRLPGTYKLSEDLKRAAWEKENSWKEVGRLAEAEDSAHYRI
                     :**  :  ::      : *** **  .: *. ::*  *:    . *:.:* *:  :*:* *:

ref|ZP_01695687.1|   QAFERQIQNLPYRFLVVHSNNLDQRKEKTLNRAIEKEEIQLKKEIEKLSKVIFHCKEDAL
ref|ZP_01695982.1|   QAFERQIQNLPYRFLVVHSNNLDQRKEKTLNRAIEKEEIQLKKEIEKLSKVIFHCKEDAL
ref|ZP_01695971.1|   QAFERQIQNLPYRFLVVHSNNLDQRKEKTLNRAIEKEEIKLKKEIEKLSKVIFHCKEDAL
ref|ZP_01695655.1|   QAFERQIQNLPYRFLVVHSNNLDQRKEKTLNRAIEKEEIQLKKEIEKLSKVIFHCKEDAL
ref|YP_430569.1|     QSFVREIDGRDYRLIVVHSTTLDKRKENSLLKKWAKQREVLEKAAKDLSRRPFACKADAR
RAAC03823            QAFRRTLYGRTYRFVVVRSSSLDTRKERKLKEVLKREKAAILEKAAKAMSQNVYSCEQDAQ
                     *:*  *  :   **:::**:*.. ** ***..*  .    ::  *:*  :  : *: **

ref|ZP_01695687.1|   EAIQSFKKKQKASYFCYKLNVQMSDQPIKRKKRGRPKKDEQTK-REQIYQIQLESFEKDH
ref|ZP_01695982.1|   EAIQSFKKKQKASYFCYKLNVQMSDQPIKRKKRGRPKKDEQTK-REQIYQIQLESFEKDH
ref|ZP_01695971.1|   EAIQSFKKKQKASYFCYKLNVQMSDQPIKRKKRGRPKKDEQTK-REQIYQIQLESFEKDH
ref|ZP_01695655.1|   EAIQSFKKKQKASYFCYKLNVQMSDQPIKRKKRGRPKKDEQTK-REQIYQIQLESFEKDH
ref|YP_430569.1|     KAIELFLREYR-------------------------------------------------
RAAC03823            MAMQTFMHEHRATLHPISARICAEQVQAKRARRGRPRKDDPPPPVHTQYRVEVAILPPSE
                     *:: *   ::  :

ref|ZP_01695687.1|   DFIENKKKMLSTFVLITNKLDEETLSNQEVLRVYKCQSAAETRFRLIKDSQMIDAIYLKT
ref|ZP_01695982.1|   DFIENKKKMLSTFVLITNKLDEETLSNQEVLRVYKGQSAAETRFRLIKDSQMIDAIYLKT
ref|ZP_01695971.1|   DFIENKKRMLSTFVLITNKLDEETLSNQEVLRVYKGQSAVETRFRLIKDSQMIDAIYLKT
ref|ZP_01695655.1|   DFIENKKKMLSTFVLITNKLDEETLSNQEVLRVYKGQSAAETRFRLIKDSQMIDAIYLKT
ref|YP_430569.1|     ------------------------------------------------------------
RAAC03823            ERVQQWREKEATFVLTDIRDDQRVSDEQILRLYKEQHEVEARFRYLKSPYHVGPIYLHK ref|ZP_01695687.1|   PERVEALGIVYVMALLIYGILEYRVRKELKEKNLSLILKGKRKLYQPTGQALLEQLEDIT
ref|ZP_01695982.1|   PERVEALGIVYVMALLIYGILEYRVRKELKEKNLSLILKGKRKLSQPTGQALLEQLEDIT
ref|ZP_01695971.1|   PERVEALGIVYVMALLIYGILEYRVRKELKEKNLSLILKGKRKLYQPTGQALLEQLEDIT
ref|ZP_01695655.1|   PERVEALGIVYVMALLIYGILEYRVRKELKEKNLSLILKGKRKLYQPTGQALLEQLEDIT
ref|YP_430569.1|     ------------------------------------------------------------
RAAC03823            PTRVKAFGFVMLLSLLLYSVLEYLIREKMKRETEPLMLPGNRKSFRPTGLAILEMLDGVT ref|ZP_01695687.1|   VILINQNQQKIRLLPDNIDSQAKKIIELCGYDLSIYA------
ref|ZP_01695982.1|   VILINQNQQKIRLLPDNIDSQAKKIIELCGYDLSIYA------
ref|ZP_01695971.1|   VILINQNRQKLRLLPDNIDSQAKKIIELCGYDLSIY-------
ref|ZP_01695655.1|   VILINQNRQKLRLLPDNIDSQAKKIIELCGYDLSIY-------
ref|YP_430569.1|     -------------------------------------------
RAAC03823            TVHMQVGDTWQRVPATPHNPQIMRVLKLLNMDLSIYAHSQKTA
```

FIG. 125

```
ref|ZP_02330348.1|      MGLWTKQQLREFIKENNLVTAQDAQNALKELFAETIQEMLEAELDTHLGYEKHEVKAKKT
ref|ZP_02328298.1|      MGLWTKQQLREFIKENNLVTAQDAQNALKELFAETIQEMLEAELDTHLGYEKHEVKAKKT
ref|ZP_02326599.1|      MGLWTKQQLREFIKENNLVTAQDAQNALKELFAETIQEMLEAELDTHLGYEKHEVKAKKT
RAAC01171               MELLSKEQIRQLIRDGKLKDIHDVQSMLKDLFASTIQEMLEAELNTHLGYAKYDAKHKDT
ref|YP_001664428.1|     MSLLTKEQLRNFISENNIQSIPDLYTSLKNLFKDTIQEMLEAELSTELGYERYDKKDKDT
ref|YP_001664274.1|     MSLLTKEQLRNFISENNIQSIPDLYTSLKNLFKDTIQEMLEAELSTELGYERYDKKDKDT
                        *  * :*:*:*::*  :.::       *  . : .**********.*.***  :::  * *.* ref|ZP_02330348.1|      PNSRNGR-SHKTVVSEYGEQQIAVPRDRMGEFEPLVVKKHQSNVTGIEDQIVALYAK---
ref|ZP_02328298.1|      PNSRNGR-SHKTVVSEYGEQQIAVPRDRMGEFEPLVVKKHQSNVTGIEDQIVALYAK---
ref|ZP_02326599.1|      PNSRNGR-SHKTVVSEYGEQQIAVPRDRMGEFEPLVVKKHQSNVTGIEDQIVALYAK---
RAAC01171               DNARNGHGAKRTVQSELGDIDIALPRDRKGEFEPLIVQKRQKRMPSIEEQVIALYLKFDS
ref|YP_001664428.1|     QNSRNGY-TQKTVKTQFGEMEIDIPRDRQGEFEPKIVPKYKRDISGIEEKVIALYAR---
ref|YP_001664274.1|     QNSRNGY-TQKTVKTQFGEMEIDIPRDRQGEFEPKIVPKYKRDISGIEEKVIALYAR---
                         *:***    :::**  ::  *:  :* :**** *****  :*  *  :  :..**:::***  :

ref|ZP_02330348.1|      --------------------
ref|ZP_02328298.1|      --------------------
ref|ZP_02326599.1|      --------------------
RAAC01171               KTPHPKVRTALQRGFFAV
ref|YP_001664428.1|     --------------------
ref|YP_001664274.1|     --------------------
```

FIG. 126

```
ref|YP_516922.1|       ---MFARIKTAYNRDGSPRRYLQIVESRREEGKVRQKVLCNLGRVEDLQNGKLDDLIRSL
ref|YP_520815.1|       ------------------------------------------------------------
ref|YP_519534.1|       ---MFARIKTAYNRDGSPRRYLQLVESRREEGKVRQKVLCNLGRVEDLQNGKLDDLIRSL
ref|ZP_01372264.1|     ---MFARIKTAYNRDGSPRRYLQLVESRREEGKVRQKVLCNLGRVEDLQNGKLDDLIRSL
ref|ZP_01370818.1|     ---MFARIKTAYNRDGSPRRYLQLVESRREEGKVRQKVLCNLGRVEDLQNGKLDDLIRSL
RAAC03825              MILLFAQIVSTKKPDGKTYKYLHIVESYREGRTVKKRRVASLGNISQYSEREIEQIIRTL ref|YP_516922.1|       AKFSDKLAVVDAAEDLFADWSKEYGPSMVFNRLWDNLGLHKILDGLFSERELSIDVREAI
ref|YP_520815.1|       -------------------------LWDNLGLHKILDGLFSERELSIDVREAI
ref|YP_519534.1|       AKFSDTLAVVDAAEDLFADWSKEFGPSMVFRRLWENLGLHKILSGLFNERELSIDVQEAI
ref|ZP_01372264.1|     AKFSDTLAVVDAAEDLFADWSKEFGPSMVFRRLWENLGLHKIFAGLFNERDLSIDVQEAI
ref|ZP_01370818.1|     AKFSDTLAVVDAAEDLFADWSKEFGPSMVFRRLWENLGLHTILDGLFNERDLSIDVQEAI
RAAC03825              ESLLQHRTTG-SLEDFEAQQVLHFGVPYVVQFLWNQLGLTEAIRDALRAREVTFDVARYV
                                                **:::***    :  :   *:::**   . :

ref|YP_516922.1|       FCMVLNRLTEPTSKLGVSDWKDSVYRPDF---ETLKLHHFYKAIDFLDENKDTIEEQLFFH
ref|YP_520815.1|       FWMVLNRLTEPTSKLGVSDWKDSVYRPDF--ETLKLHHFYKAIDFLDENKDTIEEQLFFH
ref|YP_519534.1|       FCMVLNRLTEPTSKLGVSDWKDSVYRPEF--ESLKLHHFYKAIDFLDENKESIEEQLFFH
ref|ZP_01372264.1|     FCMVLNRLTEPTSKLGVSDWKDSVYRPEF--ESLKLHHFYRAIDFLDENKDTLEEQLFFH
ref|ZP_01370818.1|     FCMVLNRLTEPTSKLGVSDWKDSVYRPEF--ESLKLHHFYKAIDFLDENKDTLEEQLFFH
RAAC03825              QAMVIHRLVDPSSKLRLFHTLDDDYLPDWGGEPWQLQHFYRALDYLVDIKPQLERVLYAR
                        ::**.:*:***    :  .   *.:* *::   *. :*:***:*:*:*  :  *:. *:  :

ref|YP_516922.1|       HTNLFTQQLDLVFFDTTSTYVEGDAGAFDLLEYGHSKDHRPDRLQVMIGILMSRDGIPIA
ref|YP_520815.1|       HTNLFTQQLDLVFFDTTSTYVEGDAGAFDLLEYGHSKDHRPDRLQVMIGILMSRDGIPIA
ref|YP_519534.1|       QTNLFTQQLDLVFFDTTSTYVEGDAGAFDLLEYGHSKDHRPDRLQVMIGILMSRDGIPIA
ref|ZP_01372264.1|     HTNLFTQQLDLVFFDTTSTYVQGDAGAFDLLEYGHSKDHRPDRLQVMIGILMSRDGIPIA
ref|ZP_01370818.1|     HTNLFTQQLDLVFFDTTSTYVEGDAGAFDLLEYGHSKDHRPDRLQVMIGILMSRDGIPIA
RAAC03825              LTDLLNFRLSLVLYDLTSTHLHG--HACPLGEHGYSRTHRPDLEQVELGLLVTPEGIPIT
                       *:*:.  :*.**::*  ***::.*     *  * *:*:*:  ****   **  :*:*:*:    :****:

ref|YP_516922.1|       HHVFPGNTPDTDAFIEAVSDLKKRFNIQRVIVVGDRGMMGKRTLELLEELQLQYILGVRM
ref|YP_520815.1|       HHVFPGNTPDTDAFIEAVSDLKKRFNIQRVIVVGDRGMMGKRTLELLEELQLQYILGVRM
ref|YP_519534.1|       HHVFPGNTPDTDAFIEAVRDLKKRFTIQRVIVVGDRGMMGKRTLELLEELELHYILGVRM
ref|ZP_01372264.1|     HHVFPGNTPDTDAFIEAVSDLKKRFTIQRVIVVGDRGMMGKRTLELLEELQLHYILGVRM
ref|ZP_01370818.1|     HHVFPGNTSDTDAFIEAVSDLKKRFTIQRVIVVGDRGMMGKRTLELLEELQLHYILGVRM
RAAC03825              HEVFAGNVSDKQTVPDILKRLKEDFAVEQCVFVGDRGMVTEKNMALMAEAGFPYIVGFHK
                       *.**.**..*.:.  :  :  **:  *  :::  :.******:  :::.:  *:  *  : **:*..

ref|YP_516922.1|       RN---IKAGPDLANSPEPYAFIKDNLKVKEVVHQ---------EKRYIVCLNEEEAKRDQ
ref|YP_520815.1|       RN---IKAGPDLANSPEPYAFIKDNLKVKEVVHQ---------EKRYIVCLNEEEAKRDQ
ref|YP_519534.1|       RN---IKAGPELAASPEPYTFLKDNLKVKEVLHQ---------EKRYIVCLNEEEAKRDR
ref|ZP_01372264.1|     RN---IKAGPELAASAQPYPFVKDNLKVKEVLHQ---------EKRYIVCLNEEEAKRDQ
ref|ZP_01370818.1|     RN---VKAGPELATSPEPYVFTKDNLKVKEVLHQ---------GKRYIVCLNEEEAKRDQ
RAAC03825              RGRIVSDALLEQFADVNAYHELKDNLRYLEVPAASVDDVEKAEGVRYILCYNPEKARQDA
                       *.     .*   :     .  :.*  **:            ***:* *  *:*::* ref|YP_516922.1|       LVREQIEIKLRS----------KLEHG---------SIKDLIGNSEYKKYINVTAEAAT
ref|YP_520815.1|       LVREQIEIKLRS----------KLEHG---------SIKDLIGNSEYKKYINVTAEAAT
ref|YP_519534.1|       LVREQIEMKLRS----------KLEHG---------SIKDLIGHSEYKKYINVTAEAAT
ref|ZP_01372264.1|     LVREHIEMKLRS----------KLEHG---------GIKDLIGHSEYKKYINVTAEAAT
ref|ZP_01370818.1|     WVREQIEVKLRS----------KLEHG---------SIKDLIGHSEYKKYLNVSAEAAT
RAAC03825              AFRESALEEAETGLKALAESLAKPKRGRKPTDKGVMLKVADLLTRKGVEAFFQVDYKDGI
                       .**     :   :            * ::*           : **:  ..   : :::*   :  .

ref|YP_516922.1|       IN----TDKLKQAAVFDGLYILQTNTELPTEEVATAYRDLWQIERAFRNLKSTLDLRPVY
ref|YP_520815.1|       IN----TDKLKQAAVFDGLYILQTNTELPTEEVATAYRDLWQIERAFRNLKSTLDLRPVY
ref|YP_519534.1|       MN----TDKLKQAAVFDGLYILQTNTELPTEEVATAYRDLWQIERAFRNLKSTLDVRPVY
ref|ZP_01372264.1|     IN----TDKLKQAAVFDGLYILQTNTELPTEEVATAYRDLWQIERAFRNLKSTLDLRPVY
ref|ZP_01370818.1|     IN----TDKLKQAAVFDGLYILQTNTELPTEEVATAYRDLWQIERAFRNLKSTLDLRPVY
RAAC03825              LTYRRDEDAITKEALRDGKFLIRTNTDLPAADVAQSYKTLMGIERAFHQIKNFLDVGPIY
                       :.      *  :: *:    :::.:****:* .:* .*  ****:::. :  *:* continued →
```

FIG. 126 continued

```
ref|YP_516922.1|      HWKERRISGHIMLCFLALVVQIKFQKLLES------------------------CGSEY
ref|YP_520815.1|      HWKERRISGHIMLCFLALVVQIKFQKLLES------------------------CGSEY
ref|YP_519534.1|      HWKERRISGHIMLCFLALVIQIRFQKLLEN------------------------CASEY
ref|ZP_01372264.1|    HWKERRISGHIMLCFLALVIQIRFQKLLEN------------------------CASEY
ref|ZP_01370818.1|    HWKERRISGHIMLCFLALVVQIRFQKLLEN------------------------CASEY
RAAC03825             HWNEQRVRGHIFVCVLAYLFEQEMQVLYRRQWAHDKAVAESLACVEEQAKVLAELESRWY
                      **:*:*: ***::*.**  :.:  .:*  *  .                         . * ref|YP_516922.1|      GYTEVIRALRKVHAVKLKIKDQDHLVRTEIHGAAAMAFKAVGLRIPER------------
ref|YP_520815.1|      GYTEVIRALRKVHAVKLKIKDQDHLVRTEIHGAAAMAFKAVGLRIPER------------
ref|YP_519534.1|      GYTEVIRALRKVHAVKLKIKDQDHLVRTEIHGAAAMAFKAVGLRIPER------------
ref|ZP_01372264.1|    GYTEVIRALRKVHAVKLKLKDQDHLVRTEIHGAAAMAFKAVGLRIPER------------
ref|ZP_01370818.1|    GYTEVIRALRKVHAVKLKLKDQDHLVRTEIHGAAAMAFRAVGLRVPER------------
RAAC03825             TGEAIVRELRRWKAVRATFLDKEFVSVTKATDQAKAILTSLGIPTPNKTLSVTKVPSMTP
                       :* **: :**: .: *::.: *:  . *    :  ::*: *::

ref|YP_516922.1|      --
ref|YP_520815.1|      --
ref|YP_519534.1|      --
ref|ZP_01372264.1|    --
ref|ZP_01370818.1|    --
RAAC03825             DE
```

FIG. 127

```
ref|ZP_02851608.1|      ------------------LSMYAKGMTVRDIQTHLQELYGVDASPTLISGITDKIVPLI
ref|YP_001307815.1|     ---------------HLESAVIGMYAKGMTTRDIATQINDIYGMDASPTLISNITDKVIPML
ref|ZP_02326599.1|      ----------------------LYAKGVSTREIQDHLQNLYGIEVSPTLISNVTNKIVPLI
RAAC03826               MRVVQTCPYNPRHIKGTVKLELYARGFSTRDIQDHLQQIYGVDMSPTLVSNLTDRLLPRI
ref|YP_001212943.1|     -------------------IAMYAKGMSTRDIEDHMRDIYGIDVSPTMVSKITDKILPMI
ref|YP_001113174.1|     -------------------IAMYGKGMSTRDIEDHMRDIYGIDVSPTMVSRITDKIMPMV
                                            :*.:*..:.*:*  ::.::**::  ***::*  :*:::*  :

ref|ZP_02851608.1|      KEWQNRPLSRIYAHVVMDAVHYKVRQDGRIVNKAAYMAIGIDLDGMKDVLGIWIGENESS
ref|YP_001307815.1|     KEWQSRPLESIYPIIFMDAIHFKVRKDNAIVSKAAYAVIGVNLEGKKDVLGIWIGASESP
ref|ZP_02326599.1|      KEWQNRPLQSVYAVVFLDATHFKVKQDGAIVSKAAYMVIGIDLDGNKDVLGMWIGENESS
RAAC03826               QEWQNRPLHPLYTVVFLDAIHYKVREEGRLVSKAAYMVIGIDIEGQKDVLGIWIGQSESS
ref|YP_001212943.1|     SEWQSRPLDRVYPVVFLDAIHFKVRKENRIINKAAYSVMAINMAGQKEVLGIWVGENESA
ref|YP_001113174.1|     IEWQSRPLDRVYPIVFLDAIHFKVRQDNRIINKAAYSVLGITMDGHKEILGIWVGEHESS
                         ***.***  :*.  :.:**:*:**::.  :: ****  ..:.:  * *::**:*:*  **.

ref|ZP_02851608.1|      KYWLKIINELKNRGVEDILIVSIDGLKGFEDAIHAVYPQTEIQSCIIHQIRNSTRYISYK
ref|YP_001307815.1|     KYWLLVLNELKNRGINDILIACVDGLNGFKEAIKAVFPNTEIQRCIIHQIRNSSKYLSYK
ref|ZP_02326599.1|      KFWLSVLNDLKNRGVQDILITCVDNLNGFSEAITASYPKTEIQKCIIHQIRNSTRYVSYK
RAAC03826               KFWLGVLNDLKNRGVQDVLVFSTDNLKGFSEAIAACFPQSDVQKCIVHQIRNSLRYVSYK
ref|YP_001212943.1|     SFWLGVCNDLKNRGVQDILIACKDGLSGFSEAISSAFPRTEIQLCIIHQIRNSMKYVPYK
ref|YP_001113174.1|     KFWLGVCNDLKSRGVEDILIACKDGLSGFSEAINTAFPKTQIQLCVIHQIRNSLKYVPYK
                        . :**    : *:** **::*:*:  . *.*.**.:** :  :*.:::*  *::****** :*:.**

ref|ZP_02851608.1|      DRKEFCSDLKNVYRAPTEEVALIELDKLEEKWGDKYEISIRSWRNNWDKLSVMFKYPEEV
ref|YP_001307815.1|     DLKAFNTDLKSVYKAPTEDVALAELDNLEEKWGGKYLIAIKSWRNNWDELSTFFKYPPEI
ref|ZP_02326599.1|      DLKKVTADLKPIYKASTEEAAVLELDRFEEVWGSKYPLIRSWRNNWAELATFFKYPPEI
RAAC03826               DFKAVAAALKPIYQAPTEEAALMELDQFERGWGARYPLCVKSWRDNWTELATFYRYPVEM
ref|YP_001212943.1|     YQKELIADLKKIYQALTIEEAEMSFTTFKGKWGKKHPIIVRSWENNWLELTAYFKYPYEI
ref|YP_001113174.1|     YRKELMKDLKKVYQALTIEEAEFAFEEFKEKWGSKYPVVIKSWENNWVELTTYFQYPRGI
                         *   .  **  :*:*  *  :  :  ::  **  ::  ::**..:**  **:.  ::**   :

ref|ZP_02851608.1|      RKLIYTNNSMESYNRQLRKVTKSKSIFPTDESLLKMLYLATMDITKKWTMRTKNWAQILG
ref|YP_001307815.1|     RKIIYTTNAMESYNRQLRKVTKSKSIFPNDESLLKILYLATIDITKKWTQGIKGWAQILA
ref|ZP_02326599.1|      RRLIYTTNMIESYHRQLRKVTKGKSIFPSDEALLK-------------------------
RAAC03826               RRIMYTTNIIEGYHRQLRKATKGKSMFPNDEALLKMLYLATMELTRKWTMRVANWGTILG
ref|YP_001212943.1|     RRMIYTTNIIEGYHRQLRKVTKTKTAYPTDEALVKIIYLATIEASKKWTMSIKDWKNCIS
ref|YP_001113174.1|     RRMIYTTNVIEGYHRQLRKVTKTKTAYPSDEALVKMLYLATLDASKKWTMPLREWRECIS
                        *:::**.*  :*.*:***.  *: :*.**:*:* ref|ZP_02851608.1|      QLSIYFEGRI-----
ref|YP_001307815.1|     QLSIFFEGRL-----
ref|ZP_02326599.1|      ---------------
RAAC03826               QLAIYFGDRVTPYIP
ref|YP_001212943.1|     QFAIYFEDRL-----
ref|YP_001113174.1|     QFLIFFGDRL-----
```

FIG. 128

```
ref|ZP_01592598.1|        ---------------RYDRKATIVTSQLPIKAWYDAMQDPTLADAILDRL----------
RAAC02717                 MNKLGGAGRNLPAAPRYALNSTCVASQLPIEAWYDTFADPTVADAVLDRLAKCSQALVEK
ref|ZP_01002160.1|        ---------------RYERKSTVITSQLPIEKWYDIIADPTLADAILDRL----------
ref|YP_771767.1|          ---------------RYEVGSTLITSQLPIDAWHDVIGEPTFADAILDRL----------
ref|YP_001229345.1|       ---------------RHGITSTIIASQIPTEKWHDAIGDPTIADAVLDRLVHNAHMITMK
ref|YP_245447.1|          --------------------SLLITSQYPQEKWYELFADPTIADAILDRIIHKSHTLQLK
                                           :  ::** * . *::  : :**.***:***:

ref|ZP_01592598.1|        ------------
RAAC02717                 AITKELIEGRRN
ref|ZP_01002160.1|        ------------
ref|YP_771767.1|          ------------
ref|YP_001229345.1|       ------------
ref|YP_245447.1|          GESMRKVRARRS
```

FIG. 129

```
ref|YP_145872.1|       ----------------------------------------------------------------
ref|YP_001124150.1|    ----------------------------------------------------------------
ref|NP_240902.1|       ----------------------------------------------------------------
ref|NP_466224.1|       INATINPRTEINRECRLISTERIAMNCYTGENESREFZPRECMBINATINPRTEINRECR
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       LISTERIAMNCYTGENESREFZPRECMBINATINPRTEINRECRLISTERIAMNCYTGEN
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       ESSREFZPRECMBINATINPRTEINRECRLISTERIAMNCYTGENESHPBREFZPRECMB
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       INATINPRTEINRECRLISTERIAMNCYTGENESFSL-REFZPRECMBINATINPRTEIN
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       RECRLISTERIAMNCYTGENESLREFZPRECMBINATINPRTEINRECRLISTERIAMNC
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       YTGENESFSLR-REFZPRECMBINATINPRTEINRECRLISTERIAMNCYTGENESFSL-
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       REFZPRECMBINATINPRTEINRECRLISTERIAMNCYTGENESFSL-REFZPRECMBIN
ref|ZP_02850412.1|     ----------------------------------------------------------------
RAAC01155              ---------------------------------------------------------------- ref|YP_145872.1|       ----------------------------------------------------------------
ref|YP_001124150.1|    ----------------------------------------------------------------
ref|NP_240902.1|       ----------------------------------------------------------------
ref|NP_466224.1|       ATINPRTEINRECRLISTERIAMNCYTGENESFSL-SPQYXRECRLISMRECMBINATIN
ref|ZP_02850412.1|     ----------------------------------------------------------------
RAAC01155              ----------------------------------------------------------------
``` continued →

FIG. 129 continued

```
ref|YP_145872.1|      ------------------------------------------------------------
ref|YP_001124150.1|   ------------------------------------------------------------
ref|NP_240902.1|      ------------------------------------------------------------
ref|NP_466224.1|      PRTEINRECRSPQWRECRLISMFRECMBINATINPRTEINRECREMBCADRECRLISTER
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      IAMNCYTGENESGBAATRECMBINATINPRTEINRECRLISTERIAMNCYTGENESSTRB
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      FGBEALRECMBINATINPRTEINRECRLISTERIAMNCYTGENESSTRAFGBEBARECMB
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      INATINPRTEINRECRLISTERIAMNCYTGENESGBEBARECMBINATINPRTEINRECR
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      LISTERIAMNCYTGENESSGBEBARECMBINATINPRTEINRECRLISTERIAMNCYTGE
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      NESGBEBARECMBINATINPRTEINRECRLISTERIAMNCYTGENESFSLN-GBEBAREC
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      MBINATINPRTEINRECRLISTERIAMNCYTGENESFSLN-GBEBARECMBINATINPRT
ref|ZP_02850412.1|    ------------------------------------------------------------
RAAC01155             ------------------------------------------------------------ ref|YP_145872.1|      ------------------------------------------------------------
ref|YP_001124150.1|   ------------------------------------------------------------
ref|NP_240902.1|      ------------------------------------------------------------
ref|NP_466224.1|      EINRECRLISTERIAMNCYTGENESFGBEBARECMBINATINPRTEINRECRLISTERIA
ref|ZP_02850412.1|    ------------------------------------------------------------
RAAC01155             ------------------------------------------------------------
``` continued →

FIG. 129 continued

```
ref|YP_145872.1|       ------------------------------------------------------YPEPLSK
ref|YP_001124150.1|    ------------------------------------------------------YPEPISK
ref|NP_240902.1|       ------------------------------------------------------YPEPIAK
ref|NP_466224.1|       MNCYTGENESHPBSCRESIGNIFICANCEE-IDENTITIESPSITIVESGAPSYPEPITK
ref|ZP_02850412.1|     ------------------------------------------------------YPEPIAK
RAAC01155              ----------------------------------------------------MGYPEPVAR
                                                                             ****:::

ref|YP_145872.1|       LIDSFMKLPGIGPKTAARLAFHVLAMKEDTVLEFAKALVDVKRHIHYCTICGHITDTDPC
ref|YP_001124150.1|    LIDSFMKLPGIGPKTAARLAFHVLAMKEDTVLEFAKALVDVKRHIHYCTICGHITDTDPC
ref|NP_240902.1|       LIEGFMRLPGIGPKTASRLAFFVLEMKEDDVLDFAKALVNVKRKLTYCSVCHNITDTDPC
ref|NP_466224.1|       LIDSFMKLPGIGPKSAARLAFYVLDMKEDDVLDFAKALVDAKRNLSFCSVCGHITDKDPC
ref|ZP_02850412.1|     LIDAFTRLPGVGPKTAARLAFHVLRMKEDDVIDFAKALVSVKRNLTYCSVCCNITDTDPC
RAAC01155              AIEHFMKLPGVGPKTAARLAFHVLEMSEADVKAFAKALIDLKTGLTECAVCCNITEASPC
                       *: * :***:***:*:****.** *.* * ***** :. * : *::* :**: .**

ref|YP_145872.1|       YICKDERRDRTTICVVQDPKDVIAMERMKEYNGLYHVLHGAISPMEGIGPEDIKIAELLT
ref|YP_001124150.1|    YICKDERRDRTMICVVQDPKDVIAMEKMKEYNGLYHVLHGAISPMEGIGPEDIKIAELLA
ref|NP_240902.1|       RICEDSKRDESVICVVQDAKDVIAMEKMKEYHGKYHVLHGAISPMDGIGPEDIKIPELIK
ref|NP_466224.1|       YICADTSRDRSVICVVQESKDVIAMEKMRDFHGLYHVLHGTISPMDGIGPEDINIPDLLK
ref|ZP_02850412.1|     RICQDKTRDNSVICVVQESKDLVAMERTKEFQGFYHVLQGAISPIEGIGPDQIKIAELLR
RAAC01155              AICRDPRRDRRVICVVQEPRDVIAMERTREYHGLYHVLHGAISPMEGVGPQDIRIRELVT
                       ** *  **. *****:.:*::***: ::::* ****:*:***:*:**:.* :*:

ref|YP_145872.1|       RLQDETVQEVILATDPNIEGEATAMYISRLLKPTGIKVTRIAHGLPVGGDLEYADEVTLS
ref|YP_001124150.1|    RLQDETIQEVILATDPNIEGEATAMYLSRLLKPTGIKITRIAHGLPVGGDLEYADEVTLS
ref|NP_240902.1|       RLQDDTIQEVIVATNPTIEGEATAMYISRLVKPTGIKVTRIAHGLPVGGDLEYADEVTLS
ref|NP_466224.1|       RLQDDTIEEVILATNPNVEGEATAMYISRLLKPSGIKVTRIAHGLPVGGDLEYADEVTLS
ref|ZP_02850412.1|     RLSDERVQELILATNPNIEGEATAMYISRLVKPFGIRVTRIAHGLPVGGDLEYADEVTLS
RAAC01155              RVGENEIEEVILATNPNVEGEATAMYISRLLKPFQVKLTRIAHGLPVGGDLEYADEVTLA
                       *:  :: ::*:*:**:*.:********:***:** :::********************:

ref|YP_145872.1|       KALEGRREL
ref|YP_001124150.1|    KALEGRREL
ref|NP_240902.1|       KAMEGRREL
ref|NP_466224.1|       KAMEGRR--
ref|ZP_02850412.1|     KALEGRREL
RAAC01155              KALEGRRAL
                       **:****
```

FIG. 130

```
dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     PSASEPRTEINDESULFVIBRIDESULFURICANSGREFYPPUTATIVETRANSPSASEP
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     RTEINDESULFVIBRIDESULFURICANSGREFYPPUTATIVETRANSPSASEPRTEIND
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     ESULFVIBRIDESULFURICANSGGBABBPUTATIVETRANSPSASEPRTEINDESULFV
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     IBRIDESULFURICANSGGBABBPUTATIVETRANSPSASEPRTEINDESULFVIBRIDE
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     SULFURICANSGGBABBPUTATIVETRANSPSASEPRTEINDESULFVIBRIDESULFUR
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     ICANSGGBABBPUTATIVETRANSPSASEPRTEINDESULFVIBRIDESULFURICANSG
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     GBABBPUTATIVETRANSPSASEPRTEINDESULFVIBRIDESULFURICANSGGBABBP
ref|YP_387237.1|     ---------------------------------------------------------- dbj|BAA94830.1|      ----------------------------------------------------------
RAAC03145            ----------------------------------------------------------
ref|ZP_01666433.1|   ----------------------------------------------------------
ref|YP_001213263.1|  ----------------------------------------------------------
ref|YP_387030.1|     UTATIVETRANSPSASEPRTEINDESULFVIBRIDESULFURICANSGGBABBPUTATIV
ref|YP_387237.1|     ----------------------------------------------------------
``` continued →

FIG. 130 continued

```
dbj|BAA94830.1|         ------------------------------------------------------------
RAAC03145               ------------------------------------------------------------
ref|ZP_01666433.1|      ------------------------------------------------------------
ref|YP_001213263.1|     ------------------------------------------------------------
ref|YP_387030.1|        ETRANSPSASEPRTEINDESULFVIBRIDESULFURICANSGGBABBPUTATIVETRANS
ref|YP_387237.1|        ------------------------------------------------------------ dbj|BAA94830.1|         ------------------------------------------------------------
RAAC03145               ------------------------------------------------------------
ref|ZP_01666433.1|      ------------------------------------------------------------
ref|YP_001213263.1|     ------------------------------------------------------------
ref|YP_387030.1|        PSASEPRTEINDESULFVIBRIDESULFURICANSGGBABBPUTATIVETRANSPSASEP
ref|YP_387237.1|        ------------------------------------------------------------ dbj|BAA94830.1|         ------------------------------------------------------------
RAAC03145               ------------------------------------------------------------
ref|ZP_01666433.1|      ------------------------------------------------------------
ref|YP_001213263.1|     ------------------------------------------------------------
ref|YP_387030.1|        RTEINDESULFVIBRIDESULFURICANSGSCRESIGNIFICANCEE-IDENTITIESPS
ref|YP_387237.1|        ------------------------------------------------------------ dbj|BAA94830.1|         -----MSKEQITLTKNELKRVMVIEKWIDGHLTEQDVARNLGISVRQAYRLKAKYRHGGA
RAAC03145               MKMSCMSKEYLVMRQEEARRLTVISKLIDGHLSVAQAAEYLQLSIRQVLRIKKRVLEEGE
ref|ZP_01666433.1|      --MSLMEKEKIFLSDKEVRRAIVIDKVIQGVCTIAEAAEVLSLSERQVKRLKAGVIKEGF
ref|YP_001213263.1|     ---------LSMTQDERNKLYVARCLLDGKMTISEAAETLGLSERQVKRIKKGVKEHGF
ref|YP_387030.1|        ITIVESGAPSVLMKAEEEARRAFVIKQAVAGAFTVREAGEVLGLSYRQVIRLKNYRKEGA
ref|YP_387237.1|        ------------MKAEEEARRAFVIKQAVAGAFTVREAGEVLGLSYRQVIRLKNYRKEGA
                              :  .* .:  *    : *  :    :... * :* **. *:*    . * dbj|BAA94830.1|         QAIAHGNRGRKPAHTLTDSLKQRVMLLYQER-YFGSNATHFAELLAEHENIHLSVSSVRR
RAAC03145               AGVIHKNRGRQPSHTLPQSLKHKIVALYQSDDYRGCNDTHFTELLAVRENIYVSTSTVRR
ref|ZP_01666433.1|      GFLAHGNRGRKPAHAISDELREQVLATIRQPVFCEANDSHLTELLAEHYNIFLSVSSIRR
ref|YP_001213263.1|     SFVIHKNRGRKPPHALTDEVRKLVVNLKKSEKYSKANFSHFQELLEEFESISLSKPSVYR
ref|YP_387030.1|        VGLVHKGRGKASNRRIAQEIRKFVAEKAKSD-FEGASCQHMEELFASRYGLELSAKSIGR
ref|YP_387237.1|        VGLVHKGRGKASNRRIAQEIRKFVAEKAKSD-FEGASCQHMEELFASRYGLELSAKSIGR
                           : * .**:  . :  :.:.::.     :  ..    *: **   .: :*   ::  * dbj|BAA94830.1|         ILLEGGLRPARLRRRPKAHRPRPRKPQAGMLWQIDASPYAWLEDRGPMLTLHGIIDDATG
RAAC03145               ILRAAGISAARKHRAPRSHRSRRRMPQAGLLWQMDASTFDWLEDRRGPRLTLHAAIDDATG
ref|ZP_01666433.1|      IRRSAGISSPRKHRRPKFHRRRRREQEGMLTQMDGSPHAWLGEDKPYISLIGAIDDATG
ref|YP_001213263.1|     ILVANGLTSPKKHSKVKRHKRRRKPQRGMLVIIDASPHAWFFNNEE-CSLHGAVDDATG
ref|YP_387030.1|        ILKEQGVACAHRHRSPKGRRCRERSRRRGDLVQMDASPFDWLG-DGVMRSLHGAIDDATG
ref|YP_387237.1|        ILKEQGVACAHRHRSPKGRRCRERSRRRGDLVQMDASPFDWLG-DGVMRSLHGAIDDATG
                        *    *:  .: :    : ::  *    *   :*.*.. *:     :* . :***** dbj|BAA94830.1|         EVVAATFRPTETLEGYVTVMIEGLRRKGVPLALYSDQHSIFHPPKG-KPTLEQELAGEPP
RAAC03145               RIVGAAFARTECLEGYWSVLHHGITAYGIPVALYVDRHTIFRSPKADKLTIDEELAGVKP
ref|ZP_01666433.1|      KIVGAIFRPTEDLNGYFEVLRQIITKYGIPIAVYTDRHSIFVSPNADKLTIEDQLEGKKA
ref|YP_001213263.1|     EILALFFMRNECLEGHYQVMKTVISNNGVPLAVYADRHTIFRSPKSDKLSLEEEELNGKKV
ref|YP_387030.1|        EVVGLWIEKNECLSGYLRVLRQMLERHGVPRAIYADRHTIFVSPKTGKLTIEEELQGKVA
ref|YP_387237.1|        EVVGLWIEKNECLSGYLRVLRQMLERHGVPRAIYADRHTIFVSPKTGKLTIEEELQGKVA
                        .::.    :   . .* *.*:  *:   :    *:* *:: .*:  ::::::* * dbj|BAA94830.1|         SLSTFGQALADLGITHIEALSPQAKGRIERLWQTFQDRLVIELRLRNVCTMEEANRVLPE
RAAC03145               S-TQLGRAVAELGISLTFARSPQAKGRIERLWETLQDRLTHELRLHRISTLEAANAFLPA
ref|ZP_01666433.1|      NLTQLGRALSELGIEHIKARSAQAKGRVERLWETLQSRLPVELNIAGITTMEEANAFLAT
ref|YP_001213263.1|     KATQFGRAMAELGINLIWAKSAQAKGRIERLWETLQSRLPVELNIAGITTMEEANAFLAT
ref|YP_387030.1|        PQTQFGRVLETLGVRFIAARSPQAKGRIERLWRTLQSRLVIAFRLAGIRTVEAANDFLGT
ref|YP_387237.1|        PQTQFGRVLETLGVRFIAARSPQAKGRIERLWRTLQSRLVIAFRLAGIRTVEAANDFLGT
                         :*: .:  **:   *  *.***:**  *: **    : :  *:* **  .* continued →
```

FIG. 130 continued

```
dbj|BAA94830.1|        LIAK-HNRQFAVAPQEAEPAYRPLPETP-LEHIFTRREYRRISGGQTFFWKGKCYMPKPV
RAAC03145              FVER-FNARFAVEPESPEPAYRPLAPHHNLHRILCYRAWRKVSPGQTISWKGQTYRIVPE
ref|ZP_01666433.1|     FILK-HNAMFEVEPANPNSAYRPAPSEESLREILCVKEKRKLKGG-VLSFQGQLYKLD--
ref|YP_001213263.1|    FINK-YNEKFAVEPKDPQPAFRKLEDNINLDYILCTKETRQIDRGSAFSYGGVYYRVICN
ref|YP_387030.1|       YAEQMHNPKFAGAPAEAQNAFLPVVEGTNLDLLLARHEQRKACGDSTVAFGGQKYRLQDS
ref|YP_387237.1|       YAEQMHNPKFAGAPAEAQNAFLPVVEGTNLDLLLARHEQRKACGDSTVAFGGQKYRLQDS
                        : .*   *    * ..: *:         *  ::   : *:    . . . : *   * dbj|BAA94830.1|        PGVPRWEAKS-VVEVRVGMDGQVWLWD--QGRAWPCVETQ---ATQTPAPTTAKKEAAPA
RAAC03145              QHRETLAPRS-TVEVRVTTNGELWIVAG-QGRLYRLEPCS---KSPAVKRREDATPTPSR
ref|ZP_01666433.1|     -GLPAYFPDT-TVLVHVHPDGKLRASYPKQNVVYDLTRVS---EPVRTKSQPKEKAGPPP
ref|YP_001213263.1|    GKTMPIAPKA-KITVLKSPQFGLKVQYG--SSIYDIEILE---QLP-PKDIAPGQPRQPR
ref|YP_387030.1|       RGRTRLLRRGKAVTVVEKLDDELMALADGEAFVLVPVVTGKSSEEPASEEKSLARGAQER
ref|YP_387237.1|       RGRTRLLRRGKAVTVVEKLDDELMALADGEAFVLVPVVTGKSSEEPASEEKSLARGAQER
                                    : *    :       :

dbj|BAA94830.1|        SPRKPAANHPWRK-----------------------
RAAC03145              QPYKPPADHPWRRMTLGRPKPKLPTPSAEAISP
ref|ZP_01666433.1|     TPRRPAPDHPWRK-----------------------
ref|YP_001213263.1|    KPVKPAENHPWRTKTTTFP--------------
ref|YP_387030.1|       EQTSPAAESSW---------------------
ref|YP_387237.1|       EQTSPAAESSW---------------------
                        *. :  .*
```

FIG. 131

```
ref|YP_148969.1|         ------------------------YLQLAHNEWDPKAKYAKAKVIYSFGREDEVDRAVLER
ref|YP_001126171.1|      ------------------------YLQLAHNEWDPKAKYAKAKVIYSFGREDEVDRAVLER
ref|YP_146154.1|         ------------------------------------------------------------
ref|YP_146741.1|         ------MYIRRVTRKNKDGTTVAYLQLAHNEWDPKAKYAKAKVIYSFGREDEVDRAVLER
RAAC03325                MSYHVDMYIRVIRRKNKNGSVTGYVQLAHNYRDPQTGQPKAKVLYTFGREDEMDLEALRR
ref|ZP_02130848.1|       ------MYIRTISRKNKDGSKVEYVQLAHNYRDPKSKQARAEVLYSFGRKDQLDMEAIRR ref|YP_148969.1|         LAKSISRFLSPEQAWEIETLTGEVSDDFQFQSSKRLGGAWLLDQLWRQLGLGEILHSLFA
ref|YP_001126171.1|      LAKSISRFLSPEQAWEIETLTGEVSDDFQFQSSKRLGGAWLLDQLWRQLGLGEILHSLFA
ref|YP_146154.1|         ------------------------------------------------------------
ref|YP_146741.1|         LAKSISRFLSPEQAWEVEKLTGEASDDFQFQSCKHLGGVWLLDQLWRQLGLGEILHSLFT
RAAC03325                LAQSIHRFVG--DEFTSGRGQSEAIQTTLLDS-RPMGGAYLLDELWRQLELDEVLRERLV
ref|ZP_02130848.1|       LAKSVERFLAKTGDVETQCKLQFPGEDVRFVESRPMGGVFVLKKIWDRLRISECLDKALA ref|YP_148969.1|         SRHHQIPLERLIFAMVANRALHPSSKLAMEEWVEKDVHIPHLPQVASHQLYRAMDELLAV
ref|YP_001126171.1|      SRHHQIPLERLIFAMVANRALHPSSKLAMEEWVEKDVHIPHLPQCASHQLYRAMDELLAV
ref|YP_146154.1|         --------LERLIFAMVANRALHPSSKLAMEEWVEKDVHIPHLPQVASHQLYRAMDELLAV
ref|YP_146741.1|         SRHHQISLERLIFAMVANRALHPSSKLAMEEWVEKDVYIPHLPQVASHQLYRAMDELLAV
RAAC03325                DRKFKAAVERVIFAMVANRALAPSSKLAMEEWVEREVALPGMTELDVWQAYRAMDVLHDV
ref|ZP_02130848.1|       DRQYTAPIGDAVFAMVANRALAPDSKLAVEDWAAKDVHLELDQPLKVQHLYRAMDFLLEN
                                     :*********  *.****:*:*. ::* :       : ***** * ref|YP_148969.1|         QPELERQVFHAVADLLNLEVDLIYFDTTSSYFEVDPSETPEGESLRKQGFSKDKRPDLVQ
ref|YP_001126171.1|      QPELERQVFHAVADLLNLEVDLIYFDTTSSYFEVDPSETPEGESLRKQGFSKDKRPDLVQ
ref|YP_146154.1|         QPELERQVFHAVADLLNLEVDLIYFDTTSSYFEVDPSETPEGESLRKQGFSKDKRPDLVQ
ref|YP_146741.1|         QPELERQVFHAVADLLNLEVDLIYFDTTSSYFEVDPSETPEGESLRKQGFSKDKRPDLVQ
RAAC03325                TEELQYEVFRRVSNLLNLDVDLLFFDTTSTYFETE--DEPE-DGLRRKGYSKDHRPDLPQ
ref|ZP_02130848.1|       QEAIQKEVFWSTANLLNLEVDLVFFDTTSTYFERD---EEDEEGLKRYGHSKDKRKDLPQ
                         ::  :   .:::*:**** *  :       : :.*::  . ***:*  ** * ref|YP_148969.1|         IVIGLAVTREGVPIRAWVWPGNTMDMTVIKQVKQDLIGWKLGRVISVMDRGFSSEENLRI
ref|YP_001126171.1|      IVIGLAVTREGVPIRAWVWPGNTMDMTVIKQVKQDLIGWKLGRVISVMDRGFSSEENLRI
ref|YP_146154.1|         IVIGLAVTREGVPIRAWVWPGNTMDMTVIKQVKQDLIGWKLGRVISVMDRGFSSEENLRI
ref|YP_146741.1|         IVIGLAVTREGIPIRAWVWPGNTMDMTVIKQVKQDLIGWKLGRVISVMDRGFSSEENLRI
RAAC03325                VVIGLAVTRDGIPVRCWTWPGNTADMSVVEEVKQGLIGWRLGRVITVVDRGFVSESNLRI
ref|ZP_02130848.1|       VVVGLAVTKEGLPIRSWVFPGNTPDVNTVEQIQKEMNDWKLGRVVWAMDRGMTSEENRAI
                         :*:******::*:*.*.*:****  *:..::::  :  .*:**:  .:*:  **.*  * ref|YP_148969.1|         LQQAGGHYIVGEKMRSGKAAVEEALNRRGRYQQVRENLHIKEIIVGDGEARQRYVLVYNP
ref|YP_001126171.1|      LQQAGGHYIVGEKMRSGKAAVEEALNRRGRYQQVRENLHIKEIIVGDGEARQRYVLVYNP
ref|YP_146154.1|         LQQAGGHYIVGEKMRSGKAAVEEALNRRGRYQQVRENLHIKEIIVGDGEARQRYVLVYNP
ref|YP_146741.1|         LQQAGGHYIVGENMRSGKAAVEEALSRRGRYHEVDENLHIKEIIVGDGEARQRYVLVYNP
RAAC03325                LQRAGGHYIAGEKMNSGKSAVEVALARPGRFRELRPNLKVKEVVVGDGEARVRYVLAFNP
ref|ZP_02130848.1|       LQRGGGNYTLGEKLR-GSNMSKAVLGSPGRFTTVRDNLEIKEVTAGDGACRRRYVIVRNP
                         **:.**:**  **::. *.  :.*  **:     ** .:**.   .*** .* ***:.  **

ref|YP_148969.1|         SEAERQRKEREKLLESLKEELEGLRQLPNEAHHKATCRLRSHPSYGKYLRQLKDGTLRID
ref|YP_001126171.1|      SEAERQRKEREKLLESLKEELEGLRQLPNEAHHKATCRLRSHPSYGKYLRQLKDGTLRID
ref|YP_146154.1|         SEAERQRKEREKLLESLKEELEGLRQLPNEAHHKATCRLRSHPSYGKYLRQLKDGTLRID
ref|YP_146741.1|         GEAERQRKERETLLESLKEELEGLRQLPNEAHHKATCRLRSHPSYGKYLRQLKDGTLRID
RAAC03325                EEAKRDEARREAMLRELRMELERLKELQGEAHTKAHCRLASHPTFKRYLKQDRWGNLRID
ref|ZP_02130848.1|       KQVKRDQATRERLIRRAEQEIEAIGDLTGKKHTKAACALLSHRSMGKYVRELKSGKLKIN
                         .:.:*:.  **  ::.  . *:  : *  .:  * ** .* **  *::: :  *.*:*:

ref|YP_148969.1|         KQAVREAEKYDGKYLIRTSDDTLSAEDVALGYKQLVDIEQAFRTLKSTLELRPMYHRLED
ref|YP_001126171.1|      KQAVREAEKYDGKYLIRTSDDTLSAEDVALGYKQLVDIEQAFRTLKSTLELRPMYHRLED
ref|YP_146154.1|         KQAVREAEKYDGKYLIRTSDDTLSAEDVALGYKQLVDIEQAFRTLKSTLELRPMYHRLED
ref|YP_146741.1|         KQAVRDAEKYDGNYLIRTSDDTLSAEDVAIGYKQLVDIEQAFRTLKSTLELRPMYHRLED
RAAC03325                PEAVRQAAHLDGKYLIRTSDDTLSTEDVALGYKQLLMVESAFRTLKTTLDIRPMYHRKDE
ref|ZP_02130848.1|       KAKITEEEKLDGKYLLSCSDDTLSPEEIALGYKQLLEVERAFRTLKSTLDLRPVYHRKDE
                         :  :  ** :** ******.*::****:  :* ******:**:**:***  ::
``` continued →

FIG. 131 continued

```
dbj|BAA94830.1|        LIAK-HNRQFAVAPQEAEPAYRPLPETP-LEHIFTRREYRRISGGQTFFWKGKCYMPKPV
RAAC03145              FVER-FNARFAVEPESPEPAYRPLAPHHNLHRILCYRAWRKVSPGQTISWKGQTYRIVPE
ref|ZP_01666433.1|     FILK-HNAMFEVEPANPNSAYRPAPSEESLREILCVKEKRKLKGG-VLSFQGQLYKLD--
ref|YP_001213263.1|    FINK-YNEKFAVEPKDPQPAFRKLEDNINLDYILCTKETRQIDRGSAFSYGGVYYRVICN
ref|YP_387030.1|       YAEQMHNPKFAGAPAEAQNAFLPVVEGTNLDLLARHEQRKACGDSTVAFGGQKYRLQDS
ref|YP_387237.1|       YAEQMHNPKFAGAPAEAQNAFLPVVEGTNLDLLARHEQRKACGDSTVAFGGQKYRLQDS
                         .*   *    *  ..: *:          *   ::   : *:    . ..: *  * ref|YP_148969.1|       RIRAHVLLSWLALLLVRIVEIRTHESWPKVRDECERLMLGHFSSKNGDLYQRTELTAKQA
ref|YP_001126171.1|    RIRAHVLLSWLALLLVRIVEIRTHESWPKVRDECERLMLGHFSSKNGDLYQRTELTAKQA
ref|YP_146154.1|       RIRAHVLLSWLALLLVRIVEIRTHESWPKVRDECERLMLGHFSSKNGDLYQRTELTAKQA
ref|YP_146741.1|       RIRAHVLLSWLALLLVRIVEIRTHESWPKVRDECERLMLGHFSSKNGDLYQRTELTAKQA
RAAC03325              RIRSHVLLCWLALLLVRIAEVQTGRTWSDIRSHMQAMHQVTKSTPDGMVVQRTETTEVQR
ref|ZP_02130848.1|     RIRSHVTLCWLALLLVRLIELETGMTWNQVRRILERLHMGEFFLNNSRILQRTELTQDQN
                       *:  *.********: *:.*    :*  .:*   : :          :. : **** *  * ref|YP_148969.1|       LFLAALGLEPPPKILGIHPRT---
ref|YP_001126171.1|    LFLAALGLEPPPKILGIHPRT---
ref|YP_146154.1|       LFLAALGLEPPPKILGIHPRT---
ref|YP_146741.1|       QLFAALGLEPPPKILGIHPR----
RAAC03325              EILRALRIKEPPRILKVEPRTRGL
ref|ZP_02130848.1|     KLLKKLKIKPPPLIKKID------
                        ::   *  ::  ** *   :.
```

FIG. 132

```
ref|ZP_02851608.1|      MNLIDKKKVREMMKEGKLKDVNDIQDLLKEQFGELIEFMLEGELDHELGYSKYDYREKET
ref|YP_001307815.1|     MSLSRDELVKLILSNSDIKTTEDIQNTLKDLFGGVLQQMLESEMESHLGYAKHDYFNKNT
ref|ZP_02326599.1|      MGLWTKQQLREFIKENNLVTAQDAQNALKELFAETIQEMLEAELDTHLGYEKHEVKAKKT
RAAC03376               MELLSKEQIRQLIRDGKLKDIHDVQSMLKDLFASTIQEMLEAELDTHLGYAKYDAKHKDT
ref|YP_001664274.1|     MSLLTKEQLRNFISENNIQSIPDLYTSLKNLFKDTIQEMLEAFLSTELGYERYDKKDKDT
ref|YP_001319448.1|     MSTVSKKVLREMITGGDLKTAGDLQSYLKELFKDTLQEMLEAETESDLGYEKGDRKNKNT
                         *     .: :: ::   ..:    *    **: *    :::***.*:. .*** : :.  *.* ref|ZP_02851608.1|      TNSRNGK-REKQLKSNYGNLEIFVPRDREGEFEPQVVKKNQRDVSSIDDQVLSMYAKGMT
ref|YP_001307815.1|     SNSRNGK-STKTMKSNLGLFDLDVPRDRECSFEPAIVKKHQTDVSHLESAVIGMYAKGMT
ref|ZP_02326599.1|      PNSRNGR-SHKTVVSEYGEQQIAVPRDRMGEFEPLVVKKHQSNVTGIEDQIVALYAKGVS
RAAC03376               DNARNGHGAKRTVQSELGDIDIALPRDRKGEFEPLIVQKRQKRMPSIEEQVIALYARGFS
ref|YP_001664274.1|     QNSRNGY-TQKTVKTQFGEMEIDTPRDRQGEFEPKIVPKYKRDISGIEEKVIALYARGMS
ref|YP_001319448.1|     QNRRNGY-SEKTVKSKFGEMEIEVPRDRNGEFEPVVVPKNKRDISGIEEKVISLYARGMS
                         *  ***    :  ::  *   ::  :****  *.***  :*  *    :.  ::.  ::.:**:*.:

ref|ZP_02851608.1|      VRDIQTHLQELYGVDASPTLISGITDKIVPLIKEWQNRPLSRIYAHVVMDAVHYKVRQDG
ref|YP_001307815.1|     TRDIATQINDIYGMDASPTLISNITDKVIPMLKEWQSRPLESIYPIIFMDAIHFKVRKDN
ref|ZP_02326599.1|      TREIQDHLQNLYGIEVSPTLISNVTNKIVPLIKEWQNRPLQSVYAVVFLDAIHFKVKQDG
RAAC03376               TRDIQDHLQQIYGVDMSPTLVSNLTDRLLPRIQEWQNRPLHPLYTVVFLDAIHYKVREEG
ref|YP_001664274.1|     TRDIHDQIKDLYGIELSAEMVSKITERIVPEIKEWQSRPLEKIYTFIFMDAIHYKVRTDG
ref|YP_001319448.1|     TRDIHDQIQDIYGIEISAEMVSKITDKVIPQVKEWQNRALEAIYPFVFMDAIHYKVREDG
                         .*:*    :::::**::  *.  .:*  :*::::*   ::***.*.*    :*.  ..::**:*:**:  :.

ref|ZP_02851608.1|      RIVNKAAYMAIGIDLDGMKDVLGIWIGENESSKYWLKIINELKNRGVEDILIVSIDGLKG
ref|YP_001307815.1|     AIVSKAAYAVIGVNLEGKKDVLGIWIGASESPKYWLLVLNELKNRGINDILIACVDGLNG
ref|ZP_02326599.1|      AIVSKAAYMVIGIDLDGNKDVLGMWIGENESSKFWLSVLNDLKNRGVQDILITCVDNLNG
RAAC03376               RLVSKAAYMVIGIDIEGQKDVLGIWIGQSESSKFWLGVLNDLKARGVQDVLVFSTDNLKG
ref|YP_001664274.1|     HIINRAAYVVLGVTIEGIKDVLGIWIGENESSRFWLGVLNELKNRGVEDVIVFSVDGLTG
ref|YP_001319448.1|     QIKSKAAYVVLGIAMDGMKDILGIWIGESESSKFWLGILNDLKNRGVNDVLIFSVDCLAG
                         :  .:***  .:*: ::  ::*  ..::**   :*:  :*::::  . *.*  * ref|ZP_02851608.1|      FEDAIHAVYPQTEIQSCIIHQIRNSTRYISYKDRKEFCSDLKNVYRAPTEEVALIELDKL
ref|YP_001307815.1|     FKEAIKAVFPNTEIQRCIIQRNSSKYLSYKDLKAFNTDLKSVYKAPTEDVALAELDNL
ref|ZP_02326599.1|      FSEAITASYPKTEIQKCIIHQIRNSTRYVSYKDLKKVTADLKPIYKASTEEAAVLELDRF
RAAC03376               FSEAIAACFPQSDVQKCIVHQIRNSLRYVSYKDFKAVAAALKPIYQAPTEEAALMELDQF
ref|YP_001664274.1|     IKEAIQAAFPKSEIQRCTIHQLRNCFKVYSYKHLKEFSKDFKAVYQSANEEIARDEFEKL
ref|YP_001319448.1|     MKEAIQASFPKSEIQRCVIHQLRYSFKYVNYKDRKEFAKDFKEVYTAVNEKAGHEKLMEL
                         :.:**  *  :*:::::*  *::**:*  .  :*:..**. *  . :* :* :. .*.  .  ::  .:

ref|ZP_02851608.1|      EEKWGDKYEISIRSWRNNWDKLSVMFKYPEEVRKLIYTNNSMESYNRQLRKVTKSKSIFP
ref|YP_001307815.1|     EEKWGGKYLIAIKSWRNNWDELSTFFKYPPEIRKIIYTTNAMESYNRQLRKVTKSKSIFP
ref|ZP_02326599.1|      EEVWGSKYPLIIRSWRNNWAELATFFKYPPEIRRLIYTTNMIESYHRQLRKVTKGKSIFP
RAAC03376               ERGWGARYPLCVKSWRDNWTELATFYRYPVEMRRIMYTTNIIEGYHRQLRKATKGKSMFP
ref|YP_001664274.1|     KNKWQNLYPYAIKSWENNWDVLSPFYKFPEEVRKIMYTTNIIEGFHRQLRKVTKSKTIFP
ref|YP_001319448.1|     ENKWGKKYPYAIKSWDANWDVLSPFFKFPSEVRKIMYTTNMIEGLHRQFRKVTKTKSIFP
                         :. *    *     ::**  **  *:  ::::*  *:*:::**.*  :*.  :**:**.**  *::**

ref|ZP_02851608.1|      TDESLLKMLYLATMDITKKWTMRTKNWAQILGQLSIYFEGRI-----
ref|YP_001307815.1|     NDESLLKILYLATIDITKKWTQGIKGWAQILAQLSIFFEGRL-----
ref|ZP_02326599.1|      SDEALLK----------------------------------------
RAAC03376               NDEALLKMLYLATMELTRKWTMRVANWGTILGQLAIYFGDRVTPYIP
ref|YP_001664274.1|     SDEALEKMLYLVTMNVLKKWTVRYKNWDIVLNQLIIMYPGRLEKYL-
ref|YP_001319448.1|     SDQALEKMLFLASQNIMKKWTLSHRNWDIVLNQLMIFFEDRLT----
                         .*::* *
```

FIG. 133

```
ref|YP_001516732.1|    ------------------------------KTRLNGICPYFTMFPLDFPYSILEE
ref|YP_318565.1|       --------------------------------------------------------
ref|YP_076090.1|       ------------------------------PHLRLNALCPYFTMFPLDFPTRYLAQ
RAAC02657              MRKRRIAMHVDPNRTDRGAAASQMELWSKRRSSDPRLRLNAISPYYTMFPLAFPLRVLAG
ref|YP_001185431.1|    --------------------------------------------------------
ref|ZP_01061333.1|     ---------------------QVTPWADKSDSDPLHSLCSYLGAFPPSLAKYFIKY ref|YP_001516732.1|    HGSRGEWVLDPFCGRGTTIYASRLLGMPSIGIDSSPVATAISEAKLVNIKPGHIVSTAIK
ref|YP_318565.1|       --------------------------------------------------------
ref|YP_076090.1|       -ARPGEWVLDPFCGRGTTNYAARLHGLPTVGIDSSPVAVAIARAKLVQVTPDELIAEAER
RAAC02657              -AERG-WVLDPFCGRGTTNFAARLAGFPTVGVDINPIAVAIAQAKLASTTVHGVVERCQQ
ref|YP_001185431.1|    -------IIDPFCGRGTSMFAARKLGLKAWGIDSSPVATAIARAKLASCSKEDILDLARD
ref|ZP_01061333.1|     FTDENDLVFDPFSGRGTTILESRILNRKSIGSDLNPIALALSKAKSHKLKKKDIIDRIDE ref|YP_001516732.1|    ILKNAEEPSDIPTG----EFWELAFHKNVLNSLCKFRE-SFLRNCRSDSRKALRAIILGA
ref|YP_318565.1|       --------------------------------------------------------
ref|YP_076090.1|       ILAG-PEPADVPEG----HFWDLAYHPRTLLDICRLRE-ALLRDCEAPVRIALRGLILGI
RAAC02657              ILES-EAPGDVPDG----EFWSWCFHQKTLEDVCRLRQ-ALS-DVQTEEDIVLRALVLGV
ref|YP_001185431.1|    LLQN--AATDMPES----EFFSKLYTSQTLKDVCALREGLLSLAHETDASVMLRALVLGA
ref|ZP_01061333.1|     LESDYDYALYLPEAQSESDEIHLIFHQATIAQLCYLKD--ILLTSKSDIDEFLIGAILGI ref|YP_001516732.1|    LHGPRPKSKQS--YFSNQSQRTYAPKPNYAVNYWKRKGLLPEEVDVIEIIREKADRYFGL
ref|YP_318565.1|       --------------------------------------------------------
ref|YP_076090.1|       LHGPRTRRAPS--YLSNQMPRTYATKPDPAVRFWVRRGMRPEEVDVLDVLARRARYSFAA
RAAC02657              LHGPRNKGLPS--YLSNQMPRTYATKPDAAVRYWKSRGIHPVYVDVLDVVRRRAEHVLSH
ref|YP_001185431.1|    LHGPLNKSLDTAIYFSNQMPRTFASKPDYSVRYWDQRSLVPPAISVLDVLKRKLDR-IPT
ref|ZP_01061333.1|     MHGGERKDGTSG-YLSISMPNTFSMSPEYVRRFVQTKELNRVKRNVFDILKEKVERVFSK ref|YP_001516732.1|    EKSQGMG---KIIVGDSRNNK---YFQKIQSQVNWVITSPPYYGMSSYIPDQWLRSWFLG
ref|YP_318565.1|       ------------------------------KFDWIITSPPYYGLRTYLPDQWIRNWFLG
ref|YP_076090.1|       LPPPVPG----CILQADSREPG---AIPVVDGGYRWVITSPPYLGMRSYQPDQWLRLWFLG
RAAC02657              VPDKVPG----FVRLADSRTLA---PEDFAMR-FRYVITSPPYFGMKTYVSDHWLRHWFLG
ref|YP_001185431.1|    LDEQFTGSFHQIIEGDSQLEI---TRAKVADDFSIVITSPPYYGMKTYVQDQWIRNWFLG
ref|ZP_01061333.1|     HKSPEKES--YIFECDAKEISKSEKLKKYQGKVDLILTSPPYLGIVNYAKQNWIRSWFLD
                                                    ::*****  *:  .*    ::*:* ***.

ref|YP_001516732.1|    DSSQVNYSSPEQLNHLSPDHFSSALKKVWENSSDICAQNATLVIRFGSINTRNVD-ALEI
ref|YP_318565.1|       GPSVVDYTSEGQLSHNGRDRFIADLRQVWANVGARCRPGATLVIRFGSIGDRLVEDPAQL
ref|YP_076090.1|       GEPTVRYIHEGQVSHLQG-EYQRDLATVWRNVAARCRPGTRLIIRFGCLPTLPCN-PKQV
RAAC02657              GPPYVDYASDPQLGRPSLLAFIEGLREVWTRVSQVCEPGALLVVRFGAIPSYEVD-PIEV
ref|YP_001185431.1|    GASTVDYTSGPQLEHGGVTTFAESLGKVWRNMADTRADSLRMFIRFGIIPSAKID-AKKI
ref|ZP_01061333.1|     SDP----------------------------------------------------------
                       . .

ref|YP_001516732.1|    IKKSLC--QTRWKTKNIKSAGFASQGRRQAIHINSKVSNPREEYDIWANL---
ref|YP_318565.1|       VSASLE--ETGWVTTEILHADNAARGRRQADTFHRKRSAPYDEVDVWA-----
ref|YP_076090.1|       LEETLARSGVPWRIVEVTGAGIPPRHRRQAVQFEKTRP-AHEEIDLVAVLGE-
RAAC02657              LRASLS--GTPWKERRLCDAGSASNGRRQADQFQFVRSRATLEVDLYASLEEA
ref|YP_001185431.1|    MQMSLEASGKEWKIISIRSAETAAEGKRQATQMKSKSS-AAIEYDFH------
ref|ZP_01061333.1|     --------------------------------------------------
```

FIG. 134

```
ref|YP_001505049.1|    ------------------------------------------------------------
ref|YP_481774.1|       ------------------------------------------------------------
ref|YP_482514.1|       ------------------------------------------------------------
ref|NP_215436.1|       MYCBACTERIUMTUBERCULSISFREFZPHYPTHETICALRESLVASEMYCBACTERIUM
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       TUBERCULSISSTRHAARLEMREFZPHYPTHETICALRESLVASEMYCBACTERIUMTUB
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       ERCULSISHRAEMBCABPSSIBLERESLVASEMYCBACTERIUMTUBERCULSISHRVGB
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       AAKISRESLVASEMYCBACTERIUMTUBERCULSISCDCEMBCADPSSIBLERESLVASE
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       MYCBACTERIUMBVISAFEMBCALPSSIBLERESLVASEMYCBACTERIUMBVISBCGST
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       RPASTEURPGBEAYHYPTHETICALPRTEINTBCGMYCBACTERIUMTUBERCULSISCG
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       BEBAHYPTHETICALRESLVASEMYCBACTERIUMTUBERCULSISSTRHAARLEMGBAB
ref|YP_001680037.1|    ------------------------------------------------------------
RAAC01373              ------------------------------------------------------------ ref|YP_001505049.1|    ------------------------------------------------------------
ref|YP_481774.1|       ------------------------------------------------------------
ref|YP_482514.1|       ------------------------------------------------------------
ref|NP_215436.1|       QISRESLVASEMYCBACTERIUMTUBERCULSISHRACBABRHYPTHETICALRESLVAS
ref|YP_001680037.1|    ------------------------------------------------------------
RAAC01373              ------------------------------------------------------------
``` continued →

FIG. 134 continued

```
ref|YP_001505049.1|    ------------------------------------------------------------
ref|YP_481774.1|       ------------------------------------------------------------
ref|YP_482514.1|       ------------------------------------------------------------
ref|NP_215436.1|       EMYCBACTERIUMTUBERCULSISFSCRESIGNIFICANCEE-IDENTITIESPSITIVE
ref|YP_001680037.1|    ------------------------------------------------------------
RAAC01373              ------------------------------------------------------MDNDVHL ref|YP_001505049.1|    -----MNLKEWAESQGVAYVTAQRWFHAGKLPVPARKVG-GLILVG-EPDRPATSGTVVV
ref|YP_481774.1|       -----MNLKEWAESQGVAYVTARRWYAAGKLPVPARRVG-GLILVG-EPDQPTGDGLTAV
ref|YP_482514.1|       -YDVRVNLKEWAAANGVGYTTARRWYRDGLLPVPARKVG-GLVLVD-ESTVPAGRPVAVV
ref|NP_215436.1|       SGAPSMNLADWAESVGVNRHTAYRWFREGTLPVPAERVG-RLILVKTAASASAAAAGVVL
ref|YP_001680037.1|    ------MKLSEWAKKNGITYRTAWQWFKAGKLPVPAVQMPTGTILIQ--EGG-KHEGKVAL
RAAC01373              VYFISMKLSDWARKNGISYKTAWRWVKEGRMPVPFEQTPSGTILVH--EPEPSTTNAVAL
                            ::* :**    *:    ** :*   *   :***   :     :*:         ...:

ref|YP_001505049.1|    YARVSSADQKSDLDRQVACVTGWATGQGLPVDRVVTEVGSALNGHRRKFLALLRDPAATT
ref|YP_481774.1|       YARVSSADQRPDLDRQVARVTAWATGQNLPVDKVVTEVGSALNGHRRKFLALLRDPDVAT
ref|YP_482514.1|       YARVSSADQKPDLDRQVARIVTWAASQNLAVGRVVTEVGSALNGHRRKFLGLLRDPAVAT
ref|NP_215436.1|       YARVSSHDRRSDLDRQVARLTAWATERDLGVGQVVCEVGSGLNGKRPKLRRILSDPDARV
ref|YP_001680037.1|    YARVSSADQKSDLDRQVSRLLTYANEQGWDVGEAVTEIGSGLNGRRPKLMKLLADPKVKV
RAAC01373              YARVSSADQKADLDRQIARLMEFAMAQKLVVVKAVTEIGSGLNGHRPKLMKMLSDPNAHT
                       ******  *::.*****::  :      :*       * ..*  *:**.***:* *:   :* **  . .

ref|YP_001505049.1|    IVVEHRDRFARFGAEYVEAALAANGRRLLVVDPAEVDDDLVRDITEILTSMCARLYGRRA
ref|YP_481774.1|       IVVEYRDRFARFGAEYVEAALSAQGRRLLVVDPGEVDDDLVGDVTEILTSLCARLYGRRA
ref|YP_482514.1|       IVVEHRDRFARFGAEYVEAALSAQGRRLLVVDPGEVDDDLVGDVTEILTSLCARLYGRRA
ref|NP_215436.1|       IVVEHRDRLARFGVEHLEAALSAQGRRIVVADPGETTDDLVCDMIEVLTGMCARLYGRRG
ref|YP_001680037.1|    IVVEHRDRLMRFGFEYVESALVAQGRRIVVVDQSELKDDLVQDMIEVLTSFCARLYGRRS
RAAC01373              IVVEHRDRLMRFGFEYVEAALAAQGRRILVVEPGEVKDDLVQDMVEVLTSFCARLYGRRS
                       ****:****: ***  *:*:** *:***::*.: .*    **** *:  *:**.:********.

ref|YP_001505049.1|    AANRARRAV-------------
ref|YP_481774.1|       AVNRATRAV-------------
ref|YP_482514.1|       AANRAARAV-------------
ref|NP_215436.1|       ARNRAMRAVTEAKREPGAG---
ref|YP_001680037.1|    AANKAKKAMEAMQCED------
RAAC01373              ARHRAKRALEVLEREDSSGVSV
                        *  ::* :*:
```

FIG. 135

```
ref|NP_756021.1|      DNAADENINEMETHYLASEEESCHERICHIACLICFTGBABEDNAADENINEMETHYLASE
ref|NP_709160.1|      ------------------------------------------------------------
ref|YP_405147.1|      ------------------------------------------------------------
ref|YP_001680296.1|   ------------------------------------------------------------
RAAC00337             ------------------------------------------------------------
ref|YP_342400.1|      ------------------------------------------------------------ ref|NP_756021.1|      ESCHERICHIACLIUTIGBABGDNAADENINEMETHYLASEESCHERICHIACLIGBABD
ref|NP_709160.1|      ------------------------------------------------------------
ref|YP_405147.1|      ------------------------------------------------------------
ref|YP_001680296.1|   ------------------------------------------------------------
RAAC00337             ------------------------------------------------------------
ref|YP_342400.1|      ------------------------------------------------------------ ref|NP_756021.1|      NAADENINEMETHYLASEESCHERICHIACLIAPECSCRESIGNIFICANCEE-IDENTI
ref|NP_709160.1|      ------------------------------------------------------------
ref|YP_405147.1|      ------------------------------------------------------------
ref|YP_001680296.1|   ------------------------------------------------------------
RAAC00337             ------------------------------------------------------------
ref|YP_342400.1|      ------------------------------------------------------------ ref|NP_756021.1|      TIESPSITIVESGAPSRAFLKWAGGKYPLLDDIKRHLPKGECLVEPFVGAGSVFLNTDFS
ref|NP_709160.1|      ---------------RAFLKWAGGKYPLLDDIKRHLPKGECLVEPFVGAGSVFLNTDFS
ref|YP_405147.1|      ----------------RAFLKWAGGKYPLLDDIKRHLPKGECLVEPFVGAGSVFLNTDFS
ref|YP_001680296.1|   ----------------RPFLKWAGNKYRIIHRIRAVLPAGNRLIEPFVGSAAVFLNTSFK
RAAC00337             --MSRLVRPRGEAAGMKPFLKWAGGKYRLLPYIQRALPPGRRLIEPFVGSGAVFLNTSYD
ref|YP_342400.1|      ----------------RPFLKWAGNKYRLLTRIISVLPPGKRLIEPFAGSAALFLNAEYE
                                      :.******.**  ::   *    ** *. *:***.*:.::***::.

ref|NP_756021.1|      RYILADINSDLISLYNIVKMRTDEYVQAARELFVPETNCAEVYYQFREEFNKSQDPFRRA
ref|NP_709160.1|      RYILADINSDLISLYNIVKMRTDEYVQAARELFVPETNCAEVYYQFREEFNKSQDPFRRA
ref|YP_405147.1|      RYILADINSDLISLYNIVKMRTDEYVQAARELFVPETNCAEVYYQFREEFNKSQDPFRRA
ref|YP_001680296.1|   ENLLADCNGDLIRLYQTVKTGGEDFIAYCRSFFTEENNRPERYYALREIFNTTDDGDLKS
RAAC00337             AYVLSDINADVIALYRVLSLHGEAFIEACRRLFVPENNCPEVYYALRDEFNASRDLVRRA
ref|YP_342400.1|      RYWVNDINPDLIALYQILQKEGKEFIHYAGCLFTPHNNTPKAYYRLRARFNTTADVAEKA
                       :  * *:* **. :.    . ::   . :*. ...*  .:  ** :*   **  : *    ::

ref|NP_756021.1|      VLFLYLNRYGYNGLCRYNLRGEFNVPFGRYKKPYFPEAELYHFAEKAQNAFFYCESYADS
ref|NP_709160.1|      VLFLYLNRYGYNGLCRYNLRGEFNVPFGRYKKPYFPEAELYHFAEKAQNAFFYCESYADS
ref|YP_405147.1|      VLFLYLNRYGYNGLCRYNLRGEFNVPFGRYKKPYFPEAELYHFAEKAQNAFFYCESYADS
ref|YP_001680296.1|   ALFIYLNRHSYNGLCRYNASGKFNAPAGRYKKPYFPERELRFFMAKARDAVFLCQDFTQT
RAAC00337             ALFVYLNRHGYNGLCRYNAEGRFNVPFGRYKRPYFPEREMRYFCEKARRAEFLCVDFREV
ref|YP_342400.1|      ALFVYLNRHGYNGLCRYSGSGIFNVPFGRYQRPYFPSKEMMAFHIKARRRFTCLDFRKV
                       .**:****:.*******.    * **.* ***::****. *:    *  **: * * *   .:  .

ref|NP_756021.1|      MARADDASVVYCDPPYAPLSATANFTAYHTNSFTLEQQAHLAEIAEGLVDRHIPVLISNH
ref|NP_709160.1|      MERADDASVVYCDPPYAPLSATANFTAYHTNSFTLEQQAHLAEIAEGLVERHIPVLISNH
ref|YP_405147.1|      MARADDASVVYCDPPYAPLSATANFTAYHTNSFTLEQQAHLAEIAEGLVERHIPVLISNH
ref|YP_001680296.1|   MGEARPGDVVYCDPPYVPLSRTSNFTGYSAGGFGEAEQWKLAELARQLADRGVSVLISNH
RAAC00337             MRMAEPGDVVYCDPPYVPLSKTANFRQYAAQGFGEAEQRDLARIAEELADRGIPVLISNH
ref|YP_342400.1|      LARIRRGTIVYADPPYTPLSQTACFTHYSGNGFGPEEQKALTQSAQRLAKRGIPVLISNH
                      :       . :..* *: *      :*.  :  *:. *.   *..*  :.****** ref|NP_756021.1|      DTMLTREWYQRAKLHVVKVRRSISSNGGTRKKVDELLALYKP---
ref|NP_709160.1|      DTMLTREWYQRAKLHVVKVRRSISSNGGTRKKVDELLALYKP---
ref|YP_405147.1|      DTMLTRKWYQRAKLHVVKVRRSISSNGGTRKKVDELLALYKP---
ref|YP_001680296.1|   DTDFTQKAYDAARIERFPVQRFVSCDGANRGKAGELLALF-----
RAAC00337             LTPFTERAYRRAECRQLQVRRATSCQGARRGYAPEVLALFAPRSR
ref|YP_342400.1|      DTPSVRQAYRNAQLTGFSVTRLISCKGTQRTPANEVLALF-----
                       *  ...  *  *.   . *  :*.* *   . *:***:
```

FIG. 136

```
emb|CAD18993.1|        MTNRTAVLSDIHGVLPALEAVLAEPEVRA-ADRVVLTGDIACGPQ-PAEVLDLLTALGD-
ref|ZP_00995572.1|     ---RVAVLSDVHGVLPVLEAVLAEPDVAS-ADLIVVTGDHTAGPM-PVETLDALTALDG-
RAAC00506              MPARVAALYDIHGNLAALDAVLQEVERAG-ADALVFGGDLAFGPQ-PRQVLERVMSLGG-
ref|YP_001115956.1|    ---KIAALSDIHGNLAALDAVLDDVRRRG-ADVIVNLGDIVSGALHPAETADRLIALD--
ref|ZP_02134324.1|     ---RIALISDIHGNDIALETVLKDMKSAGGIDQIICLGDVANLGPDPCSVVARLRDVN--
ref|YP_805441.1|       ---KIAALYDIHGNYPALKEVLKQVKKLS-PDLVVLGGDLIAGPM-PLETLSLLKHVSTT
                          :  :  *:**    .*. **  :    . *  :: **      *  ..   :  :.

emb|CAD18993.1|        -RVTWVAGNADRELVE----FRRGVRETIPDPIGPWAARQLRPDHLELLASLPLSVRLPVA
ref|ZP_00995572.1|     -RVVLVRGNADREAVA----IRSG--DDSPHPEALWAAHALREDQIAVLSALPHPVTIDIA
RAAC00506              -PVSFVRGNTDREVAERHGVEQGVRGWIAEVN-AWCHDQLTPDQREFLLSQKAHVTLHVE
ref|YP_001115956.1|    --LPTIRGNHERQLLER-------TRDAMGLSDRWAHDTLHERHRAWLAALPERATLG--
ref|ZP_02134324.1|     ---CPCVLGNHDAFLFDRDLIHQYTEVDYIIEAVDWCRDQLTQDDIDWMGDFHRVLEVLMD
ref|YP_805441.1|       FKTVGIMGNNDQDIVDIYAKKRVGLSRKATEQLTWIANQLSYKQVSFLRNLLPSISIG--
                            : **  :                                  *    *  . :      :

emb|CAD18993.1|        GLGTVLFCHATPRDDE----EVVVVDSRPDRWREVFDGLG--PDVDAVICGHTHMP-FVR
ref|ZP_00995572.1|     GFGEVLFCHGSPRDDD----EVVLVDSPPTAWQNALSIVP--DTVQTIVCGHTHMP-FVR
RAAC00506              GLGDVLFVHGSPRSDE----EAIRRDTPEAEILPMVAHVG--ESI--IVCGHTHIQ-FDR
ref|YP_001115956.1|    --DDVLLVHGTPASDLDYFLETVTRDGCRAATPDEIAQRAEDEPASLILCGHTHVPRVAR
ref|ZP_02134324.1|     KAGSLIAFHGSPLSHM----DNILSRTPDAEVDRLIQGLN----GEILACGHTHIQ-MLR
ref|YP_805441.1|       ---NYFFCHAVKNDNT----TVFSPQQNKAYIETLFKGVQ----ESYIICGHTHIQ-FEL
                          :  *. ..        .             .                :  *****:   .

emb|CAD18993.1|        LAHGRLVVNPGSVGMPYG-RSGAHWALLGPG-VDLRRTPYDTDAAIARLTRDCGYPAIAE
ref|ZP_00995572.1|     LVDRRTVINPGSIGMPYG-RAGGAWALLDRGQVSLRHTEIDLDAVCARIVAESGYPDRAA
RAAC00506              MVAGKRVVNAGSVGLPSA-ARGACWALIGPE-IELRETLYDFERAAAEIR-KSGAPKAGE
ref|YP_001115956.1|    LADGRTIVNPGSVGLPA-------------------------------------------
ref|ZP_02134324.1|     QHRGRLIINPGSVGLP--------------------------------------------
ref|YP_805441.1|       SLPNKKIINAGSIGMPFSNQFGAQWLWLDDNRIEYKRTIFN-QQAAIQLISQTEYPFKNE
                        : ::*.**:*:* emb|CAD18993.1|        WAD-----------
ref|ZP_00995572.1|     WADE----------
RAAC00506              FADDILNPPVAGP
ref|YP_001115956.1|    --------------
ref|ZP_02134324.1|     --------------
ref|YP_805441.1|       FIANNLRSTIS--
```

FIG. 137

```
ref|YP_001488901.1|    ----------------------RLPPQNIEAEQAVLGAVFLEPSALTLASEVLIPEDFYRM
ref|YP_001423303.1|    ----------------------RLPPQNIEAEQAVLGAVFLQPSALTLASEVLIPDDFYRM
ref|NP_391924.1|       ----------------------RLPPQNIEAEQAVLGAIFLQPSALTLASEVLIPDDFYRM
ref|NP_244897.1|       ----------------------RTPPQNIEAEQAVLGAIFLEDHALVTASERLAPEDFYRA
ref|ZP_01695451.1|     ----------------------RIPPQNIEAEQAVLGAIFLEPSAFITASEILTAEDFYRN
RAAC00022              MRNAMAAEETLWRDREAEAALRMPPHNLEAEQAVLGAMLISPDAVVEAMEILEADDFYRS
                                             * **:*:**********::.  *.  *  * .:**** ref|YP_001488901.1|    SHQKIYNAMLVLGDRGEPVDLVTVTSELANT-DLLEEVGGISYLTDIANSVPTAANIEYY
ref|YP_001423303.1|    SHQKIYNAMLVLGDRGEPVDLVTVTSELANT-DLLEEVGGVSYLTDIANSVPTAANIEYY
ref|NP_391924.1|       SHQKIYNAMLVLGDRGEPVDLVTVTSELANT-DLLEEVGGISYLTDIANSVPTAANIEYY
ref|NP_244897.1|       AHQRIYQVMLDLAEKGEPVDLVTVTAELQDR-KALDDVGGVAYLGDLANAVPTAANVEYY
ref|ZP_01695451.1|     AHQKIFQVFAKLNDAGKAVDLVTVAEELSAT-RQLEDAGGLSYLSELAASVPTAANIAYY
RAAC00022              AHQAIYRAIREVYEAGDPVDIITVASRLRTYGDVLDAVGGPEYLADLAAMMPTALHVVHY
                       :** *:..:  :  : *..:::.*     *: .   ::* :*** :: :* ref|YP_001488901.1|    AKIVEEKSILRRLIRTATTIAQDGYTREDEVEDLLSDAEKTIMEVAQRKNSGAFQNIKDV
ref|YP_001423303.1|    AKIVEEKSILRRLIRTATSIAQDGYTREDEVEDLLSDAEKTIMEVAQRKNSGAFQNIKDV
ref|NP_391924.1|       AKTVEEKSILRRLIRTATTIAQDGYTREDEVEDLLSEAEKTIMEVAQRKNTSAFQNIKDV
ref|NP_244897.1|       SKIVEEKSLLRRLIRVATNIAQEGYASEEEVDAILDDAEKTILDVAQRKNSSAFISIKDV
ref|ZP_01695451.1|     AGIVAEKALLRLIRTATHIAQEGYTREDDVDELLDEAERSIMEVAQRKNAGDFKHIKDV
RAAC00022              AEIVREKALLRRIISAGTRIAEAAYEPDASAMEVLADAERLVLELSQHQRTRDFTHISDV
                       : ** **:;***;*  ..* **; .*   ;  .  :*  :**: :::::*:.:  *  *.**

ref|YP_001488901.1|    LVQTYDNIEQLHNRKGDITGIPTGFSELDRMTAGFQRNDLIIVAARPSVGKTAFALNIAQ
ref|YP_001423303.1|    LVQTYDNIEQLHNRKGDITGIPTGFIELDRMTAGFQRNDLIIVAARPSVGKTAFALNIAQ
ref|NP_391924.1|       LVQTYDNIEQLYNRKGDITGIPTGFTELDRMTAGFQRNDLIIVAARPSVGKTAFALNIAQ
ref|NP_244897.1|       LVETYDKIEMLQNQKGEITGIPTGFKDLDRMTAGFQRNDLIIVAARPSVGKTAFALNISQ
ref|ZP_01695451.1|     LVSTYDNIEMLHNRKGDVTGIPTGFYELDRMTAGFQRNDLIIVAARPSVGKTAFALNIAQ
RAAC00022              LQTTFERIEQLYESDGNITGVPTGYSDLDRMTSGFQKSDLIIVAARPSVGKTAFALNIAQ
                       *  *::.**  *  :  .*:::*: :***:*:.*********************:* ref|YP_001488901.1|    NVATKTDESVAIFSLEMGSEQLVMRMLCAEGNINAQNLRTGNLTEEDWGKLTMAMGSLSN
ref|YP_001423303.1|    NVATKTDESVAIFSLEMGAEQLVMRMLCAEGNINAQNLRTGNLTEEDWGKLTMAMGSLSN
ref|NP_391924.1|       NVATKTDESVAIFSLEMGAEQLVMRMLCAEGNINAQNLRTGNLTEEDWGKLTMAMGSLSN
ref|NP_244897.1|       NVATKTDENVAIFSLEMGASQLVQRMLCAEGNIDAQRMRTGALTEEDWQKLTMAMGSLAR
ref|ZP_01695451.1|     NVGTKTEENVAIFSLEMGAEQLVMRMLCAEGNIDAQRLRTGALTDEDWRKLTMAMGSLSN
RAAC00022              NVAVRAGLPVAIFSLEMSKDQLVQRMLCAEAFIDGHKLRNGTLDDEDWPKLSMGVTTLSN
                       **..::  ********. .*** ****** . *:.:.:*.*  * ***  **:*. .*:..

ref|YP_001488901.1|    SGIFIDDTPGIRVSEIRSKCRRLKQENGLGMILIDYLQLTQGSGRSSDNRQQEVSEISRA
ref|YP_001423303.1|    SGIFIDDTPGIRVSEIRSKCRRLKQENGLGMILIDYLQLIQGSGRSSDNRQQEVSEISRA
ref|NP_391924.1|       SGIYIDDTPGIRVSEIRAKCRRLKQESGLGMILIDYLQLIQGSGRSKDNRQQEVSEISRE
ref|NP_244897.1|       AGIYIDDTPGIKVNEIRAKCREKGLGMILIDYLQLIQGRSGENRQQEVSEISRS
ref|ZP_01695451.1|     SGIYIDDTPGVRVTEIRSKCRRLKEHGLGMVVIDYLQLIQGSARSRENRQQEVSEISRS
RAAC00022              SPIYIDDTPGLTVPEMRSKLRRLKLEHGLGFVVIDYLQLIHGRRMAGENRQQEISDISRS
                        :  *:******: * *:*:* **  * ::;*******:*   : :****:*:.*** ref|YP_001488901.1|    LKSLARELEVPVIALSQLSRGVEQRQDKRPMMSDIRESGSIEQDADIVAFLYRDDYYDKE
ref|YP_001423303.1|    LKALARELEVPVIALSQLSRGVEQRQDKRPMMSDIRESGSIEQDADIVAFLYRDDYYDKE
ref|NP_391924.1|       LKSIARELQVPVIALSQLSRGVEQRQDKRPMMSDIRESGSIEQDADIVAFLYRDDYYDKE
ref|NP_244897.1|       LKGLARELEVPVIALSQLSRGVESRQDKRPMMSDIRESGSIEQDADIVAFLYRDDYYDKE
ref|ZP_01695451.1|     LKALARELEVPVIALSQLSRGVEQRQDKRPMMSDIRESGSIEQDADIVAFLYREDYYEQD
RAAC00022              LKQLARELEVPILALAQLSRSVEQRQDKRPMLSDIRESGSIEQDADVVAFLYRDDYYNPD
                       ** :****:**::**.** ** .*******:.*************:*****:***: :

ref|YP_001488901.1|    SENKNIIEIIIAKQRNGPVGTVSLAFVKEYNKFVNLER-----
ref|YP_001423303.1|    SENKNIIEIIIAKQRNGPVGTVSLAFVKEYNKFVNLER-----
ref|NP_391924.1|       TENKNIIEIIIAKQRNGPVGTVSLAFVKEYNKFVNLER-----
ref|NP_244897.1|       TENQNIIEIIIAKQRNGPVGTVELAFIKEYNKFVNLDRHHDE-
ref|ZP_01695451.1|     TENKNIIEIIIAKQRNGPVGTVQLAFIKEYNKFVNLER-----
RAAC00022              TENPNVVEVIIAKQRNGPTGKIELVFLKNFNKFVNLERAHAEP
                       :** *::*:*********.*  :**.*::*******
```

FIG. 138

```
ref|YP_001213441.1|        -------MLNKVILIGRLTQDPELRYTPGGVAVARFTLAVNRARLNKQGERETDFIDVVV
RAAC00027                  MNAEGTSMLNRVILIGRLTADPELRYTNNGTAVASFTLAVDRMRSGPNGERQTDFINVVV
ref|YP_077145.1|           -------MLNSVVLIGRLTKDPELRYTPSGKAVATLRLAVDRGTVNQQGERETDFIDIVV
ref|NP_244917.1|           -------MLNRVVLVGRLTRDPELRYTPNGVAVANFTLAVNRPFSNQQGEREADFINCVV
ref|YP_149334.1|           -------MLNRVILVGRLTRDPELRYTPSGVAVATFTLAVNRPFTNQQGERETDFIQCVV
ref|YP_001377189.1|        -------MMNRVILVGRLTKDPDLRYTPNGVAVATFTLAVNRAFTNQQGEREADFINCVI
                                  *:*  *:*:**** **:**** .*  *** : ***:*    . :***::***: *:

ref|YP_001213441.1|        WQKQAETCANYIRKGRLVAVEGRLQVRSYDDSQGIRRKAAEVVAETVRFLDR--------
RAAC00027                  WQKQAEIVAQYLQKGRLAAVDGRLQIRSYDNRDGQRVRVAEVVAETVRFLDRGPDQAQGS
ref|YP_077145.1|           WEKQAETVANYLQKGRLVAVQGRLQIRQYTTQDGQKREKAEVVATTVRFLDSARD-----
ref|NP_244917.1|           WRKQAENVANYLKKGSLAGVDGRIQTRSYDNNEGR--------------------------
ref|YP_149334.1|           WRRQAENVANFLKKGSLAGVDGRLQTRSYENQEGRRVYVTEVVADSVQFLEPKGT-SEQR
ref|YP_001377189.1|        WRKQAENVANYLKKGSLAGVDGRLQTRNYEGQDGRRVYVTEVLAESVQFLEPRNSGCEQR
                             *.:***  *:::** *..*:**:* *.*   :* ref|YP_001213441.1|        ------------------------------------------------------------
RAAC00027                  GYSAAG---------AQTRQQRPTPSSAPPFEDDPFADDSQLIDISEDDLPF
ref|YP_077145.1|           ------------------------------------------------------------
ref|NP_244917.1|           ------------------------------------------------------------
ref|YP_149334.1|           GATAGGYYGDPFPFGQDQNHQYPNEKGFGRIDDDPFANDGQPIDISDDDLPF
ref|YP_001377189.1|        GSFNQQPSGAGFGNQGSNPFGQSGNSGFTK-NDDPFSNVGQPIDISDDDLPF
```

FIG. 139

```
ref|YP_001255315.1|    -------------------------------------GAPSIKKRDGQYEPLQVEKTKK
gb|ACA43749.1|         ----------------------------------------IKKRDGQYEPLQVEKTKK
ref|YP_001392092.1|    ----------------------------------------IKKRDGQYEPLQVEKTKK
ref|ZP_02619122.1|     ----------------------------------------IKKRDGQYESLQVEKTKK
ref|YP_074151.1|       ---------------------------PERASEFIAELR--------------
RAAC01051              MQMVHPSDTSTGLMERTGQGELRSGRASHALEEWRDRVKTFTVEKRDGRIEPLSLDKIFA
                                                  : * ref|YP_001255315.1|    MVKLACEGIEGCDPLELELDSRIQFRDGMTTKEIQRTLIQTAIEKVIQNSKDNNGNNIKK
gb|ACA43749.1|         MVKLACEGIEGCDPLELELDSRIQFRDGMTTKEIQRTLIQTAIEKVIQNSKDNNGNNIKK
ref|YP_001392092.1|    MVKLACEGIEGCDPLELELDSRIQFRDGMTTKEIQRTLIQTAIEKVIQNSKDNNGNNIKK
ref|ZP_02619122.1|     MVKLACEGIEGCDPLELELDSRIQFRDGMTTKEIQRTLIQTAIEKVIQNSKDNNGNNIKK
ref|YP_074151.1|       ----------------------PLLHATTDRSQQMDLAARLAAEKTSVEEPD--------
RAAC01051              FLKRGCEAAEGCDPERLAADVWPQLRDGMRTSEIARVAIQAAVEKTSVAEPG--------
                                            ::    .:      :  * **.        . .

ref|YP_001255315.1|    TNANWQYVAARLLCFDLYKEAKISRHYNSFGYGDYYQLVKKLVKIK------LYGEYLIQ
gb|ACA43749.1|         TNANWQYVAARLLCFDLYKEAKISRHYNSFGYGDYYELVKKLVKIK------LYGEYLIQ
ref|YP_001392092.1|    TNANWQYVAARLLCFDLYKEAKISRHYNSFGYGDYYELVKKLVKIK------LYGEYLIQ
ref|ZP_02619122.1|     TNANWQYVAARLLCFDLYKEAKISRHYNSFGYGDYYELVKKLVKMK------LYGEYLIQ
ref|YP_074151.1|       ----WQYVAARLYLQKLYGEAARNRGYHQPGYGDFYELVRQLHAMGDEAGNRVYGAYMIE
RAAC01051              ----WQFVAARLLLFDAYKQASRNRGYRHLGYGDFYQLIVELERIG------RYGTYIRQ
                           **:*****  . *  :*  .* *. ****:*:*: :*  :      ** *: :

ref|YP_001255315.1|    NYSDEEIKELAKYIVPERDELFNYEGLKLLNDRYLIKGNNGEILELPQERFMTIAMHLAI
gb|ACA43749.1|         NYSDEEIKELAKYIVPERDELFNYEGLKLLNDRYLIKGHNGEILELPQERFMTIAMHLAI
ref|YP_001392092.1|    NYSDEEIKELAKYIVPERDELFNYEGLKLLNDRYLIKGHNGEILELPQERFMTIAMHLAI
ref|ZP_02619122.1|     NYSDEEIKELAKYIVPERDELFNYEGLKLLNDRYLIKGHNGEILELPQERFMTIAMHLAI
ref|YP_074151.1|       AYSEEEIRELGRYIRPERDELFTYVGLLHLADRYLIKGFHGEILELPQERYMHIAMHLAS
RAAC01051              HYSEDEIAELAAYIKPERDYLFNYVGLKQLLDRYAIRNLDNGIMELPQELFMGVSMHLAM
                        ::  .  ** .*  **    *  ***  *:..  .*:***** :*  ::**** ref|YP_001255315.1|    PEGDKKVFYAKKFYDLLSELKVTVATPTLGNAGTPFYQLSSCFISVVGDNLWSIYDVNQK
gb|ACA43749.1|         PEGDKKVFYAKKFYDILSELKVTVATPTLGNAGTPFYQLSSCFISVVGDNLWSIYDVNQK
ref|YP_001392092.1|    PEGDKKVFYAKKFYDLLSELKVTVATPTLGNAGTPFYQLSSCFISVVGDNLWSIYDVNQK
ref|ZP_02619122.1|     PEGDKKVFYAKKFYDLLSELKVTVATPTLGNAGTPFYQLSSCFISVVGDNLWSIYDVNQK
ref|YP_074151.1|       VESDR-VTWAKRFYDVLSRQEMTVATPTFRNAATPLPQLSSCFIDTVDDSLQSIYDTNQS
RAAC01051              KEKDK-VAWAKRFYDMLSTLQATVATPTLSNARKPFHQLSSCFIDMPEDDLVSIYATDEA
                         *  *:  * :**:***:**   : ******: **  .*: *******.    *.*  *** .::

ref|YP_001255315.1|    FAQVSKHGGALGIYTGKIRALNSEIRGHKNASGGVVPWIRLYNDTAVAVDQLGKRKGGAA
gb|ACA43749.1|         FAQVSKHGGALGIYTGKIRALNSEIRGHKNASGGVVPWIRLYNDTAVAVDQLGKRKGGAA
ref|YP_001392092.1|    FAQVSKHGGALGIYTGKIRALNSEIRGHKNASGGVVPWIRLYNDTAVAVDQLGKRKGGAA
ref|ZP_02619122.1|     FAQVSKHGGALGIYTGKIRALNSEIRGHKNASGGVVPWIRLYNDTAVAVDQLGKRKGGAA
ref|YP_074151.1|       FAQVSKHGGGMGIYIGKLRARGSAIRGRKGAAAGVIPWVRNYNDTAVAVDQLGARKGAVS
RAAC01051              FARVSKFGGGMGIYVGKIRARGSAIRNHPGASGGVPWIRNFNNTAVSCNQLGMRAGAAA
                        **:***.**.:*** **:**  *:** .* **.: .*:.:*:**:* :*:***  * *...:

ref|YP_001255315.1|    ITLDIWHKDIFDFLDLKTNNGDDRRKAHDIFPSVSIPDLFMKRLEKRESWSLFDPYIVEK
gb|ACA43749.1|         ITLDIWHKDIFDFLDLKTNNGDDRRKAHDIFPSVSIPDLFMKRLEKRESWSLFDPYIVEK
ref|YP_001392092.1|    ITLDIWHKDIFDFLDLKTNNGDDRRKAHDIFPSVSIPDLFMKRLEKRESWSLFDPYIVEK
ref|ZP_02619122.1|     ITLDIWHKDIFDFLDLKTNNGDDRRKAHDIFPSVSIPDLFMKRLEKRESWSLFDPYIVEK
ref|YP_074151.1|       IWLDVWHKEIFEFLALKLNNGDDRMRAHDIFPGVCVPDAFMRAVEQGDADWHLFCPHEVRT
RAAC01051              VYLDVWHKDILDFLQLRTNNGDDERMKAHDIFPGVCIPDLFMRRVEERGMWYLFCPYEVRK
                        :  **:***::** *::*:** ****.*  :******.**  :**  *    *  ** *:  *..

ref|YP_001255315.1|    IMGYKLEDYFDDEDRKEFTNKYLECERNTNIPRDTVPTLDIMKKLMKSAVETGTPFIFFR
gb|ACA43749.1|         IMGYKLEDYFDDEDRREFTNKYLECERNTNIPRDTVPTLDIMKKLMKSAVETGTPFIFFR
ref|YP_001392092.1|    IMGYKLEDYFDDEDRREFTNKYLECERNTNIPRDTVPTLDIMKKLMKSAVETGTPFIFFR
ref|ZP_02619122.1|     IMGYKLEDYFDDEDCREFTNKYLECERNTNIPRDTVPTLDIMKKLMKSAVETGTPFIFFR
ref|YP_074151.1|       EMGFSLEDAWGEEWERRYR-LCVEAAHADKLDATVVRARQVAKAMLKSQYETGGPFLFFR
RAAC01051              VMGFSLEDSWGEEFERRYE-ACVENP---NLPRVEIPAIEIMKRIMQSAFETGTPFIFFR
                        **:.*** ..:.:*  :::    :*  ::   :  : :: *  :::    *** *:***
``` continued →

FIG. 139 continued

```
ref|YP_001255315.1|    DTVNKANPNKHKGMIYSSNLCHEIAQNMSESRLLEEEIIDGNGYSEIVQRVKAGDMVTCN
gb|ACA43749.1|         DTVNKANPNKHKGMIYSSNLCHEIAQNMSESRLLEEEIIDGNGYSEIVQRVKAGDMVTCN
ref|YP_001392092.1|    DTVNKANPNKHKGMIYSSNLCHEIAQNMSESRLLEEEIIDGNGYPEVVQRVKAGDMVTCN
ref|ZP_02619122.1|     DTVNKANPNKHKGMIYSSNLCHEIAQNMSESQLLEEEIIDENGYPEVVQRVKAGDMVTCN
ref|YP_074151.1|       DTVNRLNPNKHAGMVYCSNLCTEIAQNQSPTRLIEKTDDGE----VITYRWQPGDFVVCN
RAAC01051              DTANRLNPNKHAGMVYCSNLCTEIIQNMSPSRRIEETEEGG----IITMKTEAGDFVVCN
                       **.*:.*****.**:*.****.**.**.*.::.:*:.       :..:.:.**:*.**

ref|YP_001255315.1|    LNSINLSKVKKEE-FNECIPFQIRMLDNVISLNKLPVKEAKVTSDKYRAIGLGTSGYHHF
gb|ACA43749.1|         LNSINLSKVKKEE-FNECIPFQIRMLDNVISLNKLPVKEAKVTSDKYRAIGLGTSGYHHF
ref|YP_001392092.1|    LNSINLSKVKKEE-FNECIPFQIRMLDNVISLNKLPVKEAKVTSDKYRAIGLGTSGYHHF
ref|ZP_02619122.1|     LNSINLSKVKKEE-FSECIPLQIRMLDNVISLNKLPVKEAKVTSDKYRAIGLGTSGYHHF
ref|YP_074151.1|       LASINLSKVHTEEKIAEVVPLAIRMLDNVIDLNFYPVPQAKITNKKYRAIGLGVHGYHQM
RAAC01051              LSSLNLGRCRDLDSIREIVRRQIRAMDNVIDLNHYPVPQAAVTNRKYRAVGLGVSGYHQY
                       * *:**.: :   : : * :  ** :****.** ** :* :*. ****:***. ***:

ref|YP_001255315.1|    LANNKIRWESDEHIKVADEIYEEIAYIAIKSSMELAKEKGSYPAFKDSEWETGKYFERRG
gb|ACA43749.1|         LANNKIRWESDEHIKVADEIYEEIAYIAIKSSMELAKEKGSYPAFKDSEWETGKYFERRG
ref|YP_001392092.1|    LANNKIRWESDEHIKVADEIYEEIAYIAIKSSMELAKEKGSYPAFKDSEWETGKYFERRG
ref|ZP_02619122.1|     LANNKISWESDEHIKVADEIYEEIAYIAIESSMELAKEKGSYPAFKGSEWETGKYFERRG
ref|YP_074151.1|       LAELGIHWESEDHLRKADEVFELLNYYAVKTSIELAAEKGCYPLCKGSDWETGEYFALRG
RAAC01051              LAEKGIPWESEAHVKHADELFEWINFFAIEASMELAREKGPYPLFEGSDWQTGRYFDLRG
                       **:   * ***: *:: ***::*  : : *:::*:*** ***  **  .:*:*:**.**   **

ref|YP_001255315.1|    YNS-----ERWKKLQSNIKKYGMRNGYITAIAPTGSTSNIANTTAGIDPVFKKFFMEEKKG
gb|ACA43749.1|         YNS----ERWKKLQSNIKKYGMRNGYITAIAPTGSTSNIANTTAGIDPVFKKFFMEEKKG
ref|YP_001392092.1|    YNS----ERWKKLQSNIKKYGMRNGYITAIAPTGSTSNIANTTAGIDPVFKKFFMEEKKG
ref|ZP_02619122.1|     YNS----ERWKKLQSNIKKYGMRNGYITAIAPTGSTSNIANTTAGIDPVFKKFFMEEKKG
ref|YP_074151.1|       YES----DRWQALRRQAAEVGLRNAYLLAIAPTSSTSLLCGTTASVDPIYDRVYNEGKKD
RAAC01051              YRTRPGGPDWDGLRREVAEHGVRNAYLVAIAPTSSTSLIAGSTAGIDPVYARFFLEEKKN
                       *.:       *. *: :   : :*:**.*: *****.*** :..:**.:**:: ..: * **.

ref|YP_001255315.1|    SFTPKTAPDLNEENFWYYKEAHTIDQQWSIKACAVRQKHIDQAQSFNLYITPEIKAKEIL
gb|ACA43749.1|         SFTPKTAPDLNEENFWYYKEAHTIDQQWSIKACAVRQKHIDQAQSFNLYITPEIKAKEIL
ref|YP_001392092.1|    SFTPKTAPDLNEENFWYYKEAHTIDQQWSIKACAVRQKHIDQAQSFNLYITPEIKAKEIL
ref|ZP_02619122.1|     SFTPKTAPDLNEENFWYYKEAHTIDQQWSIKACAVRQKHIDQAQSFNLYITPEIKAKEIL
ref|YP_074151.1|       QVIPLAAPGLSPKTYLYYKPAHQIDQTWSIRAAGVRQRHIDQSQSFNLYIRPDIKGRDFL
RAAC01051              GVVPQTAPNLNDKTFWYYKEAHTIDQRWSIEACAARQRHVDQSQSFNLYITPGISARQFL
                       . * :**.*. ::: *  *** .*...**:*::*****.* *..::* ref|YP_001255315.1|    NMYIESWKQGVKTIYYVRNKSLEMD--ECTSCSS
gb|ACA43749.1|         NMYMESWKQGVKTIYYVRNKSLEMD--ECTSCSS
ref|YP_001392092.1|    NMYMESWKQGVKTIYYVRNKSLEMD--ECTSCSS
ref|ZP_02619122.1|     NMYMESWRQGVKTIYYVRNRSLEMD--ECTSCSS
ref|YP_074151.1|       NLYMQAWKNGLKTVYYVRSRSLEVTEAECEACQA
RAAC01051              DLYLLAWKRGLKTVYYVRSKSVEV--EDCVACSS
                       ::*:.:*:.*:**:****.:*:*:   :* :*.:
```

FIG. 140

```
ref|YP_878438.1|        ------------------------------------------------------------
ref|ZP_02621211.1|      ------------------------------------------------------------
ref|YP_001392091.1|     ------------------------------------------------------------
ref|YP_001255314.1|     MBTULINUMASTRATCCGBABSRIBNUCLESIDE-DIPHSPHATEREDUCTASEBETASU
ref|YP_001560315.1|     ------------------------------------------------------------
RAAC01050               ------------------------------------------------------------ ref|YP_878438.1|        ------------------------------------------------------------
ref|ZP_02621211.1|      ------------------------------------------------------------
ref|YP_001392091.1|     ------------------------------------------------------------
ref|YP_001255314.1|     BUNITCLSTRIDIUMBTULINUMASTRHALLSCRESIGNIFICANCEE-IDENTITIESP
ref|YP_001560315.1|     ------------------------------------------------------------
RAAC01050               ------------------------------------------------------------ ref|YP_878438.1|        -----------IFNENGNR--GTESMINGNTTNLREWNRIKYNWANELYRTMLNNFWIPE
ref|ZP_02621211.1|      -----------IFNENGNR--GTESIINGSTTNLREWNRIKYNWANELYRNMLNNFWIPE
ref|YP_001392091.1|     -----------IFNEKGQR--GTESMINGNTTNLREWNRIKYSWASDFYRTMLNNFWIPE
ref|YP_001255314.1|     SITIVESGAPSIFNEKGQR--GTESMINGNTTNLREWNRIKYSWASDFYRTMLNNFWIPE
ref|YP_001560315.1|     ------MEKKKIFNEYGDR--GTDCLIKGNTTNLREWNRIKYDWARLIYRTMLNNFWIPE
RAAC01050               ----MQLKRTRLFNAEGDRDWGKRRIIGGNTTNMIELNNIKYEWAYKLYRAMMNNFWIPE
                                   :**  *:*  *.  :* *.***: * *.***.**  :** *:******* ref|YP_878438.1|        EISLNEDVKQFPYLTDGERNAFDKIISFLNFLDSVQSENLPNISRYITAPEVSSLLNVQT
ref|ZP_02621211.1|      EISLNEDVKQFSYLTDGERNAFDKIISFLNFLDSIQSENLPNISRYITAPEVSSILNIQA
ref|YP_001392091.1|     EISLNEDIKQFPYLTDGERNAFDKIISFLNFLDSVQSENLPNISRYITAAEVSSLLNIQT
ref|YP_001255314.1|     EISLNEDIKQFPYLTDGERNAFDKIISFLNFLDSVQSENLPNISRYITAAEVSSLLNIQT
ref|YP_001560315.1|     EISLQEDVKQFPYLTDGERNAFDKIIAFLNFLDSIQSENLPNISRYITAPEVSSLLNVQA
RAAC01050               EIPLADDARQYDLLSDDERRSYNKVLSFLIFMDSLLTHNLPNINEYITAPEVNLCLTVHA
                        **.* :* :*:  *:*.**.:::*:::** *:**: :.*****..****.**.  *.:::

ref|YP_878438.1|        FQEEIHAQSYSYILDTVTNPITRDKIYDQWREDKNLLERNKFIAGIYQSFNENPTTENFL
ref|ZP_02621211.1|      FQEEIHAQSYSYILDTVTNPITRDKIYDQWREDKNLLERNKFIAGIYQRFNENPTTENFL
ref|YP_001392091.1|     FQEEIHAQSYSYILDTVTNPITRDKIYDQWREDEHLLERNKFIAGIYEKFNKEPEIHNFL
ref|YP_001255314.1|     FQEEIHAQSYSYILDTVTNPITRDKIYDQWREDEHLLERNKFIAGIYEKFNKEPEIHNFL
ref|YP_001560315.1|     FQEEIHAQSYSYILDTVTNPVTRDRIYDIWREDKYLLERNKFIANIYQRFSDEPSDENFV
RAAC01050               FQEAVHSQSYGYVLDSVVNPATRDQIYNEWRNDDHLLRRNQFITDLFEEFIENPTDRNLM
                        *** :*:***.*:**:*.** ***:**: **:*: **:*.**.**:**:.::: * .:*  .*::

ref|YP_878438.1|        RTIMANYILEGIYFYSGFSFFYTLARQGKMTATSTIFKYINRDEITHLILFQNIIKELKN
ref|ZP_02621211.1|      RTIMANYILEGIYFYSGFSFFYTLARQGKMTATSTIFKYINRDEITHLILFQNIIKELKN
ref|YP_001392091.1|     RAIMANYILEGIYFYSGFSFFYTLARQGKMTATSTIFKYINRDEVTHLVLFQNIIKELKN
ref|YP_001255314.1|     RAIMANYILEGIYFYSGFSFFYTLARQGKMTATSTIFKYINRDEVTHLVLFQNIIKELKN
ref|YP_001560315.1|     RVVFANYILEGIYFYSGFSFFYTLARQGKMTATSTIFKYINRDEITHLVLFQNIMKELRV
RAAC01050               KTIVANYILEGVYFYAGFGFFFVLGRQGKMLGTVSEIKFIQRDELTHLAIFRNLYHEIIR
                        :.:.*******:***:**.**:.*.***** .* : :*:*:***:*** :*:*: :*: :*:

ref|YP_878438.1|        ENPDIFTESIMEEFRMMMKMGVEHEIKWGQYVTNNEILGINDNLIEKYIKYLSNLRLNAI
ref|ZP_02621211.1|      ENLDIFTESIIEEFRMMMKTGVEHEIKWGQYVTNNEILGINNNLIEKYIKYLSNLRLNAI
ref|YP_001392091.1|     ENSHIFTEELEEEFRQMMRMGVEHEIQWGQYVTNNEILGLNDELIEKYIKYLSNLRLVAI
ref|YP_001255314.1|     ENLHIFTEELEEEFRQMMRMGVEHEIQWGQYVTNNEILGLNDELIEKYIKYLSNLRLVAI
ref|YP_001560315.1|     EQKEMFTKGLEEELREMMRTGVEHEIAWGQYVTDNQILGINNELIDQYIKYLSNQRLRAV
RAAC01050               ENPGIVTPDMEEEFVEMMRTAVQHEIAWGQYVTQGKIVGLTDALIDAYIKYLANLRLQSL
                        *:  :.*  : **:  **: .*:*** ******:.:*:*:.: **: *****:* ** ::

ref|YP_878438.1|        GLEVLYPEITEHPMEWIENFSKLNNTKTDFFEAKVTNYTKAAAFDFDDL
ref|ZP_02621211.1|      GLEVLYPEITEHPMEWIENFSKLNNTKTDFFEAKVTNYTKAAAFDFDDL
ref|YP_001392091.1|     GLKPLYPEINKHPMEWIDSFSKLNSTKTDFFEAKVTNYTKAAAFDFDDL
ref|YP_001255314.1|     GLKPLYPEINKHPMEWIDSFSKLNSTKTDFFEAKVTNYTKAAAFDFDDL
ref|YP_001560315.1|     GLEILYPEITKHPMEWIESFSNINSTKTDFFEAKVTNYTKAAVFDFDDL
RAAC01050               NLPILYPEIKEHPMPWMDSFAAINSHKTDFFEQRVTNYTKAGNLNWDDL
                        .*  *****.:*** *::.*: :*. ****** :*******. :::***
```

FIG. 141

```
ref|YP_148023.1|        ------------------------------------------AEWLAQGSIAVPKLLLGHY
ref|YP_001126202.1|     ------------------------------------------AEWLAQGSVVVPKLLLDHY
ref|ZP_01697284.1|      --------------------------------------------LTVPQLLLKKY
ref|YP_001421643.1|     ---------------------------------------------SIPNLLLTHY
gb|ABN10253.1|          ----------------------------------------------IPNLLLTHY
RAAC01009               MDLWARSRPRSDSVSPHALPNGALSARGGERMEPSGRQGGNSDYLSAPFVAVPCDLLRRF
                                                                         :*  ** ::

ref|YP_148023.1|        KQLGLGEGELVLLLHMQSFFE-EGVLFPTPAELAERMTVSAAECMEMVRRLLQKGMIAIE
ref|YP_001126202.1|     KQLGLSEGELVLLLHMQSFLE-EGIVFPTPAELAEKMTVSAAECMEMVRRLLQKGMVGIE
ref|ZP_01697284.1|      KQLGLNETELVLLLQVYSFLK-EGNAFPTPEDLAGRLTIPESMCVSILRRLIQHQFLSIE
ref|YP_001421643.1|     RQLGLNETELILLLKIKMHLE-KGSYFPTPFELQSGMSISAEECTSCLRMFIQKGFLFIE
gb|ABN10253.1|          KQLGLNETELILLLKIKMHLE-KGSYFPTPNQLQEGMSTSVEECTNRLRMFIQKGFLFIE
RAAC01009               AQLGLHPHELVVLLQILASGQTEGTTELSPHELGERCGMSSKEVMACVERLVTEGFLAIG
                         **   ::**::      :  :*    :*  :*   :.      :. :: . :: * ref|YP_148023.1|        EHTDEQGIRNEKYTLEPLWEKLVHHLYTQAAQQGELGRQEEEESLYTVFEQEFGRPLSPF
ref|YP_001126202.1|     EHTDERGVRGEKYTLEPLWEQLVHHLYAQTVKDGQIGQQKEEESLYTIFEQEFGRPLSPF
ref|ZP_01697284.1|      EGEGEGGILYEKYSIMPLWAKLADEFIYEKKQDELEKSVNEETDLYTTFEQEFGRPLSPL
ref|YP_001421643.1|     ECEDHNGIKFEKYSLQPLWAKLYDYMQHSQNETQERTSERFQKSLYTIFEEEFGRPLSPL
gb|ABN10253.1|          ECEDQNGIKFEKYSLQPLWGKLYEYTQLAQTQTQERKAEGEQKSLYTIFEEEFARPLSPL
RAAC01009               ERYDDQGAHVTYFDLQPLWDKLKGRRRMVQPPP-------AEKDLVSLFEEEFGRPLSSL
                        *  ..  *    :  : *** :*              :       : .*  : **:**.****.:

ref|YP_148023.1|        ECETLAMWIDQDGHEPAIIKAALREAVLSGKLNFRYIDRILFEWKKNGIRT---------
ref|YP_001126202.1|     ECETLSMWIDQDGHEPAIIKAALREAVLSGKLNFRYIDRILFEWKKNGIRT---------
ref|ZP_01697284.1|      ECETLAMWIDQDGQSPDLIKAALREAVISGKLNFRYIDRILFEWKKNGIRT---------
ref|YP_001421643.1|     ECETLAIWQDQDQHDAILIKHALKEAVLSGKLSFRYIDRILFEWKKNGFKT---------
gb|ABN10253.1|          ECETLAIWQDQDQHDAQLIKHALKEAVLSGKLSFRYIDRILFEWKKNGLKT---------
RAAC01009               ECDQLRAWLGEHGYPEWLVVEALKESVLANKYSFRYIDRVLYNWQKNNVRSRQDLEQYRA
                        **:  *    * .:.          ::   **:*:*::.*  .******:*:: :**...::

ref|YP_148023.1|        ------------------------------------------------------------
ref|YP_001126202.1|     ------------------------------------------------------------
ref|ZP_01697284.1|      ------------------------------------------------------------
ref|YP_001421643.1|     ------------------------------------------------------------
gb|ABN10253.1|          ------------------------------------------------------------
RAAC01009               QYRERQAQWRGEPQAGQSKPRSRPASPRTAAREPVRDERYASFYELFPD
```

FIG. 142

```
ref|ZP_02175216.1|    ------------------------------------------------DKVFYPEAGFTKGE
ref|YP_464174.1|      ------------------------------------------------DKVFYPEAGFTKGE
ref|ZP_02321813.1|    ------------------------------------------------DKVFYPEAGFTKGE
ref|YP_753805.1|      -----------------------AMAGREIK----------LTNLDRVLWPEDGYCKRD
ref|ZP_01575281.1|    ------------------------------------------DKLFWPEAGITKLE
RAAC00998             MLEMGSKGRKNGIQVSSLIATGSSAHARREVKRMKRHESPPTLTHGDKIYFPAAGLCKRD
                                                                        *::  :*   *    *  :

ref|ZP_02175216.1|    VVDYYRRVAPVLLPHLRDRPLTLKRYPEGVDGPHFYEKRCPRHRPDWFRTEAIWSEGNQD
ref|YP_464174.1|      VVDYYRRVAPVLLPHLRDRPLTLKRYPEGVEGPHFYEKRCPRHRPDWFRTEAIWSEGNQE
ref|ZP_02321813.1|    VVDYYRRVAPVLLPHLRDRPLTLKRYPEGVDGPHFYEKRCPRHRPDWFRTEAIWSEGNQD
ref|YP_753805.1|      LVEYYTAIFPYMLPHLSERPLVFTRYPRGIGEKSFYQKNAPEGLPQWIKTFTWAGS-DGD
ref|ZP_01575281.1|    YVKTMTKLAPFLIKYSKHRMLTSIRYPHGINDKSFFQKEKPQGTPEWVETVEFN------
RAAC00998             YMTYLAQIGEHLVRHLRHRPVTLVRCPDGVAGRRFYQRHLPPHAPPSLPRREVQG-----
                        :       :   ::  :   .* :.   *  * *:   *:::.  *    *   .

ref|ZP_02175216.1|    YIDYCVVDDLSSLVWLASIADLELHPSLSLVDDV--ERPTALVFDLDPGPPADLLACCEV
ref|YP_464174.1|      YIDYCVVDDLSSLVWLASIADLELHPSLSLVDDV--ERPTALVFDLDPGPPADLLACCEV
ref|ZP_02321813.1|    YIDYCVVDDLSSLVWLASIADLELHPSLSRVDDV--ERPTALVFDLDPGPPAELLACCEV
ref|YP_753805.1|      SKNYVLVQQTVDLMWLANLACIEIHPWLSQINSI--EYPDFIVFDLDPSEQSTFEQVISV
ref|ZP_01575281.1|    QKNYINLNSAATLVWLCTQAALELHTSFNVHEKP--NHPSSLVFDLDPDDDLHFEDVAEL
RAAC00998             ERPLIAIPDVETLLYYGNLGAIEFHAGLHLVQGPQAGCPTALTFDLDPSDPRDFERVREL
                         :  .      *::  . . :*:*. :     :       *  :.*****.   :        .:

ref|ZP_02175216.1|    ALLLRRLLAALGLEAFPKGSGSKGMQLYVPLSG-ATYADTKPFAHAVARLLERRHPQLVV
ref|YP_464174.1|      ALLLRRLLAALGLEAFPKSSGSKGMQLYVPLSG-ATYADTKPFAHAVARLLERRHPQLVV
ref|ZP_02321813.1|    ALLLRRLLAALGLEAFPKSSGSKGMQLYVPLSG-ATYADTKPFAHAVARVLERRHPQLVV
ref|YP_753805.1|      ARLLHELMDSLSLRVYPKTSGAKGLHLYLPIAEGFTYSQIRRVAQAMAEMVCQVIPDIAT
ref|ZP_01575281.1|    AGRIHETLEALGIMDFIKTSGATGLQIFVPVAAKFDYDTARSLNEFFAQYFAEKLRSTVT
RAAC00998             ALCLREVLRGLGLDGVAKTTGASGLQVLVPLEEPLPYAVTRPVVNFVAAYCASRWPDLAT
                       *  ::. :  .*.:        *  *:.*::  :*:      *       :. . .*      ...

ref|ZP_02175216.1|    ERMAKALRGGKVLVDWSQNDPHKTTVCVYSLRARPRPTVSTPLRWAEVEKAVRTRDAGGL
ref|YP_464174.1|      ERMAKALRGGKVLVDWSQNDPHKTTVCVYSLRARPRPTVSTPLRWAEVEKAARTRDACGL
ref|ZP_02321813.1|    ERMAKALRGGKVLVDWSQNDPHKTTVCVYSLRARPRPTVSTPLRWAEVEKAVRTRDAGGL
ref|YP_753805.1|      TERALKHRGPRVYLDYLQNGLGKTVCAAYSVRPHKGAPCSTPIEWQELES-IRPDQ----
ref|ZP_01575281.1|    IERMKKKREGKIYFDWQQMWTGKSMITAYSARAVKSAAVSAPIEWSELND-VRPEM----
RAAC00998             TERRVRHRGRRVYVDAPQHGPTRTLIAAYSVRAVEKALVSAPITWAELEYGVSPDA----
                        *     ::   .*   *     ::   .**  *.   .   *:*: * *::    .

ref|ZP_02175216.1|    VFEAAAVLRRVERVGDLFAPVLTLRQRLPA-------------------
ref|YP_464174.1|      VFEAAAVLRRVERVGDLFAPVLTLRQRLPA-------------------
ref|ZP_02321813.1|    VFEAGAVLRRVERVGDLFAPVLTLRQRLPA-------------------
ref|YP_753805.1|      -FTIKTLPERLQQVGD---------------------------------
ref|ZP_01575281.1|    -FTLKNIINRLEQKGDIFE------------------------------
RAAC00998             -FDLHVVPDRLERVGDWLELAARHPASRVRAIHDALPPPWRQTRVRSV
                       *     :  *:::  **
```

FIG. 143

```
ref|NP_832076.1|         ------------------------------------------------------------
ref|YP_001645033.1|      ------------------------------------------------------------
ref|NP_844759.1|         ELREFZPCGBACTERIALNUCLEIDDNA-BINDINGPRTEINBACILLUSANTHRACISS
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         TRAREFYPDNA-BINDINGPRTEINHUBACILLUSTHURINGIENSISSTRALHAKAMRE
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         FZPDNA-BINDINGPRTEINHUBACILLUSANTHRACISSTRAREFZPDNA-BINDINGP
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         RTEINHUBACILLUSCEREUSAHREFZPDNA-BINDINGPRTEINHUBACILLUSCEREU
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         SAHREFZPDNA-BINDINGPRTEINHUBACILLUSANTHRACISSTRAREFZPDNA-BIN
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         DINGPRTEINHUBACILLUSANTHRACISSTRAREFZPDNA-BINDINGPRTEINHUBAC
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         ILLUSCEREUSWREFZPDNA-BINDINGPRTEINHUBACILLUSCEREUSNVH-REFZPD
ref|YP_001375058.1|      ------------------------------------------------------------
ref|YP_535778.1|         ------------------------------------------------------------
RAAC02359                ------------------------------------------------------------ ref|NP_832076.1|         ------------------------------------------------------------
ref|YP_001645033.1|      ------------------------------------------------------------
ref|NP_844759.1|         NA-BINDINGPRTEINHUBACILLUSCEREUSHREFZPDNA-BINDINGPRTEINHUBAC
ref|YP_001375058.1|      ------------------------------------------------------------
ref|YP_535778.1|         ------------------------------------------------------------
RAAC02359                ------------------------------------------------------------
``` continued →

FIG. 143 continued

```
ref|NP_832076.1|          ------------------------------------------------------------
ref|YP_001645033.1|       ------------------------------------------------------------
ref|NP_844759.1|          ILLUSCEREUSBBREFZPDNA-BINDINGPRTEINHUBACILLUSANTHRACISTSIANK
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          VSKII-IGBAAPDNA-BINDINGPRTEINHUBACILLUSANTHRACISSTRAMESGBAAS
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          DNA-BINDINGPRTEINHUBACILLUSCEREUSATCCGBAATDNA-BINDINGPRTEINH
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          UBACILLUSANTHRACISSTRAMESANCESTRGBEALDNA-BINDINGPRTEINHUBACI
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          LLUSCEREUSGGBAATDNA-BINDINGPRTEINHUBACILLUSANTHRACISSTRSTERN
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          EGBAATDNA-BINDINGPRTEINHUBACILLUSTHURINGIENSISSERVARKNKUKIAN
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          STR-GBAAUDNA-BINDINGPRTEINHUBACILLUSCEREUSELGBABKHUFAMILYDNA
ref|YP_001375058.1|       ------------------------------------------------------------
ref|YP_535778.1|          ------------------------------------------------------------
RAAC02359                 ------------------------------------------------------------ ref|NP_832076.1|          ------------------------------------------------------------
ref|YP_001645033.1|       ------------------------------------------------------------
ref|NP_844759.1|          -BINDINGPRTEINBACILLUSTHURINGIENSISSTRALHAKAMGBEDRDNA-BINDIN
ref|YP_001375058.1|       ------------------------------------------------------------
ref|YP_535778.1|          ------------------------------------------------------------
RAAC02359                 ------------------------------------------------------------
``` continued →

FIG. 143 continued

```
ref|NP_832076.1|          ------------------------------------------------------------
ref|YP_001645033.1|       ------------------------------------------------------------
ref|NP_844759.1|          GPRTEINHUBACILLUSANTHRACISSTRAGBEDRDNA-BINDINGPRTEINHUBACILL
ref|YP_001375058.1|       ------------------------------------------------------------
ref|YP_535778.1|          ------------------------------------------------------------
RAAC02359                 ------------------------------------------------------------ ref|NP_832076.1|          -----------------------------------------------------SISATCC
ref|YP_001645033.1|       ------------------------------------------------------------
ref|NP_844759.1|          USANTHRACISSTRAGBEDRDNA-BINDINGPRTEINHUBACILLUSANTHRACISSTRA
ref|YP_001375058.1|       ------------------------------------------------------------
ref|YP_535778.1|          ------------------------------------------------------------
RAAC02359                 ------------------------------------------------------------ ref|NP_832076.1|          SCRESIGNIFICANCEE-IDENTITIESPSITIVESGAPSMNKTELIKNVAQSADISQKD
ref|YP_001645033.1|       ----------------------------------------MNKTELVKNVAQSADISQKD
ref|NP_844759.1|          SCRESIGNIFICANCEE-IDENTITIESPSITIVESGAPSMNKTELIKNVAQSADISQKD
ref|YP_001375058.1|       ----------------------------------------MNKTELIKNVAQSADISQKD
ref|YP_535778.1|          -----------------------------------------NKAALIERVAEKTGLTKKD
RAAC02359                 ----------------------------------------MNKRDLIRKTAEETGLSQKD
                                                                   **  *:...*:.:.:::**

ref|NP_832076.1|          ASAAVQSVFDTIANALQSGDKVQLIGFGTFEVRERSARTGRNPQTGEEIQIAAGKVPAFK
ref|YP_001645033.1|       ASAAVQSVFDTIANALQSGDKVQLIGFGTFEVRERSARTGRNPQTGEEIQIAAGKVPAFK
ref|NP_844759.1|          ASAAVQSVFDTIATALQSGDKVQLIGFGTFEVRERSARTGRNPQTGEEIQIAAGKVPAFK
ref|YP_001375058.1|       ASVAVQSVFDTITNALQNGDKVQLIGFGTFEVRERAARTGRNPQTGEEIQIAAGKVPAFK
ref|YP_535778.1|          ATVAVDAVFETIQDALVDGEKVQLIGFGNFEVRERAARKGRNPQTGEEIEIPASKVPAFK
RAAC02359                 CEAVINTLFDTIRKTVESGEKVQIIGFGTFELRERAARTARNPRTGEAVEVPARRVPAFK
                          . ..::::*:**  :: .*:***:****.**:***:**..***:*** :::.* :***** ref|NP_832076.1|          AGKELKEAVK-
ref|YP_001645033.1|       AGKELKEAVK-
ref|NP_844759.1|          AGKELKEAVK-
ref|YP_001375058.1|       AGKELKEAVK-
ref|YP_535778.1|          PGKSLKDAVK-
RAAC02359                 PGAELKQAVQV
                          .* .**:**:
```

FIG. 144

```
ref|ZP_01667008.1|    ------------------------EIKWDGIRAVIYLASDNLRILSRNLKDVTRQYPEL
ref|YP_946103.1|      -MPNYSPMLATSGTTADLRGDDWLYELKWDGIRAIITGTESRIRLMSRNGNDLTAAYPEL
ref|YP_075626.1|      ---PFPPMLLER-AEAPFADDDWVYQVKWDGVRNLTLVEGGRVRHWSRRLRERTALFPEF
RAAC00997             -MPFFRPFEPISSTEVPVG-DAWIAQVKWDGVRAVAEVSGDGVQIWNRHGRLRTDRYPEI
ref|ZP_02854041.1|    MEFFQIQAMEPIPRQSVPTGDDWFYQIKWDGIRILTFFDGNSIKLRTKKGFKRTTEYPEL
ref|YP_753804.1|      ------RSMDPINCEQAFDSDDFLYQVKWDGVRMLVAVAGEQVSLLNKRGNLRSRQYPEL
                                              ::****:*  :          :  ..  :  :**:

ref|ZP_01667008.1|    MPLTQALAGHSVILDGEIVAFDINGRPS-----------------FARLQNRMGLASDRT
ref|YP_946103.1|      TDRACWPDGD-FVADGEIVALGKGSRPD-----------------FGRLQLRMNLVKAAD
ref|YP_075626.1|      DGLAAALPGRRAVLDGEIIVLQ-DGRPS-----------------FSAVLERDLAGSTAG
RAAC00997             ASALRPFRGC--AFDGEVVALT-QGRPD-----------------FYRVLRRDRAVASHE
ref|ZP_02854041.1|    NELTKEFGNTTWLLDGEIIVANQTDKSDHPKFITTNESCEEVGANFFHVLKRDRTKNPT-
ref|YP_753804.1|      QNLPNLIRASTAVLDGEIVVLREGKPS-----------------FPAVMQRDNCRNPMK
                            ***::.                                *    :  * ref|ZP_01667008.1|    IARKTTEIPATYIIFDLLYIDGQSTLSLPYIERRRLLEELDLN---GPNWQTPAYKTG-Q
ref|YP_946103.1|      IERARATVPVQLMLFDLLYDDGTDLSGLPFEHRRERLSGFAERWRVGCPLHLSAVLDH-D
ref|YP_075626.1|      AARRR---PATLMLFDLLEWDGRELYDVPLAERLALLEAVVPP---DEAWQVVSSFPGSD
RAAC00997             IEQLVREIPVWYAVFDVVRMGGEWVGDWPLAKRLDWMLEHLSG-----VEHVLTSEGEVD
ref|ZP_02854041.1|    -QKLLKTFPVRYKVFDLLMIDNQWLVNEPFIKRRELLNKHFNN-----NKFLQIIRSYSD
ref|YP_753804.1|      IQHLSKTLAISYMVFDLLYLNGRDLRSASLVDRLSQLAELFDN-----QGCLYLVESFSQ
                              :  :**::  ..    . .* :                       :

ref|ZP_01667008.1|    GRELLLASRRLGLEGIVAKKLDSIYLPGKRPGTWLKIKNVRRQEFVIGGWLPGQGTRTGM
ref|YP_946103.1|      VEDLMTSAAELGLEGVMAKKADSRYVIGRRSRSWIKLKLEQSQEVVVGGWRPGAGARAGT
ref|YP_075626.1|      GPALYAAAVARGLEGVVAKRRASRYVPGARSRDWLKVKRRSEMLAVVVGYTN----PTGR
RAAC00997             TEALFAATKQLGLEGIVCKRVDSTYAPGGKDGRWVKVKHERNAIAAVGGVVY----RDGA
ref|ZP_02854041.1|    GLSLFNITSQQNHEGIVAKKSNSIYHPGKKHSEWFKIKHLKYLQAYLGGVIVK----ENQ
ref|YP_753804.1|      GTILFDSVQRAGLEGIVAKKKNSFYRPGKQHDDWFKIKCRCSQACLVGGYTLR----GKQ
                              *   **::.*:  *  *   :   *.*:*         : * ref|ZP_01667008.1|    IGALLLGYYDRTPKEAAKAGQPQRLLFAGAVGTG-FTHTTLKKLQHLLK--PLEQAEPP-
ref|YP_946103.1|      FGALLLGIPD----------GDKLHYVGRVGSG-FKDWQLRDIMEKLE--PLAIVESP-
ref|YP_075626.1|      PGGLLLGAYR----------DGRLRYIGRVGSG-LSGADLAAIRHHLPSGPCPLAEIPR
RAAC00997             PNALMLGLFD---------DKARLFHVGNAGAGRLPRRAWRQLVERVLS---HETSLQP
ref|ZP_02854041.1|    IKSLLLGQKS--------DLADYKLNYIGRASTG-LTQKELNMLKDFAFKNRVSNSPFGN
ref|YP_753804.1|      VNALLLG-----------VMRDGSLSFAGKASNG-LDAEQLQILSETLPRLEVKDSPF--
                        .*:**            *  * ..  *  :          : .

ref|ZP_01667008.1|    FAESP-----PLKGAVFVKPALVGEVEFTEWTPGGTLRHP-----------------
ref|YP_946103.1|      FADIPR---EDAAGATWVSPELVAEVTFGEWTGPGRLRHPV----------------
ref|YP_075626.1|      LRERFG---GDPGPVVWVEPLLTVRVSFTEWTEEGRLRDPVVV--------------
RAAC00997             FARAP----KAVRTCRFAHPVVAVKVRFAEWTPKGTMRHPVLLAELDIPATPAACSFAQA
ref|ZP_02854041.1|    LSKVDLELADSKESVVFLSPQLKLQVKYTNWTPGGNLRHPVI---------------
ref|YP_753804.1|      -------LEPTPAGSHYITPQLAVEVEYLEWTDSLHLRFPVI---------------
                            :  *  :  .* :  :**   :* * ref|ZP_01667008.1|    --
ref|YP_946103.1|      --
ref|YP_075626.1|      --
RAAC00997             DP
ref|ZP_02854041.1|    --
ref|YP_753804.1|      --
```

FIG. 145

```
ref|ZP_02330146.1|        ---MRVAIYIRVSTEEQAQYGYSIDAQKERLIAYCTSQGWTDYKIYIDDG
RAAC02419                 MLLMTVALYCRVSTDEQAEHGFSIDNQKERLIAFCKSQGWDQYRLYIDDG
ref|YP_001210709.1|       ----TVACYIRVSTDEQAEQGISIPAQKSRLLAFCRSQGWNIYGFYIDDG
gb|AAD26564.1|AF124258_1  ------ALYIRVSTMEQAKEGYSIPAQTDKLKAFAKAKDMAVAKVYTDPG
ref|ZP_02184702.1|        -----VAIYVRVSTQDQAEEGYSIEEQIDKLTKYCDIKDWYVYEIYKDPG
ref|ZP_01828805.1|        ------------------------SKKDKLSSYCDIKDWNVYKVYTDGG
                                                      :  ..:*   :.   ::       .* * * ref|ZP_02330146.1|        YTGTKMMRPALNRLIRHIEDDKIDLVVVYKLDRLSRKQLDVLYLLEEVFE
RAAC02419                 YTGTNMDRPALQRLIKHIKEKKIDTVIVYKLDRLSRKQRDVLYLLEDVFD
ref|YP_001210709.1|       YSGKDLDRPAMRRLIGDTGAKKFDTVLVLKLDRLSRRQKDVLFLLEDVFE
gb|AAD26564.1|AF124258_1  FSGAKMERPALQEMISDIQNKKIDVVLVYKLDRLSRSQKNTLYLIEDVFL
ref|ZP_02184702.1|        FTGSTIDRPGMKKLVNDSKQHKFDTVLVYKLDRLSRSQKDTLYLIEDVFA
ref|ZP_01828805.1|        FSGSNTDRPALESLIKDAKKRKFDTVLVYKLDRLSRSQKDTLHLIEDVFI
                          ::*     **::.  ::  .      *:* *:* ******   *  :.*.*:*:**

ref|ZP_02330146.1|        KHNVGFKSATEPFETTTPFGKAMIGILAVFAQLERDMIVERTTIGRRQRV
RAAC02419                 KNNVVFKSATEPFDTSTPLGKAMLGILAVFAQLERDTIIERLSTGQKLRV
ref|YP_001210709.1|       PGGVGFKSVTESFDTTTPFGKAALGMMMAVFAQLERETIVERVRMAKKESA
gb|AAD26564.1|AF124258_1  KNNVDFISMQESFDTSTPFGRATIGMLSVFAQLERDTITERMHMGRTERA
ref|ZP_02184702.1|        KYNVDFVSLSENFDTSTAFGKAMIGILSVFAQLEREQITERMQMGKVGRA
ref|ZP_01828805.1|        KNGIEFLSLQENFDTSTPFGKAMIGLLSVFAQLEREQIKERMQLGKIGRA
                           .: *  *    * *:*:*.:*:*  :*:::*******: *  **    .:   .

ref|ZP_02330146.1|        SKGEWYG-GRIPFGYRMNRETKQLEIVPEEAKIIKEIYKMYLQGN-SRLS
RAAC02419                 KSGKFSG-GRIPFGYVYNSQTGKFEVSPHEAFLVREVYKKYLQGY-SLSD
ref|YP_001210709.1|       KQGRFMG-GPAPYGYRHNFETKRLEVDEVQAGTVRWIYDRYLSGAPNYRH
gb|AAD26564.1|AF124258_1  KQGYYHGSGIVPLGYDY--VHGELIINDYEAQIIQEIYDLYVNQGKGQQY
ref|ZP_02184702.1|        RSGKAMGWTRPPFGYEYT--EGKYIVDDFKAIVINKIYKEYLSGI-SITK
ref|ZP_01828805.1|        KAGKSMMWAKTSYGYDYHRDTGTITINPAQALAIKFIFESYLRGR-SITK
                              *       .  **        :        :* :.  ::. *:   .

ref|ZP_02330146.1|        IAEWAAER----TKARVIDHSVIRDILSRPVYTGKLSNAGNVVDGKHEAI
RAAC02419                 LSDWIESQ----TSARYWDHARIRDMLTRETYTGVMPYGTLRSTEIAPPI
ref|YP_001210709.1|       IAEELEHTGVPGPTNEKWNKAFVRKILTNPVYAGLIRHRENLYPGRHDPI
gb|AAD26564.1|AF124258_1  ITKRMVAK----YPDKVKTLTIVKYALTNPLYIGKISWDGKVYDGHHSPI
ref|ZP_02184702.1|        LRDKLNDEG-HLGKDIPWSYRAIRSILDNPVYAGYMNFKGEVYKGNHDAI
ref|ZP_01828805.1|        LRDDLNEK----YPKHVPWSYRAVRTILDNPVYCGFNQYKGEIYPGNHEPI
                          :  .                 ::  *  * *             .* ref|ZP_02330146.1|        IDEKTWHAVQKETQER--KEGATP------LGEYLLTGLLKCGVCGG--P
RAAC02419                 IERELWEQVQQEMVRR--REGFTP------KGEYLLSGLLRCAECGS--S
ref|YP_001210709.1|       VSPEKWQEVQKLIKSRGAVRAAAA------VHTCLLSGIIWCGECGARMR
gb|AAD26564.1|AF124258_1  IDKSMYDKAQEIIARMAQKGGEQHG-----NQLGLLLGITYCGKCGA---
ref|ZP_02184702.1|        ITKELFDKTKTELDIRQKQAYAQNNNPRPFQGKYILSGLARCGYCGAP--
ref|ZP_01828805.1|        ISKEEYDKTQSELKIRQRTA-AENVNPRPFQAKYILSGIAQCGYCGAP--
                          :    .   .:   .:                   :* *:   *. **.

ref|ZP_02330146.1|        IVHVKRITRKYGKEYLYELYACKNQHVR------KKDRNNNCSLGYIRREK
RAAC02419                 FIHVIRKK----GPYVYYLYGCRSQHQRPKKVPRRAPKQACTVGYRNREE
ref|YP_001210709.1|       VKNVWQNHPNTNPKKVTRYYVCYSQDRAGG---HMVRNPTCRCGYKHGGA
gb|AAD26564.1|AF124258_1  --EVFRYVSG-GKKYRYNYYMCRSVKKMLP---SLVKDWNCKQPSLRQEV
ref|ZP_02184702.1|        -LELMLGNIRKDGTRLKKYKCTNRIVKSR--VTFYNDNKKCTSGFYHMND
ref|ZP_01828805.1|        -LKIMLGVKRKDGSRLKKYECHQRHPRTLRGVTTYNDNKKCDSGFYYKDK
                           .:                                          . * ref|ZP_02330146.1|        VEKFVIEQIKSYT--TDDVLIKQITNEKNKFKEN--DESALNNLESQLKK
RAAC02419                 LESWVIEQVKRIARLDAEEFEHQIANIETNSDE---TEDTLRDLRKNLSD
ref|YP_001210709.1|       VEEQVLRELFCYS--YDRRLLRRALEEALAAADNRAFLRELAQARKDLAA
gb|AAD26564.1|AF124258_1  VEKKVIDSLKSLDFKKIERELKQVENKT---------KSKITTINNQISK
ref|ZP_02184702.1|        LEDYVINEVSKLQ--KNP---ETIFERTEIKN-----ENHTEIYEHRIVV
ref|ZP_01828805.1|        LEAYVLKEISKLQ--DDADYLDKIFSGDNAET-----IDR-ESYKKQIEE
                          :*  *:  .:                 .            .    :

```
ref|ZP_02330146.1|          VLTGLENLYDAIESGEIKASSISDRIRKLEEQRDVLENHIDEIKDNTPQN
RAAC02419                   IEHKLNRWYEAFEEGTIDATQLRDRIKHLEEERRRLQTNIEELQDTLVKD
ref|YP_001210709.1|         TEKKLERWYDAFEKGALEGDQLTERVKGLHQRKAYLRGQIAEMESRLKEG
gb|AAD26564.1|AF124258_1    KHNEKQKILDLYQYGTFDVTMLNERMKKIDNEINALTANIANLEGTKSES
ref|ZP_02184702.1|          IDKKIKRLSDLYMNDLINLEDMQFKAKALKDEKDHLLNKLNHSEHKLENV
ref|ZP_01828805.1|          LSKKLSRLNDLYIDDRITLEELQSKSAEFISMRGTLETELENDPALRKNK
                              ..    :    . :     :    :    :  .   *  .: .      :

ref|ZP_02330146.1|          ---ELNIQEFNIFIKEIGEAWDYLTEDEQKALIRKAFRSVTLYKD-KEIK
RAAC02419                   ---TQPQRVFN-AAKLIEEAWDYMTFDEKKNVLRAAISYIEIPRKGQPPV
ref|YP_001210709.1|         KERQTSVEEMMGILQDFPRIWENATAEERREIVVNTVKAVKV--------
gb|AAD26564.1|AF124258_1    --------LINKLETLKTFNWETETTENKILIIKEFVERIEL--------
ref|ZP_02184702.1|          -----KKDKAILFLKDIENNINDETYENKKKIINVLIKKVDVKANEIKVI
ref|ZP_01828805.1|          -----RKADMRKLLN--AEKVFSMDYENQKVLVRRLINKVKVTAEDIVIN
                                 ::: ::     . : :

ref|ZP_02330146.1|          VEWN-
RAAC02419                   IHWNV
ref|YP_001210709.1|         -----
gb|AAD26564.1|AF124258_1    -----
ref|ZP_02184702.1|          WN---
ref|ZP_01828805.1|          WKI--
```

FIG. 146

```
ref|ZP_02309926.1|      ----FSKRLSELRKKKGFSQYKLADELGFSRGQVANYEQGTREPDYQTLLKIAEFFNVST
ref|ZP_01941236.1|      ----FSKRLSELRKKKGFSQYKLADELGFSRGQVANYEQGTREPDYQTLLKIAEFFNVST
ref|ZP_01926077.1|      ----FSKRLSELRKKKGFSQYKLADELGFSRGQVANYEQGTREPDYQTLLKIAEFFNVST
ref|NP_469419.1|        ----FSKRLSELRKKKGFSQYKLADELGFSRGQVANYEQGTREPDYQTLLKIAEFFNVST
ref|YP_001111866.1|     ----------------MTQEQLAQQLGFTRGQVSNYEQGSREPDFETLKKIADFFKVTT
RAAC02417               MMMTFGERLAQLRRSKGLSQYALAEQLKMTRGQIANYEQGTREPDIETLKKLADFFDVSI
                                          :*   **::* ::***::*****:****  :**  *:*:**.*:

ref|ZP_02309926.1|      DYL-LGR----DDNNLADTIAAHID--SNATEEDIKEILAYIEEKR-KEHANEKETNITE
ref|ZP_01941236.1|      DYL-LGR----DDNNLADTIAAHID--SNATEEDIKEILAYIEEKR-KEHANEREINITE
ref|ZP_01926077.1|      DYL-LGR----DDNNLAETIAAHID--SNASEEDIKEILAYIEEKR-KEHVNEEEINITE
ref|NP_469419.1|        DYL-LGR----DDNNLADTIAAHID--SNASEEDMKEILAYIEEKR-KEHANEREIDITD
ref|YP_001111866.1|     DYM-LGR----TDD--------------PTPVDKLIELSALAGQQK-FDPMK-------E
RAAC02417               DFLVLGKPNVSDFNGLTNEVKRTLEALSQMSVEKQQEVADFAEYLRSKEEQPVVEYDVRE
                        *:: **:    :            .  . :. *:     : :                :

ref|ZP_02309926.1|      IASKEDEEINKFVDE--NEDFKVVAARVM--------------
ref|ZP_01941236.1|      IASKEDEAVDKFVEE--NEDFKAVAARVM--------------
ref|ZP_01926077.1|      IASKEDDAVDKFVEE--NEDFKAVAARVM--------------
ref|NP_469419.1|        IAAKKDADVAKFVEE--NPDFKAVAARVM--------------
ref|YP_001111866.1|     LPPEAQRSLEDFID--------YLMRK----------------
RAAC02417               IAANMEKALYAHGDEDLIQHFEEIMRRVIRRYDERASQDQQNR
                        :..: :   :    .  . :                *
```

FIG. 147

```
ref|ZP_02442523.1|       ---FQKRLKELRNAKGTSQIAIAAALGITDRGYRKYEAGDSEPTLSVIIALADYFDVSLD
ref|YP_001210714.1|      ---FAKRLSFLITKNKLSKQAVANAINVSRPAVSQFANGENLPSVEKLIALADFFDVSLD
RAAC03180                MSSFPERLSELLSATNSTKRALARAIGISERMIQYYITGAKSPTLDVLVAMADYFNVGLD
ref|YP_001664041.1|      -----KRIKELRKKKGITQKELASYLGISDRAVGYYESGQRTPPPDILQKIADFFNVSTD
ref|ZP_02589119.1|       ------RIKSLRKKENLTQKQLAEKIGVSQRMIGYYESEERFPPHDVLTKLADCFSVSAD
ref|NP_242309.1|         ---FPERLRYLRKKHGLTMKELGKKINVAESTISGYENGNRKPDMDTLVKMAEYFNSSTD
                            *:   *  .    :  :.  :.::         :     *  . :  :*: *. . * ref|ZP_02442523.1|       YLCG------------------
ref|YP_001210714.1|      YLVG------------------
RAAC03180                YLAGRSDDPTPPPRSPSSGWDP
ref|YP_001664041.1|      YLLG------------------
ref|ZP_02589119.1|       YLLG------------------
ref|NP_242309.1|         YLLG------------------
                         ** *
```

FIG. 148

```
ref|ZP_02442523.1|      --IFQKRLKELRNAKGTSQIAIAAALGITDRGYRKYEAGDSEPTLSVIIALADYFDVSLD
ref|YP_001662345.1|     ---FSQRLRQLREEKGLLQKDVAKILGITPSAYGYYEQGKREPSMEVLKKLSDFFNVSID
ref|YP_001210714.1|     --IFAKRLSFLITKNKLSKQAVANAINVSRPAVSQFANGENLPSVEKLIALADFFDVSLD
RAAC03525               MTLFSQRLTELLDRTGTTRRSFAQALGVSERMVQYYITGKKDPTVETLIAIADFFDVSLD
ref|YP_001180871.1|     MNLFRFRLKELREEKNISRSDLAEILGVSTQTIANYENGHREPNFDTLLKIADYFGVTVD
ref|ZP_02543721.1|      --MIGEKIKELRKNNKITQEQLGNAIGVSKMAISYFEKGKKSPGRESLEKIADYFNVTTD
                          ::   *    :  .. :.::      :  *.  *  . :  ::*:*.*: * ref|ZP_02442523.1|      YLCGRSDDPAR-
ref|YP_001662345.1|     YLLGRTD-----
ref|YP_001210714.1|     YLVGRSDDPRR-
RAAC03525               YLVGRSENPERK
ref|YP_001180871.1|     YLIGRSE-----
ref|ZP_02543721.1|      YLLGRSEDPE--
                        **  **::
```

FIG. 149

```
ref|YP_001038857.1|      ------------------------------YKGKQVRTFIIDGEPWWVAKDVC
ref|YP_146372.1|         -----------------------------NQLQKVFIYSGSQVRTIIKDDEVWFVAKDVC
ref|YP_001662865.1|      ------------------------------YEGNTVRTVMKDGNPWWVLKDVC
RAAC03224                MCFDPDRRGDLQLQDLHRRDTMQPVDMDGNQTMMEWMFEGHRIRVVMINDEPWWVAKDVC
ref|YP_006607.1|         -----------------------------------ENHPVRVVLVNGEPWFVAKDIC
ref|ZP_02781438.1|       ------------------------------FDSVNVRVVYLNGDPWFVAKDVC
                                                        ..  :*..  :.: *:*  **:* ref|YP_001038857.1|      DILELGDTHKAMERLDEDERNTIPVTDSLGRLQETYVVNEAGLYNLILGSRKQE-----A
ref|YP_146372.1|         EILDIADARKAVQRLDEDERSLIPVTDSLGRKQETFIVNEPGLYTLILGSRKSE-----A
ref|YP_001662865.1|      SVLDIGNSRDVMARLDSDEKG-VDIIDTPGGKQEVSIINESGLYSVILVSRKPE-----A
RAAC03224                EALQIANSRDAVSRLDEDEKNTVAITDGNRGNPNTTIINEAGLYQLTFTSRVDT-----A
ref|YP_006607.1|         DALKLVNSRKALSSLDDDEKNTVTLSDGNRGNPNMSIISESGLYTLILRCRDAVKQGTTA
ref|ZP_02781438.1|       VALEISNSRDALKALDADEKKTVALSYGIRGNPNHSLISESGFYKLIARSRKAVTPGTFA
                          *.: :::..:   :  : :        :  ::.*.*:*  :    .*        * ref|YP_001038857.1|      KEFKRWITHEVIPQIRKTGIY---------------------------------------
ref|YP_146372.1|         KQFKRWVTHEVIPTIRKTGGY---------------------------------------
ref|YP_001662865.1|      KKFKRWVTHEVLPSIRRHGLYATDELLANPDFLIQ--ALQELKAERAKNAELTTTISIQE
RAAC03224                KRFRRWLAHEVLPSIRKTGEYKTPGRRQECDIAAKQVAVMEMKARTEQAKLLVDAVHRLE
ref|YP_006607.1|         WRFRKWVTNEVLPAIRKSGEY---------------------------------------
ref|ZP_02781438.1|       HRFSNWVFRNVIPGIRKTGAYGIP-WGALQDFSRRKEQYQLSASQKGRELQACKRKKREL
                          .*  .*:  .:*:* **: * * ref|YP_001038857.1|      ------------------------------------------------
ref|YP_146372.1|         ------------------------------------------------
ref|YP_001662865.1|      QQIAEM------------------------------------------
RAAC03224                HRLSDLLIERILIASTNLMAGYDAIGIPTDGPSFTEPGRTRFPDLKPYWKPF
ref|YP_006607.1|         ------------------------------------------------
ref|ZP_02781438.1|       EEEEKRL-----------------------------------------
```

FIG. 150

```
ref|ZP_02378091.1|      ------------------------DYLPAYATTGSAGLDLRACLDAPLTLKPGETALVPT
ref|ZP_02454559.1|      ------------------------DYLPKYATTGSAGLDLRACLDAPVTLKPGDTALVPT
RAAC02915               MCVVVMGGWEMEVKVQIVSPLLTADDLPQYATQGSAGMDLRACLEAPRVVRPGEIVPVPT
ref|YP_001211829.1|     ------------------------AISLPRYATDGSAGLDLPACLDEPLAVPPGARVKVPT
ref|ZP_02091210.1|      -----------------------VPAYATPGAAAADLCAVLDAPLTVAPMQRVLVPT
ref|YP_518738.1|        ------------PSITIVESGAPSAPKLPQYATPGAAGVDLQASLDQELTIEPGQIVKIPT
                                                :* *** *:*. ** * *:    .: *  . :**

ref|ZP_02378091.1|      GLAIHLADPGYAALILPRSGLGHKHGIVLGNLVGLIDSDYQGELMISTWNRGQTEFVLNP
ref|ZP_02454559.1|      GLAIHLADPGYTALILPRSGLGHKHGIVLGNLVGLIDSDYQGELMISTWNRGQTEFALNP
RAAC02915               GLAIQLPRRDAVALVYARSGLAAKHGIALANGVGVIDSDYTGEIVVPLHHFGSKEFVLQP
ref|YP_001211829.1|     GIAIEIPHRNIAGLVFPRSGLASKHGISLANAVGVIDSDYKGEIVIAVFNQSDQEYLIKP
ref|ZP_02091210.1|      GLAIELPGAHSVALVYARSGLSIKHGLCMANGVGVVDSDYRGELKVPMVNLGAEAYTIQP
ref|YP_518738.1|        GLAIELPHAGVGAFVFARSGLASKYGLALANGVGVIDSDYRGEILVAVINQGSEPFVVKD
                        *:**.:.      .:: .****. *:*: :.* **::**** **: :.   . : ::

ref|ZP_02378091.1|      FERLAQLVIVPVVQAQFNIVDDFAASDRGAGGFGSTGR-
ref|ZP_02454559.1|      FERLAQLVIVPVVQARFNLVDDFAQSERGAGGFGSTGR-
RAAC02915               KERIAQLVIAPIYVARLVAVDHLGPTARGAGGFGSTGRV
ref|YP_001211829.1|     GERVAQLVFVPVFTATLDVVENLNCSSRGEGGFGSTGRI
ref|ZP_02091210.1|      GERVAQLCIAPVYTAAFVPAEELGDTQRGVGGFGSTGK-
ref|YP_518738.1|        GDRIAQMVFLPVFIGEFYLADQLDETGRGCGGFGSTG--
                         :*:**: : *:  . :   .:.:   : ** *******
```

FIG. 151

```
ref|YP_079090.1|         ------------------GAPSMSDRQAALDMALKQIEKQFGKGSIMKLGEQTETRIST
ref|YP_001421272.1|      ----------------------MSDRQAALDMALKQIEKQFGKGSIMKLGEKTDTRIST
emb|CAD56684.1|          ----------------------MNDRQAALDMALKQIEKQFGKGSIMKLGEQTEKRIST
ref|NP_243249.1|         ----------------------MSDRKAALDMALRQIEKQFGKGSIMKLGEQAEQRVST
ref|ZP_02850845.1|       ----------------------MSDRRAALEMALRQIEKQFGKGSIMKLGESTHMQVET
RAAC02943                MFCSRRRRGSRAYALEEIEGWCVMGDKKAALEQALRKIEKEFGKGSIMRLGEAAAMTVET
                                               *.*::*: :*:***:*  :   :.* ref|YP_079090.1|         VPSGSLALDAALGVGGYPRGRIIEVYGPESSGKTTVALHAIAEVQQQGGQAAFIDAEHAL
ref|YP_001421272.1|      VPSGSLALDTALGIGGYPRGRIIEVYGPESSGKTTVALHAIAEVQEKGGQAAFIDAEHAL
emb|CAD56684.1|          IPSGSLALDIALGVGGYPRGRVVEVYGPESSGKTTVALHAIAEVQQQGGQAAFIDAEHAL
ref|NP_243249.1|         ISSGALALDIALGVGGYPRGRVIEVYGPESSGKTTVALHAIAEVQRNGGQAAFIDAEHAL
ref|ZP_02850845.1|       VPSGSIALDIALGIGGLPRGRIIECYGPESSGKTTVALHAIAEVQRIGGQAAFIDAEHAL
RAAC02943                VPTGSIALDIALGVGGLPRGRIVEIYGPESSGKTTVALHVVAEVQKLGGQAAFIDAEHAL
                         :.:*::* *: **::* ************.:.********** ref|YP_079090.1|         DPVYAQKLGVNIDELLLSQPDTGEQALEIAEALVRSGAVDIVVIDSVAALVPKAEIEGDM
ref|YP_001421272.1|      DPVYAQKLGVNIEELLLSQPDTGEQALEIAEALVRSGAVDIVVVDSVAALVPKAEIEGDM
emb|CAD56684.1|          DPVYAQKLGVNIDELLLSQPDTGEQALEIAEALVRSGAVDIIVVDSVAALVPKAEIEGEM
ref|NP_243249.1|         DPVYAKKLGVNIDELLLSQPDTGEQALEIAEALVRSGAIDVIVIDSVAALVPKAEIEGEM
ref|ZP_02850845.1|       DPLYASKLGVNIDELLLSQPDTGEQALEIAEALVRSGAVDIIVIDSVAALVPKAEIEGDM
RAAC02943                DPVYAQKLGVNIDELLISQPDTGEQALEIAEALVRSGAVDVIVVDSVAALVPKNELEGDM
                         :.****:*:*********************:*::*:*******  :* ref|YP_079090.1|         GDSHVGLQARLMSQALRKLSGAINKSKTIAIFINQIREKVGVMFGNPETTPGGRALKFYS
ref|YP_001421272.1|      GDSHVGLQARLMSQALRKLSGAINKSKTIAIFINQIREKVGVMFGNPETTPGGRALKFYS
emb|CAD56684.1|          GDSHVGLQARLMSQALRKLSGAINKSKTIAIFINQIREKVGVMFGNPETTPGGRALKFYS
ref|NP_243249.1|         GDSHVGLQARLMSQALRKLSGAINKSKTIAIFINQIREKVGVMFGNPETTPGGRALKFYS
ref|ZP_02850845.1|       GDSHVGLQARLMSQALRKLGGAISKSKTIAIFINQLREKVGVMFGNPETTPGGRALKFYS
RAAC02943                GDSHVGLQARLMSQALRKLAGAISKSKTIAIFINQIREKVGVMFGNPETTPGGRALKFYA
                         *******************.***.*********:***************.******:

ref|YP_079090.1|         SVRLEVRRAEQLKQGNDVMGNKTKIKVVKNKVAPPFRTAEVDIMYGEGISKEGEIIDLGT
ref|YP_001421272.1|      SVRLEVRRAEQLKQGNDVMGNKTRIKVVKNKVAPPFRTAEVDIMYGEGISKEGEIIDLGT
emb|CAD56684.1|          SVRLEVRRAEQLKQGNDIVGNKTRIKVVKNKVAPPFRAAEVDIMYGEGISKEGEILDIAS
ref|NP_243249.1|         SVRLEVRRAETLKQGNDMVGNKTKIKVVKNKVAPPFKQAEVDIMYGEGISREGSILDIAS
ref|ZP_02850845.1|       SVRLEVRRIETIKQGNDMVGNRTRIKVVKNKVAPPFKQAEIDIMYGEGISREGSLVDIGV
RAAC02943                SVRLEVRRVEAIKQGNDVVGSRTRIKVVKNKVAPPFRQCDVDIMFGEGISREGSLIDIAT
                         ********  * :****::*.:*.:************:  ::***:*****.::*..:..

ref|YP_079090.1|         ELDIVQKSGAWYSYQEERLGQGRENAKQFLKENKDILLMIQEQIREHY------------
ref|YP_001421272.1|      ELDIVQKSGSWYSYEEERLGQGRENAKQFLKENKDIMLMIQEQIREYY------------
emb|CAD56684.1|          ELDIVQKSGSWYSYNDERLGQGRENAKQFLKENTDIRQETAGQVREH-------------
ref|NP_243249.1|         ELDIVQKSGAWYSFNDERLGQGRENAKQFLKENPEAAEEIESRIREHYGLN---------
ref|ZP_02850845.1|       EMDIVQKSGAWFSYNGDRLGQGRENAKQFLKDHPEVAAVIEKQIRE--------------
RAAC02943                EIDVQKSGAWYSFGEERLGQGRENAKQYLKEHPEIAEQIEAAVREYFHVNPAKPLVAAA
                         *:*:*****.*.*:  :**********:**::  :      *   :**

ref|YP_079090.1|         -------------------
ref|YP_001421272.1|      -------------------
emb|CAD56684.1|          -------------------
ref|NP_243249.1|         -------------------
ref|ZP_02850845.1|       -------------------
RAAC02943                AEDADDDADDAFDEFDAF
```

FIG. 152

```
ref|NP_242725.1|        --------------------MKAAFISDIHGNAQALEAVLTDIESKQVDQIIVLGDICFR
ref|ZP_01696769.1|      --------------------MKLAFISDIHGNAHALEAVLEDIEQKRADKIFVLGDLCFR
ref|YP_175539.1|        --------------------MRFAFLSDIHGNATALEAVLNDLQTKQIDQTYILGDLCFR
RAAC02234               MIARMETRTMDVTTMGRGVSMRLAFFSDVHGNELALDAVIADLRQVGCDGVYVLGDLAFR
ref|ZP_02170975.1|      --------------------MRLALLSDIHGNEAALRAVLEDLSRKNASHVAVLGDISYR
emb|CAJ73252.1|         --------------------MKILIISDIHGNEAALKAVLEET----ADMIFCLGDIVNY
                                            *:  ::**:***  ** **: :    .    ***:

ref|NP_242725.1|        GIEPKRSLELVRSLQVPVVKGNADEWVVRGIRKGEVPDSVLEVMRIEREWTYGKLDESDI
ref|ZP_01696769.1|      GPEPQRAYEMVMALNTEVIKGNADEWVYRGVGMNEVPEKAYEMMNRERDWTVSRMEQNAV
ref|YP_175539.1|        GPEPKRVLELVQASGARVIKGNADEWLVRGFKDGEVPVERLEMFNKERDWTLGRLSQEDL
RAAC02234               GYAPKACVEKVAEVADKVIRGNADEWVVRGVRPGEVPDERRAGMDEEAAFARGLLAREEL
ref|ZP_02170975.1|      GPKPKECLDLIRELHGKVIKGNADEWLIRGIREGELPQQAFAIMQREQAWSYGKMTDEGL
emb|CAJ73252.1|         GPYPKECIEKIRKLTDKIVRGNHDNAIGKNMECG-CSEKYKALSDQGKIFTKTILDAGEK
                         *  *:    :  :    ::*** *: : ..   . .           ::   :

ref|NP_242725.1|        DFLKQLPTVHTFSLSDTWNVLCFHATPTSLFDIVTPTAADHVVKEKLMAQNQANLYLYGH
ref|ZP_01696769.1|      ESLHQLPEEVKYEYGG-IKIHGFHATPYSLFENVPPDSENSKLKEKLMQED-ADIYLYAH
ref|YP_175539.1|        DYLKNLPTELVIDDGQDLVIHAFHASPSGLFTAIDGD-ETEKIENELMVRDEADIYIYGH
RAAC02234               EYLANLPLLQ-EESPFGRWLAFHATPLDPFPVVAADAPDDDIESRIVAGQDARLYLYGH
ref|ZP_02170975.1|      HYLNQLPTELEIPLTNRIQLYATHAFPDDLFKVIPEHAENSAFDAFFEHNPRAMYYAYGH
emb|CAJ73252.1|         EFLANLPLTNTEAGGVTFLLSHGSPGGDIYKYLRPEVSDSEMEDELKGVR-ANIVLLGH
                        . * :**          :   .: :           ..  :    *     .* ref|NP_242725.1|        IHLPYVRFIDGKIVANLGSVGLPFDGVCQASYLLVDGAEEQFSVTIQRVSYDIHSVCEQI
ref|ZP_01696769.1|      IHLPFIRTFDGKTFVNLGSVGLPFDGIAKASYAMVEIGDHDYQVSNVRVSYDVQKTIGLF
ref|YP_175539.1|        THHPYVRSLHGKNVINTGSVGMPFDGHPLASYIILDIEDGSHSVQLNRVPYNREHVVEIY
RAAC02234               IHVPYVRDIRGRTVVNLGSVGMPFDGVPQASYVILHVDEDVFRVEHRRVPYDVEAACRRY
ref|ZP_02170975.1|      IHIPHMRNITGNTLLNTGSIGLPFDGNPDASYVMLERTNDSISTSFHRVAYDIEKAVFDL
emb|CAJ73252.1|         THLPVVRKVGEITVVNPGSVGQPRDGIPLASYAIWKDG----ALEIKRVPYDIDATARGL
                         * *:*     .  * **:* * **  ***  : .         **.*: . .

ref|NP_242725.1|        EASDYPNPTF--LQNVLKHGKP-
ref|ZP_01696769.1|      EASDYPNKDK--LIDILTRAK--
ref|YP_175539.1|        KQSGYPNIEA--MSAVI------
RAAC02234               DEIGYPAAEM--MKRVLRTARPV
ref|ZP_02170975.1|      KDTDYPEDAAPLLESIYRTGK--
emb|CAJ73252.1|         QHTTIPADHVARLEEILRKGR--
                         .    *       :   :
```

FIG. 153

```
emb|CAK51299.1|         ---------RVRFLDTRPLRSSQSFRDLWIGTSVSQVGGQIANMAVLAQVWDLTGSPVGT
emb|CAI78402.1|         ---------RVRFLDTRPLRSSQSFRDLWIGTSVSQVGGQIANVAVLAQVWDLTGSPVGT
ref|YP_001362100.1|     -------------VDTRPLRSSPAFRRLWIGTTAAAFGGQVAVVAVLYQVWNLTGSTVWT
RAAC01662               MPMTLQAVFRSAMLDITPLRTSPAFLRLWIGSGISTLGGTMTPFAVMLQVYRATHSTLDV
ref|YP_832554.1|        ------------LADITPLRESPDFRRLWLGSAVSNLGSQLTLVAVSLEVYRLTQDSLYV
ref|YP_712120.1|        ------------LADLSPLREHPAYRRLWVGETISALGSQITATAVLLQVFAVTRSSFQV
                                     *  ***    :   **:*    : .*. ::  **  :*:  *  ...  .

emb|CAK51299.1|         GAIGLATGLPMVLFGLLGGTLADTFDRRAVVRATTAGQLLAAAGLCAQALADNRN--VLL
emb|CAI78402.1|         GAIGLATGLPMVLFGLLGGTLADTFDRRAVVRATTAGQLLAAAGLCAQALADNRN--VLL
ref|YP_001362100.1|     GAIGIATAVPTIVGGTVGGTLADTLDRRRLVLVTTTVSVLAALSLALQAVAGAAT--VLL
RAAC01662               GLTGLASVLPGALFVLLGGSVGDRVDRRKLALLATSGQMLVSALLAVQALIAWSA--LWL
ref|YP_832554.1|        GLLSIFALVPLVLGGLLGGSIADAHDRRKVALLATTMLWLTTAGLAAQAWLGLGN--VWL
ref|YP_712120.1|        GLVSLVALVPLVAGGLFGGAIVDAVDRRRLAMITSGGLAVVSAAFLLLTLAGAVDDVAWP
                        *    .:  : :*        :.**:: * ***  :.  ::     ..:    :     :

emb|CAK51299.1|         LLALVAMGTSSGALGAPARRTFPVRLLPGDQVAAGLALTNVSFQAAMLAGPAMAGLIIAH
emb|CAI78402.1|         LLALVAMGTSSGALGAPARRTFPVRLLPGDQVAAGLALTNVSFQAAMLAGPAMAGLIIAR
ref|YP_001362100.1|     VLVLVAAQTSAAAVGAAARRTFISRLLPSDLVRAGVALNHIGFQIAMLTGPAVAGVVLAA
RAAC01662               IYALLCAQSVLGAINAPARRTFVPRLLPKEQVRAGQTLNTLAIRFGEVAGPSLAGVIASF
ref|YP_832554.1|        LYVLVAVQSGAQAINQPARSAIIPALVRKELLPAANALSMITFGLCMTAGPLLAGVLAVW
ref|YP_712120.1|        LMCLVAVQSALLAADQPARRAMTPNLIPLEHLPAASALAQIGGTAAGVFGPLIAGVSVAA
                        :  *:.   :   *  .** ::   *:  : :  *, :*          **  :**. :

emb|CAK51299.1|         WDLSAAYATQAVAMVLSMLTVLRLPAMRPEGADAAGGRRRPERG----------GWRIVL
emb|CAI78402.1|         WDLSAAYATQAVAMVVSMLTVIRLPAMRPEGADAAGGRRRPERG----------GWRIVL
ref|YP_001362100.1|     GGLRAAYLTDAVGLTVSLYGVLRLPAIRPQ-SLADTGTARAARGGLPAVRATWEGWRYLL
RAAC01662               AGLGWCYACDAATFLAALYAIYRLPPMLPEANAKQRSMLDGVME----------GLRFLG
ref|YP_832554.1|        VGFGWTYTLDVASFAFAFWALLRLPPMPPGKTTHRAGLRSVVEG----------FRFLG
ref|YP_712120.1|        GGFSIAYAIDLVTFAAPLYGLARLPAMPPRGGRGAGVASVAEG----------LRFLR
                         .:  *  :  .:   .:  : ***.: *           .              * :

emb|CAK51299.1|         RRPTLWGSMATDLSATLLAMPVALFPLVNEIRFGGNPQTLGLFLSAVAVGGITAGLLSGT
emb|CAI78402.1|         RRPTLWGSMATDLSATLLAMPVALFPLVNEIRFGGNPQTLGLFLSAVAVGGITAGLLSGT
ref|YP_001362100.1|     RRPVLRGCLATDLAATVLAMPIALFPAINAQRFDGEEATLGLFLSAIAVGGLLAGFTSGT
RAAC01662               RSRALLGAMLADLSVTLGVPTALLPALVSERFGGRPETLGLMMGATCIGGLVILALSGP
ref|YP_832554.1|        TRPNLRMTFVIDLVAMIFAQPRALMPAIGAVMIGGGEATVGVLLASTAVGAFLAGLFSGP
ref|YP_712120.1|        GQPVLLMTFVVDIIAMVFGMPRALFPALAEGRFGGGSATAGAMYSAVAVGSLLAAGLSGP
                         *   :  *:.  ::. * **:* :      :.*     *  * :  .: ..*.:  **.

emb|CAK51299.1|         VTRWHRGGLVQMSAAGVWGLALACFGLAGPLW------------LALGCL-AVAGAADTV
emb|CAI78402.1|         VTRWHRGGLVQMSAAGVWGLALACFGLAGPLW------------LALGCL-AVAGAADTV
ref|YP_001362100.1|     LTRARRTGRVMLIAAATWGTSLTTFALVDSLP------------ATLACL-AVAGAADTV
RAAC01662               VRHIRSECKAILVACAAWAIAAGGLGLAPFVW------------LCVALL-GLMGAADSI
ref|YP_832554.1|        LGGIRRQGSAVVWSVMGWGASIAGFGLVVVLAGRSGADGVTWWLLPAALCCALAGIADSV
ref|YP_712120.1|        LGGVRRQGLAVVVSIVLWGGAIAGFGLAHDIA------------LGLALL-ALAGAADMV
                          :   :   * .::   *.:   :.*.   :                .:  * ** :

emb|CAK51299.1|         SVVTRSALVQLETPDAYRGRVSSVEHVIGVAGPELGNFRGGLLASATSASFSLVFGGLSA
emb|CAI78402.1|         SVVTRSALVQLETPDAYRGRVSSVEHVIGVAGPELGNFRGGLSASATSASFSLVFGGLSA
ref|YP_001362100.1|     AVISRGTIVQLSTPDAFLGRVSAAEGTVGVAGPGLGNARAGAVAGVTSTAVSSLTGGLAC
RAAC01662               LVVMRSTLIQQGTPDGLRGRISSVDYLVGTGGPQLGNLRAGLVGSLLPPGASIAVGGLST
ref|YP_832554.1|        SAVFRTTILQAATPDIILRGRLQGVFVVVAGGPRIGDMLAGGGTKLLSEGWVLLLGGLL-
ref|YP_712120.1|        SAILRNAILNVATPDEMRGRLQGVFLVVVTGGPRLGDLEAGSVAAVTSPAFSVVSGGLAC
                         .: *  :::: *    :...    : ..**  *:   .*             *** emb|CAK51299.1|         ILAIAAV-------------------
emb|CAI78402.1|         ILAIAAV-------------------
ref|YP_001362100.1|     VLAVAVIAATTPALRR----------
RAAC01662               LAAILCVGWFVPELRRAQAEEGVGASD
ref|YP_832554.1|        --CTAVAWTV----------------
ref|YP_712120.1|        IGCLLLATAAVPALIRYDARAAV----
                             .:
```

FIG. 154

```
ref|ZP_02620185.1|        -----------MALYAISDLHLSLN------------CDKPMDVFGDHWMNHDNRIKENW
ref|YP_877450.1|          -----------MALYAISDLHLSLN------------CDKPMDVFGDHWMNHDNRIKENW
ref|YP_001512273.1|       -----------MAIFAIGDLHLSGY------------SNKPMDIFGEHWTEHDKKIMESW
ref|ZP_01188667.1|        -------------IYAIGDLHLSFENKVIPGDWEKVSQYKPMSLFGDKWVEHYRKIYKNW
RAAC02171                 MISWNGQGGTTVAIYAIADLHLDTS------------QSKPMDVFGHEWRDHAEKIAHHW
ref|YP_001275096.1|       -------------VWSISDLHLSFA-----------RPKPMDIFGSRWKDHPERIAAAW
                                       :::*.**.            *.:**. *. *  .:*   * ref|ZP_02620185.1|        INKITNEDTVLIAGDISWSMKMEDGMADLEWIHKLPGRKIISKGNHDYWWGS--ISKLNS
ref|YP_877450.1|          INKITNEDTVLIAGDISWSMKMEDGMADLEWIHKLPGRKIISKGNHDYWWGS--ISKLNS
ref|YP_001512273.1|       QKNVKDEDAVLIPGDISWAMTLEDAKIDLNWIADLPGQKYLIRGNHDYWWGS--LTKLNS
ref|ZP_01188667.1|        KAEVTCKDLVLVPGDISWAMKLEEAVYDLEFIGSMPGKKIFIRGNHDYWWSG--ISKVRS
RAAC02171                 QDQIHDDDIVLIPGDISWAMKLEEAAPDLVWIGRLPGRKVLIRGNHDFWWGG--IQRVRK
ref|YP_001275096.1|       RARVKPDDVVLLAGDTSWAMKLQDALVDLQWIAALPGRKIISRGNHDYWWSSERTNRVRR
                           .:  .* **:.** **:*.:::.  ** :*  :**:*  : :****:**..    ::.

ref|ZP_02620185.1|        LY-DDMLFIQNNFFIYEDYAICGTRGWTPP-ADKYS-EHDDKIYKREQIRLKISLDAAK-
ref|YP_877450.1|          LY-DDIRFIQNNFFVYEDYAICGTRGWNPP-TDKYS-EHDDKIYKREQIRLRISLDAAK-
ref|YP_001512273.1|       LF-DSMHFTQNNFFTYNQYATCGTRGWNCPNHYKFT-EHDGKIFTREVNRLELSLKAAK-
ref|ZP_01188667.1|        ILPDGCFALQNDCLEFEGVSITGTRGWICPNEDNFT-EHDEKVYKREVNRLKLSLESIK-
RAAC02171                 ALPPRMYALQNDCLVLDNVCFAGTRGWTLPHHPSYNAEQDEPILKREILRLELSLKAAV-
ref|YP_001275096.1|       SLPPGIDILEASAIDIGEAVVCATRGWNTPETPGFQESTDRPYYERELMRLDTALAAAQH
                           :   .  :       . .:    .****  *  :   .  *    ** **  :*  :

ref|ZP_02620185.1|        -KAGYEKIIVMIHYPPVNDKFQKNELTEIFNEYNVEKVIYGHLHGP-SLKTIFEGKHEGV
ref|YP_877450.1|          -KAGFEKIIVMVHYPPVNDKFEKTELTEIFNEYNVEKVIYGHLHGP-SLKNIFEGEHEGV
ref|YP_001512273.1|       -EKGYEDIIVMLHYPPTNDKLEPSLFTEMLEKYKVKQVVYGHLHGETSYDAGLKGEYNGV
ref|ZP_01188667.1|        -NTD-KKKIVMMHYMPVNENHEHNDFIKVMIDYNVDICIYGHLHGEDSHKIRLPEEKWGI
RAAC02171                 -KEG-KPILCLMHYPPVDSNHPHSPFHELLAAYGVRACVYGHLHGP-AHRFAFNGEIDSV
ref|YP_001275096.1|       LASGKRPIIVMIHFPPFAGRRP-TEFARRIAAAKAAACVYGHLHRPEDWAVATQGLVDGV
                                 . . :   : ::*: *     . . : :        . :*****       .:

ref|ZP_02620185.1|        EYIMTSCDYIDFDPIKI-------
ref|YP_877450.1|          EYIMTSCDYIDFDPIKI-------
ref|YP_001512273.1|       YYNLVSCDYAGF------------
ref|ZP_01188667.1|        RFYLVSSDFLNFKPLRI-------
RAAC02171                 RYQLVSCDYLQFIPWKIPEEWLQP
ref|YP_001275096.1|       YYQLTSCDYLGFGP----------
                           : :.*.*:   *
```

FIG. 155

```
sp|P80579|THIO_ALIAC      ------------------------------------------------------------
RAAC01696                 ------------------------------------------------------------
pdb|1NW2|A                EFTHIREDXINFRMALICYCLBACILLUSACIDCALDARIUSPDBNWFCHAINFTHECRY
pdb|1NSW|A                ------------------------------------------------------------
pdb|1RQM|A                ------------------------------------------------------------
ref|YP_703612.1|          ------------------------------------------------------------ sp|P80579|THIO_ALIAC      ------------------------------------------------------------
RAAC01696                 ------------------------------------------------------------
pdb|1NW2|A                STALSTRUCTUREFTHEMUTANTREFTHIREDXINFRMALICYCLBACILLUSACIDCAL
pdb|1NSW|A                ------------------------------------------------------------
pdb|1RQM|A                ------------------------------------------------------------
ref|YP_703612.1|          ------------------------------------------------------------ sp|P80579|THIO_ALIAC      ------------------------------------------------------------
RAAC01696                 ------------------------------------------------------------
pdb|1NW2|A                DARIUSPDBNWGCHAINGTHECRYSTALSTRUCTUREFTHEMUTANTREFTHIREDXINF
pdb|1NSW|A                ------------------------------------------------------------
pdb|1RQM|A                ------------------------------------------------------------
ref|YP_703612.1|          ------------------------------------------------------------ sp|P80579|THIO_ALIAC      ------------------------------------------------------------
RAAC01696                 ------------------------------------------------------------
pdb|1NW2|A                RMALICYCLBACILLUSACIDCALDARIUSPDBNWHCHAINHTHECRYSTALSTRUCTUR
pdb|1NSW|A                ------------------------------------------------------------
pdb|1RQM|A                ------------------------------------------------------------
ref|YP_703612.1|          ------------------------------------------------------------ sp|P80579|THIO_ALIAC      ------------------------------------------------------------
RAAC01696                 ------------------------------------------------------------
pdb|1NW2|A                EFTHEMUTANTREFTHIREDXINFRMALICYCLBACILLUSACIDCALDARIUSSCRESI
pdb|1NSW|A                ------------------------------------------------------------
pdb|1RQM|A                ------------------------------------------------------------
ref|YP_703612.1|          ------------------------------------------------------------ sp|P80579|THIO_ALIAC      -----------------------------------ATMTLTDANFQQ-AIQGDKPVLVDFW
RAAC01696                 ----------------------------MQVSTLG-GIPMATMTLTDANFQQ-AIQGDKPVLVDFW
pdb|1NW2|A                GNIFICANCEE-IDENTITIESPSITIVESGAPSATMTLTDANFQQ-AIQGDKPVLVDFW
pdb|1NSW|A                ----------------------------PSITIVESGAPSATMTLTDANFQQ-AIQGDGPVLVDFW
pdb|1RQM|A                ----------------------------------ATMTLTDANFQQ-AIQGDGPVLVDFW
ref|YP_703612.1|          ---------------------------------TVTITDDSFQQDVISSDKPVLVDFW
                                                             *:*: .* .*..* ******* sp|P80579|THIO_ALIAC      AAWCGPCRMMAPVLEEFAEAHADKVTVAKLNVDENPETTSQFGIMSIPTLILFKGGRPVK
RAAC01696                 AAWCGPCRMMAPVLEEFAEAHADKVTVAKLNVDENPETTSQFGIMSIPTLILFKGGRPVK
pdb|1NW2|A                AAWCGPCRMMAPVLEEFAEAHADKVTVAKLNVDENPETTSQFGIMSIPTLILFKGGEPVK
pdb|1NSW|A                AAWCGPCRMMAPVLEEFAEAHADKVTVAKLNVDENPETTSQFGIMSIPTLILFKGGRPVK
pdb|1RQM|A                AAWCGPCRMMAPVLEEFAEAHADKVTVAKLNVDENPETTSQFGIMSIPTLILFKGGEPVK
ref|YP_703612.1|          ATWCGPCKMIAPVLEEIAGEHSEKLTIAKLDIDANPGAARDFQVMSIPTLILFKDGKPIN
                          *:*****:*:******:*  *::*:*:***::** ::  :* :**********.*.*::

sp|P80579|THIO_ALIAC      QLIGYQPKEQLEAQLADVLQ
RAAC01696                 QLIGYQPKEQLEAQLADVLQ
pdb|1NW2|A                QLIGYQPKEQLEAQLADVLQ
pdb|1NSW|A                QLIGYQPKEQLEAQLADVLQ
pdb|1RQM|A                QLIGYQPKEQLEAQLADVLQ
ref|YP_703612.1|          TIVGTKGKAALLKELADVL-
                          ::* : *  *  :*****
```

FIG. 156

```
ref|ZP_02850022.1|        MNKLTTD--AAFREAVQGDGITVVVFKTTWCADCHYIDPFMPDVEQQYNGKFSFHEIDRD
RAAC01724                 MEEIRTS--ERYREAVQ-SGRVVVEFYATWCPDCRRIEPYLGEWEEKYREQFTMVRVNRD
ref|NP_244119.1|          MEQIKTL--EQFQQVKN-QENVVFLFSADWCPDCRVIEPFLPELEQTY-DFYQFYYVNRD
ref|YP_001422284.1|       MKKIEST--EELQKAVQ-DDWAVFMFSADWCPDCRFVEPFLPELEADF-PEFTYYYVDRD
ref|YP_815236.1|          MEEIKELTPEKLKEITA-NGKVVLLFLATWCPDCRFLDPFLPQIEKDN-SDAKFYKIDRD
ref|NP_965472.1|          MEEIKELTPEKLKEITK-NGKVVLLFSATWCPDCRFLDPFLPQIEKDN-PDAKFYKIDRD
                          *:::         ::      .*. *  : **.**: ::*::  *   .      ::**

ref|ZP_02850022.1|        ELPDLCSELNILGIPSFIAFRNGKELIRYVNKLRKTREEIEQFLDRA--
RAAC01724                 EVPDLAEELQILGIPTFLVYDQGREVKRLFSRDAKSKEQVEQFLDQAYA
ref|NP_244119.1|          DFIELCQELDIFGIPSFLFYSNGEERSRFVSKDRKTKEEIERFLTEA--
ref|YP_001422284.1|       QFIDTCAEWEIYGIPSFVVFNGGKEVNRFVSKDRKTKEEIEQFLTDSLA
ref|YP_815236.1|          GSIDVAKELNIFGIPSFVVYQDGKEIGRLVNKDRKTKEEVENFLN----
ref|NP_965472.1|          GSIDVAKELNIFGIPSFVVYQDGKEIGRLVNKDRKTKEEVENFLN----
                          :  . *  :* ***:*:  :   *.*   *  ..:  *::*::*.**
```

FIG. 157

```
ref|YP_001212789.1|   -MRAAIYLRVSTEDQAKHGYSLPDQRTACREKAAALGAG--EVMEFADEGISGELLDRPG
ref|YP_001211675.1|   -MRAAVYVRVSTEDQARHGYSLQEQKEACRCRAVDLGAK--TVLEFADEGVSGATLDRPG
ref|ZP_01666637.1|    ----AIYARVSTDEQARTGYSLQDQVNQCRKKLLSLGLS--NIKEYIDDGYSGEFLDRPA
ref|ZP_02326197.1|    -MHAAIYVRVSTGLQAVEGTSLETQLDYCLRKAFELGTSQNDIHIYREEGASGEDLDRPA
RAAC01817             MMWTAIYTRVSTEHQAQAGHGLDVQREACVQYALSLGVAPHDIRLYEEAGGSGEDMDRPE
ref|ZP_01126596.1|    MKIAAIYARVSSDQQKGAN-TIASQTAALIEFAREQGFTVPDEWIIEDEGFSGASLLRPG
                        :* ***:   *   . :  *            *          :  * **  : **

ref|YP_001212789.1|   LSALREAVKAGQLDLVVCFDPDRLARKLAHQLTITDEIEKAGVRLEFVNF-EWQNTPDGR
ref|YP_001211675.1|   LQGLRELIRSGQTDLVVVRDPDRLSRKLSHQLILTEEIEKAGVRLEFLDF-DWKDTPDGR
ref|ZP_01666637.1|    LSRLRDDLRAGLIKTVMVYDPDRLSRNLTNQLIIADEIEKYGAKLEFITG-SYDASPEGR
ref|ZP_02326197.1|    LNRLRQDVASGTFSVLILTHPDRLTRDLTDKLFICRELESRNIRLVFVDT-EYKNTPEGQ
RAAC01817             LLRLLDDVRRGLVDRVVVKHPDRLSRNVADKAIVVRELSACGVKLHFVDVPNWDESDEAV
ref|ZP_01126596.1|    LERLRDLAAEGQIQAVLIHSPDRLSRKYAYQVLLTEEFARHGVEAIFIKA-PHSATPEDQ
                       *  *    *  ..  ::  ****:*. : :: *:  .  .*:     . : :

ref|YP_001212789.1|   LFYALRGAIAEYEKEKIRERTVRGKLQKARLGGLPVQADSYGYIYD--------NGTVKP
ref|YP_001211675.1|   LFYAIRGAIAEFEKEKIRERMARGKTQKAKQGGMPIGFYNYGVVYEPE------TGKVRL
ref|ZP_01666637.1|    LFFSIRGAIAEFEKEKIRERSLRGKRAKVLSGKPLFGRDPYGYICDRD------TGQYVI
ref|ZP_02326197.1|    LFFNLMSVIAQYELSLIKKRTVRGRLKAVEKENKIMPMRTAPYGYDII------GSKLVI
RAAC01817             LLFHVISSIAEYELRQIRRRTLAGKLKAVR-GGKVMPSGVDPYGYRYE------DGRYVV
ref|ZP_01126596.1|    LMLQFQGMIAEYERAQILERSRRGKRHRAKSGEISVLGG-APYGYRYIRKMPETPARYEI
                      *:      .  **::*    * .*    *:      .           *          .

ref|YP_001212789.1|   HPVESEVVKMIFRWFTTEDIGVNGVAARLSEQGIPTRKGRP-AWQRCVVKTILTNPMYVG
ref|YP_001211675.1|   HETEAKVVEEIFKWFVQEDIGINGVAKRLNEAEVPSRKGK--RWHKQVVRQVLVNPVYKG
ref|ZP_01666637.1|    NEEEAKIVRLIFKLYTENRYSVAKLHAQLKAMGVVNRSGK--PFSLSVLDHILANEMYAG
ref|ZP_02326197.1|    NEEEARFVRYIYEWYVHQRWTIRQTGEKLVELGAIPKRKESRSWSASSIQRILTSEIYIG
RAAC01817             VPEEAEIVRLIYQWYGIDGMSLRAIAERLDAMGVPTKTRQSARWHHSTVARILDNPLYRG
ref|ZP_01126596.1|    DAAEAAVVRLVFEKYTVDGLSIGAIARLLREMGPPTRRRVT-RWERSVVWGMLRNPAYKG
                       *: .*. ::.  :      .          *      :      :  :*.  * * ref|YP_001212789.1|   TFYYNRRDCRGTCYNK-------HLPPEKRVKVKEKPGEEWIAVPVPAIIDRETWEKAQE
ref|YP_001211675.1|   TWQYKD-----------------------------ICIPVPAIIDEAVWLKAQE
ref|ZP_01666637.1|    TKWYFQKYQKTVG-------------QKKRKVLKRNVNEWVSIDVPAIIDKETFQKAAE
ref|ZP_02326197.1|    RYYYNRRKTGKVKGQK-------TPSGSNRKLLEWRKEEDWIRVEVPAIIDTGIYEQAMQ
RAAC01817             TWYYNRRRTRKRQGVRG------ARRGRGRQVVAVRDPGEWIAVSVPPVVDPDLARSVAL
ref|ZP_01126596.1|    TACFNKTQVGPRQKVTKPFRLSGRSVHGEKTSAHERPREEWIEVPVPALVSEETFALAAE
                                                          : :  **.::.          .

ref|YP_001212789.1|   KIKAARRLWSGWSREEYLLSGLISCADCGNTMHGAVKTKSGG------------------
ref|YP_001211675.1|   KIRGARRLWAGQRKHDYLLSGIVTCGECGQTMTG--VYSKWWN-----------------
ref|ZP_01666637.1|    VRRQNKVTAKRNTKFEYLLSGIIKCPKCGYAMRG---TRFPK------------------
ref|ZP_02326197.1|    Q-RQRNRKKSGHVKESYLLRGLIRCGECGRSWQATSYS----------------------
RAAC01817             R-KQGS-PRGGSTSAHTFLSGKLVCAHCQRAWRHEACRTAGGIVRKFRRPPAERGADPCA
ref|ZP_01126596.1|    RLADNKRFAPRRTIEPSLVQGLVSCRKCGYALYRASTRTSAR------------------
                           ::  *   :  .* :

ref|YP_001212789.1|   ------------------------------------------------------------
ref|YP_001211675.1|   ------------------------------------------------------------
ref|ZP_01666637.1|    ------------------------------------------------------------
ref|ZP_02326197.1|    ---------------------------------GRADP---------------------
RAAC01817             YRCARVPADEIERAVWRELVRRMRALGIGRELAAGGRASPGDPLMEDVARLRREMRAAVE
ref|ZP_01126596.1|    ------------------------------------------------------------ ref|YP_001212789.1|   -----------SRERGYTCVKTAAGAS-----------------------NQGC
ref|YP_001211675.1|   -----------KKDRRYTCFKGYQGAR-----------------------HRGC
ref|ZP_01666637.1|    -----------RNNKDYAYYVCSAYVN-----------------------AYEC
ref|ZP_02326197.1|    ---------MSGAKKKYLCYRCPNKTPATFG-----------------TTRLI
RAAC01817             RRDRARELYLRGHLDRTAALRAMSEEARRLREGRAEACRLCHARQRRLNAWEDLWTALET
ref|ZP_01126596.1|    -----------KIHYYRCLGSDGWRHLG----------------------GSV ref|YP_001212789.1|   RPIKRVPAEIVEKAVW--------------------------
ref|YP_001211675.1|   LPSKYVLAGYVESAVWEQVKDWLQDPGALASEAYASSPRVED-------
ref|ZP_01666637.1|    DNRRCVPSQELDEAVWQEIVNMFKKSG---------------
ref|ZP_02326197.1|    CTAPSLKAEWLDQNVWKSVL----------------------
RAAC01817             HDGVELRRLWLEAAVSRVEMDASGGEVVLTLFARIGEQTGARVDDTLAT
ref|ZP_01126596.1|    CDSRPIRQDLLDHIWQEVMRLIADPGL---------------
                             ::  *
```

FIG. 158

```
ref|YP_001514193.1|   ------------------------------------------------------------
ref|YP_001317996.1|   ------------------------------------------------------------
ref|YP_001090064.1|   ------------------------------------------------------------
ref|ZP_01995293.1|    ------------------------------------------------------------
ref|YP_517020.1|      ------------------------------------------------------------
RAAC01840             MTHGGGVLRFARLSRVSSSSRGGRSHDQALSDRVGGGDQIVAGGRGDRRRSRLRGGHPPH ref|YP_001514193.1|   ------------------------------------------------------------
ref|YP_001317996.1|   ------------------------------------------------------------
ref|YP_001090064.1|   ------------------------------------------------------------
ref|ZP_01995293.1|    ------------------------------------------------------------
ref|YP_517020.1|      ------------------------------------------------------------
RAAC01840             TLRRVSSSSRSGRRGRPARAGSGGRSPGELPRLHGSLDCRSAGRHHELCPSAAAQRRLHR ref|YP_001514193.1|   ------------------------------------------------------------
ref|YP_001317996.1|   ------------------------------------------------------------
ref|YP_001090064.1|   --------------------ATEPHSPHRIBSYLTRANSFERASECLSTRIDIUMDIFF
ref|ZP_01995293.1|    ------------------------------------------------------------
ref|YP_517020.1|      ------------------------------------------------------------
RAAC01840             VRERRRGELRRRPGSLSGRVVLRAPRARRVCRGRSRRPRVARRAVRGLAGQAHARVRGVR ref|YP_001514193.1|   ------------------------------------------------------------
ref|YP_001317996.1|   ------------------------------------------------------------
ref|YP_001090064.1|   ICILEQCD-BEMBCAPUTATIVENICTINATEPHSPHRIBSYLT----------------
ref|ZP_01995293.1|    ------------------------------------------------------------
ref|YP_517020.1|      ------------------------------------------------------------
RAAC01840             IAARGHGHGAPRPAPRSKARDAKSYGRDRRGEEPANARRGRAAPGLRGRRAHRRLLGIRS ref|YP_001514193.1|   ------------------------------------------------------------
ref|YP_001317996.1|   ------------------------------------------------------------
ref|YP_001090064.1|   ----------------RANSFERASECLSTRIDIUMDIFFICILESCRESIGNIFICANC
ref|ZP_01995293.1|    ------------------------------------------------------------
ref|YP_517020.1|      ------------------------------------------------------------
RAAC01840             QRLGHRRGGAFGPGSRRRHPVDARRTLFAPRAGRVRGIRWRDAPGARGASCSRMSKAISR ref|YP_001514193.1|   -------------------------------KNLTLLTDLYQLTMMNGYLKNGADENVVIFD
ref|YP_001317996.1|   -------------------------------RNHTLLTDLYQLTMMNGYFENNSHEDTVIFD
ref|YP_001090064.1|   EE-IDENTITIESPSITIVES----GAPSRNLTLLTDLYQLTMLNGYFEKNIHEDIVVFD
ref|ZP_01995293.1|    -------------------------------RNLTLLTDLYELTMMQGYYEKGQNEN-VIFD
ref|YP_517020.1|      -------------------------------VALLTDLYQLTMMQGYYQNGYENKEAVFD
RAAC01840             AKDGDEGMDIKERARARVEEIGALPVYRDRHLTLLTDLYQLTMMYGHFRAGRHETRVVFD
                                                     :******:***: *:  . .:  .:**

ref|YP_001514193.1|   LFFRTNPCNNSYTMIAGIEQVIDYIENLKFDEESLVYLKGLNLFDDEFIDYLRNFKFTGT
ref|YP_001317996.1|   LFFRKNPCNNSFTIIAGIEQVIDYIENLGFTEEDIQYLRSLNLFGEAFLDMLKQFTFTGT
ref|YP_001090064.1|   MFFRKNACDGGYTIVCGIDQVVEYIDNLHFSDEDLEYLKNLNLFSDKFLKFLKEFKFTGD
ref|ZP_01995293.1|    VFFRQNPCNNGYSVCAGLDQVIDYIKNLHFTYDDVDYLRGLGIFKEDFLHYLSGFHFSGD
ref|YP_517020.1|      LYFRKIPSGGGYVIAAGLEQVVEYIENLRFSSEDMAYLRGLNIFDEGFLNLLKDFRFHGD
RAAC01840             LFYRKNPCNGYVIAAGLEQVVWYIYNLAFSEDDLAYLRSLGMFSEDFLSYLRHFRFRGD
                      : :: *   .....:  : .*:::   ** *  :.:  **:.*.:*   *  * * * ref|YP_001514193.1|   IYGVDEGTVMFPYEPILRVKAPVIQAQLIETTLLNIVNFQSLIATKAARICSAAD-----
ref|YP_001317996.1|   IYGVQEGSIMFPHEPILRVKASVLQAQLIETALLNMINFQSLIATKASRIVEAAK-----
ref|YP_001090064.1|   IYAVEEGTIMFPNEPLITVKAPLYQAQLIETALLTIVNFQSLIATKASRVCFAAQ-----
ref|ZP_01995293.1|    IYAIPEGTVVFPKEPLLKVVAPIMEAQLVETAILNIINHQSLIATKTSRIVFAAN-----
ref|YP_517020.1|      IDAVPEGTVVFPYEPLVRVKGRILEAQLIETALLNIINFETLIATKASRVVAAAG-----
RAAC01840             VYAVPEGTVVFPNEPILRVEGPIAEVQLIESAVLAFINHQSLIATKARRIVEAARTNVRH
                      :  .:  **::** **:: *    .   :  *.**:*::::*  :* .::*****  *: **
``` continued →

FIG. 158 continued

```
ref|YP_001514193.1|    -GDPVFEFGLRRAQGPDAGVYGARAAVIGGCVGTSNVLAGKRFDIPVVGTHAHSWIQSFD
ref|YP_001317996.1|    -GDPVFEFGLRRAQGPDAGIYGARAAVIGGCVATSNILAGKLFDLPVVGTHAHSWIQKFD
ref|YP_001090064.1|    -GDPVFEFGLRRAQGPDAGIYGARAAVVGGCAGTANVLAGKMFDIPIIGTQAHSWVQKFD
ref|ZP_01995293.1|     -GDGIMEFGLRRAQGPDAGLYGARAAMIGGCVGTSNVLAGQMFDVPVMGTHAHSWIMSFP
ref|YP_517020.1|       -GGSVMEFGLRRAQGPDAGILGSRAAFIGCCQFTSNVLAGKRYGIPLSGTQAHSWIQCFP
RAAC01840              PGSTVIEMGLRRSQNADAAVFGARAAFIGGCVATSNVLAAQSYNIPVAGTQAHSWIQSFP
                        *. ::******:*..**.: *:*.:*  *:*:**.: :.:*: :**:  * ref|YP_001514193.1|    SELEAFRAYARSYPNSTTLLVDTYNVLHSGVPNAITVFNELKEQGYEPK--GIRIDSGDI
ref|YP_001317996.1|    SELEAFRAYAKAYPDKCLLLVDTYDTLKSGIPNALTVFNELREKGYEPK--GIRIDSGDL
ref|YP_001090064.1|    NELEAFQAYADVYPDKCLLLVDTYDVLNSGVPNAIKVFKNISEKGYKPM--GIRLDSGDL
ref|ZP_01995293.1|     DEYTAFKTYAEMYPDNCTLLVDTYDTLKSGVPNAIRVFQEFKDAGKPLIKYGIRLDSGDL
ref|YP_517020.1|       DELEAFRAYARTFPDQCLLLVDTYNVLKSGVPNAIKVGLELEAEGHRFL--GIRIDSGDL
RAAC01840              SEYEAFQAYRAAFPDNTVLLVDTYDVLRSGVPNAIRVGLEMKAAGQSLK--AIRIDSGDL
                       .*  **::*   :*:. ******:.*.**:***: *  ::  *     .**:****:

ref|YP_001514193.1|    AYLSKEARKMLDAAGLPNVKITASSDLDEDVINNLKLQGAAIDFWGVGTNLITSKSCPAL
ref|YP_001317996.1|    AYISKQARRMLDDAGYEKVGIVASSDLDEDTIDSLKLQGASINSWGVGTNLITSKDCPAL
ref|YP_001090064.1|    AYLSKEAKKQLDNAGFSDISITASNDLDEYTITSLKAEGATINSWGVGTKLITSFDSPSL
ref|ZP_01995293.1|     AYLSKEARKMLDEAGFPEATICASNDLDEFLLHDLKMQGAAIDSWGVGTNLITSKDCPSF
ref|YP_517020.1|       TYLSREARKMLDQAGLEHARIVASNDLDEHTISAIRAQGAAIDSWGVGTHLITSKDTPAL
RAAC01840              AYLSKRARQMLNDAGLADVQIIASSDLDEYTIRDLLTQGAEIDAWGVGTRLITSEDCPSL
                       :*:*:*..*::  *: **  . * **.****  :  : :** *: *****.****  . *::

ref|YP_001514193.1|    GGVYKLSAIE-VDGQIIPKIKISENPEKITNPGYKKVVRIYDKENKKAQADLIMLDSEEI
ref|YP_001317996.1|    GGVYKLSAVE-KSGTLIPKMKLSDNPGKITNPGYKKVIRIYEAENNRAQADLILLEEEEI
ref|YP_001090064.1|    GGVYKLAASC-EKGVLEPKIKISENPEKINNPGYKKVIRIYN-EDNKAEADLIMLHDEVI
ref|ZP_01995293.1|     GGVYKLAAIQNEEGEFVPKIKISENTEKITNPGNKTIYRIYEKASGKIKADLICFADEVI
ref|YP_517020.1|       GGVYKLSAEG-QKGVFEPRLKVSENISKITNPGIKKIVRFYD-RRGKAMADLIALEDEHF
RAAC01840              GCVYKLVAQQ-FGDRMEPRIKISENPNKITNPGKKKVLRLYV--NGSATADLIALDEEVY
                       * **** *          . : *::*:*:* .* *.: *:*      **** : .* ref|YP_001514193.1|    NTNEPLTIFHPIYTWKKKTFRN--YETKDLLVPIYEQGKLVYERKTIKEIRKHAQSELDS
ref|YP_001317996.1|    DTTKPLTIFHPLYTWKKKTFSN--YKVREMLMPIYEDGKLVYPRKTVNEIRAYVRQELST
ref|YP_001090064.1|    DESKPLEIFHPTYTWKTKVFTN--YKVKELLKPLYIKGRCKYNKKAVLEIKNHVQYELST
ref|ZP_01995293.1|     DPKQDLLLFDPMDTWKKTKLAGGTYNVREILLPIFKNGECLYKSPTLKEIAAYCREEKDT
ref|YP_517020.1|       E--EPLTIFDPIETWKRKTLTD--FKTRELLRPVFRGGRRVYELPYLKDIQTYAQHECET
RAAC01840              DPSEPLELFHPIHTYKRKVVQN--YEMEELLRPVFVGGELVYELPTVQEIQARVETQLSA
                         :  * :*.* *:*     ..   :: .::* *::   *.    :  * :*    . :.:

ref|YP_001514193.1|    LWPEYRRLNRPQLYKVDLSKKLWDLKNQMMDQFR-
ref|YP_001317996.1|    LWPEYKRLNRPQLYKVDLSQKLWSLKHNMIQSLKK
ref|YP_001090064.1|    IWEQYKRLSKPHIYKVDLSRNLWYLKTQMI-----
ref|ZP_01995293.1|     LWDETKRLFYPHRVYVDLSQKLYAVKQSLLDQ---
ref|YP_517020.1|       LWDEVKRLVNPHRYIVDLSPKLFELRQSLLLE---
RAAC01840              FSSEVRRHLNPHEYHVDLSKPLWDLKQRLLHEWRR
                       :  :  *  *:   **** * *   ::  ::
```

FIG. 159

```
ref|YP_604970.1|    ------------------------AHQGGEERWPSNTMLAYRNAAALGVDMLDTDLHA
ref|NP_295807.1|    ------------------------AHQGGEALWPSNTLTAYRGAVALGVDLLEMDLHA
RAAC01875           MARAVEEFVEGRMQMDGTRRPRVRIFAHRGASREAPENTLPAFQIALRQGADVIETDVHW
ref|YP_076566.1|    ---------------------PRPVVLAHQGASGHAPSNTMEAFRLALEQGADILELDVHM
ref|YP_644758.1|    ------------------------FAHRGASARAPENTLEAFRLGVEAGAGGLEMDLHM
ref|YP_357266.1|    ---------------------PRPRLFGHRGNSGDFPENTLPAFSDALACGTPYLELDVRA
                                            . *:*  .    *.**: *:    *.   :: *::

ref|YP_604970.1|    TRDGALVLSHDETLDRLTDTQGRIADMTLAQVLAADAGYAFTPDGGKTFPFRGQGVRVAQ
ref|NP_295807.1|    TRDGALVLSHDATLDRLTDTQGRIADLTLEQVLRADAGYTLTPAGGSGFPFRGQGVQVAQ
RAAC01875           TKDRELVICHDPRIDAVSDGTGAIADMTYEELLRYDFGYRFTRDGGRTYPYRGCGIRMAT
ref|YP_076566.1|    TRDGVVVSHDETIDRMSDGTGLIKEMTLAELRRYDFGYRFTPDGGLTYPYRGKGVTIPT
ref|YP_644758.1|    TRDGEIVVIHDHTVDRTTDGSGAVREMSLRELRRLDAGYRFSPDGGRSHPYRGRGLRVPT
ref|YP_357266.1|    TKDDEVVVIHDESLLRTCGIDRPVAGLTFAELQNYDAGATFTPDQGRSYPHRGCGIRVPL
                    *:*  :*: **  :      .    :  ::  ::     *  *  ::   *  .*.** *: :.

ref|YP_604970.1|    LAEVLAAFPNMPLTIEIKQTSPSLAAPFCKALRDAGVTDHVIVASFSDKALNEFRAACPE
ref|NP_295807.1|    LKDVLREFPNTPLIIELKQASPSIAAPFCAELRRAGATGRVIAASFSDAALNEFRRLCPE
RAAC01875           LREALRAFPGAHFNVDLKPKCPHVG-LFLRMLEEEDSLERVTLASFHHRTLVEARARCPR
ref|YP_076566.1|    LEEVLQAFPEVPVNIEIKQADPPMEAQLWELIQRYGAEDRVLVASFHGTVAKRWRDLAGD
ref|YP_644758.1|    LREVYEAFPRAAVNMEIKEPVPGIERRVLEVIDGAGARGRTLVAAFDHGIVRRFREASGG
ref|YP_357266.1|    LADVLQAFPRALFNIEIKQETPAMETATLEVIRRADMTEQVLLAAENDAVMARLRPLCQT
                    *   :.   **    . :::*   * :     :    .  :.  *:          .  *  .

ref|YP_604970.1|    V--ITSMTEKELRPLVLLSKVGLA--HLAPLPGRAAQVPVRSGN----IEVVTPAFVRAM
ref|NP_295807.1|    V--MTSMTERELRPLVLLSKVGLS--ALAPTPGQVAQVPVRSGG----IEIVTPAFVRAL
RAAC01875           L--KTSASPFEVARLAAMARAGWERGGRARMPFQAVQVPLRQYG----VRVVTPRFIEFA
ref|YP_076566.1|    R--VATSAPVEHMYLVAAHYLSHLD-RLYAPAHDAFQVPVAQKAGPLTVRFDTERFLRMA
ref|YP_644758.1|    E-VATSASRLEVVAFYALVRLGLW--RFARPGYAALQIPVRRRG----IELITPSLVAAA
ref|YP_357266.1|    AGIPTSFSYGELVSFFTWLQAGGQ--SPYHPPAQALQIPETYEG----QTLVTPQSIAAA
                       ::: :  *   :   .    :       . *:*       . *    :

ref|YP_604970.1|    HARGVAVHVWTINDPAEMRRLIAMGVDGIITDRPDL----------
ref|NP_295807.1|    HARGVAVQVWTIDDEAEMRRLVQMGVDGVITNRPDL----------
RAAC01875           HRLGLEVDVWTVDDPNVIRGLIRQGVDGIVTNSPQILQKLLLELEQ
ref|YP_076566.1|    ERVNVAVHYWTINDEDEMRRLYQLGAHGIITDYP------------
ref|YP_644758.1|    HALGVRVDAWTINEPEEMRRLLGLGVDVVMTDRPE-----------
ref|YP_357266.1|    HTLGIEIHVWTVNQAQDMERLLRMGVDGVMSDRPAV----------
                    .  .: :. **::  :. *  :: . *  *.. ::::  *
```

FIG. 160

```
ref|ZP_01034116.1|      ------------------------------------------------------MRSVELFVGAG
ref|ZP_02297879.1|      ------------------------------------------------------MRAIELFAGAG
RAAC02539               MRHYAFRRMLTMWTRWMAIETVLFRKQLVGFEGNRHDLKNSYSGERSVRMRSVELFVGAG
gb|ABY83631.1|          ------------------------------------------------------MKSVELFAGAG
ref|YP_208280.1|        ------------------------------------------------------MKSLEIFSGAG
ref|YP_001516905.1|     ------------------------------------------------------KLSCLELFTGAG
                                                                              :  .:*:* *** ref|ZP_01034116.1|      GLGIGVSQAGFRPAAVMDWDRWACDTLRENKERGLDPIAHWPI-HEGDIRQFDFGTVDGT
ref|ZP_02297879.1|      GLGMGVSRAGFTPQAVVEWDRWCCDTIRENREKGIASLAGWPMPIEGDVRGVNFRGFEGK
RAAC02539               GLAMGISNAGFRHVGLYEWDRYACDTIRFNKERNVGPVRDWPI-YQLDVRSVDFTQYRG-
gb|ABY83631.1|          GLAMGCEIAGFEHLAVVEWDKWACDTVRENKKSGFPLLSDWDL-FEGDVREFDWSKIPKG
ref|YP_208280.1|        GLAKGLELAGFQHASFIELNKDACNSLRSNFNP--------KLVYQGDVADFDLSSQEG-
ref|YP_001516905.1|     GLAKGLEKAGVQHTAFVEWNKDACITLANNYSA--------QLVHNVDIRTFKFSQFGH-
                        **. *  . **.    ..  ::  .*  ::   * .          : : *:  ..

ref|ZP_01034116.1|      VDLVTGGPPCQPFSMGGRHRAFLDGRDMFPQAIRAVRELRPRAFIFENVKGLTRSSFANY
ref|ZP_02297879.1|      LDLVTGGPPCQPFSLGGKHQAHADRRDMWPEAVRAVRETRPRAFIFENVKGLTRESFATY
RAAC02539               IELLAGGPPCQPFSLGGKHRGREDHRNMFPEMIRAVREIQPKVVLIENVKGLLRESFAKY
gb|ABY83631.1|          IDLLAGGPPCQPFSIGGKHKANSDSRDMFPATAEAIRQIRPKAFIVENVKGLTRATFATY
ref|YP_208280.1|        IEVIAGGPPCQPFSLGGKHLAHEDRRDMFPHAVRYVEYYRPKAFIFENVKGLLRKSFADY
ref|YP_001516905.1|     VDIVSGGPPCQPFSMGGKIIKGNMDKRDMFPYACKAISVCTPKAFVFENVKGLLRKSFSSY
                        : :::******: :*  .  * *:*:*   . :    *:..:.****** * :*: * ref|ZP_01034116.1|      LEYIRLQLTYPDLVAKRDEEWLAHLARLEDHHT--KGTEKGLRYRVVMRVLNSANYGVPQ
ref|ZP_02297879.1|      VSHIVLQMTYPDIVAKSEEGWEGHLQRLERHHTS-RRRVTGLEYRVVYRVLNAANHGVPQ
RAAC02539               FEYILLQICYPEIVPKENEDWTDHLSRLEQQHT--KGRYHGLSYRVVFRLLNAADYGVPQ
gb|ABY83631.1|          FQYIQLQLEFPEVAPRNGEDWSEHLKRLQEEKTSGKNKGRGLTYNVLATLVNAADYGIPQ
ref|YP_208280.1|        FEYILLRLTYPNLGILQNEDWKGHLTRLKEIEFN---LYKGIKYKVSYQLLNAADYGVPQ
ref|YP_001516905.1|     FEYILLRLRYPDLSLQASERWEDHLARLEKIHTS--GKYDGIKYNVVFRLVDAANYGVPQ
                        ..:* *:: :*::      *  *  **  **:.        *: *.*  ::::*::*:**

ref|ZP_01034116.1|      RRERVFLVGFRADTGIEWHFPKPTHSRDALLWSQWRDEVYWDLHRVARK--NRP-EGGAA
ref|ZP_02297879.1|      RRERVVFVGFRSDLDIKWAFPAETHSLDALLWDQVHGD-YWDRHRVRKA--DRN-IGDRY
RAAC02539               KRERVFIVGFRSDLNIEWSFPNPTHSFDALLYDQWVTGEYWERHRVAKK--HRPDIPDKL
gb|ABY83631.1|          KRERVFIVGFRDDLEIEWSFPKPTHSYDALIYDQWVTGDYWKRHGLEMP--TVP---SQM
ref|YP_208280.1|        KRERVVIVGIRADLDIDWKFPKRTHSEDRLNWEKYVTGEYWEKHNE--------PKRFNKD
ref|YP_001516905.1|     RRERVFIVGIREDLNIEWSFPEESHSLDSLLWSQFITGAYWIRNAVNPLEIEHLDQRTQQ
                        :****.:**:* *  *.*  ** :** *  :..       **  :

ref|ZP_01034116.1|      KAR--SLKIADRPLD-EPWLTVRDAISDLPDPEHAPGTARGFHDHRFQPGARSYAGHTGS
ref|ZP_02297879.1|      RQR--AARLGQQPDT-LPWRTTRDAIADLPDPEREPKQSMTYLNHRFQPGARSYPGHTGS
RAAC02539               KKRIESLRMGLRLIQQGAPWVTVRDAISGLPDPESE--QDCGVPNHRFNPGARVYPGHTGS
gb|ABY83631.1|          VSR--IAKLRKNPPDTLPWKTVRDAIADLPDPETK--AAKMIRNHGFQAGARTYPGHTGS
ref|YP_208280.1|        IAEKLQKKYGIFEPEKKPWQTVRDTLSDIPHP-LGN---HKITGHEYRDGARIYPGHTGS
ref|YP_001516905.1|     RAKQLMQQPSLFSPSLEPWKTVRDQIGKLPAPDIQG---SFDNEHVLREGARSYPGHTGS
                          .        :      ** *.** :.  :* *           *    *** *.***** ref|ZP_01034116.1|      PLDEPAKTLKAGVHGVPGGENMLRRPDGSVRYFTIRESARLQTFPDDMVFHGSWTETMRQ
ref|ZP_02297879.1|      PLDEPAKTLKAGVHGVPGGENMLLRPDGSVRYTVRESARLQTFPDDFRLHGSWSFAMRQ
RAAC02539               PLDEPAKTLKAGDHGVPGGENMLVKPDGTVRYFTVRESARLQTFPDEYVFSGSWTESMRQ
gb|ABY83631.1|          PLDLPAKTLKAGAHGVPGGENMLVRDDGSVRYFTVRESARTQTFPDSYRFHGSWTETMRQ
ref|YP_208280.1|        GIDEPSKTIKAGGHGVPGGENMIRYDDGTVRYFTSYEAKLLQTFPEEFVISGAWGEAMRQ
ref|YP_001516905.1|     YIDMPSKALKAGDHGVPGGENMIRYQDGRIRYYTTFEAKRIQTFPDNYRISGSWTEAMRQ
                         :*  *:*::* ****   :*  :*:  :*::.    : *:* *:*** ref|ZP_01034116.1|      LGNAVPCQLARIVASGVRHKL-----------
ref|ZP_02297879.1|      LGNAVPVELAHVVASSVNAHLQFKAS------
RAAC02539               LGNAVPVRLAHFITKDIRTRLEWSVADAGKAV
gb|ABY83631.1|          LGNAVPVHLAYCVASSVAEKL-----------
ref|YP_208280.1|        IGNAVPVKLSEILGKHL---------------
ref|YP_001516905.1|     IGNAVPVELGYRIANSL---------------
                        :*****  .*.   : . :
```

FIG. 161

```
gb|AB014793.1|         ---MKKQRAFLKWAGGKYGLVEDIQRHLPPARKLVEPFVGAGSVFLNTDYDHYLLADINP
ref|YP_001443312.1|    ---MKKQRAFLKWAGGKYGLVEDIQRHLPPARKLVEPFVGAGSVFLNTDYDHYLLADINP
ref|ZP_01815366.1|     ---MKKQRAFLKWAGGKYGLVEDIQRHLPPARKLVEPFVGAGSVFLNTDYEQYLLADINP
ref|YP_205672.1|       ---MKKHRAFLKWAGGKYSLVEEIQRHLPDARKLIEPFVGAGSVFLNTDYDHYLLADINP
ref|ZP_01042597.1|     ---MKRNRAFLKWAGGKYGLVEPIKACLPEGRKLIEPFVGAGSVFLNTDYDRYLLNDINP
RAAC02543              MQSMPIRRSYLQWPGGKSHIVSALRAFLPPGRRLIEPFVGASSVFLNTDYPEYLLGDANP
                          *  .*::*:*.***  :*.  ::  ** .*:*:***.**** .* * ** gb|AB014793.1|         DLINLYNLLKERPEEYISEAKRWFVAENNRKEAYLNIRAEFNKTDDVMYRSLAFLYMNRF
ref|YP_001443312.1|    DLINLYNLLKERPEEYISEAKRWFVAENNRKEAYLDIRAEFNKTDDVMYRSLAFLYMNRF
ref|ZP_01815366.1|     DLINLYNLLKTDPETYIAEAKRWFCPENNRKEVFLDIRAQFNDTDNVMYRSLAFLYMNRF
ref|YP_205672.1|       DLINLYNHLKDEPERFIEDARALFQPEYNKKEVYLALRVEFNQCTDTYRRSLLFLYMNRH
ref|ZP_01042597.1|     DLITLYQFVKRRPKTFIADARRLFTARNNQSDAYYALRKSFNESNDPYYRSLLFLYLNRH
RAAC02543              DLILVHRTLQAYGEAFIGACRELFVPENNAPERYYALRQEFNATQNLWRRAILFVYLNRH
                       *** ::. ::    : :*  .: *  .. *   : :* .**      :    *:: *:*:**.

gb|AB014793.1|         GFNGLCRYNKKGGFNVPFGSYKKPYFPEAELEFFAEKAKKATFVCEGYPETFSRARKGSV
ref|YP_001443312.1|    GFNGLCRYNKKGGFNVPFGSYKKPYFPEAELEFFAEKAKKATFVCEGYPETFSRARKGSV
ref|ZP_01815366.1|     GFNGLCRYNKKGGFNVPFGSYKKPYFPEAELEFFAEKAKKATFVCEGYHETFSRARKGCV
ref|YP_205672.1|       GFNGLCRYNKKGGFNVPFGSYKKPYFPEKMVFFAEKAKKATFVCEGYMDTFKRARKGAV
ref|ZP_01042597.1|     GYNGLCRYNSRGIFNVPFGDYRKPYFPEAEIEVFAEKAKRAKFVCSSFEQVFRRARKGDV
RAAC02543              GIHGLMRYNRRGAFNTPFGYRRKIYFPEAEMRLFAEHAKRASFVHADFRDLMSQARPGDV
                       * : * :* .*  :* **** *: .*::*.  .: : : : * * gb|AB014793.1|         VYCDPPYAPLSNTANFTSYAGNGFTLDDQAALADIAEKAATERGIPVLISNHDTTLTRRL
ref|YP_001443312.1|    VYCDPPYAPLSNTANFTSYAGNGFTLDDQAALADIAERAATERGIPVLISNHDTTLTRRL
ref|ZP_01815366.1|     VYCDPPYAPLSNTANFTSYAGNGFSLDDQAALADVAEKAATERGIPVLISNHDTTLTRRL
ref|YP_205672.1|       VYCDPPYAPLSTTANFTSYAGNGFSLDDQAALADIAEKAAFERDIPVLISNHDTTLTRRL
ref|ZP_01042597.1|     IYCDPPYAPLVQASNFTSYATGGFSLDEQSELARHAIRAACKRHIPVLISNHDTPLTRAL
RAAC02543              VYCDPPYVPLSDTANFTEYAPGGFSWHDHMALAGYARELA-RRGVTVEISNHRTPATESL
                       :****.  ::*. .*:: .::  **   *  . * :.* **** *. *. * gb|AB014793.1|         YHGAELNVVKVKRTIS-RNGSGRNKVDELLALFRAP
ref|YP_001443312.1|    YHGAELNVVKVKRTIS-RNGSGRNKVDELLALFRAP
ref|ZP_01815366.1|     YHGAELNVVKVKRTIS-RNGAGRNKVDELLALF---
ref|YP_205672.1|       YHGATLNTIKVKRTIS-RNGAGRNKVDELMALFHAP
ref|ZP_01042597.1|     YERAKISSLKVARNIS-QKGDARKPVAELLALF---
RAAC02543              YRGAQLVSVRAPRNIGVQHRQAARTAEEILAIFWPP
                       *. * :  ::. *.*. ::   . . . *::*:*
```

FIG. 162

```
ref|YP_001275109.1|    ------------------------------RRERKRVIAFGWYGGKYSHLDWLLPLLPFCHHY
ref|ZP_01514022.1|     -----------------------------KRSKKRILAFGWYGGKYSHLDWLLPLLPSCHHY
ref|YP_001633718.1|    ----------------------------QRRTRRLIAFGWYGGKYSHLDWLLPLLPPCHHY
ref|ZP_01631840.1|     ------------------------------KKIAFGWYGGKYSHLDWLLPLLPTITHY
gb|AAZ73681.1|         -----------------------------KNKLIAFGWYGGKYSHLDWLLPLLPKTTHY
RAAC02564              MGVMLLSFIEGLPPFTALMIDHVSTARQKPRRKRIAFGWYGGKYSHLSWLLPLLPRAHHY
                                                      :.*********.*** ref|YP_001275109.1|    CEPFGGSAAVLFNREPSPVETYNDIDGEVVNFFRVLRDDPERLVRAIGLTPFSREEFAIA
ref|ZP_01514022.1|     CEPFGGSAAVLLNREPSPVETYNDIDGDVVHFFRVLRDEPERLVRAIGLTPFSREEFAIA
ref|YP_001633718.1|    CEPFGGSAAVLLNRDPAPVETYNDIDGEVTNFFRVLRDQPDQLTRAIALTPFSREEFALA
ref|ZP_01631840.1|     CEPFGGSAAVLLNREPAPVETYNDIDGQVVNFFRVLRDQRDELIQAIGLTPFSREEFRIA
gb|AAZ73681.1|         CEPFGGSASILINREPSPVETYNDIDGELVNFFRVLRDEKNELIRAIAFTPFSRSEFELA
RAAC02564              CEPFGGSAAVLLNRDPSPVETYNDLDGEVVNFFRVLREQRDALIEAIALTPFSREEFVRA
                       ********::*:**:*:*****:::.:******::  : *...:.  * ref|YP_001275109.1|    CEIDPA-LDPVERARRFYVRARQVRTGLAQSATLGRWANCKNTSRSGMAGAVSRWLGAVE
ref|ZP_01514022.1|     CEIDPS-LDPVECARRFYVRARQVRTGLAQSATLGRWANCKNTSRAGMAGAVSRWLGAIE
ref|YP_001633718.1|    CEIDPS-LEPIERARRFYVRARQVRTGLAQSASLGRWANCKQTSRSGMAGAISRWFGAIE
ref|ZP_01631840.1|     IAKDETGLSDLEKARRFFVRARQVRTGLAQTASIGRWAHCKLTSRAGMAGAVSRWLGSVE
gb|AAZ73681.1|         ISKDTTNLSNLERARRFFIRARQVRTGLAQTASSGRWAHCLLTSRAGMAGAVSRWLGSID
RAAC02564              IVEPTGGLTELERARRFYVRARQARMALAQTATPGRWAACRNTSQRGMAGNVSRWLGSAA
                         :  :* ****::****.* .***:*: ****  **: **** :****:***:*:

ref|YP_001275109.1|    DLPEIALRLLRVQIENRPAIEVIRLYDSADTLFYCDPPYIHETRGDDNAYAYEMNYEEHC
ref|ZP_01514022.1|     DLPDIALRLLRVQIENRPSIEVIRLYDSPDTLFYCDPPYVHDTWGDNNAYAYEMNNEEHR
ref|YP_001633718.1|    DLPDIAIRLLRVQIENRPALEVIRLYDSPDTLFYCDPPYVHETRGDNNAYAYEMSNEEHQ
ref|ZP_01631840.1|     HLPEIVQRLLRVQIENDTAIDIIQRYDSSETLFYCDPPYPHDSRGDSKAYAYEMTDDEHR
gb|AAZ73681.1|         DLSKIVQRLQRVQIENSSSFDIIRRYDSEETLFYCDPPYPHNTRGDSKAYAYEMTDEEHR
RAAC02564              NLAEIAARLVRVQIEHRPAMDVIRAYDSPDTLFYCDPPYIHATRTDPRAYRYEMSDEEHM
                        .*..*.  ** *****:  .:::.:*: *** :********  *   *..** ***. :**

ref|YP_001275109.1|    ELAMSLNSVRGLVAISGYECDLMNDLYPSSRWYKSVAPSKTIHSTKDKRTEILWTNY
ref|ZP_01514022.1|     QLALVLNSVQGFVAISGYDCDLMNDLYPSNWYKNIAPTKTIHSTK-----------
ref|YP_001633718.1|    QLADVLNSVQGFVAISGYDCDLMNELYSPPKWIKHVGPTRTIHSTKDQRTEILWTNY
ref|ZP_01631840.1|     QLAGVLRSVKGKVALSGYDCTIMQELYG--DWNCIKAPQKQCHSIKELRQEVLWVNY
gb|AAZ73681.1|         KLAEIVHNIKGKVAVSGYECTLMNELYG--DWKQISAPTKSCHSVKKPRTERLWINY
RAAC02564              ELARVLHNVRGKVAISGYHCDLMDELYR--DWRCIDAPPKQCHASKRWRQEALWVNY
                        :**    :..::* **:***.* **::**     *   .* :  *:  *
```

FIG. 163

```
ref|YP_853610.1|            ------------------------FESQADIRVIVINGEPWFIASDVCRAIGIANHRDAVR
ref|YP_512277.1|            ------------------------FESQADIRVIVINGEPWFIASDVCRAIGIANHRDAVR
ref|ZP_01959153.1|          ------------------------NSTPIRVQVINNEPWFVAKDVCDVLGISKYRDAIA
ref|YP_001038857.1|         ------------------------GKQVRTFIIDGEPWWVAKDVCDILELGDTHKAME
ref|YP_001662865.1|         ------------------------GNTVRTVMKDGNPWWVLKDVCSVLDIGNSRDVMA
RAAC02566                   MPFCPADIALRRGRSLMQQTWAVFANGAQVRVFWVDGEPWFDAVGVCEAMGLRNIEKAIR
                                                    :*.    :.:**:  .**   : :   ...:

ref|YP_853610.1|            KLDDDEKG-VASTDTPGGEQESIIISESGLYTLILRCRDAVTPGTIPYRFRKWVTGEVLP
ref|YP_512277.1|            KLDDDEKG-VASTDTPGGEQESIIISESGLYTLILRCRDAVTPGTIPYRFRKWVTGEVLP
ref|ZP_01959153.1|          RLDDDEGC-PIEVDTLGGMQKMAAVNESGLYTLILQSR---KPEAKP--FRKWVTSEVLP
ref|YP_001038857.1|         RLDEDERNTIPVTDSLGRLQETYVVNEAGLYNLILGSR---KQEAKE--FKRWITHEVIP
ref|YP_001662865.1|         RLDSDEKG-VDIIDTPGGKQEVSIINESGLYSVILVSR---KPEAKK--FKRWVTHEVLP
RAAC02566                   RLDDDEKG-LVTVDNAGGREEILVVRESGMLRLALAGR---EPHARA--FQRWVVREVLP
                            :.    *. *   ::   :  *:*: : *  *     :    *::*:. **:* ref|YP_853610.1|            -QIRRTGSYIKNSLPQEERIKMVA-------------------------
ref|YP_512277.1|            -QIRRTGSYIKNSLPQEERIKMVA-------------------------
ref|ZP_01959153.1|          -------------------------------------------------
ref|YP_001038857.1|         -QIRKTGIYALEPKQLLAVAIIEAQKIIEEQDR----------------
ref|YP_001662865.1|         -SIRRHGLYATD--ELL--------------------------------
RAAC02566                   LAIRGQRPNALEEQLRLEKVSLLVEILAAYQDRLSDGGIEHLAKTIANLLT
```

FIG. 164

```
ref|YP_375842.1|        --------------------MSKAELVEKIAAQAKLTKVDAERAVNAFINVVTSSLKGGD
ref|YP_001131112.1|     --------------------MSKAELVEKIAAQANLTKVDAEKSVNAFINVVTSSLKAGD
ref|ZP_00591928.1|      -------------------LMSKAELVEKIASQAGLTKADAERAVNSFVSVVTDSLKAGE
ref|YP_001003150.1|     --------------------MNKADLAEKVAAETGVSKRVATDAVSAVFTGIEESLASGE
ref|NP_046614.1|        ----------------GAPSMNKTELIAKVAEKQGVSKKEGAPSVEKVFDTISEALKSGE
RAAC02589               MCCLTGLERMRDLLEKERELVNKGELVAEVQARVGLPKSQVLQVLNTFCEVTTERLQAGE
                                            :..* :*  ::    . :.*     :. .    . * .*:

ref|YP_375842.1|        DVTLVGFGTFTTGDRAARQGRNPQTGKAITIPAKKVVKFKPGKALKDEV-
ref|YP_001131112.1|     DVTLVGFGTFTTGDRAERQGRNPQTGKTITIPAKTVVKFKPGKALKDEV-
ref|ZP_00591928.1|      DVTLVGFGTFSVGERAERQGRNPQTGETITIAARKAVKFKPGKALKEEVD
ref|YP_001003150.1|     DVSIPGFGKFAVVARPERQGRNPQTGELIDIPAGMNVRFKPGAPLKRSVD
ref|NP_046614.1|        KVSIPGFGTFEVRERAARKGRNPQTGEEIDIPATKAPAFKPAKALKDAV-
RAAC02589               EVSLPPLGKFQYVMRSARRQRNPQTGEMIDVPEKATVRFRPSGALKGRVN
                        .*::   :*.*     *. *: ******: * :.     *:*. .** *
```

FIG. 165

```
ref|YP_001127101.1|        --------------------------------YLTPTVIEQTNRGERAYDIYSRLLKD
ref|YP_148915.1|           --------------------------------YLIPTVIEQTNRGERAYDIYSRLLKD
ref|YP_080797.1|           SIGNIFICANCEE-IDENTITIESPSITIVESGAPSIPTVIEQTNRGERAYDIYSRLLKD
ref|YP_001488316.1|        --------------------------------IPTVIEQTNRGERAYDIYSRLLKD
ref|ZP_02848186.1|         --------------------------------VPIVVEQTNRGERSYDIYSRLLKD
RAAC02045                  ------------------MSSTWPQGEGGCCMYYPIPYVIEQTSRGERTYDIYSRLLKD
                                                              :*  *:*.******** ref|YP_001127101.1|        RIIFLGSPIDDQVANSIVSQLLFLAAEDPEKDISLYINSPGGSITAGLAIYDTMQFIKPD
ref|YP_148915.1|           RIVFLGSPIDDQVANSIVSQLLFLAAEDPDKDISLYINSPGGSITAGLAIYDTMQFIKPD
ref|YP_080797.1|           RIIMLGSAIDDNVANSIVSQLLFLEAEDPEKDISIYINSPGGSITAGMAIYDTMQFIKPQ
ref|YP_001488316.1|        RIIMLGSAIDDNVANSIVSQLLFLEAEDPEKDISIYINSPGGSITAGMAIYDTMQFIKPK
ref|ZP_02848186.1|         RIIFLGSAIDDDVANSIAQLLFLAADDPEKDIHLYINSPGGSVTAGMAIYDTMQYIKPD
RAAC02045                  RIVILGTPIDDQVANSIVAQLLFLAADDPEKDIQMYINSPGGSVTAGMAIYDTMQHIRPA
                           :::.*:::**  *::*  :*******:*:*******. *:* ref|YP_001127101.1|        VSTICIGMAASMGAFLLAAGAKGKRFALPNSEVMIHQPLGGAQGQATEIEIAAKRILFLR
ref|YP_148915.1|           VSTICIGMAASMGAFLLAAGAKGKRFALPNSEIMIHQPLGGAQGQATEIEIAAKRILFLR
ref|YP_080797.1|           VSTICTGMAASMGAFLLAAGEKGKRYALPNSEVMIHQPLGGAQGQATEIEIAAKRILSLR
ref|YP_001488316.1|        VSTICIGMAASMGAFLLAAGEKGKRYALPNSEVMIHQPLGGAQGQATEIEIAAKRILSLR
ref|ZP_02848186.1|         VSTICMGMAASMGSLLLTAGAKGKRFALPNAEVMIHQPLGGVRGQASDIKIHADWILKTK
RAAC02045                  VSTLCIGMAASMGAFLLAAGEKGKRYALPNAEIMIHQPLGGVEGQASDIKIHAEWILKTK
                           ***:*  ******* :**.**  ****:*:******** .***:.:**  *.  **   :

ref|YP_001127101.1|        DKLNRILAENTGQPIEVIERDTDRDNFMTAQKAQEYGIIDRVL-------
ref|YP_148915.1|           DKLNRILSENTGQPIEVIERDTDRDNFMTAQKAMEYGIIDRVL-------
ref|YP_080797.1|           DKLNKILAERTGQPLEVIERDTDRDNFKTAEEAKEYGLIDKVL-------
ref|YP_001488316.1|        DKLNQVLAERTGQPIEVIERDTDRDNFKTAEEALQYGLIDKVL-------
ref|ZP_02848186.1|         QKLNEIYVERTGQPYEKIDRDTDRDNFMSAEDALNYGLIDKVI-------
RAAC02045                  DKLNRLLSERTGQPLEVIERDTDRDHFMTAEEEAKAYGLIDEVLHPLHPVR
                           :***.:  *.**** * *:****** * :*:.*   **:**:**.*:
```

FIG. 166

```
ref|YP_866618.1|    ------IKAPKKLIEVALPLDDINAAAAREKSIRHG-HPSTLHLWWARRPLAAARAVLFA
ref|YP_342704.1|    -----EIKTPKKLIEVALPLDDINTAAAREKSIRHG-HPSTLHLWWARRPLAAARAVLFA
ref|NP_384606.1|    ------VRTPKKLIEVALPLDAINEAAAREKSIRHG-HPSTLHLWWARRPLAAARAVIFA
ref|YP_911114.1|    ------IKSPRKLIEVALPLDAINAACAYEKMPGIGAHPRGIHLWWARRPLAAARAVLFA
ref|YP_115396.1|    ------VKAPKKLIEVALPLDAINEASAREKSIRHG-HPSTLHLWWARRPLAAARAVIFA
RAAC02635           MYVVPKVKAPKKLIEVTLPLDDINAEAAREKSIRHG-HPSTLHLWWARRPLAAARAVLFA
                          :::*:*****:**** ** .* **     * **  :***************:**

ref|YP_866618.1|    QMVNDP----GGERG--YYAGKTKAQADAEREELFKIIRELVLWENTNNEEVLNKARAAI
ref|YP_342704.1|    QMVNDP----GYQQGEGFKYGVNKKEAEIKREKLFQIIRDLVKWENTNNEEVLNRAREAI
ref|NP_384606.1|    QMVNDPSWKWELEHPGEIPPNNIKASWAASRNRLFAIIKDLVEWENTTNEVVLEKARAEI
ref|YP_911114.1|    QLVNDP----GYQQGCGFKYGKNKKEAAIERKRLFKIIEELVLWENTTNEEVLERARVEI
ref|YP_115396.1|    QMVNDP----GYQQGGGFRYGVNKEKAQLERERLFKIIEELVQWENTNNEAVLSRARAEI
RAAC02635           QLVNDP----GGERG--YKPGMTREQAQKERERLFGIMRRLVKWENSNDEEVLREAREEI
                    *:****    :     :      .  :  .*:.** *:.  *:.:* .  * ref|YP_866618.1|    RKSWRETCELNK----GKSGFDPDKLPAFHDPFAGGGAIPLEAQRLGMESHASDLNPVAV
ref|YP_342704.1|    WESWRETCHLNRNHPQAAELFNPDKLPAFHDPFAGGGAIPLEAQRLGLESYASDLNPVAV
ref|NP_384606.1|    RKSWRETCDLNKDHPQAAGLFNPERLPAFHDPFAGGGALPLEAQRLGLASYASDLNPVAV
ref|YP_911114.1|    RRSWREVCELNKEHPQAAELFNPEKMPAFHDPFAGGGAIPLEAQRLGLEAYASDLNPVAV
ref|YP_115396.1|    WKSWRETCELNKNHPCAAELFNPDKLPAFHDPFAGGGAIPLEAQRLGLESYASDLNPVAV
RAAC02635           WKSWRETCEMNK----GLPGFDPDKLPAFHDPFAGGGSIPLEAQRLGLEAYASDLNPVAV
                     .****.*.:*:        .    *:*:::*********:.**:  ::******* ref|YP_866618.1|    LINKAMIEIPPKFAGRKPVGPIPEGEKQG------RMESDWPGATGLAEDVRRYGHWMRE
ref|YP_342704.1|    MINKAMIEIPPKFAGQRPVGPLPQGEKQG------KLMDDWSGARGLAEDVRRYGHWMRE
ref|NP_384606.1|    LINKATIEIPPKFAGRPPVNPEARTSRD-------AWSKQWFRAQGLAEDVRYYGRWMRM
ref|YP_911114.1|    LINKAMIEIPPKFAGRPPVGPEIENKQGKSL----ELPKIWPGATGLAEDVRRYGSWMRD
ref|YP_115396.1|    TINKAMIEIPPRFAGRAPVGPVPPSPDGRGVGGEGLFAQDWAGAKGLAEDVRRYGAWMRS
RAAC02635           LINKALIEIPPKFSGRPPVNPEARSKVG--------LLEQEWKGASGLADDIRYYGEWMRD
                    **.***:*:*: **.*         .   *   * ***:*:*     * ref|YP_866618.1|    EAFKRIGHLYPQVEITAEMAKERPDLKGIVGQKLTVIAWLWARTVRSPNPAFSHIAVPLV
ref|YP_342704.1|    EAFERIGNLYPRIKITQEMVAERPDLKPYQGQELTVIAWLWARTVKSPNPAFSHADIPLA
ref|NP_384606.1|    VAQKRIGHLYPPVEITSDMAKERPDLRPLVGQQLTVIAWLWARTVKSPNPAFRHVDVPLA
ref|YP_911114.1|    EAQKRIGHLYPPVEVTEEMARERSDLKPLVGKKLTVIAWLWTRTVKSPNPAFTHVNVPLV
ref|YP_115396.1|    EAEKRIGHLYPQVEVTRELAQGRQDLQPLVGQKLTVIAWLWARTVKSPNPAFSHVEVPLA
RAAC02635           EAFKRIGHLYPQVELPPEYG---------GGKATVIAWIWARTVKSPNPAYSHVDVPLV
                    * :***:***  :::. :           *  : *****:*:***:  *   :**.

ref|YP_866618.1|    SSFLLSTKKGKEAYIEPVVD--------------ANSYYFSVKKGTPS-------KDSAR
ref|YP_342704.1|    SSFLLSTKKGKESYVNPLVE--------------GHNYQFEVCMGVPP-------AEARN
ref|NP_384606.1|    SSFVLSTKTGAEAYVDPVID--------------KDTYHFAVRSGRAP-------SQARE
ref|YP_911114.1|    SSYILANKDGKEVYVKPVIE--------------GDKYYFLIKNGTPT-------TEAKD
ref|YP_115396.1|    STFVLSSKAGKEAYVQPMISPLPLGEGLGVRAGSEGYYRFTVQVAGTPGFDKADYARAKS
RAAC02635           RSFWLSTKKGKEVWVEPVIHE-----------DGSGYHFEVRTEGKP---------KIE
                    ::  *:.* * *  ::.*::                * * :     .

ref|YP_866618.1|    GTSAGK-RGGFRCIFSDAPIDYNYIRDEGSAGRIGTRLMAIVAEGVRGRIYLSATPELEI
ref|YP_342704.1|    GTKLGR-GANFTCLLSDTPIDPKYIYAQQSGNLGQRLMAVVAEGKSGRIYLTPTAEMEQ
ref|NP_384606.1|    GTKFSR--GNFRCLLSQAPIDGDYIKAEAKAGRMGERLMAIVAEGRNGRIYLSPSSDQEN
ref|YP_911114.1|    GTKATVRGANFRCIVSGAVIGSDYIKTEGKAGRIGQRLMAIVAEGTRGRVYLPPTLDAET
ref|YP_115396.1|    GTKLAR-GANFECLLSNTPIEPNHIYTEANAGRMGARLMAIVAECARGRVYLPPLPEHEA
RAAC02635           GTVNRR---GGTCIMSGSPIPFDYIRAEGKAERMGQRLMTVVVEGPRGRLYIAPTDDMEG
                    **        . *:.* : *   .:*  ::...: :* ***::*.   :*::..   : * ref|YP_866618.1|    IANSAK-PEWSPDVKLHGKCR-VNVSNYGLDVYSDLFTPRQLVALTTFSNLVQEARVKAV
ref|YP_342704.1|    AASAAS-PDWKPDALMPENPRWFSPPMYGMKSYGDLFTPRQLVALNTFSDLVQEACYKAI
ref|NP_384606.1|    IASAAH-PDWKPDVEFFQQALGFRVGNYGMTKWSDLFTARQLVALTTFTELIAEVRKQIV
ref|YP_911114.1|    VAKDAA-PTWRPSGDVPERLTGGTCVPYGLKEWGDIFTPRQLVALTILSDLLSEVRELVR
ref|YP_115396.1|    IARQAQ-PEWKPEVAMPDNPRWFSPPLYGLKNYGDLFTPRQLVALTFSDLVIDAIERCR
RAAC02635           MALSLKEPDGLPQTQLPKRALGFRVQEYGMTMHKHLFTNRQLVALKTFSDLV*: :.
                        *    *     *.    .         .      **:  .:****.*******.   :::*: :.

```
ref|YP_866618.1|    NDAKITGMADDGMGIDEGGFGAGAYGDAVAVYLGFIVDKVSESLSTICTWSSSPKNE---
ref|YP_342704.1|    ADAKAAGMTDDGIGIDDGGRGATAYGDALAVYLTFAINKLADRGSTICTWDSSRSS----
ref|NP_384606.1|    ADAIAAGMIDDQTGLDKGGEGASAYAEAVSVYLAIALSRLTDICNALCRWEVTKT-----
ref|YP_911114.1|    EDALASGLSDSEKGLGDGGSGVIAYAEAVSVYLAFAINRCADFCNSVTRWVPGNQ-----
ref|YP_115396.1|    RDAAAAGLPDDGVPLDAGGTGATAYAQAVGVYLAIAISRFSDRNNSICTWDSGPTGTKAS
RAAC02635           EDALSSGMTDDGIGLEDGGIGARAYADAVAVYLGLVLDKCADYWSSICSWNSPKE-----
                     **  *:  *.    :   ** *. **.:*:.***  :  :.:  ::    .::   * ref|YP_866618.1|    --------LIVSTFRRQAIPMTWDFGEANPFANSSGSLEKIVPAVSKVIKTSLCGSVDGN
ref|YP_342704.1|    --------TRNTFGRQAIPMTWDFAEPNPLSDSTGNFMGGIGWANDVLSRMIP-SSGGI
ref|NP_384606.1|    --------QVRNLFSRQAIPMLWDFAENNVFGGAAGDYIISLGNMVKALE-KLPARDPGV
ref|YP_911114.1|    --------KVMNLFGKQAIPMTWDYPEAAILADTVGGFAPASKYVADCIG-KLSPAAVGF
ref|YP_115396.1|    TGGSARTASLRNLFARQAIPMAWDFGEANPFSDSGGGFSSAFEWIEPAVR-SLRGGCAGY
RAAC02635           --------LVRNTFSRQAIPMVWDFAEANPFSDSTGNWMGMVDWVWKAVENAPIKTTLGE
                           .  * :*** : *    :..: *.         :         * ref|YP_866618.1|    AIQFDARTVNLS-DRVVSTDPPYYDNIGYADLSDFFYVWSRRALKSIFPSLYSTLAVPKA
ref|YP_342704.1|    AVQQDAATQNISAEKVISTDPPYYDNIGYADLSDFFYVWMRRSLKSFYPSLFATMAVPKA
ref|NP_384606.1|    SRQQDAQTQSISACKAISTDPPYYDNIGYADLSDFFYVWLREPLRSIYPGLFATVVTPKA
ref|YP_911114.1|    ASQADAQTQSISMAKIISTDPPYYDNIAYADLSDFFYVWLRKSLRLFLPGLFSTITVPKV
ref|YP_115396.1|    GDGADAQTQTLSRDKVVSTDPPYYDNIGYADLSDFFYVWLRRSLKPIFPGLYATLAVPKA
RAAC02635           AHLADAQTQSISVGKIVSTDPPYYDNVGYSDLSDFFYVWLRRSLNPILPGLFATLMTPKE
                    .   ** *  .:*    :  :********:.*:*******  *..*.  :  *.::*:  .**

ref|YP_866618.1|    EELVATPYRHGSKEEAEAFFMNCMICAINNFANQAHPSFPVTIYYAFKQSETK-ETGTTS
ref|YP_342704.1|    EELVAIPYRHGTKEKAETFFLDGMTQAIHNMADKGHPAFPVSIYYAFKQSETK-EGATSN
ref|NP_384606.1|    EELVATPARHGGSEAAELFFLGGMTAAMQRLAELAHPSTPVTIYYAFKQSETSGQDGTSS
ref|YP_911114.1|    EELVAAPYRHGTKQKAETFFLTGMTEAIHNLAEQAHPEGPVTIYYAFKQSETSGQDGTSS
ref|YP_115396.1|    EELVATPYRHGSKEAAEAFFLDGMRRALKNLAEQAHPAFPVTIYYAFKQSETTDAAGTSS
RAAC02635           DELVAAPERHQSKGDANSFFIHGMSKAMSTLANSTHPGFPVTIYYAFKQSDTE-NEGTSS
                    :**** * **   .  *: **:  **  *:  :*:  **  **:*********:*   .*:..

ref|YP_866618.1|    TGWETFLEAVIQAGFGITGTWPMRTERGARSIGIGANALASSIILVCRKRDNSAESISRR
ref|YP_342704.1|    TGWETFLEAVIRAGFSIDGTWPMRTEMSNRMIGSGTNALASSVVLVCKKREIEAESISRR
ref|NP_384606.1|    TGWETFLDAVIRSGLALTGTWPMRTELGNRMRGQDSNALASSIVMVCRPRPATAETVSRR
ref|YP_911114.1|    PGWVTFLSAVLSAGFAIVGTWPLRSEQEFRMIGMCANALASSIVLVCRKRSADAPSVSRR
ref|YP_115396.1|    TGWETFLQAVLDAGFALTGTWPMRTELGNRMIGAGTNALASSIVLVCRQRATDAPTASRR
RAAC02635           EGWVAFLEALLQAGFAVTGTWPLRTEMSNRMRGLDSNALASSIVIVCRRRPANAETISRR
                      :.*::  :*:.:  ****:*:*    *    * .: :****::: * * : *** ref|YP_866618.1|    QFQRELREILPEALETMIGG---KEGASP-------VAPVDLAQASIGPGMAVYSKYAAV
ref|YP_342704.1|    DFQRELREQMPDALEAMIGG---ETGTTP-------IAPVDLAQAAIGPGMAIFSKYEAV
ref|NP_384606.1|    AFLRELNQVLPEALDEMTRG---SGDDRSP------VAPVDLSQAIIGPGMAVFSKYAAV
ref|YP_911114.1|    EFIRELNGVLPEALDEMTKG---SGEERSP------VAPVDLSQAIIGPGMAVFSKYSAV
ref|YP_115396.1|    EFLRELNATLPEAIADMIGADPSPQPLSPRERGYCRVAPVDLSQAIIGPGMAIFSQYAAV
RAAC02635           AFLRELNTVIPDALSDMMHG---GPDRSP-------IAAVDLQQAAIGPGMAVFSKYAAV
                     * ***. :*:*: *   . :           :*.*   ******:*:* ** ref|YP_866618.1|    LNQDCNPMSVHDALILINREITDFLTPDSGSFDNDTLFCSTWFDQYGWKAGPFGEADTLS
ref|YP_342704.1|    LNQDGSRMSVHDALILINRAITEYLSPESGSFDADTQFCSSWFDQYGWSTGPFGEANVLA
ref|NP_384606.1|    LEADGTPMTVQAALRLINR----FLAEDD--FDHDSQFCLHWFEQYGWKEGRFGEADTLA
ref|YP_911114.1|    LEADGTPMSVRTALQLINR----FLAEDD--FDPDTQFCLHWFEQGWNENLFGEADVLA
ref|YP_115396.1|    LEADGTPMTVKTALALINR----FLAEDD--FDHDTQFCLHWFQQGWASGKYGEADVLA
RAAC02635           LEADGSPMTVKTALQLINRVVDAYLHASEAEVDADTLFCINWFDQFGWSEADFGRADVLA
                    *: **. *:*: ** ****     :*    .* *: ** **:*  **      :*.:.*:

ref|YP_866618.1|    RAKGTSVDGVQEAGVVQSGGGKVRLFKWDEYPDDWDPKKDNRTPVWEALHHLIRALNKDG
ref|YP_342704.1|    QAKGTTVDGVNTAGVVESGGGKVRLLKWAEYEADWDPIKDNRTPIWEACHQMIRSLNNQG
ref|NP_384606.1|    RAKGTSVDGVKQSGVIYASGGIVRLLKWAEYPSDWDPVGDGRLPVWEALHHLIRIFKSEG
ref|YP_911114.1|    RSKSTSVDAMKEAGVLQSCSGKVRLLKWAEYPSDWDPRTDKRMPVWEALHQLIRALKQGG
ref|YP_115396.1|    RAKGTAVDALVAAGVAESAKGSVRLLKWPEYPADWSPESDTRTPIWEALHQLIRALNQAG
RAAC02635           RAKGTSVDAVRAAGVLTADHGKVRLLRWQDYPSDWSPGKDYDTPVWEALHHLIRALQQDC
                    ::*.*.** *  *:. ***  :** : ***.* * :.*:** ** *: :::.*
                                                                    continued →
```

FIG. 166 continued

```
ref|YP_866618.1|    ESVSGGLLARMPERAEAIRQLAYHLYTLCERKKWADDARAYNELITSWHGIAAASHEVGH
ref|YP_342704.1|    ESAAGELLAKMPEKGEPIRQLAYHLYTLCERKKWAEDARAYNELIGSWHAIVTASHEVGH
ref|NP_384606.1|    ESGAGNVLAAVAAKAEPARQLAYRLYTLCERAGWAEDARAYNDIITSWSAIESAAAAA--
ref|YP_911114.1|    ESASGALLAALGGKAEAVRQLAYRLYTLCERLGQAEDARAYNELITSWTGIESVA-----
ref|YP_115396.1|    ETEAGRLLARMPARAEPIRALAYRLYTLCERKGWAEDARAYNELVTAWSGIEQAANEAGV
RAAC02635           EQAAGALLAGMYSVSESIRSLAYRLYTLCERKGWAEDARAYNELIASWDAIAEVAQKAGL
                      :*  :**  :    .*. * ***:*******   *:******::: :* .*   .:

ref|YP_866618.1|    LGTQCTLDL-
ref|YP_342704.1|    SGSQAELGLD
ref|NP_384606.1|    ----------
ref|YP_911114.1|    ----------
ref|YP_115396.1|    VGAQMQLEL-
RAAC02635           SGSQLTLDVE
```

FIG. 167

```
ref|NP_244431.1|      MNLIPTVIEQTNRGERAYDIYSRLLKDRIIMLGTAIDDNVANSIVAQLLFLQAEDPDKDI
ref|YP_176521.1|      MNLIPTVIEQTNRGERAYDIYSRLLKDRIIMLGSGVDDNVANSIVAQMLFLQAEDPEKDI
ref|ZP_02171648.1|    MNLVPTVIEQTNRGERAYDIYSRLLKDRIIMLGTPIDDNVANSIVAQLLFLAADDPDKDI
RAAC00088             MSLIPYVIEQTSRGERSYDIYSRLLKDRIIFLGTPIDDDVANAVVAQLLFLAADDPDKDI
ref|ZP_02848186.1|    MNLVPIVVEQTNRGERSYDIYSRLLKDRITFLGSAIDDDVANSVIAQLLFLAADDPEKDI
ref|ZP_02210735.1|    MALVPTVVEQTGRGERAYDIYSRLLKDRIIFLSDEVNDTTASLVVAQLLFLEAEDPDKDI
                      * *:*  *:* .*:************:*.   ::* .*.  :::* *::* ref|NP_244431.1|      SLYINSPGGSITAGMAIYDTMQYIKPNVSTICIGMAASMGAFLLAAGAKGKRFALPNSEV
ref|YP_176521.1|      SLYINSPGGSITAGMAIYDTMQFIKPDVSTICIGMAASMGAFLLTAGAKGKRMALPNSEV
ref|ZP_02171648.1|    SLYINSPGGSITAGMAIYDTMQFIKPKVQTICIGMAASMGAFLLTAGEPGKRYALPNSEV
RAAC00088             QMYINSPGGSVSAGLAIYDTMQHIKPDVSTMCVGMAASMAAVLLAAGAKGKRYALPNSEV
ref|ZP_02848186.1|    HLYINSPGGSVTAGMAIYDTMQYIKPDVSTICMGMAASMGSLLLTAGAKGKRFALPNAEV
ref|ZP_02210735.1|    HLYINSPGGSVTAGMAIYDTMQYIKPDVSTICIGMAASMGAFLLNAGAKGKRFALPNSEI
                      :*********::**:******.***.*.*:*:******.:.**  ** *** ****:*:

ref|NP_244431.1|      MIHQPLGGTRGQASDIEIHTRRILEMRETLNRILAERTGQPLEQIAKDTDRDNFMTAEKA
ref|YP_176521.1|      MIHQPLGGMQGQAADMEIHARRIIQMREKLNQIMAERSGQPYERIARDTDRDNFMTAEQA
ref|ZP_02171648.1|    MIHQPLGGAQGQASDIEIHAKRIVEMKEKLNQILAERTGQDIEQIRKDTDRDNFLSAAQA
RAAC00088             MIHQPLGGARGQASDIEIHARHILKTRERLNRILAERTGQPLERVAQDTDRDNFMSAEEA
ref|ZP_02848186.1|    MIHQPLGGVRGQASDKIHADWILKTKQKLNEIYVERTGQPYEKIDRDTDRDNFMSAEDA
ref|ZP_02210735.1|    MIHQPLGGAKGQATDIEIIAKWILKIKERLNKILSERTGQPIEKIQEDTFRDNFMSAQEA
                      ****** :*:*:::**:   *:: ::  **.*   :   *:: .:**::*  .* ref|NP_244431.1|      REYGLIDKVI--
ref|YP_176521.1|      KEYGLIDKVI--
ref|ZP_02171648.1|    KEYGLIDEVM--
RAAC00088             KAYGLIDEVIYR
ref|ZP_02848186.1|    LNYGLIDKVI--
ref|ZP_02210735.1|    KEYGLIDEVI--
                       *****:*:
```

FIG. 168

```
ref|YP_146448.1|      --ERSIALYCRVSTDEQAREGISLDEQQERLKAYCRAMGWSEEPLLFIDDGYSAKNLDRP
ref|ZP_02848045.1|    ---RFVALYCRVSTDEQAREGVSLDEQVERLKAYCRAMGWSEQVQTYIDDGYSAKNLDRP
ref|NP_977168.1|      -SSQFIALYCRVSTDDQAKEGVSLEEQQERLEAYCRAMGWGEDVVVYVEDGYSAKSTDRP
ref|ZP_02261191.1|    -SSQFIALYCRVSTDDQAKEGVSLEEQQERLEAYCRAMGWGEDVVVYVEDGYSAKSTDRP
RAAC00111             MTERHLALYVRVSTEEQAASGHSLREQEEQLVEYARSHGFPR-YELYCDDGYSGKSLNRP
ref|NP_981890.1|      -SKRKVAIYIRVSTEEQANEGFSLGAQEDYLKQYANTKGYEV-YDIYIDDGYSGKDYNRP
                        : :* ****::** .* **   * :  *  *..: *:        :: :****.*. :**

ref|YP_146448.1|      ELNRLLKEVKKGTISKILVTKLDRLSRRLLDLLKLIDMFQEHNVSFISISES-FDTNTPS
ref|ZP_02848045.1|    ELKRLLHAVKSGAVSRIMVTKLDRMSRRLLDLLNIIDLFQDHEVSFVSISES-FDTNTPS
ref|NP_977168.1|      HLKRLIEDVKAGEIKKIIVTKLDRMSRKLLDLLTLIDLFQEHDVSFVSISES-FDTNTPS
ref|ZP_02261191.1|    HLKRLIEDVKAGEIKKIIVTKLDRMSRKLLDLLTLIDLFQEHDVSFVSISES-FDTNTPS
RAAC00111             AMERLRADTRAGCVLGVVTTRIDRLTRSVADFARLVDEMNLHGVFYRSTRQN-FEISTAM
ref|NP_981890.1|      EIQRLFKDLYQEKFTGILVKSVDRISRRVSDVTKLIDDVLAPRKCYVLVSDNNLDSSTTG
                       :** .    :  : ::.. :**::*  : *. ::* .  :        :. :: .*.

ref|YP_146448.1|      GRLTLQVLGAVAEFERERIRERVFENMLHAARQGKWLTQSPYGYRLQNKELVIYEPEAQI
ref|ZP_02848045.1|    GRLTLQVLGAVAEFERERIRERVFENMLHAATTGKWLTQSPYGYDLVDKSLVVNIVESQI
ref|NP_977168.1|      GRLTLQVLGAVAEFERERIRERVFENMYHAASKGKWLTQHPFGYRLENKELVTYENEAKI
ref|ZP_02261191.1|    GRLTLQVLGAVAEFERERIRERVFENMYHAASKGKWLTQHPFGYRLENKELVIYENEAKI
RAAC00111             GRLVAQMLSVIAEFEREMIAERVHENLLAMAQRGELATKPPFGYRLVNGRLTPDPREARW
ref|NP_981890.1|      GTAFIQLLATFAEYERSMIVQRVKAGMSKRAELGYWNGGHVLGYDVKNKELKVNKEEAEV
                      *  :*...**:**. * :**   .:   *  *     **  :  *       *:.

ref|YP_146448.1|      VRNVYDWYLNKGLGYYAIAKKLNEEGIPSRQKKEWSIRAIKLMLTNPVYKGTLFWNRMDS
ref|ZP_02848045.1|    VKRVYDMYLNEGLGFYSIAKRLNEEGVPSRHRKEWSIRAIKLMLTNPAYKGTLVWNRKDS
ref|NP_977168.1|      VRDIFIWYTQEGHGFYAIAKKLNLLGIPSRQNKQWSIRSVKLLLSNPVYKGTVVWNRKDR
ref|ZP_02261191.1|    VRDIFIWYTQEGHGFYAIAKKLNLLGIPSRQNKQWSIRSVKLLLSNPVYKGTVVWNRKDR
RAAC00111             VREG-ARLLLTGASPRDVAMEFNALGVRTKTGRLWTDRTVRTLFSNPALAGVSVWNRRKT
ref|NP_981890.1|      VRKIFHLRT-EGKGYKSIALILNQQGFKTKRGRLFSIGTIKTILENPLYIGYCRWGRHKN
                      *:           *   :*   :* *.. ::  : ::  :::  :: **   *  *.*.

ref|YP_146448.1|      SKSKRVKKDDADWVVLEDACPAIIDQATWEQVQKR--VNK-KQMAPRAQTSPHLLGGLLK
ref|ZP_02848045.1|    SKTQRKDKDEAEWVSVEECLPVIIDQPMWDKVQQR--INQPSNIAPRAKTSPHLLGGMLR
ref|NP_977168.1|      SKKKEQFKKEDEWVIQENAAPAIVTDELWNEAQKR--MQT-STLAPRAQTSPHLLGGLLK
ref|ZP_02261191.1|    SKKKEQFKKEDEWVIQENAAPAIVTDELWNEAQKR--MQT-STLAPRAQTSPHLLGGLLK
RAAC00111             QGSRRTEREPTEWVCVEGAHEAILSREEFEALRGM--LERRRALSPRSQGSKRPLAGIAR
ref|NP_981890.1|      WNVERRKGKTDEYKFVKGKIIEPIVSEDLWKRVQGVNYAHKKSISKNRNFNGEFVLSGILR
                       .   :   :    *:   :.   *:   . .  *       * .*.:

ref|YP_146448.1|      CGRCGSGMSIGWSGSAKNRYR----VYRCSANKNKGTCTSKQYRADDVESWFKHGLLKLA
ref|ZP_02848045.1|    CGNCGSGMSIGFSGSPNKRYR----VYRCSANKNKGTCTSKQYRA---------------
ref|NP_977168.1|      CGKCGSGMSIGWSGSTKNRYR----VYRCSANKNKGTCTSKQYKA---------------
ref|ZP_02261191.1|    CGKCGSGMSIGWSGSTKNRYR----VYRCSANKNKGTCTSKQYKA---------------
RAAC00111             CGFCGSAMYAGWQVSKRGHERQKRPIYRCGRYVTGGGCTPNQVDASALEMLVVEELLRRV
ref|NP_981890.1|      CPSCGAGM----------------------------------------------------
                      *  **:.* ref|YP_146448.1|      DSINSQMIPHLTQKAAENEESTIEQKIRTAKNRYKRKVEAYTAGLIELEDLNEEKKRMEQ
ref|ZP_02848045.1|    ------------------------------------------------------------
ref|NP_977168.1|      ------------------------------------------------------------
ref|ZP_02261191.1|    ------------------------------------------------------------
RAAC00111             RPELEPVVSAYRAHAASNELRTVQRKRRVALARLSRLAEAYASGVVSEEAFSREQVRLLR
ref|NP_981890.1|      ------------------------------------------------------------ ref|YP_146448.1|      II----------------------------------------------------------
ref|ZP_02848045.1|    ------------------------------------------------------------
ref|NP_977168.1|      ------------------------------------------------------------
ref|ZP_02261191.1|    ------------------------------------------------------------
RAAC00111             VLEACREAEAQAAALSTTDGWDAWVRELCARLAGDPHLERALFLTVVREVRVFRPKRSRE
ref|NP_981890.1|      ------------------------------------------------------------ ref|YP_146448.1|      ----------
ref|ZP_02848045.1|    ----------
ref|NP_977168.1|      ----------
ref|ZP_02261191.1|    ----------
RAAC00111             VDVDLVLRLE
ref|NP_981890.1|      ----------
```

FIG. 169

```
ref|ZP_01236658.1|    ---------RAFLKWAGGKYSLVEDIKRHLPPARKLVEPFVGAGSVFLNTDYDHYLLADI
ref|ZP_01161642.1|    ---------RAFLKWAGGKYSLVEDIKRHLPPARKLVEPFVGAGSVFLNTDYDHYLLADI
ref|ZP_01221581.1|    ---------RAFLKWAGGKYSLVEEIQRHLPPARKLVEPFVGAGSVFLNTDFEQYLLADI
ref|YP_128524.1|      ---------RAFLKWAGGKYSLVEEIQRHLPPARKLVEPFVGAGSVFLNTDFEQYLLADI
ref|ZP_01898092.1|    -----MQKTRAFLKWAGGKYSLVDHLREKLPAGKRLVEPFVGAGSVFLNTDYDEYLLNDI
RAAC03161             MEVQFMTVLRSYLQWPGGKSHIVTALRAFLPPGRRLIEPFVGAGSVFLNANYPEYLLGDA
                           *::*:*.***   :*   ::   **..::*:**********:::  .* * ref|ZP_01236658.1|    NPDLINLYNILKHEPERYIEDARKLFTPEYNNKEAYLKIREEFNASDDPYLRSLYFLYMN
ref|ZP_01161642.1|    NPDLINLYNILKHEPERYVEDARKLFTPEYNNKEAYLKIREEFNASDDPYLRSLYFLYMN
ref|ZP_01221581.1|    NPDLINLYNILKDDPEKYVEDVRKLFTPEFNQKEEYLKIREEFNKTQDPYVRSLYFLYMN
ref|YP_128524.1|      NPDLINLYNILKDDPEKYIEDVRKLFTPEFNQKEEYLKIREEFNKTQDPYVRSLYFLYMN
ref|ZP_01898092.1|    NPDLINMYKILQHKPEQFIADAQRFFTPEFNDKERYYKIREKFNKTSNPYQRSLMFLYMN
RAAC03161             NGDLILTHQMLQAHGEAFIEACRDLFVPENNTPDRYYELRDEFNSTADPWRKAILFVYLN
                      * ***   :::*:   .  *  :: :  :*.**  *  :*  ::**   :*:  ***  *:*:* ref|ZP_01236658.1|    RHGFNGLCRYNKKGGFNVPFGSYKKPYFPEAEMYYFSEKAKRATFVCEGYLQTFSRARKG
ref|ZP_01161642.1|    RHGFNGLCRYNKKGGFNVPFGSYKKPYFPEAEMYYFSEKAKRATFVCEGYLQTFSRARKG
ref|ZP_01221581.1|    RHGFNGLCRYNKKGGFNVPFGSYKKPYFPEKEMYFFAEKAKRATFVCEGYQQTFSRARKG
ref|YP_128524.1|      RHGFNGLCRYNKKGGFNVPFGSYKKPYFPEKEMYFFAEKAKRATFVCEGYQQTFSRARKG
ref|ZP_01898092.1|    RHGFNGLCRYNKSGGFNVPFGSYKKPYFPLKELRFFAEKSKKATFICESYSDVYKRLGSD
RAAC03161             RHGFHGLCRYTRNGDFNVSFGYRKTVYFPEEEMRYFAEKAKQATFVCADFRDLLERVEPG
                      ****:*****.:.*.***.**   *.  ***    *: :*:**:*:***:*   .: :   .*   .

ref|ZP_01236658.1|    CVVYCDPPYAPLSSTANFTSYSGNGFSLDDQATLADVAEKAAAERDIAVLISNHDTALTR
ref|ZP_01161642.1|    CVVYCDPPYAPLSSTANFTSYSGNGFSLDDQATLADVAEKAAAERDIAVLISNHDTALTR
ref|ZP_01221581.1|    CVVYCDPPYAPLSTTANFTSYAGNGFSLDDQADLADVAEKAATEREIPVLISNHDTKLTR
ref|YP_128524.1|      CVVYCDPPYAPLSSTANFTSYTGNGFSLDDQADLADVAEKAATEREIPVLISNHDTKLTR
ref|ZP_01898092.1|    DVVYCDPPYAPLSRTASFTSYSASGFSLDDQALLAKVSRETSQERNIPILISNHDIPLTR
RAAC03161             DVVYCDPPYVPLSRTSNFTEYAPTRFSWRDHTQLAGYAQALT-ERGVTVVISNHRRPAVE
                      ********.*** *:.**.*:   . ** *::  **   :.  : ** ..::****   ..

ref|ZP_01236658.1|    RLYTGADLSVVKAKRTIS-RNGSGRNKVDELLALF---
ref|ZP_01161642.1|    RLYTGADLSVVKVKRTIS-RNGSGRNKVDELLALF---
ref|ZP_01221581.1|    RLYHGADLSVVKVRRTIS-RNGSGRNKVDELLALFKS-
ref|YP_128524.1|      RLYHGADLSVVKVRRTIS-RNGSGRNKVDELLALFKS-
ref|ZP_01898092.1|    ELYHGSTFEVVQVKRTIS-RNAGKRNKVDELLALYR--
RAAC03161             SLYRGAEIIVVEAPRNIVNRYRQATHVIEELIAVFRAL
                      **  *:  :  **:. *.*  *      :  ::**:*::
```

FIG. 170

```
ref|YP_001567845.1|    ------------------------------------------------------------
RAAC03110              MTSLSQGRRAIGLRYPGHDTLECASQLQALSRAVKQAYGGEASAARMTSRDNIGEAHVTA
gb|ACA00199.1|         ------------------------------------------------------------
ref|NP_490383.1|       ------------------------------------------------------------
ref|YP_319960.1|       ------------------------------------------------------------
ref|ZP_01731959.1|     ------------------------------------------------------------ ref|YP_001567845.1|    --------------RVEVLDKNKQPLMPCHPARARELLKKGKAAVFRYHPFTIILKDR-EG
RAAC03110              ERRDEEVTLMRQNRVLVLDTHRRPLMPCHPARARQLLKAGRASVFRRYPFTIILHDR-NG
gb|ACA00199.1|         --------------RVLVLDKNRQPLMPCHPARARQLLRRGKAAVFRRFPFTIILKDR-ES
ref|NP_490383.1|       --------------KVFVIDNEKRSLNPIHPAQARQLLKRGKAAVFRRFPFTIVVKESYTD
ref|YP_319960.1|       --------------KVFVINKEKRPLNPIHPAQARQLLRSGKAAVFKRFPFTIIVKESNVN
ref|ZP_01731959.1|     --------------VFVLSKDKRPLSPCHQARARKLLKQGKAAVYRKYPFTIILKEEVNP
                                     *:*:.....:.* * * *:*:**:**: *:*:*:: .****:::.

ref|YP_001567845.1|    GDTQPIQVKIDPGSKITGVTLVGDFKN-GKKVIWGAEIHHRGQSIKKALDTRRGVRRSRR
RAAC03110              GDVQPMQLKLAPGSKTTGVALVADFQR-GKTVVWAAEIQHRGDQIRQALLRRRMLRRGRR
gb|ACA00199.1|         GVTQPTVLKLDPGSNTTGLALVADFARRGKVLVWAAELRHRGAAIRKALADRRAHRRFRR
ref|NP_490383.1|       ATVSPLRLKFDPGAKYTGIALVNDVNG---EVVFAAELKHRGFAIRDALTSRRQLRRSRR
ref|YP_319960.1|       TNVSPLRLKLDPGAKTTGIAIINDAND---EVVFAAELKHRGFAIRDAITSRRQLRRSRR
ref|ZP_01731959.1|     NKPKPCRTKLDPGAKVTGIALIQ--GD----RVIFGAELEHRGFRIKDSLESRQLRRGRR
                         .*   :*: **:: **::::      :::.**:.*** .*:..::  **  ** **

ref|YP_001567845.1|    NRKTRYRIARFDNRKRSKGWLPPSLISRVENILTWIKRIRRFSPITGISLELVRFDTQKL
RAAC03110              YRKTRYRKPRFDNRRRLEGWLPPSLMSRVHNIETWVARLRRWAPITHLSMQLVSFDTQKL
gb|ACA00199.1|         -FKLRYRPARFNNRTRPSGWLAPSLQHRVDTMTWVQRLMRWTPVTSLSQELVRFDTQAM
ref|NP_490383.1|       SRKTRYRQPRFFNRTRPQGWLAPSLQSRVENIKTWVNRLRKVAPITAISQELVKFDTQLI
ref|YP_319960.1|       NRKTRYRQPRFLNRTKPEGWLAPSLQSRVENIKTWVSKLRKVAPITAISQELVKFDMQLI
ref|ZP_01731959.1|     GRKTRYRKPRFLNRTPKGWLPPSLQSRVENINTWVNRLRKLCPVDSISVELVRFDTQQL
                         * *** .** **   :  .***.***   **..  **: ::  :   *:  :* :** ** * :

ref|YP_001567845.1|    QDPEINGIEYQRGTLYGYEIKEYLLEKWGRKCVYCGKENVPLEIEHIVPKSKGGSDRISN
RAAC03110              QYPEISGEEYQQGTLYGYEVREYLLEKWGRKCAYCGAENVPLEIDHVIPRSRGGSDRVSN
gb|ACA00199.1|         QNPEISGVEYQQGTLFGYEVREYLLEKWVRKCAYCDAENVPLTIDHIHPRSKGGSNRVSN
ref|NP_490383.1|       RHPDIQGKEYQQGTLAGFETRQYFLEKWNRECAYCGIKDVPLQIEHIHPKSKGGSNSITN
ref|YP_319960.1|       RRPDIQGKEYQQGTLAGFETRQYLLEKWNRECAYCGIKDVPLQIEHIHPKSKGGSNSITN
ref|ZP_01731959.1|     ENPEISGVEYQQGTLFGYEVREYLLEKYNRTCQYCGAKEVPFEIEHIVPKSKGGSDRVSN
                         . *:*:* * * *:*  ::*:*** * * . ::: *:*: *:*:***: ::* ref|YP_001567845.1|    LTLACHECNQKKGNQSIEEFLTNNPERLKQIKSESKRPLKDTAALNATRWYIFNQLRGNS
RAAC03110              LVLACHRCNQAKANRPVEEFLAHDQERLHRIQAQLKLSLRDAAAMNATRWAVFRRLKDT-
gb|ACA00199.1|         LTLACFPCNQRKGNRDVAEFLDRDPKRLARIEAQRRAPLQDAAAVNSIRWALWRNLVAT-
ref|NP_490383.1|       LTLSCEKCNLKKGTQDIKNFLKKDKSRLEKILALTKKSLADAAAVNTTRFALLEVLKST-
ref|YP_319960.1|       LTLSCEKCNLRKCNQDIRDYLEKDKPRLEKILALTKKPLADAAAVNATRFALLYALKST-
ref|ZP_01731959.1|     LTLSCHKCNQKKGNRSVEEFLKGKPEVLKRVKANAKKPLRDAAAVNAARWAVFNRLKAS-
                         *.*:* ** *..: : ::*  .  *  :: :  : .*:**:*: *:     *    .

ref|YP_001567845.1|    LTAGKEELPIEVGTGGRTKYNRETQNYPKKHWIDAACVGESGQNVQIEPDMQVLEIKAMG
RAAC03110              ------GLPVEAGSGGRTKYNRFSQGYPKAKWIDAACVGESGQCVRLDTQMQVLTIVAKG
gb|ACA00199.1|         ------GLDVEVGTGGRTKRNRSQQQYPKEHWIDAACVGESGANVRLDPFHKPLAIQAMG
ref|NP_490383.1|       ------GLPVEIGSGGLTKFNRTQQGLNKSHWLDACCVGASTP-ILKIKGIRLLLITANG
ref|YP_319960.1|       ------GLPIETGSGGLTKFNRTQQALNKSHWLDACCVGASTP-ILKIKGIKPLLITANG
ref|ZP_01731959.1|     ------GLEVEAGSGGLTKFNRTKHELPKTHWLDAACVGKSTPSKLRMLVQKPLKIKATG
                              * :* *:  **   :   *:.* *       :  * * * ref|YP_001567845.1|    HGMRRMCFVDKYGFPKKYRPKERTYMGYKTGDIVLAVIPKGKNMGIHIGRIAIRHRPSFL
RAAC03110              HGKRQRCITDKYGFPRSHAPSSRSYMGFRTGDLVQAHVPRGKYAGTHVGRIVIRHRPSFQ
gb|ACA00199.1|         HGRRQRARLNRYGFPRGYKLRARSYLGFRTGDVVFCAKPK---IEVFAGRVAIRFRPSFV
ref|NP_490383.1|       HGTRQSCRTDKYGFPIRHCSRTKFHFGFQTGDIVKAVVTKGKKIGTYIGRIATRATGSFN
ref|YP_319960.1|       HGTRQSCRTDKYGLPVRHCSRTKFHFGFQTGDIVKAVVTKGKKVGTYIGRIATRATGSFN
ref|ZP_01731959.1|     HGTRQMCRTNKYGFPTRYVPHKKDVKGFQTGDIVKAVVTKGKKTGIYVGRVAVRSTGSFN
                        ** *:  .  :**.*   :    *::***:*  .  :    .  **:. *  ** ref|YP_001567845.1|    LNGVG----DVHPKYLTLLQKNDGYGY---
RAAC03110              LNGF-----NVHPKYLKVLQRGDGYGYAME
gb|ACA00199.1|         VTGAD-RKVESHPKYLSMIQKGDGYAYA--
ref|NP_490383.1|       ISTVQGLIQGISHKYCKTIHKKDGAYAI-
ref|YP_319960.1|       ISTAKGLIQGISHKYCKTIHKKDGAYGI-
ref|ZP_01731959.1|     TSTAKGVIQGINHKYCRQIHKKDGYSYA--
                        :.           **   ::: ***.*
```

FIG. 171

```
ref|NP_852746.1|         --------------IRTLAINNEPWFIAKDVCDAIGIDNNRKALLALDEDEK-GVTLSNTL
ref|YP_853610.1|         --------FESQADIRVIVINGEPWFIASDVCRAIGIANHRDAVRKLDDDEK-GVASTDTP
emb|CAP00374.1|          --------FEQNSQIRIIMINSNPWFVAKDICDALGLSNHRDAISKLDKDEK-GVALTDTL
ref|ZP_01959153.1|       ----------NSTPIRVQVINNEPWFVAKDVCDVLGISKYRDAIARLDDDEG-CPIEVDTL
ref|YP_001038857.1|      ----------GKQVRTFIIDGEPWWVAKDVCDILELGDTHKAMERLDEDERNTIPVTDSL
RAAC03810                MQQTWAVFANGTQVRVFWVDGEPLFDAMGVCEAVGLRNVEKALRRLDDDEQ-GSVILEGL
                                          :*    ::.:*  : *  .:*    :  :   ..*:   **.**         :

ref|NP_852746.1|         GGKQEMNIISESGMYTLILRCRDAVKKGSVPHRFRKWVTAEVLPAIRKTGKYEAKTTVDD
ref|YP_853610.1|         GGEQESIIISESGLYTLILRCRDAVTPGTIPYRFRKWVTGEVLPQIRRTGSYIKNSLPQF
emb|CAP00374.1|          GGQQELSVINESGMYALVMRSRDAMKEGTPQHKFRKWVTSEVLPSIRKTGKYEAP-----
ref|ZP_01959153.1|       GGMQKMAAVNESGLYTLILQSR---KPEAKP--FRKWVTSEVLPSIRKKGYYG-------
ref|YP_001038857.1|      GRLQETYVVNEAGLYNLILGSR---KQEAKE--FKRWITHEVIPQIRKTGIYALEPKQL-
RAAC03810                DGREEIHVVRESGMLRLSLVGK-----DEHARALQRWATREVLPSVIRTGRYGEPDIEQE
                          . ::    :  *:*:  *  :  :            :::* * **:* : :.* * ref|NP_852746.1|         RTGLRNA-----------------------------
ref|YP_853610.1|         E-------------------------------
emb|CAP00374.1|          --------------------------------
ref|ZP_01959153.1|       --------------------------------
ref|YP_001038857.1|      --------------------------------
RAAC03810                QLQLQKATLLFNTLAMFRDRLFDETVQNLANAMADVLRG
```

FIG. 172

```
emb|CAP00374.1|              --------------------FEQNSQIRIIMINSNPWFVAKDICDALGLSNHRDAISKL
ref|NP_852746.1|             --------------------------IRTLAINNEPWFIAKDVCDAIGIDNNRKALLAL
ref|ZP_01959153.1|           --------------------NSTPIRVQVINNEPWFVAKDVCDVLGTSKYRDAIARL
ref|YP_001038857.1|          -----------------------GKQVRTFIIDGEPWWVAKDVCDILELGDTHKAMERL
ref|ZP_02327844.1|           --------GKETNIIMNQLQVFNFTGKDVRVVVKDGHPWWVAKDVSELLGFRMASDFTRTL
RAAC03316                    MSCTTHSIGRRRSPMQQTWAVFANGTQVRVFWVDGEPLFDAMGVCEAVGLRNVEKALRRL
                                                   :*     :..* : * .:.: : :   .    * emb|CAP00374.1|              DKDEKGVALTD-TLGGQQELSVINESGMYALVMRSRDAMKEGTPQHKFRKWVTSEVLPSI
ref|NP_852746.1|             DEDEKGVTLSN-TLGGKQEMNIISESGMYTLILRCRDAVKKGSVPHRFRKWVTAEVLPAI
ref|ZP_01959153.1|           DDDEGCPIEVD-TLGGMQKMAAVNESGLYTLILQSRKPEAKP-----FRKWVTSEVLPSI
ref|YP_001038857.1|          DEDERNTIPVTDSLGRLQETYVVNEAGLYNLILGSRKQEAKE-----FKRWITHEVIPQI
ref|ZP_02327844.1|           DDDEKDTQIVR-TPGGNQEVTIINESGLYSAILKSRKPEAKQ-----FKRWVTHEVLPAI
RAAC03316                    DDDEQGSVILE-GLDGREEIHVVRESGMLRLSLVGKDEHARA-----LQRWATREVLPSV
                             *.**         .  ::   : *:*:   :  :.   .       :::* * **:* :

emb|CAP00374.1|              RKTGKYEAP---------------------------------
ref|NP_852746.1|             RKTGKYEAKTTVDDRTGLRNA---------------------
ref|ZP_01959153.1|           RKKGYYG-------------------------------------
ref|YP_001038857.1|          RKTGIYALE------PKQL-------------------------
ref|ZP_02327844.1|           RKTGMYATDELLDDPELLIQAVTKL-------------------
RAAC03316                    IRTGRYGEPDIEQEQLQLQKATLLFNTLAMFRDRLFDETVQNLANAMADVLRG
                              :.* *
```

FIG. 173

```
ref|YP_148854.1|         ------------------------------DRNDVMRVVEVEPLLALYLYTPLCGTCQLARRM
ref|YP_001127043.1|      ------------------------PIERTEIQQTITEQPLMALYLYTPLCGTCQLAKRM
ref|YP_080555.1|         ---------------------------LKRLEHETCL-LYVYTPFCCTCQLAGRM
ref|NP_693306.1|         ---------------------------------VI--YIYTPFCGTCSVARAM
RAAC03018                MVRANVQGPRQVHTEGRRIPMFTPFPGDRPEALGTLPHEALV--FVHTPLCGTCQLARRM
ref|ZP_02170973.1|       ------------------------------KGVL--FLHTPLCGTCKMAGQF
                                                    :  :::**:****.:*  :

ref|YP_148854.1|         LTVVEQLF-PALPFYETDINYIPEQAVAWKIESVPCLLLFRDGTVAGKWYAFHSVPYLYE
ref|YP_001127043.1|      LTVVEELF-PALPFYETDVNYIPEQAVVWKIESVPCLLLFVDGTMVGKWYAFHSVPYLYE
ref|YP_080555.1|         LEVVDEMM-KDIPFYKNNLNYSPSFAKQQEIESVPCFILYKKGRVVKKEYAFHSVSYLYD
ref|NP_693306.1|         LENIERLHRQDI-FYEMNAAVHPEYMHDNQIESVPCLLFVENGEIVERIYTFYSTANIYD
RAAC03018                LEVVDAAHTNRLPLYDLDANLAPEAMQSWKIESVPALLYVKNGEIAHVQYRFGDVVDLAD
ref|ZP_02170973.1|       LQIAEQIP-DIPEIFSMDLNMAPHIAKDWKIESVPCLVVIDDGNVTDRMYAFKSIPDI--
                         *  :      ::. :    *       :*****.::   .* :.   * * .   :

ref|YP_148854.1|         VIQACL--
ref|YP_001127043.1|      EIQARLPR
ref|YP_080555.1|         TIKQNL--
ref|NP_693306.1|         YLIQY---
RAAC03018                AIRQFLER
ref|ZP_02170973.1|       --------
```

FIG. 174

```
ref|YP_001178926.1|     -----FPAVFEPGENGGYCVTFPDLPGCITEGETLEEALYMAKEALELHLYGLEEDNEEI
ref|YP_001211485.1|     -----FPAIFEVGEIKGYCVTFPDLPGCITEGNTLEEALQMAREALELHLYGMEEDEDEI
ref|YP_001180877.1|     -----FPAIFEPAEKEGYVVTFPDLPGCITEGKNLEEALYMAKEALELHIFGLEEDGEEI
ref|YP_001219837.1|     -----YPALFEAYEDGGYTVSFPDLPGCITEGDSLTEALTMAKEALELFLWNMEDDNEEI
ref|YP_001211518.1|     -----YPAIFDYAED-GISVEFPDLPGCYTCGDNDEEALRMAKEALALHLYGLEEDGFPI
RAAC02718               MATRGYPAIFDPYEDGSFVVLFPDFPGCVTQGCNLDDAVAMAEEALTLQLYGIERDGEDL
                            :**:*:    *   .  * ***:***   * *  .  :*:  **.***  * ::.:*  *      :

ref|YP_001178926.1|     PEPTPPEKLDIP--------------------
ref|YP_001211485.1|     PSPTPPERVDVPEKGF----VAIVEARMPL---
ref|YP_001180877.1|     PEPTPPEKLNV---------------------
ref|YP_001219837.1|     PEPTPPEKI-----------------------
ref|YP_001211518.1|     PEPSPASRIKVEPNQV----------------
RAAC02718               PEPSDPSHVTVPEEVQGQWFVMLIHPRPELFHP
                        *.*:  ..::
```

FIG. 175

```
ref|YP_001035109.1|    ------------------------------------MAQLYYKYGTMNSGKTIEILKVA
ref|YP_001450442.1|    ------------------------------------MAQLYYKYGTMNSCKTIEILKVA
ref|ZP_01818216.1|     ------------------------------------MAQLYYRYGTMNSGKTIEILKVA
ref|ZP_01830009.1|     ------------------------------------MAQLYYRYGTMNSGKTIEILKVA
ref|ZP_01819917.1|     ------------------------------------MAQLYYRYGTMNSGKTIEILKVA
RAAC01115              MERLARDDGHSARRLVRARGRVTCAITRSREPERGIDVAKLYFRFGQMNASKSIQLLTVA
                                                           :*:**::: * **:.*:*::*.**

ref|YP_001035109.1|    HNYEEQGKSVVIMTSAVDTRDGFGVVSSRIGMKRNAIAIEDQTDIFGYIQQLPEKPYCVL
ref|YP_001450442.1|    HNYEEQGKGVVIMTSAVDTRDGVGYVSSRIGMKRQAMAIEDDTDILGYIKNLPEKPYCIL
ref|ZP_01818216.1|     YNYEEQGKGVVIMTSALDTRDGVGYVSSRIGMKRPALAIEETTDIFGYIRDLPEKPCCVL
ref|ZP_01830009.1|     YNYEEQGKGVVIMTSALDTRDGVGYVSSRIGMKRPALAIEETTDIFGYIRDLPEKPYCVL
ref|ZP_01819917.1|     YNYEEQGKGVVIMTSALDTRDGVGYVSSRIGMKRPALAIEETTDIFGYIRGLPEKPYCVL
RAAC01115              HSYEEQGKKVALFTPAIDDRYGRGVIASRVGIAKRAVVVEEDTDLFACVR--AQMPDCVL
                       :.****** *.::*.*:* * * * ::**:*: : *:..*: **::. ::   .: * *:* ref|YP_001035109.1|    IDEAQFLKRHHVYDLARVVDELDVPVMAFGLKNDFRNELFEGSKHLLLLADKIEEIKTIC
ref|YP_001450442.1|    IDEAQFLKRHHVYDLARVVDELDVPVMAFGLKNDFRNELFEGSKHLLLLADKIEEIKTIC
ref|ZP_01818216.1|     VDEAQFLKRHHVYDLARVVDELDIPVMAFGLKNDFRNELFEGSKYLLLLADKIDEIKTIC
ref|ZP_01830009.1|     VDEAQFLKRHHVYDLARVVDELDIPVMAFGLKNDFRNELFEGSKYLLLLADKIDEIKTIC
ref|ZP_01819917.1|     VDEAQFLKRHHVYDLARVVDELDIPVMAFGLKNDFRNELFEGSKYLLLLADKIDEIKTIC
RAAC01115              VDEVQFLRAYHVRQLARVADDLDIPVIMYGLLKDYRNRLFEGSEAAILWADRIEEIKTIC
                       :.*: : :**.*:.: :** :*:.***:    :* **:*:****** ref|YP_001035109.1|    QY--CSRKATMVLRTDNGKPVYDGEQIKIGGHETYISVCRKHYFNPDIK--------
ref|YP_001450442.1|    QY--CSRKATMVLRTDHGKPVYDGEQIQIGGNETYIPVCRKHYFKPDI---------
ref|ZP_01818216.1|     QY--CKKKATMVLRTQDGLPVYDGEQIQIGGNETYISVCRKHYFAPEI---------
ref|ZP_01830009.1|     QY--CKKKATMVLRTQDGLPVYDGEQIQIGGNETYISVCRKHYFAPEI---------
ref|ZP_01819917.1|     QY--CKKKATMVLRTQDGLPVYDGEQIQIGGNETYISVCRKHYFAPEI---------
RAAC01115              AHPGCDRKATMILKVKDGRPVYEGEQIEVGGNDLYKSVCRKHYFHPDVEGLMRATGP
                       :    *.:****:*:...* ***.****::**:: *  .******* *::
```

FIG. 176

```
ref|NP_622644.1|          ------------------------------------------------------------
ref|YP_001664955.1|       ------------------------------------------------------------
ref|ZP_02616274.1|        ------------------------------------------------------------
ref|YP_001255422.1|       TEINCLSTRIDIUMBTULINUMASTRATCCGBABSGLYCERPHSPHRYLDIESTERPHSP
ref|YP_076287.1|          ------------------------------------------------------------
RAAC01119                 ------------------------------------------------------------ ref|NP_622644.1|          ------------------------------------------------------------
ref|YP_001664955.1|       ------------------------------------------------------------
ref|ZP_02616274.1|        ------------------------------------------------------------
ref|YP_001255422.1|       HDIESTERASEFAMILYPRTEINCLSTRIDIUMBTULINUMASTRHALLSCRESIGNIFI
ref|YP_076287.1|          ------------------------------------------------------------
RAAC01119                 ------------------------------------------------------------ ref|NP_622644.1|          -----------------------------TLVIAHRGDSKNVPENTIAAFKRAMELGADG
ref|YP_001664955.1|       -----------------------------LVIAHRGDSRNAPENTLASFKSALEMGADG
ref|ZP_02616274.1|        -----------------------------TKILAHRGASAYAPENTMAAFKKAIEMNADG
ref|YP_001255422.1|       CANCEE-IDENTITIESPSITIVESGAPSTKILAHRGASAYAPENTMAAFKKAIEMNADG
ref|YP_076287.1|          --------------------------------IGHRGAAGTHPENTMVSFRRAFELGVDG
RAAC01119                 ------------------MIRELLMRDDTLFIAHRGASAECPENTLPAFVRAAELGADM
                                                          :.*** :    ****: :*  * *:..* ref|NP_622644.1|          IELDVQLTKDGHLVVIHDETVDRTTNGEGFVKDFTLEEIKKLDAGIKFGEKFAGERIPTL
ref|YP_001664955.1|       IELDVQLTKDGQLVVIHDERVDRTTDGIGFVKDFTLKELKRLDAGIKFDKKFAGERIPSL
ref|ZP_02616274.1|        IELDVHLSKDGYIVIIHDERVDRTTDGKCEVKDFSLYELKKLDAGSWFSDEYKDEKIPTL
ref|YP_001255422.1|       IELDVHLSKDGYIVIIHDERVDRTTDGKGEVKDFSLDELKKLDAGSWFSYEYKDEKIPTL
ref|YP_076287.1|          IEFDVHRTADGHLVVIHDPAVDRTTDGSGLVMAMTLEQIRALDAGSWKDPRFAGERVPTL
RAAC01119                 IELDVRLTGDGGVVVLHDPTVDRTTNGSGLAADMRLADLRKLDAGSWFDARFRGTLIPTL
                          **:**: : ** :*::**  *****:* * .  : * ::: ****   . .: .  :*:* ref|NP_622644.1|          YEVFELIGDKDFLVNIEIKSGIVLYP-GIEEKLIKAIKEYNFEERVIISSFNHYSLRDVK
ref|YP_001664955.1|       YEVFELIGHKNFIVNIEIKSGIVLYP-GIEEKLIKAIEDYDFEDRVVISSFNHYSLRDVK
ref|ZP_02616274.1|        EELLKLIKNTELYLNIEIKAGYRVYP-NIEEKVIAMIEKYKMLDRVIISSFDHYSLVRVK
ref|YP_001255422.1|       EELLKLIKNTEIYLNIEIKAGYRLYP-NIEEKVIAMIEKYKMLDRVIISSFDHYSLVRVK
ref|YP_076287.1|          QELVRATP-PGVRLYLELKAGSVHYP-GIEQELVDLLKAEGVLDRTQVSSFDHRALVKLK
RAAC01119                 DEVFATVP--HMCLNIELKTSPVAHTRQLIRRVLGAIYRHNARDRVLISSFDHAALAEVR
                           *:.        . : :*:*:.   :.  : ..::  :       :*. :***:* :*  ::

ref|NP_622644.1|          KMAPHLKIGLLYQCGLVEPWHMALRMEAYSLHPFYFNIIPELVEGCKKNGVKLFPWTVDR
ref|YP_001664955.1|       RMAPELKIGLLYQCGLVEPWHMAIRMKAYSLHPFYFNIIPELVEGCKKNNIKLFPWTVDR
ref|ZP_02616274.1|        EINSNIKTGMLYEAALYEPWEYARSIKVEALHPNYITLTKEFIDKAYINSFEVNSYTIND
ref|YP_001255422.1|       EINSNIKTGMLYEAALYEPWEYARSIKVEALHPNYITLTKEFIDKAYINSFEVNPYTIND
ref|YP_076287.1|          EICPELPLGMLTSSNLVDPVGMAKAIGCEAIHPAWPWVTPEYVEAAHAAGLKVNCWTVND
RAAC01119                 RFDRDIAIGVLFTGRLLEPIQLAERLGAQSLHPDIEHLDPLFVAEAKSHHLAVYAWTAKS
                          .:  .:  *:*    * :*    *  :    ::**    :    :  .    . :  :* .

ref|NP_622644.1|          KEDMERMIKAGVDGIITDD-------------------
ref|YP_001664955.1|       KEDMEMMIKAGVDAIITDD-------------------
ref|ZP_02616274.1|        ETNMKSLIKNKVTSII----------------------
ref|YP_001255422.1|       ETNMESLIENKITSII----------------------
ref|YP_076287.1|          PLALALMQNAGVDGIMTD--------------------
RAAC01119                 ELAVNRALACQVSGIILDDLRLRQIATKAVPSPTPPSA
                              :        : .*:
```

FIG. 177

```
ref|YP_001433837.1|   ------------------------VFVTTS-RGLRRDSVPMRLFEKAKRLGVWNPSDIDFSQD
ref|YP_001276310.1|   ---------------------------TTS-RGLRRDTVPMRLFEKAKRLGVWNPSDIDFSQD
ref|ZP_01514627.1|    ---------------------------TTS-RGLRRNSPPMRLFEKAKQFGIWNPSLLDFSRD
ref|YP_001636906.1|   ---------------------------TTS-RGLNRNSPPMRLFEKAKRFGIWNPSLIDLSRD
RAAC00203             MVGVEFDVLEATPMALTEMPRVFQTTSEKRLNHSILPMRLYHKAKKLGTWDPRDIDFTKD
ref|YP_001102862.1|   ----------------------------LNWDSLPLRLFGKGN-AKFWDPADIDFTRD
                                                  *.. *:**: *.:    *:* :*:::* ref|YP_001433837.1|   MRDWQTLTDDERDLVLRLTSLFQAGEEAVTLDLLPLVATIAAEGRIEEELFLTSFLWEEA
ref|YP_001276310.1|   VRDWQTLTADERDLVLRLTSLFQAGEEAVTLDLLPLVATIAAEGRIEEELFLTSFLWEEA
ref|ZP_01514627.1|    IDDWNRLSDEERDLLLRLTALFQAGEEAVTLDLLPLIKAIAHDGRLEEELFLTTFLFEEA
ref|YP_001636906.1|   IRDWEQLRDEERDLLLRLTALFQAGEEAVTLDLLPLIRTIAREGRLEEELYLTTFLFEEA
RAAC00203             KEDWQGMNEAERRVILRLCSLFVAGEEAVTLDLLPLIMAVAREGRLEEEMYLTTFLFEEA
ref|YP_001102862.1|   AEDWQGLTEEERRSVAMLCSQFIAGEEAVTQDLQPFMAAMAAEGRFGDEMYLTQFCFEEA
                       : :      :   * :* *****  *:: ::* :**: :*::** * :*** ref|YP_001433837.1|   KHTDFFNRFLTEVAGVTGDLSHYHTAN--YRALIHEALPAAMERLRDDPSPEAQAIASLT
ref|YP_001276310.1|   KHTDFFNRFLTEVGVTGDLSHYHTSN--YRALIHEALPAAMGRLRDDPSPEAQAIASLT
ref|ZP_01514627.1|    KHTDFFARFISEVARVDPDLSRYHTPS--YRALIYDALPRAMQRLEHDPSPFNLAEASLT
ref|YP_001636906.1|   KHTDFFARFISEVARVDPDLSRYHTAS--YRALIYEALPAALHRLDHDPSPLNLAEASLT
RAAC00203             KHTEVFRRFLDEVAGETSDLSVFHKDH--YRKIFYEYLPQAMGRLVHDPSPEAQAEASVT
ref|YP_001102862.1|   KHTQVFRLWMDAVG-LTGDLHSHVAENPGYRAIFYEELPRSLNALHDDPSPANQVRASVT
                      ***:.*  ::  *        .        :::: **  ::   * .**   . :* ref|YP_001433837.1|   YNMIVEGVLAETGYHAYFTMLERRNLMPGTRKGIGLLKQDESRHIAYGVYLLSRLINAEP
ref|YP_001276310.1|   YNMIVEGVLAETGYHAYFTMLERRDLMPGTRKGIGLLKQDESRHIAYGVYLLSRLINAEP
ref|ZP_01514627.1|    YNMIVEGVLAETGYHGYFTIIDTHNLMPGVREGIRLLKQDESRHIAYGIYLLSRLIAADR
ref|YP_001636906.1|   YNMIVEGVLAETGYHAYFTILDSQDIMPGTREGIRLLKQDESRHIAYGVYLLSRLIATDP
RAAC00203             YNMVVEGVLAETGYYAFYTALQKENKLPGLIQAIRLLQRDESRHIGYGTYLLSRLISENA
ref|YP_001102862.1|   YNHVVEGTLALTGYFAWQKICRSRGILPGMQEVVRRIGDDERRHMAWGTFTCRRHVAADE
                      ** :***.** ***..: .   ..:**  : :  :  ** **:.*  *  :  :

ref|YP_001433837.1|   RLWDVVVERMNELVVYAMGVIDDAFACYEV-------------VPFGLSHDDFMQFAMG
ref|YP_001276310.1|   RLWDVIVERMNELVVYAMGVIDDAFACYEV-------------VPFGLSHDDFMHFAMG
ref|ZP_01514627.1|    QIWDHIVERMNELVIHALGVIDEIFTSYDT-------------MPFGLQIETFSTFALN
ref|YP_001636906.1|   QVWDHIVERMNELVLYAMGVIDEIFACYDP-------------MPFNLQIETFSTFALN
RAAC00203             HIWDVVNRRINLLLPHAIGVVQDLNAELDTEEAQKLAEELGTTDVPFGLNPDEFVAYAQK
ref|YP_001102862.1|   SNWDVVQEQMQHLLPLAVTQIQWRPEDAPEE-------------TPFRLDIDELAAYASD
                        **  : .:::   *:  *:  ::                    ** *. : : :* ref|YP_001433837.1|   QFERRLDRIERARNQTVE-------------
ref|YP_001276310.1|   QFQRRLDRIERARDQTLESI------------
ref|ZP_01514627.1|    QFQRRLNRLELACQQSLAEI------------
ref|YP_001636906.1|   QFQRRLNRLELASRQSMNEI------------
RAAC00203             QFATRLGVLQRARGKSVDEIYYYTEETVGVEQ
ref|YP_001102862.1|   RAGRRLGAISAARGVPVEQI------------
                      :  **. :. *    .:
```

FIG. 178

```
ref|ZP_02849297.1|      --------ERTLVISDIHGCYDAFNRLLERVNYEPVKDQLILLGDFVSKGPDSKLVVEQSAS
RAAC01413               MGSTPPERTIFISDIHGHLRPFARLLERLGYRPDRDQLVLVGDYISGGPDSLGVLRLVRN
ref|NP_815033.1|        -----------ISDIHGQADLFDALLT---DYDPVEHQLVLIGDLNDRGSDSKACFLKCKE
ref|ZP_00604769.1|      -----------IGDVHGKHELFEKLIII--YYDPKIHQLVLLGDLNDRGPRTKECFLLGKQ
ref|YP_796463.1|        -----------VSDIHGEYKKFKEILK--YWDSNRQQLILLGDLCDRGLQSYECFYLAKY
ref|NP_862606.1|        -----------VGDIHGEYKKFKEILK--YWDSNRQQLILLGDLCDRGLQSYECFYLAKY
                                      :.*:**     *  ::      :  .**:*:**   . *   :   .

ref|ZP_02849297.1|      LVREHGAIAVQGNHDERFVDIVRNKTKEAREKFFRHGGRQTVYSYLKGSDMTGSEEDLLN
RAAC01413               LCSEG-AVALRGNHEEAVVNWMR---------------------RGMKPLGPVRDSLY
ref|NP_815033.1|        LVEQHGAVYLRGNHEEYFLQFLQNPEDWFAGYVRNGGKETIESLLHPGATAEYSPTEMAL
ref|ZP_00604769.1|      LVEETGAIYLRGNHEEYFLQFLQSPEDWYAPYMRNGGKETFESLIHPGASEEYSPTEISM
ref|YP_796463.1|        LCDNYGAILIKGNHEDLFLKFLNKTEDFKENYIKNGGLKTLESF---GYSENNTFKDIVL
ref|NP_862606.1|        LCDNYGAILIKGNHEDLFLKFLNKTEDFKENYIKNGGLKTLESF---GYSENNTFKDIVL
                         *  :  *:  ::***::  .:.  :.                    *       .  :

ref|ZP_02849297.1|      RLRETVLERYPYHADFLEQLPYYYEDKHFIYVHAGLNPKYPNWKEQPKRDFLYIKDSFHK
RAAC01413               R----AIAADASLAAFLSTLPYAWEGERWVAVHAGIDPDKPHWRQTAKRDLLTIRERFYA
ref|NP_815033.1|        MIR----SRYPELIDFLTKRPLYFEWQHYLFVHAGVDLTMEDWRQTAPKDFLWIREPFHQ
ref|ZP_00604769.1|      MIQ----SRYSELIKFLVQRPLYYEWENYLFVHAGVDLTKKDWRKTSLRDFIWIREPFHE
ref|YP_796463.1|        DIK----KNNDKLIEFLTYLPNFYEWNDYIFVHAGVNLKINNWKDTSIRDFMWIREDFHF
ref|NP_862606.1|        DIK----KNNDKLIEFLTYLPNFYEWNDYIFVHAGVNLKINNWKDTSIRDFMWIREDFHF
                                    **    *  :*  ::  ****::    .*::. .:*::  *:: *:

ref|ZP_02849297.1|      SDTVVNKVVVFGHTKTVDLH---GRADVWYGKGKIGIDGGCASGLQLNALEIIGEEVRSF
RAAC01413               RPHRVGKLVVFGHTPCVVLH---GTHDVWYGSDKVGIDGGARIIGGQVNALVDAGGALTST
ref|NP_815033.1|        GKNNTGKTIVFGHTITPMLHGDMQTTDLWQSDGKIGIDGGAIFGGSVIIGVI---------
ref|ZP_00604769.1|      GKNNTGKTIVFGHTITPMLHGDMQTTDLWIQDHKIGMDGGAVFGGSLHGVV---------
ref|YP_796463.1|        TPNRLNKTIVFGHTETKILN-KNNKYDIWIHDNKIGIDGGAVYGGYLYGVI---------
ref|NP_862606.1|        TPNRLNKTIVFGHTETKILN-KNNKYDIWIHDNKIGIDGGAVYGGYLYGVI---------
                          .*  :*****   *:       *:*  . *:*:***. *   :  ..:

ref|ZP_02849297.1|      SVP-
RAAC01413               AEPV
ref|NP_815033.1|        ----
ref|ZP_00604769.1|      ----
ref|YP_796463.1|        ----
ref|NP_862606.1|        ----
```

FIG. 179

```
ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         SISFALLSTERICINHIBITINANDACTIVATINPDBDKUACHAINACRYSTALSTRUCT
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         URESFBACILLUSSUBTILISPHSPHRIBSYLPYRPHSPHATESYNTHETASEMLECULA
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         RBASISFALLSTERICINHIBITINANDACTIVATINPDBDKUBCHAINBCRYSTALSTR
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         UCTURESFBACILLUSSUBTILISPHSPHRIBSYLPYRPHSPHATESYNTHETASEMLEC
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         ULARBASISFALLSTERICINHIBITINANDACTIVATINPDBIBSACHAINAPHSPHRI
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         BSYLDIPHSPHATESYNTHETASEINCMPLEXWITHCADMIUMINSPDBIBSBCHAINBP
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         HSPHRIBSYLDIPHSPHATESYNTHETASEINCMPLEXWITHCADMIUMINSEMBCAAUN
RAAC01435                ------------------------------------------------------------
ref|YP_359065.1|         ------------------------------------------------------------ ref|YP_145897.2|         ------------------------------------------------------------
sp|P42816|KPRS_BACCL     ------------------------------------------------------------
ref|YP_001124176.1|      ------------------------------------------------------------
ref|NP_387932.1|         NAMEDPRTEINPRDUCTBACILLUSSUBTILISDBBAAPHSPHRIBSYLPYRPHSPHATE
RAAC01435                ------------------------------------------------------------
ref|YP_359065.1|         ------------------------------------------------------------
``` continued →

FIG. 179 continued

```
ref|YP_145897.2|       ------------------------------------------------------------
sp|P42816|KPRS_BACCL   ------------------------------------------------------------
ref|YP_001124176.1|    ------------------------------------------------------------
ref|NP_387932.1|       SYNTHETASEBACILLUSSUBTILISEMBCABPHSPHRIBSYLPYRPHSPHATESYNTHE
RAAC01435              ------------------------------------------------------------
ref|YP_359065.1|       ------------------------------------------------------------ ref|YP_145897.2|       ------------------------------------------------------------
sp|P42816|KPRS_BACCL   ------------------------------------------------------------
ref|YP_001124176.1|    ------------------------------------------------------------
ref|NP_387932.1|       TASEBACILLUSSUBTILISSUBSPSUBTILISSTRSCRESIGNIFICANCEE-IDENTI
RAAC01435              ------------------------------------------------------------
ref|YP_359065.1|       ------------------------------------------------------------ ref|YP_145897.2|       ------------------LKLFALNSNMKLAKEIAEVMGIELGKCSVSRFSDGEIQINI
sp|P42816|KPRS_BACCL   ------------------LKLFALNSNMKLAKEIAEVMGIELGKCSVSRFSDGEIQINI
ref|YP_001124176.1|    ------------------LKLFALNSNMKLAKQIAETMGIELGKCSVSRFSDGEIQINI
ref|NP_387932.1|       TIESPSITIVESGAPSDKNLKIFSLNSNPELAKEIADIVGVQLGKCSVTRFSDGEVQINI
RAAC01435              -------------MAIDADLKLVTGNANPALAQEIADYIGVPLADCQVGRFSDGEVRIRL
ref|YP_359065.1|       ------------------DLKIFSGNANPDLAREIASFLGVEVGDARVSRFSDGEIQVKI
                                         **::  *:*  **::**. :*: :... * ******::.:

ref|YP_145897.2|       EESIRGDDVFVIQSTSVPVNEHLMELLIMIDALKRASARTINIVMPYYGYARQDRKARSR
sp|P42816|KPRS_BACCL   EESIRGDDVFVIQSTSVPVNEHLMELLIMIDALKRASARTINIVMPYYGYARQDRKARSR
ref|YP_001124176.1|    EESIRGDDVFVIQSTSVPVNEHLMELLIMIDALKRASARTINIVMPYYGYARQDRKARSR
ref|NP_387932.1|       EESIRGCDCYIIQSTSDPVNEHIMELLIMVDALKRASAKTINIVIPYYGYARQDRKARSR
RAAC01435              GESVRGANVFIIQPTSQPVNEHLMELLILMDAVKRASARTINVVIPYYGYARQDRKARAR
ref|YP_359065.1|       NESVRGADVFIIQPTCTPVNENLMELLILIDAIRRASARRITAVLPYFGYARQDRKTRAR
                        :  : ::**.*. **::*::::****:  *. *::*****:*:* ref|YP_145897.2|       EPITAKLVANLLETAGASRVITLDLHAPQIQGFFDIPIDHLMGVPILADYFKSKQLEDIV
sp|P42816|KPRS_BACCL   NPITAKLVANLLETAGASRVITLDLHAPQIQGFFDIPIDHLMGVPILADYFKSKQLEDIV
ref|YP_001124176.1|    EPITAKLVANLLETAGASRVITLDLHAPQIQGFFDIPIDHLMGVPILADYFKSKQLDDVV
ref|NP_387932.1|       EPITAKLFANLLETAGATRVIALDLHAPQIQGFFDIPIDHLMGVPILGEYFEGKNLEDIV
RAAC01435              DPITAKLVANLLQTAGASRVISMDLHAGQIQGFFDIPVDHLIGMPILADYFLDKQIENPV
ref|YP_359065.1|       DPITAKLVSNLITVSGARRVIAMDLHAGQIQGFFDIPVDHLVGVPILAKYFNEKGLENKV
                       :****.::  .: *:** *****:*.*:*.. * ::: * ref|YP_145897.2|       VVSPDHGGVTRARKLADRLKAPIAIIDKRRPKPNVAEVMNIVGQVAGKTAILIDDIIDTA
sp|P42816|KPRS_BACCL   VVSPDHGGVTRARKLADRLKAPIAIIDKRRPKPNVAEVMNIVGQVAGKTAILIDDIIDTA
ref|YP_001124176.1|    IVSPDHGGVTRARKLADRLKAPIAIIDKRRPRPNVAEVMNIIGQVKGKTAILIDDIIDTA
ref|NP_387932.1|       IVSPDHGGVTRARKLADRLKAPIAIIDKRRPRPNVAEVMNIVGNIEGKTAILIDDIIDTA
RAAC01435              VVSPDMGGVTRARAFAERLGAPLAIIDKRRPDANVAQVMNIIGDIEGKTAILIDDMIDTA
ref|YP_359065.1|       VVSPDLGGVTRARDLAERIGAPIAIIDKRRPEPNVAEIMNIIGEIEGKTVIMIDDIIDTA
                       :**** *******  :*:*: **:********  .*  ::***:*:: ***.*:*****:****

ref|YP_145897.2|       GTITLAANALAENGAKEVYACCTHPVLSGPAIERIQNSRIKELVVTNSIALPEEKKIDKI
sp|P42816|KPRS_BACCL   GTITLAANALAENGAKEVYACCTHPVLSGPAIERIQSSKIKELVVTNSIALPEEKKIDKI
ref|YP_001124176.1|    GTITLGANALVENGAKEVYACCTHPVLSGPAIERIQNSKIKELVVTNSIALPEEKKIDKI
ref|NP_387932.1|       GTITLAANALVENGAKEVYACCTHPVLSGPAVERINNSTIKELVVTNSIKLPEEKKIERF
RAAC01435              GTITAGAAELLKRGARGVYACCIHPVLSGQGVERLQNSAIEEVVVTNTIALPEHKRIDKI
ref|YP_359065.1|       GTITQGAQALMERGAKEVYVCCTHPILSGPAVDRLANAPIKEVVVTNTIPLPPEKKLPKI
                       ****  .* *   *   **: ** **:***  .: *:  :  *:*:****:* **  .*:: ::

ref|YP_145897.2|       VELSVAPLIAEAISRVYEMKSVSVLFD
sp|P42816|KPRS_BACCL   VKLSVRPLIAEAITRVYEMKSVSVLFD
ref|YP_001124176.1|    VELSVAPLIAEAITRVYEMQSVSVLFD
ref|NP_387932.1|       KQLSVGPLLAEAIIRVIEQQSVSYLF-
RAAC01435              KVLSVAELIAEAIIRVHTQRSVSQLFD
ref|YP_359065.1|       KVLSVAPLMGEAIRRIHEDLSVSELF-
                        ***    *::***    ***  *** **
```

FIG. 180

```
ref|ZP_02170919.1|    MNKTELINAVAESADLSKKDATSAVDAVFEVITDSLKKGDKVQLIGFGNFEVRERAARKG
ref|ZP_01862118.1|    MNKTELINAVAEAAELSKKDATKAVDAVFESIQDALANGDKVQLIGFGNFEVRERAARKG
ref|NP_692713.1|      MNKTDLVNAVAEKSELSKKDATKAVDAVFESVMDSLKNGEKVQLIGFGNFEVRERSARKG
ref|YP_535778.1|      -NKAALIERVAEKTGLTKKDATVAVDAVFETIQDALVDGEKVQLIGFGNFEVRERAARKG
ref|YP_359077.1|      MNKAELVSVIAEKAEMTKKDAEKALNAVLAAIEEALKKGEKVQLVGFGTFEVRERAARKG
RAAC01442             MNKMELINRVAEKTNLKKKDAESAVNAVFEIIEEALANGEKVQIIGFGTFETRSRAARSG
                       **   *:. :  : :.**   *::**:    : ::* .*:*::*.**.*:**.* ref|ZP_02170919.1|    RNPQTGEEIEIPASNVPAFKPGKALKDAVK
ref|ZP_01862118.1|    RNPQTGEEIEISASKVPAFKPGKALKDAVK
ref|NP_692713.1|      RNPQTGEEIEIPASKVPAFKPGKALKD---
ref|YP_535778.1|      RNPQTGEEIEIPASKVPAFKPGKSLKDAVK
ref|YP_359077.1|      RNPQTGQEIEIPASKVPVFKPGKLLKE---
RAAC01442             RNPQTGEVIEIPASTVPAFKPGNKLKEVTR
                      ******: ***.**.**.****: **:
```

FIG. 181

```
ref|ZP_02583512.1|    ----------IPEEVVEQIRTSSDIVEVIGEYVQLRKQGRNYFGLCPFHGENSPSFSVS
ref|NP_834002.1|      ----------IPEEVVEQIRTSSDIVEVIGEYVQLRKQGRNYFGLCPFHGENSPSFSVS
ref|ZP_00238564.1|    SITIVESGAPSIPEEVVEQIRTSSDIVEVIGEYVQLRKQGRNYFGLCPFHGENSPSFSVS
ref|ZP_02604064.1|    ----------IPEEVVEQIRTSSDIVEVIGEYVQLRKQGRNYFGLCPFHGENSPSFSVS
ref|NP_846740.1|      ----------IPEEVVEQIRTSSDIVEVIGEYVQLRKQGRNYFGLCPFHGENSPSFSVS
RAAC00895             --------MMNVPETFIDTLRQKVDIVEVISEYVPLRKSGRSYVGLCPFHNERTPSFSVS
                              :**  .:: :*  .  ***** *.* *.**.* ****** .*.:****** ref|ZP_02583512.1|    SDKQIFHCFGCGEGGNVFSFLMKMEGLAFTEAVQKLGERNGIAVAEYTSGQGQQEDISDD
ref|NP_834002.1|      SDKQIFHCFGCGEGGNVFSFLMKMEGLAFTEAVQKLGERNGIAVAEYTSGQGQQEDISDD
ref|ZP_00238564.1|    SDKQIFHCFGCGEGGNVFSFLMKMEGLAFTEAVQKLGERNGIAVAEYTSGQGQQEDISDD
ref|ZP_02604064.1|    SDKQIFHCFGCGEGGNVFSFLMKMEGLAFTEAVQKLGERNGIAVAEYTSGQGQQEDISDD
ref|NP_846740.1|      SDKQIFHCFGCGEGGNVFSFLMKMEGLAFTEAVQKLGERNGIAVAEYTSGQGQQEDISDD
RAAC00895             PERQVYHCFGCGAGGTVFRFLMDIEGISFAETVTLLAERCGIPLPDSLHAPAPR---SPR
                       .::*::****  . *.:**::*:*:  *. .::.        . .:  * ref|ZP_02583512.1|    TVIMQQAHELLKKYYHHLLVNTEEGNEALSYLLNRGITKEMIEKFEIGYASPAWDAATKI
ref|NP_834002.1|      TVIMQQAHELLKKYYHHLLVNTEEGNEALSYLLNRGITKEMIEKFEIGYASPAWDAATKI
ref|ZP_00238564.1|    TVIMQQAHELLKKYYHHLLVNTEEGNEALSYLLKRGITKEMIEKFEIGYASPAWDAATKI
ref|ZP_02604064.1|    TVIMQQAHELLKKYYHHLLVNTEEGNEALSYLLKRGITKEMIEKFEIGYASPAWDAATKI
ref|NP_846740.1|      TVIMQQAHELLKKYYHHLLVNTEEGNEALSYLLKRGITKEMIEKFEIGYASPAWDAATKI
RAAC00895             LERYRQAHDLAAKAFNHILMNTDAGVQALRYLLSRGISRTTMATFQLGYAPPSGRAMMSF
                       :***:*      * ::*:*:**: *   :** ***.***::    : .*::***.*:  *    .:

ref|ZP_02583512.1|    LQKRGLSLSSMEQAGLLIRSEKDGSHYDRFRGRVMFPIYTLQGKVIAFSGRALGDDT-PK
ref|NP_834002.1|      LQKRGLSLSTMEQAGLLIRSEKDGSHYDRFRGRVMFPIYTLQGKVIAFSGRALGDDT-PK
ref|ZP_00238564.1|    LQKRGLSLSSMEQAGLLIRSEKDGSHYDRFRGRVMFPIYTLQGKVIAFSGRALGDDT-PK
ref|ZP_02604064.1|    LQKRGLSLSSMEQAGLLIRSEKDGSHYDRFRGRVMFPIYTLQGKVIAFSGRALGDDT-PK
ref|NP_846740.1|      LQKRGLSLSSMEQAGLLIRSEKDGSHYDRFRGRVMFPIYTLQGKVIAFSGRALGDDT-PK
RAAC00895             LQQKGFSAEEELIACGLAVDLG--GELVDRFRGRVIIPIADRRCQVVAFGARALDDDAKPK
                       **::*:*   .  : .**  :       *.  ******::**    :*:*:**.  ***.**:   **

ref|ZP_02583512.1|    YLNSPETPIFHKSKLLYNFHQARPFIRKRGQVVLFEGYADVLAAVKSGVEEAVATMGTAL
ref|NP_834002.1|      YLNSPETPIFHKSKLLYNFHQARPFIRKRGQVVLFEGYADVLAAVKSGVEEAVATMGTAL
ref|ZP_00238564.1|    YLNSPETPIFHKSKLLYNFHQARPFIRKRGQVVLFEGYADVLAAVKSGVEEAVATMGTAL
ref|ZP_02604064.1|    YLNSPETPIFHKSKLLYNFHQARPFIRKRGQVVLFEGYADVLAAVKSGVEEAVATMGTAL
ref|NP_846740.1|      YLNSPETPIFHKSKLLYNFHQARPFIRKRGQVVLFEGYADVLAAVKSGVEEAVATMGTAL
RAAC00895             YLNSPEYELFHKGRMLFNVHRARKAIRRERRALLLEGYMDVLAVAQAGIECAVATLGTSL
                       ****  :*.::*:*.*:  :.*  .  ** :::*:*  **:*:* ref|ZP_02583512.1|    TEEQAKLLRRNVETVVLCYDGDKAGREATMKAGQLLLKVGCQVKVTSLPDKLDPDEYVQQ
ref|NP_834002.1|      TEEQAKLLRRNVETVVLCYDGDKAGREATMKAGQLLLKVGCQVKVTSLPDKLDPDEYVQQ
ref|ZP_00238564.1|    TEEQAKLLRRNVETVVLCYDGDKAGREATMKAGQLLLQVGCQVKVTSLPDKLDPDEYVQQ
ref|ZP_02604064.1|    TEEQAKLLRRNVETVVLCYDGDKAGREATMKAGQLLLQVGCQVKVTSLPNKLDPDEYVQQ
ref|NP_846740.1|      TEEQAKLLRRNVETVVLCYDGDKAGREATMKAGQLLLQVGCQVKVTSLPDKLDPDEYVQQ
RAAC00895             TEEQAQLLKADCDKVVIAYDGDEAGRKATVRAIEVLEQAGVTPVVLRLPDGMDPDEYIRA
                       *****:**:  :  :.**:****:***:**:.*  ::* :.*   *   **:  :*****::

ref|ZP_02583512.1|    YGTTAFEN-LVKSSVSFVGFKINYLRLGKNLQDESGKEEYVKSVLKELSLLQDAMQAESY
ref|NP_834002.1|      YGTTAFEN-LVKSSVSFVGFKINYLRLGKNLQDESGKEEYVKSVLKELSLLQDAMQAESY
ref|ZP_00238564.1|    YGTTAFEN-LVKSSISFVGFKINYLRLGKNLQDESGKEEYVKSVLKELSLLQDAMQAESY
ref|ZP_02604064.1|    YGTTAFEN-LVKSSISFVGFKINYLRLGKNLQDESGKEEYVKSVLKELSLLQDAMQAESY
ref|NP_846740.1|      YGTTAFEN-LVKSSISFVGFKINYLRLGKNLQDESGKEEYVKSVLKELSLLQDAMQAESY
RAAC00895             HGARAFERMLSESTWTAVQFLEDMRARAEWVSPAGRTEFLRQVLRLLAERASPVEQEYQ
                       :*: ***. * :*:  :   *  *::  :*  .    :*: *:::.**.  *:     ..:: * ref|ZP_02583512.1|    LKSLSQEFSYSMETLLNQLHQYRKEQKVQQKQIKQVAKPSQVVQTKPKLTGFERAEREII
ref|NP_834002.1|      LKSLSQEFSYSMETLLNQLHQYRKEQKVQQKQIKQVAKPSQVVQTKPKLTGFERAEREII
ref|ZP_00238564.1|    LKSLSQEFSYSMETLLNQLHQYRKEQKVQQKQVKQVSKPSQIVQTKPKLTGFERAEREII
ref|ZP_02604064.1|    LKSLSQEFSYSMETLLNQLHQYRKEQKVQQKQVKQVSKPSQIVQTKPKLTGFERAEREII
ref|NP_846740.1|      LKSLSQEFSYSMETLLNQLHQYRKEQKVQQKQVKQVSKPSQIVQTKPKLTGFERAEREII
RAAC00895             LRNLSQEFNLSVETLKEEMRGFAKPLRRRSPPREEVTP---WVNSPRAAKGKDQVSLRIL
                       *:.*****. :*:***  :: : *  : :.    ::*:        *::  .*  :::.. .*:
``` continued →

FIG. 181 continued

```
ref|ZP_02583512.1|        YHMLQSAEVAVR-MESHIEDFHTEEHKGILYELYAYYEKGNEPSVGTFLSWLSDEKLKNI
ref|NP_834002.1|          YHMLQSAEVAVR-MESHIEDFHTEEHKGILYELYAYYEKGNEPSVGTFLSWLSDEKLKNI
ref|ZP_00238564.1|        YHMLQSPEVAVR-MESHIEDFHTEEHKGILYELYAYYEKGNEPSVGTFLSWLSDEKLKNI
ref|ZP_02604064.1|        YHMLQSPEVAVR-MESHIEDFHTEEHKGILYELYAYYEKGNEPSVGTFLSWLSDEKLKNI
ref|NP_846740.1|          YHMLQSPEVAVR-MESHIEDFHTEEHKGILYELYAYYEKGNEPSVGTFLSWLSDEKLKNI
RAAC00895                 QAALFSQEAAEYLMEKGVTELAHPLHTALLSHVYSWRLEQPGQPPSAFIDRLEDEELVRL
                           *  *  *.*    **. :  ::    *...* .:*::  :       . .:*:. *.**:* .:

ref|ZP_02583512.1|        ITDISTDEF--INPEYTEEVLQGHLETLRRHQEKLEKMEIIFKVKQMEKTDPVEAAKYYV
ref|NP_834002.1|          ITDISTDEF--INPEYTEEVLQGHLETLRRHQEKLEKMEIIFKVKQMEKTDPVEAAKYYV
ref|ZP_00238564.1|        ITDISTDEF--INPEYTEEVLQGHLETLRRHQEKLEKMEIIFKIKQMEKTDPVEAAKYYV
ref|ZP_02604064.1|        ITDISTDEF---INPEYTEEVLQGHLETLRRHQEKLEKMEIIFKIKQMEKTDPVEAAKYYV
ref|NP_846740.1|          ITDISTDEF--INPEYTEEVLQSHLETLRRHQEKLEKMEIIFKIKQMEKTDPVEAAKYYV
RAAC00895                 ASSLLFDEPPEITVELVEDYLR-ALELFRLEQELKEKVRAWNEAEAAGDQEKSREIKLQV
                          :.:    **      *. *  .*: *:  ** :* . :.   : :   . :  .   *  * ref|ZP_02583512.1|        AYLQNQKA-----------
ref|NP_834002.1|          AYLQNQKA-----------
ref|ZP_00238564.1|        AYLQNQKA-----------
ref|ZP_02604064.1|        AYLQNQKA-----------
ref|NP_846740.1|          AYLQNQKA-----------
RAAC00895                 EWIQSQMATMKQPRALHAE
                          ::*.* *
```

FIG. 182

```
ref|YP_001180871.1|    ----MNLFRFRLKELREEKNISRSDLAEILGVSTQTIANYENGHREPNFDTLLKIADYFG
ref|YP_001114120.1|    ---VMSTIGERLRQLRKEKNINREDVANLLGVTVRSVTNYESGQRNLDPDQLIALADYYD
ref|YP_001662345.1|    --EKLNPFSQRLRQLREEKGLLQKDVAKILGITPSAYGYYEQGKREPSMEVLKKLSDFFN
ref|YP_001210714.1|    ------IFAKRLSFLITKNKLSKQAVANAINVSRPAVSQFANGENLPSVEKLIALADFFD
RAAC03475              MEEVMTLFSQRLTELLDRTGTTRRSFAQALGVSERMVQYYITGKKDPTVETLIAIADFFD
ref|ZP_02442523.1|     ------IFQKRLKELRNAKGTSQIAIAAALGITDRGYRKYEAGDSEPTLSVIIALADYFD
                             :  **  *       .    :   .*   :.::          :  *.      . :  ::*::.

ref|YP_001180871.1|    VTVDYLIGRSE-----
ref|YP_001114120.1|    VSMDYLTGRSDNPK--
ref|YP_001662345.1|    VSIDYLLGRTD-----
ref|YP_001210714.1|    VSLDYLVGRSDDPRR-
RAAC03475              VSLDYLVGRSENPERK
ref|ZP_02442523.1|     VSLDYLCGRSDDPAR-
                       *::*** **::
```

FIG. 183

```
ref|YP_001114120.1|    --GERLRQLRKEKNINREDVANLLGVTVRSVTNYESGQRNLDPDQLIALADYYDVSMDYL
RAAC03560              MNGERLRALRKSLGLKRDEVAQAIGVTPRIITDYETETKRPTLDTAVKLADFFNVSLDYL
ref|YP_001662345.1|    ---QRLRQLREEKGLLQKDVAKILGITPSAYGYYEQGKREPSMEVLKKLSDFFNVSIDYL
ref|NP_242309.1|       ---ERLRYLRKKHGLTMKELGKKINVAESTISGYENGNRKPDMDTLVKMAEYFNSSTDYL
ref|YP_146346.1|       --GDRLRKLRQEKKLTQEELGKKINVTKVSISGYENGNRTPDTETLQKLADFFNVTTDYL
ref|YP_146347.1|       ----RLKMLRLQKKLTHQDMADFLGITRQGYSKYENGQSQPDIDTINKLAEFFNVTTDYL
                           :    .   :   .::..  :.::                 :     :::::: : * ref|YP_001114120.1|    TGRSDNPKPPQTTTIDDE---
RAAC03560              VGRTDDPTPPKRSSPSNEPGS
ref|YP_001662345.1|    LGRTDIRSP------------
ref|NP_242309.1|       LGRTEEP-APYQKQPPEKQ--
ref|YP_146346.1|       LGRTDHPNPPDQDDIPEE---
ref|YP_146347.1|       LGRTDDPTPPEQDDIPEE---
                        **::    .
```

TYPE II RESTRICTION-MODIFICATION SYSTEM METHYLATION SUBUNIT OF *ALICYCLOBACILLUS ACIDOCALDARIUS*

CROSS-REFERENCE TO RELATED APPLICATIONS

This application is a divisional of U.S. patent application Ser. No. 13/604,979, filed Sep. 6, 2012, now U.S. Pat. No. 8,569,030, issued Oct. 29, 2013, which application is a divisional of U.S. patent application Ser. No. 12/800,045, filed May 5, 2010, abandoned, the disclosure of which is hereby incorporated herein by this reference in its entirety.

GOVERNMENT RIGHTS

This invention was made with government support under Contract No. DE-AC07-99ID13727 and Contract No. DE-AC07-05ID14517 awarded by the United States Department of Energy. The government has certain rights in the invention.

STATEMENT ACCORDING TO 37 C.F.R. §1.821(c) or (e)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

TECHNICAL FIELD

The present invention relates generally to biotechnology. More specifically, embodiments of the present invention relate to isolated and/or purified polypeptides and nucleic acid sequences encoding polypeptides from *Alicyclobacillus acidocaldarius* and methods for their use.

BACKGROUND

Thermophilic and/or acidophilic bacteria have great potential for production of useful chemicals in industrial processes. However, most systems for promoting genetic recombination for the purposes of introducing nucleic acids of interest are not well suited for such thermophilic and/or acidophilic bacteria.

BRIEF SUMMARY OF THE INVENTION

Embodiments of the invention relate to purified and/or isolated nucleotide sequences of the genome of *Alicyclobacillus acidocaldarius*, or a homologue or fragment thereof. In one embodiment of the invention, the nucleotide sequence is selected from at least one of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, and 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 or a homologue or fragment thereof. In another embodiment of the invention, the homologue is selected from the group consisting of a nucleotide sequence having at least 80% sequence identity to at least one of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283.

Embodiments of the invention may further relate to an isolated and/or purified nucleic acid sequence comprising a nucleic acid sequence encoding a polypeptide selected from the group consisting of a polypeptide having at least 90% sequence identity to at least one of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282.

Embodiments of the invention also relate to isolated and/or purified polypeptides coded for by a nucleotide sequence comprising a nucleotide sequence of the genome of *Alicyclobacillus acidocaldarius*, or a homologue or fragment thereof. In one embodiment, the nucleotide sequence comprises a nucleotide sequence selected from the group consisting of a nucleotide sequence having at least 80% sequence identity to at least one of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283.

In another embodiment of the invention, the nucleotide sequence comprises a nucleotide sequence selected from at least one of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, and 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 or a homologue or fragment thereof. In still another embodiment, the polypeptide comprises an amino acid sequence of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282. In yet another embodiment, the polypeptide comprises an amino acid sequence selected from the group consisting of a polypeptide having at least 90% sequence identity to at least one of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282.

In embodiments of the invention, the polypeptides may be acidophilic and/or thermophilic. In further embodiments, the polypeptides may be glycosylated, pegylated, and/or otherwise post-translationally modified.

Embodiments of methods include methods of altering genetic recombination inside or outside of a cell, the methods comprising providing a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 to a nucleotide sequence with which recombination is desired.

Further embodiments of methods include placing a cell producing or encoding a recombinant, purified, and/or isolated nucleotide sequence comprising a nucleotide sequence selected from the group consisting of a nucleotide sequences having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 in a environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

These and other aspects of the invention will become apparent to the skilled artisan in view of the teachings contained herein.

BRIEF DESCRIPTION OF THE SEVERAL VIEWS OF THE DRAWINGS

FIG. 1 depicts a sequence alignment between SEQ ID NO:1 (RAAC03697) and ref|ZP_01916690.1|, ref|YP_308280.1|, ref|XP_001525241.1|, gb|AAY21825.1|, and ref|XP_001743680.1| (SEQ ID NOS:3-7 respectively). Amino acids conserved among all sequences are indicated by a "*" and generally conserved amino acids are indicated by a ":".

FIG. 2 depicts a sequence alignment between SEQ ID NO:18 (RAAC02297) and ref|ZP_01171092.1|, ref|YP_429214.1|, gb|EAZ41188.1|, gb|AAR38445.1|, and ref|ZP_01774730.1| (SEQ ID NOS:20-24 respectively). Amino acids conserved among all sequences are indicated by a "*" and generally conserved amino acids are indicated by a ":".

FIG. 3 depicts a sequence alignment between SEQ ID NO:35 (RAAC02298) and ref|ZP_01575699.1|, ref|ZP_01171091.1|, ref|ZP_02598168.1|, ref|ZP_01900573.1|, and ref|ZP_01301851.1| (SEQ ID NOS:37-41 respectively). Amino acids conserved among all sequences are indicated by a "*" and generally conserved amino acids are indicated by a ":".

FIG. 4 depicts a sequence alignment between SEQ ID NO:52 (RAAC02299) and ref|ZP_01171090.1|, ref|ZP_02598167.1|, ref|ZP_01575700.1|, ref|ZP_02849387.1|, and ref|NP_627754.1| (SEQ ID NOS:54-58 respectively). Amino acids conserved among all sequences are indicated by a "*" and generally conserved amino acids are indicated by a ":".

FIG. 5 depicts a sequence alignment between SEQ ID NO:69 (RAAC02300) and ref|ZP_02598166.1|, ref|ZP_01171089.1|, ref|ZP_02849386.1|, ref|YP_159112.1|, and ref|ZP_02007550.1| (SEQ ID NOS:71-75 respectively). Amino acids conserved among all sequences are indicated by a "*" and generally conserved amino acids are indicated by a ":".

FIG. 6 depicts a sequence alignment between SEQ ID NO:86 (RAAC02301) and ref|ZP_02756760.1|, ref|ZP_01171088.1|, emb|CAE47790.1|, emb|CAE47778.1|, and ref|NP_967133.1| (SEQ ID NOS:88-92 respectively). Amino acids conserved among all sequences are indicated by a "*" and generally conserved amino acids are indicated by a ":".

FIG. 7 depicts a sequence alignment between SEQ ID NO:103 (RAAC02302) and ref|ZP_01171087.1|, ref|YP_061819.1|, emb|CAJ49597.1|, ref|YP_158155.1|, and ref|NP_779769.1| (SEQ ID NOS:105-109 respectively). Amino acids conserved among all sequences are indicated by a "*" and generally conserved amino acids are indicated by a ":".

FIG. 8 depicts a sequence alignment between SEQ ID NO:120 (RAAC02303) and ref|YP_001371728.1|, ref|YP_001235767.1|, ref|YP_674884.1|, ref|NP_046584.1|, and ref|ZP_00630666.1| (SEQ ID NOS:122-126 respectively). Amino acids conserved among all sequences are indicated by a "*" and generally conserved amino acids are indicated by a ":".

FIG. 9 depicts a sequence alignment between SEQ ID NO:137 (RAAC02304) and ref|YP_793245.1|, ref|YP_386759.1|, ref|YP_868126.1|, ref|NP 253469.1|, and ref|ZP_01591801.1| (SEQ ID NOS:139-143 respectively). Amino acids conserved among all sequences are indicated by a "*" and generally conserved amino acids are indicated by a ":".

FIG. 10 depicts a sequence alignment between SEQ ID NO:154 (RAAC02305) and ref|YP_645800.1|, ref|ZP_01697403.1|, ref|NP_111721.1|, dbj|BAB60367.1|, and ref|YP_950098.1| (SEQ ID NOS:156-160 respectively). Amino acids conserved among all sequences are indicated by a "*" and generally conserved amino acids are indicated by a ":".

FIG. 11 depicts a sequence alignment between SEQ ID NO:171 (RAAC02306) and gb|EAU91762.1|, ref|ZP_01035289.1|, ref|ZP_01076306.1|, ref|YP_173223.1|, and ref|ZP_01500882.1| (SEQ ID NOS:173-177 respectively). Amino acids conserved among all sequences are indicated by a "*" and generally conserved amino acids are indicated by a ":".

FIG. 12 depicts a sequence alignment between SEQ ID NO:188 (RAAC02289) and ref|YP_517477.1|, ref|YP_001568284.1|, ref|YP_503850.1|, ref|NP_783815.1|, and ref|YP_149134.1| (SEQ ID NOS:190-194 respectively). Amino acids conserved among all sequences are indicated by a "*" and generally conserved amino acids are indicated by a ":".

FIG. 13 depicts a sequence alignment between SEQ ID NO:205 (RAAC02307) and ref|XP_001317319.1|, ref|YP_303751.1|, ref|ZP_01222568.1|, ref|XP_001191064.1|, and ref|ZP_01697132.1| (SEQ ID NOS:207-211 respectively). Amino acids conserved among all sequences are indicated by a "*" and generally conserved amino acids are indicated by a ":".

FIG. 14 depicts a sequence alignment between SEQ ID NO:222 (RAAC02309) and ref|NP_623664.1|, ref|ZP_02755290.1|, ref|YP_001662357.1|, ref|YP_001666189.1|, and ref|YP_001181426.1| (SEQ ID NOS:224-228 respectively). Amino acids conserved among all sequences are indicated by a "*" and generally conserved amino acids are indicated by a ":".

FIG. 15 depicts a sequence alignment between SEQ ID NO:239 (RAAC02310) and ref|NP_735797.1|, ref|XP_001247966.1|, gb|AAG38042.1|AF295925_7, ref|ZP_00874806.1|, and gb|ABV55445.1| (SEQ ID NOS:241-245 respectively). Amino acids conserved among all sequences are indicated by a "*" and generally conserved amino acids are indicated by a ":".

FIG. 16 depicts a sequence alignment between SEQ ID NO:256 (RAAC02311) and ref|YP_001205829.1|, ref|YP_001240062.1|, ref|YP_359336.1|, ref|YP_001451893.1|, and ref|YP_466026.1| (SEQ ID NOS:258-262 respectively). Amino acids conserved among all sequences are indicated by a "*" and generally conserved amino acids are indicated by a ":".

FIG. 17 depicts a sequence alignment between SEQ ID NO:273 (RAAC02312) and ref|YP_001506532.1|, ref|NP_279998.1|, ref|ZP_02850831.1|, ref|ZP_02248080.1|, and ref|XP_001637270.1| (SEQ ID NOS:275-279 respectively).

Amino acids conserved among all sequences are indicated by a "*" and generally conserved amino acids are indicated by a ":".

FIG. 18 depicts a sequence alignment between SEQ ID NO:290 (RAAC02313) and ref|YP_245669.1|, ref|ZP_02369868.1|, ref|YP_438666.1|, ref|NP_695275.1|, and emb|CAB06069.2| (SEQ ID NOS:292-296 respectively). Amino acids conserved among all sequences are indicated by a "*" and generally conserved amino acids are indicated by a ":".

FIG. 19 depicts a sequence alignment between SEQ ID NO:307 (RAAC02314) and ref|XP_503244.1|, ref|NP_218466.1|, ref|ZP_01058859.1|, ref|NP_126488.1|, and ref|YP_754274.1| (SEQ ID NOS:309-313 respectively). Amino acids conserved among all sequences are indicated by a "*" and generally conserved amino acids are indicated by a ":".

FIG. 20 depicts a sequence alignment between SEQ ID NO:324 (RAAC02315) and ref|ZP_02854145.1|, ref|YP_145847.1|, ref|YP_536482.1|, ref|YP_799230.1|, and ref|NP_714527.1| (SEQ ID NOS:326-330 respectively). Amino acids conserved among all sequences are indicated by a "*" and generally conserved amino acids are indicated by a ":".

FIG. 21 depicts a sequence alignment between SEQ ID NO:341 (RAAC02316) and ref|ZP_02180762.1|, ref|ZP_02077766.1|, ref|ZP_01893908.1|, ref|XP_001444409.1|, and ref|XP_624126.2| (SEQ ID NOS:343-347 respectively). Amino acids conserved among all sequences are indicated by a "*" and generally conserved amino acids are indicated by a ":".

FIG. 22 depicts a sequence alignment between SEQ ID NO:358 (RAAC02290) and emb|CAJ50746.1|, gb|AAM28266.1|, ref|XP_816394.1|, ref|XP_001585185.1|, and gb|EAU92316.1| (SEQ ID NOS:360-364 respectively). Amino acids conserved among all sequences are indicated by a "*" and generally conserved amino acids are indicated by a ":".

FIG. 23 depicts a sequence alignment between SEQ ID NO:375 (RAAC02317) and ref|YP_001210712.1|, ref|ZP_02727046.1|, ref|ZP_02758954.1|, ref|ZP_01593342.1|, and ref|ZP_00235902.1| (SEQ ID NOS:377-381 respectively). Amino acids conserved among all sequences are indicated by a "*" and generally conserved amino acids are indicated by a ":".

FIG. 24 depicts a sequence alignment between SEQ ID NO:409 (RAAC02319) and ref|YP_431168.1|, ref|YP_001212944.1|, ref|YP_754944.1|, ref|YP_754864.1|, and ref|ZP_02171383.1| (SEQ ID NOS:411-415 respectively). Amino acids conserved among all sequences are indicated by a "*" and generally conserved amino acids are indicated by a ":".

FIG. 25 depicts a sequence alignment between SEQ ID NO:426 (RAAC02320) and ref|YP_431169.1|, ref|YP_754945.1|, ref|YP_754863.1|, ref|ZP_01287154.1|, and ref|ZP_01287577.1| (SEQ ID NOS:428-432 respectively). Amino acids conserved among all sequences are indicated by a "*" and generally conserved amino acids are indicated by a ":".

FIG. 26 depicts a sequence alignment between SEQ ID NO:443 (RAAC02321) and ref|NP_982177.1|, ref|ZP_02595431.1|, ref|NP_927486.1|, ref|YP_001108426.1|, and emb|CAN89659.1| (SEQ ID NOS:445-449 respectively). Amino acids conserved among all sequences are indicated by a "*" and generally conserved amino acids are indicated by a ":".

FIG. 27 depicts a sequence alignment between SEQ ID NO:460 (RAAC02322) and ref|YP_504284.1|, ref|YP_001046337.1|, ref|ZP_02131576.1|, ref|ZP_01288161.1|, and ref|ZP_02132246.1| (SEQ ID NOS:462-466 respectively). Amino acids conserved among all sequences are indicated by a "*" and generally conserved amino acids are indicated by a ":".

FIG. 28 depicts a sequence alignment between SEQ ID NO:477 (RAAC02323) and ref|ZP_01287831.1|, ref|YP_076198.1|, ref|YP_446560.1|, ref|NP_634267.1|, and ref|ZP_01106621.1| (SEQ ID NOS:479-483 respectively). Amino acids conserved among all sequences are indicated by a "*" and generally conserved amino acids are indicated by a ":".

FIG. 29 depicts a sequence alignment between SEQ ID NO:494 (RAAC02324) and ref|ZP_02595423.1|, ref|NP_982173.1|, ref|_02367476.1|, ref|YP_001616264.1|, and ref|YP_827637.1| (SEQ ID NOS:496-500 respectively). Amino acids conserved among all sequences are indicated by a "*" and generally conserved amino acids are indicated by a ":".

FIG. 30 depicts a sequence alignment between SEQ ID NO:511 (RAAC02326) and ref|NP_982172.1|, ref|ZP_01872101.1|, ref|NP_922949.1|, emb|CAO48005.1|, and sp|P08995|NO26_SOYBN (SEQ ID NOS:513-517 respectively). Amino acids conserved among all sequences are indicated by a "*" and generally conserved amino acids are indicated by a ":".

FIG. 31 depicts a sequence alignment between SEQ ID NO:528 (RAAC02327) and ref|NP_982171.1|, ref|ZP_01090358.1|, ref|ZP_01856486.1|, ref|ZP_02736297.1|, and ref|ZP_01311632.1| (SEQ ID NOS:530-534 respectively). Amino acids conserved among all sequences are indicated by a "*" and generally conserved amino acids are indicated by a ":".

FIG. 32 depicts a sequence alignment between SEQ ID NO:545 (RAAC02328) and ref|NP_982170.1|, ref|XP_955124.1|, ref|XP_763458.1|, ref|XP_845342.1|, and ref|XP_666904.1| (SEQ ID NOS:547-551 respectively). Amino acids conserved among all sequences are indicated by a "*" and generally conserved amino acids are indicated by a ":".

FIG. 33 depicts a sequence alignment between SEQ ID NO:562 (RAAC02332) and ref|YP_079109.1|, ref|ZP_01858609.1|, gb|AAV70501.1|, ref|YP_001319533.1|, and ref|ZP_00539168.1| (SEQ ID NOS:564-568 respectively). Amino acids conserved among all sequences are indicated by a "*" and generally conserved amino acids are indicated by a ":".

FIG. 34 depicts a sequence alignment between SEQ ID NO:596 (RAAC02334) and ref|YP_001485227.1|, ref|YP_001358015.1|, ref|ZP_02013298.1|, ref|ZP_02178354.1|, and ref|YP_001356736.1| (SEQ ID NOS:598-602 respectively). Amino acids conserved among all sequences are indicated by a "*" and generally conserved amino acids are indicated by a ":".

FIG. 35 depicts a sequence alignment between SEQ ID NO:613 (RAAC02335) and dbj|BAF91394.1|, gb|AAL17690.1|, dbj|BAF91409.1|, ref|NP_001058416.1|, and dbj|BAD45624.1| (SEQ ID NOS:615-619 respectively). Amino acids conserved among all sequences are indicated by a "*" and generally conserved amino acids are indicated by a ":".

FIG. 36 depicts a sequence alignment between SEQ ID NO:630 (RAAC02336) and ref|YP_517477.1|, ref|YP_517489.1|, ref|ZP_01370335.1|, gb|ACA46983.1|, and ref|YP_001568284.1| (SEQ ID NOS:632-636 respectively).

Amino acids conserved among all sequences are indicated by a "*" and generally conserved amino acids are indicated by a ":".

FIG. 37 depicts a sequence alignment between SEQ ID NO:647 (RAAC02292) and gb|AAB91591.1|, ref|YP_001422657.1|, ref|NP_391247.1|, ref|YP_093160.1|, and ref|NP_391246.1| (SEQ ID NOS:649-653 respectively). Amino acids conserved among all sequences are indicated by a "*" and generally conserved amino acids are indicated by a ":".

FIG. 38 depicts a sequence alignment between SEQ ID NO:664 (RAAC02337) and gb|ACA41259.1|, ref|ZP_02626811.1|, ref|NP_664934.1|, ref|YP_195796.1|, and ref|NP_817052.1| (SEQ ID NOS:666-670 respectively). Amino acids conserved among all sequences are indicated by a "*" and generally conserved amino acids are indicated by a ":".

FIG. 39 depicts a sequence alignment between SEQ ID NO:681 (RAAC02338) and gb|ACA41261.1|, ref|ZP_02626812.1|, ref|NP_664935.1|, ref|XP_001701427.1|, and sp|Q2M3V2|ANR43_HUMAN (SEQ ID NOS:683-687 respectively). Amino acids conserved among all sequences are indicated by a "*" and generally conserved amino acids are indicated by a ":".

FIG. 40 depicts a sequence alignment between SEQ ID NO:698 (RAAC02339) and gb|AAU83457.1|, emb|CAJ70907.1|, ref|ZP_00514953.1|, ref|YP_322920.1|, and ref|YP_183482.1| (SEQ ID NOS:700-704 respectively). Amino acids conserved among all sequences are indicated by a "*" and generally conserved amino acids are indicated by a ":".

FIG. 41 depicts a sequence alignment between SEQ ID NO:715 (RAAC02340) and ref|ZP_01731985.1|, ref|ZP_02429891.1|, ref|ZP_02432977.1|, ref|ZP_02085861.1|, and ref|ZP_02207628.1| (SEQ ID NOS:717-721 respectively). Amino acids conserved among all sequences are indicated by a "*" and generally conserved amino acids are indicated by a ":".

FIG. 42 depicts a sequence alignment between SEQ ID NO:732 (RAAC02341) and ref|ZP_02596024.1|, ref|NP_150014.1|, ref|ZP_00231288.1|, ref|YP_001213007.1|, and ref|YP_001113884.1| (SEQ ID NOS:734-738 respectively). Amino acids conserved among all sequences are indicated by a "*" and generally conserved amino acids are indicated by a ":".

FIG. 43 depicts a sequence alignment between SEQ ID NO:749 (RAAC02342) and ref|NP_783868.1|, ref|YP_805310.1|, ref|ZP_01273840.1|, ref|YP_803555.1|, and ref|YP_001270615.1| (SEQ ID NOS:751-755 respectively). Amino acids conserved among all sequences are indicated by a "*" and generally conserved amino acids are indicated by a ":".

FIG. 44 depicts a sequence alignment between SEQ ID NO:766 (RAAC02293) and ref|ZP_01171099.1|, ref|ZP_02598174.1|, ref|YP_429218.1|, ref|YP_001112194.1|, and ref|YP_001112320.1| (SEQ ID NOS:768-772 respectively). Amino acids conserved among all sequences are indicated by a "*" and generally conserved amino acids are indicated by a ":".

FIG. 45 depicts a sequence alignment between SEQ ID NO:783 (RAAC02346) and ref|NP_623604.1|, ref|ZP_00235040.1|, ref|ZP_02327783.1|, ref|ZP_02082031.1|, and ref|ZP_02846176.1| (SEQ ID NOS:785-789 respectively). Amino acids conserved among all sequences are indicated by a "*" and generally conserved amino acids are indicated by a ":".

FIG. 46 depicts a sequence alignment between SEQ ID NO:800 (RAAC02347) and ref|XP_001383704.2|, ref|XP_001664270.1|, ref|YP_113896.1|, ref|XP_761114.1|, and ref|XP_001015776.2| (SEQ ID NOS:802-806 respectively). Amino acids conserved among all sequences are indicated by a "*" and generally conserved amino acids are indicated by a ":".

FIG. 47 depicts a sequence alignment between SEQ ID NO:817 (RAAC03510) and gb|ACA42330.1|, ref|ZP_02605128.1|, ref|ZP_02586769.1|, ref|YP_001049647.1|, and ref|YP_913053.1| (SEQ ID NOS:819-823 respectively). Amino acids conserved among all sequences are indicated by a "*" and generally conserved amino acids are indicated by a ":".

FIG. 48 depicts a sequence alignment between SEQ ID NO:834 (RAAC02348) and ref|XP_414088.2|, ref|ZP_01171110.1|, gb|AAF98351.1|, ref|NP_607899.1|, and ref|NP_269831.1| (SEQ ID NOS:836-840 respectively). Amino acids conserved among all sequences are indicated by a "*" and generally conserved amino acids are indicated by a ":".

FIG. 49 depicts a sequence alignment between SEQ ID NO:851 (RAAC02349) and ref|YP_001038860.1|, ref|YP_754926.1|, ref|YP_001396671.1|, ref|YP_001254879.1|, and ref|YP_001396310.1| (SEQ ID NOS:853-857 respectively). Amino acids conserved among all sequences are indicated by a "*" and generally conserved amino acids are indicated by a ":".

FIG. 50 depicts a sequence alignment between SEQ ID NO:868 (RAAC03270) and ref|YP_001655174.1|, emb|CAJ73677.1|, emb|CAJ73386.1|, emb|CAJ74660.1|, and ref|ZP_00516046.1| (SEQ ID NOS:870-874 respectively). Amino acids conserved among all sequences are indicated by a "*" and generally conserved amino acids are indicated by a ":".

FIG. 51 depicts a sequence alignment between SEQ ID NO:885 (RAAC03271) and sp|P26545|VE2_HPV5B, ref|XP_001371550.1|, sp|P36786|VE2_HPV19, ref|NP_041368.1|, and ref|XP_001131003.1| (SEQ ID NOS:887-891 respectively). Amino acids conserved among all sequences are indicated by a "*" and generally conserved amino acids are indicated by a ":".

FIG. 52 depicts a sequence alignment between SEQ ID NO:902 (RAAC02294) and ref|YP_941474.2|, gb|AAZ42391.1|, ref|ZP_01171098.1|, prf||2123261AD, and ref|NP_498368.2| (SEQ ID NOS:904-908 respectively). Amino acids conserved among all sequences are indicated by a "*" and generally conserved amino acids are indicated by a ":".

FIG. 53 depicts a sequence alignment between SEQ ID NO:919 (RAAC02353) and ref|YP_430185.1|, ref|YP_001233893.1|, emb|CAO81523.1|, ref|YP_001603689.1|, and ref|YP_719187.1| (SEQ ID NOS:921-925 respectively). Amino acids conserved among all sequences are indicated by a "*" and generally conserved amino acids are indicated by a ":".

FIG. 54 depicts a sequence alignment between SEQ ID NO:936 (RAAC02354) and ref|YP_001438903.1|, ref|YP_001251565.1|, ref|YP_126374.1|, ref|YP_123382.1|, and ref|YP_001251158.1| (SEQ ID NOS:938-942 respectively). Amino acids conserved among all sequences are indicated by a "*" and generally conserved amino acids are indicated by a ":".

FIG. 55 depicts a sequence alignment between SEQ ID NO:953 (RAAC02355) and ref|ZP_02758276.1|, gb|ACA42232.1|, ref|ZP_02602342.1|, ref|ZP_02597242.1|, and ref|ZP_02524501.1| (SEQ ID NOS:955-

959 respectively). Amino acids conserved among all sequences are indicated by a "*" and generally conserved amino acids are indicated by a ":".

FIG. 56 depicts a sequence alignment between SEQ ID NO:970 (RAAC02356) and ref|NP_347717.1|, ref|YP_423535.1|, ref|ZP_01860459.1|, ref|YP_429187.1|, and ref|YP_645289.1| (SEQ ID NOS:972-976 respectively). Amino acids conserved among all sequences are indicated by a "*" and generally conserved amino acids are indicated by a ":".

FIG. 57 depicts a sequence alignment between SEQ ID NO:987 (RAAC02357) and gb|EAY58379.1|, ref|ZP_01505670.1|, ref|NP_856790.1|, ref|NP_217638.1|, and ref|ZP_00876805.1| (SEQ ID NOS:989-993 respectively). Amino acids conserved among all sequences are indicated by a "*" and generally conserved amino acids are indicated by a ":".

FIG. 58 depicts a sequence alignment between SEQ ID NO:1004 (RAAC02358) and ref|YP_024839.1|, ref|YP_001456771.1|, ref|YP_655149.1|, ref|XP_748956.1|, and ref|NP_943831.1| (SEQ ID NOS:1006-1010 respectively). Amino acids conserved among all sequences are indicated by a "*" and generally conserved amino acids are indicated by a ":".

FIG. 59 depicts a sequence alignment between SEQ ID NO:1038 (RAAC02361) and ref|ZP_01966753.1|, ref|YP_001086797.1|, ref|ZP_01805266.1|, ref|YP_001681547.1|, and ref|ZP_01188985.1| (SEQ ID NOS:1040-1044 respectively). Amino acids conserved among all sequences are indicated by a "*" and generally conserved amino acids are indicated by a ":".

FIG. 60 depicts a sequence alignment between SEQ ID NO:1055 (RAAC02362) and ref|YP_157691.1|, ref|ZP_02509777.1|, ref|ZP_02485527.1|, ref|ZP_02406784.1|, and ref|YP_335221.1| (SEQ ID NOS:1057-1061 respectively). Amino acids conserved among all sequences are indicated by a "*" and generally conserved amino acids are indicated by a ":".

FIG. 61 depicts a sequence alignment between SEQ ID NO:1072 (RAAC02363) and ref|YP_001681084.1|, ref|YP_177318.1|, ref|ZP_02329650.1|, ref|NP_243607.1|, and ref|YP_001421775.1| (SEQ ID NOS:1074-1078 respectively). Amino acids conserved among all sequences are indicated by a "*" and generally conserved amino acids are indicated by a ":".

FIG. 62 depicts a sequence alignment between SEQ ID NO:1089 (RAAC02364) and ref|YP_079689.1|, ref|ZP_02329649.1|, ref|ZP_01860132.1|, ref|ZP_01171904.1|, and ref|YP_001487332.1| (SEQ ID NOS:1091-1095 respectively). Amino acids conserved among all sequences are indicated by a "*" and generally conserved amino acids are indicated by a ":".

FIG. 63 depicts a sequence alignment between SEQ ID NO:1106 (RAAC02366) and ref|ZP_01614696.1|, gb|ABH06559.1|, gb|AAB95339.1|, ref|YP_161675.1|, and ref|YP_001202661.1| (SEQ ID NOS:1108-1112 respectively). Amino acids conserved among all sequences are indicated by a "*" and generally conserved amino acids are indicated by a ":".

FIG. 64 depicts a sequence alignment between SEQ ID NO:1123 (RAAC02367) and ref|ZP_02093159.1|, ref|ZP_02026447.1|, ref|YP_001127515.1|, ref|ZP_02091713.1|, and ref|ZP_02423704.1| (SEQ ID NOS:1125-1129 respectively). Amino acids conserved among all sequences are indicated by a "*" and generally conserved amino acids are indicated by a ":".

FIG. 65 depicts a sequence alignment between SEQ ID NO:1140 (RAAC02370) and ref|ZP_00960984.1|, ref|ZP_01035782.1|, ref|ZP_01903846.1|, ref|ZP_01880414.1|, and ref|ZP_01742943.1| (SEQ ID NOS:1142-1146 respectively). Amino acids conserved among all sequences are indicated by a "*" and gene conserved amino acids are indicated by a ":".

FIG. 66 depicts a sequence alignment between SEQ ID NO:1157 (RAAC02371) and ref|ZP_02756730.1|, ref|ZP_02833143.1|, ref|YP_521772.1|, ref|ZP_01551668.1|, and ref|YP_887014.1| (SEQ ID NOS:1159-1163 respectively). Amino acids conserved among all sequences are indicated by a "*" and generally conserved amino acids are indicated by a ":".

FIG. 67 depicts a sequence alignment between SEQ ID NO:1174 (RAAC02372) and sp|Q7ZXB1|MCM7B_XENLA, ref|YP_324842.1|, ref|NP_486002.1|, ref|XP_660834.1|, and ref|ZP_01733540.1| (SEQ ID NOS:1176-1180 respectively). Amino acids conserved among all sequences are indicated by a "*" and generally conserved amino acids are indicated by a ":".

FIG. 68 depicts a sequence alignment between SEQ ID NO:1191 (RAAC02296) and ref|XP_001563017.1|, ref|XP_001615133.1|, ref|YP_001236354.1|, ref|ZP_01776409.1|, and ref|ZP_01565636.1| (SEQ ID NOS:1193-1197 respectively). Amino acids conserved among all sequences are indicated by a "*" and generally conserved amino acids are indicated by a ":".

FIG. 69 depicts a sequence alignment between SEQ ID NO:1208 (RAAC02373) and ref|YP_001376930.1|, gb|AAW81277.1|, ref|ZP_02852259.1|, ref|YP_001642790.1|, and ref|YP_001312077.1| (SEQ ID NOS:1210-1214 respectively). Amino acids conserved among all sequences are indicated by a "*" and generally conserved amino acids are indicated by a ":".

FIG. 70 depicts a sequence alignment between SEQ ID NO:1225 (RAAC02374) and ref|XP_001467069.1|, ref|YP_001376929.1|, ref|YP_001208199.1|, gb|EAU86007.1|, and ref|YP_946581.1| (SEQ ID NOS:1227-1231 respectively). Amino acids conserved among all sequences are indicated by a "*" and generally conserved amino acids are indicated by a ":".

FIG. 71 depicts a sequence alignment between SEQ ID NO:1242 (RAAC02375) and ref|XP_975359.1|, ref|XP_001315633.1|, ref|ZP_02840410.1|, ref|ZP_01467536.1|, and ref|YP_001016790.1| (SEQ ID NOS:1244-1248 respectively). Amino acids conserved among all sequences are indicated by a "*" and generally conserved amino acids are indicated by a ":".

FIG. 72 depicts a sequence alignment between SEQ ID NO:1259 (RAAC03273) and ref|YP_502758.1|, gb|EAU81483.1|, ref|ZP_01091610.1|, ref|YP_944003.1|, and ref|YP_462360.1| (SEQ ID NOS:1261-1265 respectively). Amino acids conserved among all sequences are indicated by a "*" and generally conserved amino acids are indicated by a ":".

FIG. 73 depicts a sequence alignment between SEQ ID NO:1276 (RAAC02967) and ref|YP_074959.1|, ref|YP_594046.1|, ref|ZP_01846154.1|, sp|Q45618|TRA6_BACST, and ref|YP_828009.1| (SEQ ID NOS:1278-1282 respectively). Amino acids conserved among all sequences are indicated by a "*" and generally conserved amino acids are indicated by a ":".

FIG. 74 depicts a sequence alignment between SEQ ID NO:1293 (RAAC03589) and ref|YP_146741.1|, ref|YP_148969.1|, ref|YP_001126171.1|, ref|ZP_02130848.1|, and ref|YP_146154.1| (SEQ ID NOS:1295-1299 respec- FIG. 75 depicts a sequence alignment between SEQ ID NO:1310 (RAAC03695) and ref|ZP_01665148.1|, ref|YP_001111903.1|, ref|YP_752864.1|, ref|YP_753434.1|, and ref|YP_753226.1| (SEQ ID NOS:1312-1316 respectively). Amino acids conserved among all sequences are indicated by a "*" and generally conserved amino acids are indicated by a ":".

FIG. 76 depicts a sequence alignment between SEQ ID NO:1327 (RAAC02318) and ref|YP_754943.1|, ref|YP_754865.1|, ref|YP_431166.1|, ref|ZP_02171171.1|, and ref|YP_519650.1| (SEQ ID NOS:1329-1333 respectively). Amino acids conserved among all sequences are indicated by a "*" and generally conserved amino acids are indicated by a ":".

FIG. 77 depicts a sequence alignment between SEQ ID NO:1344 (RAAC02319) and ref|YP_431168.1|, ref|YP_001212944.1|, ref|YP_754944.1|, ref|YP_754864.1|, and ref|ZP_02171383.1| (SEQ ID NOS:1346-1350 respectively). Amino acids conserved among all sequences are indicated by a "*" and generally conserved amino acids are indicated by a ":".

FIG. 78 depicts a sequence alignment between SEQ ID NO:1361 (RAAC02333) and ref|ZP_02734990.1|, ref|ZP_01265219.1|, ref|YP_266430.1|, ref|YP_008142.1|, and ref|YP_713924.1| (SEQ ID NOS:1363-1367 respectively). Amino acids conserved among all sequences are indicated by a "*" and generally conserved amino acids are indicated by a ":".

FIG. 79 depicts a sequence alignment between SEQ ID NO:1378 (RAAC03703) and ref|YP_001036724.1|, ref|YP_001039064.1|, ref|YP_001039349.1|, ref|YP_076118.1|, and ref|YP_074958.1|X (SEQ ID NOS:1380-1384 respectively). Amino acids conserved among all sequences are indicated by a "*" and generally conserved amino acids are indicated by a ":".

FIG. 80 depicts a sequence alignment between SEQ ID NO:1395 (RAAC03568) and ref|YP_001039349.1|, ref|YP_001036724.1|, ref|YP_001039064.1|, ref|YP_076118.1|, and ref|YP_074958.1|X (SEQ ID NOS:1397-1401 respectively). Amino acids conserved among all sequences are indicated by a "*" and generally conserved amino acids are indicated by a ":".

FIG. 81 depicts a sequence alignment between SEQ ID NO:1412 (RAAC03707) and ref|YP_519534.1|, ref|ZP_01370818.1|, ref|ZP_01372264.1|, ref|YP_516922.1|, and ref|YP_519084.1|X (SEQ ID NOS:1414-1418 respectively). Amino acids conserved among all sequences are indicated by a "*" and generally conserved amino acids are indicated by a ":".

FIG. 82 depicts a sequence alignment between SEQ ID NO:1429 (RAAC03173) and ref|YP_431168.1|, ref|YP_001212944.1|, ref|YP_754944.1|, ref|YP_754864.1|, and ref|ZP_02171383.1|X (SEQ ID NOS:1431-1435 respectively). Amino acids conserved among all sequences are indicated by a "*" and generally conserved amino acids are indicated by a ":".

FIG. 83 depicts a sequence alignment between SEQ ID NO:1446 (RAAC02966) and ref|YP_074959.1|, ref|NP_634718.1|, ref|NP_1616807.1|, gb|AAR99616.1|, and sp|Q456181TRA6_BACSTX (SEQ ID NOS:1448-1452 respectively). Amino acids conserved among all sequences are indicated by a "*" and generally conserved amino acids are indicated by a ":".

FIG. 84 depicts a sequence alignment between SEQ ID NO:1463 (RAAC00757) and ref|YP_430545.1|, ref|YP_148444.1|, ref|NP_980798.1|, ref|YP_001211577.1|, and sp|Q9 KDI8|RUVB_BACHDX (SEQ ID NOS:1465-1469 respectively). Amino acids conserved among all sequences are indicated by a "*" and generally conserved amino acids are indicated by a ":".

FIG. 85 depicts a sequence alignment between SEQ ID NO:1480 (RAAC00756) and ref|YP_234498.1|, ref|NP_793742.1|, ref|YP_275913.1|, ref|ZP_00991066.1|, and ref|YP_001186768.1|X (SEQ ID NOS:1482-1486 respectively). Amino acids conserved among all sequences are indicated by a "*" and generally conserved amino acids are indicated by a ":".

FIG. 86 depicts a sequence alignment between SEQ ID NO:1497 (RAAC00755) and ref|YP_644098.1|, ref|ZP_02848139.1|, ref|YP_518701.1|, ref|YP_074988.1|, and ref|YP_001180347.1|X (SEQ ID NOS:1499-1503 respectively). Amino acids conserved among all sequences are indicated by a "*" and generally conserved amino acids are indicated by a ":".

FIG. 87 depicts a sequence alignment between SEQ ID NO:1514 (RAAC01468) and ref|YP_146341.1|, ref|YP_001513188.1|, ref|ZP_02261478.1|, ref|YP_001373830.1|, and ref|ZP_02257063.1|X (SEQ ID NOS:1516-1520 respectively). Amino acids conserved among all sequences are indicated by a "*" and generally conserved amino acids are indicated by a ":".

FIG. 88 depicts a sequence alignment between SEQ ID NO:1531 (RAAC03178) and ref|ZP_01665148.1|, ref|YP_752864.1|, ref|YP_001111903.1|, ref|YP_753434.1|, and ref|YP_753226.1|X (SEQ ID NOS:1533-1537 respectively). Amino acids conserved among all sequences are indicated by a "*" and generally conserved amino acids are indicated by a ":".

FIG. 89 depicts a sequence alignment between SEQ ID NO:1548 (RAAC01937) and dbj|BAF33373.1|, ref|YP_01126744.1|, gb|AAB52611.1|, gb|ABM97416.1|, and sp|P520261DPO1_BACSTX (SEQ ID NOS:1550-1554 respectively). Amino acids conserved among all sequences are indicated by a "*" and generally conserved amino acids are indicated by a ":".

FIG. 90 depicts a sequence alignment between SEQ ID NO:1565 (RAAC01372) and ref|YP_001681573.1|, ref|ZP_00651175.1|, ref|YP_473713.1|, gb|ACA11657.1|, and ref|YP_475384.1|X (SEQ ID NOS:1567-1571 respectively). Amino acids conserved among all sequences are indicated by a "*" and generally conserved amino acids are indicated by a ":".

FIG. 91 depicts a sequence alignment between SEQ ID NO:1582 (RAAC00062) and ref|ZP_01695687.1|, ref|ZP_01695971.1|, ref|ZP_01695982.1|, ref|ZP_01695655.1|, and ref|YP_430569.1|X (SEQ ID NOS:1584-1588 respectively). Amino acids conserved among all sequences are indicated by a "*" and generally conserved amino acids are indicated by a ":".

FIG. 92 depicts a sequence alignment between SEQ ID NO:1599 (RAAC02377) and ref|YP_752864.1|, ref|ZP_01665148.1|, ref|YP_001111903.1|, ref|YP_754667.1|, and ref|YP_753226.1|X (SEQ ID NOS:1601-1605 respectively). Amino acids conserved among all sequences are indicated by a "*" and generally conserved amino acids are indicated by a ":".

FIG. 93 depicts a sequence alignment between SEQ ID NO:1633 (RAAC03117) and ref|YP_754865.1|, ref|YP_754943.1|, ref|YP_431166.1|, ref|ZP_02171171.1|, and ref|YP_001318017.1|X (SEQ ID NOS:1635-1639 respectively). Amino acids conserved among all sequences are indicated by a "*" and generally conserved amino acids are indicated by a ":".

FIG. 94 depicts a sequence alignment between SEQ ID NO:1650 (RAAC00037) and ref|YP_001514390.1|, ref|NP_780819.1|, ref|YP_001663996.1|, ref|YP_699899.1|, and ref|YP_077153.1|X (SEQ ID NOS:1652-1656 respectively). Amino acids conserved among all sequences are indicated by a "*" and generally conserved amino acids are indicated by a ":".

FIG. 95 depicts a sequence alignment between SEQ ID NO:1667 (RAAC00054) and ref|NP_387885.1|, ref|YP_803557.1|, ref|YP_077286.1|, ref|ZP_02326643.1|, and ref|YP_001419683.1|X (SEQ ID NOS:1669-1673 respectively). Amino acids conserved among all sequences are indicated by a "*" and generally conserved amino acids are indicated by a ":".

FIG. 96 depicts a sequence alignment between SEQ ID NO:1684 (RAAC03102) and ref|YP_074959.1|, gb|AAR99616.1|, sp|Q456181TRA6_BACST, ref|YP_075129.1|, and ref|YP_359963.1|X (SEQ ID NOS:1686-1690 respectively). Amino acids conserved among all sequences are indicated by a "*" and generally conserved amino acids are indicated by a ":".

FIG. 97 depicts a sequence alignment between SEQ ID NO:1701 (RAAC03103) and ref|YP_074959.1|, ref|YP_594046.1|, ref|ZP_02563000.1|, ref|ZP_02516401.1|, and ref|ZP_02335796.1|X (SEQ ID NOS:1703-1707 respectively). Amino acids conserved among all sequences are indicated by a "*" and generally conserved amino acids are indicated by a ":".

FIG. 98 depicts a sequence alignment between SEQ ID NO:1718 (RAAC03341) and ref|YP_076075.1|, ref|YP_074958.1|, ref|YP_076118.1|, ref|YP_001039349.1|, and ref|YP_001036724.1|X (SEQ ID NOS:1720-1724 respectively). Amino acids conserved among all sequences are indicated by a "*" and generally conserved amino acids are indicated by a ":".

FIG. 99 depicts a sequence alignment between SEQ ID NO:1786 (RAAC02852) and ref|YP_001125185.1|, ref|YP_147064.1|, ref|YP_001486753.1|, ref|NP_389494.1|, and ref|YP_091420.1|X (SEQ ID NOS:1788-1792 respectively). Amino acids conserved among all sequences are indicated by a "*" and generally conserved amino acids are indicated by a ":".

FIG. 100 depicts a sequence alignment between SEQ ID NO:1803 (RAAC02854) and ref|YP_001125186.1|, ref|ZP_01775043.1|, ref|YP_175772.1|, ref|NP_243331.1|, and ref|YP_740910.1|X (SEQ ID NOS:1805-1809 respectively). Amino acids conserved among all sequences are indicated by a "*" and generally conserved amino acids are indicated by a ":".

FIG. 101 depicts a sequence alignment between SEQ ID NO:1820 (RAAC03166) and ref|YP_001211938.1|, dbj|BAD22831.1|, ref|ZP_01666445.1|, ref|ZP_01665334.1|, and gb|EAY56013.1|X (SEQ ID NOS:1822-1826 respectively). Amino acids conserved among all sequences are indicated by a "*" and generally conserved amino acids are indicated by a ":".

FIG. 102 depicts a sequence alignment between SEQ ID NO:1854 (RAAC02961) and ref|ZP_02330756.1|, ref|ZP_02327778.1|, ref|ZP_02330395.1|, ref|ZP_02327484.1|, and ref|ZP_02326400.1|X (SEQ ID NOS:1856-1860 respectively). Amino acids conserved among all sequences are indicated by a "*" and generally conserved amino acids are indicated by a ":".

FIG. 103 depicts a sequence alignment between SEQ ID NO:1871 (RAAC02202) and ref|YP_146129.1|, sp|O877031DNLJ_BACST, gb|ABN05294.1|, ref|YP_001124385.1|, and ref|ZP_01169975.1|X (SEQ ID NOS:1873-1877 respectively). Amino acids conserved among all sequences are indicated by a "*" and generally conserved amino acids are indicated by a ":".

FIG. 104 depicts a sequence alignment between SEQ ID NO:1888 (RAAC03682) and ref|ZP_01695687.1|, ref|ZP_01695971.1|, ref|ZP_01695982.1|, ref|ZP_01695655.1|, and ref|YP_430569.1|X (SEQ ID NOS:1890-1894 respectively). Amino acids conserved among all sequences are indicated by a "*" and generally conserved amino acids are indicated by a ":".

FIG. 105 depicts a sequence alignment between SEQ ID NO:1922 (RAAC03770) and ref|ZP_01695687.1|, ref|ZP_01695971.1|, ref|ZP_01695982.1|, ref|ZP_01695655.1|, and ref|YP_430569.1|X (SEQ ID NOS:1924-1928 respectively). Amino acids conserved among all sequences are indicated by a "*" and generally conserved amino acids are indicated by a ":".

FIG. 106 depicts a sequence alignment between SEQ ID NO:1939 (RAAC02738) and ref|NP_842969.1|, ref|YP_430640.1|, ref|ZP_02596019.1|, ref|YP_001666203.1|, and ref|YP_001512589.1|X (SEQ ID NOS:1941-1945 respectively). Amino acids conserved among all sequences are indicated by a "*" and generally conserved amino acids are indicated by a ":".

FIG. 107 depicts a sequence alignment between SEQ ID NO:1956 (RAAC02514) and ref|YP_001114460.1|, ref|YP_001111555.1|, ref|YP_001112147.1|, ref|YP_001111684.1|, and ref|YP_001113963.1|X (SEQ ID NOS:1958-1962 respectively). Amino acids conserved among all sequences are indicated by a "*" and generally conserved amino acids are indicated by a ":".

FIG. 108 depicts a sequence alignment between SEQ ID NO:1973 (RAAC02515) and ref|YP_001111555.1|, ref|YP_001111684.1|, ref|YP_001114460.1|, ref|YP_001113963.1|, and dbj|BAD18231.1|X (SEQ ID NOS:1975-1979 respectively). Amino acids conserved among all sequences are indicated by a "*" and generally conserved amino acids are indicated by a ":".

FIG. 109 depicts a sequence alignment between SEQ ID NO:1990 (RAAC02530) and ref|YP_001212947.1|, ref|YP_431166.1|, ref|YP_754943.1|, ref|YP_754865.1|, and ref|YP_001318017.1|X (SEQ ID NOS:1992-1996 respectively). Amino acids conserved among all sequences are indicated by a "*" and generally conserved amino acids are indicated by a ":".

FIG. 110 depicts a sequence alignment between SEQ ID NO:2007 (RAAC02533) and ref|YP_001039349.1|, ref|YP_001036724.1|, ref|YP_001039064.1|, ref|YP_076118.1|, and ref|YP_076073.1|X (SEQ ID NOS:2009-2013 respectively). Amino acids conserved among all sequences are indicated by a "*" and generally conserved amino acids are indicated by a ":".

FIG. 111 depicts a sequence alignment between SEQ ID NO:2024 (RAAC02534) and ref|YP_076118.1|, ref|YP_074958.1|, ref|YP_001039349.1|, ref|YP_001036724.1|, and ref|YP_001039064.1|X (SEQ ID NOS:2026-2030 respectively). Amino acids conserved among all sequences are indicated by a "*" and generally conserved amino acids are indicated by a ":".

FIG. 112 depicts a sequence alignment between SEQ ID NO:2041 (RAAC02562) and ref|YP_148733.1|, ref|YP_146224.1|, ref|ZP_02619781.1|, ref|ZP_02171259.1|, and ref|NP_977687.1|X (SEQ ID NOS:2043-2047 respec- FIG. 113 depicts a sequence alignment between SEQ ID NO:2058 (RAAC03229) and ref|YP_519534.1|, ref|ZP_01370818.1|, ref|ZP_01372264.1|, ref|YP_516922.1|, and ref|YP_520815.1|X (SEQ ID NOS:2060-2064 respectively). Amino acids conserved among all sequences are indicated by a "*" and generally conserved amino acids are indicated by a ":".

FIG. 114 depicts a sequence alignment between SEQ ID NO:2092 (RAAC00160) and ref|YP_001125159.1|, ref|ZP_02849289.1|, ref|ZP_02329219.1|, ref|YP_147039.1|, and ref|NP_816723.1|X (SEQ ID NOS:2094-2098 respectively). Amino acids conserved among all sequences are indicated by a "*" and generally conserved amino acids are indicated by a ":".

FIG. 115 depicts a sequence alignment between SEQ ID NO:2109 (RAAC03182) and ref|YP_146741.1|, ref|YP_148969.1|, ref|YP_001126171.1|, ref|ZP_02130848.1|, and ref|YP_146154.1|X (SEQ ID NOS:2111-2115 respectively). Amino acids conserved among all sequences are indicated by a "*" and generally conserved amino acids are indicated by a ":".

FIG. 116 depicts a sequence alignment between SEQ ID NO:2126 (RAAC03163) and ref|YP_148733.1|, ref|YP_146224.1|, ref|ZP_02171259.1|, ref|ZP_02619781.1|, and ref|NP_977687.1|X (SEQ ID NOS:2128-2132 respectively). Amino acids conserved among all sequences are indicated by a "*" and generally conserved amino acids are indicated by a ":".

FIG. 117 depicts a sequence alignment between SEQ ID NO:2143 (RAAC01387) and ref|YP_148733.1|, ref|YP_146224.1|, ref|ZP_02171259.1|, ref|ZP_02619781.1|, and ref|YP_001396471.1|X (SEQ ID NOS:2145-2149 respectively). Amino acids conserved among all sequences are indicated by a "*" and generally conserved amino acids are indicated by a ":".

FIG. 118 depicts a sequence alignment between SEQ ID NO:2160 (RAAC03385) and gb|AAL87775.1|AF403183_1286, ref|YP_517288.1|, ref|YP_517659.1|, ref|ZP_01368657.1|, and ref|YP_001212990.1|X (SEQ ID NOS: 2162-2166 respectively). Amino acids conserved among all sequences are indicated by a "*" and generally conserved amino acids are indicated by a ":".

FIG. 119 depicts a sequence alignment between SEQ ID NO:2177 (RAAC03398) and ref|YP_001126171.1|, ref|YP_148969.1|, ref|YP_146154.1|, ref|YP_146741.1|, and ref|ZP_02172080.1|X (SEQ ID NOS:2179-2183 respectively). Amino acids conserved among all sequences are indicated by a "*" and generally conserved amino acids are indicated by a ":".

FIG. 120 depicts a sequence alignment between SEQ ID NO:2194 (RAAC03177) and ref|YP_148969.1|, ref|YP_146154.1|, ref|YP_001126171.1|, ref|YP_146741.1|, and ref|ZP_02172080.1|X (SEQ ID NOS:2196-2200 respectively). Amino acids conserved among all sequences are indicated by a "*" and generally conserved amino acids are indicated by a ":".

FIG. 121 depicts a sequence alignment between SEQ ID NO:2211 (RAAC03588) and ref|YP_001036724.1|, ref|YP_001039064.1|, ref|YP_001039349.1|, ref|YP_074105.1|, and ref|YP_076073.1|X (SEQ ID NOS:2213-2217 respectively). Amino acids conserved among all sequences are indicated by a "*" and generally conserved amino acids are indicated by a ":".

FIG. 122 depicts a sequence alignment between SEQ ID NO:2228 (RAAC03818) and ref|YP_074959.1|, ref|NP_634718.1|, gb|AAR99616.1|, sp|Q45618|TRA6_BACST, and ref|NP_616807.1|X (SEQ ID NOS:2230-2234 respectively). Amino acids conserved among all sequences are indicated by a "*" and generally conserved amino acids are indicated by a ":".

FIG. 123 depicts a sequence alignment between SEQ ID NO:2245 (RAAC03819) and ref|YP_594046.1|, ref|YP_074959.1|, ref|YP_359963.1|, ref|YP_361300.1|, and ref|NP_622784.1|X (SEQ ID NOS:2247-2251 respectively). Amino acids conserved among all sequences are indicated by a "*" and generally conserved amino acids are indicated by a ":".

FIG. 124 depicts a sequence alignment between SEQ ID NO:2262 (RAAC03823) and ref|ZP_01695687.1|, ref|ZP_01695971.1|, ref|ZP_01695982.1|, ref|ZP_01695655.1|, and ref|YP_430569.1|X (SEQ ID NOS:2264-2268 respectively). Amino acids conserved among all sequences are indicated by a "*" and generally conserved amino acids are indicated by a ":".

FIG. 125 depicts a sequence alignment between SEQ ID NO:2279 (RAAC01171) and ref|ZP_02330348.1|, ref|ZP_02328298.1|, ref|ZP_02326599.1|, ref|YP_001664428.1|, and ref|YP_001664274.1| (SEQ ID NOS:2281-2285 respectively). Amino acids conserved among all sequences are indicated by a "*" and generally conserved amino acids are indicated by a ":".

FIG. 126 depicts a sequence alignment between SEQ ID NO:2296 (RAAC03825) and ref|YP_0519534.1|, ref|ZP_01370818.1|, ref|ZP_01372264.1|, ref|YP_516922.1|, and ref|YP_520815.1| (SEQ ID NOS:2298-2302 respectively). Amino acids conserved among all sequences are indicated by a "*" and generally conserved amino acids are indicated by a ":".

FIG. 127 depicts a sequence alignment between SEQ ID NO:2313 (RAAC03826) and ref|ZP_02851608.1|, ref|ZP_02326599.1|, ref|YP_001307815.1|, ref|YP_001212943.1|, and ref|YP_001113174.1| (SEQ ID NOS: 2315-2319 respectively). Amino acids conserved among all sequences are indicated by a "*" and generally conserved amino acids are indicated by a ":".

FIG. 128 depicts a sequence alignment between SEQ ID NO:2330 (RAAC02717) and ref|ZP_01002160.1|, ref|ZP_01592598.1|, ref|YP_001229345.1|, ref|YP_771767.1|, and ref|YP_245447.1| (SEQ ID NOS:2332-2336 respectively). Amino acids conserved among all sequences are indicated by a "*" and generally conserved amino acids are indicated by a ":".

FIG. 129 depicts a sequence alignment between SEQ ID NO:2347 (RAAC01155) and ref|YP_145872.1|, ref|YP_001124150.1|, ref|ZP_02850412.1|, ref|NP_240902.1|, and ref|NP_466224.1| (SEQ ID NOS:2349-2353 respectively). Amino acids conserved among all sequences are indicated by a "*" and generally conserved amino acids are indicated by a ":".

FIG. 130 depicts a sequence alignment between SEQ ID NO:2364 (RAAC03145) and dbj|BAA94830.1|, ref|ZP_01666433.1|, ref|YP_001213263.1|, ref|YP_387030.1|, and ref|YP_387237.1| (SEQ ID NOS:2366-2370 respectively). Amino acids conserved among all sequences are indicated by a "*" and generally conserved amino acids are indicated by a ":".

FIG. 131 depicts a sequence alignment between SEQ ID NO:2381 (RAAC03325) and ref|YP_146741.1|, ref|YP_148969.1|, ref|YP_001126171.1|, ref|ZP_02130848.1|, and ref|YP_146154.1| (SEQ ID NOS:2383-2387 respectively). Amino acids conserved among all sequences are indicated by a "*" and generally conserved amino acids are indicated by a ":".

FIG. 132 depicts a sequence alignment between SEQ ID NO:2398 (RAAC03376) and ref|ZP_02851608.1|, ref|ZP_02326599.1|, ref|YP_001664274.1|, ref|YP_001307815.1|, and ref|YP_001319448.1| (SEQ ID NOS: 2400-2404 respectively). Amino acids conserved among all sequences are indicated by a "*" and generally conserved amino acids are indicated by a ":".

FIG. 133 depicts a sequence alignment between SEQ ID NO:2415 (RAAC02657) and ref|YP_076090.1|, ref|YP_001516732.1|, ref|YP_001185431.1|, ref|YP_318565.1|, and ref|ZP_01061333.1| (SEQ ID NOS:2417-2421 respectively). Amino acids conserved among all sequences are indicated by a "*" and generally conserved amino acids are indicated by a ":".

FIG. 134 depicts a sequence alignment between SEQ ID NO:2432 (RAAC01373) and ref|YP_001680037.1|, ref|YP_001505049.1|, ref|YP_482514.1|, ref|YP_481774.1|, and ref|NP_215436.1| (SEQ ID NOS:2434-2438 respectively). Amino acids conserved among all sequences are indicated by a "*" and generally conserved amino acids are indicated by a ":".

FIG. 135 depicts a sequence alignment between SEQ ID NO:2449 (RAAC00337) and ref|YP_001680296.1|, ref|YP_342400.1|, ref|NP_756021.1|, ref|YP_405147.1|, and ref|NP_709160.1| (SEQ ID NOS:2451-2455 respectively). Amino acids conserved among all sequences are indicated by a "*" and generally conserved amino acids are indicated by a ":".

FIG. 136 depicts a sequence alignment between SEQ ID NO:2466 (RAAC00506) and emb|CAD18993.1|, ref|ZP_00995572.1|, ref|YP_805441.1|, ref|YP_001115956.1|, and ref|ZP_02134324.1| (SEQ ID NOS:2468-2472 respectively). Amino acids conserved among all sequences are indicated by a "*" and generally conserved amino acids are indicated by a ":".

FIG. 137 depicts a sequence alignment between SEQ ID NO:2483 (RAAC00022) and ref|ZP_01695451.1|, ref|NP_391924.1|, ref|YP_001488901.1|, ref|NP_244897.1|, and ref|YP_001423303.1| (SEQ ID NOS:2485-2489 respectively). Amino acids conserved among all sequences are indicated by a "*" and generally conserved amino acids are indicated by a ":".

FIG. 138 depicts a sequence alignment between SEQ ID NO:2500 (RAAC00027) and ref|YP_001213441.1|, ref|NP_244917.1|, ref|YP_001377189.1|, ref|YP_149334.1|, and ref|YP_077145.1| (SEQ ID NOS:2502-2506 respectively). Amino acids conserved among all sequences are indicated by a "*" and generally conserved amino acids are indicated by a ":".

FIG. 139 depicts a sequence alignment between SEQ ID NO:2517 (RAAC01051) and ref|YP_074151.1|, ref|YP_001255315.1|, ref|YP_001392092.1|, gb|ACA43749.1|, and ref|ZP_02619122.1|X (SEQ ID NOS:2519-2523 respectively). Amino acids conserved among all sequences are indicated by a "*" and generally conserved amino acids are indicated by a ":".

FIG. 140 depicts a sequence alignment between SEQ ID NO:2534 (RAAC01050) and ref|YP_878438.1|, ref|ZP_02621211.1|, ref|YP_001560315.1|, ref|YP_001255314.1|X (SEQ ID NOS: 2536-2540 respectively). Amino acids conserved among all sequences are indicated by a "*" and generally conserved amino acids are indicated by a ":".

FIG. 141 depicts a sequence alignment between SEQ ID NO:2551 (RAAC01009) and ref|YP_148023.1|, ref|YP_001126202.1|, ref|YP_001421643.1|, ref|ZP_01697284.1|, and gb|ABN10253.1|X (SEQ ID NOS:2553-2557 respectively). Amino acids conserved among all sequences are indicated by a "*" and generally conserved amino acids are indicated by a ":".

FIG. 142 depicts a sequence alignment between SEQ ID NO:2568 (RAAC00998) and ref|ZP_02175216.1|, ref|YP_464174.1|, ref|YP_753805.1|, ref|ZP_02321813.1|, and ref|ZP_01575281.1|X (SEQ ID NOS:2570-2574 respectively). Amino acids conserved among all sequences are indicated by a "*" and generally conserved amino acids are indicated by a ":".

FIG. 143 depicts a sequence alignment between SEQ ID NO:2585 (RAAC02359) and ref|NP_832076.1|, ref|YP_001645033.1|, ref|NP_844759.1|, ref|YP_001375058.1|, and ref|YP_535778.1|X (SEQ ID NOS:2587 FIG. 153-2591 respectively). Amino acids conserved among all sequences are indicated by a "*" and generally conserved amino acids are indicated by a ":".

FIG. 144 depicts a sequence alignment between SEQ ID NO:2602 (RAAC00997) and ref|ZP_02854041.1|, ref|YP_075626.1|, ref|YP_753804.1|, ref|ZP_01667008.1|, and ref|YP_946103.1|X (SEQ ID NOS:2604-2608 respectively). Amino acids conserved among all sequences are indicated by a "*" and generally conserved amino acids are indicated by a ":".

FIG. 145 depicts a sequence alignment between SEQ ID NO:2619 (RAAC02419) and ref|ZP_02330146.1|, ref|YP_001210709.1|, ref|ZP_02184702.1|, gb|AAD26564.1|AF124258_1, and ref|ZP_01828805.1|X (SEQ ID NOS:2621-2625 respectively). Amino acids conserved among all sequences are indicated by a "*" and generally conserved amino acids are indicated by a ":".

FIG. 146 depicts a sequence alignment between SEQ ID NO:2636 (RAAC02417) and ref|NP_469419.1|, ref|ZP_02309926.1|, ref|ZP_01926077.1|, ref|ZP_01941236.1|, and ref|YP_001111866.1|X (SEQ ID NOS:2638-2642 respectively). Amino acids conserved among all sequences are indicated by a "*" and generally conserved amino acids are indicated by a ":".

FIG. 147 depicts a sequence alignment between SEQ ID NO:2653 (RAAC03180) and ref|ZP_02442523.1|, ref|YP_001664041.1|, ref|YP_001210714.1|, ref|ZP_02589119.1|, and ref|NP_242309.1|X (SEQ ID NOS:2655-2659 respectively). Amino acids conserved among all sequences are indicated by a "*" and generally conserved amino acids are indicated by a ":".

FIG. 148 depicts a sequence alignment between SEQ ID NO:2670 (RAAC03525) and ref|ZP_02442523.1|, ref|YP_001210714.1|, ref|YP_001180871.1|, ref|YP_001662345.1|, and ref|ZP_02543721.1|X (SEQ ID NOS: 2672-2676 respectively). Amino acids conserved among all Sequences are indicated by a "*" and generally conserved amino acids are indicated by a ":".

FIG. 149 depicts a sequence alignment between SEQ ID NO:2687 (RAAC03224) and ref|YP_006607.1|, ref|YP_001038857.1|, ref|YP_146372.1|, ref|YP_001662865.1|, and ref|ZP_02781438.1|X (SEQ ID NOS:2689-2693 respectively). Amino acids conserved among all sequences are indicated by a "*" and generally conserved amino acids are indicated by a ":".

FIG. 150 depicts a sequence alignment between SEQ ID NO:2704 (RAAC02915) and ref|YP_001211829.1|, ref|ZP_02091210.1|, ref|YP_518738.1|, ref|ZP_02378091.1|, and ref|ZP_02454559.1|X (SEQ ID NOS:

2706-2710 respectively). Amino acids conserved among all sequences are indicated by a "*" and generally conserved amino acids are indicated by a ":".

FIG. 151 depicts a sequence alignment between SEQ ID NO:2721 (RAAC02943) and ref|ZP_02850845.1|, ref|NP_243249.1|, emb|CAD56684.1|, ref|YP_079090.1|, and ref|YP_001421272.1|X (SEQ ID NOS:2723-2727 respectively). Amino acids conserved among all sequences are indicated by a "*" and generally conserved amino acids are indicated by a ":".

FIG. 152 depicts a sequence alignment between SEQ ID NO:2738 (RAAC02234) and ref|NP_242725.1|, ref|YP_175539.1|, ref|ZP_02170975.1|, ref|ZP_01696769.1|, and emb|CAJ73252.1|X (SEQ ID NOS:2740-2744 respectively). Amino acids conserved among all sequences are indicated by a "*" and generally conserved amino acids are indicated by a ":".

FIG. 153 depicts a sequence alignment between SEQ ID NO:2755 (RAAC01662) and emb|CAK51299.1|, ref|YP_832554.1|, emb|CAI78402.1|, ref|YP_001362100.1|, and ref|YP_712120.1|X (SEQ ID NOS:2757-2761 respectively). Amino acids conserved among all sequences are indicated by a "*" and generally conserved amino acids are indicated by a ":".

FIG. 154 depicts a sequence alignment between SEQ ID NO:2772 (RAAC02171) and ref|ZP_01188667.1|, ref|ZP_02620185.1|, ref|YP_001512273.1|, ref|YP_877450.1|, and ref|YP_001275096.1|X (SEQ ID NOS:2774-2778 respectively). Amino acids conserved among all sequences are indicated by a "*" and generally conserved amino acids are indicated by a ":".

FIG. 155 depicts a sequence alignment between SEQ ID NO:2789 (RAAC01696) and sp|P80579|THIO_ALIAC, pdb|1NW2|A, pdb|1NSW|A, pdb|1RQM|A, and ref|YP_703612.1|X (SEQ ID NOS:2791-2795 respectively). Amino acids conserved among all sequences are indicated by a "*" and generally conserved amino acids are indicated by a ":".

FIG. 156 depicts a sequence alignment between SEQ ID NO:2806 (RAAC01724) and ref|NP_244119.1|, ref|ZP_02850022.1|, ref|YP_815236.1|, ref|NP_965472.1|, and ref|YP_001422284.1|X (SEQ ID NOS:2808-2812 respectively). Amino acids conserved among all sequences are indicated by a "*" and generally conserved amino acids are indicated by a ":".

FIG. 157 depicts a sequence alignment between SEQ ID NO:2823 (RAAC01817) and ref|ZP_02326197.1|, ref|YP_001212789.1|, ref|ZP_01666637.1|, ref|YP_001211675.1|, and ref|ZP_101126596.1|X (SEQ ID NOS:2825-2829 respectively). Amino acids conserved among all sequences are indicated by a "*" and generally conserved amino acids are indicated by a ":".

FIG. 158 depicts a sequence alignment between SEQ ID NO:2840 (RAAC01840) and ref|YP_001514193.1|, ref|YP_517020.1|, ref|YP_001317996.1|, ref|YP_001090064.1|, and ref|ZP_01995293.1|X (SEQ ID NOS:2842-2846 respectively). Amino acids conserved among all sequences are indicated by a "*" and generally conserved amino acids are indicated by a ":".

FIG. 159 depicts a sequence alignment between SEQ ID NO:2857 (RAAC01875) and ref|YP_644758.1|, ref|YP_604970.1|, ref|YP_076566.1|, ref|NP_295807.1|, and ref|YP_357266.1|X (SEQ ID NOS:2859-2863 respectively). Amino acids conserved among all sequences are indicated by a "*" and generally conserved amino acids are indicated by a ":".

FIG. 160 depicts a sequence alignment between SEQ ID NO:2874 (RAAC02539) and ref|ZP_01034116.1|, gb|ABY83631.1|, ref|ZP_02297879.1|, ref|YP_208280.1|, and ref|YP_001516905.1|X (SEQ ID NOS:2876-2880 respectively). Amino acids conserved among all sequences are indicated by a "*" and generally conserved amino acids are indicated by a ":".

FIG. 161 depicts a sequence alignment between SEQ ID NO:2891 (RAAC02543) and ref|ZP_01042597.1|, gb|ABO14793.1|, ref|YP_001443312.1|, ref|ZP_01815366.1|, and ref|YP_205672.1|X (SEQ ID NOS:2893-2897 respectively). Amino acids conserved among all sequences are indicated by a "*" and generally conserved amino acids are indicated by a ":".

FIG. 162 depicts a sequence alignment between SEQ ID NO:2908 (RAAC02564) and ref|ZP_01631840.1|, gb|AAZ73681.1|, ref|YP_001633718.1|, ref|YP_001275109.1|, and ref|ZP_01514022.1|X (SEQ ID NOS:2910-2914 respectively). Amino acids conserved among all sequences are indicated by a "*" and generally conserved amino acids are indicated by a ":".

FIG. 163 depicts a sequence alignment between SEQ ID NO:2925 (RAAC02566) and ref|YP_853610.1|, ref|YP_512277.1|, ref|YP_001038857.1|, ref|ZP_01959153.1|, and ref|YP_001662865.1|X (SEQ ID NOS:2927-2931 respectively). Amino acids conserved among all sequences are indicated by a "*" and generally conserved amino acids are indicated by a ":".

FIG. 164 depicts a sequence alignment between SEQ ID NO:2942 (RAAC02589) and ref|ZP_00591928.1|, ref|YP_001003150.1|, ref|NP_046614.1|, ref|YP_375842.1|, and ref|YP_001131112.1|X (SEQ ID NOS:2944-2948 respectively). Amino acids conserved among all sequences are indicated by a "*" and generally conserved amino acids are indicated by a ":".

FIG. 165 depicts a sequence alignment between SEQ ID NO:2959 (RAAC02045) and ref|ZP_02848186.1|, ref|YP_080797.1|, ref|YP_001127101.1|, ref|YP_148915.1|, and ref|YP_001488316.1|X (SEQ ID NOS:2961-2965 respectively). Amino acids conserved among all sequences are indicated by a "*" and generally conserved amino acids are indicated by a ":".

FIG. 166 depicts a sequence alignment between SEQ ID NO:2976 (RAAC02635) and ref|YP_866618.1|, ref|YP_342704.1|, ref|NP_384606.1|, ref|YP_115396.1|, and ref|YP_911114.1|X (SEQ ID NOS:2978-2982 respectively). Amino acids conserved among all sequences are indicated by a "*" and generally conserved amino acids are indicated by a ":".

FIG. 167 depicts a sequence alignment between SEQ ID NO:2993 (RAAC00088) and ref|NP 244431.1|, ref|ZP_02848186.1|, ref|ZP_02171648.1|, ref|ZP_02210735.1|, and ref|YP_176521.1|X (SEQ ID NOS:2995-2999 respectively). Amino acids conserved among all sequences are indicated by a "*" and generally conserved amino acids are indicated by a ":".

FIG. 168 depicts a sequence alignment between SEQ ID NO:3010 (RAAC00111) and ref|YP_46448.1|, ref|NP_977168.1|, ref|ZP_02261191.1|, ref|ZP_02848045.1|, and ref|NP_981890.1|X (SEQ ID NOS:3012-3016 respectively). Amino acids conserved among all sequences are indicated by a "*" and generally conserved amino acids are indicated by a ":".

FIG. 169 depicts a sequence alignment between SEQ ID NO:3027 (RAAC03161) and ref|ZP_01898092.1|, ref|ZP_01221581.1|, ref|YP_128524.1|, ref|ZP_01236658.1|, and ref|ZP_01161642.1|X (SEQ ID NOS:3029-3033 respec- FIG. 170 depicts a sequence alignment between SEQ ID NO:3044 (RAAC03110) and ref|YP_001567845.1|, gb|ACA00199.1|, ref|ZP_01731959.1|, ref|NP_490383.1|, and ref|YP_319960.1|X (SEQ ID NOS:3046-3050 respectively). Amino acids conserved among all sequences are indicated by a "*" and generally conserved amino acids are indicated by a ":".

FIG. 171 depicts a sequence alignment between SEQ ID NO:3061 (RAAC03810) and emb|CAP00374.1|, ref|YP_001038857.1|, ref|NP_852746.1|, ref|ZP_01959153.1|, and ref|YP_853610.1|X (SEQ ID NOS:3063-3067 respectively). Amino acids conserved among all sequences are indicated by a "*" and generally conserved amino acids are indicated by a ":".

FIG. 172 depicts a sequence alignment between SEQ ID NO:3078 (RAAC03316) and emb|CAP00374.1|, ref|YP_001038857.1|, ref|ZP_02327844.1|, ref|NP_852746.1|, and ref|ZP_01959153.1|X (SEQ ID NOS:3080-3084 respectively). Amino acids conserved among all sequences are indicated by a "*" and generally conserved amino acids are indicated by a ":".

FIG. 173 depicts a sequence alignment between SEQ ID NO:3095 (RAAC03018) and ref|YP_148854.1|, ref|YP_001127043.1|, ref|YP_080555.1|, ref|NP_693306.1|, and ref|ZP_02170973.1|X (SEQ ID NOS:3097-3101 respectively). Amino acids conserved among all sequences are indicated by a "*" and generally conserved amino acids are indicated by a ":".

FIG. 174 depicts a sequence alignment between SEQ ID NO:3112 (RAAC02718) and ref|YP_001178926.1|, ref|YP_001180877.1|, ref|YP_001219837.1|, ref|YP_001211485.1|, and ref|YP_001211518.1|X (SEQ ID NOS:3114-3118 respectively). Amino acids conserved among all sequences are indicated by a "*" and generally conserved amino acids are indicated by a ":".

FIG. 175 depicts a sequence alignment between SEQ ID NO:3129 (RAAC01115) and ref|YP_001035109.1|, ref|ZP_01819917.1|, ref|YP_001450442.1|, ref|ZP_01818216.1|, and ref|ZP_01830009.1|X (SEQ ID NOS:3131-3135 respectively). Amino acids conserved among all sequences are indicated by a "*" and generally conserved amino acids are indicated by a ":".

FIG. 176 depicts a sequence alignment between SEQ ID NO:3146 (RAAC01119) and ref|NP_622644.1|, ref|YP_001664955.1|, ref|YP_076287.1|, ref|ZP_02616274.1|, and ref|YP_001255422.1|X (SEQ ID NOS:3148-3152 respectively). Amino acids conserved among all sequences are indicated by a "*" and generally conserved amino acids are indicated by a ":".

FIG. 177 depicts a sequence alignment between SEQ ID NO:3163 (RAAC00203) and ref|YP_001433837.1|, ref|YP_001276310.1|, ref|ZP_01514627.1|, ref|YP_001636906.1|, and ref|YP_001102862.1|X (SEQ ID NOS:3165-3169 respectively). Amino acids conserved among all sequences are indicated by a "*" and generally conserved amino acids are indicated by a ":".

FIG. 178 depicts a sequence alignment between SEQ ID NO:3180 (RAAC01413) and ref|ZP_02849297.1|, ref|NP_815033.1|, ref|YP_796463.1|, ref|NP_862606.1|, and ref|ZP_00604769.1|X (SEQ ID NOS:3182-3186 respectively). Amino acids conserved among all sequences are indicated by a "*" and generally conserved amino acids are indicated by a ":".

FIG. 179 depicts a sequence alignment between SEQ ID NO:3197 (RAAC01435) and ref|YP_359065.1|, ref|YP_145897.21, ref|NP_387932.1|, ref|YP_001124176.1|, and sp|P42816|KPPRS_BACCLX (SEQ ID NOS:3199-3203 respectively). Amino acids conserved among all sequences are indicated by a "*" and generally conserved amino acids are indicated by a ":".

FIG. 180 depicts a sequence alignment between SEQ ID NO:3214 (RAAC01442) and ref|ZP_02170919.1|, ref|YP_535778.1|, ref|ZP_01862118.1|, ref|NP_692713.1|, and ref|YP_359077.1|X (SEQ ID NOS:3216-3220 respectively). Amino acids conserved among all sequences are indicated by a "*" and generally conserved amino acids are indicated by a ":".

FIG. 181 depicts a sequence alignment between SEQ ID NO:3231 (RAAC00895) and ref|NP_846740.1|, ref|ZP_00238564.1|, ref|ZP_02583512.1|, ref|NP 834002.1|, and ref|ZP_02604064.1|X (SEQ ID NOS:3233-3237 respectively). Amino acids conserved among all sequences are indicated by a "*" and generally conserved amino acids are indicated by a ":".

FIG. 182 depicts a sequence alignment between SEQ ID NO:3248 (RAAC03475) and ref|ZP_02442523.1|, ref|YP_001210714.1|, ref|YP_001180871.1|, ref|YP_001662345.1|, and ref|YP_001114120.1|X (SEQ ID NOS:3250-3254 respectively). Amino acids conserved among all sequences are indicated by a "*" and generally conserved amino acids are indicated by a ":".

FIG. 183 depicts a sequence alignment between SEQ ID NO:3265 (RAAC03560) and ref|YP_001114120.1|, ref|NP_242309.1|, ref|YP_146346.1|, ref|YP_146347.1|, and ref|YP_001662345.1|X (SEQ ID NOS:3267-3271 respectively). Amino acids conserved among all sequences are indicated by a "*" and generally conserved amino acids are indicated by a ":".

DETAILED DESCRIPTION OF THE INVENTION

Embodiments of the invention include genes and associated proteins related to genetic recombination from the thermoacidophile *Alicyclobacillus acidocaldarius*. Coding sequences for genes related to recombination were determined from sequence information generated from sequencing the genome of *Alicyclobacillus acidocaldarius*. These genes and proteins may represent targets and/or elements of transformation systems or vectors for genetic engineering for introducing nucleotide sequences of interest into *Alicyclobacillus acidocaldarius*, Gram positive thermophiles, or other organisms. Non-limiting examples of nucleotide sequences found within the genome of *Alicyclobacillus acidocaldarius*, and amino acids coded thereby, associated with recombination are listed in the sequence listing. Examples of these nucleotide sequences and the proteins they encode can be found in Table 1. Proteins related to recombination may be, without limitation, one of any of the following: ATP-dependent DNA helicase recG, ATP-dependent DNA ligase, ATP-dependent endopeptidase clp proteolytic subunit, Chromosome partitioning protein, Crossover junction endodeoxyribonuclease ruvC, Deoxyuridine 5'-triphosphate nucleotidohydrolase, DNA adenine methylase, DNA helicase, DNA integration/recombination/inversion, DNA polymerase I, DNA polymerase III beta chain, DNA polymerase IV, DNA primase, DNA repair protein radC, DNA replication and repair protein recF, DNA replication protein dnaD, DNA topoisomerase I, DNA/RNA helicase (DEAD/DEAH box family), DNA-binding protein HU, Fe—S oxidoreductase, Glycerophosphoryl diester phosphodiesterase, HNH endonuclease family protein, Holliday junction DNA helicase ruvB, Integrase/recombinase (XerC/CodV family), Ligase/carboxyalse family protein, LtrC-like protein, Macrolide-efflux protein, NAD-dependent DNA ligase, Nicotinate phosphoribosyltransferase, nodulin-26, Phage antirepressor protein, Phage protein, Phosphinothricin N-acetyltransferase, Phosphohydrolase, RecA protein, Recombination protein recR, Replicative DNA helicase, Ribonucleoside-diphosphate reductase alpha chain, Ribonucleoside-diphosphate reductase beta chain, Ribose-phosphate pyrophosphokinase, Serine/threonine protein phosphatase, Single-strand DNA binding protein, Single-stranded DNA-binding protein, Site-specific recombinase, Site-specific resolvase/integrase, Thioredoxin, Thymidine kinase, Transcriptional regulator/Lex A repressor, Transcriptional regulator, Cro/CI family, Transposase, TRSE protein, Two-component response regulator, Type II restriction-modification system methylation subunit, and others.

Embodiments of the invention relate in part to the gene sequences and/or protein sequences comprising genes and/or proteins of *Alicyclobacillus acidocaldarius*. Genes and proteins included are those which play a role in genetic manipulation. Intracellular enzyme activities may be thermophilic and/or acidophilic in nature and general examples of similar genes are described in the literature. Classes of genes, sequences, enzymes and factors include, but are not limited to, those listed in Table 1. FIGS. 1-183 provide sequence alignments between polypeptide sequences of the present invention and closely related proteins. Areas of high homology between the polypeptide sequences of the present invention and closely related proteins are indicative of functionality for polypeptide sequences of the present invention for the same purposes as the sequences to which they are aligned.

TABLE 1

*Alicyclobacillus acidocaldarius* coding sequences related to recombination

| Reference | Protein Sequence | Coding Sequence | Function |
| --- | --- | --- | --- |
| RAAC02304 | SEQ ID NO: 137 | SEQ ID NO: 138 | Two-component response regulator |
| RAAC02309 | SEQ ID NO: 222 | SEQ ID NO: 223 | TRSE PROTEIN |
| RAAC02315 | SEQ ID NO: 324 | SEQ ID NO: 325 | Chromosome partitioning protein parA |
| RAAC02319 | SEQ ID NO: 409 | SEQ ID NO: 410 | Transposase |
| RAAC02321 | SEQ ID NO: 443 | SEQ ID NO: 444 | Ligase/carboxyalse family protein |
| RAAC02324 | SEQ ID NO: 494 | SEQ ID NO: 495 | Fe—S OXIDOREDUCTASE |
| RAAC02326 | SEQ ID NO: 511 | SEQ ID NO: 512 | nodulin-26 |
| RAAC02332 | SEQ ID NO: 562 | SEQ ID NO: 563 | Phosphinothricin N-acetyltransferase |
| RAAC02292 | SEQ ID NO: 647 | SEQ ID NO: 648 | Transcriptional regulator/Lex A repressor |
| RAAC02340 | SEQ ID NO: 715 | SEQ ID NO: 716 | LtrC-like protein |
| RAAC02341 | SEQ ID NO: 732 | SEQ ID NO: 733 | DNA repair protein radC |
| RAAC02342 | SEQ ID NO: 749 | SEQ ID NO: 750 | DNA polymerase III, beta chain |
| RAAC02348 | SEQ ID NO: 834 | SEQ ID NO: 835 | Single-stranded DNA-binding protein |
| RAAC02358 | SEQ ID NO: 1004 | SEQ ID NO: 1005 | DNA/RNA helicase (DEAD/DEAH box family) |
| RAAC02361 | SEQ ID NO: 1038 | SEQ ID NO: 1039 | DNA helicase II |
| RAAC02363 | SEQ ID NO: 1072 | SEQ ID NO: 1073 | DNA polymerase IV |
| RAAC02318 | SEQ ID NO: 1327 | SEQ ID NO: 1328 | Transposase |
| RAAC02319 | SEQ ID NO: 1344 | SEQ ID NO: 1345 | Transposase |
| RAAC02333 | SEQ ID NO: 1361 | SEQ ID NO: 1362 | DNA integration/recombination/inversion protein |
| RAAC03173 | SEQ ID NO: 1429 | SEQ ID NO: 1430 | Transposase |
| RAAC00757 | SEQ ID NO: 1463 | SEQ ID NO: 1464 | Holliday junction DNA helicase ruvB |
| RAAC00756 | SEQ ID NO: 1480 | SEQ ID NO: 1481 | Holliday junction DNA helicase ruvB |
| RAAC00755 | SEQ ID NO: 1497 | SEQ ID NO: 1498 | Crossover junction endodeoxyribonuclease ruvC |
| RAAC01468 | SEQ ID NO: 1514 | SEQ ID NO: 1515 | Site-specific recombinase |
| RAAC03178 | SEQ ID NO: 1531 | SEQ ID NO: 1532 | Transposase |
| RAAC01937 | SEQ ID NO: 1548 | SEQ ID NO: 1549 | DNA polymerase I |
| RAAC01372 | SEQ ID NO: 1565 | SEQ ID NO: 1566 | Transposase |
| RAAC02377 | SEQ ID NO: 1599 | SEQ ID NO: 1600 | Transposase |
| RAAC00037 | SEQ ID NO: 1650 | SEQ ID NO: 1651 | ATP-dependent DNA helicase recG |
| RAAC00054 | SEQ ID NO: 1667 | SEQ ID NO: 1668 | DNA replication and repair protein recF |
| RAAC03102 | SEQ ID NO: 1684 | SEQ ID NO: 1685 | Transposase |
| RAAC03103 | SEQ ID NO: 1701 | SEQ ID NO: 1702 | Transposase |
| RAAC03341 | SEQ ID NO: 1718 | SEQ ID NO: 1719 | Transposase |
| RAAC02852 | SEQ ID NO: 1786 | SEQ ID NO: 1787 | DNA topoisomerase I (EC 1280.1374.1276.1277) |
| RAAC02854 | SEQ ID NO: 1803 | SEQ ID NO: 1804 | Integrase/recombinase (XerC/CodV family) |
| RAAC03166 | SEQ ID NO: 1820 | SEQ ID NO: 1821 | Transposase |
| RAAC02961 | SEQ ID NO: 1854 | SEQ ID NO: 1855 | DNA integration/recombination/inversion protein |
| RAAC02202 | SEQ ID NO: 1871 | SEQ ID NO: 1872 | NAD-dependent DNA ligase |
| RAAC03682 | SEQ ID NO: 1888 | SEQ ID NO: 1889 | Transposase |
| RAAC02738 | SEQ ID NO: 1939 | SEQ ID NO: 1940 | DNA integration/recombination/inversion protein |
| RAAC02514 | SEQ ID NO: 1956 | SEQ ID NO: 1957 | Transposase |
| RAAC02515 | SEQ ID NO: 1973 | SEQ ID NO: 1974 | Transposase |
| RAAC02530 | SEQ ID NO: 1990 | SEQ ID NO: 1991 | Transposase |
| RAAC02533 | SEQ ID NO: 2007 | SEQ ID NO: 2008 | Transposase |
| RAAC02534 | SEQ ID NO: 2024 | SEQ ID NO: 2025 | Transposase |
| RAAC02562 | SEQ ID NO: 2041 | SEQ ID NO: 2042 | Transposase |
| RAAC03229 | SEQ ID NO: 2058 | SEQ ID NO: 2059 | Transposase |
| RAAC00160 | SEQ ID NO: 2092 | SEQ ID NO: 2093 | ATP-dependent DNA helicase recG |
| RAAC03182 | SEQ ID NO: 2109 | SEQ ID NO: 2110 | Transposase |
| RAAC03163 | SEQ ID NO: 2126 | SEQ ID NO: 2127 | Transposase |
| RAAC01387 | SEQ ID NO: 2143 | SEQ ID NO: 2144 | Transposase |
| RAAC01171 | SEQ ID NO: 2279 | SEQ ID NO: 2280 | Transposase |
| RAAC03825 | SEQ ID NO: 2296 | SEQ ID NO: 2297 | Transposase |
| RAAC03826 | SEQ ID NO: 2313 | SEQ ID NO: 2314 | Transposase |
| RAAC02717 | SEQ ID NO: 2330 | SEQ ID NO: 2331 | Transposase |

TABLE 1-continued

*Alicyclobacillus acidocaldarius* coding sequences related to recombination

| Reference | Protein Sequence | Coding Sequence | Function |
|---|---|---|---|
| RAAC01155 | SEQ ID NO: 2347 | SEQ ID NO: 2348 | Recombination protein recR |
| RAAC03145 | SEQ ID NO: 2364 | SEQ ID NO: 2365 | Transposase |
| RAAC03325 | SEQ ID NO: 2381 | SEQ ID NO: 2382 | Transposase |
| RAAC03376 | SEQ ID NO: 2398 | SEQ ID NO: 2399 | Transposase |
| RAAC02657 | SEQ ID NO: 2415 | SEQ ID NO: 2416 | Type II restriction-modification system methylation subunit |
| RAAC01373 | SEQ ID NO: 2432 | SEQ ID NO: 2433 | Site-specific resolvase/integrase |
| RAAC00337 | SEQ ID NO: 2449 | SEQ ID NO: 2450 | DNA adenine methylase |
| RAAC00506 | SEQ ID NO: 2466 | SEQ ID NO: 2467 | Serine/threonine protein phosphatase |
| RAAC00022 | SEQ ID NO: 2483 | SEQ ID NO: 2484 | Replicative DNA helicase |
| RAAC00027 | SEQ ID NO: 2500 | SEQ ID NO: 2501 | Single-strand DNA binding protein |
| RAAC01051 | SEQ ID NO: 2517 | SEQ ID NO: 2518 | Ribonucleoside-diphosphate reductase alpha chain |
| RAAC01050 | SEQ ID NO: 2534 | SEQ ID NO: 2535 | Ribonucleoside-diphosphate reductase beta chain |
| RAAC01009 | SEQ ID NO: 2551 | SEQ ID NO: 2552 | DNA replication protein dnaD |
| RAAC00998 | SEQ ID NO: 2568 | SEQ ID NO: 2569 | ATP-dependent DNA ligase |
| RAAC02359 | SEQ ID NO: 2585 | SEQ ID NO: 2586 | DNA-binding protein HU |
| RAAC00997 | SEQ ID NO: 2602 | SEQ ID NO: 2603 | ATP-dependent DNA ligase |
| RAAC02419 | SEQ ID NO: 2619 | SEQ ID NO: 2620 | Site-specific recombinase |
| RAAC02417 | SEQ ID NO: 2636 | SEQ ID NO: 2637 | Transcriptional regulator, Cro/CI family |
| RAAC03180 | SEQ ID NO: 2653 | SEQ ID NO: 2654 | Transcriptional regulator, Cro/CI family |
| RAAC03224 | SEQ ID NO: 2687 | SEQ ID NO: 2688 | Phage antirepressor protein |
| RAAC02915 | SEQ ID NO: 2704 | SEQ ID NO: 2705 | Deoxyuridine 5'-triphosphate nucleotidohydrolase |
| RAAC02943 | SEQ ID NO: 2721 | SEQ ID NO: 2722 | RecA protein |
| RAAC02234 | SEQ ID NO: 2738 | SEQ ID NO: 2739 | Serine/threonine protein phosphatase |
| RAAC01662 | SEQ ID NO: 2755 | SEQ ID NO: 2756 | Macrolide-efflux protein |
| RAAC02171 | SEQ ID NO: 2772 | SEQ ID NO: 2773 | Phosphohydrolase |
| RAAC01696 | SEQ ID NO: 2789 | SEQ ID NO: 2790 | Thioredoxin |
| RAAC01724 | SEQ ID NO: 2806 | SEQ ID NO: 2807 | Thioredoxin |
| RAAC01817 | SEQ ID NO: 2823 | SEQ ID NO: 2824 | Site-specific recombinase |
| RAAC01840 | SEQ ID NO: 2840 | SEQ ID NO: 2841 | Nicotinate phosphoribosyltransferase |
| RAAC01875 | SEQ ID NO: 2857 | SEQ ID NO: 2858 | Glycerophosphoryl diester phosphodiesterase |
| RAAC02539 | SEQ ID NO: 2874 | SEQ ID NO: 2875 | Type II restriction-modification system methylation subunit |
| RAAC02543 | SEQ ID NO: 2891 | SEQ ID NO: 2892 | DNA adenine methylase |
| RAAC02564 | SEQ ID NO: 2908 | SEQ ID NO: 2909 | DNA adenine methylase |
| RAAC02566 | SEQ ID NO: 2925 | SEQ ID NO: 2926 | Phage antirepressor protein |
| RAAC02589 | SEQ ID NO: 2942 | SEQ ID NO: 2943 | DNA-binding protein HU |
| RAAC02045 | SEQ ID NO: 2959 | SEQ ID NO: 2960 | ATP-dependent endopeptidase clp proteolytic subunit clpP |
| RAAC02635 | SEQ ID NO: 2976 | SEQ ID NO: 2977 | Type II restriction-modification system methylation subunit |
| RAAC00088 | SEQ ID NO: 2993 | SEQ ID NO: 2994 | ATP-dependent endopeptidase clp proteolytic subunit clpP |
| RAAC00111 | SEQ ID NO: 3010 | SEQ ID NO: 3011 | Site-specific recombinase |
| RAAC03161 | SEQ ID NO: 3027 | SEQ ID NO: 3028 | DNA adenine methylase |
| RAAC03110 | SEQ ID NO: 3044 | SEQ ID NO: 3045 | HNH endonuclease family protein |
| RAAC03316 | SEQ ID NO: 3078 | SEQ ID NO: 3079 | Phage antirepressor protein |
| RAAC03018 | SEQ ID NO: 3095 | SEQ ID NO: 3096 | Thioredoxin |
| RAAC02718 | SEQ ID NO: 3112 | SEQ ID NO: 3113 | Phage protein |
| RAAC01115 | SEQ ID NO: 3129 | SEQ ID NO: 3130 | Thymidine kinase |
| RAAC01119 | SEQ ID NO: 3146 | SEQ ID NO: 3147 | Glycerophosphoryl diester phosphodiesterase |
| RAAC00203 | SEQ ID NO: 3163 | SEQ ID NO: 3164 | Ribonucleoside-diphosphate reductase beta chain |
| RAAC01413 | SEQ ID NO: 3180 | SEQ ID NO: 3181 | Serine/threonine protein phosphatase |
| RAAC01435 | SEQ ID NO: 3197 | SEQ ID NO: 3198 | Ribose-phosphate pyrophosphokinase |
| RAAC01442 | SEQ ID NO: 3214 | SEQ ID NO: 3215 | DNA-binding protein HU |
| RAAC00895 | SEQ ID NO: 3231 | SEQ ID NO: 3232 | DNA primase |
| RAAC03475 | SEQ ID NO: 3248 | SEQ ID NO: 3249 | Transcriptional regulator, Cro/CI family |

The present invention relates to nucleotides sequences comprising isolated and/or purified nucleotide sequences of the genome of *Alicyclobacillus acidocaldarius* selected from the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 or one of their fragments.

The present invention likewise relates to isolated and/or purified nucleotide sequences, characterized in that they comprise at least one of: a) a nucleotide sequence of at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present invention as meaning both a double-stranded or single-stranded DNA in the monomeric and dimeric (so-called in tandem) forms and the transcription products of said DNAs.

Aspects of the invention relate to nucleotide sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning, and subcloning, it being possible for the sequences of the invention to be carried by vectors.

Isolated and/or purified nucleotide sequence fragment according to the invention will be understood as designating any nucleotide fragment of the genome of *Alicyclobacillus acidocaldarius*, and may include, by way of non-limiting examples, length of at least 8, 12, 20 25, 50, 75, 100, 200, 300, 400, 500, 1000, or more, consecutive nucleotides of the sequence from which it originates.

Specific fragment of an isolated and/or purified nucleotide sequence according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

Homologous isolated and/or purified nucleotide sequence in the sense of the present invention is understood as meaning isolated and/or purified a nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. Said "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. Said homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotide sequences are said to be "identical" if the sequence of amino-acids or nucleotide residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *J Mol Biol,* 147, 195-197, by the homology alignment algorithm of Needleman and Wunsch, *J. Mol. Biol.* 48: 443 (1970), by the search for similarity method of Pearson and Lipman, *Proc. Natl. Acad. Sci.* (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence," software that is available in the web site worldwideweb.blast.ncbi.nlm.nih.gov/Blast.cgi?PAGE_TYPE=BlastSearch&PROG_DEF=blastn&BLAST_PROG_DEF=megaBlast&SHOW_DEFAULTS=on&BLAST_SPEC=blast2seq&LINK_LOC=align2seq, and habitually used by the inventors and in general by the skilled person for comparing and determining the identity between two sequences, gap cost that depends on the sequence length to be compared is directly selected by the software (i.e., 11.2 for substitution matrix BLOSUM-62 for length>85).

Complementary nucleotide sequence of a sequence of the invention is understood as meaning any DNA whose nucleotides are complementary to those of the sequence of the invention, and whose orientation is reversed (antisense sequence).

Hybridization under conditions of stringency with a nucleotide sequence according to the invention is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example, a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by the person skilled in the art for oligonucleotides of greater or smaller size, according to the teaching of Sambrook et al., 1989.

Among the isolated and/or purified nucleotide sequences according to the invention, are those that can be used as a primer or probe in methods allowing the homologous sequences according to the invention to be obtained, these methods, such as the polymerase chain reaction (PCR), nucleic acid cloning, and sequencing, being well known to the person skilled in the art.

The terms "recombination," "genetic recombination," and "genetic engineering" are used interchangeable herein and refer to the process by which a first stretch of one or more nucleic acids are removed from or added to a second stretch of nucleic acids. Such addition or removal may occur in vivo or ex vivo. The terms also refer to the introduction of coding sequences or genes into cells or organisms for the purposes of expression or regulation of other nucleotide sequences or polypeptides. The terms further refer to the alteration of nucleic acid structure or topology. By way of non-limiting example, altering the "twist," supercoiling, helicity, separation and/or annealing of a nucleotide sequence.

Among the isolated and/or purified nucleotide sequences according to the invention, those are again preferred that can be used as a primer or probe in methods allowing the presence of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283, and one of their fragments, or one of their variants such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to the person skilled in the art, and containing modifications with respect to the normal sequences according to the invention, for example, mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

The present invention relates to nucleotide sequence comprising isolated and/or purified nucleotide sequences of *Alicyclobacillus acidocaldarius*, characterized in that they are selected from the sequences SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 or one of their fragments.

Embodiments of the invention likewise relate to isolated and/or purified nucleotide sequences characterized in that they comprise a nucleotide sequence selected from: a) at least one of a nucleotide sequence of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 or one of their fragments or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID NOS:13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1220-1224, 1237-1241, 1254-1258, 1271-1275, 1288-1292, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581, 1594-1598, 1611-1615, 1628-1632, 1645-1649, 1662-1666, 1679-1683, 1696-1700, 1713-1717, 1730-1734, 1747-1751, 1764-1768, 1781-1785, 1798-1802, 1815-1819, 1832-1836, 1849-1853, 1866-1870, 1883-1887, 1900-1904, 1917-1921, 1934-1938, 1951-1955, 1968-1972, 1985-1989, 2002-2006, 2019-2023, 2036-2040, 2053-2057, 2070-2074, 2087-2091, 2104-2108, 2121-2125, 2138-2142, 2155-2159, 2172-2176, 2189-2193, 2206-2210, 2223-2227, 2240-2244, 2257-2261, 2274-2278, 2291-2295, 2308-2312, 2325-2329, 2342-2346, 2359-2363, 2376-2380, 2393-2397, 2410-2414, 2427-2431, 2444-2448, 2461-2465, 2478-2482, 2495-2499, 2512-2516, 2529-2533, 2546-2550, 2563-2567, 2580-2584, 2597-2601, 2614-2618, 2631-2635, 2648-2652, 2665-2669, 2682-2686, 2699-2703, 2716-2720, 2733-2737, 2750-2754, 2767-2771, 2784-2788, 2801-2805, 2818-2822, 2835-2839, 2852-2856, 2869-2873, 2886-2890, 2903-2907, 2920-2924, 2937-2941, 2954-2958, 2971-2975, 2988-2992, 3005-3009, 3022-3026, 3039-3043, 3056-3060, 3073-3077, 3090-3094, 3107-3111, 3124-3128, 3141-3145, 3158-3162, 3175-3179, 3192-3196, 3209-3213, 3226-3230, 3243-3247, 3260-3264, 3277-3281, and 3294-3298; or fragments thereof and any isolated and/or purified nucleotide sequences that have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283; or fragments thereof. Such homologous sequences can comprise, for example, the sequences corresponding to the genomic sequences *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide. As will be apparent to one of ordinary skill in the art, such homologues are easily created and identified using conventional techniques and publicly available computer programs such as BLAST. Accordingly, each homologue referenced above should be considered as set forth herein and fully described.

Embodiments of the invention comprise the isolated and/or purified polypeptides coded for by a nucleotide sequence according to the invention, or fragments thereof, whose sequence is represented by a fragment. Amino acid sequences corresponding to the isolated and/or purified polypeptides that can be coded for according to one of the three possible reading frames of at least one of the sequences SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283.

Embodiments of the invention likewise relate to the isolated and/or purified polypeptides, characterized in that they comprise a polypeptide selected from at least one of the amino acid sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, and 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282; or one of their fragments.

Among the isolated and/or purified polypeptides, according to embodiments of the invention, are the isolated and/or purified polypeptides of amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1215-1219, 1232-1236, 1249-1253, 1266-1270, 1283-1287, 1300-

1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2439-2443, 2456-2460, 2473-2477, 2490-2494, 2507-2511, 2524-2528, 2541-2545, 2558-2562, 2575-2579, 2592-2596, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2864-2868, 2881-2885, 2898-2902, 2915-2919, 2932-2936, 2949-2953, 2966-2970, 2983-2987, 3000-3004, 3017-3021, 3034-3038, 3051-3055, 3068-3072, 3085-3089, 3102-3106, 3119-3123, 3136-3140, 3153-3157, 3170-3174, 3187-3191, 3204-3208, 3221-3225, 3238-3242, 3255-3259, 3272-3276, and 3289-3293; or fragments thereof or any other isolated and/or purified polypeptides that have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with at least one of the sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282; or fragments thereof. As will be apparent to one of ordinary skill in the art, such homologues are easily created and identified using conventional techniques and publicly available computer programs such as BLAST. Accordingly, each homologue referenced above should be considered as set forth herein and fully described.

Embodiments of the invention also relate to the polypeptides, characterized in that they comprise a polypeptide selected from: a) a specific fragment of at least 5 amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the invention, the isolated and/or purified polypeptides according to the invention may be glycosylated, pegylated, and/or otherwise post-translationally modified. In further embodiments, glycosylation, pegylation, and/or other post-translational modifications may occur in vivo or in vitro and/or may be performed using chemical techniques. In additional embodiments, any glycosylation, pegylation and/or other post-translational modifications may be N-linked or O-linked.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other posttranslational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

Aspects of the invention relate to polypeptides that are isolated or obtained by purification from natural sources, or else obtained by genetic recombination, or alternatively by chemical synthesis and that they may thus contain unnatural amino acids, as will be described below.

A "polypeptide fragment" according to the embodiments of the invention is understood as designating a polypeptide containing at least 5 consecutive amino acids, preferably 10 consecutive amino acids or 15 consecutive amino acids.

In the present invention, a specific polypeptide fragment is understood as designating the consecutive polypeptide fragment coded for by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the invention.

"Specific homologous polypeptide" will be understood as designating the homologous polypeptides such as defined above and having a specific fragment of polypeptide according to the invention. In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. As will be apparent to one of ordinary skill in the art, such substitutions are easily created and identified using standard molecular biology techniques and publicly available computer programs such as BLAST. Accordingly, each substitution referenced above should be considered as set forth herein and fully described. Examples of such substitutions in the amino acid sequences SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 may include those isolated and/or purified polypeptides of amino acid sequence SEQ ID NOS:8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1215-1219, 1232-1236, 1249-1253, 1266-1270, 1283-1287, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2439-2443, 2456-2460, 2473-2477, 2490-2494, 2507-2511, 2524-2528, 2541-2545, 2558-2562, 2575-2579, 2592-2596, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2864-2868, 2881-2885, 2898-2902, 2915-2919, 2932-2936, 2949-2953, 2966-2970, 2983-2987, 3000-3004, 3017-3021, 3034-3038, 3051-3055, 3068-3072, 3085-3089, 3102-3106, 3119-3123, 3136-3140, 3153-3157, 3170-3174, 3187-3191, 3204-3208, 3221-3225, 3238-3242, 3255-3259, 3272-3276, and 3289-3293. These equivalent amino acids may be determined either by depending on their structural homology with the amino acids that they substitute, or on results of comparative tests of biological activity between the different polypeptides, which are capable of being carried out.

By way of nonlimiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

In a further embodiment, substitutions are limited to substitutions in amino acids not conserved among other proteins that have similar identified enzymatic activity. For example, one of ordinary skill in the art may align proteins of the same function in similar organisms and determine which amino acids are generally conserved among proteins of that function. One example of a program that may be used to generate such alignments is worldwideweb.charite.de/bioinf/strap/ in conjunction with the databases provided by the NCBI. Examples of such polypeptides may include, but are not limited to, those found in amino acid sequence SEQ ID NOS:8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1215-1219, 1232-1236, 1249-1253, 1266-1270, 1283-1287, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2439-2443, 2456-2460, 2473-2477, 2490-2494, 2507-2511, 2524-2528, 2541-2545, 2558-2562, 2575-2579, 2592-2596, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2864-2868, 2881-2885, 2898-2902, 2915-2919, 2932-2936, 2949-2953, 2966-2970, 2983-2987, 3000-3004, 3017-3021, 3034-3038, 3051-3055, 3068-3072, 3085-3089, 3102-3106, 3119-3123, 3136-3140, 3153-3157, 3170-3174, 3187-3191, 3204-3208, 3221-3225, 3238-3242, 3255-3259, 3272-3276, and 3289-3293.

Thus, according to one embodiment of the invention, substitutions or mutation may be made at positions that are generally conserved among proteins of that function. In a further embodiment, nucleic acid sequences may be mutated or substituted such that the amino acid they code for is unchanged (degenerate substitutions and/mutations) and/or mutated or substituted such that any resulting amino acid substitutions or mutations are made at positions that are generally conserved among proteins of that function. Examples of such nucleic acid sequences may include, but are not limited to, those found in the nucleotide sequences of SEQ ID NOS:13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850; 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1220-1224, 1237-1241, 1254-1258, 1271-1275, 1288-1292, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581, 1594-1598, 1611-1615, 1628-1632, 1645-1649, 1662-1666, 1679-1683, 1696-1700, 1713-1717, 1730-1734, 1747-1751, 1764-1768, 1781-1785, 1798-1802, 1815-1819, 1832-1836, 1849-1853, 1866-1870, 1883-1887, 1900-1904, 1917-1921, 1934-1938, 1951-1955, 1968-1972, 1985-1989, 2002-2006, 2019-2023, 2036-2040, 2053-2057, 2070-2074, 2087-2091, 2104-2108, 2121-2125, 2138-2142, 2155-2159, 2172-2176, 2189-2193, 2206-2210, 2223-2227, 2240-2244, 2257-2261, 2274-2278, 2291-2295, 2308-2312, 2325-2329, 2342-2346, 2359-2363, 2376-2380, 2393-2397, 2410-2414, 2427-2431, 2444-2448, 2461-2465, 2478-2482, 2495-2499, 2512-2516, 2529-2533, 2546-2550, 2563-2567, 2580-2584, 2597-2601, 2614-2618, 2631-2635, 2648-2652, 2665-2669, 2682-2686, 2699-2703, 2716-2720, 2733-2737, 2750-2754, 2767-2771, 2784-2788, 2801-2805, 2818-2822, 2835-2839, 2852-2856, 2869-2873, 2886-2890, 2903-2907, 2920-2924, 2937-2941, 2954-2958, 2971-2975, 2988-2992, 3005-3009, 3022-3026, 3039-3043, 3056-3060, 3073-3077, 3090-3094, 3107-3111, 3124-3128, 3141-3145, 3158-3162, 3175-3179, 3192-3196, 3209-3213, 3226-3230, 3243-3247, 3260-3264, 3277-3281, and 3294-3298; or fragments thereof.

The specific homologous polypeptides likewise correspond to polypeptides coded for by the specific homologous nucleotide sequences such as defined above and thus comprise in the present definition the polypeptides that are mutated or correspond to variants that can exist in *Alicyclobacillus acidocaldarius*, and that especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, having at least one of the characteristics of polypeptides according to the invention. In certain embodiments the peptide is capable of behaving as at least one of the types of proteins outlined in Table 1.

The polypeptide fragments according to embodiments of the invention can correspond to isolated or purified fragments naturally present in *Alicyclobacillus acidocaldarius* or correspond to fragments that can be obtained by cleavage of said polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, from hosts transformed by an expression vector according to the invention containing a nucleic acid allowing the expression of said fragments, placed under the control of appropriate regulation and/or expression elements.

"Modified polypeptide" of a polypeptide according to an embodiment of the invention is understood as designating a polypeptide obtained by genetic recombination or by chemical synthesis as will be described below, having at least one modification with respect to the normal sequence. These modifications may or may not be able to bear on amino acids at the origin of specificity, and/or of activity, or at the origin of the structural conformation, localization, and of the capacity of membrane insertion of the polypeptide according to the invention. It will thus be possible to create polypeptides of equivalent, increased, or decreased activity, and of equivalent, narrower, or wider specificity. Among the modified polypeptides, it is necessary to mention the polypeptides in which up to 5 or more amino acids can be modified, truncated at the N- or C-terminal end, or even deleted or added.

The methods allowing said modulations on eukaryotic or prokaryotic cells to be demonstrated are well known to the person of ordinary skill in the art. It is likewise well understood that it will be possible to use the nucleotide sequences coding for said modified polypeptides for said modulations, for example through vectors according to the invention and described below.

The preceding modified polypeptides can be obtained by using combinatorial chemistry, in which it is possible to systematically vary parts of the polypeptide before testing them on models, cell cultures or microorganisms for example, to select the compounds that are most active or have the properties sought.

Chemical synthesis likewise has the advantage of being able to use nonnatural amino acids, or nonpeptide bonds.

Thus, in order to improve the duration of life of the polypeptides according to the invention, it may be of interest to use nonnatural amino acids, for example in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends molecules not recognized by proteases.

The nucleotide sequences coding for a polypeptide according to the invention are likewise part of the invention.

The invention likewise relates to nucleotide sequences utilizable as a primer or probe, characterized in that said sequences are selected from the nucleotide sequences according to the invention.

It is well understood that the present invention, in various embodiments, likewise relates to specific polypeptides of *Alicyclobacillus acidocaldarius*, coded for by nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides coded for by said nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., NAR, 1992); the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive isotope ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes that are utilizable for numerous applications.

Examples of nonradioactive labeling of nucleotide sequences are described, for example, in French Patent No. 78.10975 or by Urdea et al. or by Sanchez-Pescador et al. in 1988.

In the latter case; it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

Another aspect of the present invention is a vector for the cloning and/or expression of a sequence, characterized in that it contains a nucleotide sequence according to the invention.

The vectors according to the invention, characterized in that they contain the elements allowing the integration, expression and/or the secretion of said nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by the person skilled in the art, and it will be possible to introduce the resulting vectors into an appropriate host by standard methods, such as, for example, lipofection, electroporation, conjugation, and thermal shock.

The vectors according to the invention are, for example, vectors of plasmid or viral origin. One example of a vector for the expression of polypeptides of the invention is baculovirus.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of said cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example, sf9 insect cells (Luckow, 1993).

Embodiments of the invention likewise relate to organisms comprising one of such transformed cells according to the invention.

The obtainment of transgenic organisms according to the invention expressing one or more of the coding sequences of *Alicyclobacillus acidocaldarius* or part of the coding sequences may be carried out in, for example, rats, mice, or rabbits according to methods well known to the person skilled in the art, such as by viral or nonviral transfections. It will be possible to obtain the transgenic organisms expressing one or more of such coding sequences by transfection of multiple copies of such coding sequences under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of said chimeras.

The transformed cells as well as the transgenic organisms according to the invention are utilizable in procedures for preparation of recombinant polypeptides.

It is today possible to produce recombinant polypeptides in relatively large quantity by genetic engineering using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of said transformed cells according to the invention are themselves comprised in the present invention.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among the procedures for preparation of a polypeptide of the invention in recombinant form, the preparation procedures employing a vector, and/or a cell transformed by the vector and/or a transgenic organism comprising one of the transformed cells, containing a nucleotide sequence according to the invention coding for a polypeptide of *Alicyclobacillus acidocaldarius*.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of nucleotide sequence according to the invention; b) if need be, recovery of the recombinant polypeptide.

When the procedure for preparation of a polypeptide of the invention employs a transgenic organism according to the invention, the recombinant polypeptide is then extracted from said organism.

The invention also relates to a polypeptide that is capable of being obtained by a procedure of the invention such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques that are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield in 1966.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids that are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated, pegylated, and/or otherwise post-translationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

The hybrid nucleotide sequences coding for a hybrid polypeptide as well as the hybrid polypeptides according to the invention characterized in that they are recombinant polypeptides obtained by the expression of the hybrid nucleotide sequences are likewise part of the invention.

The invention likewise comprises the vectors characterized in that they contain one of the hybrid nucleotide sequences. The host cells transformed by the vectors, the transgenic organisms comprising one of said transformed cells as well as the procedures for preparation of recombinant polypeptides using the vectors, the transformed cells and/or said transgenic organisms are, of course, likewise part of the invention.

The polypeptides according to the invention, the antibodies according to the invention described below and the nucleotide sequences according to the invention can advantageously be employed in procedures for the detection and/or identification of *Alicyclobacillus acidocaldarius*, in a sample capable of containing them. These procedures, according to the specificity of the polypeptides, the antibodies and the nucleotide sequences according to the invention that will be used, will in particular be able to detect and/or to identify *Alicyclobacillus acidocaldarius*.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between said polypeptide and the antibodies possibly present in the biological sample); b) demonstration of the antigen-antibody complexes possibly formed.

Any conventional procedure can be employed for carrying out such a detection of the antigen-antibody complexes possibly formed.

By way of nonlimiting example, one method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label, such as, of the enzymatic, fluorescent or radioactive type.

Such methods comprise, for example, the following acts: deposition of determined quantities of a polypeptide composition according to the invention in the wells of a microtiter plate, introduction into the wells of increasing dilutions of serum, or of a biological sample other than that defined previously, having to be analyzed, incubation of the microtiter plate, introduction into the wells of the microtiter plate of labeled antibodies directed against pig immunoglobulins, the labeling of these antibodies having been carried out with the aid of an enzyme selected from those that are capable of hydrolyzing a substrate by modifying the absorption of the radiation of the latter, at least at a determined wavelength, for example at 550 nm, detection, by comparison with a control test, of the quantity of hydrolyzed substrate.

The polypeptides according to the invention allow monoclonal or polyclonal antibodies to be prepared that are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide that has served as an antigen has previously been immobilized. The polyclonal antibodies according to the invention can also be prepared by purification, on an affinity column on which a polypeptide according to the invention has previously been immobilized, of the antibodies contained in the serum of an animal immunologically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* in a sample, characterized in that it comprises the following steps: a) contacting of the sample with a mono- or polyclonal antibody according to the invention (under conditions allowing an immunological reaction between said antibodies and the polypeptides of *Alicyclobacillus acidocaldarius* possibly present in the biological sample); b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* in a sample, characterized in that it contains the following steps: a) if need be, isolation of the DNA from the sample to be analyzed; b) specific amplification of the DNA of the sample with the aid of at least one primer, or a pair of primers, according to the invention; c) demonstration of the amplification products.

These can be detected, for example, by the technique of molecular hybridization utilizing a nucleic probe according to the invention. This probe will advantageously be labeled with a nonradioactive (cold probe) or radioactive isotope.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

A further embodiment of the invention comprises a method, characterized in that it comprises the following acts: a) contacting of a nucleotide probe according to the invention with a biological sample, the DNA contained in the biological sample having, if need be, previously been made accessible to hybridization under conditions allowing the hybridization of the probe with the DNA of the sample; b) demonstration of the hybrid formed between the nucleotide probe and the DNA of the biological sample.

The present invention also relates to a procedure according to the invention, characterized in that it comprises the following acts: a) contacting of a nucleotide probe immobilized on a support according to the invention with a biological sample, the DNA of the sample having, if need be, previously been made accessible to hybridization, under conditions allowing the hybridization of the probe with the DNA of the sample; b) contacting of the hybrid formed between the nucleotide probe immobilized on a support and the DNA contained in the biological sample, if need be after elimination of the DNA of the biological sample that has not hybridized with the probe, with a nucleotide probe labeled according to the invention; c) demonstration of the novel hybrid formed in act b).

According to an advantageous embodiment of the procedure for detection and/or identification defined previously, this is characterized in that, prior to act a), the DNA of the biological sample is first amplified with the aid of at least one primer according to the invention. Embodiments of methods include methods of altering recombination inside or outside of a cell, the methods comprising: providing a recombinant, purified, and/or isolated nucleotide sequence comprising a nucleotide sequence selected from the group consisting of nucleotide sequences having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283; and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 to a nucleotide sequence with which recombination event is desired.

Further embodiments of methods include placing a cell producing or encoding a recombinant, purified, and/or isolated nucleotide sequence comprising a nucleotide sequence selected from the group consisting of a nucleotide sequence having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283; and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 in a environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and/or wherein one or more chromosomal genes have been deleted from the *Bacillus* chromosome. In some further embodiments, one or more indigenous chromosomal regions have been deleted from a corresponding wild-type *Bacillus* host chromosome. In further embodiments, the *Bacillus* is an *Alicyclobacillus* sp. or *Alicyclobacillus acidocaldarius*.

Additional embodiments, include methods of modulating recombination at temperatures at or above about 25, 30, 35, 40, 45, 50, 55, 60, 65, 70, 75, 80, 85, 90, and/or 95 degrees Celsius and/or at a pH at, below, and/or above 8, 7, 6, 5, 4, 3, 2, 1, and/or 0 via providing a recombinant, purified, and/or isolated nucleotide sequence comprising a nucleotide sequence selected from the group consisting of a nucleotide sequences having at least 90% sequence identity to at least one of the sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283; and/or a recombinant, purified, and/or isolated polypeptide selected from the group consisting of a polypeptide having at least 90% sequence identity to at least one of the sequences of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 to a nucleotide sequence in with which a recombination event is desired.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other posttranslational modification may be required for the isolated and/or purified polypeptides according to the invention to be enzymatically or functionally active at pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

The invention is described in additional detail in the following illustrative examples. Although the examples may represent only selected embodiments of the invention, it should be understood that the following examples are illustrative and not limiting.

EXAMPLES

Example 1

Recombination Using Nucleotide and Amino Acid Sequences from *Alicyclobacillus acidocaldarius*

Provided in SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 are a nucleotide sequences isolated from *Alicyclobacillus acidocaldarius* and coding for the polypeptides of SEQ ID NOS: 1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282, and respectively. The nucleotide sequences of SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOS:2, 19, 36, 53, 70, 87, 104, 121, 138, 155, 172, 189, 206, 223, 240, 257, 274, 291, 308, 325, 359, 376, 410, 427, 444, 512, 529, 546, 597, 614, 648, 665, 682, 699, 716, 733, 750, 767, 784, 818, 835, 852, 886, 903, 920, 937, 954, 971, 988, 1005, 1039, 1056, 1073, 1090, 1107, 1124, 1141, 1158, 1175, 1192, 1209, 1226, 1243, 1260, 1277, 1294, 1311, 1328, 1345, 1362, 1379, 1396, 1413, 1430, 1447, 1464, 1481, 1498, 1515, 1532, 1549, 1566, 1583, 1600, 1634, 1651, 1685, 1702, 1719, 1787, 1804, 1821, 1872, 1889, 1923, 1940, 1957, 1974, 1991, 2008, 2025, 2042, 2059, 2093, 2110, 2127, 2161, 2178, 2195, 2212, 2229, 2246, 2263, 2280, 2314, 2331, 2348, 2365, 2382, 2399, 2416, 2433, 2450, 2467, 2484, 2501, 2518, 2535, 2552, 2569, 2586, 2603, 2620, 2637, 2654, 2671, 2688, 2705, 2722, 2739, 2773, 2790, 2824, 2841, 2858, 2926, 2943, 2960, 3011, 3028, 3062, 3079, 3096, 3113, 3130, 3147, 3164, 3181, 3198, 3232, 3249, 3266, and 3283. The polypeptides of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 are then isolated and/or purified. The isolated and/or purified polypeptides of SEQ ID NOS:1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 are then each demonstrated to have one or more of the activities provided in Table 1.

The isolated and/or purified polypeptides of SEQ ID NOS: 1, 18, 35, 52, 69, 86, 103, 120, 137, 154, 171, 188, 205, 222, 239, 256, 273, 290, 307, 324, 358, 375, 409, 426, 443, 511, 528, 545, 596, 613, 647, 664, 681, 698, 715, 732, 749, 766, 783, 817, 834, 851, 885, 902, 819, 936, 953, 970, 987, 1004, 1038, 1055, 1072, 1089, 1106, 1123, 1140, 1157, 1174, 1191, 1208, 1225, 1242, 1259, 1276, 1293, 1310, 1327, 1344, 1361, 1378, 1395, 1412, 1429, 1446, 1463, 1480, 1497, 1514, 1531, 1548, 1565, 1582, 1599, 1633, 1650, 1684, 1701, 1718, 1786, 1803, 1820, 1871, 1888, 1922, 1939, 1956, 1973, 1990, 2007, 2024, 2041, 2058, 2092, 2109, 2126, 2160, 2177, 2094, 2211, 2228, 2245, 2262, 2279, 2313, 2330, 2347, 2364, 2381, 2398, 2415, 2432, 2449, 2466, 2483, 2500, 2517, 2534, 2551, 2568, 2585, 2602, 2619, 2636, 2653, 2670, 2687, 2704, 2721, 2738, 2772, 2789, 2823, 2840, 2857, 2925, 2942, 2959, 3010, 3027, 3061, 3078, 3095, 3112, 3129, 3146, 3163, 3180, 3197, 3231, 3248, 3265, and 3282 are demonstrated to have activity as at least one of a ATP-dependent DNA helicase recG, ATP-dependent DNA ligase, ATP-dependent endopeptidase clp proteolytic subunit, Chromosome partitioning protein, Crossover junction endodeoxyribonuclease ruvC, Deoxyuridine 5'-triphosphate nucleotidohydrolase, DNA adenine methylase, DNA helicase, DNA integration/recombination/inversion, DNA polymerase I, DNA polymerase III beta chain, DNA polymerase IV, DNA primase, DNA repair protein radC, DNA replication and repair protein recF, DNA replication protein dnaD, DNA topoisomerase I, DNA/RNA helicase (DEAD/DEAH box family), DNA-binding protein HU, Fe—S oxidoreductase, Glycerophosphoryl diester phosphodiesterase, HNH endonuclease family protein, Holliday junction DNA helicase ruvB, Integrase/recombinase (XerC/CodV family), Ligase/carboxyalse family protein, LtrC-like protein, Macrolide-efflux protein, NAD-dependent DNA ligase, Nicotinate phosphoribosyltransferase, nodulin-26, Phage antirepressor protein, Phage protein, Phosphinothricin N-acetyltransferase, Phosphohydrolase, RecA protein, Recombination protein recR, Replicative DNA helicase, Ribonucleoside-diphosphate reductase alpha chain, Ribonucleoside-diphosphate reductase beta chain, Ribose-phosphate pyrophosphokinase, Serine/threonine protein phosphatase, Single-strand DNA binding protein, Single-stranded DNA-binding protein, Site-specific recombinase, Site-specific resolvase/integrase, Thioredoxin, Thymidine kinase, Transcriptional regulator/Lex A repressor, Transcriptional regulator, Cro/CI family, Transposase, TRSE protein, Two-component response regulator, Type II restriction-modification system methylation subunit.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and that fall within the limits of the appended claims and their legal equivalents.

BIBLIOGRAPHIC REFERENCES

Barany, F., 1991, *PNAS. USA* 88:189-193.
Buckholz, R. G., 1993, Yeast systems for the expression of heterologous gene products. *Curr. Op. Biotechnology* 4:538-542.
Burg, J. L. et al., 1996, *Mol. and Cell. Probes* 10:257-271.
Chu, B. C. F. et al., 1986, *NAR* 14:5591-5603.
Duck, P. et al., 1990, *Biotechniques* 9:142-147.
Edwards, C. P., and A. Aruffo, 1993, Current applications of COS cell based transient expression systems. *Curr. Op. Biotechnology* 4:558-563.
Guatelli, J. C. et al., 1990, *PNAS. USA* 87:1874-1878.
Houben-Weyl, 1974, in *Methoden der Organischen Chemie*, E. Wunsch Ed., Volume 15-I and 15-II, Thieme, Stuttgart.
Innis, M. A. et al., 1990, in *PCR Protocols. A guide to Methods and Applications*, San Diego, Academic Press.
Kievitis, T. et al., 1991, *J. Virol. Methods* 35:273-286.
Kohler, G. et al., 1975, *Nature* 256(5517):495497.
Kwoh, D. Y. et al., 1989, *PNAS. USA* 86:1173-1177.
Luckow, V. A., 1993, Baculovirus systems for the expression of human gene products. *Curr. Op. Biotechnology* 4:564-572.
Matthews, J. A. et al., 1988, *Anal. Biochem.* 169:1-25.
Merrifield, R. D., 1966, *J. Am. Chem. Soc.* 88(21):5051-5052.
Miele, E. A. et al., 1983, *J. Mol. Biol.* 171:281-295.
Olins, P. O., and S. C. Lee, 1993, Recent advances in heterologous gene expression in *E. coli. Curr. Op. Biotechnology* 4:520-525.
Rolfs, A. et al., 1991, In *PCR Topics. Usage of Polymerase Chain reaction in Genetic and Infectious Disease*. Berlin: Springer-Verlag.
Sambrook, J. et al., 1989, *In Molecular cloning: A Laboratory Manual*. Cold Spring Harbor, N.Y.: Cold Spring Harbor Laboratory Press.
Sanchez-Pescador, R., 1988, *J. Clin. Microbiol.* 26(10):1934-1938.
Segev D., 1992, in *Non-radioactive Labeling and Detection of Biomolecules*. Kessler C. Springer Verlag, Berlin, New-York: 197-205.
Urdea, M. S., 1988, *Nucleic Acids Research* 11:4937-4957.
Walker, G. T. et al., 1992, *NAR* 20:1691-1696.
Walker, G. T. et al., 1992, *PNAS. USA* 89:392-396.
White, B. A. et al., 1997, *Methods in Molecular Biology* 67, Humana Press, Totowa, N.J.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09029114B2). An electronic copy of the "Sequence Listing" will also be available from the USPTO upon request and payment of the fee set forth in 37 CFR 1.19(b)(3).

What is claimed is:

1. A method of modulating or altering recombination, the method comprising:
   providing an isolated or purified polypeptide having at least 90% sequence identity to SEQ ID No. 2976 to a nucleotide sequence in which a genetic recombination event is desired.

2. The method according to claim 1, wherein the polypeptide has activity at or below about pH 8.

3. The method according to claim 1, wherein the polypeptide has activity at a temperature at or above about 50 degrees Celsius.

4. The method according to claim 1, wherein the modulation or alteration of recombination occurs at or below about pH 8.

5. The method according to claim 1, wherein the modulation or alteration of recombination occurs at a temperature at or above about 50 degrees Celsius.

6. The method according to claim 1, wherein the purified or isolated polypeptide is glycosylated, pegylated, or otherwise post-translationally modified.

7. The method according to claim 1, wherein the polypeptide has as a Type II restriction-modification system methylation subunit.

* * * * *